US012433508B2

(12) United States Patent
Harris et al.

(10) Patent No.: US 12,433,508 B2
(45) Date of Patent: Oct. 7, 2025

(54) SURGICAL SYSTEM HAVING A SURGICAL INSTRUMENT CONTROLLED BASED ON COMPARISON OF SENSOR AND DATABASE DATA

(71) Applicant: Cilag GmbH International, Zug (CH)

(72) Inventors: Jason L. Harris, Lebanon, OH (US); Frederick E. Shelton, IV, Hillsboro, OH (US); Chad E. Eckert, Terrace Park, OH (US); Jordan B. Wong, Cincinnati, OH (US); David C. Yates, Morrow, OH (US); Tamara S. Widenhouse, Clarksville, OH (US); Chester O. Baxter, III, Loveland, OH (US)

(73) Assignee: Cilag GmbH International, Zug (CH)

( * ) Notice: Subject to any disclaimer, the term of this patent is extended or adjusted under 35 U.S.C. 154(b) by 215 days.

(21) Appl. No.: 17/960,604

(22) Filed: Oct. 5, 2022

(65) Prior Publication Data

US 2023/0098870 A1 Mar. 30, 2023

Related U.S. Application Data

(63) Continuation of application No. 16/676,652, filed on Nov. 7, 2019, now Pat. No. 11,596,291, which is a
(Continued)

(51) Int. Cl.
*A61B 5/107* (2006.01)
*A61B 1/00* (2006.01)
(Continued)

(52) U.S. Cl.
CPC ...... *A61B 5/1076* (2013.01); *A61B 1/000094* (2022.02); *A61B 1/00045* (2013.01);
(Continued)

(58) Field of Classification Search
CPC .......... A61B 1/000094; A61B 17/1285; A61B 18/085; A61B 2017/00017;
(Continued)

(56) References Cited

U.S. PATENT DOCUMENTS

| | | |
|---|---|---|
| 1,853,416 A | 4/1932 | Hall |
| 2,222,125 A | 11/1940 | Stehlik |

(Continued)

FOREIGN PATENT DOCUMENTS

| | | |
|---|---|---|
| AU | 2015201140 A1 | 3/2015 |
| CA | 2795323 A1 | 5/2014 |

(Continued)

OTHER PUBLICATIONS

US 10,504,709, 8/2018, Karancsi et al. (withdrawn)
(Continued)

*Primary Examiner* — Mohamed G Gabr

(57) ABSTRACT

A surgical system comprising a surgical instrument and a surgical hub is disclosed. The surgical instrument is configured to perform a surgical procedure and comprises a housing, a shaft assembly, an end effector, and a sensor configured to sense a parameter associated with a function of the surgical instrument. The surgical hub comprises a processor and a memory. The memory stores instructions executable by the processor to receive data from the sensor, wherein the data comprises the parameter associated with the function of the surgical instrument; infer a step of the surgical procedure being performed by the surgical instrument, based on the data from the sensor; receive data from a database, wherein the data from the database is associated with the step of the surgical procedure; compare a value of the parameter to the data received from the database; and control the surgical instrument based on the comparison.

14 Claims, 150 Drawing Sheets

Related U.S. Application Data continuation of application No. 16/209,423, filed on Dec. 4, 2018, now Pat. No. 11,969,142.

(60) Provisional application No. 62/773,778, filed on Nov. 30, 2018, provisional application No. 62/773,728, filed on Nov. 30, 2018, provisional application No. 62/773,741, filed on Nov. 30, 2018, provisional application No. 62/773,742, filed on Nov. 30, 2018, provisional application No. 62/750,529, filed on Oct. 25, 2018, provisional application No. 62/750,539, filed on Oct. 25, 2018, provisional application No. 62/750,555, filed on Oct. 25, 2018, provisional application No. 62/729,183, filed on Sep. 10, 2018, provisional application No. 62/729,177, filed on Sep. 10, 2018, provisional application No. 62/729,176, filed on Sep. 10, 2018, provisional application No. 62/729,185, filed on Sep. 10, 2018, provisional application No. 62/729,184, filed on Sep. 10, 2018, provisional application No. 62/729,182, filed on Sep. 10, 2018, provisional application No. 62/729,191, filed on Sep. 10, 2018, provisional application No. 62/729,195, filed on Sep. 10, 2018, provisional application No. 62/729,186, filed on Sep. 10, 2018, provisional application No. 62/721,995, filed on Aug. 23, 2018, provisional application No. 62/721,998, filed on Aug. 23, 2018, provisional application No. 62/721,999, filed on Aug. 23, 2018, provisional application No. 62/721,994, filed on Aug. 23, 2018, provisional application No. 62/721,996, filed on Aug. 23, 2018, provisional application No. 62/692,747, filed on Jun. 30, 2018, provisional application No. 62/692,748, filed on Jun. 30, 2018, provisional application No. 62/692,768, filed on Jun. 30, 2018, provisional application No. 62/691,228, filed on Jun. 28, 2018, provisional application No. 62/691,227, filed on Jun. 28, 2018, provisional application No. 62/691,230, filed on Jun. 28, 2018, provisional application No. 62/691,219, filed on Jun. 28, 2018, provisional application No. 62/691,257, filed on Jun. 28, 2018, provisional application No. 62/691,262, filed on Jun. 28, 2018, provisional application No. 62/691,251, filed on Jun. 28, 2018, provisional application No. 62/665,129, filed on May 1, 2018, provisional application No. 62/665,139, filed on May 1, 2018, provisional application No. 62/665,177, filed on May 1, 2018, provisional application No. 62/665,128, filed on May 1, 2018, provisional application No. 62/665,192, filed on May 1, 2018, provisional application No. 62/665,134, filed on May 1, 2018, provisional application No. 62/659,900, filed on Apr. 19, 2018, provisional application No. 62/650,898, filed on Mar. 30, 2018, provisional application No. 62/650,887, filed on Mar. 30, 2018, provisional application No. 62/650,882, filed on Mar. 30, 2018, provisional application No. 62/650,877, filed on Mar. 30, 2018, provisional application No. 62/649,302, filed on Mar. 28, 2018, provisional application No. 62/649,300, filed on Mar. 28, 2018, provisional application No. 62/649,309, filed on Mar. 28, 2018, provisional application No. 62/649,310, filed on Mar. 28, 2018, provisional application No. 62/649,291, filed on Mar. 28, 2018, provisional application No. 62/649,296, filed on Mar. 28, 2018, provisional application No. 62/649,333, filed on Mar. 28, 2018, provisional application No. 62/649,327, filed on Mar. 28, 2018, provisional application No. 62/649,315, filed on Mar. 28, 2018, provisional application No. 62/649,313, filed on Mar. 28, 2018, provisional application No. 62/649,320, filed on Mar. 28, 2018, provisional application No. 62/649,307, filed on Mar. 28, 2018, provisional application No. 62/649,323, filed on Mar. 28, 2018, provisional application No. 62/611,341, filed on Dec. 28, 2017, provisional application No. 62/611,340, filed on Dec. 28, 2017, provisional application No. 62/611,339, filed on Dec. 28, 2017.

(51) Int. Cl.

| | |
|---|---|
| ***A61B 1/05*** | (2006.01) |
| ***A61B 1/06*** | (2006.01) |
| ***A61B 5/00*** | (2006.01) |
| ***A61B 5/02*** | (2006.01) |
| ***A61B 5/026*** | (2006.01) |
| ***A61B 5/06*** | (2006.01) |
| ***A61B 5/287*** | (2021.01) |
| ***A61B 6/00*** | (2006.01) |
| ***A61B 17/068*** | (2006.01) |
| ***A61B 17/072*** | (2006.01) |
| ***A61B 17/11*** | (2006.01) |
| ***A61B 17/115*** | (2006.01) |
| ***A61B 17/128*** | (2006.01) |
| ***A61B 17/32*** | (2006.01) |
| ***A61B 18/14*** | (2006.01) |
| ***A61B 34/00*** | (2016.01) |
| ***A61B 34/10*** | (2016.01) |
| ***A61B 34/20*** | (2016.01) |
| ***A61B 34/32*** | (2016.01) |
| ***A61B 90/00*** | (2016.01) |
| ***A61B 90/35*** | (2016.01) |
| ***A61M 1/00*** | (2006.01) |
| ***B25J 9/16*** | (2006.01) |
| ***B25J 13/00*** | (2006.01) |
| ***G06K 7/10*** | (2006.01) |
| ***G06K 19/077*** | (2006.01) |
| ***G16H 10/60*** | (2018.01) |
| ***G16H 40/63*** | (2018.01) |
| ***G16H 40/67*** | (2018.01) |
| ***G16H 50/20*** | (2018.01) |
| ***G16H 70/20*** | (2018.01) |
| ***H01Q 1/22*** | (2006.01) |
| ***H04L 9/40*** | (2022.01) |
| ***H04L 67/10*** | (2022.01) |
| ***H04L 67/12*** | (2022.01) |
| ***H04N 5/272*** | (2006.01) |
| ***H04N 7/18*** | (2006.01) |
| ***H05K 1/02*** | (2006.01) |
| ***H05K 1/18*** | (2006.01) |
| *A61B 17/00* | (2006.01) |
| *A61B 18/00* | (2006.01) |
| *A61B 34/30* | (2016.01) |
| *A61B 90/30* | (2016.01) |
| *A61M 13/00* | (2006.01) |

(52) U.S. Cl.

CPC ............ *A61B 1/051* (2013.01); *A61B 1/0661* (2013.01); *A61B 5/0066* (2013.01); *A61B 5/0075* (2013.01); *A61B 5/02* (2013.01); *A61B 5/0261* (2013.01); *A61B 5/062* (2013.01); *A61B 5/065* (2013.01); *A61B 5/1073* (2013.01); *A61B 5/287* (2021.01); *A61B*

*5/6852* (2013.01); *A61B 5/6857* (2013.01); *A61B 5/6859* (2013.01); *A61B 5/7278* (2013.01); *A61B 5/743* (2013.01); *A61B 6/5247* (2013.01); *A61B 17/0682* (2013.01); *A61B 17/072* (2013.01); *A61B 17/1114* (2013.01); *A61B 17/1155* (2013.01); *A61B 17/1285* (2013.01); *A61B 17/320092* (2013.01); *A61B 18/1442* (2013.01); *A61B 18/1445* (2013.01); *A61B 34/10* (2016.02); *A61B 34/20* (2016.02); *A61B 34/32* (2016.02); *A61B 34/71* (2016.02); *A61B 90/35* (2016.02); *A61B 90/361* (2016.02); *A61B 90/37* (2016.02); *A61M 1/73* (2021.05); *A61M 1/79* (2021.05); *B25J 9/1697* (2013.01); *B25J 13/006* (2013.01); *G06K 7/10316* (2013.01); *G06K 19/07749* (2013.01); *G16H 10/60* (2018.01); *G16H 40/63* (2018.01); *G16H 40/67* (2018.01); *G16H 50/20* (2018.01); *G16H 70/20* (2018.01); *H01Q 1/22* (2013.01); *H04L 63/1416* (2013.01); *H04L 67/10* (2013.01); *H04L 67/12* (2013.01); *H04N 5/272* (2013.01); *H04N 7/183* (2013.01); *H05K 1/028* (2013.01); *H05K 1/189* (2013.01); *A61B 2017/00022* (2013.01); *A61B 2017/00026* (2013.01); *A61B 2017/0003* (2013.01); *A61B 2017/00039* (2013.01); *A61B 2017/00044* (2013.01); *A61B 2017/00057* (2013.01); *A61B 2017/00061* (2013.01); *A61B 2017/00075* (2013.01); *A61B 2017/00084* (2013.01); *A61B 2017/00097* (2013.01); *A61B 2017/00106* (2013.01); *A61B 2017/0011* (2013.01); *A61B 2017/00115* (2013.01); *A61B 2017/00119* (2013.01); *A61B 2017/00199* (2013.01); *A61B 2017/00203* (2013.01); *A61B 2017/00221* (2013.01); *A61B 2017/00398* (2013.01); *A61B 2017/00402* (2013.01); *A61B 2017/00734* (2013.01); *A61B 2017/00809* (2013.01); *A61B 2017/00818* (2013.01); *A61B 2017/07257* (2013.01); *A61B 2017/07271* (2013.01); *A61B 2017/07278* (2013.01); *A61B 2017/07285* (2013.01); *A61B 2017/1132* (2013.01); *A61B 2017/32007* (2017.08); *A61B 2017/320074* (2017.08); *A61B 2017/320084* (2013.01); *A61B 2017/320095* (2017.08); *A61B 2017/320097* (2017.08); *A61B 2018/00541* (2013.01); *A61B 2018/00589* (2013.01); *A61B 2018/00595* (2013.01); *A61B 2018/00601* (2013.01); *A61B 2018/00607* (2013.01); *A61B 2018/0063* (2013.01); *A61B 2018/00642* (2013.01); *A61B 2018/00684* (2013.01); *A61B 2018/00791* (2013.01); *A61B 2018/00827* (2013.01); *A61B 2018/00875* (2013.01); *A61B 2018/00892* (2013.01); *A61B 2018/00988* (2013.01); *A61B 2018/00994* (2013.01); *A61B 2034/105* (2016.02); *A61B 2034/2051* (2016.02); *A61B 2034/2055* (2016.02); *A61B 2034/2057* (2016.02); *A61B 2034/2061* (2016.02); *A61B 34/30* (2016.02); *A61B 2034/301* (2016.02); *A61B 2034/305* (2016.02); *A61B 2090/309* (2016.02); *A61B 2217/005* (2013.01); *A61B 2217/007* (2013.01); *A61B 2218/002* (2013.01); *A61B 2218/007* (2013.01); *A61B 2218/008* (2013.01); *A61M 1/80* (2021.05); *A61M 13/003* (2013.01); *A61M 2205/3306* (2013.01); *A61M 2205/3327* (2013.01); *A61M 2205/3331* (2013.01); *A61M 2205/3365* (2013.01); *A61M 2205/3368* (2013.01); *G05B 2219/40174* (2013.01); *G05B 2219/45119* (2013.01)

(58) Field of Classification Search

CPC .. A61B 2017/00026; A61B 2017/0003; A61B 2017/00039; A61B 2017/00199; A61B 2017/00123; A61B 2017/00119; A61B 2018/00642; A61B 2018/00684; A61B 2018/00988; A61B 2090/0811; A61B 2090/064; A61B 2090/0807; A61B 2034/256; A61B 2034/2059; A61B 2562/0261; A61B 2562/0247; A61B 34/20; A61B 34/25; A61B 34/30; A61B 34/32; A61B 5/068; A61M 1/73

See application file for complete search history.

(56) References Cited

U.S. PATENT DOCUMENTS

| | | | |
|---|---|---|---|
| 3,082,426 | A | 3/1963 | Miles |
| 3,503,396 | A | 3/1970 | Pierie et al. |
| 3,584,628 | A | 6/1971 | Green |
| 3,626,457 | A | 12/1971 | Duerr et al. |
| 3,633,584 | A | 1/1972 | Farrell |
| 3,759,017 | A | 9/1973 | Young |
| 3,863,118 | A | 1/1975 | Lander et al. |
| 3,898,545 | A | 8/1975 | Coppa et al. |
| 3,912,121 | A | 10/1975 | Steffen |
| 3,915,271 | A | 10/1975 | Harper |
| 3,932,812 | A | 1/1976 | Milligan |
| 4,041,362 | A | 8/1977 | Ichiyanagi |
| 4,052,649 | A | 10/1977 | Greenwell et al. |
| 4,087,730 | A | 5/1978 | Goles |
| 4,157,859 | A | 6/1979 | Terry |
| 4,171,700 | A | 10/1979 | Farin |
| 4,202,722 | A | 5/1980 | Paquin |
| 4,412,539 | A | 11/1983 | Jarvik |
| 4,448,193 | A | 5/1984 | Ivanov |
| 4,523,695 | A | 6/1985 | Braun et al. |
| 4,608,160 | A | 8/1986 | Zoch |
| 4,614,366 | A | 9/1986 | North et al. |
| 4,633,874 | A | 1/1987 | Chow et al. |
| 4,701,193 | A | 10/1987 | Robertson et al. |
| 4,735,603 | A | 4/1988 | Goodson et al. |
| 4,788,977 | A | 12/1988 | Farin et al. |
| 4,849,752 | A | 7/1989 | Bryant |
| D303,787 | S | 10/1989 | Messenger et al. |
| 4,892,244 | A | 1/1990 | Fox et al. |
| 4,976,173 | A | 12/1990 | Yang |
| 5,010,341 | A | 4/1991 | Huntley et al. |
| 5,026,387 | A | 6/1991 | Thomas |
| 5,035,692 | A | 7/1991 | Lyon et al. |
| 5,042,460 | A | 8/1991 | Sakurai et al. |
| 5,047,043 | A | 9/1991 | Kubota et al. |
| 5,084,057 | A | 1/1992 | Green et al. |
| 5,100,402 | A | 3/1992 | Fan |
| D327,061 | S | 6/1992 | Soren et al. |
| 5,129,570 | A | 7/1992 | Schulze et al. |
| 5,151,102 | A | 9/1992 | Kamiyama et al. |
| 5,156,315 | A | 10/1992 | Green et al. |
| 5,158,585 | A | 10/1992 | Saho et al. |
| 5,171,247 | A | 12/1992 | Hughett et al. |
| 5,189,277 | A | 2/1993 | Boisvert et al. |
| 5,197,962 | A | 3/1993 | Sansom et al. |
| 5,204,669 | A | 4/1993 | Dorfe et al. |
| 5,217,003 | A | 6/1993 | Wilk |
| 5,242,474 | A | 9/1993 | Herbst et al. |
| 5,253,793 | A | 10/1993 | Green et al. |
| 5,271,543 | A | 12/1993 | Grant et al. |
| RE34,519 | E | 1/1994 | Fox et al. |
| 5,275,323 | A | 1/1994 | Schulze et al. |
| 5,318,516 | A | 6/1994 | Cosmescu |
| 5,318,563 | A | 6/1994 | Malis et al. |

(56) References Cited

U.S. PATENT DOCUMENTS

| | | | |
|---|---|---|---|
| 5,322,055 | A | 6/1994 | Davison et al. |
| 5,342,349 | A | 8/1994 | Kaufman |
| 5,364,003 | A | 11/1994 | Williamson, IV |
| 5,383,880 | A | 1/1995 | Hooven |
| 5,385,544 | A | 1/1995 | Edwards et al. |
| 5,396,900 | A | 3/1995 | Slater et al. |
| 5,397,046 | A | 3/1995 | Savage et al. |
| 5,403,312 | A | 4/1995 | Yates et al. |
| 5,403,327 | A | 4/1995 | Thornton et al. |
| 5,413,267 | A | 5/1995 | Solyntjes et al. |
| 5,415,335 | A | 5/1995 | Knodell, Jr. |
| 5,417,699 | A | 5/1995 | Klein et al. |
| 5,439,468 | A | 8/1995 | Schulze et al. |
| 5,445,304 | A | 8/1995 | Plyley et al. |
| 5,462,545 | A | 10/1995 | Wang et al. |
| 5,465,895 | A | 11/1995 | Knodel et al. |
| 5,467,911 | A | 11/1995 | Tsuruta et al. |
| 5,474,566 | A | 12/1995 | Alesi et al. |
| 5,485,947 | A | 1/1996 | Olson et al. |
| 5,496,315 | A | 3/1996 | Weaver et al. |
| 5,496,317 | A | 3/1996 | Goble et al. |
| 5,503,320 | A | 4/1996 | Webster et al. |
| 5,529,235 | A | 6/1996 | Boiarski et al. |
| 5,531,743 | A | 7/1996 | Nettekoven et al. |
| 5,545,148 | A | 8/1996 | Wurster |
| 5,552,685 | A | 9/1996 | Young et al. |
| 5,560,372 | A | 10/1996 | Cory |
| 5,584,425 | A | 12/1996 | Savage et al. |
| 5,610,379 | A | 3/1997 | Muz et al. |
| 5,610,811 | A | 3/1997 | Honda |
| 5,613,966 | A | 3/1997 | Makower et al. |
| 5,624,452 | A | 4/1997 | Yates |
| D379,346 | S | 5/1997 | Mieki |
| 5,626,587 | A | 5/1997 | Bishop et al. |
| 5,643,291 | A | 7/1997 | Pier et al. |
| 5,654,750 | A | 8/1997 | Weil et al. |
| 5,673,841 | A | 10/1997 | Schulze et al. |
| 5,673,842 | A | 10/1997 | Bittner et al. |
| 5,675,227 | A | 10/1997 | Roos et al. |
| 5,693,042 | A | 12/1997 | Boiarski et al. |
| 5,693,052 | A | 12/1997 | Weaver |
| 5,695,502 | A | 12/1997 | Pier et al. |
| 5,697,926 | A | 12/1997 | Weaver |
| 5,706,998 | A | 1/1998 | Plyley et al. |
| 5,718,359 | A | 2/1998 | Palmer et al. |
| 5,724,468 | A | 3/1998 | Leone et al. |
| 5,725,536 | A | 3/1998 | Oberlin et al. |
| 5,725,542 | A | 3/1998 | Yoon |
| 5,735,445 | A | 4/1998 | Vidal et al. |
| 5,735,848 | A | 4/1998 | Yates et al. |
| 5,746,209 | A | 5/1998 | Yost et al. |
| 5,749,362 | A | 5/1998 | Funda et al. |
| 5,749,893 | A | 5/1998 | Vidal et al. |
| 5,752,644 | A | 5/1998 | Bolanos et al. |
| 5,762,255 | A | 6/1998 | Chrisman et al. |
| 5,762,458 | A | 6/1998 | Wang et al. |
| 5,766,186 | A | 6/1998 | Faraz et al. |
| 5,769,791 | A | 6/1998 | Benaron et al. |
| 5,775,331 | A | 7/1998 | Raymond et al. |
| 5,797,537 | A | 8/1998 | Oberlin et al. |
| 5,800,350 | A | 9/1998 | Coppleson et al. |
| D399,561 | S | 10/1998 | Ellingson |
| 5,817,093 | A | 10/1998 | Williamson, IV et al. |
| 5,820,009 | A | 10/1998 | Melling et al. |
| 5,833,690 | A | 11/1998 | Yates et al. |
| 5,836,849 | A | 11/1998 | Mathiak et al. |
| 5,836,869 | A | 11/1998 | Kudo et al. |
| 5,836,909 | A | 11/1998 | Cosmescu |
| 5,843,080 | A | 12/1998 | Fleenor et al. |
| 5,846,237 | A | 12/1998 | Nettekoven |
| 5,849,022 | A | 12/1998 | Sakashita et al. |
| 5,873,873 | A | 2/1999 | Smith et al. |
| 5,878,938 | A | 3/1999 | Bittner et al. |
| 5,893,849 | A | 4/1999 | Weaver |
| 5,906,625 | A | 5/1999 | Bito et al. |
| 5,942,333 | A | 8/1999 | Arnett et al. |
| 5,947,996 | A | 9/1999 | Logeman |
| 5,968,032 | A | 10/1999 | Sleister |
| 5,980,510 | A | 11/1999 | Tsonton et al. |
| 5,987,346 | A | 11/1999 | Benaron et al. |
| 5,997,528 | A | 12/1999 | Bisch et al. |
| 6,004,269 | A | 12/1999 | Crowley et al. |
| 6,010,054 | A | 1/2000 | Johnson et al. |
| 6,030,437 | A | 2/2000 | Gourrier et al. |
| 6,036,637 | A | 3/2000 | Kudo |
| 6,039,734 | A | 3/2000 | Goble |
| 6,039,735 | A | 3/2000 | Greep |
| 6,059,799 | A | 5/2000 | Aranyi et al. |
| 6,066,137 | A | 5/2000 | Greep |
| 6,079,606 | A | 6/2000 | Milliman et al. |
| 6,090,107 | A | 7/2000 | Borgmeier et al. |
| 6,099,537 | A | 8/2000 | Sugai et al. |
| 6,102,907 | A | 8/2000 | Smethers et al. |
| 6,109,500 | A | 8/2000 | Alli et al. |
| 6,113,598 | A | 9/2000 | Baker |
| 6,126,592 | A | 10/2000 | Proch et al. |
| 6,126,658 | A | 10/2000 | Baker |
| 6,131,789 | A | 10/2000 | Schulze et al. |
| 6,155,473 | A | 12/2000 | Tompkins et al. |
| 6,214,000 | B1 | 4/2001 | Fleenor et al. |
| 6,258,105 | B1 | 7/2001 | Hart et al. |
| 6,269,411 | B1 | 7/2001 | Reasoner |
| 6,273,887 | B1 | 8/2001 | Yamauchi et al. |
| 6,283,960 | B1 | 9/2001 | Ashley |
| 6,301,495 | B1 | 10/2001 | Gueziec et al. |
| 6,302,881 | B1 | 10/2001 | Farin |
| 6,308,089 | B1 | 10/2001 | von der Ruhr et al. |
| 6,325,808 | B1 | 12/2001 | Bernard et al. |
| 6,325,811 | B1 | 12/2001 | Messerly |
| 6,331,181 | B1 | 12/2001 | Tierney et al. |
| 6,341,164 | B1 | 1/2002 | Dilkie et al. |
| 6,391,102 | B1 | 5/2002 | Bodden et al. |
| 6,423,057 | B1 | 7/2002 | He et al. |
| 6,434,416 | B1 | 8/2002 | Mizoguchi et al. |
| 6,443,973 | B1 | 9/2002 | Whitman |
| 6,451,015 | B1 | 9/2002 | Rittman, III et al. |
| 6,454,781 | B1 | 9/2002 | Witt et al. |
| 6,457,625 | B1 | 10/2002 | Tormala et al. |
| 6,461,352 | B2 | 10/2002 | Morgan et al. |
| 6,466,817 | B1 | 10/2002 | Kaula et al. |
| 6,480,796 | B2 | 11/2002 | Wiener |
| 6,524,307 | B1 | 2/2003 | Palmerton et al. |
| 6,530,933 | B1 | 3/2003 | Yeung et al. |
| 6,551,243 | B2 | 4/2003 | Bocionek et al. |
| 6,569,109 | B2 | 5/2003 | Sakurai et al. |
| 6,582,424 | B2 | 6/2003 | Fleenor et al. |
| 6,584,358 | B2 | 6/2003 | Carter et al. |
| 6,585,791 | B1 | 7/2003 | Garito et al. |
| 6,611,793 | B1 | 8/2003 | Burnside et al. |
| 6,618,626 | B2 | 9/2003 | West, Jr. et al. |
| 6,633,234 | B2 | 10/2003 | Wiener et al. |
| 6,648,223 | B2 | 11/2003 | Boukhny et al. |
| 6,678,552 | B2 | 1/2004 | Pearlman |
| 6,679,899 | B2 | 1/2004 | Wiener et al. |
| 6,685,704 | B2 | 2/2004 | Greep |
| 6,699,187 | B2 | 3/2004 | Webb et al. |
| 6,731,514 | B2 | 5/2004 | Evans |
| 6,742,895 | B2 | 6/2004 | Robin |
| 6,752,816 | B2 | 6/2004 | Culp et al. |
| 6,760,616 | B2 | 7/2004 | Hoey et al. |
| 6,770,072 | B1 | 8/2004 | Truckai et al. |
| 6,773,444 | B2 | 8/2004 | Messerly |
| 6,775,575 | B2 | 8/2004 | Bommannan et al. |
| 6,778,846 | B1 | 8/2004 | Martinez et al. |
| 6,781,683 | B2 | 8/2004 | Kacyra et al. |
| 6,783,524 | B2 | 8/2004 | Anderson et al. |
| 6,783,525 | B2 | 8/2004 | Greep et al. |
| 6,793,652 | B1 | 9/2004 | Whitman et al. |
| 6,793,663 | B2 | 9/2004 | Kneifel et al. |
| 6,824,539 | B2 | 11/2004 | Novak |
| 6,846,308 | B2 | 1/2005 | Whitman et al. |
| 6,849,074 | B2 | 2/2005 | Chen et al. |
| 6,852,219 | B2 | 2/2005 | Hammond |
| 6,863,650 | B1 | 3/2005 | Irion |

(56) References Cited

U.S. PATENT DOCUMENTS

| | | | |
|---|---|---|---|
| 6,869,430 | B2 | 3/2005 | Balbierz et al. |
| 6,869,435 | B2 | 3/2005 | Blake, III |
| 6,911,033 | B2 | 6/2005 | de Guillebon et al. |
| 6,913,471 | B2 | 7/2005 | Smith |
| 6,937,892 | B2 | 8/2005 | Leyde et al. |
| 6,945,981 | B2 | 9/2005 | Donofrio et al. |
| 6,951,559 | B1 | 10/2005 | Greep |
| 6,962,587 | B2 | 11/2005 | Johnson et al. |
| 6,978,921 | B2 | 12/2005 | Shelton, IV et al. |
| 6,988,649 | B2 | 1/2006 | Shelton, IV et al. |
| 7,000,818 | B2 | 2/2006 | Shelton, IV et al. |
| 7,009,511 | B2 | 3/2006 | Mazar et al. |
| 7,030,146 | B2 | 4/2006 | Baynes et al. |
| 7,032,798 | B2 | 4/2006 | Whitman et al. |
| 7,041,941 | B2 | 5/2006 | Faries, Jr. et al. |
| 7,044,352 | B2 | 5/2006 | Shelton, IV et al. |
| 7,044,911 | B2 | 5/2006 | Drinan et al. |
| 7,044,949 | B2 | 5/2006 | Orszulak et al. |
| 7,048,775 | B2 | 5/2006 | Jornitz et al. |
| 7,053,752 | B2 | 5/2006 | Wang et al. |
| 7,055,730 | B2 | 6/2006 | Ehrenfels et al. |
| 7,073,765 | B2 | 7/2006 | Newkirk |
| 7,077,853 | B2 | 7/2006 | Kramer et al. |
| 7,077,856 | B2 | 7/2006 | Whitman |
| 7,081,096 | B2 | 7/2006 | Brister et al. |
| 7,097,640 | B2 | 8/2006 | Wang et al. |
| 7,103,688 | B2 | 9/2006 | Strong |
| 7,104,949 | B2 | 9/2006 | Anderson et al. |
| 7,118,564 | B2 | 10/2006 | Ritchie et al. |
| 7,121,460 | B1 | 10/2006 | Parsons et al. |
| 7,137,980 | B2 | 11/2006 | Buysse et al. |
| 7,140,528 | B2 | 11/2006 | Shelton, IV |
| 7,143,923 | B2 | 12/2006 | Shelton, IV et al. |
| 7,143,925 | B2 | 12/2006 | Shelton, IV et al. |
| 7,147,139 | B2 | 12/2006 | Schwemberger et al. |
| 7,155,316 | B2 | 12/2006 | Sutherland et al. |
| 7,164,940 | B2 | 1/2007 | Hareyama et al. |
| 7,169,145 | B2 | 1/2007 | Isaacson et al. |
| 7,177,533 | B2 | 2/2007 | McFarlin et al. |
| 7,182,775 | B2 | 2/2007 | de Guillebon et al. |
| 7,207,472 | B2 | 4/2007 | Wukusick et al. |
| 7,208,005 | B2 | 4/2007 | Frecker et al. |
| 7,217,269 | B2 | 5/2007 | El-Galley et al. |
| 7,230,529 | B2 | 6/2007 | Ketcherside, Jr. et al. |
| 7,232,447 | B2 | 6/2007 | Gellman et al. |
| 7,236,817 | B2 | 6/2007 | Papas et al. |
| 7,246,734 | B2 | 7/2007 | Shelton, IV |
| 7,252,664 | B2 | 8/2007 | Nasab et al. |
| 7,278,563 | B1 | 10/2007 | Green |
| 7,294,106 | B2 | 11/2007 | Birkenbach et al. |
| 7,294,116 | B1 | 11/2007 | Ellman et al. |
| 7,296,724 | B2 | 11/2007 | Green et al. |
| 7,317,955 | B2 | 1/2008 | McGreevy |
| 7,328,828 | B2 | 2/2008 | Ortiz et al. |
| 7,334,717 | B2 | 2/2008 | Rethy et al. |
| 7,343,565 | B2 | 3/2008 | Ying et al. |
| 7,344,532 | B2 | 3/2008 | Goble et al. |
| 7,353,068 | B2 | 4/2008 | Tanaka et al. |
| 7,362,228 | B2 | 4/2008 | Nycz et al. |
| 7,371,227 | B2 | 5/2008 | Zeiner |
| 7,380,695 | B2 | 6/2008 | Doll et al. |
| 7,383,088 | B2 | 6/2008 | Spinelli et al. |
| 7,391,173 | B2 | 6/2008 | Schena |
| 7,407,074 | B2 | 8/2008 | Ortiz et al. |
| 7,408,439 | B2 | 8/2008 | Wang et al. |
| 7,413,541 | B2 | 8/2008 | Konishi |
| 7,422,136 | B1 | 9/2008 | Marczyk |
| 7,422,139 | B2 | 9/2008 | Shelton, IV et al. |
| 7,423,972 | B2 | 9/2008 | Shaham et al. |
| D579,876 | S | 11/2008 | Novotney et al. |
| 7,457,804 | B2 | 11/2008 | Uber, III et al. |
| D583,328 | S | 12/2008 | Chiang |
| 7,464,847 | B2 | 12/2008 | Viola et al. |
| 7,464,849 | B2 | 12/2008 | Shelton, IV et al. |
| 7,496,418 | B2 | 2/2009 | Kim et al. |
| D589,447 | S | 3/2009 | Sasada et al. |
| 7,515,961 | B2 | 4/2009 | Germanson et al. |
| 7,518,502 | B2 | 4/2009 | Austin et al. |
| 7,554,343 | B2 | 6/2009 | Bromfield |
| 7,563,259 | B2 | 7/2009 | Takahashi |
| 7,568,604 | B2 | 8/2009 | Ehrenfels et al. |
| 7,575,144 | B2 | 8/2009 | Ortiz et al. |
| 7,597,731 | B2 | 10/2009 | Palmerton et al. |
| 7,617,137 | B2 | 11/2009 | Kreiner et al. |
| 7,621,192 | B2 | 11/2009 | Conti et al. |
| 7,621,898 | B2 | 11/2009 | Lalomia et al. |
| 7,631,793 | B2 | 12/2009 | Rethy et al. |
| 7,637,410 | B2 | 12/2009 | Marczyk |
| 7,637,907 | B2 | 12/2009 | Blaha |
| 7,641,092 | B2 | 1/2010 | Kruszynski et al. |
| 7,644,848 | B2 | 1/2010 | Swayze et al. |
| 7,667,592 | B2 | 2/2010 | Ohyama et al. |
| 7,667,839 | B2 | 2/2010 | Bates |
| 7,670,334 | B2 | 3/2010 | Hueil et al. |
| 7,694,865 | B2 | 4/2010 | Scirica |
| 7,699,860 | B2 | 4/2010 | Huitema et al. |
| 7,720,306 | B2 | 5/2010 | Gardiner et al. |
| 7,721,934 | B2 | 5/2010 | Shelton, IV et al. |
| 7,721,936 | B2 | 5/2010 | Shalton, IV et al. |
| 7,736,357 | B2 | 6/2010 | Lee, Jr. et al. |
| 7,742,176 | B2 | 6/2010 | Braunecker et al. |
| 7,743,960 | B2 | 6/2010 | Whitman et al. |
| 7,753,245 | B2 | 7/2010 | Boudreaux et al. |
| 7,757,028 | B2 | 7/2010 | Druke et al. |
| 7,766,207 | B2 | 8/2010 | Mather et al. |
| 7,766,905 | B2 | 8/2010 | Paterson et al. |
| 7,770,773 | B2 | 8/2010 | Whitman et al. |
| 7,771,429 | B2 | 8/2010 | Ballard et al. |
| 7,776,037 | B2 | 8/2010 | Odom |
| 7,782,789 | B2 | 8/2010 | Stultz et al. |
| 7,784,663 | B2 | 8/2010 | Shelton, IV |
| 7,803,151 | B2 | 9/2010 | Whitman |
| 7,810,692 | B2 | 10/2010 | Hall et al. |
| 7,818,041 | B2 | 10/2010 | Kim et al. |
| 7,819,298 | B2 | 10/2010 | Hall et al. |
| 7,832,612 | B2 | 11/2010 | Baxter, III et al. |
| 7,833,219 | B2 | 11/2010 | Tashiro et al. |
| 7,836,085 | B2 | 11/2010 | Petakov et al. |
| 7,837,079 | B2 | 11/2010 | Holsten et al. |
| 7,837,680 | B2 | 11/2010 | Isaacson et al. |
| 7,841,980 | B2 | 11/2010 | Minosawa et al. |
| 7,845,537 | B2 | 12/2010 | Shelton, IV et al. |
| 7,857,185 | B2 | 12/2010 | Swayze et al. |
| D631,252 | S | 1/2011 | Leslie |
| 7,862,560 | B2 | 1/2011 | Marion |
| 7,862,579 | B2 | 1/2011 | Ortiz et al. |
| 7,865,236 | B2 | 1/2011 | Cory et al. |
| 7,884,735 | B2 | 2/2011 | Newkirk |
| 7,887,530 | B2 | 2/2011 | Zemlok et al. |
| 7,892,337 | B2 | 2/2011 | Palmerton et al. |
| 7,907,166 | B2 | 3/2011 | Lamprecht et al. |
| 7,913,891 | B2 | 3/2011 | Doll et al. |
| 7,918,230 | B2 | 4/2011 | Whitman et al. |
| 7,918,377 | B2 | 4/2011 | Measamer et al. |
| 7,920,706 | B2 | 4/2011 | Asokan et al. |
| 7,927,014 | B2 | 4/2011 | Dehler |
| 7,932,826 | B2 | 4/2011 | Fritchie et al. |
| 7,942,300 | B2 | 5/2011 | Rethy et al. |
| 7,945,065 | B2 | 5/2011 | Menzl et al. |
| 7,945,342 | B2 | 5/2011 | Tsai et al. |
| 7,951,148 | B2 | 5/2011 | McClurken |
| 7,954,682 | B2 | 6/2011 | Giordano et al. |
| 7,954,687 | B2 | 6/2011 | Zemlok et al. |
| 7,955,322 | B2 | 6/2011 | Devengenzo et al. |
| 7,956,620 | B2 | 6/2011 | Gilbert |
| 7,963,433 | B2 | 6/2011 | Whitman et al. |
| 7,966,269 | B2 | 6/2011 | Bauer et al. |
| 7,967,180 | B2 | 6/2011 | Scirica |
| 7,976,553 | B2 | 7/2011 | Shelton, IV et al. |
| 7,979,157 | B2 | 7/2011 | Anvari |
| 7,980,443 | B2 | 7/2011 | Scheib et al. |
| 7,982,776 | B2 | 7/2011 | Dunki-Jacobs et al. |
| 7,988,028 | B2 | 8/2011 | Farascioni et al. |
| 7,993,140 | B2 | 8/2011 | Sakezles |

(56) References Cited

U.S. PATENT DOCUMENTS

| | | | |
|---|---|---|---|
| 7,993,354 | B1 | 8/2011 | Brecher et al. |
| 7,995,045 | B2 | 8/2011 | Dunki-Jacobs |
| 8,005,947 | B2 | 8/2011 | Morris et al. |
| 8,007,494 | B1 | 8/2011 | Taylor et al. |
| 8,007,513 | B2 | 8/2011 | Nalagatla et al. |
| 8,010,180 | B2 | 8/2011 | Quaid et al. |
| 8,012,170 | B2 | 9/2011 | Whitman et al. |
| 8,015,976 | B2 | 9/2011 | Shah |
| 8,016,855 | B2 | 9/2011 | Whitman et al. |
| 8,019,094 | B2 | 9/2011 | Hsieh et al. |
| 8,025,199 | B2 | 9/2011 | Whitman et al. |
| 8,027,710 | B1 | 9/2011 | Dannan |
| 8,035,685 | B2 | 10/2011 | Jensen |
| 8,038,686 | B2 | 10/2011 | Huitema et al. |
| 8,038,693 | B2 | 10/2011 | Allen |
| 8,043,560 | B2 | 10/2011 | Okumoto et al. |
| 8,054,184 | B2 | 11/2011 | Cline et al. |
| 8,054,752 | B2 | 11/2011 | Druke et al. |
| 8,062,306 | B2 | 11/2011 | Nobis et al. |
| 8,062,330 | B2 | 11/2011 | Prommersberger et al. |
| 8,066,721 | B2 | 11/2011 | Kortenbach et al. |
| 8,074,861 | B2 | 12/2011 | Ehrenfels et al. |
| 8,075,571 | B2 | 12/2011 | Vitali et al. |
| 8,096,459 | B2 | 1/2012 | Ortiz et al. |
| 8,118,206 | B2 | 2/2012 | Zand et al. |
| 8,120,301 | B2 | 2/2012 | Goldberg et al. |
| 8,123,764 | B2 | 2/2012 | Meade et al. |
| D655,678 | S | 3/2012 | Kobayashi et al. |
| 8,128,625 | B2 | 3/2012 | Odom |
| 8,131,565 | B2 | 3/2012 | Dicks et al. |
| 8,136,712 | B2 | 3/2012 | Zingman |
| 8,146,149 | B2 | 3/2012 | Steinkogler et al. |
| D657,368 | S | 4/2012 | Magee et al. |
| 8,147,486 | B2 | 4/2012 | Honour et al. |
| 8,155,479 | B2 | 4/2012 | Hoffman et al. |
| 8,157,145 | B2 | 4/2012 | Shelton, IV et al. |
| 8,157,150 | B2 | 4/2012 | Viola et al. |
| 8,157,151 | B2 | 4/2012 | Ingmanson et al. |
| 8,160,098 | B1 | 4/2012 | Yan et al. |
| 8,160,690 | B2 | 4/2012 | Wilfley et al. |
| 8,161,977 | B2 | 4/2012 | Shelton, IV et al. |
| 8,170,396 | B2 | 5/2012 | Kuspa et al. |
| 8,172,836 | B2 | 5/2012 | Ward |
| 8,181,839 | B2 | 5/2012 | Beetel |
| 8,185,409 | B2 | 5/2012 | Putnam et al. |
| 8,206,345 | B2 | 6/2012 | Abboud et al. |
| 8,208,707 | B2 | 6/2012 | Mendonca et al. |
| 8,210,411 | B2 | 7/2012 | Yates et al. |
| 8,214,007 | B2 | 7/2012 | Baker et al. |
| 8,216,849 | B2 | 7/2012 | Petty |
| 8,220,688 | B2 | 7/2012 | Laurent et al. |
| 8,225,643 | B2 | 7/2012 | Abboud et al. |
| 8,225,979 | B2 | 7/2012 | Farascioni et al. |
| 8,229,549 | B2 | 7/2012 | Whitman et al. |
| 8,231,042 | B2 | 7/2012 | Hessler et al. |
| 8,239,066 | B2 | 8/2012 | Jennings et al. |
| 8,241,322 | B2 | 8/2012 | Whitman et al. |
| 8,255,045 | B2 | 8/2012 | Gharib et al. |
| D667,838 | S | 9/2012 | Magee et al. |
| 8,257,387 | B2 | 9/2012 | Cunningham |
| 8,260,016 | B2 | 9/2012 | Maeda et al. |
| 8,262,560 | B2 | 9/2012 | Whitman |
| 8,292,639 | B2 | 10/2012 | Achammer et al. |
| 8,292,888 | B2 | 10/2012 | Whitman |
| 8,295,902 | B2 | 10/2012 | Salahieh et al. |
| 8,308,040 | B2 | 11/2012 | Huang et al. |
| 8,321,581 | B2 | 11/2012 | Katis et al. |
| 8,322,590 | B2 | 12/2012 | Patel et al. |
| 8,328,065 | B2 | 12/2012 | Shah |
| 8,335,590 | B2 | 12/2012 | Costa et al. |
| D675,164 | S | 1/2013 | Kobayashi et al. |
| 8,343,065 | B2 | 1/2013 | Bartol et al. |
| 8,346,392 | B2 | 1/2013 | Walser et al. |
| 8,360,299 | B2 | 1/2013 | Zemlok et al. |
| 8,364,222 | B2 | 1/2013 | Cook et al. |
| D676,392 | S | 2/2013 | Gassauer |
| 8,365,975 | B1 | 2/2013 | Manoux et al. |
| D678,196 | S | 3/2013 | Miyauchi et al. |
| D678,304 | S | 3/2013 | Yakoub et al. |
| 8,388,652 | B2 | 3/2013 | Viola |
| 8,393,514 | B2 | 3/2013 | Shelton, IV et al. |
| 8,397,972 | B2 | 3/2013 | Kostrzewski |
| 8,398,541 | B2 | 3/2013 | DiMaio et al. |
| 8,403,944 | B2 | 3/2013 | Pain et al. |
| 8,403,945 | B2 | 3/2013 | Whitfield et al. |
| 8,403,946 | B2 | 3/2013 | Whitfield et al. |
| 8,406,859 | B2 | 3/2013 | Zuzak et al. |
| 8,411,034 | B2 | 4/2013 | Boillot et al. |
| 8,413,871 | B2 | 4/2013 | Racenet et al. |
| 8,422,035 | B2 | 4/2013 | Hinderling et al. |
| 8,423,182 | B2 | 4/2013 | Robinson et al. |
| 8,428,722 | B2 | 4/2013 | Verhoef et al. |
| 8,429,153 | B2 | 4/2013 | Birdwell et al. |
| 8,439,910 | B2 | 5/2013 | Greep et al. |
| 8,444,663 | B2 | 5/2013 | Houser et al. |
| 8,452,615 | B2 | 5/2013 | Abri |
| 8,454,506 | B2 | 6/2013 | Rothman et al. |
| 8,461,744 | B2 | 6/2013 | Wiener et al. |
| 8,468,030 | B2 | 6/2013 | Stroup et al. |
| 8,469,973 | B2 | 6/2013 | Meade et al. |
| 8,472,630 | B2 | 6/2013 | Konrad et al. |
| 8,473,066 | B2 | 6/2013 | Aghassian et al. |
| D687,146 | S | 7/2013 | Juzkiw et al. |
| 8,476,227 | B2 | 7/2013 | Kaplan et al. |
| 8,478,418 | B2 | 7/2013 | Fahey |
| 8,489,235 | B2 | 7/2013 | Moll et al. |
| 8,499,992 | B2 | 8/2013 | Whitman et al. |
| 8,500,728 | B2 | 8/2013 | Newton et al. |
| 8,500,756 | B2 | 8/2013 | Papa et al. |
| 8,503,759 | B2 | 8/2013 | Greer et al. |
| 8,505,801 | B2 | 8/2013 | Ehrenfels et al. |
| 8,506,478 | B2 | 8/2013 | Mizuyoshi |
| 8,512,325 | B2 | 8/2013 | Mathonnet |
| 8,512,365 | B2 | 8/2013 | Wiener et al. |
| 8,515,520 | B2 | 8/2013 | Brunnett et al. |
| 8,517,239 | B2 | 8/2013 | Scheib et al. |
| 8,521,331 | B2 | 8/2013 | Itkowitz |
| 8,523,043 | B2 | 9/2013 | Ullrich et al. |
| 8,533,475 | B2 | 9/2013 | Frikart et al. |
| 8,540,709 | B2 | 9/2013 | Allen |
| 8,546,996 | B2 | 10/2013 | Messerly et al. |
| 8,554,697 | B2 | 10/2013 | Claus et al. |
| 8,560,047 | B2 | 10/2013 | Haider et al. |
| 8,561,870 | B2 | 10/2013 | Baxter, III et al. |
| 8,562,598 | B2 | 10/2013 | Falkenstein et al. |
| 8,566,115 | B2 | 10/2013 | Moore |
| 8,567,393 | B2 | 10/2013 | Hickle et al. |
| 8,568,411 | B2 | 10/2013 | Falkenstein et al. |
| 8,571,598 | B2 | 10/2013 | Valavi |
| 8,573,459 | B2 | 11/2013 | Smith et al. |
| 8,573,465 | B2 | 11/2013 | Shelton, IV |
| 8,574,229 | B2 | 11/2013 | Eder et al. |
| 8,585,631 | B2 | 11/2013 | Dacquay |
| 8,585,694 | B2 | 11/2013 | Amoah et al. |
| 8,590,762 | B2 | 11/2013 | Hess et al. |
| 8,591,536 | B2 | 11/2013 | Robertson |
| 8,595,607 | B2 | 11/2013 | Nekoomaram et al. |
| 8,596,513 | B2 | 12/2013 | Olson et al. |
| 8,596,515 | B2 | 12/2013 | Okoniewski |
| 8,604,709 | B2 | 12/2013 | Jalbout et al. |
| 8,608,044 | B2 | 12/2013 | Hueil et al. |
| 8,608,045 | B2 | 12/2013 | Smith et al. |
| 8,616,431 | B2 | 12/2013 | Timm et al. |
| 8,617,155 | B2 | 12/2013 | Johnson et al. |
| 8,620,055 | B2 | 12/2013 | Barratt et al. |
| 8,620,473 | B2 | 12/2013 | Diolaiti et al. |
| 8,622,275 | B2 | 1/2014 | Baxter, III et al. |
| 8,623,027 | B2 | 1/2014 | Price et al. |
| 8,627,483 | B2 | 1/2014 | Rachlin et al. |
| 8,627,993 | B2 | 1/2014 | Smith et al. |
| 8,627,995 | B2 | 1/2014 | Smith et al. |
| 8,628,518 | B2 | 1/2014 | Blumenkranz et al. |
| 8,628,545 | B2 | 1/2014 | Cabrera et al. |
| 8,631,987 | B2 | 1/2014 | Shelton, IV et al. |

(56) References Cited

U.S. PATENT DOCUMENTS

| | | | |
|---|---|---|---|
| 8,632,525 | B2 | 1/2014 | Kerr et al. |
| 8,636,190 | B2 | 1/2014 | Zemlok et al. |
| 8,636,736 | B2 | 1/2014 | Yates et al. |
| 8,641,621 | B2 | 2/2014 | Razzaque et al. |
| 8,652,086 | B2 | 2/2014 | Gerg et al. |
| 8,652,121 | B2 | 2/2014 | Quick et al. |
| 8,652,128 | B2 | 2/2014 | Ward |
| 8,657,176 | B2 | 2/2014 | Shelton, IV et al. |
| 8,657,177 | B2 | 2/2014 | Scirica et al. |
| 8,663,220 | B2 | 3/2014 | Wiener et al. |
| 8,663,222 | B2 | 3/2014 | Anderson et al. |
| 8,666,544 | B2 | 3/2014 | Moll et al. |
| 8,679,114 | B2 | 3/2014 | Chapman et al. |
| 8,682,049 | B2 | 3/2014 | Zhao et al. |
| 8,682,489 | B2 | 3/2014 | Itkowitz et al. |
| 8,685,056 | B2 | 4/2014 | Evans et al. |
| 8,688,188 | B2 | 4/2014 | Heller et al. |
| 8,690,864 | B2 | 4/2014 | Hoarau |
| 8,701,962 | B2 | 4/2014 | Kostrzewski |
| D704,839 | S | 5/2014 | Juzkiw et al. |
| 8,719,061 | B2 | 5/2014 | Birchall |
| 8,720,766 | B2 | 5/2014 | Hess et al. |
| 8,733,613 | B2 | 5/2014 | Huitema et al. |
| 8,740,840 | B2 | 6/2014 | Foley et al. |
| 8,740,866 | B2 | 6/2014 | Reasoner et al. |
| 8,747,238 | B2 | 6/2014 | Shelton, IV et al. |
| 8,752,749 | B2 | 6/2014 | Moore et al. |
| 8,757,465 | B2 | 6/2014 | Woodard, Jr. et al. |
| 8,761,717 | B1 | 6/2014 | Buchheit |
| 8,763,879 | B2 | 7/2014 | Shelton, IV et al. |
| 8,768,251 | B2 | 7/2014 | Claus et al. |
| 8,771,270 | B2 | 7/2014 | Burbank |
| 8,775,196 | B2 | 7/2014 | Simpson et al. |
| 8,779,648 | B2 | 7/2014 | Giordano et al. |
| 8,790,253 | B2 | 7/2014 | Sunagawa et al. |
| 8,794,497 | B2 | 8/2014 | Zingman |
| 8,795,001 | B1 | 8/2014 | Lam et al. |
| 8,799,008 | B2 | 8/2014 | Johnson et al. |
| 8,799,009 | B2 | 8/2014 | Mellin et al. |
| 8,800,838 | B2 | 8/2014 | Shelton, IV |
| 8,801,703 | B2 | 8/2014 | Gregg et al. |
| 8,814,996 | B2 | 8/2014 | Giurgiutiu et al. |
| 8,818,556 | B2 | 8/2014 | Sanchez et al. |
| 8,819,581 | B2 | 8/2014 | Nakamura et al. |
| 8,820,603 | B2 | 9/2014 | Shelton, IV et al. |
| 8,820,608 | B2 | 9/2014 | Miyamoto |
| 8,827,134 | B2 | 9/2014 | Viola et al. |
| 8,827,136 | B2 | 9/2014 | Hessler |
| 8,840,003 | B2 | 9/2014 | Morgan et al. |
| D716,333 | S | 10/2014 | Chotin et al. |
| 8,851,354 | B2 | 10/2014 | Swensgard et al. |
| 8,852,174 | B2 | 10/2014 | Burbank |
| 8,875,973 | B2 | 11/2014 | Whitman |
| 8,876,857 | B2 | 11/2014 | Burbank |
| 8,882,662 | B2 | 11/2014 | Charles |
| 8,885,032 | B2 | 11/2014 | Igarashi et al. |
| 8,886,790 | B2 | 11/2014 | Harrang et al. |
| 8,893,949 | B2 | 11/2014 | Shelton, IV et al. |
| 8,899,479 | B2 | 12/2014 | Cappuzzo et al. |
| 8,905,977 | B2 | 12/2014 | Shelton et al. |
| 8,912,746 | B2 | 12/2014 | Reid et al. |
| 8,914,098 | B2 | 12/2014 | Brennan et al. |
| 8,917,513 | B1 | 12/2014 | Hazzard |
| 8,918,207 | B2 | 12/2014 | Prisco |
| 8,920,186 | B2 | 12/2014 | Shishikura |
| 8,920,414 | B2 | 12/2014 | Stone et al. |
| 8,920,433 | B2 | 12/2014 | Barrier et al. |
| 8,930,203 | B2 | 1/2015 | Kiaie et al. |
| 8,930,214 | B2 | 1/2015 | Woolford |
| 8,931,679 | B2 | 1/2015 | Kostrzewski |
| 8,934,684 | B2 | 1/2015 | Mohamed |
| 8,936,614 | B2 | 1/2015 | Allen, IV |
| 8,945,095 | B2 | 2/2015 | Blumenkranz et al. |
| 8,945,163 | B2 | 2/2015 | Voegele et al. |
| 8,955,732 | B2 | 2/2015 | Zemlok et al. |
| 8,956,581 | B2 | 2/2015 | Rosenbaum et al. |
| 8,960,519 | B2 | 2/2015 | Whitman et al. |
| 8,960,520 | B2 | 2/2015 | McCuen |
| 8,962,062 | B2 | 2/2015 | Podhajsky et al. |
| 8,967,443 | B2 | 3/2015 | McCuen |
| 8,967,455 | B2 | 3/2015 | Zhou |
| 8,968,276 | B2 | 3/2015 | Zemlok et al. |
| 8,968,296 | B2 | 3/2015 | McPherson |
| 8,968,309 | B2 | 3/2015 | Roy et al. |
| 8,968,312 | B2 | 3/2015 | Marczyk et al. |
| 8,968,337 | B2 | 3/2015 | Whitfield et al. |
| 8,968,358 | B2 | 3/2015 | Reschke |
| 8,974,429 | B2 | 3/2015 | Gordon et al. |
| 8,979,890 | B2 | 3/2015 | Boudreaux |
| 8,986,288 | B2 | 3/2015 | Konishi |
| 8,986,302 | B2 | 3/2015 | Aldridge et al. |
| 8,989,903 | B2 | 3/2015 | Weir et al. |
| 8,991,678 | B2 | 3/2015 | Wellman et al. |
| 8,992,565 | B2 | 3/2015 | Brisson et al. |
| 8,998,797 | B2 | 4/2015 | Omori |
| 9,002,518 | B2 | 4/2015 | Manzo et al. |
| 9,010,608 | B2 | 4/2015 | Casasanta, Jr. et al. |
| 9,010,611 | B2 | 4/2015 | Ross et al. |
| 9,011,366 | B2 | 4/2015 | Dean et al. |
| 9,011,427 | B2 | 4/2015 | Price et al. |
| 9,016,539 | B2 | 4/2015 | Kostrzewski et al. |
| 9,017,326 | B2 | 4/2015 | DiNardo et al. |
| 9,020,240 | B2 | 4/2015 | Pettersson et al. |
| D729,267 | S | 5/2015 | Yoo et al. |
| 9,023,032 | B2 | 5/2015 | Robinson |
| 9,023,071 | B2 | 5/2015 | Miller et al. |
| 9,027,431 | B2 | 5/2015 | Tang et al. |
| 9,028,494 | B2 | 5/2015 | Shelton, IV et al. |
| 9,035,568 | B2 | 5/2015 | Ganton et al. |
| 9,038,882 | B2 | 5/2015 | Racenet et al. |
| 9,043,027 | B2 | 5/2015 | Durant et al. |
| 9,044,227 | B2 | 6/2015 | Shelton, IV et al. |
| 9,044,244 | B2 | 6/2015 | Ludwin et al. |
| 9,044,261 | B2 | 6/2015 | Houser |
| 9,050,063 | B2 | 6/2015 | Roe et al. |
| 9,050,083 | B2 | 6/2015 | Yates et al. |
| 9,050,120 | B2 | 6/2015 | Swarup et al. |
| 9,052,809 | B2 | 6/2015 | Vesto |
| 9,055,035 | B2 | 6/2015 | Porsch et al. |
| 9,055,870 | B2 | 6/2015 | Meador et al. |
| 9,060,770 | B2 | 6/2015 | Shelton, IV et al. |
| 9,060,775 | B2 | 6/2015 | Wiener et al. |
| 9,066,650 | B2 | 6/2015 | Sekiguchi |
| 9,072,523 | B2 | 7/2015 | Houser et al. |
| 9,072,535 | B2 | 7/2015 | Shelton, IV et al. |
| 9,072,536 | B2 | 7/2015 | Shelton, IV et al. |
| 9,078,653 | B2 | 7/2015 | Leimbach et al. |
| 9,078,727 | B2 | 7/2015 | Miller |
| 9,084,606 | B2 | 7/2015 | Greep |
| 9,089,360 | B2 | 7/2015 | Messerly et al. |
| 9,095,362 | B2 | 8/2015 | Dachs, II et al. |
| 9,095,367 | B2 | 8/2015 | Olson et al. |
| 9,099,863 | B2 | 8/2015 | Smith et al. |
| 9,101,358 | B2 | 8/2015 | Kerr et al. |
| 9,101,359 | B2 | 8/2015 | Smith et al. |
| 9,101,374 | B1 | 8/2015 | Hoch et al. |
| 9,106,270 | B2 | 8/2015 | Puterbaugh et al. |
| 9,107,573 | B2 | 8/2015 | Birnkrant |
| 9,107,662 | B2 | 8/2015 | Kostrzewski |
| 9,107,684 | B2 | 8/2015 | Ma |
| 9,107,688 | B2 | 8/2015 | Kimball et al. |
| 9,107,689 | B2 | 8/2015 | Robertson et al. |
| 9,107,694 | B2 | 8/2015 | Hendriks et al. |
| 9,111,548 | B2 | 8/2015 | Nandy et al. |
| 9,113,880 | B2 | 8/2015 | Zemlok et al. |
| 9,114,494 | B1 | 8/2015 | Mah |
| 9,116,597 | B1 | 8/2015 | Gulasky |
| 9,119,617 | B2 | 9/2015 | Souls et al. |
| 9,119,655 | B2 | 9/2015 | Bowling et al. |
| 9,119,657 | B2 | 9/2015 | Shelton, IV et al. |
| 9,123,155 | B2 | 9/2015 | Cunningham et al. |
| 9,125,644 | B2 | 9/2015 | Lane et al. |
| 9,129,054 | B2 | 9/2015 | Nawana et al. |
| 9,137,254 | B2 | 9/2015 | Bilbrey et al. |

(56) References Cited

U.S. PATENT DOCUMENTS

| | | | |
|---|---|---|---|
| 9,138,129 | B2 | 9/2015 | Diolaiti |
| 9,138,225 | B2 | 9/2015 | Huang et al. |
| 9,149,322 | B2 | 10/2015 | Knowlton |
| 9,155,503 | B2 | 10/2015 | Cadwell |
| 9,160,853 | B1 | 10/2015 | Daddi et al. |
| 9,161,803 | B2 | 10/2015 | Yates et al. |
| 9,168,054 | B2 | 10/2015 | Turner et al. |
| 9,168,091 | B2 | 10/2015 | Janssen et al. |
| 9,168,104 | B2 | 10/2015 | Dein |
| 9,179,912 | B2 | 11/2015 | Yates et al. |
| 9,183,723 | B2 | 11/2015 | Sherman et al. |
| 9,186,143 | B2 | 11/2015 | Timm et al. |
| 9,192,375 | B2 | 11/2015 | Skinlo et al. |
| 9,192,447 | B2 | 11/2015 | Choi et al. |
| 9,192,707 | B2 | 11/2015 | Gerber et al. |
| 9,198,711 | B2 | 12/2015 | Joseph |
| 9,202,078 | B2 | 12/2015 | Abuelsaad et al. |
| 9,204,830 | B2 | 12/2015 | Zand et al. |
| 9,204,879 | B2 | 12/2015 | Shelton, IV |
| 9,204,995 | B2 | 12/2015 | Scheller et al. |
| 9,211,120 | B2 | 12/2015 | Scheib et al. |
| 9,216,062 | B2 | 12/2015 | Duque et al. |
| 9,218,053 | B2 | 12/2015 | Komuro et al. |
| 9,220,502 | B2 | 12/2015 | Zemlok et al. |
| 9,226,689 | B2 | 1/2016 | Jacobsen et al. |
| 9,226,751 | B2 | 1/2016 | Shelton, IV et al. |
| 9,226,766 | B2 | 1/2016 | Aldridge et al. |
| 9,226,767 | B2 | 1/2016 | Stulen et al. |
| 9,226,791 | B2 | 1/2016 | McCarthy et al. |
| 9,232,883 | B2 | 1/2016 | Ozawa et al. |
| 9,237,891 | B2 | 1/2016 | Shelton, IV |
| 9,237,921 | B2 | 1/2016 | Messerly et al. |
| 9,241,728 | B2 | 1/2016 | Price et al. |
| 9,241,730 | B2 | 1/2016 | Babaev |
| 9,241,731 | B2 | 1/2016 | Boudreaux et al. |
| 9,247,996 | B1 | 2/2016 | Merana et al. |
| 9,250,172 | B2 | 2/2016 | Harris et al. |
| 9,255,907 | B2 | 2/2016 | Heanue et al. |
| 9,259,282 | B2 | 2/2016 | Azizian et al. |
| 9,265,429 | B2 | 2/2016 | St. Pierre et al. |
| 9,265,585 | B2 | 2/2016 | Wingardner et al. |
| 9,265,959 | B2 | 2/2016 | Drew et al. |
| 9,272,406 | B2 | 3/2016 | Aronhalt et al. |
| 9,277,956 | B2 | 3/2016 | Zhang |
| 9,277,961 | B2 | 3/2016 | Panescu et al. |
| 9,277,969 | B2 | 3/2016 | Brannan et al. |
| 9,280,884 | B1 | 3/2016 | Schultz et al. |
| 9,282,962 | B2 | 3/2016 | Schmid et al. |
| 9,282,974 | B2 | 3/2016 | Shelton, IV |
| 9,283,045 | B2 | 3/2016 | Rhee et al. |
| 9,283,054 | B2 | 3/2016 | Morgan et al. |
| 9,289,211 | B2 | 3/2016 | Williams et al. |
| 9,289,212 | B2 | 3/2016 | Shelton, IV et al. |
| 9,295,514 | B2 | 3/2016 | Shelton, IV et al. |
| 9,301,691 | B2 | 4/2016 | Hufnagel et al. |
| 9,301,753 | B2 | 4/2016 | Aldridge et al. |
| 9,301,755 | B2 | 4/2016 | Shelton, IV et al. |
| 9,301,759 | B2 | 4/2016 | Spivey et al. |
| 9,301,810 | B2 | 4/2016 | Amiri et al. |
| 9,302,213 | B2 | 4/2016 | Manahan et al. |
| 9,307,894 | B2 | 4/2016 | von Grunberg et al. |
| 9,307,914 | B2 | 4/2016 | Fahey |
| 9,307,986 | B2 | 4/2016 | Hall et al. |
| 9,314,246 | B2 | 4/2016 | Shelton, IV et al. |
| 9,314,308 | B2 | 4/2016 | Parihar et al. |
| 9,320,563 | B2 | 4/2016 | Brustad et al. |
| 9,325,732 | B1 | 4/2016 | Stickle et al. |
| 9,326,767 | B2 | 5/2016 | Koch, Jr. et al. |
| 9,326,770 | B2 | 5/2016 | Shelton, IV et al. |
| 9,331,422 | B2 | 5/2016 | Nazzaro et al. |
| 9,332,987 | B2 | 5/2016 | Leimbach et al. |
| 9,333,042 | B2 | 5/2016 | Diolaiti et al. |
| 9,336,385 | B1 | 5/2016 | Spencer et al. |
| 9,341,704 | B2 | 5/2016 | Picard et al. |
| 9,345,481 | B2 | 5/2016 | Hall et al. |
| 9,345,490 | B2 | 5/2016 | Ippisch |
| 9,345,544 | B2 | 5/2016 | Hourtash et al. |
| 9,345,546 | B2 | 5/2016 | Toth et al. |
| 9,345,900 | B2 | 5/2016 | Wu et al. |
| 9,351,726 | B2 | 5/2016 | Leimbach et al. |
| 9,351,727 | B2 | 5/2016 | Leimbach et al. |
| 9,358,003 | B2 | 6/2016 | Hall et al. |
| 9,358,685 | B2 | 6/2016 | Meier et al. |
| 9,360,449 | B2 | 6/2016 | Duric |
| 9,364,230 | B2 | 6/2016 | Shelton, IV et al. |
| 9,364,231 | B2 | 6/2016 | Wenchell |
| 9,364,249 | B2 | 6/2016 | Kimball et al. |
| 9,364,294 | B2 | 6/2016 | Razzaque et al. |
| 9,370,400 | B2 | 6/2016 | Parihar |
| 9,375,282 | B2 | 6/2016 | Nau, Jr. et al. |
| 9,375,539 | B2 | 6/2016 | Stearns et al. |
| 9,381,003 | B2 | 7/2016 | Todor et al. |
| 9,381,058 | B2 | 7/2016 | Houser et al. |
| 9,386,984 | B2 | 7/2016 | Aronhalt et al. |
| 9,386,988 | B2 | 7/2016 | Baxter, III et al. |
| 9,387,295 | B1 | 7/2016 | Mastri et al. |
| 9,393,017 | B2 | 7/2016 | Flanagan et al. |
| 9,393,037 | B2 | 7/2016 | Olson et al. |
| 9,398,905 | B2 | 7/2016 | Martin |
| 9,398,911 | B2 | 7/2016 | Auld |
| 9,402,629 | B2 | 8/2016 | Ehrenfels et al. |
| 9,414,776 | B2 | 8/2016 | Sillay et al. |
| 9,414,940 | B2 | 8/2016 | Stein et al. |
| 9,419,018 | B2 | 8/2016 | Sasagawa et al. |
| 9,421,014 | B2 | 8/2016 | Ingmanson et al. |
| 9,433,470 | B2 | 9/2016 | Choi |
| 9,439,622 | B2 | 9/2016 | Case et al. |
| 9,439,668 | B2 | 9/2016 | Timm et al. |
| 9,439,736 | B2 | 9/2016 | Olson |
| 9,445,764 | B2 | 9/2016 | Gross et al. |
| 9,445,813 | B2 | 9/2016 | Shelton, IV et al. |
| 9,450,701 | B2 | 9/2016 | Do et al. |
| 9,451,949 | B2 | 9/2016 | Gorek et al. |
| 9,451,958 | B2 | 9/2016 | Shelton, IV et al. |
| 9,463,022 | B2 | 10/2016 | Swayze et al. |
| 9,463,646 | B2 | 10/2016 | Payne et al. |
| 9,468,438 | B2 | 10/2016 | Baber et al. |
| 9,474,565 | B2 | 10/2016 | Shikhman et al. |
| D772,252 | S | 11/2016 | Myers et al. |
| 9,480,492 | B2 | 11/2016 | Aranyi et al. |
| 9,485,475 | B2 | 11/2016 | Speier et al. |
| 9,486,271 | B2 | 11/2016 | Dunning |
| 9,492,146 | B2 | 11/2016 | Kostrzewski et al. |
| 9,492,237 | B2 | 11/2016 | Kang et al. |
| 9,493,807 | B2 | 11/2016 | Little et al. |
| 9,498,182 | B2 | 11/2016 | Case et al. |
| 9,498,215 | B2 | 11/2016 | Duque et al. |
| 9,498,231 | B2 | 11/2016 | Haider et al. |
| 9,509,566 | B2 | 11/2016 | Chu et al. |
| 9,516,239 | B2 | 12/2016 | Blanquart et al. |
| 9,519,753 | B1 | 12/2016 | Gerdeman et al. |
| 9,522,003 | B2 | 12/2016 | Weir et al. |
| 9,526,407 | B2 | 12/2016 | Hoeg et al. |
| 9,526,499 | B2 | 12/2016 | Kostrzewski et al. |
| 9,526,587 | B2 | 12/2016 | Zhao et al. |
| 9,532,827 | B2 | 1/2017 | Morgan et al. |
| 9,532,845 | B1 | 1/2017 | Dossett et al. |
| 9,539,007 | B2 | 1/2017 | Dhakad et al. |
| 9,539,020 | B2 | 1/2017 | Conlon et al. |
| 9,542,481 | B2 | 1/2017 | Halter et al. |
| 9,546,662 | B2 | 1/2017 | Shener-Irmakoglu et al. |
| 9,549,781 | B2 | 1/2017 | He et al. |
| 9,554,692 | B2 | 1/2017 | Levy |
| 9,554,794 | B2 | 1/2017 | Baber et al. |
| 9,554,854 | B2 | 1/2017 | Yates et al. |
| 9,561,038 | B2 | 2/2017 | Shelton, IV et al. |
| 9,561,045 | B2 | 2/2017 | Hinman et al. |
| 9,561,082 | B2 | 2/2017 | Yen et al. |
| 9,561,982 | B2 | 2/2017 | Enicks et al. |
| 9,566,708 | B2 | 2/2017 | Kurnianto |
| 9,572,592 | B2 | 2/2017 | Price et al. |
| 9,579,099 | B2 | 2/2017 | Penna et al. |
| 9,579,503 | B2 | 2/2017 | McKinney et al. |
| 9,585,657 | B2 | 3/2017 | Shelton, IV et al. |

(56) References Cited

U.S. PATENT DOCUMENTS

| | | | |
|---|---|---|---|
| 9,592,095 | B2 | 3/2017 | Panescu et al. |
| 9,597,081 | B2 | 3/2017 | Swayze et al. |
| 9,600,031 | B2 | 3/2017 | Kaneko et al. |
| 9,600,138 | B2 | 3/2017 | Thomas et al. |
| 9,603,024 | B2 | 3/2017 | Wang et al. |
| 9,603,277 | B2 | 3/2017 | Morgan et al. |
| D783,675 | S | 4/2017 | Yagisawa et al. |
| D784,270 | S | 4/2017 | Bhattacharya |
| 9,610,114 | B2 | 4/2017 | Baxter, III et al. |
| 9,610,412 | B2 | 4/2017 | Zemlok et al. |
| 9,615,877 | B2 | 4/2017 | Tyrrell et al. |
| 9,622,684 | B2 | 4/2017 | Wybo |
| 9,622,808 | B2 | 4/2017 | Beller et al. |
| 9,628,501 | B2 | 4/2017 | Datta Ray et al. |
| 9,629,560 | B2 | 4/2017 | Joseph |
| 9,629,623 | B2 | 4/2017 | Lytle, IV et al. |
| 9,629,628 | B2 | 4/2017 | Aranyi |
| 9,629,629 | B2 | 4/2017 | Leimbach et al. |
| 9,630,318 | B2 | 4/2017 | Ibarz Gabardos et al. |
| 9,636,112 | B2 | 5/2017 | Penna et al. |
| 9,636,188 | B2 | 5/2017 | Gattani et al. |
| 9,636,239 | B2 | 5/2017 | Durand et al. |
| 9,636,825 | B2 | 5/2017 | Penn et al. |
| 9,641,596 | B2 | 5/2017 | Unagami et al. |
| 9,641,815 | B2 | 5/2017 | Richardson et al. |
| 9,642,620 | B2 | 5/2017 | Baxter, III et al. |
| 9,643,022 | B2 | 5/2017 | Mashiach et al. |
| 9,649,110 | B2 | 5/2017 | Parihar et al. |
| 9,649,111 | B2 | 5/2017 | Shelton, IV et al. |
| 9,649,126 | B2 | 5/2017 | Robertson et al. |
| 9,649,169 | B2 | 5/2017 | Cinquin et al. |
| 9,652,655 | B2 | 5/2017 | Satish et al. |
| 9,655,616 | B2 | 5/2017 | Aranyi |
| 9,656,092 | B2 | 5/2017 | Golden |
| 9,662,116 | B2 | 5/2017 | Smith et al. |
| 9,662,177 | B2 | 5/2017 | Weir et al. |
| 9,668,729 | B2 | 6/2017 | Williams et al. |
| 9,668,732 | B2 | 6/2017 | Patel et al. |
| 9,668,765 | B2 | 6/2017 | Grace et al. |
| 9,671,860 | B2 | 6/2017 | Ogawa et al. |
| 9,675,264 | B2 | 6/2017 | Acquista et al. |
| 9,675,354 | B2 | 6/2017 | Weir et al. |
| 9,681,870 | B2 | 6/2017 | Baxter, III et al. |
| 9,686,306 | B2 | 6/2017 | Chizeck et al. |
| 9,687,230 | B2 | 6/2017 | Leimbach et al. |
| 9,690,362 | B2 | 6/2017 | Leimbach et al. |
| 9,700,292 | B2 | 7/2017 | Nawana et al. |
| 9,700,309 | B2 | 7/2017 | Jaworek et al. |
| 9,700,312 | B2 | 7/2017 | Kostrzewski et al. |
| 9,700,320 | B2 | 7/2017 | Dinardo et al. |
| 9,706,993 | B2 | 7/2017 | Hessler et al. |
| 9,710,214 | B2 | 7/2017 | Lin et al. |
| 9,710,644 | B2 | 7/2017 | Reybok et al. |
| 9,713,424 | B2 | 7/2017 | Spaide |
| 9,713,503 | B2 | 7/2017 | Goldschmidt |
| 9,717,141 | B1 | 7/2017 | Tegg |
| 9,717,498 | B2 | 8/2017 | Aranyi et al. |
| 9,717,525 | B2 | 8/2017 | Ahluwalia et al. |
| 9,717,548 | B2 | 8/2017 | Couture |
| 9,724,094 | B2 | 8/2017 | Baber et al. |
| 9,724,100 | B2 | 8/2017 | Scheib et al. |
| 9,724,118 | B2 | 8/2017 | Schulte et al. |
| 9,733,663 | B2 | 8/2017 | Leimbach et al. |
| 9,737,301 | B2 | 8/2017 | Baber et al. |
| 9,737,310 | B2 | 8/2017 | Whitfield et al. |
| 9,737,335 | B2 | 8/2017 | Butler et al. |
| 9,737,355 | B2 | 8/2017 | Yates et al. |
| 9,737,371 | B2 | 8/2017 | Romo et al. |
| 9,740,826 | B2 | 8/2017 | Raghavan et al. |
| 9,743,016 | B2 | 8/2017 | Nestares et al. |
| 9,743,929 | B2 | 8/2017 | Leimbach et al. |
| 9,743,946 | B2 | 8/2017 | Faller et al. |
| 9,743,947 | B2 | 8/2017 | Price et al. |
| 9,750,499 | B2 | 9/2017 | Leimbach et al. |
| 9,750,500 | B2 | 9/2017 | Malkowski |
| 9,750,522 | B2 | 9/2017 | Scheib et al. |
| 9,750,523 | B2 | 9/2017 | Tsubuku |
| 9,750,560 | B2 | 9/2017 | Ballakur et al. |
| 9,750,563 | B2 | 9/2017 | Shikhman et al. |
| 9,753,135 | B2 | 9/2017 | Bosch |
| 9,753,568 | B2 | 9/2017 | McMillen |
| 9,757,126 | B2 | 9/2017 | Cappola |
| 9,757,128 | B2 | 9/2017 | Baber et al. |
| 9,757,142 | B2 | 9/2017 | Shimizu |
| 9,757,152 | B2 | 9/2017 | Ogilvie et al. |
| 9,763,741 | B2 | 9/2017 | Alvarez et al. |
| 9,764,164 | B2 | 9/2017 | Wiener et al. |
| 9,770,541 | B2 | 9/2017 | Carr et al. |
| 9,775,611 | B2 | 10/2017 | Kostrzewski |
| 9,777,913 | B2 | 10/2017 | Talbert et al. |
| 9,782,164 | B2 | 10/2017 | Mumaw et al. |
| 9,782,169 | B2 | 10/2017 | Kimsey et al. |
| 9,782,212 | B2 | 10/2017 | Wham et al. |
| 9,782,214 | B2 | 10/2017 | Houser et al. |
| 9,788,835 | B2 | 10/2017 | Morgan et al. |
| 9,788,836 | B2 | 10/2017 | Overmyer et al. |
| 9,788,851 | B2 | 10/2017 | Dannaher et al. |
| 9,788,902 | B2 | 10/2017 | Inoue et al. |
| 9,788,907 | B1 | 10/2017 | Alvi et al. |
| 9,795,436 | B2 | 10/2017 | Yates et al. |
| 9,797,486 | B2 | 10/2017 | Zergiebel et al. |
| 9,801,531 | B2 | 10/2017 | Morita et al. |
| 9,801,626 | B2 | 10/2017 | Parihar et al. |
| 9,801,627 | B2 | 10/2017 | Harris et al. |
| 9,801,679 | B2 | 10/2017 | Trees et al. |
| 9,802,033 | B2 | 10/2017 | Hibner et al. |
| 9,804,618 | B2 | 10/2017 | Leimbach et al. |
| 9,805,472 | B2 | 10/2017 | Chou et al. |
| 9,808,244 | B2 | 11/2017 | Leimbach et al. |
| 9,808,245 | B2 | 11/2017 | Richard et al. |
| 9,808,246 | B2 | 11/2017 | Shelton, IV et al. |
| 9,808,248 | B2 | 11/2017 | Hoffman |
| 9,808,249 | B2 | 11/2017 | Shelton, IV |
| 9,814,457 | B2 | 11/2017 | Martin et al. |
| 9,814,460 | B2 | 11/2017 | Kimsey et al. |
| 9,814,462 | B2 | 11/2017 | Woodard, Jr. et al. |
| 9,814,463 | B2 | 11/2017 | Williams et al. |
| 9,820,699 | B2 | 11/2017 | Bingley et al. |
| 9,820,738 | B2 | 11/2017 | Lytle, IV et al. |
| 9,820,741 | B2 | 11/2017 | Kostrzewski |
| 9,820,768 | B2 | 11/2017 | Gee et al. |
| 9,826,976 | B2 | 11/2017 | Parihar et al. |
| 9,826,977 | B2 | 11/2017 | Leimbach et al. |
| 9,827,054 | B2 | 11/2017 | Richmond et al. |
| 9,827,059 | B2 | 11/2017 | Robinson et al. |
| 9,830,424 | B2 | 11/2017 | Dixon et al. |
| 9,833,241 | B2 | 12/2017 | Huitema et al. |
| 9,833,254 | B1 | 12/2017 | Barral et al. |
| 9,839,419 | B2 | 12/2017 | Deck et al. |
| 9,839,424 | B2 | 12/2017 | Zergiebel et al. |
| 9,839,428 | B2 | 12/2017 | Baxter, III et al. |
| 9,839,467 | B2 | 12/2017 | Harper et al. |
| 9,839,470 | B2 | 12/2017 | Gilbert et al. |
| 9,839,487 | B2 | 12/2017 | Dachs, II |
| 9,844,321 | B1 | 12/2017 | Ekvall et al. |
| 9,844,368 | B2 | 12/2017 | Boudreaux et al. |
| 9,844,369 | B2 | 12/2017 | Huitema et al. |
| 9,844,374 | B2 | 12/2017 | Lytle, IV et al. |
| 9,844,375 | B2 | 12/2017 | Overmyer et al. |
| 9,844,376 | B2 | 12/2017 | Baxter, III et al. |
| 9,844,379 | B2 | 12/2017 | Shelton, IV et al. |
| 9,848,058 | B2 | 12/2017 | Johnson et al. |
| 9,848,877 | B2 | 12/2017 | Shelton, IV et al. |
| 9,861,354 | B2 | 1/2018 | Saliman et al. |
| 9,861,363 | B2 | 1/2018 | Chen et al. |
| 9,861,428 | B2 | 1/2018 | Trees et al. |
| 9,864,839 | B2 | 1/2018 | Baym et al. |
| 9,867,612 | B2 | 1/2018 | Parihar et al. |
| 9,867,651 | B2 | 1/2018 | Wham |
| 9,867,670 | B2 | 1/2018 | Brannan et al. |
| 9,867,914 | B2 | 1/2018 | Bonano et al. |
| 9,872,609 | B2 | 1/2018 | Levy |
| 9,872,683 | B2 | 1/2018 | Hopkins et al. |
| 9,877,718 | B2 | 1/2018 | Weir et al. |

(56) References Cited

U.S. PATENT DOCUMENTS

| | | | |
|---|---|---|---|
| 9,877,721 | B2 | 1/2018 | Schellin et al. |
| 9,883,860 | B2 | 2/2018 | Leimbach et al. |
| 9,888,864 | B2 | 2/2018 | Rondoni et al. |
| 9,888,914 | B2 | 2/2018 | Martin et al. |
| 9,888,919 | B2 | 2/2018 | Leimbach et al. |
| 9,888,921 | B2 | 2/2018 | Williams et al. |
| 9,888,975 | B2 | 2/2018 | Auld |
| 9,895,148 | B2 | 2/2018 | Shelton, IV et al. |
| 9,900,787 | B2 | 2/2018 | Ou |
| 9,901,342 | B2 | 2/2018 | Shelton, IV et al. |
| 9,901,406 | B2 | 2/2018 | State et al. |
| 9,905,000 | B2 | 2/2018 | Chou et al. |
| 9,907,196 | B2 | 2/2018 | Susini et al. |
| 9,907,550 | B2 | 3/2018 | Sniffin et al. |
| 9,913,642 | B2 | 3/2018 | Leimbach et al. |
| 9,913,645 | B2 | 3/2018 | Zerkle et al. |
| 9,918,326 | B2 | 3/2018 | Gilson et al. |
| 9,918,730 | B2 | 3/2018 | Trees et al. |
| 9,918,778 | B2 | 3/2018 | Walberg et al. |
| 9,918,788 | B2 | 3/2018 | Paul et al. |
| 9,922,304 | B2 | 3/2018 | DeBusk et al. |
| 9,924,941 | B2 | 3/2018 | Burbank |
| 9,924,944 | B2 | 3/2018 | Shelton, IV et al. |
| 9,924,961 | B2 | 3/2018 | Shelton, IV et al. |
| 9,931,040 | B2 | 4/2018 | Homyk et al. |
| 9,931,118 | B2 | 4/2018 | Shelton, IV et al. |
| 9,931,124 | B2 | 4/2018 | Gokharu |
| 9,936,863 | B2 | 4/2018 | Tesar |
| 9,936,942 | B2 | 4/2018 | Chin et al. |
| 9,936,955 | B2 | 4/2018 | Miller et al. |
| 9,936,961 | B2 | 4/2018 | Chien et al. |
| 9,937,012 | B2 | 4/2018 | Hares et al. |
| 9,937,014 | B2 | 4/2018 | Bowling et al. |
| 9,937,626 | B2 | 4/2018 | Rockrohr |
| 9,938,972 | B2 | 4/2018 | Walley |
| 9,943,230 | B2 | 4/2018 | Kaku et al. |
| 9,943,309 | B2 | 4/2018 | Shelton, IV et al. |
| 9,943,312 | B2 | 4/2018 | Posada et al. |
| 9,943,377 | B2 | 4/2018 | Yates et al. |
| 9,943,379 | B2 | 4/2018 | Gregg, II et al. |
| 9,943,918 | B2 | 4/2018 | Grogan et al. |
| 9,943,964 | B2 | 4/2018 | Hares |
| 9,949,785 | B2 | 4/2018 | Price et al. |
| 9,962,157 | B2 | 5/2018 | Sapre |
| 9,968,355 | B2 | 5/2018 | Shelton, IV et al. |
| 9,974,595 | B2 | 5/2018 | Anderson et al. |
| 9,980,140 | B1 | 5/2018 | Spencer et al. |
| 9,980,769 | B2 | 5/2018 | Trees et al. |
| 9,980,778 | B2 | 5/2018 | Ohline et al. |
| 9,987,000 | B2 | 6/2018 | Shelton, IV et al. |
| 9,987,068 | B2 | 6/2018 | Anderson et al. |
| 9,987,072 | B2 | 6/2018 | McPherson |
| 9,990,856 | B2 | 6/2018 | Kuchenbecker et al. |
| 9,993,248 | B2 | 6/2018 | Shelton, IV et al. |
| 9,993,258 | B2 | 6/2018 | Shelton, IV et al. |
| 9,993,305 | B2 | 6/2018 | Andersson |
| 10,004,491 | B2 | 6/2018 | Martin et al. |
| 10,004,497 | B2 | 6/2018 | Overmyer et al. |
| 10,004,500 | B2 | 6/2018 | Shelton, IV et al. |
| 10,004,501 | B2 | 6/2018 | Shelton, IV et al. |
| 10,004,527 | B2 | 6/2018 | Gee et al. |
| 10,004,557 | B2 | 6/2018 | Gross |
| D822,206 | S | 7/2018 | Shelton, IV et al. |
| 10,010,322 | B2 | 7/2018 | Shelton, IV et al. |
| 10,010,324 | B2 | 7/2018 | Huitema et al. |
| 10,013,049 | B2 | 7/2018 | Leimbach et al. |
| 10,016,199 | B2 | 7/2018 | Baber et al. |
| 10,021,318 | B2 | 7/2018 | Hugosson et al. |
| 10,022,090 | B2 | 7/2018 | Whitman |
| 10,022,120 | B2 | 7/2018 | Martin et al. |
| 10,022,391 | B2 | 7/2018 | Ruderman Chen et al. |
| 10,022,568 | B2 | 7/2018 | Messerly et al. |
| 10,028,402 | B1 | 7/2018 | Walker |
| 10,028,744 | B2 | 7/2018 | Shelton, IV et al. |
| 10,028,761 | B2 | 7/2018 | Leimbach et al. |
| 10,028,788 | B2 | 7/2018 | Kang |
| 10,034,704 | B2 | 7/2018 | Asher et al. |
| 10,037,641 | B2 | 7/2018 | Hyde et al. |
| 10,037,715 | B2 | 7/2018 | Toly et al. |
| D826,405 | S | 8/2018 | Shelton, IV et al. |
| 10,039,546 | B2 | 8/2018 | Williams et al. |
| 10,039,564 | B2 | 8/2018 | Hibner et al. |
| 10,039,565 | B2 | 8/2018 | Vezzu |
| 10,039,589 | B2 | 8/2018 | Virshek et al. |
| 10,041,822 | B2 | 8/2018 | Zemlok |
| 10,044,791 | B2 | 8/2018 | Kamen et al. |
| 10,045,704 | B2 | 8/2018 | Fagin et al. |
| 10,045,776 | B2 | 8/2018 | Shelton, IV et al. |
| 10,045,779 | B2 | 8/2018 | Savage et al. |
| 10,045,781 | B2 | 8/2018 | Cropper et al. |
| 10,045,782 | B2 | 8/2018 | Murthy Aravalli |
| 10,045,813 | B2 | 8/2018 | Mueller |
| 10,048,379 | B2 | 8/2018 | Markendorf et al. |
| 10,052,044 | B2 | 8/2018 | Shelton, IV et al. |
| 10,052,102 | B2 | 8/2018 | Baxter, III et al. |
| 10,052,104 | B2 | 8/2018 | Shelton, IV et al. |
| 10,054,441 | B2 | 8/2018 | Schorr et al. |
| 10,058,393 | B2 | 8/2018 | Bonutti et al. |
| 10,069,633 | B2 | 9/2018 | Gulati et al. |
| 10,076,326 | B2 | 9/2018 | Yates et al. |
| 10,080,618 | B2 | 9/2018 | Marshall et al. |
| 10,084,833 | B2 | 9/2018 | McDonnell et al. |
| D831,209 | S | 10/2018 | Huitema et al. |
| 10,085,748 | B2 | 10/2018 | Morgan et al. |
| 10,085,749 | B2 | 10/2018 | Cappola et al. |
| 10,092,355 | B1 | 10/2018 | Hannaford et al. |
| 10,095,942 | B2 | 10/2018 | Mentese et al. |
| 10,097,578 | B2 | 10/2018 | Baldonado et al. |
| 10,098,527 | B2 | 10/2018 | Weisenburgh, II et al. |
| 10,098,635 | B2 | 10/2018 | Burbank |
| 10,098,642 | B2 | 10/2018 | Baxter, III et al. |
| 10,098,705 | B2 | 10/2018 | Brisson et al. |
| 10,102,926 | B1 | 10/2018 | Leonardi |
| 10,105,140 | B2 | 10/2018 | Malinouskas et al. |
| 10,105,142 | B2 | 10/2018 | Baxter, III et al. |
| 10,105,470 | B2 | 10/2018 | Reasoner et al. |
| 10,111,658 | B2 | 10/2018 | Chowaniec et al. |
| 10,111,665 | B2 | 10/2018 | Aranyi et al. |
| 10,111,679 | B2 | 10/2018 | Baber et al. |
| 10,111,703 | B2 | 10/2018 | Cosman, Jr. et al. |
| D834,541 | S | 11/2018 | You et al. |
| 10,117,649 | B2 | 11/2018 | Baxter, III et al. |
| 10,117,651 | B2 | 11/2018 | Whitman et al. |
| 10,117,702 | B2 | 11/2018 | Danziger et al. |
| 10,118,119 | B2 | 11/2018 | Sappok et al. |
| 10,130,359 | B2 | 11/2018 | Hess et al. |
| 10,130,360 | B2 | 11/2018 | Olson et al. |
| 10,130,361 | B2 | 11/2018 | Yates et al. |
| 10,130,367 | B2 | 11/2018 | Cappola et al. |
| 10,130,432 | B2 | 11/2018 | Auld et al. |
| 10,133,248 | B2 | 11/2018 | Fitzsimmons et al. |
| 10,135,242 | B2 | 11/2018 | Baber et al. |
| 10,136,246 | B2 | 11/2018 | Yamada |
| 10,136,887 | B2 | 11/2018 | Shelton, IV et al. |
| 10,136,891 | B2 | 11/2018 | Shelton, IV et al. |
| 10,136,949 | B2 | 11/2018 | Felder et al. |
| 10,136,954 | B2 | 11/2018 | Johnson et al. |
| 10,137,245 | B2 | 11/2018 | Melker et al. |
| 10,143,526 | B2 | 12/2018 | Walker et al. |
| 10,143,948 | B2 | 12/2018 | Bonifas et al. |
| 10,147,148 | B2 | 12/2018 | Wu et al. |
| 10,149,680 | B2 | 12/2018 | Parihar et al. |
| 10,152,789 | B2 | 12/2018 | Carnes et al. |
| 10,154,841 | B2 | 12/2018 | Weaner et al. |
| 10,159,044 | B2 | 12/2018 | Hrabak |
| 10,159,481 | B2 | 12/2018 | Whitman et al. |
| 10,159,483 | B2 | 12/2018 | Beckman et al. |
| 10,164,466 | B2 | 12/2018 | Calderoni |
| 10,166,025 | B2 | 1/2019 | Leimbach et al. |
| 10,166,061 | B2 | 1/2019 | Berry et al. |
| 10,169,862 | B2 | 1/2019 | Andre et al. |
| 10,172,618 | B2 | 1/2019 | Shelton, IV et al. |
| 10,172,687 | B2 | 1/2019 | Garbus et al. |
| 10,175,096 | B2 | 1/2019 | Dickerson |

(56) References Cited

U.S. PATENT DOCUMENTS

| | | | |
|---|---|---|---|
| 10,175,127 | B2 | 1/2019 | Collins et al. |
| 10,178,992 | B2 | 1/2019 | Wise et al. |
| 10,179,413 | B2 | 1/2019 | Rockrohr |
| 10,180,463 | B2 | 1/2019 | Beckman et al. |
| 10,182,814 | B2 | 1/2019 | Okoniewski |
| 10,182,816 | B2 | 1/2019 | Shelton, IV et al. |
| 10,182,818 | B2 | 1/2019 | Hensel et al. |
| 10,188,385 | B2 | 1/2019 | Kerr et al. |
| 10,189,157 | B2 | 1/2019 | Schlegel et al. |
| 10,190,888 | B2 | 1/2019 | Hryb et al. |
| 10,194,891 | B2 | 2/2019 | Jeong et al. |
| 10,194,907 | B2 | 2/2019 | Marczyk et al. |
| 10,194,913 | B2 | 2/2019 | Nalagatla et al. |
| 10,194,972 | B2 | 2/2019 | Yates et al. |
| 10,197,803 | B2 | 2/2019 | Badiali et al. |
| 10,198,965 | B2 | 2/2019 | Hart |
| 10,201,311 | B2 | 2/2019 | Chou et al. |
| 10,201,349 | B2 | 2/2019 | Leimbach et al. |
| 10,201,364 | B2 | 2/2019 | Leimbach et al. |
| 10,201,365 | B2 | 2/2019 | Boudreaux et al. |
| 10,205,708 | B1 | 2/2019 | Fletcher et al. |
| 10,206,605 | B2 | 2/2019 | Shelton, IV et al. |
| 10,206,752 | B2 | 2/2019 | Hares et al. |
| 10,213,201 | B2 | 2/2019 | Shelton, IV et al. |
| 10,213,203 | B2 | 2/2019 | Swayze et al. |
| 10,213,266 | B2 | 2/2019 | Zemlok et al. |
| 10,213,268 | B2 | 2/2019 | Dachs, II |
| 10,219,491 | B2 | 3/2019 | Stiles, Jr. et al. |
| 10,220,522 | B2 | 3/2019 | Rockrohr |
| 10,222,750 | B2 | 3/2019 | Bang et al. |
| 10,226,249 | B2 | 3/2019 | Jaworek et al. |
| 10,226,250 | B2 | 3/2019 | Beckman et al. |
| 10,226,254 | B2 | 3/2019 | Cabrera et al. |
| 10,226,302 | B2 | 3/2019 | Lacal et al. |
| 10,231,634 | B2 | 3/2019 | Zand et al. |
| 10,231,733 | B2 | 3/2019 | Ehrenfels et al. |
| 10,231,775 | B2 | 3/2019 | Shelton, IV et al. |
| 10,238,413 | B2 | 3/2019 | Hibner et al. |
| 10,245,027 | B2 | 4/2019 | Shelton, IV et al. |
| 10,245,028 | B2 | 4/2019 | Shelton, IV et al. |
| 10,245,029 | B2 | 4/2019 | Hunter et al. |
| 10,245,030 | B2 | 4/2019 | Hunter et al. |
| 10,245,033 | B2 | 4/2019 | Overmyer et al. |
| 10,245,037 | B2 | 4/2019 | Conklin et al. |
| 10,245,038 | B2 | 4/2019 | Hopkins et al. |
| 10,245,040 | B2 | 4/2019 | Milliman |
| 10,251,661 | B2 | 4/2019 | Collings et al. |
| 10,251,725 | B2 | 4/2019 | Valentine et al. |
| 10,258,331 | B2 | 4/2019 | Shelton, IV et al. |
| 10,258,359 | B2 | 4/2019 | Kapadia |
| 10,258,362 | B2 | 4/2019 | Conlon |
| 10,258,363 | B2 | 4/2019 | Worrell et al. |
| 10,258,415 | B2 | 4/2019 | Harrah et al. |
| 10,258,418 | B2 | 4/2019 | Shelton, IV et al. |
| 10,258,425 | B2 | 4/2019 | Mustufa et al. |
| 10,263,171 | B2 | 4/2019 | Wiener et al. |
| 10,265,004 | B2 | 4/2019 | Yamaguchi et al. |
| 10,265,035 | B2 | 4/2019 | Fehre et al. |
| 10,265,066 | B2 | 4/2019 | Measamer et al. |
| 10,265,068 | B2 | 4/2019 | Harris et al. |
| 10,265,072 | B2 | 4/2019 | Shelton, IV et al. |
| 10,265,090 | B2 | 4/2019 | Ingmanson et al. |
| 10,265,130 | B2 | 4/2019 | Hess et al. |
| 10,271,840 | B2 | 4/2019 | Sapre |
| 10,271,844 | B2 | 4/2019 | Valentine et al. |
| 10,271,850 | B2 | 4/2019 | Williams |
| 10,271,851 | B2 | 4/2019 | Shelton, IV et al. |
| D847,989 | S | 5/2019 | Shelton, IV et al. |
| 10,278,698 | B2 | 5/2019 | Racenet |
| 10,278,778 | B2 | 5/2019 | State et al. |
| 10,283,220 | B2 | 5/2019 | Azizian et al. |
| 10,285,694 | B2 | 5/2019 | Viola et al. |
| 10,285,698 | B2 | 5/2019 | Cappola et al. |
| 10,285,700 | B2 | 5/2019 | Scheib |
| 10,285,705 | B2 | 5/2019 | Shelton, IV et al. |
| 10,292,610 | B2 | 5/2019 | Srivastava |
| 10,292,704 | B2 | 5/2019 | Harris et al. |
| 10,292,707 | B2 | 5/2019 | Shelton, IV et al. |
| 10,292,758 | B2 | 5/2019 | Boudreaux et al. |
| 10,292,769 | B1 | 5/2019 | Yu |
| 10,292,771 | B2 | 5/2019 | Wood et al. |
| 10,293,129 | B2 | 5/2019 | Fox et al. |
| 10,299,792 | B2 | 5/2019 | Huitema et al. |
| 10,299,870 | B2 | 5/2019 | Connolly et al. |
| 10,305,926 | B2 | 5/2019 | Mihan et al. |
| D850,617 | S | 6/2019 | Shelton, IV et al. |
| 10,307,159 | B2 | 6/2019 | Harris et al. |
| 10,307,170 | B2 | 6/2019 | Parfett et al. |
| 10,307,199 | B2 | 6/2019 | Farritor et al. |
| 10,311,036 | B1 | 6/2019 | Hussam et al. |
| 10,313,137 | B2 | 6/2019 | Aarnio et al. |
| 10,314,577 | B2 | 6/2019 | Laurent et al. |
| 10,314,582 | B2 | 6/2019 | Shelton, IV et al. |
| 10,321,907 | B2 | 6/2019 | Shelton, IV et al. |
| 10,321,964 | B2 | 6/2019 | Grover et al. |
| 10,327,764 | B2 | 6/2019 | Harris et al. |
| 10,327,779 | B2 | 6/2019 | Richard et al. |
| 10,335,147 | B2 | 7/2019 | Rector et al. |
| 10,335,149 | B2 | 7/2019 | Baxter, III et al. |
| 10,335,180 | B2 | 7/2019 | Johnson et al. |
| 10,335,227 | B2 | 7/2019 | Heard |
| 10,339,496 | B2 | 7/2019 | Matson et al. |
| 10,342,543 | B2 | 7/2019 | Shelton, IV et al. |
| 10,342,602 | B2 | 7/2019 | Strobl et al. |
| 10,342,623 | B2 | 7/2019 | Huelman et al. |
| 10,343,102 | B2 | 7/2019 | Reasoner et al. |
| 10,349,824 | B2 | 7/2019 | Claude et al. |
| 10,349,939 | B2 | 7/2019 | Shelton, IV et al. |
| 10,349,941 | B2 | 7/2019 | Marczyk et al. |
| 10,350,016 | B2 | 7/2019 | Burbank et al. |
| 10,357,184 | B2 | 7/2019 | Crawford et al. |
| 10,357,246 | B2 | 7/2019 | Shelton, IV et al. |
| 10,357,247 | B2 | 7/2019 | Shelton, IV et al. |
| 10,362,179 | B2 | 7/2019 | Harris |
| 10,363,032 | B2 | 7/2019 | Scheib et al. |
| 10,363,037 | B2 | 7/2019 | Aronhalt et al. |
| 10,368,861 | B2 | 8/2019 | Baxter, III et al. |
| 10,368,865 | B2 | 8/2019 | Harris et al. |
| 10,368,867 | B2 | 8/2019 | Harris et al. |
| 10,368,876 | B2 | 8/2019 | Bhatnagar et al. |
| 10,368,894 | B2 | 8/2019 | Madan et al. |
| 10,368,903 | B2 | 8/2019 | Morales et al. |
| 10,376,263 | B2 | 8/2019 | Morgan et al. |
| 10,376,305 | B2 | 8/2019 | Yates et al. |
| 10,376,337 | B2 | 8/2019 | Kilroy et al. |
| 10,376,338 | B2 | 8/2019 | Taylor et al. |
| 10,378,893 | B2 | 8/2019 | Mankovskii |
| 10,383,518 | B2 | 8/2019 | Abu-Tarif et al. |
| 10,383,699 | B2 | 8/2019 | Kilroy et al. |
| 10,384,021 | B2 | 8/2019 | Koeth et al. |
| 10,386,990 | B2 | 8/2019 | Shikhman et al. |
| 10,390,718 | B2 | 8/2019 | Chen et al. |
| 10,390,794 | B2 | 8/2019 | Kuroiwa et al. |
| 10,390,825 | B2 | 8/2019 | Shelton, IV et al. |
| 10,390,831 | B2 | 8/2019 | Holsten et al. |
| 10,390,895 | B2 | 8/2019 | Henderson et al. |
| 10,398,348 | B2 | 9/2019 | Osadchy et al. |
| 10,398,434 | B2 | 9/2019 | Shelton, IV et al. |
| 10,398,517 | B2 | 9/2019 | Eckert et al. |
| 10,398,521 | B2 | 9/2019 | Itkowitz et al. |
| 10,404,521 | B2 | 9/2019 | McChord et al. |
| 10,404,801 | B2 | 9/2019 | Martch |
| 10,405,857 | B2 | 9/2019 | Shelton, IV et al. |
| 10,405,859 | B2 | 9/2019 | Harris et al. |
| 10,405,863 | B2 | 9/2019 | Wise et al. |
| 10,413,291 | B2 | 9/2019 | Worthington et al. |
| 10,413,293 | B2 | 9/2019 | Shelton, IV et al. |
| 10,413,297 | B2 | 9/2019 | Harris et al. |
| 10,417,446 | B2 | 9/2019 | Takeyama |
| 10,420,552 | B2 | 9/2019 | Shelton, IV et al. |
| 10,420,558 | B2 | 9/2019 | Nalagatla et al. |
| 10,420,559 | B2 | 9/2019 | Marczyk et al. |
| 10,420,620 | B2 | 9/2019 | Rockrohr |
| 10,420,865 | B2 | 9/2019 | Reasoner et al. |

(56) References Cited

U.S. PATENT DOCUMENTS

| | | | |
|---|---|---|---|
| 10,422,727 | B2 | 9/2019 | Pliskin |
| 10,426,466 | B2 | 10/2019 | Contini et al. |
| 10,426,467 | B2 | 10/2019 | Miller et al. |
| 10,426,468 | B2 | 10/2019 | Contini et al. |
| 10,426,471 | B2 | 10/2019 | Shelton, IV et al. |
| 10,426,481 | B2 | 10/2019 | Aronhalt et al. |
| 10,433,837 | B2 | 10/2019 | Worthington et al. |
| 10,433,844 | B2 | 10/2019 | Shelton, IV et al. |
| 10,433,849 | B2 | 10/2019 | Shelton, IV et al. |
| 10,433,918 | B2 | 10/2019 | Shelton, IV et al. |
| 10,441,279 | B2 | 10/2019 | Shelton, IV et al. |
| 10,441,345 | B2 | 10/2019 | Aldridge et al. |
| 10,448,948 | B2 | 10/2019 | Shelton, IV et al. |
| 10,448,950 | B2 | 10/2019 | Shelton, IV et al. |
| 10,456,137 | B2 | 10/2019 | Vendely et al. |
| 10,456,140 | B2 | 10/2019 | Shelton, IV et al. |
| 10,456,193 | B2 | 10/2019 | Yates et al. |
| 10,463,365 | B2 | 11/2019 | Williams |
| 10,463,367 | B2 | 11/2019 | Kostrzewski et al. |
| 10,463,371 | B2 | 11/2019 | Kostrzewski |
| 10,463,436 | B2 | 11/2019 | Jackson et al. |
| 10,470,762 | B2 | 11/2019 | Leimbach et al. |
| 10,470,764 | B2 | 11/2019 | Baxter, III et al. |
| 10,470,768 | B2 | 11/2019 | Harris et al. |
| 10,470,791 | B2 | 11/2019 | Houser |
| 10,471,254 | B2 | 11/2019 | Sano et al. |
| 10,478,181 | B2 | 11/2019 | Shelton, IV et al. |
| 10,478,182 | B2 | 11/2019 | Taylor |
| 10,478,185 | B2 | 11/2019 | Nicholas |
| 10,478,189 | B2 | 11/2019 | Bear et al. |
| 10,478,190 | B2 | 11/2019 | Miller et al. |
| 10,478,544 | B2 | 11/2019 | Friederichs et al. |
| 10,485,450 | B2 | 11/2019 | Gupta et al. |
| 10,485,542 | B2 | 11/2019 | Shelton, IV et al. |
| 10,485,543 | B2 | 11/2019 | Shelton, IV et al. |
| 10,492,783 | B2 | 12/2019 | Shelton, IV et al. |
| 10,492,784 | B2 | 12/2019 | Beardsley et al. |
| 10,492,785 | B2 | 12/2019 | Overmyer et al. |
| 10,496,788 | B2 | 12/2019 | Amarasingham et al. |
| 10,498,269 | B2 | 12/2019 | Zemlok et al. |
| 10,499,847 | B2 | 12/2019 | Latimer et al. |
| 10,499,891 | B2 | 12/2019 | Chaplin et al. |
| 10,499,914 | B2 | 12/2019 | Huang et al. |
| 10,499,915 | B2 | 12/2019 | Aranyi |
| 10,499,994 | B2 | 12/2019 | Luks et al. |
| 10,507,068 | B2 | 12/2019 | Kopp et al. |
| 10,510,267 | B2 | 12/2019 | Jarc et al. |
| 10,512,413 | B2 | 12/2019 | Schepis et al. |
| 10,512,461 | B2 | 12/2019 | Gupta et al. |
| 10,512,499 | B2 | 12/2019 | McHenry et al. |
| 10,512,509 | B2 | 12/2019 | Bowling et al. |
| 10,512,514 | B2 | 12/2019 | Nowlin et al. |
| 10,517,588 | B2 | 12/2019 | Gupta et al. |
| 10,517,595 | B2 | 12/2019 | Hunter et al. |
| 10,517,596 | B2 | 12/2019 | Hunter et al. |
| 10,517,686 | B2 | 12/2019 | Vokrot et al. |
| 10,524,789 | B2 | 1/2020 | Swayze et al. |
| 10,531,579 | B2 | 1/2020 | Hsiao et al. |
| 10,531,874 | B2 | 1/2020 | Morgan et al. |
| 10,531,929 | B2 | 1/2020 | Widenhouse et al. |
| 10,532,330 | B2 | 1/2020 | Diallo et al. |
| 10,536,617 | B2 | 1/2020 | Liang et al. |
| 10,537,324 | B2 | 1/2020 | Shelton, IV et al. |
| 10,537,325 | B2 | 1/2020 | Bakos et al. |
| 10,537,351 | B2 | 1/2020 | Shelton, IV et al. |
| 10,542,978 | B2 | 1/2020 | Chowaniec et al. |
| 10,542,979 | B2 | 1/2020 | Shelton, IV et al. |
| 10,542,982 | B2 | 1/2020 | Beckman et al. |
| 10,542,991 | B2 | 1/2020 | Shelton, IV et al. |
| D876,466 | S | 2/2020 | Kobayashi et al. |
| 10,548,504 | B2 | 2/2020 | Shelton, IV et al. |
| 10,548,612 | B2 | 2/2020 | Martinez et al. |
| 10,548,673 | B2 | 2/2020 | Harris et al. |
| 10,552,574 | B2 | 2/2020 | Sweeney |
| 10,555,675 | B2 | 2/2020 | Satish et al. |
| 10,555,748 | B2 | 2/2020 | Yates et al. |
| 10,555,750 | B2 | 2/2020 | Conlon et al. |
| 10,555,769 | B2 | 2/2020 | Worrell et al. |
| 10,561,349 | B2 | 2/2020 | Wedekind et al. |
| 10,561,422 | B2 | 2/2020 | Schellin et al. |
| 10,561,470 | B2 | 2/2020 | Hourtash et al. |
| 10,561,471 | B2 | 2/2020 | Nichogi |
| 10,561,560 | B2 | 2/2020 | Boutoussov et al. |
| 10,561,753 | B2 | 2/2020 | Thompson et al. |
| 10,568,625 | B2 | 2/2020 | Harris et al. |
| 10,568,626 | B2 | 2/2020 | Shelton, IV et al. |
| 10,568,632 | B2 | 2/2020 | Miller et al. |
| 10,568,704 | B2 | 2/2020 | Savall et al. |
| 10,575,868 | B2 | 3/2020 | Hall et al. |
| 10,582,928 | B2 | 3/2020 | Hunter et al. |
| 10,582,931 | B2 | 3/2020 | Mujawar |
| 10,582,964 | B2 | 3/2020 | Weinberg et al. |
| 10,586,074 | B2 | 3/2020 | Rose et al. |
| 10,588,623 | B2 | 3/2020 | Schmid et al. |
| 10,588,625 | B2 | 3/2020 | Weaner et al. |
| 10,588,629 | B2 | 3/2020 | Malinouskas et al. |
| 10,588,630 | B2 | 3/2020 | Shelton, IV et al. |
| 10,588,631 | B2 | 3/2020 | Shelton, IV et al. |
| 10,588,632 | B2 | 3/2020 | Shelton, IV et al. |
| 10,588,711 | B2 | 3/2020 | DiCarlo et al. |
| 10,592,067 | B2 | 3/2020 | Merdan et al. |
| 10,595,844 | B2 | 3/2020 | Nawana et al. |
| 10,595,882 | B2 | 3/2020 | Parfett et al. |
| 10,595,887 | B2 | 3/2020 | Shelton, IV et al. |
| 10,595,930 | B2 | 3/2020 | Scheib et al. |
| 10,595,952 | B2 | 3/2020 | Forrest et al. |
| 10,602,007 | B2 | 3/2020 | Takano |
| 10,602,848 | B2 | 3/2020 | Magana |
| 10,603,036 | B2 | 3/2020 | Hunter et al. |
| 10,603,128 | B2 | 3/2020 | Zergiebel et al. |
| 10,610,223 | B2 | 4/2020 | Wellman et al. |
| 10,610,224 | B2 | 4/2020 | Shelton, IV et al. |
| 10,610,286 | B2 | 4/2020 | Wiener et al. |
| 10,610,313 | B2 | 4/2020 | Bailey et al. |
| 10,617,412 | B2 | 4/2020 | Shelton, IV et al. |
| 10,617,414 | B2 | 4/2020 | Shelton, IV et al. |
| 10,617,482 | B2 | 4/2020 | Houser et al. |
| 10,617,484 | B2 | 4/2020 | Kilroy et al. |
| 10,624,635 | B2 | 4/2020 | Harris et al. |
| 10,624,667 | B2 | 4/2020 | Faller et al. |
| 10,624,691 | B2 | 4/2020 | Wiener et al. |
| 10,631,423 | B2 | 4/2020 | Collins et al. |
| 10,631,858 | B2 | 4/2020 | Burbank |
| 10,631,912 | B2 | 4/2020 | McFarlin et al. |
| 10,631,916 | B2 | 4/2020 | Horner et al. |
| 10,631,917 | B2 | 4/2020 | Ineson |
| 10,631,939 | B2 | 4/2020 | Dachs, II et al. |
| 10,639,027 | B2 | 5/2020 | Shelton, IV et al. |
| 10,639,034 | B2 | 5/2020 | Harris et al. |
| 10,639,035 | B2 | 5/2020 | Shelton, IV et al. |
| 10,639,036 | B2 | 5/2020 | Yates et al. |
| 10,639,037 | B2 | 5/2020 | Shelton, IV et al. |
| 10,639,039 | B2 | 5/2020 | Vendely et al. |
| 10,639,098 | B2 | 5/2020 | Cosman et al. |
| 10,639,111 | B2 | 5/2020 | Kopp |
| 10,639,185 | B2 | 5/2020 | Agrawal et al. |
| 10,653,413 | B2 | 5/2020 | Worthington et al. |
| 10,653,476 | B2 | 5/2020 | Ross |
| 10,653,489 | B2 | 5/2020 | Kopp |
| 10,656,720 | B1 | 5/2020 | Holz |
| 10,660,705 | B2 | 5/2020 | Piron et al. |
| 10,667,809 | B2 | 6/2020 | Bakos et al. |
| 10,667,810 | B2 | 6/2020 | Shelton, IV et al. |
| 10,667,811 | B2 | 6/2020 | Harris et al. |
| 10,667,877 | B2 | 6/2020 | Kapadia |
| 10,674,897 | B2 | 6/2020 | Levy |
| 10,675,021 | B2 | 6/2020 | Harris et al. |
| 10,675,023 | B2 | 6/2020 | Cappola |
| 10,675,024 | B2 | 6/2020 | Shelton, IV et al. |
| 10,675,025 | B2 | 6/2020 | Swayze et al. |
| 10,675,026 | B2 | 6/2020 | Harris et al. |
| 10,675,035 | B2 | 6/2020 | Zingman |
| 10,675,100 | B2 | 6/2020 | Frushour |
| 10,675,104 | B2 | 6/2020 | Kapadia |

(56) References Cited

U.S. PATENT DOCUMENTS

| | | | |
|---|---|---|---|
| 10,677,764 | B2 | 6/2020 | Ross et al. |
| 10,679,758 | B2 | 6/2020 | Fox et al. |
| 10,682,136 | B2 | 6/2020 | Harris et al. |
| 10,682,138 | B2 | 6/2020 | Shelton, IV et al. |
| 10,686,805 | B2 | 6/2020 | Reybok, Jr. et al. |
| 10,687,806 | B2 | 6/2020 | Shelton, IV et al. |
| 10,687,809 | B2 | 6/2020 | Shelton, IV et al. |
| 10,687,810 | B2 | 6/2020 | Shelton, IV et al. |
| 10,687,884 | B2 | 6/2020 | Wiener et al. |
| 10,687,905 | B2 | 6/2020 | Kostrzewski |
| 10,695,055 | B2 | 6/2020 | Shelton, IV et al. |
| 10,695,081 | B2 | 6/2020 | Shelton, IV et al. |
| 10,695,134 | B2 | 6/2020 | Barral et al. |
| 10,702,270 | B2 | 7/2020 | Shelton, IV et al. |
| 10,702,271 | B2 | 7/2020 | Aranyi et al. |
| 10,709,446 | B2 | 7/2020 | Harris et al. |
| 10,716,489 | B2 | 7/2020 | Kalvoy et al. |
| 10,716,615 | B2 | 7/2020 | Shelton, IV et al. |
| 10,716,639 | B2 | 7/2020 | Kapadia et al. |
| 10,717,194 | B2 | 7/2020 | Griffiths et al. |
| 10,722,222 | B2 | 7/2020 | Aranyi |
| 10,722,233 | B2 | 7/2020 | Wellman |
| 10,722,292 | B2 | 7/2020 | Arya et al. |
| D893,717 | S | 8/2020 | Messerly et al. |
| 10,729,458 | B2 | 8/2020 | Stoddard et al. |
| 10,729,509 | B2 | 8/2020 | Shelton, IV et al. |
| 10,733,267 | B2 | 8/2020 | Pedersen |
| 10,736,219 | B2 | 8/2020 | Seow et al. |
| 10,736,616 | B2 | 8/2020 | Scheib et al. |
| 10,736,628 | B2 | 8/2020 | Yates et al. |
| 10,736,629 | B2 | 8/2020 | Shelton, IV et al. |
| 10,736,636 | B2 | 8/2020 | Baxter, III et al. |
| 10,736,705 | B2 | 8/2020 | Scheib et al. |
| 10,743,872 | B2 | 8/2020 | Leimbach et al. |
| 10,748,115 | B2 | 8/2020 | Laster et al. |
| 10,751,052 | B2 | 8/2020 | Stokes et al. |
| 10,751,136 | B2 | 8/2020 | Farritor et al. |
| 10,751,768 | B2 | 8/2020 | Hersey et al. |
| 10,755,813 | B2 | 8/2020 | Shelton, IV et al. |
| D896,379 | S | 9/2020 | Shelton, IV et al. |
| 10,758,229 | B2 | 9/2020 | Shelton, IV et al. |
| 10,758,230 | B2 | 9/2020 | Shelton, IV et al. |
| 10,758,294 | B2 | 9/2020 | Jones |
| 10,758,310 | B2 | 9/2020 | Shelton, IV et al. |
| 10,765,376 | B2 | 9/2020 | Brown, III et al. |
| 10,765,424 | B2 | 9/2020 | Baxter, III et al. |
| 10,765,427 | B2 | 9/2020 | Shelton, IV et al. |
| 10,765,470 | B2 | 9/2020 | Yates et al. |
| 10,772,630 | B2 | 9/2020 | Wixey |
| 10,772,651 | B2 | 9/2020 | Shelton, IV et al. |
| 10,772,673 | B2 | 9/2020 | Allen, IV et al. |
| 10,772,688 | B2 | 9/2020 | Peine et al. |
| 10,779,818 | B2 | 9/2020 | Zemlok et al. |
| 10,779,821 | B2 | 9/2020 | Harris et al. |
| 10,779,823 | B2 | 9/2020 | Shelton, IV et al. |
| 10,779,897 | B2 | 9/2020 | Rockrohr |
| 10,779,900 | B2 | 9/2020 | Pedros et al. |
| 10,783,634 | B2 | 9/2020 | Nye et al. |
| 10,786,298 | B2 | 9/2020 | Johnson |
| 10,786,317 | B2 | 9/2020 | Zhou et al. |
| 10,786,327 | B2 | 9/2020 | Anderson et al. |
| 10,792,038 | B2 | 10/2020 | Becerra et al. |
| 10,792,118 | B2 | 10/2020 | Prpa et al. |
| 10,792,422 | B2 | 10/2020 | Douglas et al. |
| 10,799,304 | B2 | 10/2020 | Kapadia et al. |
| 10,803,977 | B2 | 10/2020 | Sanmugalingham |
| 10,806,445 | B2 | 10/2020 | Penna et al. |
| 10,806,453 | B2 | 10/2020 | Chen et al. |
| 10,806,454 | B2 | 10/2020 | Kopp |
| 10,806,499 | B2 | 10/2020 | Castaneda et al. |
| 10,806,506 | B2 | 10/2020 | Gaspredes et al. |
| 10,806,532 | B2 | 10/2020 | Grubbs et al. |
| 10,813,638 | B2 | 10/2020 | Shelton, IV et al. |
| 10,813,703 | B2 | 10/2020 | Swayze et al. |
| 10,818,383 | B2 | 10/2020 | Sharifi Sedeh et al. |
| 10,828,028 | B2 | 11/2020 | Harris et al. |
| 10,828,030 | B2 | 11/2020 | Weir et al. |
| 10,835,206 | B2 | 11/2020 | Bell et al. |
| 10,835,245 | B2 | 11/2020 | Swayze et al. |
| 10,835,246 | B2 | 11/2020 | Shelton, IV et al. |
| 10,835,247 | B2 | 11/2020 | Shelton, IV et al. |
| 10,842,473 | B2 | 11/2020 | Scheib et al. |
| 10,842,490 | B2 | 11/2020 | DiNardo et al. |
| 10,842,492 | B2 | 11/2020 | Shelton, IV et al. |
| 10,842,522 | B2 | 11/2020 | Messerly et al. |
| 10,842,523 | B2 | 11/2020 | Shelton, IV et al. |
| 10,842,575 | B2 | 11/2020 | Panescu et al. |
| 10,842,897 | B2 | 11/2020 | Schwartz et al. |
| D904,612 | S | 12/2020 | Wynn et al. |
| 10,849,697 | B2 | 12/2020 | Yates et al. |
| 10,849,700 | B2 | 12/2020 | Kopp et al. |
| 10,856,768 | B2 | 12/2020 | Osadchy et al. |
| 10,856,867 | B2 | 12/2020 | Shelton, IV et al. |
| 10,856,868 | B2 | 12/2020 | Shelton, IV et al. |
| 10,856,870 | B2 | 12/2020 | Harris et al. |
| 10,863,984 | B2 | 12/2020 | Shelton, IV et al. |
| 10,864,037 | B2 | 12/2020 | Mun et al. |
| 10,864,050 | B2 | 12/2020 | Tabandeh et al. |
| 10,872,684 | B2 | 12/2020 | McNutt et al. |
| 10,881,399 | B2 | 1/2021 | Shelton, IV et al. |
| 10,881,401 | B2 | 1/2021 | Baber et al. |
| 10,881,446 | B2 | 1/2021 | Strobl |
| 10,881,464 | B2 | 1/2021 | Odermatt et al. |
| 10,888,321 | B2 | 1/2021 | Shelton, IV et al. |
| 10,888,322 | B2 | 1/2021 | Morgan et al. |
| 10,892,899 | B2 | 1/2021 | Shelton, IV et al. |
| 10,892,995 | B2 | 1/2021 | Shelton, IV et al. |
| 10,893,863 | B2 | 1/2021 | Shelton, IV et al. |
| 10,893,864 | B2 | 1/2021 | Harris et al. |
| 10,893,884 | B2 | 1/2021 | Stoddard et al. |
| 10,898,183 | B2 | 1/2021 | Shelton, IV et al. |
| 10,898,186 | B2 | 1/2021 | Bakos et al. |
| 10,898,189 | B2 | 1/2021 | McDonald, II |
| 10,898,256 | B2 | 1/2021 | Yates et al. |
| 10,898,280 | B2 | 1/2021 | Kopp |
| 10,898,622 | B2 | 1/2021 | Shelton, IV et al. |
| 10,902,944 | B1 | 1/2021 | Casey et al. |
| 10,903,685 | B2 | 1/2021 | Yates et al. |
| 10,905,415 | B2 | 2/2021 | DiNardo et al. |
| 10,905,418 | B2 | 2/2021 | Shelton, IV et al. |
| 10,905,420 | B2 | 2/2021 | Jasemian et al. |
| 10,912,559 | B2 | 2/2021 | Harris et al. |
| 10,912,567 | B2 | 2/2021 | Shelton, IV et al. |
| 10,912,580 | B2 | 2/2021 | Green et al. |
| 10,912,619 | B2 | 2/2021 | Jarc et al. |
| 10,916,415 | B2 | 2/2021 | Karancsi et al. |
| 10,918,385 | B2 | 2/2021 | Overmyer et al. |
| 10,930,400 | B2 | 2/2021 | Robbins et al. |
| D914,878 | S | 3/2021 | Shelton, IV et al. |
| 10,932,705 | B2 | 3/2021 | Muhsin et al. |
| 10,932,772 | B2 | 3/2021 | Shelton, IV et al. |
| 10,932,784 | B2 | 3/2021 | Mozdzierz et al. |
| 10,932,804 | B2 | 3/2021 | Scheib et al. |
| 10,932,806 | B2 | 3/2021 | Shelton, IV et al. |
| 10,932,872 | B2 | 3/2021 | Shelton, IV et al. |
| 10,939,313 | B2 | 3/2021 | Eom et al. |
| 10,943,454 | B2 | 3/2021 | Shelton, IV et al. |
| 10,944,728 | B2 | 3/2021 | Wiener et al. |
| 10,945,727 | B2 | 3/2021 | Shelton, IV et al. |
| 10,950,982 | B2 | 3/2021 | Regnier et al. |
| 10,952,708 | B2 | 3/2021 | Scheib et al. |
| 10,954,935 | B2 | 3/2021 | O'Shea et al. |
| 10,959,727 | B2 | 3/2021 | Hunter et al. |
| 10,959,729 | B2 | 3/2021 | Ehrenfels et al. |
| 10,959,744 | B2 | 3/2021 | Shelton, IV et al. |
| 10,959,788 | B2 | 3/2021 | Grover et al. |
| 10,960,150 | B2 | 3/2021 | Zergiebel et al. |
| 10,966,590 | B2 | 4/2021 | Takahashi et al. |
| 10,966,791 | B2 | 4/2021 | Harris et al. |
| 10,966,798 | B2 | 4/2021 | Tesar et al. |
| 10,973,516 | B2 | 4/2021 | Shelton, IV et al. |
| 10,973,517 | B2 | 4/2021 | Wixey |
| 10,973,520 | B2 | 4/2021 | Shelton, IV et al. |
| 10,973,682 | B2 | 4/2021 | Vezzu et al. |

(56) References Cited

U.S. PATENT DOCUMENTS

| | | | |
|---|---|---|---|
| 10,980,536 | B2 | 4/2021 | Weaner et al. |
| 10,980,537 | B2 | 4/2021 | Shelton, IV et al. |
| 10,980,560 | B2 | 4/2021 | Shelton, IV et al. |
| 10,980,595 | B2 | 4/2021 | Wham |
| 10,980,610 | B2 | 4/2021 | Rosenberg et al. |
| 10,987,102 | B2 | 4/2021 | Gonzalez et al. |
| 10,987,178 | B2 | 4/2021 | Shelton, IV et al. |
| 10,992,698 | B2 | 4/2021 | Patel et al. |
| 10,993,715 | B2 | 5/2021 | Shelton, IV et al. |
| 10,998,098 | B2 | 5/2021 | Greene et al. |
| 11,000,276 | B2 | 5/2021 | Shelton, IV et al. |
| 11,000,278 | B2 | 5/2021 | Shelton, IV et al. |
| 11,007,004 | B2 | 5/2021 | Shelton, IV et al. |
| 11,007,022 | B2 | 5/2021 | Shelton, IV et al. |
| 11,013,563 | B2 | 5/2021 | Shelton, IV et al. |
| 11,026,687 | B2 | 6/2021 | Shelton, IV et al. |
| 11,026,712 | B2 | 6/2021 | Shelton, IV et al. |
| 11,026,713 | B2 | 6/2021 | Stokes et al. |
| 11,026,751 | B2 | 6/2021 | Shelton, IV et al. |
| 11,039,834 | B2 | 6/2021 | Harris et al. |
| 11,045,191 | B2 | 6/2021 | Shelton, IV et al. |
| 11,045,192 | B2 | 6/2021 | Harris et al. |
| 11,045,197 | B2 | 6/2021 | Shelton, IV et al. |
| 11,045,591 | B2 | 6/2021 | Shelton, IV et al. |
| 11,051,817 | B2 | 7/2021 | Shelton, IV et al. |
| 11,051,836 | B2 | 7/2021 | Shelton, IV et al. |
| 11,051,873 | B2 | 7/2021 | Wiener et al. |
| 11,051,876 | B2 | 7/2021 | Shelton, IV et al. |
| 11,051,902 | B2 | 7/2021 | Kruecker et al. |
| 11,056,244 | B2 | 7/2021 | Shelton, IV et al. |
| 11,058,423 | B2 | 7/2021 | Shelton, IV et al. |
| 11,058,498 | B2 | 7/2021 | Shelton, IV et al. |
| 11,058,501 | B2 | 7/2021 | Tokarchuk et al. |
| 11,064,997 | B2 | 7/2021 | Shelton, IV et al. |
| 11,069,012 | B2 | 7/2021 | Shelton, IV et al. |
| 11,071,560 | B2 | 7/2021 | Deck et al. |
| 11,071,595 | B2 | 7/2021 | Johnson et al. |
| 11,076,921 | B2 | 8/2021 | Shelton, IV et al. |
| 11,083,458 | B2 | 8/2021 | Harris et al. |
| 11,090,047 | B2 | 8/2021 | Shelton, IV et al. |
| 11,090,048 | B2 | 8/2021 | Fanelli et al. |
| 11,090,075 | B2 | 8/2021 | Hunter et al. |
| 11,096,688 | B2 | 8/2021 | Shelton, IV et al. |
| 11,096,693 | B2 | 8/2021 | Shelton, IV et al. |
| 11,100,631 | B2 | 8/2021 | Yates et al. |
| 11,103,268 | B2 | 8/2021 | Shelton, IV et al. |
| 11,109,866 | B2 | 9/2021 | Shelton, IV et al. |
| 11,109,878 | B2 | 9/2021 | Shelton, IV et al. |
| 11,114,195 | B2 | 9/2021 | Shelton, IV et al. |
| 11,116,485 | B2 | 9/2021 | Scheib et al. |
| 11,123,070 | B2 | 9/2021 | Shelton, IV et al. |
| 11,129,611 | B2 | 9/2021 | Shelton, IV et al. |
| 11,129,634 | B2 | 9/2021 | Scheib et al. |
| 11,129,636 | B2 | 9/2021 | Shelton, IV et al. |
| 11,129,669 | B2 | 9/2021 | Stulen et al. |
| 11,129,670 | B2 | 9/2021 | Shelton, IV et al. |
| 11,132,462 | B2 | 9/2021 | Shelton, IV et al. |
| 11,134,942 | B2 | 10/2021 | Harris et al. |
| 11,141,160 | B2 | 10/2021 | Shelton, IV et al. |
| 11,141,213 | B2 | 10/2021 | Yates et al. |
| 11,147,607 | B2 | 10/2021 | Yates et al. |
| 11,160,551 | B2 | 11/2021 | Shelton, IV et al. |
| 11,160,605 | B2 | 11/2021 | Shelton, IV et al. |
| 11,166,716 | B2 | 11/2021 | Shelton, IV et al. |
| 11,166,772 | B2 | 11/2021 | Shelton, IV et al. |
| 11,179,150 | B2 | 11/2021 | Yates et al. |
| 11,179,151 | B2 | 11/2021 | Shelton, IV et al. |
| 11,179,155 | B2 | 11/2021 | Shelton, IV et al. |
| 11,179,175 | B2 | 11/2021 | Houser et al. |
| 11,179,204 | B2 | 11/2021 | Shelton, IV et al. |
| 11,179,208 | B2 | 11/2021 | Yates et al. |
| 11,185,325 | B2 | 11/2021 | Shelton, IV et al. |
| 11,185,330 | B2 | 11/2021 | Huitema et al. |
| 11,191,539 | B2 | 12/2021 | Overmyer et al. |
| 11,191,540 | B2 | 12/2021 | Aronhalt et al. |
| 11,197,668 | B2 | 12/2021 | Shelton, IV et al. |
| 11,202,570 | B2 | 12/2021 | Shelton, IV et al. |
| 11,207,065 | B2 | 12/2021 | Harris et al. |
| 11,207,067 | B2 | 12/2021 | Shelton, IV et al. |
| 11,207,090 | B2 | 12/2021 | Shelton, IV et al. |
| 11,213,293 | B2 | 1/2022 | Worthington et al. |
| 11,213,294 | B2 | 1/2022 | Shelton, IV et al. |
| 11,213,359 | B2 | 1/2022 | Shelton, IV et al. |
| 11,218,822 | B2 | 1/2022 | Morgan et al. |
| 11,219,453 | B2 | 1/2022 | Shelton, IV et al. |
| 11,224,426 | B2 | 1/2022 | Shelton, IV et al. |
| 11,229,436 | B2 | 1/2022 | Shelton, IV et al. |
| 11,229,471 | B2 | 1/2022 | Shelton, IV et al. |
| 11,234,756 | B2 | 2/2022 | Shelton, IV et al. |
| 11,241,230 | B2 | 2/2022 | Shelton, IV et al. |
| 11,253,256 | B2 | 2/2022 | Harris et al. |
| 11,253,315 | B2 | 2/2022 | Yates et al. |
| 11,257,589 | B2 | 2/2022 | Shelton, IV et al. |
| 11,259,806 | B2 | 3/2022 | Shelton, IV et al. |
| 11,259,807 | B2 | 3/2022 | Shelton, IV et al. |
| 11,259,830 | B2 | 3/2022 | Nott et al. |
| 11,266,409 | B2 | 3/2022 | Huitema et al. |
| 11,266,468 | B2 | 3/2022 | Shelton, IV et al. |
| 11,272,931 | B2 | 3/2022 | Boudreaux et al. |
| 11,273,001 | B2 | 3/2022 | Shelton, IV et al. |
| 11,273,290 | B2 | 3/2022 | Kowshik |
| 11,278,280 | B2 | 3/2022 | Shelton, IV et al. |
| 11,278,281 | B2 | 3/2022 | Shelton, IV et al. |
| 11,284,890 | B2 | 3/2022 | Nalagatla et al. |
| 11,284,936 | B2 | 3/2022 | Shelton, IV et al. |
| 11,291,440 | B2 | 4/2022 | Harris et al. |
| 11,291,441 | B2 | 4/2022 | Giordano et al. |
| 11,291,444 | B2 | 4/2022 | Boudreaux et al. |
| 11,291,445 | B2 | 4/2022 | Shelton, IV et al. |
| 11,291,465 | B2 | 4/2022 | Parihar et al. |
| 11,291,495 | B2 | 4/2022 | Yates et al. |
| 11,291,510 | B2 | 4/2022 | Shelton, IV et al. |
| 11,298,128 | B2 | 4/2022 | Messerly et al. |
| 11,298,129 | B2 | 4/2022 | Bakos et al. |
| 11,298,130 | B2 | 4/2022 | Bakos et al. |
| 11,298,148 | B2 | 4/2022 | Jayme et al. |
| 11,304,699 | B2 | 4/2022 | Shelton, IV et al. |
| 11,304,720 | B2 | 4/2022 | Kimball et al. |
| 11,304,745 | B2 | 4/2022 | Shelton, IV et al. |
| 11,304,763 | B2 | 4/2022 | Shelton, IV et al. |
| 11,308,075 | B2 | 4/2022 | Shelton, IV et al. |
| 11,311,306 | B2 | 4/2022 | Shelton, IV et al. |
| 11,311,342 | B2 | 4/2022 | Parihar et al. |
| D950,728 | S | 5/2022 | Bakos et al. |
| D952,144 | S | 5/2022 | Boudreaux |
| 11,317,915 | B2 | 5/2022 | Boudreaux et al. |
| 11,317,919 | B2 | 5/2022 | Shelton, IV et al. |
| 11,317,937 | B2 | 5/2022 | Nott et al. |
| 11,324,557 | B2 | 5/2022 | Shelton, IV et al. |
| 11,331,100 | B2 | 5/2022 | Boudreaux et al. |
| 11,331,101 | B2 | 5/2022 | Harris et al. |
| 11,337,746 | B2 | 5/2022 | Boudreaux |
| 11,344,326 | B2 | 5/2022 | Faller et al. |
| 11,350,959 | B2 | 6/2022 | Messerly et al. |
| 11,350,978 | B2 | 6/2022 | Henderson et al. |
| 11,357,503 | B2 | 6/2022 | Bakos et al. |
| 11,364,075 | B2 | 6/2022 | Yates et al. |
| 11,369,377 | B2 | 6/2022 | Boudreaux et al. |
| 11,376,002 | B2 | 7/2022 | Shelton, IV et al. |
| 11,382,697 | B2 | 7/2022 | Shelton, IV et al. |
| 11,382,715 | B2 | 7/2022 | Arai et al. |
| 11,389,164 | B2 | 7/2022 | Yates et al. |
| 11,389,188 | B2 | 7/2022 | Gee et al. |
| 11,399,858 | B2 | 8/2022 | Sawhney et al. |
| 11,406,382 | B2 | 8/2022 | Shelton, IV et al. |
| 11,406,390 | B2 | 8/2022 | Shelton, IV et al. |
| 11,410,259 | B2 | 8/2022 | Harris et al. |
| 11,413,042 | B2 | 8/2022 | Shelton, IV et al. |
| 11,419,606 | B2 | 8/2022 | Overmyer et al. |
| 11,419,630 | B2 | 8/2022 | Yates et al. |
| 11,419,667 | B2 | 8/2022 | Messerly et al. |
| 11,423,007 | B2 | 8/2022 | Shelton, IV et al. |
| 11,424,027 | B2 | 8/2022 | Shelton, IV |
| D964,564 | S | 9/2022 | Boudreaux |

(56) References Cited

U.S. PATENT DOCUMENTS

| | | | |
|---|---|---|---|
| 11,432,885 | B2 | 9/2022 | Shelton, IV et al. |
| 11,446,052 | B2 | 9/2022 | Shelton, IV et al. |
| 11,457,944 | B2 | 10/2022 | Scoggins |
| 11,464,511 | B2 | 10/2022 | Timm et al. |
| 11,464,513 | B2 | 10/2022 | Shelton, IV et al. |
| 11,464,532 | B2 | 10/2022 | Nott et al. |
| 11,464,535 | B2 | 10/2022 | Shelton, IV et al. |
| 11,464,559 | B2 | 10/2022 | Nott et al. |
| 11,471,156 | B2 | 10/2022 | Shelton, IV et al. |
| 11,471,206 | B2 | 10/2022 | Henderson et al. |
| 11,478,244 | B2 | 10/2022 | DiNardo et al. |
| 11,504,192 | B2 | 11/2022 | Shelton, IV et al. |
| 11,510,671 | B2 | 11/2022 | Shelton, IV et al. |
| 11,510,675 | B2 | 11/2022 | Shelton, IV et al. |
| 11,510,720 | B2 | 11/2022 | Morgan et al. |
| 11,510,741 | B2 | 11/2022 | Shelton, IV et al. |
| 11,517,309 | B2 | 12/2022 | Bakos et al. |
| 11,517,315 | B2 | 12/2022 | Huitema et al. |
| 2001/0056237 | A1 | 12/2001 | Cane et al. |
| 2002/0049551 | A1 | 4/2002 | Friedman et al. |
| 2002/0052616 | A1 | 5/2002 | Wiener et al. |
| 2002/0072746 | A1 | 6/2002 | Lingenfelder et al. |
| 2002/0138642 | A1 | 9/2002 | Miyazawa et al. |
| 2002/0169584 | A1 | 11/2002 | Fu et al. |
| 2003/0009111 | A1 | 1/2003 | Cory et al. |
| 2003/0009154 | A1 | 1/2003 | Whitman |
| 2003/0018329 | A1 | 1/2003 | Hooven |
| 2003/0046109 | A1 | 3/2003 | Uchikubo |
| 2003/0069573 | A1 | 4/2003 | Kadhiresan et al. |
| 2003/0093503 | A1 | 5/2003 | Yamaki et al. |
| 2003/0114851 | A1 | 6/2003 | Truckai et al. |
| 2003/0130711 | A1 | 7/2003 | Pearson et al. |
| 2003/0210812 | A1 | 11/2003 | Khamene et al. |
| 2003/0223877 | A1 | 12/2003 | Anstine et al. |
| 2004/0015053 | A1 | 1/2004 | Bieger et al. |
| 2004/0078236 | A1 | 4/2004 | Stoodley et al. |
| 2004/0108825 | A1 | 6/2004 | Lee et al. |
| 2004/0199180 | A1 | 10/2004 | Knodel et al. |
| 2004/0199659 | A1 | 10/2004 | Ishikawa et al. |
| 2004/0206365 | A1 | 10/2004 | Knowlton |
| 2004/0229496 | A1 | 11/2004 | Robinson et al. |
| 2004/0243147 | A1 | 12/2004 | Lipow |
| 2004/0243148 | A1 | 12/2004 | Wasielewski |
| 2004/0243435 | A1 | 12/2004 | Williams |
| 2005/0020909 | A1 | 1/2005 | Moctezuma de la Barrera et al. |
| 2005/0020918 | A1 | 1/2005 | Wilk et al. |
| 2005/0021027 | A1 | 1/2005 | Shields et al. |
| 2005/0023324 | A1 | 2/2005 | Doll et al. |
| 2005/0063575 | A1 | 3/2005 | Ma et al. |
| 2005/0065438 | A1 | 3/2005 | Miller |
| 2005/0070800 | A1 | 3/2005 | Takahashi |
| 2005/0100867 | A1 | 5/2005 | Hilscher et al. |
| 2005/0131390 | A1 | 6/2005 | Heinrich et al. |
| 2005/0139629 | A1 | 6/2005 | Schwemberger et al. |
| 2005/0143759 | A1 | 6/2005 | Kelly |
| 2005/0148854 | A1 | 7/2005 | Ito et al. |
| 2005/0149001 | A1 | 7/2005 | Uchikubo et al. |
| 2005/0149356 | A1 | 7/2005 | Cyr et al. |
| 2005/0165390 | A1 | 7/2005 | Mauti et al. |
| 2005/0182655 | A1 | 8/2005 | Merzlak et al. |
| 2005/0192633 | A1 | 9/2005 | Montpetit |
| 2005/0203380 | A1 | 9/2005 | Sauer et al. |
| 2005/0203384 | A1 | 9/2005 | Sati et al. |
| 2005/0203504 | A1 | 9/2005 | Wham et al. |
| 2005/0213832 | A1 | 9/2005 | Schofield et al. |
| 2005/0222631 | A1 | 10/2005 | Dalal et al. |
| 2005/0228246 | A1 | 10/2005 | Lee et al. |
| 2005/0228425 | A1 | 10/2005 | Boukhny et al. |
| 2005/0236474 | A1 | 10/2005 | Onuma et al. |
| 2005/0251233 | A1 | 11/2005 | Kanzius |
| 2005/0277913 | A1 | 12/2005 | McCary |
| 2006/0020272 | A1 | 1/2006 | Gildenberg |
| 2006/0025816 | A1 | 2/2006 | Shelton |
| 2006/0059018 | A1 | 3/2006 | Shiobara et al. |
| 2006/0069388 | A1 | 3/2006 | Truckai et al. |
| 2006/0079872 | A1 | 4/2006 | Eggleston |
| 2006/0079874 | A1 | 4/2006 | Faller et al. |
| 2006/0116908 | A1 | 6/2006 | Dew et al. |
| 2006/0136622 | A1 | 6/2006 | Rouvelin et al. |
| 2006/0142739 | A1 | 6/2006 | DiSilestro et al. |
| 2006/0184160 | A1 | 8/2006 | Ozaki et al. |
| 2006/0241399 | A1 | 10/2006 | Fabian |
| 2006/0282009 | A1 | 12/2006 | Oberg et al. |
| 2006/0287645 | A1 | 12/2006 | Tashiro et al. |
| 2007/0010838 | A1 | 1/2007 | Shelton et al. |
| 2007/0016235 | A1 | 1/2007 | Tanaka et al. |
| 2007/0016979 | A1 | 1/2007 | Damaj et al. |
| 2007/0027459 | A1 | 2/2007 | Horvath et al. |
| 2007/0038080 | A1 | 2/2007 | Salisbury et al. |
| 2007/0049947 | A1 | 3/2007 | Menn et al. |
| 2007/0066970 | A1 | 3/2007 | Ineson |
| 2007/0078678 | A1 | 4/2007 | DiSilvestro et al. |
| 2007/0084896 | A1 | 4/2007 | Doll et al. |
| 2007/0085528 | A1 | 4/2007 | Govari et al. |
| 2007/0156019 | A1 | 7/2007 | Larkin et al. |
| 2007/0167702 | A1 | 7/2007 | Hasser et al. |
| 2007/0168461 | A1 | 7/2007 | Moore |
| 2007/0173803 | A1 | 7/2007 | Wham et al. |
| 2007/0175955 | A1 | 8/2007 | Shelton et al. |
| 2007/0179482 | A1 | 8/2007 | Anderson |
| 2007/0179508 | A1 | 8/2007 | Arndt |
| 2007/0191713 | A1 | 8/2007 | Eichmann et al. |
| 2007/0192139 | A1 | 8/2007 | Cookson et al. |
| 2007/0203744 | A1 | 8/2007 | Scholl |
| 2007/0225556 | A1 | 9/2007 | Ortiz et al. |
| 2007/0225690 | A1 | 9/2007 | Sekiguchi et al. |
| 2007/0239028 | A1 | 10/2007 | Houser et al. |
| 2007/0244478 | A1 | 10/2007 | Bahney |
| 2007/0249990 | A1 | 10/2007 | Cosmescu |
| 2007/0270660 | A1 | 11/2007 | Caylor et al. |
| 2007/0282195 | A1 | 12/2007 | Masini et al. |
| 2007/0282321 | A1 | 12/2007 | Shah et al. |
| 2007/0282333 | A1 | 12/2007 | Fortson et al. |
| 2007/0293218 | A1 | 12/2007 | Meylan et al. |
| 2008/0013460 | A1 | 1/2008 | Allen et al. |
| 2008/0015664 | A1 | 1/2008 | Podhajsky |
| 2008/0015912 | A1 | 1/2008 | Rosenthal et al. |
| 2008/0019393 | A1 | 1/2008 | Yamaki |
| 2008/0033404 | A1 | 2/2008 | Romoda et al. |
| 2008/0039742 | A1 | 2/2008 | Hashimshony et al. |
| 2008/0040151 | A1 | 2/2008 | Moore |
| 2008/0058593 | A1 | 3/2008 | Gu et al. |
| 2008/0059658 | A1 | 3/2008 | Williams |
| 2008/0077158 | A1 | 3/2008 | Haider et al. |
| 2008/0083414 | A1 | 4/2008 | Messerges |
| 2008/0091071 | A1 | 4/2008 | Kumar et al. |
| 2008/0114212 | A1 | 5/2008 | Messerges |
| 2008/0114350 | A1 | 5/2008 | Park et al. |
| 2008/0129465 | A1 | 6/2008 | Rao |
| 2008/0140090 | A1 | 6/2008 | Aranyi et al. |
| 2008/0167644 | A1 | 7/2008 | Shelton et al. |
| 2008/0177258 | A1 | 7/2008 | Govari et al. |
| 2008/0177362 | A1 | 7/2008 | Phillips et al. |
| 2008/0200940 | A1 | 8/2008 | Eichmann et al. |
| 2008/0234708 | A1 | 9/2008 | Houser et al. |
| 2008/0235052 | A1 | 9/2008 | Node-Langlois et al. |
| 2008/0255413 | A1 | 10/2008 | Zemlok et al. |
| 2008/0262654 | A1 | 10/2008 | Omori et al. |
| 2008/0272172 | A1 | 11/2008 | Zemlok et al. |
| 2008/0281301 | A1 | 11/2008 | DeBoer et al. |
| 2008/0281678 | A1 | 11/2008 | Keuls et al. |
| 2008/0296346 | A1 | 12/2008 | Shelton, IV et al. |
| 2008/0306759 | A1 | 12/2008 | Ilkin et al. |
| 2008/0312953 | A1 | 12/2008 | Claus |
| 2009/0017910 | A1 | 1/2009 | Rofougaran et al. |
| 2009/0030437 | A1 | 1/2009 | Houser et al. |
| 2009/0036750 | A1 | 2/2009 | Weinstein et al. |
| 2009/0036794 | A1 | 2/2009 | Stubhaug et al. |
| 2009/0043253 | A1 | 2/2009 | Podaima |
| 2009/0046146 | A1 | 2/2009 | Hoyt |
| 2009/0048589 | A1 | 2/2009 | Takashino et al. |
| 2009/0048611 | A1 | 2/2009 | Funda et al. |
| 2009/0076409 | A1 | 3/2009 | Wu et al. |
| 2009/0090763 | A1 | 4/2009 | Zemlok et al. |

(56) References Cited

U.S. PATENT DOCUMENTS

| | | | |
|---|---|---|---|
| 2009/0099866 | A1 | 4/2009 | Newman |
| 2009/0114699 | A1 | 5/2009 | Viola |
| 2009/0128084 | A1 | 5/2009 | Johnson et al. |
| 2009/0182577 | A1 | 7/2009 | Squilla et al. |
| 2009/0206131 | A1 | 8/2009 | Weisenburgh, II et al. |
| 2009/0217932 | A1 | 9/2009 | Voegele |
| 2009/0234352 | A1 | 9/2009 | Behnke et al. |
| 2009/0259149 | A1 | 10/2009 | Tahara et al. |
| 2009/0259221 | A1 | 10/2009 | Tahara et al. |
| 2009/0259489 | A1 | 10/2009 | Kimura et al. |
| 2009/0270678 | A1 | 10/2009 | Scott et al. |
| 2009/0299214 | A1 | 12/2009 | Wu et al. |
| 2009/0306581 | A1 | 12/2009 | Claus |
| 2009/0307681 | A1 | 12/2009 | Armado et al. |
| 2009/0326321 | A1 | 12/2009 | Jacobsen et al. |
| 2009/0326336 | A1 | 12/2009 | Lemke et al. |
| 2010/0036374 | A1 | 2/2010 | Ward |
| 2010/0036405 | A1 | 2/2010 | Giordano et al. |
| 2010/0038403 | A1 | 2/2010 | D'Arcangelo |
| 2010/0057106 | A1 | 3/2010 | Sorrentino et al. |
| 2010/0065604 | A1 | 3/2010 | Weng |
| 2010/0069939 | A1 | 3/2010 | Konishi |
| 2010/0069942 | A1 | 3/2010 | Shelton, IV |
| 2010/0070417 | A1 | 3/2010 | Flynn et al. |
| 2010/0120266 | A1 | 5/2010 | Rimborg |
| 2010/0132334 | A1 | 6/2010 | Duclos et al. |
| 2010/0137845 | A1 | 6/2010 | Ramstein et al. |
| 2010/0137886 | A1 | 6/2010 | Zergiebel et al. |
| 2010/0168561 | A1 | 7/2010 | Anderson |
| 2010/0179831 | A1 | 7/2010 | Brown et al. |
| 2010/0191100 | A1 | 7/2010 | Anderson et al. |
| 2010/0198200 | A1 | 8/2010 | Horvath |
| 2010/0198248 | A1 | 8/2010 | Vakharia |
| 2010/0204717 | A1 | 8/2010 | Knodel |
| 2010/0217991 | A1 | 8/2010 | Choi |
| 2010/0234996 | A1 | 9/2010 | Schreiber et al. |
| 2010/0235689 | A1 | 9/2010 | Tian et al. |
| 2010/0250571 | A1 | 9/2010 | Pierce et al. |
| 2010/0258327 | A1 | 10/2010 | Esenwein et al. |
| 2010/0292535 | A1 | 11/2010 | Paskar |
| 2010/0292684 | A1 | 11/2010 | Cybulski et al. |
| 2010/0301095 | A1 | 12/2010 | Shelton, IV et al. |
| 2011/0022032 | A1 | 1/2011 | Zemlok et al. |
| 2011/0036890 | A1 | 2/2011 | Ma |
| 2011/0043612 | A1 | 2/2011 | Keller et al. |
| 2011/0046618 | A1 | 2/2011 | Minar et al. |
| 2011/0071530 | A1 | 3/2011 | Carson |
| 2011/0077512 | A1 | 3/2011 | Boswell |
| 2011/0087238 | A1 | 4/2011 | Wang et al. |
| 2011/0087502 | A1 | 4/2011 | Yelton et al. |
| 2011/0105277 | A1 | 5/2011 | Shauli |
| 2011/0105895 | A1 | 5/2011 | Kornblau et al. |
| 2011/0112569 | A1 | 5/2011 | Friedman et al. |
| 2011/0118708 | A1 | 5/2011 | Burbank et al. |
| 2011/0119075 | A1 | 5/2011 | Dhoble |
| 2011/0125149 | A1 | 5/2011 | El-Galley et al. |
| 2011/0152712 | A1 | 6/2011 | Cao et al. |
| 2011/0163147 | A1 | 7/2011 | Laurent et al. |
| 2011/0166883 | A1 | 7/2011 | Palmer et al. |
| 2011/0196398 | A1 | 8/2011 | Robertson et al. |
| 2011/0237883 | A1 | 9/2011 | Chun |
| 2011/0251612 | A1 | 10/2011 | Faller et al. |
| 2011/0264000 | A1 | 10/2011 | Paul et al. |
| 2011/0264078 | A1 | 10/2011 | Lipow et al. |
| 2011/0265311 | A1 | 11/2011 | Kondo et al. |
| 2011/0273465 | A1 | 11/2011 | Konishi et al. |
| 2011/0278343 | A1 | 11/2011 | Knodel et al. |
| 2011/0290024 | A1 | 12/2011 | Lefler |
| 2011/0295270 | A1 | 12/2011 | Giordano et al. |
| 2011/0306840 | A1 | 12/2011 | Allen et al. |
| 2012/0012638 | A1 | 1/2012 | Huang et al. |
| 2012/0021684 | A1 | 1/2012 | Schultz et al. |
| 2012/0022519 | A1 | 1/2012 | Huang et al. |
| 2012/0029354 | A1 | 2/2012 | Mark et al. |
| 2012/0046662 | A1 | 2/2012 | Gilbert |
| 2012/0059684 | A1 | 3/2012 | Hampapur et al. |
| 2012/0078247 | A1 | 3/2012 | Worrell et al. |
| 2012/0080336 | A1 | 4/2012 | Shelton, IV et al. |
| 2012/0083786 | A1 | 4/2012 | Artale et al. |
| 2012/0100517 | A1 | 4/2012 | Bowditch et al. |
| 2012/0101488 | A1 | 4/2012 | Aldridge et al. |
| 2012/0116265 | A1 | 5/2012 | Houser et al. |
| 2012/0116381 | A1 | 5/2012 | Houser et al. |
| 2012/0116394 | A1 | 5/2012 | Timm et al. |
| 2012/0130217 | A1 | 5/2012 | Kauphusman et al. |
| 2012/0145714 | A1 | 6/2012 | Farascioni et al. |
| 2012/0172696 | A1 | 7/2012 | Kallback et al. |
| 2012/0190981 | A1 | 7/2012 | Harris et al. |
| 2012/0191091 | A1 | 7/2012 | Allen |
| 2012/0191162 | A1 | 7/2012 | Villa |
| 2012/0197619 | A1 | 8/2012 | Namer Yelin et al. |
| 2012/0203067 | A1 | 8/2012 | Higgins et al. |
| 2012/0203785 | A1 | 8/2012 | Awada |
| 2012/0211542 | A1 | 8/2012 | Racenet |
| 2012/0226150 | A1 | 9/2012 | Balicki et al. |
| 2012/0245958 | A1 | 9/2012 | Lawrence et al. |
| 2012/0253329 | A1 | 10/2012 | Zemlok et al. |
| 2012/0253847 | A1 | 10/2012 | Dell'Anno et al. |
| 2012/0265555 | A1 | 10/2012 | Cappuzzo et al. |
| 2012/0292367 | A1 | 11/2012 | Morgan et al. |
| 2012/0319859 | A1 | 12/2012 | Taub et al. |
| 2013/0001121 | A1 | 1/2013 | Metzger |
| 2013/0006241 | A1 | 1/2013 | Takashino |
| 2013/0008677 | A1 | 1/2013 | Huifu |
| 2013/0024213 | A1 | 1/2013 | Poon |
| 2013/0046182 | A1 | 2/2013 | Hegg et al. |
| 2013/0046279 | A1 | 2/2013 | Niklewski et al. |
| 2013/0046295 | A1 | 2/2013 | Kerr et al. |
| 2013/0066647 | A1 | 3/2013 | Andrie et al. |
| 2013/0090526 | A1 | 4/2013 | Suzuki et al. |
| 2013/0090755 | A1 | 4/2013 | Kiryu et al. |
| 2013/0093829 | A1 | 4/2013 | Rosenblatt et al. |
| 2013/0096597 | A1 | 4/2013 | Anand et al. |
| 2013/0116218 | A1 | 5/2013 | Kaplan et al. |
| 2013/0131845 | A1 | 5/2013 | Guilleminot |
| 2013/0144284 | A1 | 6/2013 | Behnke, II et al. |
| 2013/0153635 | A1 | 6/2013 | Hodgkinson |
| 2013/0165776 | A1 | 6/2013 | Blomqvist |
| 2013/0178853 | A1 | 7/2013 | Hyink et al. |
| 2013/0191647 | A1 | 7/2013 | Ferrara, Jr. et al. |
| 2013/0193188 | A1 | 8/2013 | Shelton, IV et al. |
| 2013/0197531 | A1 | 8/2013 | Boukhny et al. |
| 2013/0201356 | A1 | 8/2013 | Kennedy et al. |
| 2013/0206813 | A1 | 8/2013 | Nalagatla |
| 2013/0214025 | A1 | 8/2013 | Zemlok et al. |
| 2013/0253480 | A1 | 9/2013 | Kimball et al. |
| 2013/0256373 | A1 | 10/2013 | Schmid et al. |
| 2013/0267874 | A1 | 10/2013 | Marcotte et al. |
| 2013/0268283 | A1 | 10/2013 | Vann et al. |
| 2013/0277410 | A1 | 10/2013 | Fernandez et al. |
| 2013/0317837 | A1 | 11/2013 | Ballantyne et al. |
| 2013/0321425 | A1 | 12/2013 | Greene et al. |
| 2013/0325809 | A1 | 12/2013 | Kim et al. |
| 2013/0331873 | A1 | 12/2013 | Ross et al. |
| 2013/0331875 | A1 | 12/2013 | Ross et al. |
| 2014/0001231 | A1 | 1/2014 | Shelton, IV et al. |
| 2014/0001234 | A1 | 1/2014 | Shelton, IV et al. |
| 2014/0005640 | A1 | 1/2014 | Shelton, IV et al. |
| 2014/0006132 | A1 | 1/2014 | Barker |
| 2014/0009894 | A1 | 1/2014 | Yu |
| 2014/0013565 | A1 | 1/2014 | MacDonald et al. |
| 2014/0018788 | A1 | 1/2014 | Engelman et al. |
| 2014/0029411 | A1 | 1/2014 | Nayak et al. |
| 2014/0033926 | A1 | 2/2014 | Fassel et al. |
| 2014/0035762 | A1 | 2/2014 | Shelton, IV et al. |
| 2014/0066700 | A1 | 3/2014 | Wilson et al. |
| 2014/0073893 | A1 | 3/2014 | Bencini |
| 2014/0074076 | A1 | 3/2014 | Gertner |
| 2014/0081255 | A1 | 3/2014 | Johnson et al. |
| 2014/0081659 | A1 | 3/2014 | Nawana et al. |
| 2014/0084949 | A1 | 3/2014 | Smith et al. |
| 2014/0087999 | A1 | 3/2014 | Kaplan et al. |
| 2014/0092089 | A1 | 4/2014 | Kasuya et al. |
| 2014/0107697 | A1 | 4/2014 | Patani et al. |

(56) References Cited

U.S. PATENT DOCUMENTS

| | | | |
|---|---|---|---|
| 2014/0108035 | A1 | 4/2014 | Akbay et al. |
| 2014/0108983 | A1 | 4/2014 | William R. et al. |
| 2014/0117256 | A1 | 5/2014 | Mueller et al. |
| 2014/0121669 | A1 | 5/2014 | Claus |
| 2014/0148729 | A1 | 5/2014 | Schmitz et al. |
| 2014/0148803 | A1 | 5/2014 | Taylor |
| 2014/0163359 | A1 | 6/2014 | Sholev et al. |
| 2014/0166724 | A1 | 6/2014 | Schellin et al. |
| 2014/0171778 | A1 | 6/2014 | Tsusaka et al. |
| 2014/0176576 | A1 | 6/2014 | Spencer |
| 2014/0187856 | A1 | 7/2014 | Holoien et al. |
| 2014/0188440 | A1 | 7/2014 | Donhowe et al. |
| 2014/0194864 | A1 | 7/2014 | Martin et al. |
| 2014/0195052 | A1 | 7/2014 | Tsusaka et al. |
| 2014/0204190 | A1 | 7/2014 | Rosenblatt, III et al. |
| 2014/0226572 | A1 | 8/2014 | Thota et al. |
| 2014/0243799 | A1 | 8/2014 | Parihar |
| 2014/0243809 | A1 | 8/2014 | Gelfand et al. |
| 2014/0243811 | A1 | 8/2014 | Reschke et al. |
| 2014/0246475 | A1 | 9/2014 | Hall et al. |
| 2014/0249557 | A1 | 9/2014 | Koch, Jr. et al. |
| 2014/0252064 | A1 | 9/2014 | Mozdzierz et al. |
| 2014/0263541 | A1 | 9/2014 | Leimbach et al. |
| 2014/0263552 | A1 | 9/2014 | Hall et al. |
| 2014/0275760 | A1 | 9/2014 | Lee et al. |
| 2014/0276749 | A1 | 9/2014 | Johnson |
| 2014/0287393 | A1 | 9/2014 | Kumar et al. |
| 2014/0296694 | A1 | 10/2014 | Jaworski |
| 2014/0303660 | A1 | 10/2014 | Boyden et al. |
| 2014/0303990 | A1 | 10/2014 | Schoenefeld et al. |
| 2014/0336943 | A1 | 11/2014 | Pellini et al. |
| 2014/0337052 | A1 | 11/2014 | Pellini et al. |
| 2014/0364691 | A1 | 12/2014 | Krivopisk et al. |
| 2015/0006201 | A1 | 1/2015 | Pait et al. |
| 2015/0025549 | A1 | 1/2015 | Kilroy et al. |
| 2015/0032150 | A1 | 1/2015 | Ishida et al. |
| 2015/0051452 | A1 | 2/2015 | Ciaccio |
| 2015/0051598 | A1 | 2/2015 | Orszulak et al. |
| 2015/0051617 | A1 | 2/2015 | Takemura et al. |
| 2015/0053737 | A1 | 2/2015 | Leimbach et al. |
| 2015/0053743 | A1 | 2/2015 | Yates et al. |
| 2015/0057675 | A1 | 2/2015 | Akeel et al. |
| 2015/0062316 | A1 | 3/2015 | Haraguchi et al. |
| 2015/0066000 | A1 | 3/2015 | An et al. |
| 2015/0070187 | A1 | 3/2015 | Wiesner et al. |
| 2015/0073400 | A1 | 3/2015 | Sverdlik et al. |
| 2015/0077528 | A1 | 3/2015 | Awdeh |
| 2015/0083774 | A1 | 3/2015 | Measamer et al. |
| 2015/0108198 | A1 | 4/2015 | Estrella |
| 2015/0133945 | A1 | 5/2015 | Dushyant et al. |
| 2015/0136833 | A1 | 5/2015 | Shelton, IV et al. |
| 2015/0140982 | A1 | 5/2015 | Postrel |
| 2015/0145682 | A1 | 5/2015 | Harris |
| 2015/0148830 | A1 | 5/2015 | Stulen et al. |
| 2015/0157354 | A1 | 6/2015 | Bales, Jr. et al. |
| 2015/0173673 | A1 | 6/2015 | Toth et al. |
| 2015/0173756 | A1 | 6/2015 | Baxter, III et al. |
| 2015/0182220 | A1 | 7/2015 | Yates et al. |
| 2015/0196295 | A1 | 7/2015 | Shelton, IV et al. |
| 2015/0199109 | A1 | 7/2015 | Lee |
| 2015/0202014 | A1 | 7/2015 | Kim et al. |
| 2015/0208934 | A1 | 7/2015 | Sztrubel et al. |
| 2015/0223725 | A1 | 8/2015 | Engel et al. |
| 2015/0223868 | A1 | 8/2015 | Brandt et al. |
| 2015/0237502 | A1 | 8/2015 | Schmidt et al. |
| 2015/0272557 | A1 | 10/2015 | Overmyer et al. |
| 2015/0272571 | A1 | 10/2015 | Leimbach et al. |
| 2015/0272580 | A1 | 10/2015 | Leimbach et al. |
| 2015/0272582 | A1 | 10/2015 | Leimbach et al. |
| 2015/0272694 | A1 | 10/2015 | Charles |
| 2015/0282821 | A1 | 10/2015 | Look et al. |
| 2015/0296042 | A1 | 10/2015 | Aoyama |
| 2015/0297200 | A1 | 10/2015 | Fitzsimmons et al. |
| 2015/0297222 | A1 | 10/2015 | Huitema et al. |
| 2015/0297311 | A1 | 10/2015 | Tesar |
| 2015/0302157 | A1 | 10/2015 | Collar et al. |
| 2015/0310174 | A1 | 10/2015 | Coudert et al. |
| 2015/0313538 | A1 | 11/2015 | Bechtel et al. |
| 2015/0317899 | A1 | 11/2015 | Dumbauld et al. |
| 2015/0320423 | A1 | 11/2015 | Aranyi |
| 2015/0324114 | A1 | 11/2015 | Hurley et al. |
| 2015/0328474 | A1 | 11/2015 | Flyash et al. |
| 2015/0332003 | A1 | 11/2015 | Stamm et al. |
| 2015/0332196 | A1 | 11/2015 | Stiller et al. |
| 2015/0335344 | A1 | 11/2015 | Aljuri et al. |
| 2015/0374259 | A1 | 12/2015 | Garbey et al. |
| 2016/0000437 | A1 | 1/2016 | Giordano et al. |
| 2016/0001411 | A1 | 1/2016 | Alberti |
| 2016/0015471 | A1 | 1/2016 | Piron et al. |
| 2016/0022374 | A1 | 1/2016 | Haider et al. |
| 2016/0034648 | A1 | 2/2016 | Mohlenbrock et al. |
| 2016/0038224 | A1 | 2/2016 | Couture et al. |
| 2016/0038253 | A1 | 2/2016 | Piron et al. |
| 2016/0048780 | A1 | 2/2016 | Sethumadhavan et al. |
| 2016/0058439 | A1 | 3/2016 | Shelton, IV et al. |
| 2016/0066913 | A1 | 3/2016 | Swayze et al. |
| 2016/0100837 | A1 | 4/2016 | Huang et al. |
| 2016/0106516 | A1 | 4/2016 | Mesallum |
| 2016/0106934 | A1 | 4/2016 | Hiraga et al. |
| 2016/0121143 | A1 | 5/2016 | Mumaw et al. |
| 2016/0157717 | A1 | 6/2016 | Gaster |
| 2016/0158468 | A1 | 6/2016 | Tang et al. |
| 2016/0166336 | A1 | 6/2016 | Razzaque et al. |
| 2016/0174998 | A1 | 6/2016 | Lal et al. |
| 2016/0175025 | A1 | 6/2016 | Strobl |
| 2016/0180045 | A1 | 6/2016 | Syed |
| 2016/0182637 | A1 | 6/2016 | Adriaens et al. |
| 2016/0184054 | A1 | 6/2016 | Lowe |
| 2016/0192960 | A1 | 7/2016 | Bueno et al. |
| 2016/0203599 | A1 | 7/2016 | Gillies et al. |
| 2016/0206202 | A1 | 7/2016 | Frangioni |
| 2016/0206362 | A1 | 7/2016 | Mehta et al. |
| 2016/0224760 | A1 | 8/2016 | Petak et al. |
| 2016/0225551 | A1 | 8/2016 | Shedletsky |
| 2016/0228061 | A1 | 8/2016 | Kallback et al. |
| 2016/0228204 | A1 | 8/2016 | Quaid et al. |
| 2016/0235303 | A1 | 8/2016 | Fleming et al. |
| 2016/0242836 | A1 | 8/2016 | Eggers et al. |
| 2016/0249910 | A1 | 9/2016 | Shelton, IV et al. |
| 2016/0249920 | A1 | 9/2016 | Gupta et al. |
| 2016/0256184 | A1* | 9/2016 | Shelton, IV ......... A61B 17/295 |
| 2016/0270861 | A1 | 9/2016 | Guru et al. |
| 2016/0275259 | A1 | 9/2016 | Nolan et al. |
| 2016/0278841 | A1 | 9/2016 | Panescu et al. |
| 2016/0287312 | A1 | 10/2016 | Tegg et al. |
| 2016/0287316 | A1 | 10/2016 | Worrell et al. |
| 2016/0287912 | A1 | 10/2016 | Warnking |
| 2016/0292456 | A1 | 10/2016 | Dubey et al. |
| 2016/0296246 | A1 | 10/2016 | Schaller |
| 2016/0302210 | A1 | 10/2016 | Thornton et al. |
| 2016/0310055 | A1 | 10/2016 | Zand et al. |
| 2016/0310204 | A1 | 10/2016 | Mchenry et al. |
| 2016/0314716 | A1 | 10/2016 | Grubbs |
| 2016/0314717 | A1 | 10/2016 | Grubbs |
| 2016/0321400 | A1 | 11/2016 | Durrant et al. |
| 2016/0323283 | A1 | 11/2016 | Kang et al. |
| 2016/0331460 | A1 | 11/2016 | Cheatham, III et al. |
| 2016/0342753 | A1 | 11/2016 | Feazell |
| 2016/0342916 | A1 | 11/2016 | Arceneaux et al. |
| 2016/0345857 | A1 | 12/2016 | Jensrud et al. |
| 2016/0350490 | A1 | 12/2016 | Martinez et al. |
| 2016/0354160 | A1 | 12/2016 | Crowley et al. |
| 2016/0354162 | A1 | 12/2016 | Yen et al. |
| 2016/0361070 | A1 | 12/2016 | Ardel et al. |
| 2016/0367305 | A1 | 12/2016 | Hareland |
| 2016/0367401 | A1 | 12/2016 | Claus |
| 2016/0374710 | A1 | 12/2016 | Sinelnikov et al. |
| 2016/0374723 | A1 | 12/2016 | Frankhouser et al. |
| 2016/0374762 | A1 | 12/2016 | Case et al. |
| 2016/0379504 | A1 | 12/2016 | Bailey et al. |
| 2017/0005911 | A1 | 1/2017 | Kasargod et al. |
| 2017/0007247 | A1 | 1/2017 | Shelton, IV et al. |
| 2017/0027603 | A1 | 2/2017 | Pandey |
| 2017/0042604 | A1 | 2/2017 | McFarland et al. |

(56) References Cited

U.S. PATENT DOCUMENTS

2017/0068792 A1 3/2017 Reiner
2017/0079530 A1 3/2017 DiMaio et al.
2017/0079730 A1 3/2017 Azizian et al.
2017/0086829 A1 3/2017 Vendely et al.
2017/0086930 A1 3/2017 Thompson et al.
2017/0105754 A1 4/2017 Boudreaux et al.
2017/0105787 A1 4/2017 Witt et al.
2017/0116873 A1 4/2017 Lendvay et al.
2017/0127499 A1 5/2017 Unoson et al.
2017/0132374 A1 5/2017 Lee et al.
2017/0132385 A1 5/2017 Hunter et al.
2017/0132785 A1 5/2017 Wshah et al.
2017/0143284 A1 5/2017 Sehnert et al.
2017/0164997 A1 6/2017 Johnson et al.
2017/0165008 A1 6/2017 Finley
2017/0165012 A1 6/2017 Chaplin et al.
2017/0172550 A1 6/2017 Mukherjee et al.
2017/0172565 A1 6/2017 Heneveld
2017/0172614 A1 6/2017 Scheib et al.
2017/0172674 A1 6/2017 Hanuschik et al.
2017/0172676 A1 6/2017 Itkowitz et al.
2017/0173262 A1 6/2017 Veltz
2017/0177807 A1 6/2017 Fabian
2017/0178069 A1 6/2017 Paterra et al.
2017/0185732 A1 6/2017 Niklewski et al.
2017/0196583 A1 7/2017 Sugiyama
2017/0202595 A1 7/2017 Shelton, IV
2017/0202608 A1 7/2017 Shelton, IV et al.
2017/0209145 A1 7/2017 Swayze et al.
2017/0215944 A1 8/2017 Keffeler
2017/0224332 A1 8/2017 Hunter et al.
2017/0224428 A1 8/2017 Kopp
2017/0231553 A1 8/2017 Igarashi et al.
2017/0231628 A1 8/2017 Shelton, IV et al.
2017/0245809 A1 8/2017 Ma et al.
2017/0249431 A1 8/2017 Shelton, IV et al.
2017/0249432 A1 8/2017 Grantcharov
2017/0262604 A1 9/2017 Francois
2017/0265864 A1 9/2017 Hessler et al.
2017/0265943 A1 9/2017 Sela et al.
2017/0273715 A1 9/2017 Piron et al.
2017/0281186 A1 10/2017 Shelton, IV et al.
2017/0296173 A1 10/2017 Shelton, IV et al.
2017/0296185 A1 10/2017 Swensgard et al.
2017/0296213 A1 10/2017 Swensgard et al.
2017/0303984 A1 10/2017 Malackowski
2017/0304007 A1 10/2017 Piron et al.
2017/0304020 A1 10/2017 Ng et al.
2017/0311777 A1 11/2017 Hirayama et al.
2017/0312456 A1 11/2017 Phillips
2017/0325876 A1 11/2017 Nakadate et al.
2017/0325878 A1 11/2017 Messerly et al.
2017/0333152 A1 11/2017 Wade
2017/0337043 A1 11/2017 Brincat et al.
2017/0360358 A1 12/2017 Amiot et al.
2017/0360499 A1 12/2017 Greep et al.
2017/0367583 A1 12/2017 Black et al.
2017/0367754 A1 12/2017 Narisawa
2017/0367771 A1 12/2017 Tako et al.
2017/0367772 A1 12/2017 Gunn et al.
2017/0370710 A1 12/2017 Chen et al.
2018/0008359 A1 1/2018 Randle
2018/0011983 A1 1/2018 Zuhars et al.
2018/0021058 A1 1/2018 Meglan
2018/0042659 A1 2/2018 Rupp et al.
2018/0050196 A1 2/2018 Pawsey et al.
2018/0052971 A1 2/2018 Hanina et al.
2018/0065248 A1 3/2018 Barral et al.
2018/0078170 A1 3/2018 Panescu et al.
2018/0098049 A1 4/2018 Sugano et al.
2018/0098816 A1 4/2018 Govari et al.
2018/0108438 A1 4/2018 Ryan et al.
2018/0116735 A1 5/2018 Tierney et al.
2018/0122506 A1 5/2018 Grantcharov et al.
2018/0132895 A1 5/2018 Silver
2018/0144243 A1 5/2018 Hsieh et al.
2018/0153436 A1 6/2018 Olson
2018/0153574 A1 6/2018 Faller et al.
2018/0153632 A1 6/2018 Tokarchuk et al.
2018/0154297 A1 6/2018 Maletich et al.
2018/0161062 A1 6/2018 Kaga et al.
2018/0161716 A1 6/2018 Li et al.
2018/0165780 A1 6/2018 Romeo
2018/0168574 A1 6/2018 Robinson et al.
2018/0168575 A1 6/2018 Simms et al.
2018/0168577 A1 6/2018 Aronhalt et al.
2018/0168579 A1 6/2018 Aronhalt et al.
2018/0168598 A1 6/2018 Shelton, IV et al.
2018/0168608 A1 6/2018 Shelton, IV et al.
2018/0168609 A1 6/2018 Fanelli et al.
2018/0168610 A1 6/2018 Shelton, IV et al.
2018/0168615 A1 6/2018 Shelton, IV et al.
2018/0168618 A1 6/2018 Scott et al.
2018/0168619 A1 6/2018 Scott et al.
2018/0168623 A1 6/2018 Simms et al.
2018/0168625 A1 6/2018 Posada et al.
2018/0168633 A1 6/2018 Shelton, IV et al.
2018/0168647 A1 6/2018 Shelton, IV et al.
2018/0168648 A1 6/2018 Shelton, IV et al.
2018/0168650 A1 6/2018 Shelton, IV et al.
2018/0172420 A1 6/2018 Hein et al.
2018/0177383 A1 6/2018 Noonan et al.
2018/0182475 A1 6/2018 Cossler et al.
2018/0183684 A1 6/2018 Jacobson et al.
2018/0193579 A1 7/2018 Hanrahan et al.
2018/0206884 A1 7/2018 Beaupre
2018/0206905 A1 7/2018 Batchelor et al.
2018/0211726 A1 7/2018 Courtemanche et al.
2018/0214025 A1 8/2018 Homyk et al.
2018/0221005 A1 8/2018 Hamel et al.
2018/0221598 A1 8/2018 Silver
2018/0228557 A1 8/2018 Darisse et al.
2018/0233222 A1 8/2018 Daley et al.
2018/0235719 A1 8/2018 Jarc
2018/0235722 A1 8/2018 Baghdadi et al.
2018/0242967 A1 8/2018 Meade
2018/0247128 A1 8/2018 Alvi et al.
2018/0247711 A1 8/2018 Terry
2018/0250086 A1 9/2018 Grubbs
2018/0250825 A1 9/2018 Hashimoto et al.
2018/0263699 A1 9/2018 Murphy et al.
2018/0263710 A1 9/2018 Sakaguchi et al.
2018/0268320 A1 9/2018 Shekhar
2018/0271520 A1 9/2018 Shelton, IV et al.
2018/0271603 A1 9/2018 Nir et al.
2018/0289427 A1 10/2018 Griffiths et al.
2018/0294060 A1 10/2018 Kassab
2018/0296286 A1 10/2018 Peine et al.
2018/0303552 A1 10/2018 Ryan et al.
2018/0304471 A1 10/2018 Tokuchi
2018/0310986 A1 11/2018 Batchelor et al.
2018/0315492 A1 11/2018 Bishop et al.
2018/0317916 A1 11/2018 Wixey
2018/0333188 A1 11/2018 Nott et al.
2018/0333207 A1 11/2018 Moctezuma De La Barrera
2018/0333209 A1 11/2018 Frushour et al.
2018/0353186 A1 12/2018 Mozdzierz et al.
2018/0357383 A1 12/2018 Allen et al.
2018/0360456 A1 12/2018 Shelton, IV et al.
2018/0366213 A1 12/2018 Fidone et al.
2018/0368930 A1 12/2018 Esterberg et al.
2019/0000569 A1 1/2019 Crawford et al.
2019/0001079 A1 1/2019 Zergiebel et al.
2019/0005641 A1 1/2019 Yamamoto
2019/0006047 A1 1/2019 Gorek et al.
2019/0025040 A1 1/2019 Andreason et al.
2019/0036688 A1 1/2019 Wasily et al.
2019/0038335 A1 2/2019 Mohr et al.
2019/0038364 A1 2/2019 Enoki
2019/0045515 A1 2/2019 Kwasnick et al.
2019/0046198 A1 2/2019 Stokes et al.
2019/0053801 A1 2/2019 Wixey et al.
2019/0053866 A1 2/2019 Seow et al.
2019/0059986 A1 2/2019 Shelton, IV et al.

(56) References Cited

U.S. PATENT DOCUMENTS

| | | | |
|---|---|---|---|
| 2019/0069949 | A1 | 3/2019 | Vrba et al. |
| 2019/0069964 | A1 | 3/2019 | Hagn |
| 2019/0069966 | A1 | 3/2019 | Petersen et al. |
| 2019/0070550 | A1 | 3/2019 | Lalomia et al. |
| 2019/0070731 | A1 | 3/2019 | Bowling et al. |
| 2019/0083190 | A1 | 3/2019 | Graves et al. |
| 2019/0087544 | A1 | 3/2019 | Peterson |
| 2019/0099221 | A1 | 4/2019 | Schmidt et al. |
| 2019/0104919 | A1 | 4/2019 | Shelton, IV et al. |
| 2019/0110828 | A1 | 4/2019 | Despatie |
| 2019/0110855 | A1 | 4/2019 | Barral et al. |
| 2019/0115108 | A1 | 4/2019 | Hegedus et al. |
| 2019/0122330 | A1 | 4/2019 | Saget et al. |
| 2019/0125320 | A1 | 5/2019 | Shelton, IV et al. |
| 2019/0125335 | A1 | 5/2019 | Shelton, IV et al. |
| 2019/0125336 | A1 | 5/2019 | Deck et al. |
| 2019/0125338 | A1 | 5/2019 | Shelton, IV et al. |
| 2019/0125361 | A1 | 5/2019 | Shelton, IV et al. |
| 2019/0125377 | A1 | 5/2019 | Shelton, IV |
| 2019/0125378 | A1 | 5/2019 | Shelton, IV et al. |
| 2019/0125388 | A1 | 5/2019 | Shelton, IV et al. |
| 2019/0125430 | A1 | 5/2019 | Shelton, IV et al. |
| 2019/0125431 | A1 | 5/2019 | Shelton, IV et al. |
| 2019/0125432 | A1 | 5/2019 | Shelton, IV et al. |
| 2019/0125454 | A1 | 5/2019 | Stokes et al. |
| 2019/0125455 | A1 | 5/2019 | Shelton, IV et al. |
| 2019/0125476 | A1 | 5/2019 | Shelton, IV et al. |
| 2019/0133703 | A1 | 5/2019 | Seow et al. |
| 2019/0142535 | A1 | 5/2019 | Seow et al. |
| 2019/0145942 | A1 | 5/2019 | Dutriez et al. |
| 2019/0150975 | A1 | 5/2019 | Kawasaki et al. |
| 2019/0163875 | A1 | 5/2019 | Allen et al. |
| 2019/0167296 | A1 | 6/2019 | Tsubuku et al. |
| 2019/0192044 | A1 | 6/2019 | Ravi et al. |
| 2019/0192157 | A1 | 6/2019 | Scott et al. |
| 2019/0200844 | A1 | 7/2019 | Shelton, IV et al. |
| 2019/0200905 | A1 | 7/2019 | Shelton, IV et al. |
| 2019/0200906 | A1 | 7/2019 | Shelton, IV et al. |
| 2019/0200977 | A1 | 7/2019 | Shelton, IV et al. |
| 2019/0200980 | A1 | 7/2019 | Shelton, IV et al. |
| 2019/0200981 | A1 | 7/2019 | Harris et al. |
| 2019/0200984 | A1 | 7/2019 | Shelton, IV et al. |
| 2019/0200985 | A1 | 7/2019 | Shelton, IV et al. |
| 2019/0200987 | A1 | 7/2019 | Shelton, IV et al. |
| 2019/0200988 | A1 | 7/2019 | Shelton, IV |
| 2019/0200997 | A1 | 7/2019 | Shelton, IV et al. |
| 2019/0201021 | A1 | 7/2019 | Shelton, IV et al. |
| 2019/0201024 | A1 | 7/2019 | Shelton, IV et al. |
| 2019/0201025 | A1 | 7/2019 | Shelton, IV et al. |
| 2019/0201026 | A1 | 7/2019 | Shelton, IV et al. |
| 2019/0201027 | A1 | 7/2019 | Shelton, IV et al. |
| 2019/0201029 | A1 | 7/2019 | Shelton, IV et al. |
| 2019/0201030 | A1 | 7/2019 | Shelton, IV et al. |
| 2019/0201034 | A1 | 7/2019 | Shelton, IV et al. |
| 2019/0201036 | A1 | 7/2019 | Nott et al. |
| 2019/0201038 | A1 | 7/2019 | Yates et al. |
| 2019/0201039 | A1 | 7/2019 | Widenhouse et al. |
| 2019/0201040 | A1 | 7/2019 | Messerly et al. |
| 2019/0201042 | A1 | 7/2019 | Nott et al. |
| 2019/0201045 | A1 | 7/2019 | Yates et al. |
| 2019/0201046 | A1 | 7/2019 | Shelton, IV et al. |
| 2019/0201047 | A1 | 7/2019 | Yates et al. |
| 2019/0201075 | A1 | 7/2019 | Shelton, IV et al. |
| 2019/0201076 | A1 | 7/2019 | Honda et al. |
| 2019/0201083 | A1 | 7/2019 | Shelton, IV et al. |
| 2019/0201085 | A1 | 7/2019 | Shelton, IV et al. |
| 2019/0201087 | A1 | 7/2019 | Shelton, IV et al. |
| 2019/0201090 | A1 | 7/2019 | Shelton, IV et al. |
| 2019/0201102 | A1 | 7/2019 | Shelton, IV et al. |
| 2019/0201104 | A1 | 7/2019 | Shelton, IV et al. |
| 2019/0201112 | A1 | 7/2019 | Wiener et al. |
| 2019/0201113 | A1 | 7/2019 | Shelton, IV et al. |
| 2019/0201115 | A1 | 7/2019 | Shelton, IV et al. |
| 2019/0201118 | A1 | 7/2019 | Shelton, IV et al. |
| 2019/0201123 | A1 | 7/2019 | Shelton, IV et al. |
| 2019/0201126 | A1 | 7/2019 | Shelton, IV et al. |
| 2019/0201127 | A1 | 7/2019 | Shelton, IV et al. |
| 2019/0201128 | A1 | 7/2019 | Yates et al. |
| 2019/0201130 | A1 | 7/2019 | Shelton, IV et al. |
| 2019/0201136 | A1 | 7/2019 | Shelton, IV et al. |
| 2019/0201137 | A1 | 7/2019 | Shelton, IV et al. |
| 2019/0201139 | A1 | 7/2019 | Shelton, IV et al. |
| 2019/0201140 | A1 | 7/2019 | Yates et al. |
| 2019/0201142 | A1 | 7/2019 | Shelton, IV et al. |
| 2019/0201146 | A1 | 7/2019 | Shelton, IV et al. |
| 2019/0201158 | A1 | 7/2019 | Shelton, IV et al. |
| 2019/0201594 | A1 | 7/2019 | Shelton, IV et al. |
| 2019/0204201 | A1 | 7/2019 | Shelton, IV et al. |
| 2019/0205001 | A1 | 7/2019 | Messerly et al. |
| 2019/0205567 | A1 | 7/2019 | Shelton, IV et al. |
| 2019/0206551 | A1 | 7/2019 | Yates et al. |
| 2019/0206555 | A1 | 7/2019 | Morgan et al. |
| 2019/0206561 | A1 | 7/2019 | Shelton, IV et al. |
| 2019/0206562 | A1 | 7/2019 | Shelton, IV et al. |
| 2019/0206564 | A1 | 7/2019 | Shelton, IV et al. |
| 2019/0206569 | A1 | 7/2019 | Shelton, IV et al. |
| 2019/0224434 | A1 | 7/2019 | Silver et al. |
| 2019/0254759 | A1 | 8/2019 | Azizian |
| 2019/0261984 | A1 | 8/2019 | Nelson et al. |
| 2019/0269476 | A1 | 9/2019 | Bowling et al. |
| 2019/0272917 | A1 | 9/2019 | Couture et al. |
| 2019/0274662 | A1 | 9/2019 | Rockman et al. |
| 2019/0274705 | A1 | 9/2019 | Sawhney et al. |
| 2019/0274710 | A1 | 9/2019 | Black |
| 2019/0274711 | A1 | 9/2019 | Scoggins et al. |
| 2019/0274713 | A1 | 9/2019 | Scoggins et al. |
| 2019/0274714 | A1 | 9/2019 | Cuti et al. |
| 2019/0274718 | A1 | 9/2019 | Denzinger et al. |
| 2019/0274719 | A1 | 9/2019 | Stulen |
| 2019/0274749 | A1 | 9/2019 | Brady et al. |
| 2019/0274752 | A1 | 9/2019 | Denzinger et al. |
| 2019/0278262 | A1 | 9/2019 | Taylor et al. |
| 2019/0282311 | A1 | 9/2019 | Nowlin et al. |
| 2019/0290389 | A1 | 9/2019 | Kopp |
| 2019/0298350 | A1 | 10/2019 | Shelton, IV et al. |
| 2019/0298353 | A1 | 10/2019 | Shelton, IV et al. |
| 2019/0298464 | A1 | 10/2019 | Abbott |
| 2019/0307520 | A1 | 10/2019 | Peine et al. |
| 2019/0311802 | A1 | 10/2019 | Kokubo et al. |
| 2019/0314081 | A1 | 10/2019 | Brogna |
| 2019/0320929 | A1 | 10/2019 | Spencer et al. |
| 2019/0321117 | A1 | 10/2019 | Itkowitz et al. |
| 2019/0333626 | A1 | 10/2019 | Mansi et al. |
| 2019/0343594 | A1 | 11/2019 | Garcia Kilroy et al. |
| 2019/0374140 | A1 | 12/2019 | Tucker et al. |
| 2019/0374292 | A1 | 12/2019 | Barral et al. |
| 2019/0378610 | A1 | 12/2019 | Barral et al. |
| 2020/0000470 | A1 | 1/2020 | Du et al. |
| 2020/0000509 | A1 | 1/2020 | Hayashida et al. |
| 2020/0038120 | A1 | 2/2020 | Ziraknejad et al. |
| 2020/0046353 | A1 | 2/2020 | Deck et al. |
| 2020/0054317 | A1 | 2/2020 | Pisarnwongs et al. |
| 2020/0054321 | A1 | 2/2020 | Harris et al. |
| 2020/0078070 | A1 | 3/2020 | Henderson et al. |
| 2020/0078071 | A1 | 3/2020 | Asher |
| 2020/0078076 | A1 | 3/2020 | Henderson et al. |
| 2020/0078078 | A1 | 3/2020 | Henderson et al. |
| 2020/0078080 | A1 | 3/2020 | Henderson et al. |
| 2020/0078081 | A1 | 3/2020 | Jayme et al. |
| 2020/0078082 | A1 | 3/2020 | Henderson et al. |
| 2020/0078089 | A1 | 3/2020 | Henderson et al. |
| 2020/0078096 | A1 | 3/2020 | Barbagli et al. |
| 2020/0078110 | A1 | 3/2020 | Henderson et al. |
| 2020/0078111 | A1 | 3/2020 | Oberkircher et al. |
| 2020/0078112 | A1 | 3/2020 | Henderson et al. |
| 2020/0078113 | A1 | 3/2020 | Sawhney et al. |
| 2020/0078114 | A1 | 3/2020 | Asher et al. |
| 2020/0078115 | A1 | 3/2020 | Asher et al. |
| 2020/0078116 | A1 | 3/2020 | Oberkircher et al. |
| 2020/0078117 | A1 | 3/2020 | Henderson et al. |
| 2020/0078118 | A1 | 3/2020 | Henderson et al. |
| 2020/0078119 | A1 | 3/2020 | Henderson et al. |
| 2020/0078120 | A1 | 3/2020 | Aldridge et al. |
| 2020/0081585 | A1 | 3/2020 | Petre et al. |

(56) References Cited

U.S. PATENT DOCUMENTS

| | | | |
|---|---|---|---|
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0162896 A1 | 5/2020 | Su et al. |
| 2020/0168323 A1 | 5/2020 | Bullington et al. |
| 2020/0178760 A1 | 6/2020 | Kashima et al. |
| 2020/0178971 A1 | 6/2020 | Harris et al. |
| 2020/0193600 A1 | 6/2020 | Shameli et al. |
| 2020/0197027 A1 | 6/2020 | Hershberger et al. |
| 2020/0203004 A1 | 6/2020 | Shanbhag et al. |
| 2020/0214699 A1 | 7/2020 | Shelton, IV et al. |
| 2020/0226751 A1 | 7/2020 | Jin et al. |
| 2020/0230803 A1 | 7/2020 | Yamashita et al. |
| 2020/0237372 A1 | 7/2020 | Park |
| 2020/0261086 A1 | 8/2020 | Zeiner et al. |
| 2020/0275930 A1 | 9/2020 | Harris et al. |
| 2020/0281665 A1 | 9/2020 | Kopp |
| 2020/0305924 A1 | 10/2020 | Carroll |
| 2020/0305945 A1 | 10/2020 | Morgan et al. |
| 2020/0348662 A1 | 11/2020 | Cella et al. |
| 2020/0405304 A1 | 12/2020 | Mozdzierz et al. |
| 2020/0405375 A1 | 12/2020 | Shelton, IV et al. |
| 2021/0007760 A1 | 1/2021 | Reisin |
| 2021/0015568 A1 | 1/2021 | Liao et al. |
| 2021/0022731 A1 | 1/2021 | Eisinger |
| 2021/0022738 A1 | 1/2021 | Weir et al. |
| 2021/0022809 A1 | 1/2021 | Crawford et al. |
| 2021/0059674 A1 | 3/2021 | Shelton, IV et al. |
| 2021/0076966 A1 | 3/2021 | Grantcharov et al. |
| 2021/0128149 A1 | 5/2021 | Whitfield et al. |
| 2021/0153889 A1 | 5/2021 | Nott et al. |
| 2021/0169516 A1 | 6/2021 | Houser et al. |
| 2021/0176179 A1 | 6/2021 | Shelton, IV |
| 2021/0177452 A1 | 6/2021 | Nott et al. |
| 2021/0177489 A1 | 6/2021 | Yates et al. |
| 2021/0186454 A1 | 6/2021 | Behzadi et al. |
| 2021/0192914 A1 | 6/2021 | Shelton, IV et al. |
| 2021/0201646 A1 | 7/2021 | Shelton, IV et al. |
| 2021/0205020 A1 | 7/2021 | Shelton, IV et al. |
| 2021/0205021 A1 | 7/2021 | Shelton, IV et al. |
| 2021/0205028 A1 | 7/2021 | Shelton, IV et al. |
| 2021/0205029 A1 | 7/2021 | Wiener et al. |
| 2021/0205030 A1 | 7/2021 | Shelton, IV et al. |
| 2021/0205031 A1 | 7/2021 | Shelton, IV et al. |
| 2021/0212602 A1 | 7/2021 | Shelton, IV et al. |
| 2021/0212694 A1 | 7/2021 | Shelton, IV et al. |
| 2021/0212717 A1 | 7/2021 | Yates et al. |
| 2021/0212719 A1 | 7/2021 | Houser et al. |
| 2021/0212770 A1 | 7/2021 | Messerly et al. |
| 2021/0212771 A1 | 7/2021 | Shelton, IV et al. |
| 2021/0212774 A1 | 7/2021 | Shelton, IV et al. |
| 2021/0212775 A1 | 7/2021 | Shelton, IV et al. |
| 2021/0212782 A1 | 7/2021 | Shelton, IV et al. |
| 2021/0220058 A1 | 7/2021 | Messerly et al. |
| 2021/0240852 A1 | 8/2021 | Shelton, IV et al. |
| 2021/0241898 A1 | 8/2021 | Shelton, IV et al. |
| 2021/0249125 A1 | 8/2021 | Morgan et al. |
| 2021/0251487 A1 | 8/2021 | Shelton, IV et al. |
| 2021/0259687 A1 | 8/2021 | Gonzalez et al. |
| 2021/0259697 A1 | 8/2021 | Shelton, IV et al. |
| 2021/0259698 A1 | 8/2021 | Shelton, IV et al. |
| 2021/0282780 A1 | 9/2021 | Shelton, IV et al. |
| 2021/0282781 A1 | 9/2021 | Shelton, IV et al. |
| 2021/0306176 A1 | 9/2021 | Park et al. |
| 2021/0315579 A1 | 10/2021 | Shelton, IV et al. |
| 2021/0315580 A1 | 10/2021 | Shelton, IV et al. |
| 2021/0315581 A1 | 10/2021 | Shelton, IV et al. |
| 2021/0315582 A1 | 10/2021 | Shelton, IV et al. |
| 2021/0322014 A1 | 10/2021 | Shelton, IV et al. |
| 2021/0322015 A1 | 10/2021 | Shelton, IV et al. |
| 2021/0322017 A1 | 10/2021 | Shelton, IV et al. |
| 2021/0322018 A1 | 10/2021 | Shelton, IV et al. |
| 2021/0322019 A1 | 10/2021 | Shelton, IV et al. |
| 2021/0322020 A1 | 10/2021 | Shelton, IV et al. |
| 2021/0336939 A1 | 10/2021 | Wiener et al. |
| 2021/0353287 A1 | 11/2021 | Shelton, IV et al. |
| 2021/0353288 A1 | 11/2021 | Shelton, IV et al. |
| 2021/0358599 A1 | 11/2021 | Alvi et al. |
| 2021/0361284 A1 | 11/2021 | Shelton, IV et al. |
| 2022/0000484 A1 | 1/2022 | Shelton, IV et al. |
| 2022/0054158 A1 | 2/2022 | Shelton, IV et al. |
| 2022/0079591 A1 | 3/2022 | Bakos et al. |
| 2022/0160438 A1 | 5/2022 | Shelton, IV et al. |
| 2022/0175374 A1 | 6/2022 | Shelton, IV et al. |
| 2022/0230738 A1 | 7/2022 | Shelton, IV et al. |
| 2022/0241027 A1 | 8/2022 | Shelton, IV et al. |
| 2022/0249097 A1 | 8/2022 | Shelton, IV et al. |

FOREIGN PATENT DOCUMENTS

| | | | |
|---|---|---|---|
| CN | 101617950 | A | 1/2010 |
| CN | 104490448 | B | 3/2017 |
| CN | 206097107 | U | 4/2017 |
| CN | 107811710 | A | 3/2018 |
| CN | 108652695 | A | 10/2018 |
| DE | 3016131 | A1 | 10/1981 |
| DE | 3824913 | A1 | 2/1990 |
| DE | 4002843 | C1 | 4/1991 |
| DE | 102005051367 | A1 | 4/2007 |
| DE | 102016207666 | A1 | 11/2017 |
| EP | 0000756 | B1 | 10/1981 |
| EP | 0408160 | A1 | 1/1991 |
| EP | 0473987 | A1 | 3/1992 |
| EP | 0929263 | B1 | 7/1999 |
| EP | 1214913 | A2 | 6/2002 |
| EP | 2730209 | A1 | 5/2014 |
| EP | 2732772 | A1 | 5/2014 |
| EP | 2942023 | A2 | 11/2015 |
| EP | 3047806 | A1 | 7/2016 |
| EP | 3056923 | A1 | 8/2016 |
| EP | 3095399 | A2 | 11/2016 |
| EP | 3120781 | A2 | 1/2017 |
| EP | 3135225 | A2 | 3/2017 |
| EP | 3141181 | A1 | 3/2017 |
| FR | 2838234 | A1 | 10/2003 |
| GB | 2037167 | A1 | 7/1980 |
| GB | 2509523 | A | 7/2014 |
| JP | S5373315 | A | 6/1978 |
| JP | H07132122 | A | 5/1995 |
| JP | H08332169 | A | 12/1996 |
| JP | 2001029353 | A | 2/2001 |
| JP | 2001340350 | A | 12/2001 |
| JP | 2002272758 | A | 9/2002 |
| JP | 2007123394 | A | 5/2007 |
| JP | 2007300312 | A | 11/2007 |
| JP | 2009039515 | A | 2/2009 |
| JP | 2010057642 | A | 3/2010 |
| JP | 2010131265 | A | 6/2010 |
| JP | 2012065698 | A | 4/2012 |
| JP | 2014155207 | A | 8/2014 |
| JP | 2016174836 | A | 10/2016 |
| JP | 2017047022 | A | 3/2017 |
| JP | 2017513561 | A | 6/2017 |
| JP | 2017526510 | A | 9/2017 |
| JP | 2017532168 | A | 11/2017 |
| KR | 20140104587 | A | 8/2014 |
| KR | 101587721 | B1 | 1/2016 |
| WO | WO-9734533 | A1 | 9/1997 |
| WO | WO-0024322 | A1 | 5/2000 |
| WO | WO-0108578 | A1 | 2/2001 |
| WO | WO-0112089 | A1 | 2/2001 |
| WO | WO-0120892 | A2 | 3/2001 |
| WO | WO-03079909 | A2 | 10/2003 |
| WO | WO-2007137304 | A2 | 11/2007 |
| WO | WO-2008053485 | A1 | 5/2008 |
| WO | WO-2008056618 | A2 | 5/2008 |
| WO | WO-2008069816 | A1 | 6/2008 |
| WO | WO-2008147555 | A2 | 12/2008 |
| WO | WO-2011112931 | A1 | 9/2011 |
| WO | WO-2013143573 | A1 | 10/2013 |
| WO | WO-2014031800 | A1 | 2/2014 |
| WO | WO-2014071184 | A1 | 5/2014 |
| WO | WO-2014134196 | A1 | 9/2014 |

(56) References Cited

FOREIGN PATENT DOCUMENTS

| | | | |
|---|---|---|---|
| WO | WO-2015054665 | A1 | 4/2015 |
| WO | WO-2015129395 | A1 | 9/2015 |
| WO | WO-2016093049 | A1 | 6/2016 |
| WO | WO-2016100719 | A1 | 6/2016 |
| WO | WO-2016118752 | A1 | 7/2016 |
| WO | WO-2016206015 | A1 | 12/2016 |
| WO | WO-2017011382 | A1 | 1/2017 |
| WO | WO-2017011646 | A1 | 1/2017 |
| WO | WO-2017058617 | A2 | 4/2017 |
| WO | WO-2017058695 | A1 | 4/2017 |
| WO | WO-2017151996 | A1 | 9/2017 |
| WO | WO-2017183353 | A1 | 10/2017 |
| WO | WO-2017189317 | A1 | 11/2017 |
| WO | WO-2017205308 | A1 | 11/2017 |
| WO | WO-2017210499 | A1 | 12/2017 |
| WO | WO-2017210501 | A1 | 12/2017 |
| WO | WO-2018116247 | A1 | 6/2018 |
| WO | WO-2018152141 | A1 | 8/2018 |
| WO | WO-2018176414 | A1 | 10/2018 |

OTHER PUBLICATIONS

Engel et al. “A safe robot system for craniofacial surgery”, 2013 IEEE International Conference on Robotics and Automation (ICRA); May 6-10, 2013; Karlsruhe, Germany, vol. 2, Jan. 1, 2001, pp. 2020-2024.

Miller, et al., “Impact of Powered and Tissue-Specific Endoscopic Stapling Technology on Clinical and Economic Outcomes of Video-Assisted Thoracic Surgery Lobectomy Procedures: A Retrospective, Observational Study,” Article, Apr. 2018, pp. 707-723, vol. 35 (Issue 5), Advances in Therapy.

Choi et al., A haptic augmented reality surgeon console for a laparoscopic surgery robot system, 2013, IEEE, p. 355-357 (Year: 2013).

“Surgical instrumentation: the true cost of instrument trays and a potential strategy for optimization”; Mhlaba et al.; Sep. 23, 2015 (Year: 2015).

Anonymous: “Titanium Key Chain Tool 1.1, Ultralight Multipurpose Key Chain Tool, Forward Cutting Can Opener—Vargo Titanium,” vargooutdoors.com, Jul. 5, 2014 (Jul. 5, 2014), retrieved from the internet: https://vargooutdoors.com/titanium-key-chain-tool-1-1.html.

Shi et al., An intuitive control console for robotic surgery system, 2014, IEEE, p. 404-407 (Year: 2014).

Slocinski et al., “Distance measure for impedance spectra for quantified evaluations,” Lecture Notes on Impedance Spectroscopy, vol. 3, Taylor and Francis Group (Jul. 2012)—Book Not Attached.

Zoccali, Bruno, “A Method for Approximating Component Temperatures at Altitude Conditions Based on CFD Analysis at Sea Level Conditions,” (white paper), www.tdmginc.com, Dec. 6, 2018 (9 pages).

Flores et al., “Large-scale Offloading in the Internet of Things,” 2017 IEEE International Conference on Pervasive Computing and Communications Workshops (PERCOM Workshops), IEEE, pp. 479-484, Mar. 13, 2017.

Kalantarian et al., “Computation Offloading for Real-Time Health-Monitoring Devices,” 2016 38th Annual International Conference of the IEEE Engineering in Medicine and Biology Society (EBMC), IEEE, pp. 4971-4974, Aug. 16, 2016.

Yuyi Mao et al., “A Survey on Mobile Edge Computing: The Communication Perspective,” IEEE Communications Surveys & Tutorials, pp. 2322-2358, Jun. 13, 2017.

Khazaei et al., “Health Informatics for Neonatal Intensive Care Units: An Analytical Modeling Perspective,” IEEE Journal of Translational Engineering in Health and Medicine, vol. 3, pp. 1-9, Oct. 21, 2015.

Benkmann et al., “Concept of iterative optimization of minimally invasive surgery,” 2017 22nd International Conference on Methods and Models in Automation and Robotics (MMAR), IEEE pp. 443-446, Aug. 28, 2017.

Trautman, Peter, “Breaking the Human-Robot Deadlock: Surpassing Shared Control Performance Limits with Sparse Human-Robot Interaction,” Robotics: Science and Systems XIIII, pp. 1-10, Jul. 12, 2017.

Miksch et al., “Utilizing temporal data abstraction for data validation and therapy planning for artificially ventilated newborn infants,” Artificial Intelligence in Medicine, vol. 8, No. 6, pp. 543-576 (1996).

Horn et al., “Effective data validation of high-frequency data: Time-point-time-interval-, and trend-based methods,” Computers in Biology and Medic, New York, NY, vol. 27, No. 5, pp. 389-409 (1997).

Stacey et al., “Temporal abstraction in intelligent clinical data analysis: A survey,” Artificial Intelligence in Medicine, vol. 39, No. 1, pp. 1-24 (2006).

Yang et al., “A dynamic stategy for packet scheduling and bandwidth allocation based on channel quality in IEEE 802.16e OFDMA system,” Journal of Network and Computer Applications, vol. 39, pp. 52-60, May 2, 2013.

Hsiao-Wei Tang, “*ARCM*”, Video, Sep. 2012, YouTube, 5 screenshots, Retrieved from internet: <https://www.youtube.com/watch?v=UldQaxb3fRw&feature=youtu.be>.

Giannios, et al., “Visible to near-infrared refractive properties of freshly-excised human-liver tissues: marking hepatic malignancies,” Article, Jun. 14, 2016, pp. 1-10, Scientific Reports 6, Article No. 27910, Nature.

Vander Heiden, et al., “Understanding the Warburg effect: the metabolic requirements of cell proliferation,” Article, May 22, 2009, pp. 1-12, vol. 324, Issue 5930, Science.

Hirayama et al., “Quantitative Metabolome Profiling of Colon and Stomach Cancer Microenvironment by Capillary Electrophoresis Time-of-Flight Mass Spectrometry,” Article, Jun. 2009, pp. 4918-4925, vol. 69, Issue 11, Cancer Research.

Cengiz, et al., “A Tale of Two Compartments: Interstitial Versus Blood Glucose Monitoring,” Article, Jun. 2009, pp. S11-S16, vol. 11, Supplement 1, Diabetes Technology & Therapeutics.

Shen, et al., “An iridium nanoparticles dispersed carbon based thick film electrochemical biosensor and its application for a single use, disposable glucose biosensor,” Article, Feb. 3, 2007, pp. 106-113, vol. 125, Issue 1, Sensors and Actuators B: Chemical, Science Direct.

IEEE Std No. 177, “Standard Definitions and Methods of Measurement for Piezoelectric Vibrators,” published May 1966, The Institute of Electrical and Electronics Engineers, Inc., New York, N.Y.

CRC Press, “The Measurement, Instrumentation and Sensors Handbook,” 1999, Section VII, Chapter 41, Peter O’Shea, “Phase Measurement,” pp. 1303-1321, ISBN 0-8493-2145-X.

“ATM-MPLS Network Interworking Version 2.0, af-aic-0178.001” ATM Standard, The ATM Forum Technical Committee, published Aug. 2003.

IEEE Std 802.3-2012 (Revision of IEEE Std 802.3-2008, published Dec. 28, 2012.

Bonaci et al., “To Make a Robot Secure: An Experimental Analysis of Cyber Security Threats Against Teleoperated Surgical Robots,” May 13, 2015. Retrieved from the Internet: URL:https://arxiv.org/pdf/1504.04339v2.pdf [retrieved on Aug. 24, 2019].

Homa Alemzadeh et al., “Targeted Attacks on Teleoperated Surgical Robots: Dynamic Model-Based Detection and Mitigation,” 2016 46th Annual IEEE/IFIP International Conference on Dependable Systems and Networks (DSN), IEEE, Jun. 28, 2016, pp. 395-406.

Harold I. Brandon and V. Leroy Young, Mar. 1997, Surgical Services Management vol. 3 No. 3. retrieved from the internet <https://www.surgimedics.com/Research%20Articles/Electrosurgical%20Plume/Characterization%20And%20Removal%20Of%20Electrosurgical%20Smoke.pdf> (Year: 1997).

Marshall Brain, How Microcontrollers Work, 2006, retrieved from the internet <https://web.archive.org/web/20060221235221/http://electronics.howstuffworks.com/microcontroller.htm/printable> (Year: 2006).

Sorrells, P., “Application Note AN680. Passive RFID Basics,” retrieved from http://ww1.microchip.com/downloads/en/AppNotes/00680b.pdf on Feb. 26, 2020, Dec. 31, 1998, pp. 1-7.

(56) References Cited

OTHER PUBLICATIONS

Staub et al., "Contour-based Surgical Instrument Tracking Supported by Kinematic Prediction," Proceedings of the 2010 3rd IEEE RAS & EMBS International Conference on Biomedical Robotics and Biomechatronics, Sep. 1, 2010, pp. 746-752.
Phumzile Malindi, "5. QoS in Telemedicine," "Telemedicine," Jun. 20, 2011, IntechOpen, pp. 119-138.
Allan et al., "3-D Pose Estimation of Articulated Instruments in Robotic Minimally Invasive Surgery," IEEE Transactions on Medical Imaging, vol. 37, No. 5, May 1, 2018, pp. 1204-1213.
Kassahun et al., "Surgical Robotics Beyond Enhanced Dexterity Instrumentation: A Survey of the Machine Learning Techniques and their Role in Intelligent and Autonomous Surgical Actions." International Journal of Computer Assisted Radiology and Surgery, vol. 11, No. 4, Oct. 8, 2015, pp. 553-568.
Weede et al. "An Intelligent and Autonomous Endoscopic Guidance System for Minimally Invasive Surgery," 2013 IEEE International Conference on Robotics ad Automation (ICRA), May 6-10, 2013. Karlsruhe, Germany, May 1, 2011, pp. 5762-5768.
Altenberg et al., "Genes of Glycolysis are Ubiquitously Overexpressed in 24 Cancer Classes," Genomics, vol. 84, pp. 1014-1020 (2004).
Jiang, "'Sound of Silence' : a secure indoor wireless ultrasonic communication system," Article, 2014, pp. 46-50, Snapshots of Doctoral Research at University College Cork, School of Engineering—Electrical & Electronic Engineering, UCC, Cork, Ireland.
Li, et al., "Short-range ultrasonic communications in air using quadrature modulation," Journal, Oct. 30, 2009, pp. 2060-2072, IEEE Transactions on Ultrasonics, Ferroelectrics, and Frequency Control, vol. 56, No. 10, IEEE.
Salamon, "AI Detects Polyps Better Than Colonoscopists" Online Article, Jun. 3, 2018, Medscape Medical News, Digestive Disease Week (DDW) 2018: Presentation 133.
Misawa, et al. "Artificial Intelligence-Assisted Polyp Detection for Colonoscopy: Initial Experience," Article, Jun. 2018, pp. 2027-2029, vol. 154, Issue 8, American Gastroenterolgy Association.
Dottorato, "Analysis and Design of the Rectangular Microstrip Patch Antennas for TM0n0 operating mode,"Article, Oct. 8, 2010, pp. 1-9, Microwave Journal.
Xie et al., Development of stereo vision and master-slave controller for a compact surgical robot system, 2015, IEEE, p. 403-407 (Year: 2015).
Sun et al., Innovative effector design for simulation training in robotic surgery, 2010, IEEE, p. 1755-1759 (Year: 2010).
Nabil Simaan et al., "Intelligent Surgical Robots with Situational Awareness: From Good to Great Surgeons", DOI: 10.1115/1.2015-Sep-6 external link, Sep. 2015 (Sep. 2015), p. 3-6, Retrieved from the Internet: URL:http://memagazineselect.asmedigitalcollection.asme.org/data/journals/meena/936888/me-2015-sep6.pdf XP055530863.
Nordlinger, Christopher, "The Internet of Things and the Operating Room of the Future," May 4, 2015, https://medium.com/@chrisnordlinger/the-internet-of-things-and-the-operating-room-of-the-future-8999a143d7b1, retrieved from the internet on Apr. 27, 2021, 9 pages.
Screen captures from YouTube video clip entitled "Four ways to use the Lego Brick Separator Tool," 2 pages, uploaded on May 29, 2014 by user "Sarah Lewis". Retrieved from internet: https://www.youtube.com/watch?v=ucKiRD6U1LU (Year: 2014).
Anonymous, "Internet of Things Powers Connected Surgical Device Infrastructure Case Study", Dec. 31, 2016 (Dec. 31, 2016), Retrieved from the Internet: URL:https://www.cognizant.com/services-resources/150110_IoT_connected_surgical_devices.pdf.
Roy D Cullum, "Handbook of Engineering Design", ISBN: 9780408005586, Jan. 1, 1988 (Jan. 1, 1988), XP055578597, ISBN: 9780408005586, 10-20, Chapter 6, p. 138, right-hand column, paragraph 3.
Draijer, Matthijs et al., "Review of laser speckle contrast techniques for visualizing tissue perfusion," Lasers in Medical Science, Springer-Verlag, LO, vol. 24, No. 4, Dec. 3, 2008, pp. 639-651.
Lalys, et al., "Automatic knowledge-based recognition of low-level tasks in ophthalmological procedures", Int J CARS, vol. 8, No. 1, pp. 1-49, Apr. 19, 2012.
Hu, Jinwen, Stimulations of adaptive temperature control with self-focused hyperthermia system for tumor treatment, Jan. 9, 2012, Ultrasonics 53, pp. 171-177, (Year: 2012).
Hussain et al., "A survey on resource allocation in high performance distributed computing systems", Parallel Computing, vol. 39, No. 11, pp. 709-736 (2013).
Anonymous: "Screwdriver—Wikipedia", en.wikipedia.org, Jun. 23, 2019, XP055725151, Retrieved from the Internet: URL:https://en.wikipedia.org/w/index.php?title=Screwdriver&oldid=903111203 [retrieved on Mar. 20, 2021].
Takahashi et al., "Automatic smoke evacuation in laparoscopic surgery: a simplified method for objective evaluation," Surgical Endoscopy, vol. 27, No. 8, pp. 2980-2987, Feb. 23, 2013.

* cited by examiner

| Sensor Signal | Proximity |
|---|---|
| R1 | D1 |
| R2 | D2 |
| R3 | D3 |
| . | . |
| . | . |
| . | . |
| Rn | Dn |

SURGICAL SYSTEM HAVING A SURGICAL INSTRUMENT CONTROLLED BASED ON COMPARISON OF SENSOR AND DATABASE DATA

CROSS-REFERENCE TO RELATED APPLICATIONS

The present application claims priority under 35 U.S.C. § 120 to U.S. patent application Ser. No. 16/676,652, titled METHOD OF COMPRESSING TISSUE WITHIN A STAPLING DEVICE AND SIMULTANEOUSLY DISPLAYING THE LOCATION OF THE TISSUE WITHIN THE JAWS, filed Nov. 7, 2019, now U.S. Patent Application Publication No. 2020/0178971, which claims priority under 35 U.S.C. § 120 to U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, filed Dec. 4, 2018, now U.S. Patent Application Publication No. 2019/0200981, which claims priority under 35 U.S.C. § 119(e) to U.S. Provisional Patent Application No. 62/773,778, titled METHOD FOR ADAPTIVE CONTROL SCHEMES FOR SURGICAL NETWORK CONTROL AND INTERACTION, filed Nov. 30, 2018, to U.S. Provisional Patent Application No. 62/773,728, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, filed Nov. 30, 2018, to U.S. Provisional Patent Application No. 62/773,741, titled METHOD FOR FACILITY DATA COLLECTION AND INTERPRETATION, filed Nov. 30, 2018, and to U.S. Provisional Patent Application No. 62/773,742, titled METHOD FOR CIRCULAR STAPLER CONTROL ALGORITHM ADJUSTMENT BASED ON SITUATIONAL AWARENESS, filed Nov. 30, 2018, the disclosure of each of which is herein incorporated by reference in its entirety.

The present application claims priority under 35 U.S.C. § 120 to U.S. patent application Ser. No. 16/676,652, titled METHOD OF COMPRESSING TISSUE WITHIN A STAPLING DEVICE AND SIMULTANEOUSLY DISPLAYING THE LOCATION OF THE TISSUE WITHIN THE JAWS, filed Nov. 7, 2019, now U.S. Patent Application Publication No. 2020/0178971, which claims priority under 35 U.S.C. § 120 to U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, filed Dec. 4, 2018, now U.S. Patent Application Publication No. 2019/0200981, which claims priority under 35 U.S.C. § 119(e) to U.S. Provisional Patent Application No. 62/750,529, titled METHOD FOR OPERATING A POWERED ARTICULATING MULTI-CLIP APPLIER, filed Oct. 25, 2018, to U.S. Provisional Patent Application No. 62/750,539, titled SURGICAL CLIP APPLIER, filed Oct. 25, 2018, and to U.S. Provisional Patent Application No. 62/750,555, titled SURGICAL CLIP APPLIER, filed Oct. 25, 2018, the disclosure of each of which is herein incorporated by reference in its entirety.

The present application claims priority under 35 U.S.C. § 120 to U.S. patent application Ser. No. 16/676,652, titled METHOD OF COMPRESSING TISSUE WITHIN A STAPLING DEVICE AND SIMULTANEOUSLY DISPLAYING THE LOCATION OF THE TISSUE WITHIN THE JAWS, filed Nov. 7, 2019, now U.S. Patent Application Publication No. 2020/0178971, which claims priority under 35 U.S.C. § 120 to U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, filed Dec. 4, 2018, now U.S. Patent Application Publication No. 2019/0200981, which also claims priority under 35 U.S.C. § 119(e) to U.S. Provisional Patent Application No. 62/729,183, titled CONTROL FOR A SURGICAL NETWORK OR SURGICAL NETWORK CONNECTED DEVICE THAT ADJUSTS ITS FUNCTION BASED ON A SENSED SITUATION OR USAGE, filed Sep. 10, 2018, to U.S. Provisional Patent Application No. 62/729,177, titled AUTOMATED DATA SCALING, ALIGNMENT, AND ORGANIZING BASED ON PREDEFINED PARAMETERS WITHIN A SURGICAL NETWORK BEFORE TRANSMISSION, filed Sep. 10, 2018, to U.S. Provisional Patent Application No. 62/729,176, titled INDIRECT COMMAND AND CONTROL OF A FIRST OPERATING ROOM SYSTEM THROUGH THE USE OF A SECOND OPERATING ROOM SYSTEM WITHIN A STERILE FIELD WHERE THE SECOND OPERATING ROOM SYSTEM HAS PRIMARY AND SECONDARY OPERATING MODES, filed Sep. 10, 2018, to U.S. Provisional Patent Application No. 62/729,185, titled POWERED STAPLING DEVICE THAT IS CAPABLE OF ADJUSTING FORCE, ADVANCEMENT SPEED, AND OVERALL STROKE OF CUTTING MEMBER OF THE DEVICE BASED ON SENSED PARAMETER OF FIRING OR CLAMPING, filed Sep. 10, 2018, to U.S. Provisional Patent Application No. 62/729,184, titled POWERED SURGICAL TOOL WITH A PREDEFINED ADJUSTABLE CONTROL ALGORITHM FOR CONTROLLING AT LEAST ONE END EFFECTOR PARAMETER AND A MEANS FOR LIMITING THE ADJUSTMENT, filed Sep. 10, 2018, to U.S. Provisional Patent Application No. 62/729,182, titled SENSING THE PATIENT POSITION AND CONTACT UTILIZING THE MONO-POLAR RETURN PAD ELECTRODE TO PROVIDE SITUATIONAL AWARENESS TO THE HUB, filed Sep. 10, 2018, to U.S. Provisional Patent Application No. 62/729,191, titled SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION, filed Sep. 10, 2018, to U.S. Provisional Patent Application No. 62/729,195, titled ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION, filed Sep. 10, 2018, and to U.S. Provisional Patent Application No. 62/729,186, titled WIRELESS PAIRING OF A SURGICAL DEVICE WITH ANOTHER DEVICE WITHIN A STERILE SURGICAL FIELD BASED ON THE USAGE AND SITUATIONAL AWARENESS OF DEVICES, filed Sep. 10, 2018, the disclosure of each of which is herein incorporated by reference in its entirety.

The present application claims priority under 35 U.S.C. § 120 to U.S. patent application Ser. No. 16/676,652, titled METHOD OF COMPRESSING TISSUE WITHIN A STAPLING DEVICE AND SIMULTANEOUSLY DISPLAYING THE LOCATION OF THE TISSUE WITHIN THE JAWS, filed Nov. 7, 2019, now U.S. Patent Application Publication No. 2020/0178971, which claims priority under 35 U.S.C. § 120 to U.S. patent application Ser. No. 16/209,423, titled METHOD OF COMPRESSING TISSUE WITHIN A STAPLING DEVICE AND SIMULTANE- OUSLY DISPLAYING THE LOCATION OF THE TISSUE WITHIN THE JAWS, filed Dec. 4, 2018, now U.S. Patent Application Publication No. 2019/0200981, which also claims priority under 35 U.S.C. § 119(e) to U.S. Provisional Patent Application No. 62/721,995, titled CONTROLLING AN ULTRASONIC SURGICAL INSTRUMENT ACCORDING TO TISSUE LOCATION, filed Aug. 23, 2018, to U.S. Provisional Patent Application No. 62/721,998, titled SITUATIONAL AWARENESS OF ELECTROSURGICAL SYSTEMS, filed Aug. 23, 2018, to U.S. Provisional Patent Application No. 62/721,999, titled INTERRUPTION OF ENERGY DUE TO INADVERTENT CAPACITIVE COUPLING, filed Aug. 23, 2018, to U.S. Provisional Patent Application No. 62/721,994, titled BIPOLAR COMBINATION DEVICE THAT AUTOMATICALLY ADJUSTS PRESSURE BASED ON ENERGY MODALITY, filed Aug. 23, 2018, and to U.S. Provisional Patent Application No. 62/721,996, titled RADIO FREQUENCY ENERGY DEVICE FOR DELIVERING COMBINED ELECTRICAL SIGNALS, filed Aug. 23, 2018, the disclosure of each of which is herein incorporated by reference in its entirety.

The present application claims priority under 35 U.S.C. § 120 to U.S. patent application Ser. No. 16/676,652, titled METHOD OF COMPRESSING TISSUE WITHIN A STAPLING DEVICE AND SIMULTANEOUSLY DISPLAYING THE LOCATION OF THE TISSUE WITHIN THE JAWS, filed Nov. 7, 2019, now U.S. Patent Application Publication No. 2020/0178971, which claims priority under 35 U.S.C. § 120 to U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, filed Dec. 4, 2018, now U.S. Patent Application Publication No. 2019/0200981, which also claims priority under 35 U.S.C. § 119(e) to U.S. Provisional Patent Application No. 62/692,747, titled SMART ACTIVATION OF AN ENERGY DEVICE BY ANOTHER DEVICE, filed on Jun. 30, 2018, to U.S. Provisional Patent Application No. 62/692,748, titled SMART ENERGY ARCHITECTURE, filed on Jun. 30, 2018, and to U.S. Provisional Patent Application No. 62/692,768, titled SMART ENERGY DEVICES, filed on Jun. 30, 2018, the disclosure of each of which is herein incorporated by reference in its entirety.

The present application claims priority under 35 U.S.C. § 120 to U.S. patent application Ser. No. 16/676,652, titled METHOD OF COMPRESSING TISSUE WITHIN A STAPLING DEVICE AND SIMULTANEOUSLY DISPLAYING THE LOCATION OF THE TISSUE WITHIN THE JAWS, filed Nov. 7, 2019, now U.S. Patent Application Publication No. 2020/0178971, which claims priority under 35 U.S.C. § 120 to U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, filed Dec. 4, 2018, now U.S. Patent Application Publication No. 2019/0200981, which also claims priority under 35 U.S.C. § 119(e) to U.S. Provisional Patent Application No. 62/691,228, titled METHOD OF USING REINFORCED FLEX CIRCUITS WITH MULTIPLE SENSORS WITH ELECTROSURGICAL DEVICES, filed Jun. 28, 2018, to U.S. Provisional Patent Application No. 62/691,227, titled CONTROLLING A SURGICAL INSTRUMENT ACCORDING TO SENSED CLOSURE PARAMETERS, filed Jun. 28, 2018, to U.S. Provisional Patent Application No. 62/691,230, titled SURGICAL INSTRUMENT HAVING A FLEXIBLE ELECTRODE, filed Jun. 28, 2018, to U.S. Provisional Patent Application No. 62/691,219, titled SURGICAL EVACUATION SENSING AND MOTOR CONTROL, filed Jun. 28, 2018, to U.S. Provisional Patent Application No. 62/691,257, titled COMMUNICATION OF SMOKE EVACUATION SYSTEM PARAMETERS TO HUB OR CLOUD IN SMOKE EVACUATION MODULE FOR INTERACTIVE SURGICAL PLATFORM, filed Jun. 28, 2018, to U.S. Provisional Patent Application No. 62/691,262, titled SURGICAL EVACUATION SYSTEM WITH A COMMUNICATION CIRCUIT FOR COMMUNICATION BETWEEN A FILTER AND A SMOKE EVACUATION DEVICE, filed Jun. 28, 2018, and to U.S. Provisional Patent Application No. 62/691,251, titled DUAL IN-SERIES LARGE AND SMALL DROPLET FILTERS, filed Jun. 28, 2018, the disclosure of each of which is herein incorporated by reference in its entirety.

The present application claims priority under 35 U.S.C. § 120 to U.S. patent application Ser. No. 16/676,652, titled METHOD OF COMPRESSING TISSUE WITHIN A STAPLING DEVICE AND SIMULTANEOUSLY DISPLAYING THE LOCATION OF THE TISSUE WITHIN THE JAWS, filed Nov. 7, 2019, now U.S. Patent Application Publication No. 2020/0178971, which claims priority under 35 U.S.C. § 120 to U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, filed Dec. 4, 2018, now U.S. Patent Application Publication No. 2019/0200981, which claims priority under 35 U.S.C. § 119(e) to U.S. Provisional Patent Application No. 62/665,129, titled SURGICAL SUTURING SYSTEMS, filed May 1, 2018, to U.S. Provisional Patent Application No. 62/665,139, titled SURGICAL INSTRUMENTS COMPRISING CONTROL SYSTEMS, filed May 1, 2018, to U.S. Provisional Patent Application No. 62/665,177, titled SURGICAL INSTRUMENTS COMPRISING HANDLE ARRANGEMENTS, filed May 1, 2018, to U.S. Provisional Patent Application No. 62/665,128, titled MODULAR SURGICAL INSTRUMENTS, filed May 1, 2018, to U.S. Provisional Patent Application No. 62/665,192, titled SURGICAL DISSECTORS, filed May 1, 2018, and to U.S. Provisional Patent Application No. 62/665,134, titled SURGICAL CLIP APPLIER, filed May 1, 2018, the disclosure of each of which is herein incorporated by reference in its entirety.

The present application claims priority under 35 U.S.C. § 120 to U.S. patent application Ser. No. 16/676,652, titled METHOD OF COMPRESSING TISSUE WITHIN A STAPLING DEVICE AND SIMULTANEOUSLY DISPLAYING THE LOCATION OF THE TISSUE WITHIN THE JAWS, filed Nov. 7, 2019, now U.S. Patent Application Publication No. 2020/0178971, which claims priority under 35 U.S.C. § 120 to U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, filed Dec. 4, 2018, now U.S. Patent Application Publication No. 2019/0200981, which also claims priority under 35 U.S.C. § 119(e) to U.S. Provisional Patent Application No. 62/659,900, titled METHOD OF HUB COMMUNICATION, filed on Apr. 19, 2018, the disclosure of which is herein incorporated by reference in its entirety.

The present application claims priority under 35 U.S.C. § 120 to U.S. patent application Ser. No. 16/676,652, titled METHOD OF COMPRESSING TISSUE WITHIN A STAPLING DEVICE AND SIMULTANEOUSLY DISPLAYING THE LOCATION OF THE TISSUE WITHIN THE JAWS, filed Nov. 7, 2019, now U.S. Patent Application Publication No. 2020/0178971, which claims priority under 35 U.S.C. § 120 to U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, filed Dec. 4, 2018, now U.S. Patent Application Publication No. 2019/0200981, which also claims priority under 35 U.S.C. § 119(e) to U.S. Provisional Patent Application No. 62/650,898, filed on Mar. 30, 2018, titled CAPACITIVE COUPLED RETURN PATH PAD WITH SEPARABLE ARRAY ELEMENTS, to U.S. Provisional Patent Application No. 62/650,887, titled SURGICAL SYSTEMS WITH OPTIMIZED SENSING CAPABILITIES, filed Mar. 30, 2018, to U.S. Provisional Patent Application No. 62/650,882, titled SMOKE EVACUATION MODULE FOR INTERACTIVE SURGICAL PLATFORM, filed Mar. 30, 2018, and to U.S. Provisional Patent Application No. 62/650,877, titled SURGICAL SMOKE EVACUATION SENSING AND CONTROLS, filed Mar. 30, 2018, the disclosure of each of which is herein incorporated by reference in its entirety.

The present application claims priority under 35 U.S.C. § 120 to U.S. patent application Ser. No. 16/676,652, titled METHOD OF COMPRESSING TISSUE WITHIN A STAPLING DEVICE AND SIMULTANEOUSLY DISPLAYING THE LOCATION OF THE TISSUE WITHIN THE JAWS, filed Nov. 7, 2019, now U.S. Patent Application Publication No. 2020/0178971, which claims priority under 35 U.S.C. § 120 to U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, filed Dec. 4, 2018, now U.S. Patent Application Publication No. 2019/0200981, which also claims the benefit of priority under 35 U.S.C. § 119(e) to U.S. Provisional Patent Application No. 62/649,302, titled INTERACTIVE SURGICAL SYSTEMS WITH ENCRYPTED COMMUNICATION CAPABILITIES, filed Mar. 28, 2018, to U.S. Provisional Patent Application No. 62/649,294, titled DATA STRIPPING METHOD TO INTERROGATE PATIENT RECORDS AND CREATE ANONYMIZED RECORD, filed Mar. 28, 2018, to U.S. Provisional Patent Application No. 62/649,300, titled SURGICAL HUB SITUATIONAL AWARENESS, filed Mar. 28, 2018, to U.S. Provisional Patent Application No. 62/649,309, titled SURGICAL HUB SPATIAL AWARENESS TO DETERMINE DEVICES IN OPERATING THEATER, filed Mar. 28, 2018, to U.S. Provisional Patent Application No. 62/649,310, titled COMPUTER IMPLEMENTED INTERACTIVE SURGICAL SYSTEMS, filed Mar. 28, 2018, to U.S. Provisional Patent Application No. 62/649,291, titled USE OF LASER LIGHT AND RED-GREEN-BLUE COLORATION TO DETERMINE PROPERTIES OF BACK SCATTERED LIGHT, filed Mar. 28, 2018, to U.S. Provisional Patent Application No. 62/649,296, titled ADAPTIVE CONTROL PROGRAM UPDATES FOR SURGICAL DEVICES, filed Mar. 28, 2018, to U.S. Provisional Patent Application No. 62/649,333, titled CLOUD-BASED MEDICAL ANALYTICS FOR CUSTOMIZATION AND RECOMMENDATIONS TO A USER, filed Mar. 28, 2018, to U.S. Provisional Patent Application No. 62/649,327, titled CLOUD-BASED MEDICAL ANALYTICS FOR SECURITY AND AUTHENTICATION TRENDS AND REACTIVE MEASURES, filed Mar. 28, 2018, to U.S. Provisional Patent Application No. 62/649,315, titled DATA HANDLING AND PRIORITIZATION IN A CLOUD ANALYTICS NETWORK, filed Mar. 28, 2018, to U.S. Provisional Patent Application No. 62/649,313, titled CLOUD INTERFACE FOR COUPLED SURGICAL DEVICES, filed Mar. 28, 2018, to U.S. Provisional Patent Application No. 62/649,320, titled DRIVE ARRANGEMENTS FOR ROBOT-ASSISTED SURGICAL PLATFORMS, filed Mar. 28, 2018, to U.S. Provisional Patent Application No. 62/649,307, titled AUTOMATIC TOOL ADJUSTMENTS FOR ROBOT-ASSISTED SURGICAL PLATFORMS, filed Mar. 28, 2018, and to U.S. Provisional Patent Application No. 62/649,323, titled SENSING ARRANGEMENTS FOR ROBOT-ASSISTED SURGICAL PLATFORMS, filed Mar. 28, 2018, the disclosure of each of which is herein incorporated by reference in its entirety.

The present application claims priority under 35 U.S.C. § 120 to U.S. patent application Ser. No. 16/676,652, titled METHOD OF COMPRESSING TISSUE WITHIN A STAPLING DEVICE AND SIMULTANEOUSLY DISPLAYING THE LOCATION OF THE TISSUE WITHIN THE JAWS, filed Nov. 7, 2019, now U.S. Patent Application Publication No. 2020/0178971, which claims priority under 35 U.S.C. § 120 to U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, filed Dec. 4, 2018, now U.S. Patent Application Publication No. 2019/0200981, which also claims the benefit of priority under 35 U.S.C. § 119(e) to U.S. Provisional Patent Application No. 62/611,341, titled INTERACTIVE SURGICAL PLATFORM, filed Dec. 28, 2017, to U.S. Provisional Patent Application No. 62/611,340, titled CLOUD-BASED MEDICAL ANALYTICS, filed Dec. 28, 2017, and to U.S. Provisional Patent Application No. 62/611,339, titled ROBOT ASSISTED SURGICAL PLATFORM, filed Dec. 28, 2017, the disclosure of each of which is herein incorporated by reference in its entirety.

BACKGROUND

The present disclosure relates to various surgical systems.

SUMMARY

In one aspect, a method of compressing tissue during a surgical procedure is provided. The method comprises: obtaining a surgical instrument comprising an end effector, wherein the end effector comprises a first jaw and a second jaw; establishing a communication pathway between the surgical instrument and a surgical hub; inserting the surgical instrument into a surgical site; compressing tissue between the first jaw and the second jaw; determining a location of the compressed tissue with respect to at least one of the first jaw and the second jaw; communicating the determined location of the compressed tissue to the surgical hub; and displaying the determined location of the compressed tissue on a visual feedback device.

In another aspect, a method of compressing tissue during a surgical procedure. The method comprises: inserting a surgical instrument comprising an end effector into a surgical site, wherein the end effector comprises a first jaw and a second jaw; compressing tissue between the first jaw and the second jaw; determining a location of the compressed tissue within a surgical site; communicating the determined location of the compressed tissue to a surgical hub; and displaying the determined location of the compressed tissue on a display.

In another aspect, a method of grasping tissue during a surgical procedure. The method comprises: obtaining a surgical instrument comprising an end effector, wherein the end effector comprises a first jaw and a second jaw; establishing a communication pathway between the surgical instrument and a surgical hub; grasping tissue between the first jaw and the second jaw; determining a location of the grasped tissue with respect to at least one of the first jaw and the second jaw; communicating the determined location of the grasped tissue to the surgical hub; and displaying the determined location of the grasped tissue on a visual feedback display.

FIGURES

The features of various aspects are set forthwith particularity in the appended claims. The various aspects, however, both as to organization and methods of operation, together with further objects and advantages thereof, may best be understood by reference to the following description, taken in conjunction with the accompanying drawings as follows.

Figure 35:
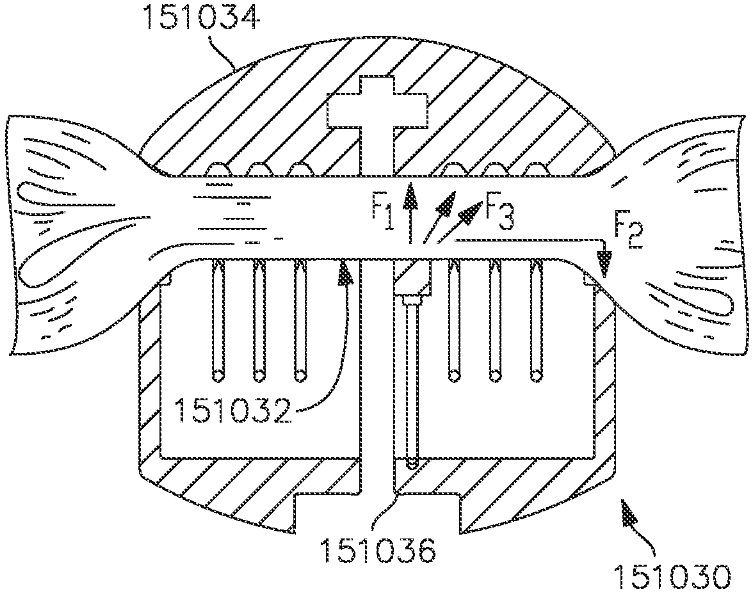

FIG. 35 also depicts example forces exerted by an end-effector of a medical device compressing tissue in accordance with one or more aspects of the present disclosure.

Figure 36:
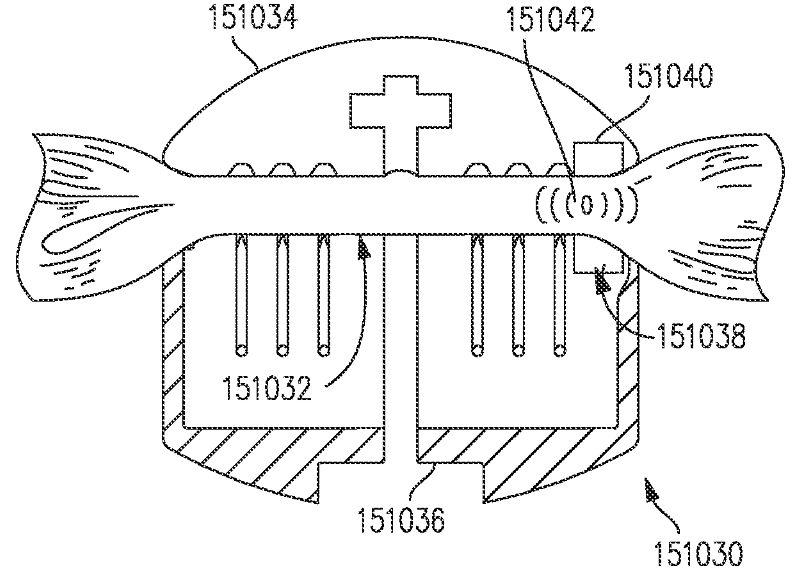

FIG. 36 depicts an example tissue compression sensor system in accordance with one or more aspects of the present disclosure.

Figure 37:
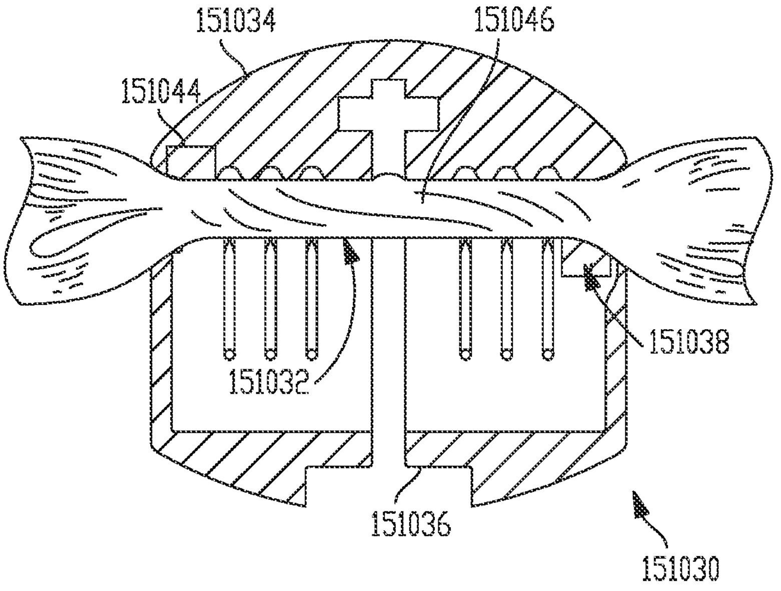

FIG. 37 also depicts an example tissue compression sensor system in accordance with one or more aspects of the present disclosure.

Figure 38:
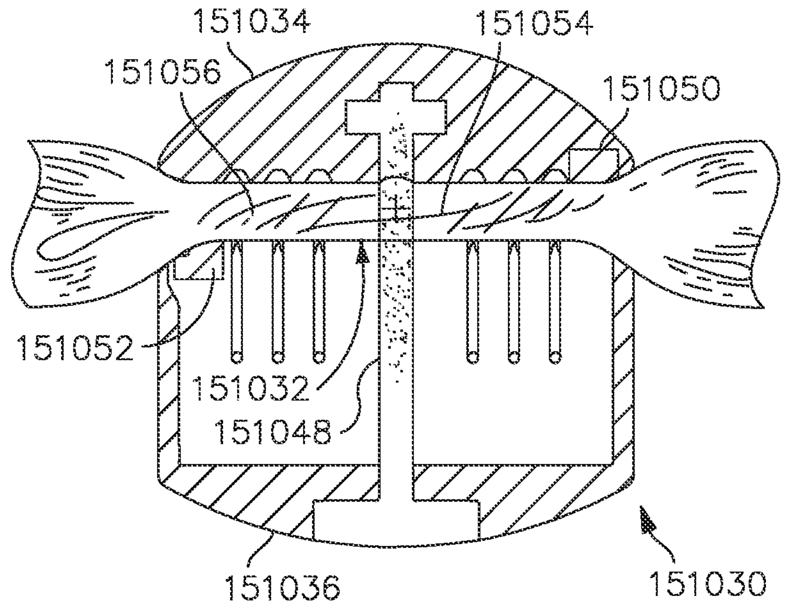

FIG. 38 also depicts an example tissue compression sensor system in accordance with one or more aspects of the present disclosure.

Figure 39:
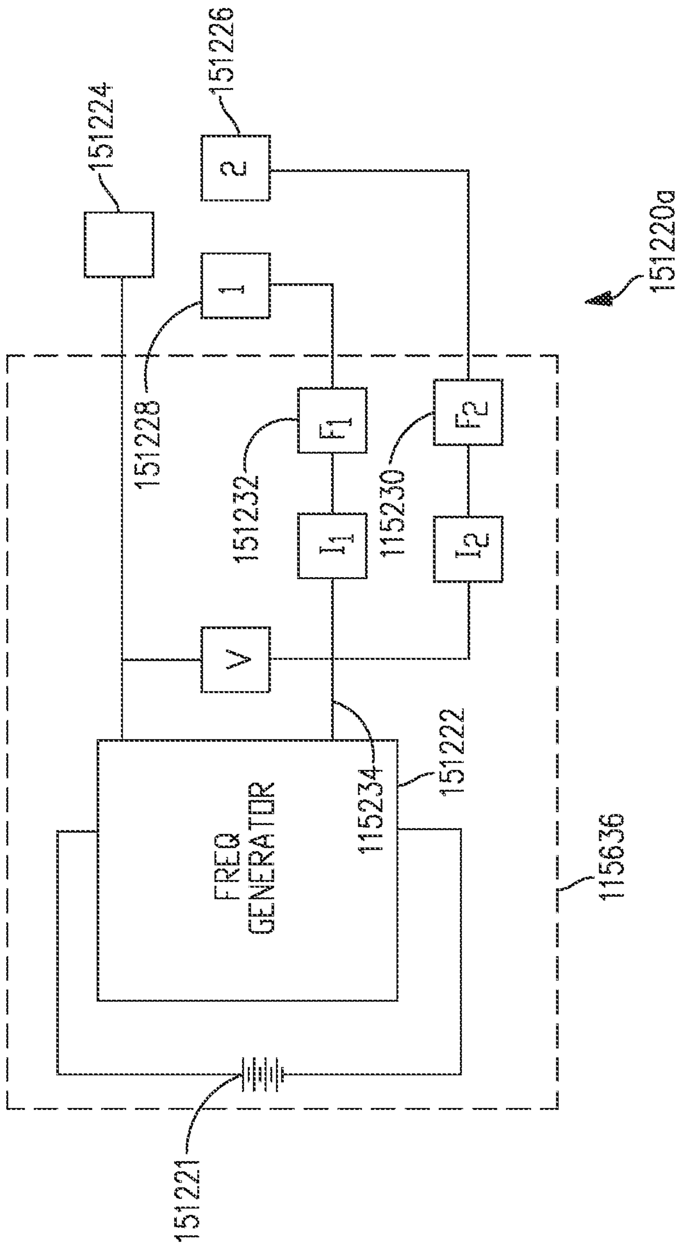

FIG. 39 is also an example circuit diagram in accordance with one or more aspects of the present disclosure.

Figure 40:
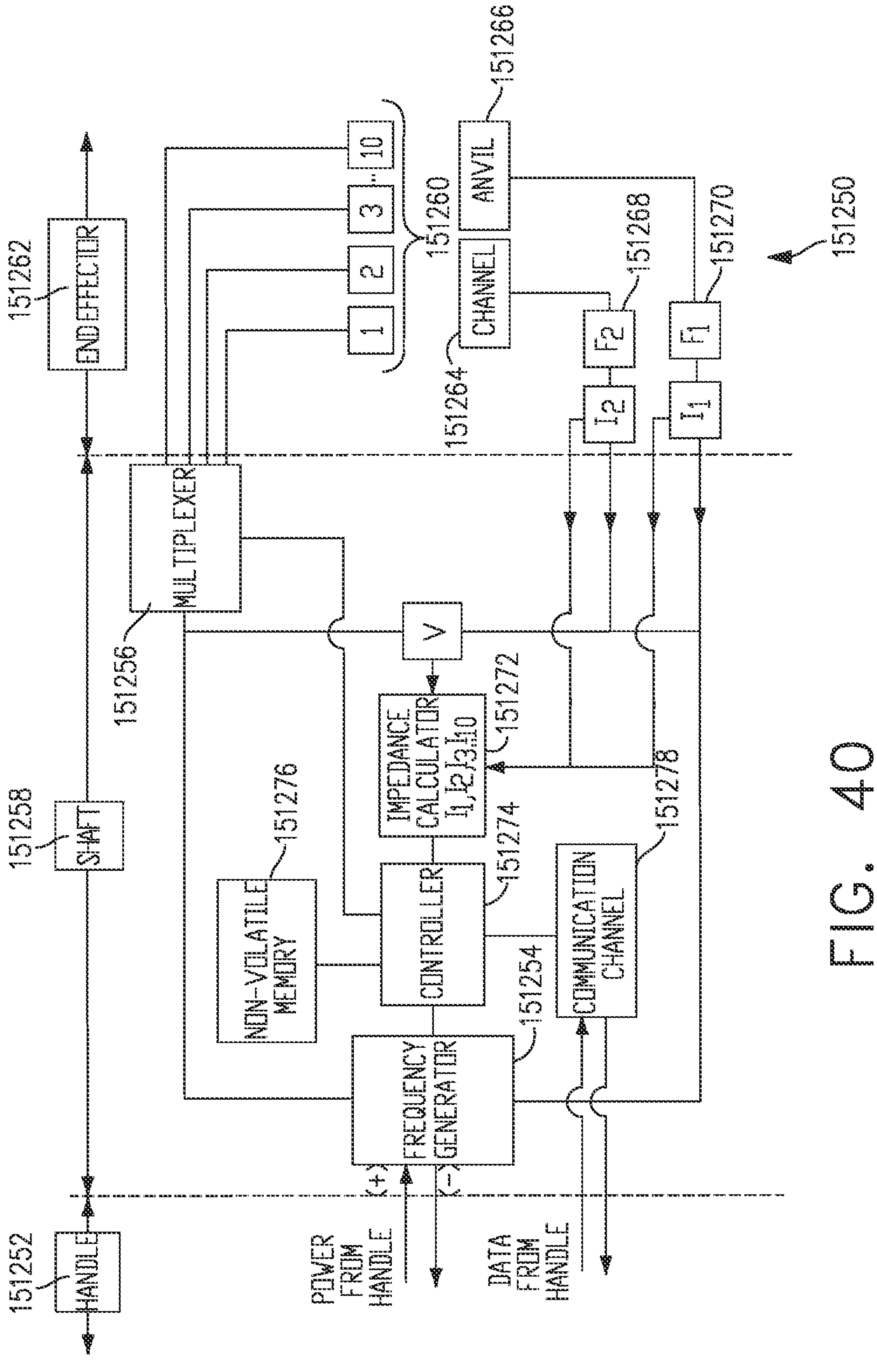

FIG. 40 is also an example circuit diagram in accordance with one or more aspects of the present disclosure.

Figure 41:
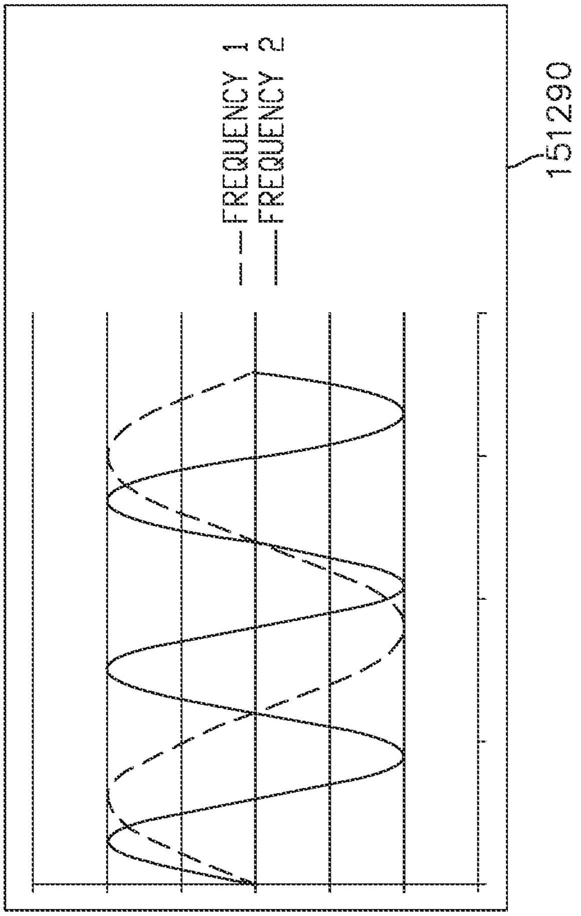

FIG. 41 is graph depicting an example frequency modulation in accordance with one or more aspects of the present disclosure.

Figure 42:
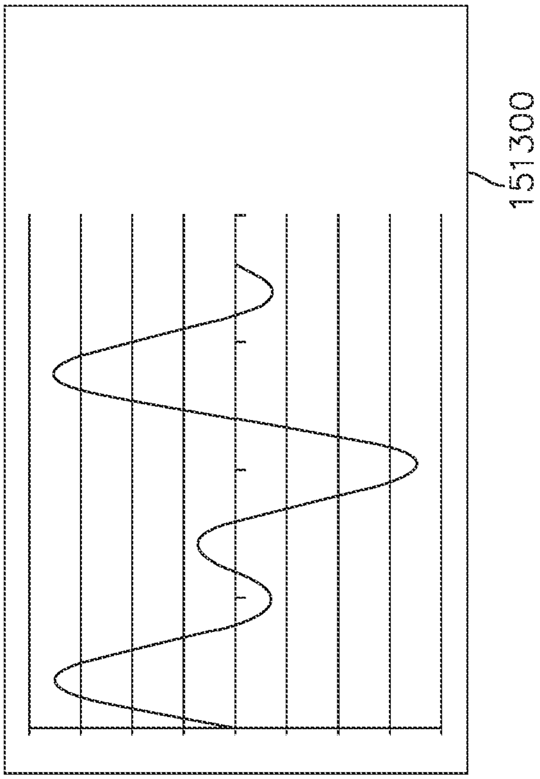

FIG. 42 is graph depicting a compound RF signal in accordance with one or more aspects of the present disclosure.

Figure 43:
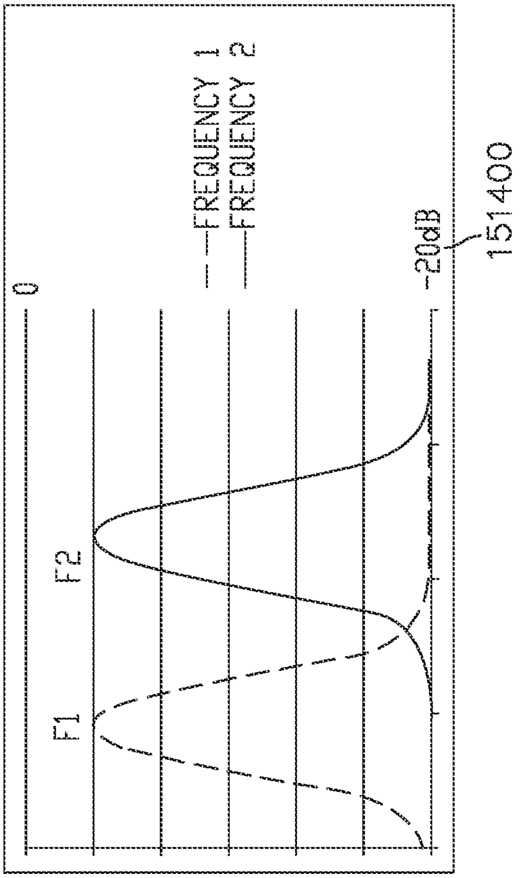

FIG. 43 is graph depicting filtered RF signals in accordance with one or more aspects of the present disclosure.

Figure 44:
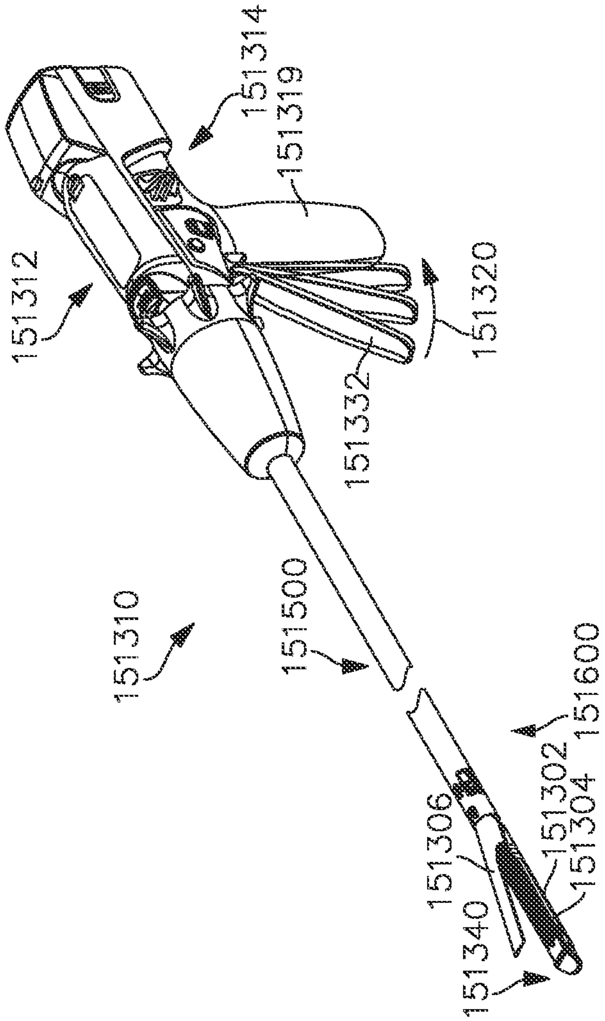

FIG. 44 is a perspective view of a surgical instrument with an articulable, interchangeable shaft.

Figure 45:
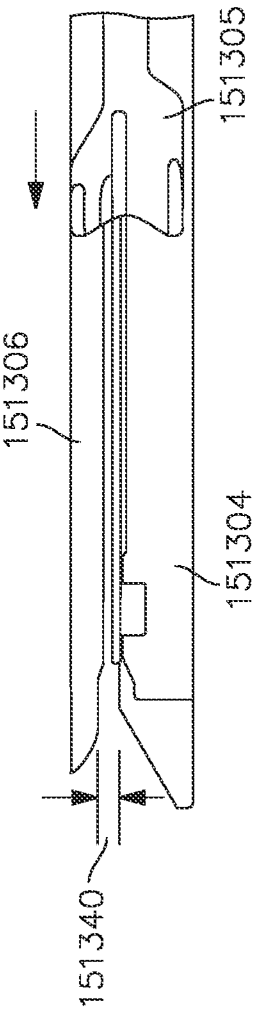

FIG. 45 is a side view of the tip of the surgical instrument.

Figure 48:
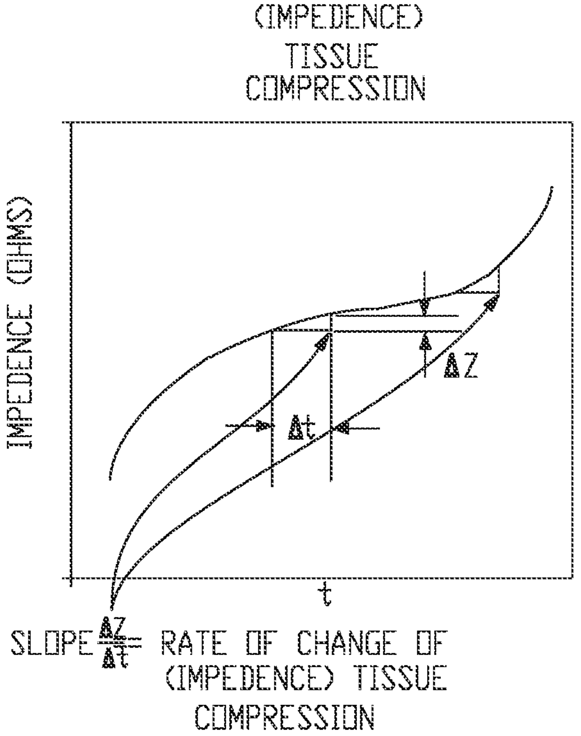
Figure 49:
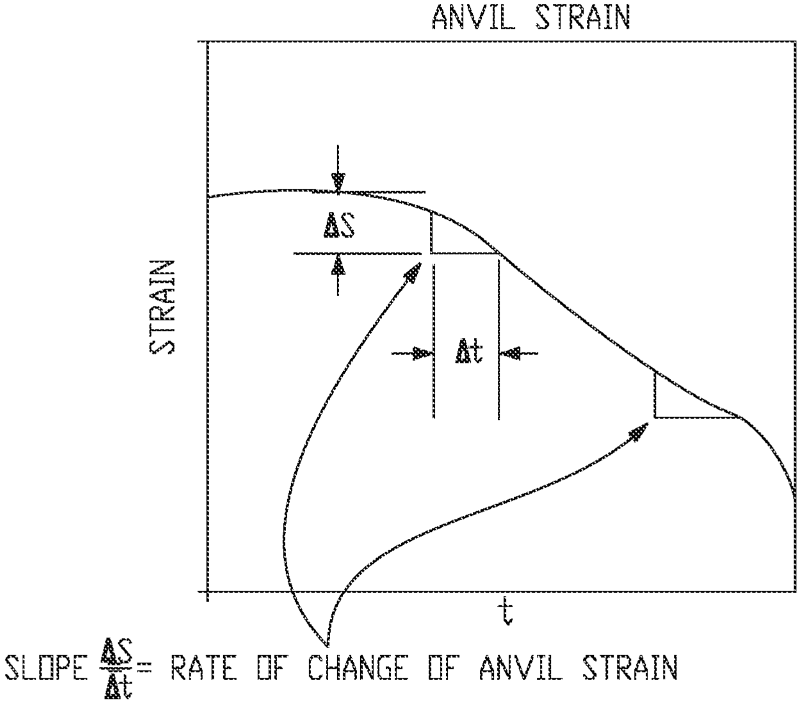
Figure 50:
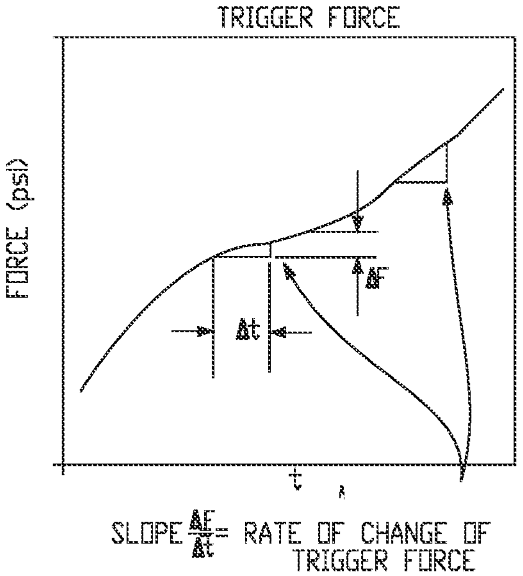

FIGS. 46 to 50 are graphs plotting gap size over time (FIG. 46), firing current over time (FIG. 47), tissue compression over time (FIG. 48), anvil strain over time (FIG. 49), and trigger force over time (FIG. 50).

Figure 51:
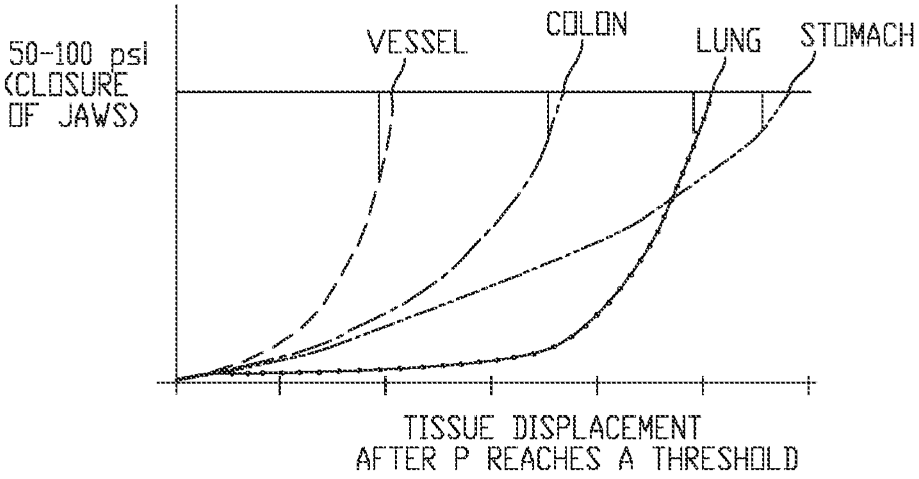

FIG. 51 is a graph plotting tissue displacement as a function of tissue compression for normal tissues.

Figure 52:
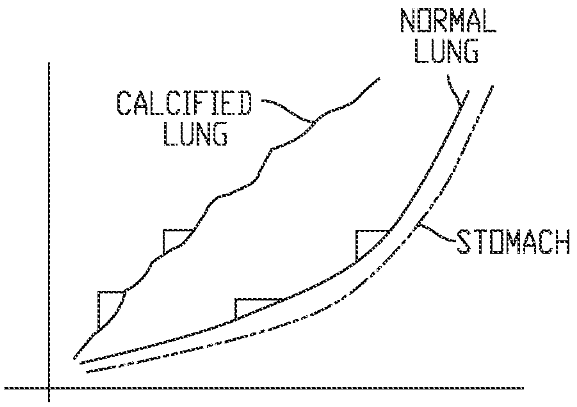

FIG. 52 is a graph plotting tissue displacement as a function of tissue compression to distinguish normal and diseased tissues.

Figure 53:
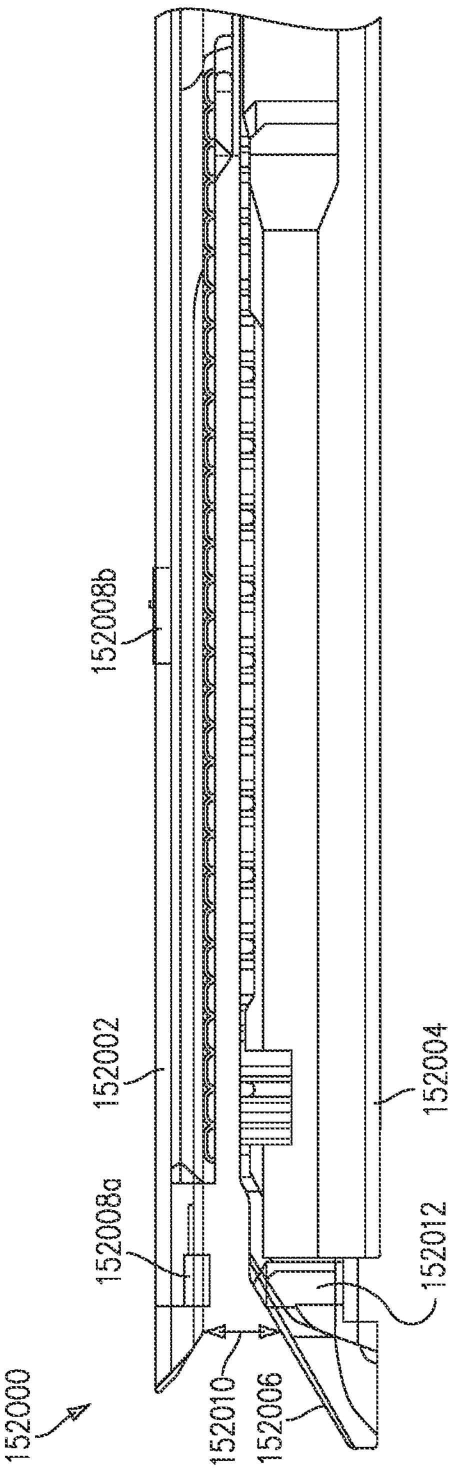

FIG. 53 illustrates one embodiment of an end effector comprising a first sensor and a second sensor.

Figure 54:
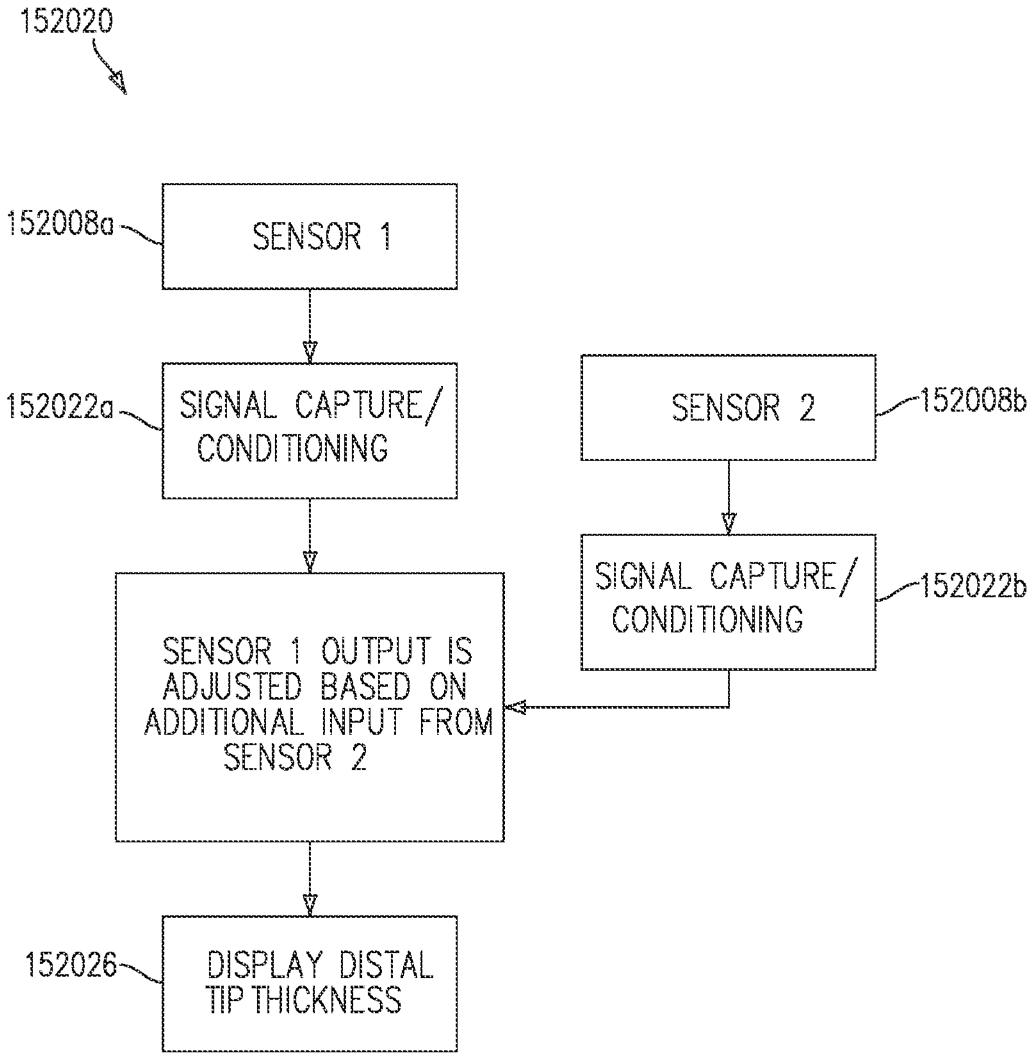

FIG. 54 is a logic diagram illustrating one embodiment of a process for adjusting the measurement of the first sensor based on input from the second sensor of the end effector illustrated in FIG. 53.

Figure 55:
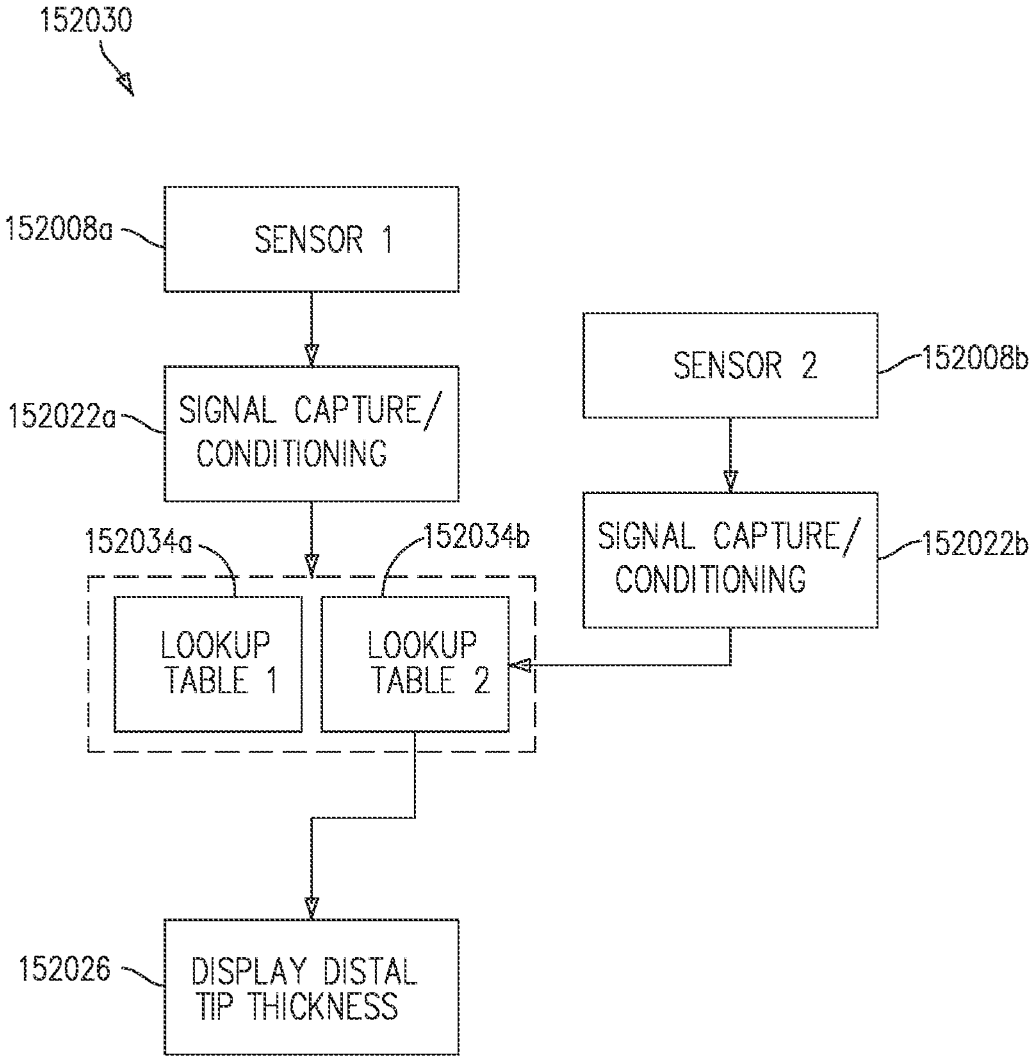

FIG. 55 is a logic diagram illustrating one embodiment of a process for determining a look-up table for a first sensor based on the input from a second sensor.

Figure 56:
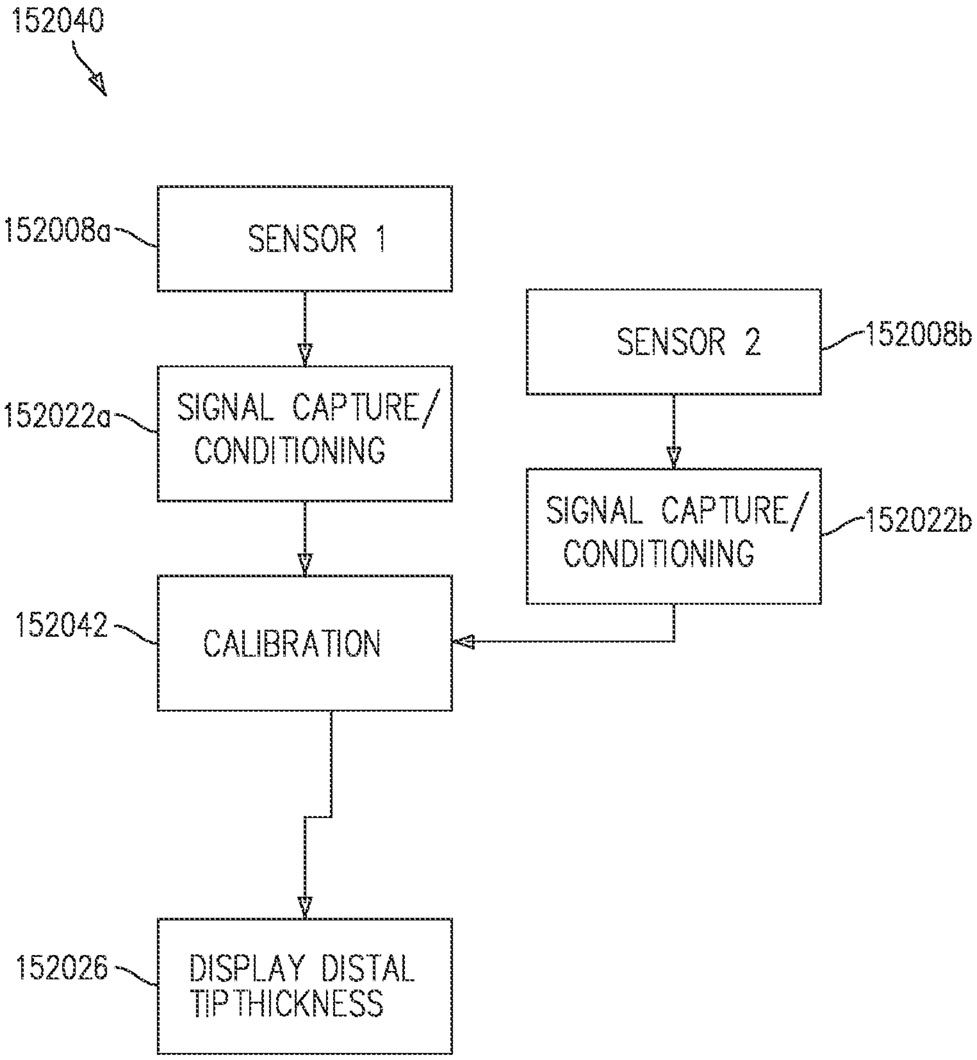

FIG. 56 is a logic diagram illustrating one embodiment of a process for calibrating a first sensor in response to an input from a second sensor.

Figure 57:
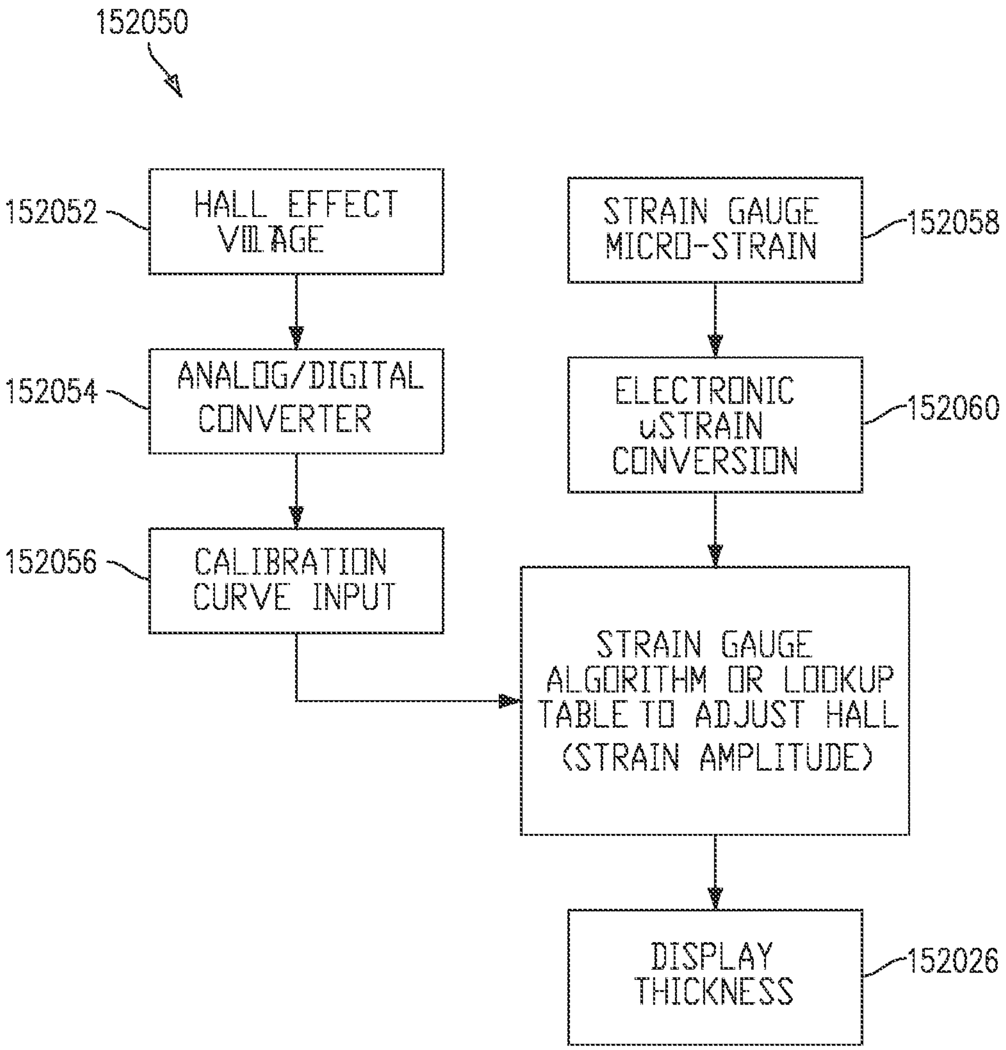

FIG. 57 is a logic diagram illustrating one embodiment of a process for determining and displaying the thickness of a tissue section clamped between an anvil and a staple cartridge of an end effector.

Figure 58:
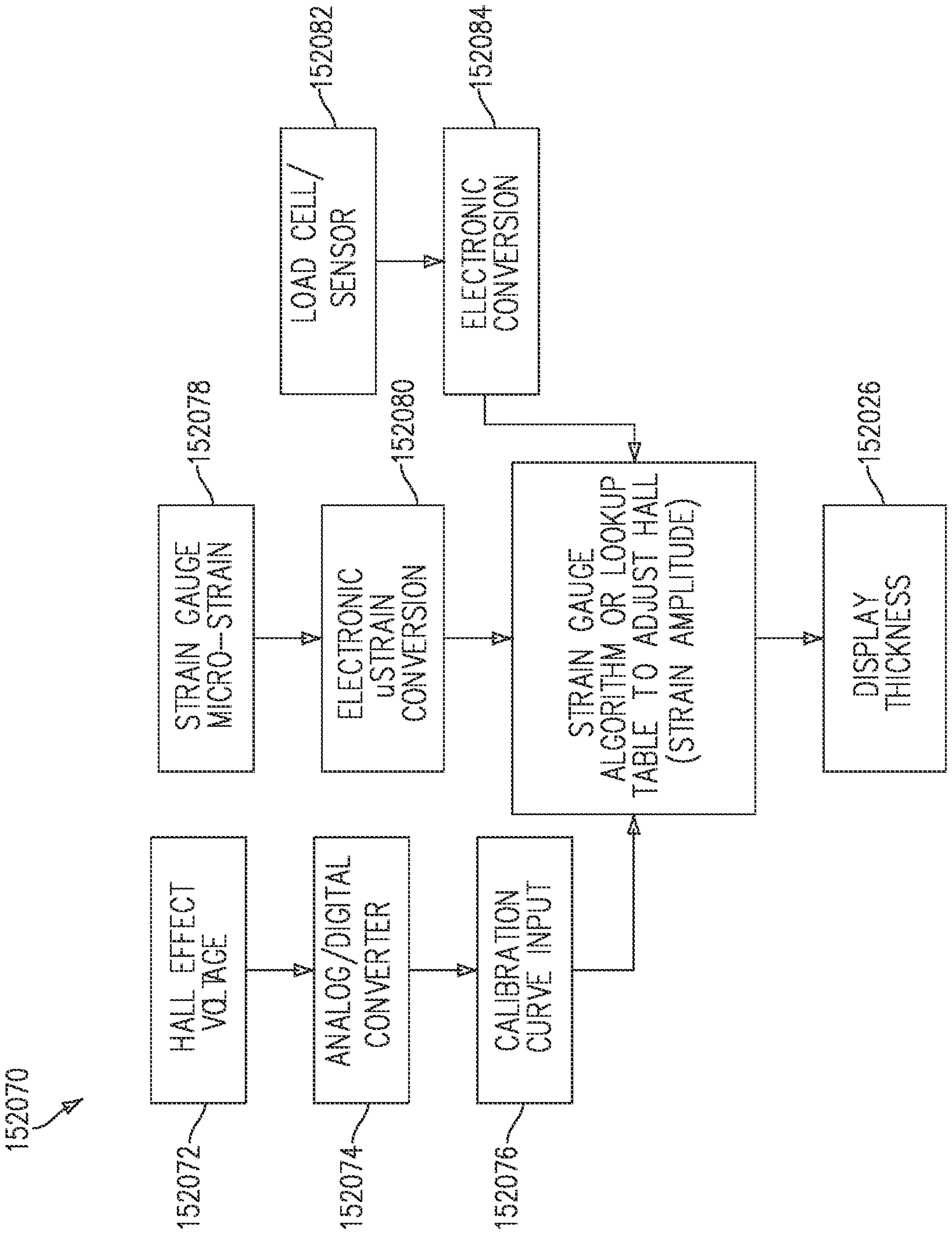

FIG. 58 is a logic diagram illustrating one embodiment of a process for determining and displaying the thickness of a tissue section clamped between the anvil and the staple cartridge of the end effector.

Figure 59:
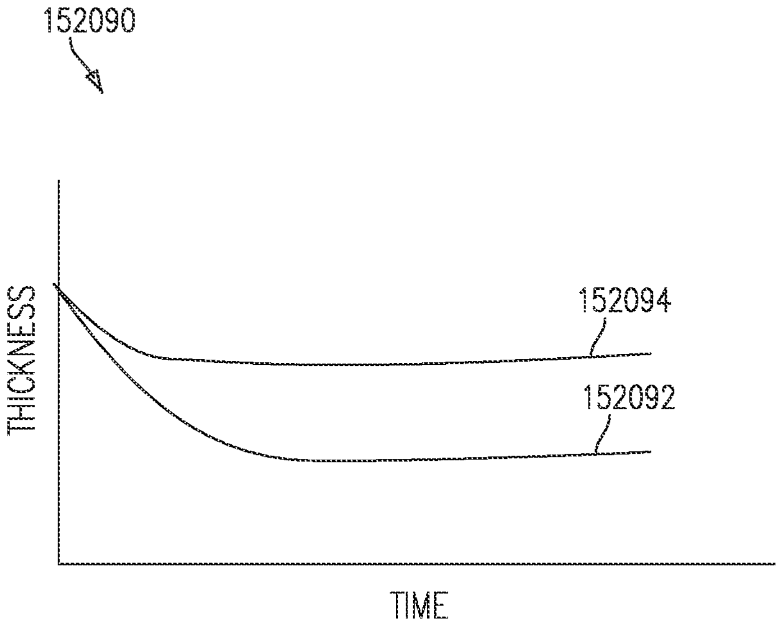

FIG. 59 is a graph illustrating an adjusted Hall effect thickness measurement compared to an unmodified Hall effect thickness measurement.

Figure 60:
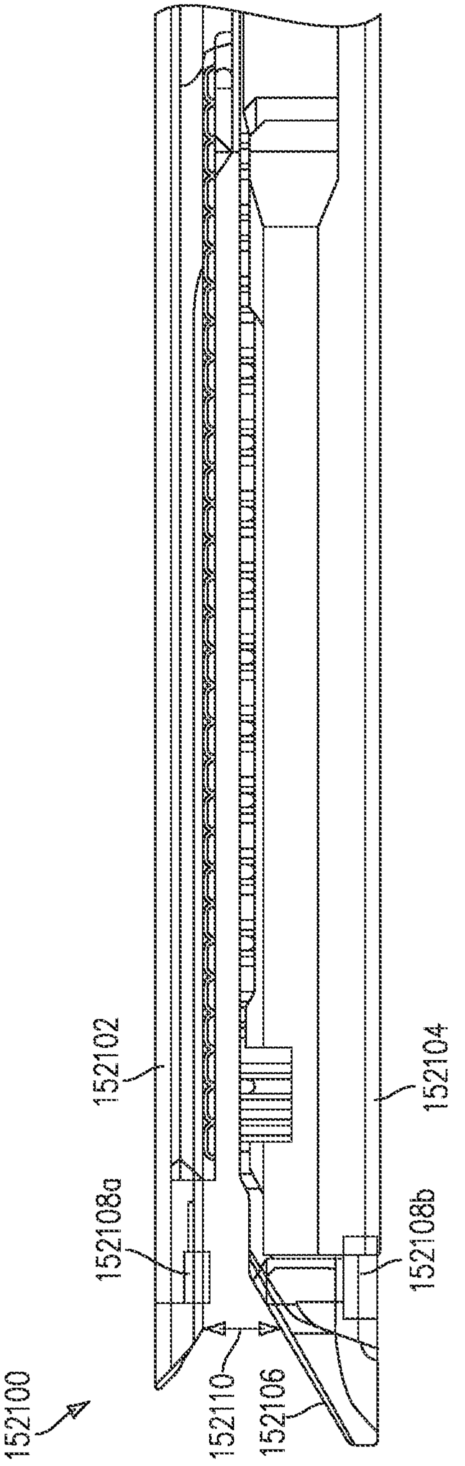

FIG. 60 illustrates one embodiment of an end effector comprising a first sensor and a second sensor.

Figure 61:
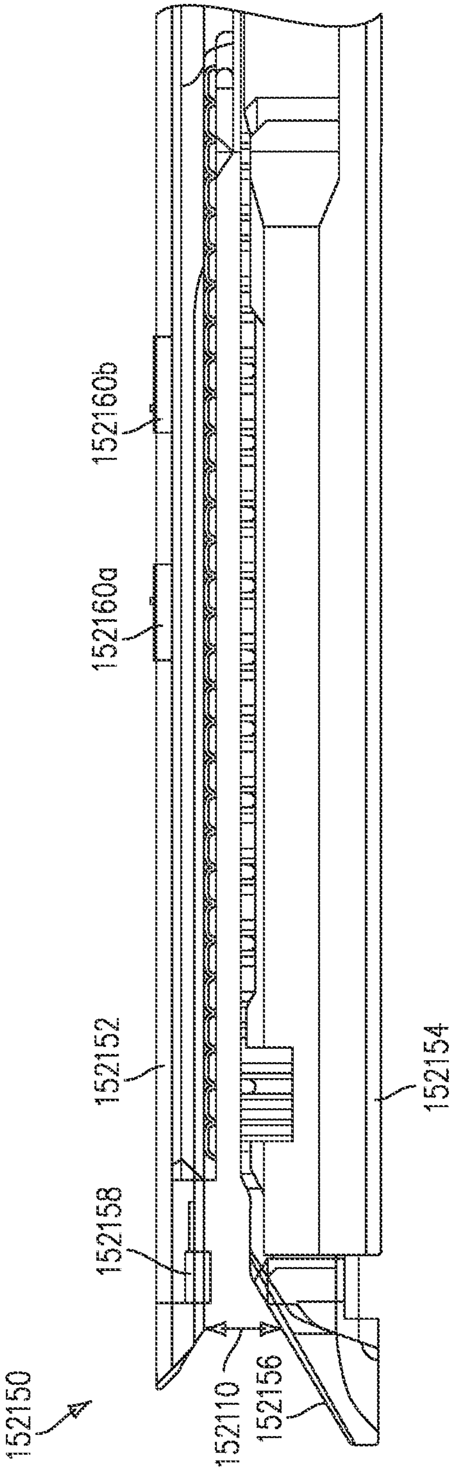

FIG. 61 illustrates one embodiment of an end effector comprising a first sensor and a plurality of second sensors.

Figure 62:
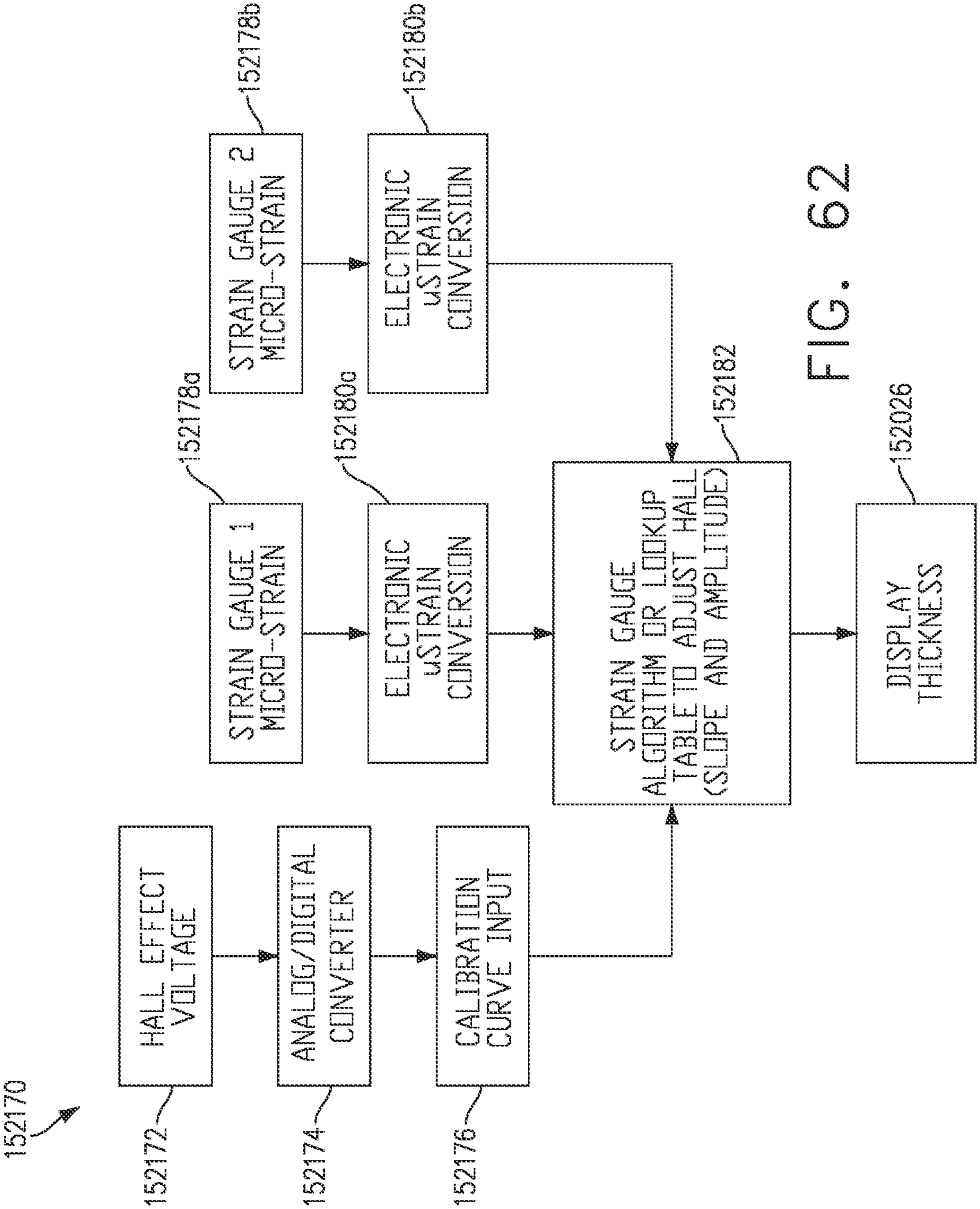

FIG. 62 is a logic diagram illustrating one embodiment of a process for adjusting a measurement of a first sensor in response to a plurality of secondary sensors.

Figure 63:
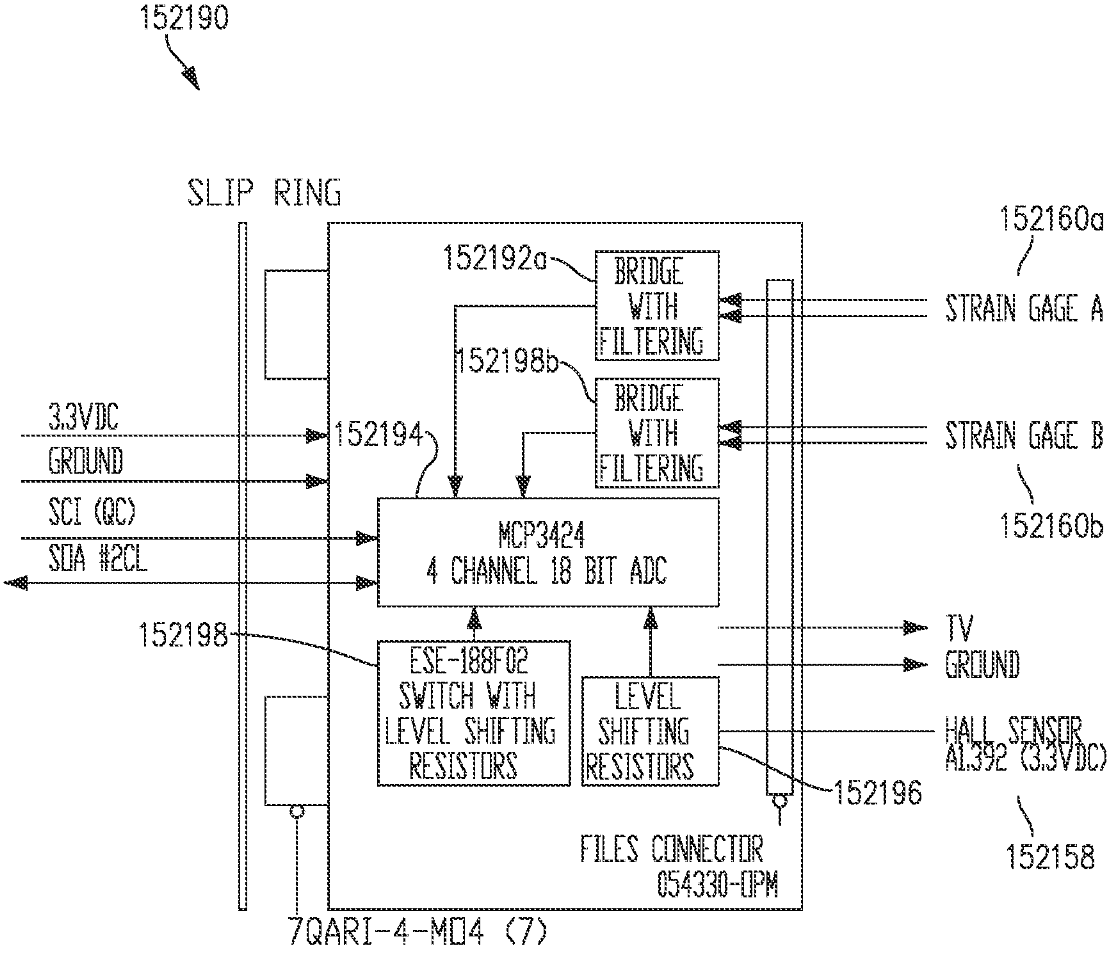

FIG. 63 illustrates one embodiment of a circuit configured to convert signals from a first sensor and a plurality of secondary sensors into digital signals receivable by a processor.

Figure 64:
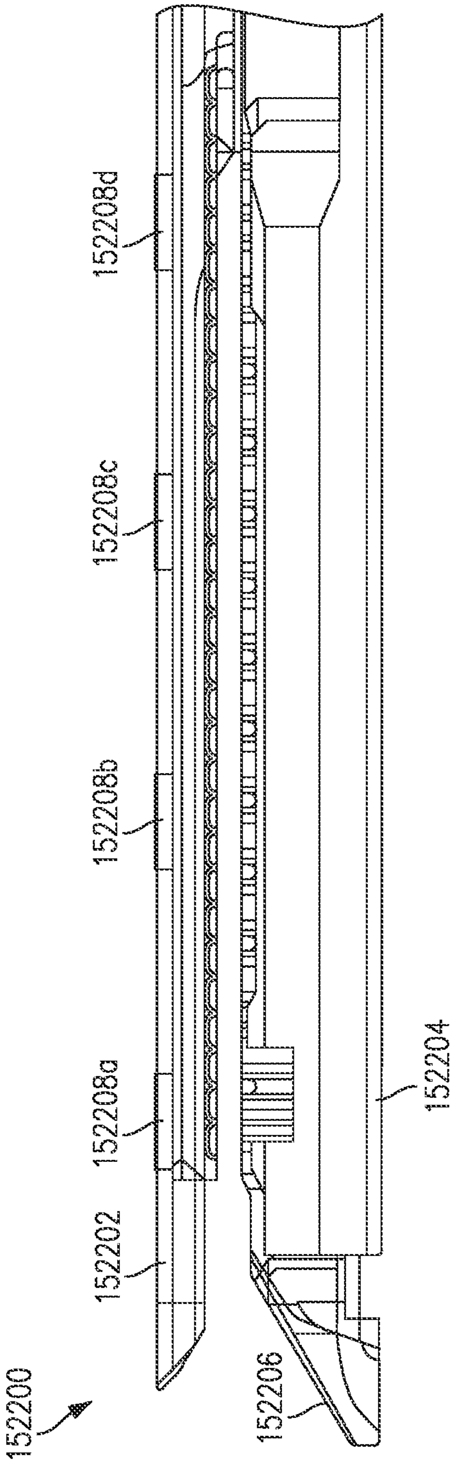

FIG. 64 illustrates one embodiment of an end effector comprising a plurality of sensors.

Figure 65:
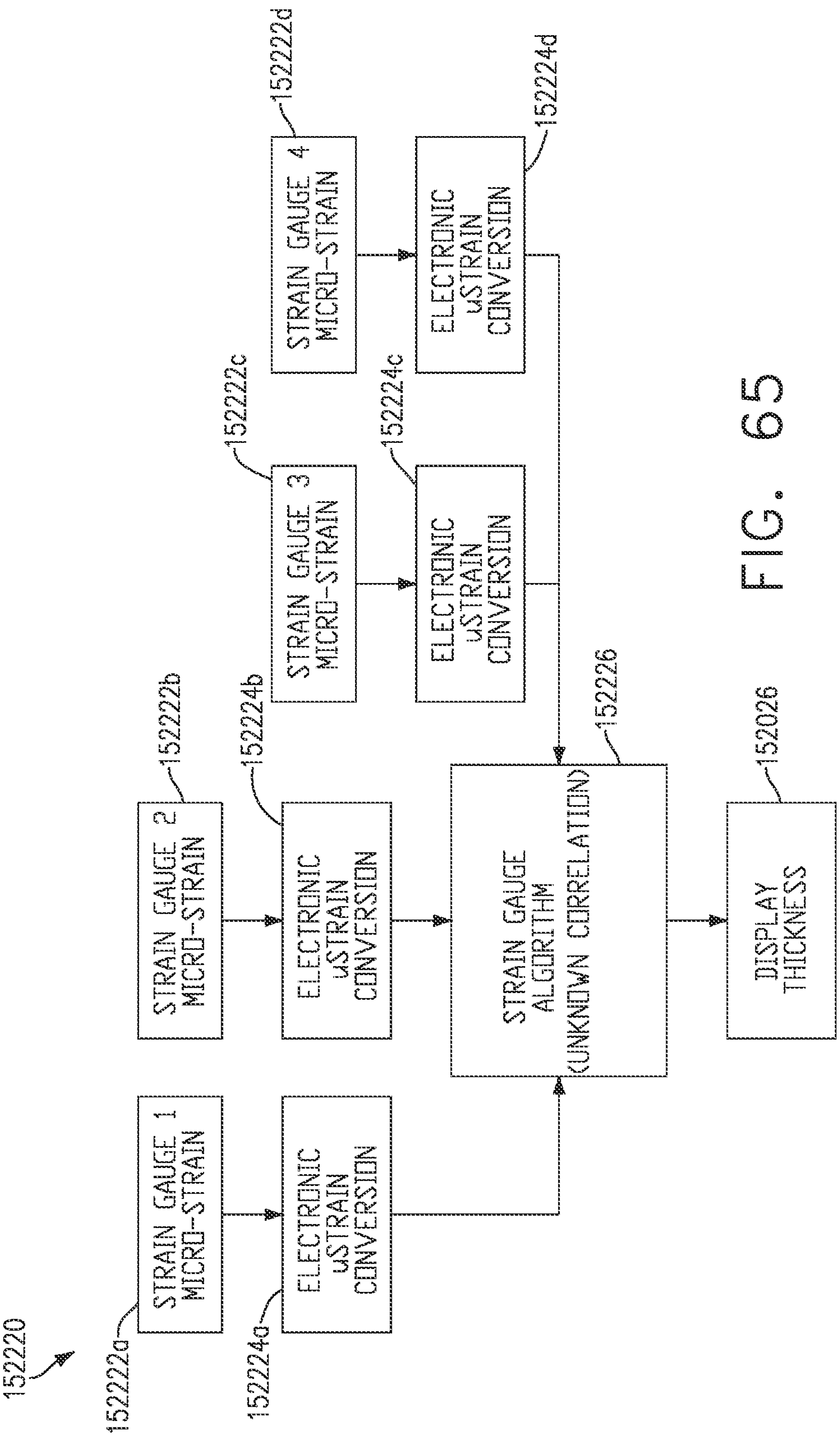

FIG. 65 is a logic diagram illustrating one embodiment of a process for determining one or more tissue properties based on a plurality of sensors.

Figure 66:
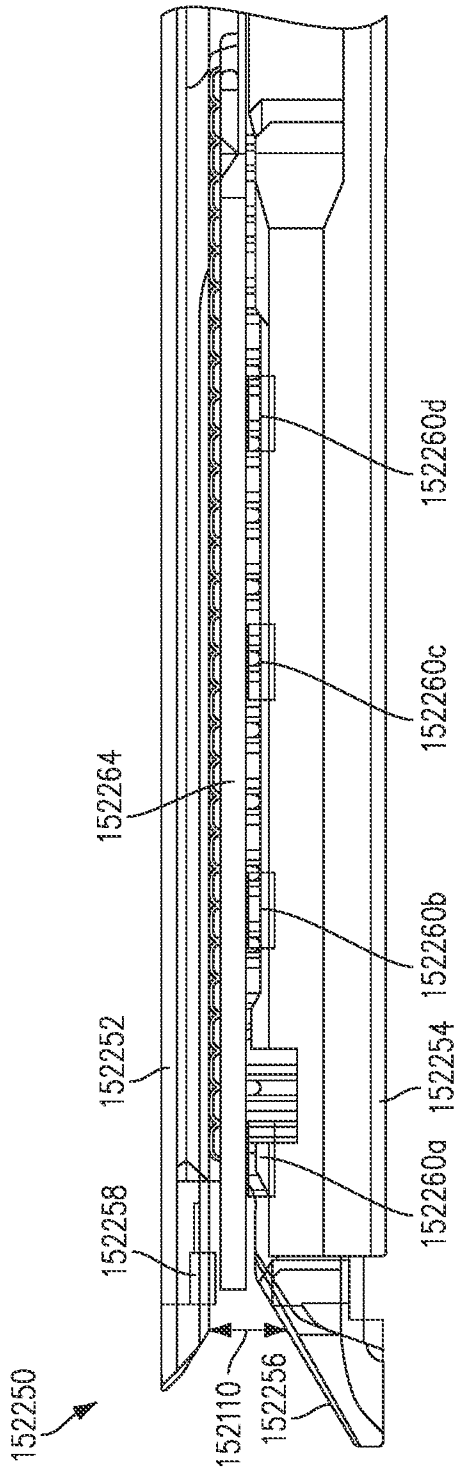

FIG. 66 illustrates one embodiment of an end effector comprising a plurality of sensors coupled to a second jaw member.

Figure 67:
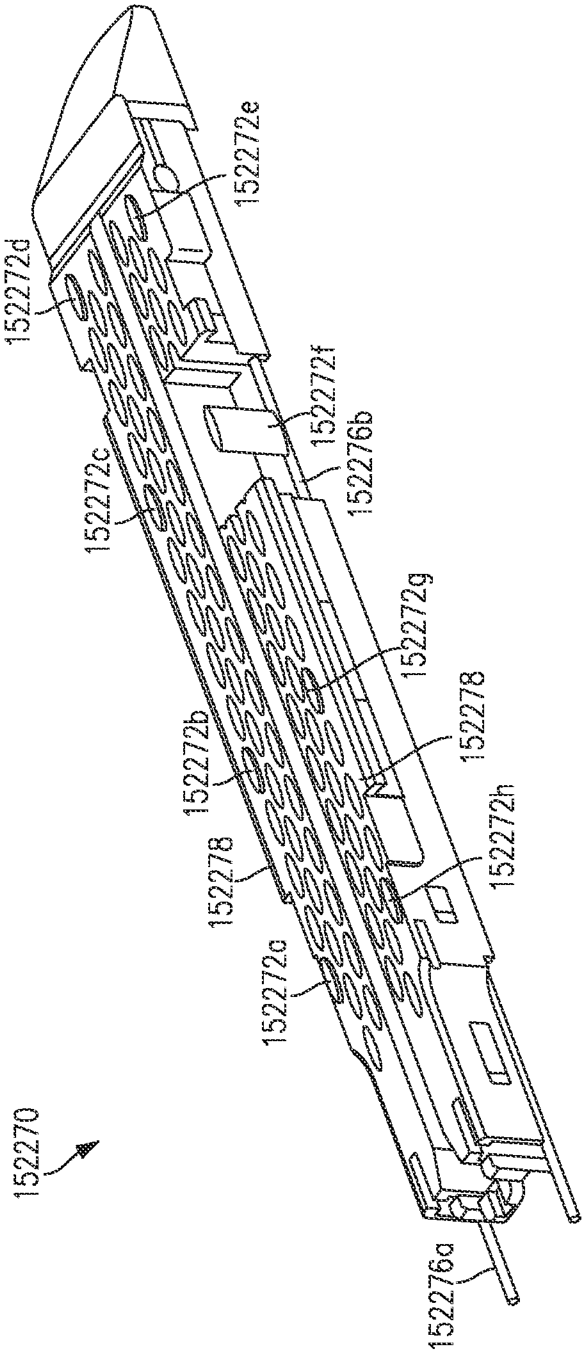

FIG. 67 illustrates one embodiment of a staple cartridge comprising a plurality of sensors formed integrally therein.

Figure 68:
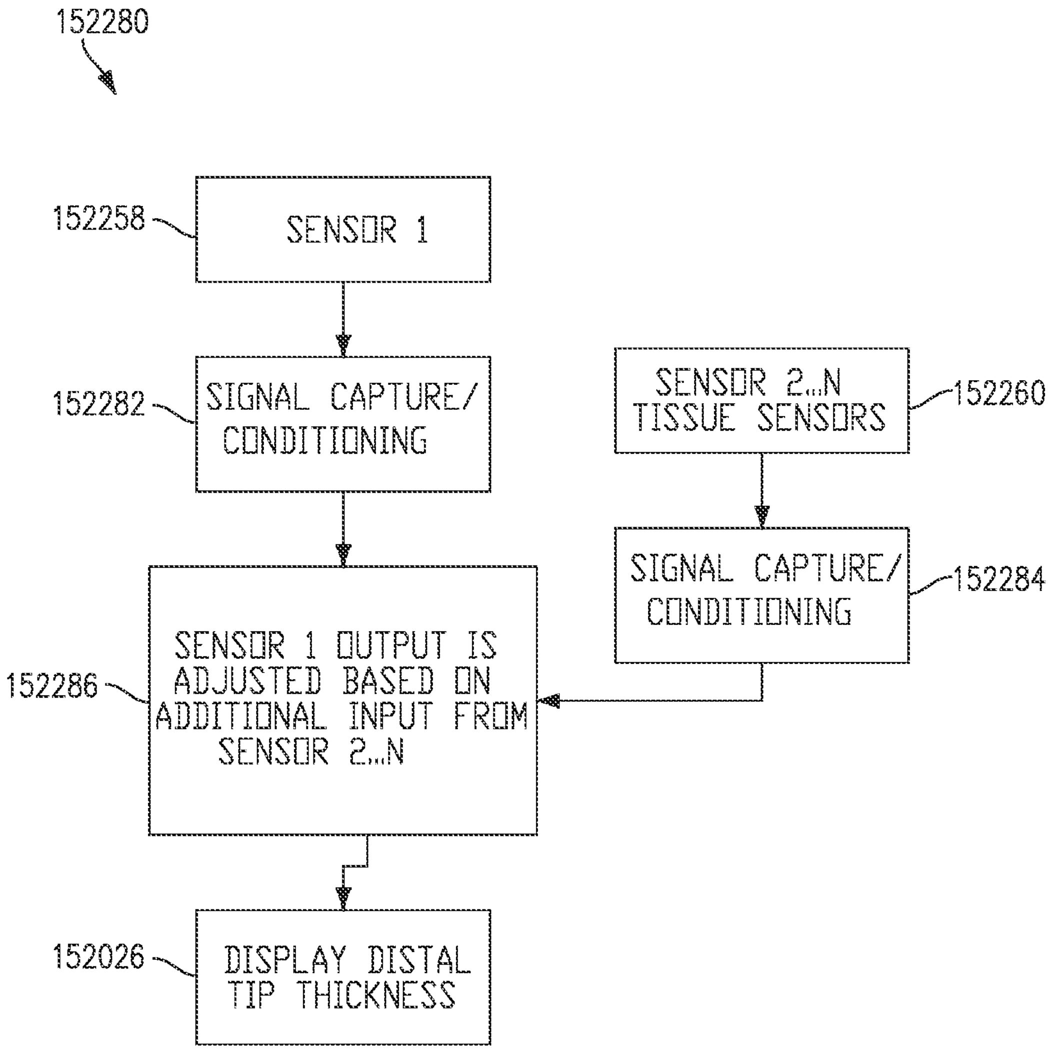

FIG. 68 is a logic diagram illustrating one embodiment of a process for determining one or more parameters of a tissue section clamped within an end effector.

Figure 69:
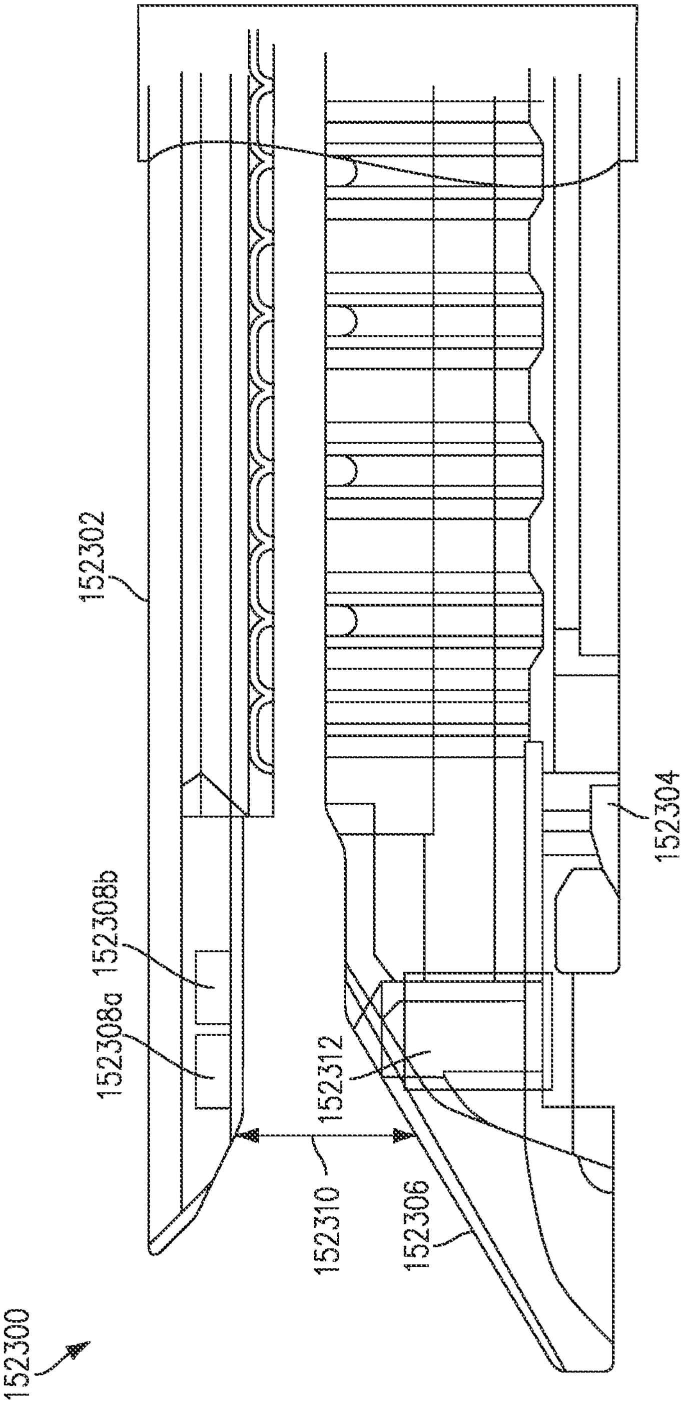

FIG. 69 illustrates one embodiment of an end effector comprising a plurality of redundant sensors.

Figure 70:
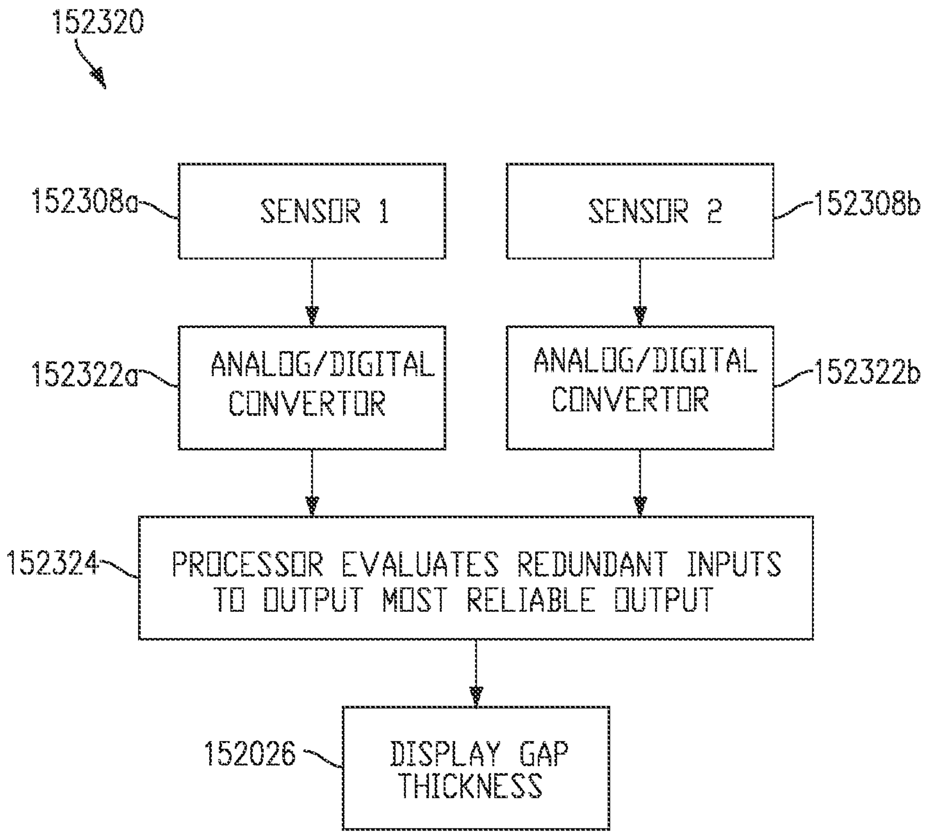

FIG. 70 is a logic diagram illustrating one embodiment of a process for selecting the most reliable output from a plurality of redundant sensors.

Figure 71:
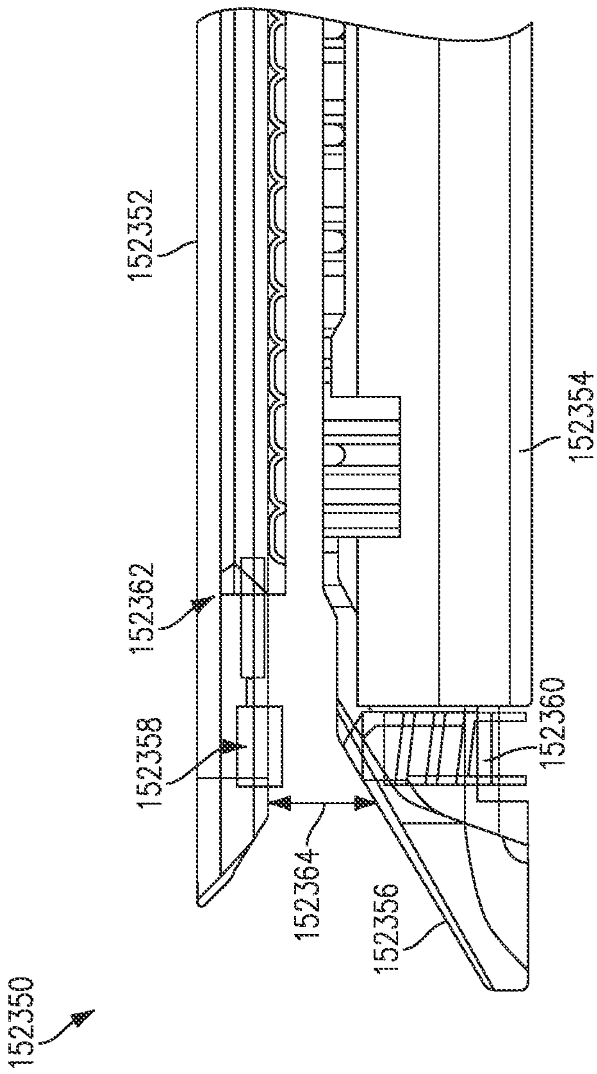

FIG. 71 illustrates one embodiment of an end effector comprising a sensor comprising a specific sampling rate to limit or eliminate false signals.

Figure 72:
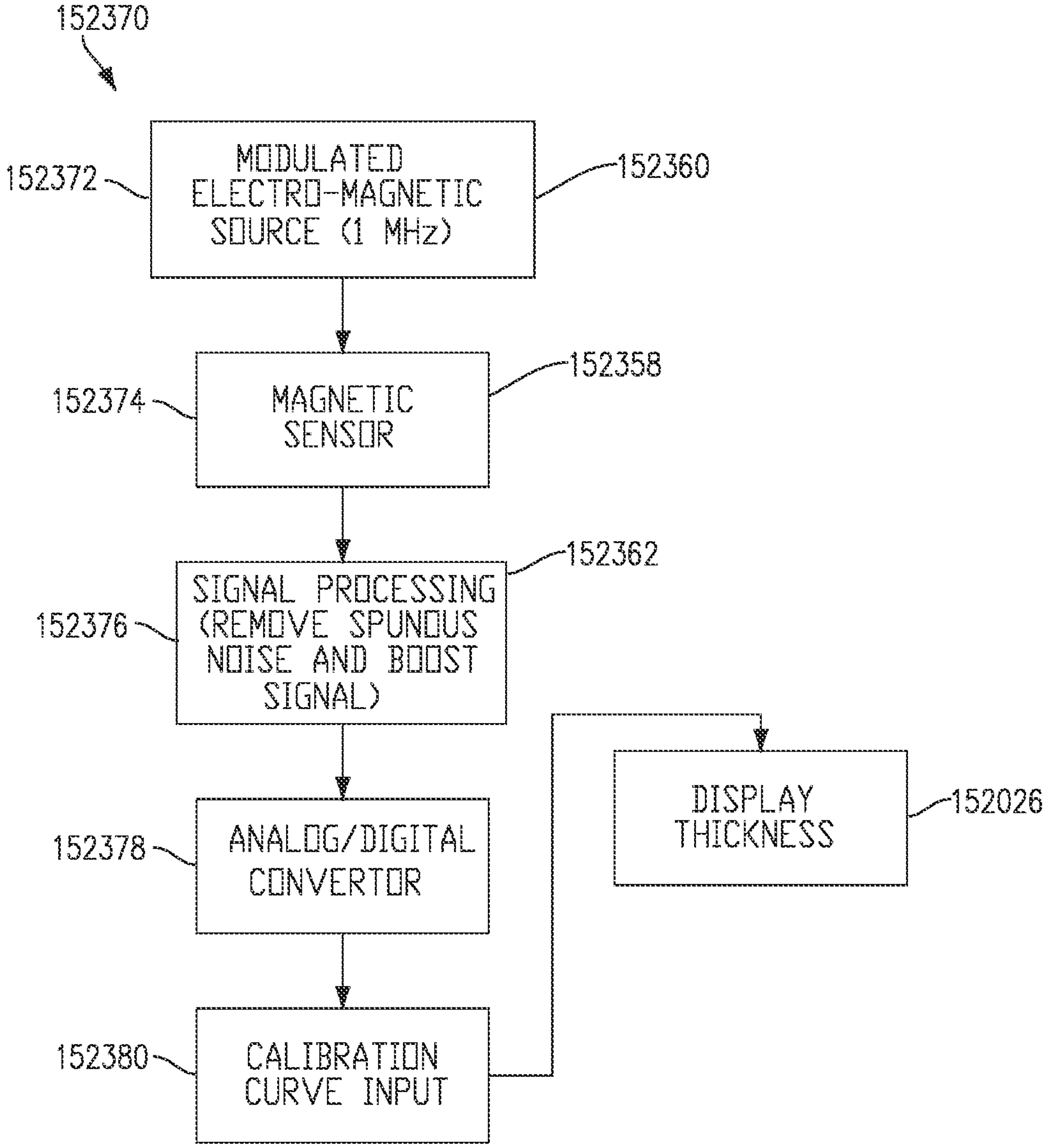

FIG. 72 is a logic diagram illustrating one embodiment of a process for generating a thickness measurement for a tissue section located between an anvil and a staple cartridge of an end effector.

Figure 73:
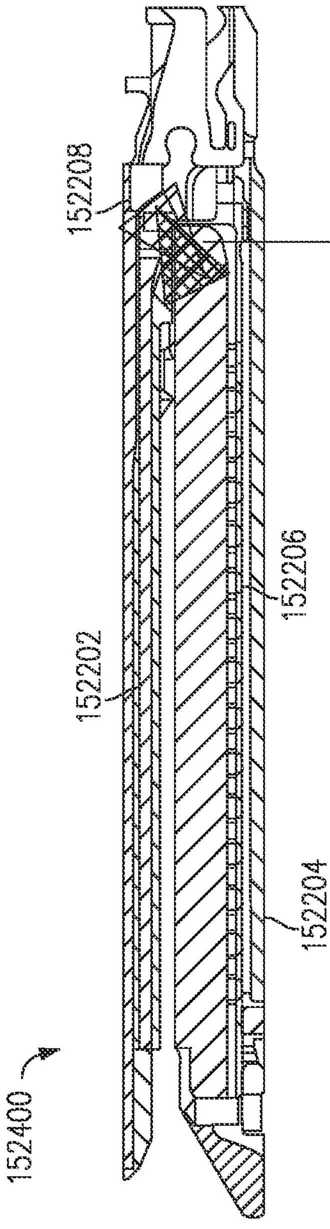
Figure 74:
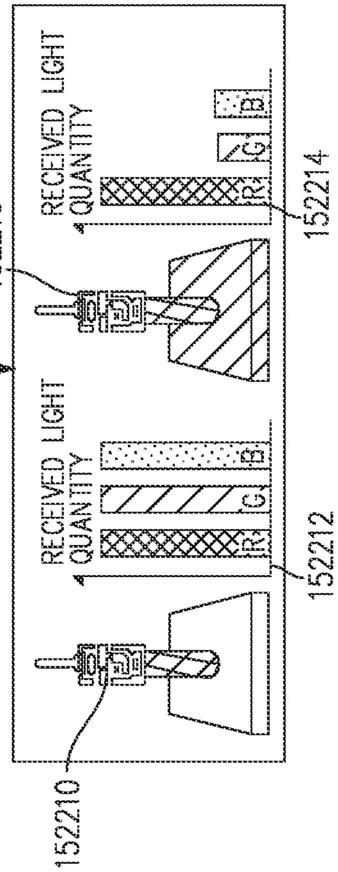

FIGS. 73 and 74 illustrate one embodiment of an end effector comprising a sensor for identifying staple cartridges of different types.

Figure 75:
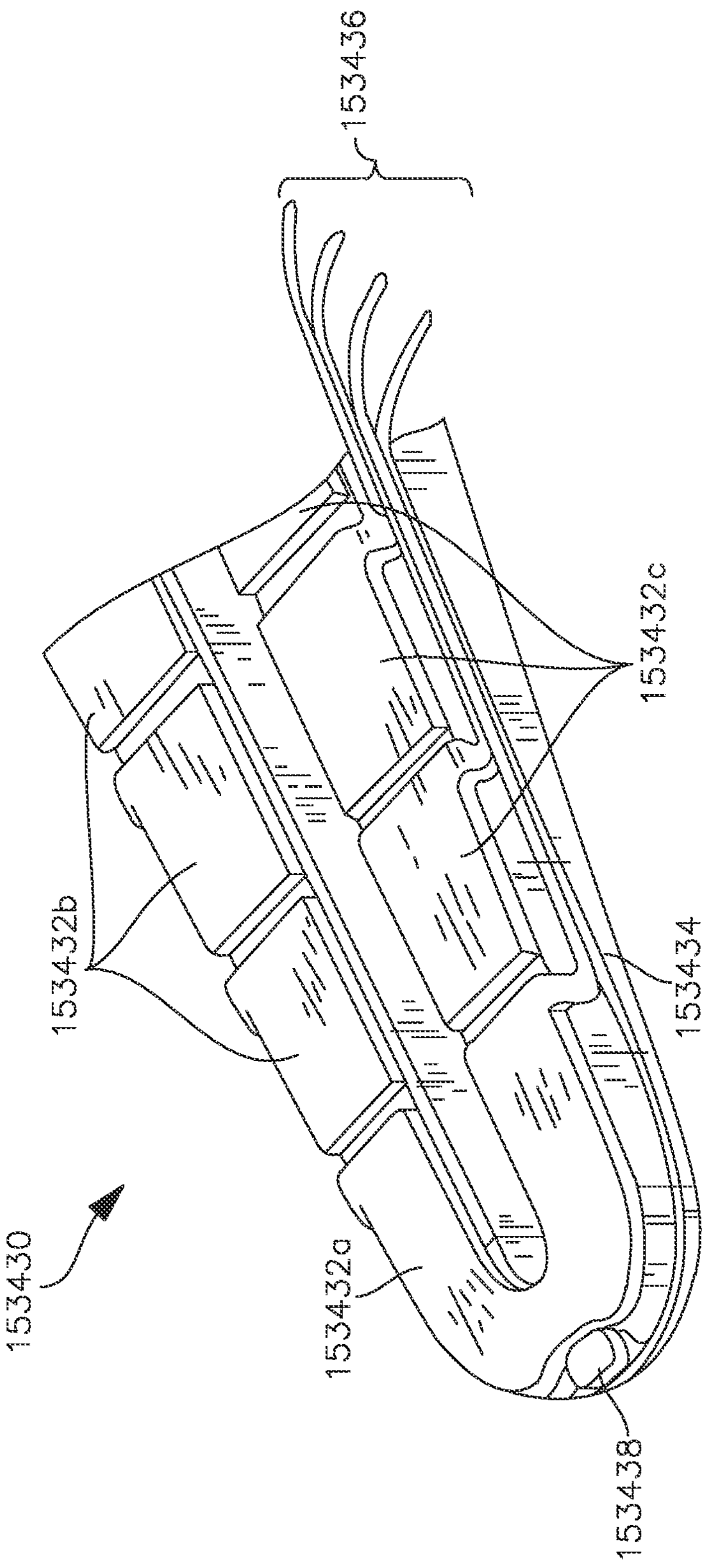

FIG. 75 illustrates one aspect of a segmented flexible circuit configured to fixedly attach to a jaw member of an end effector, in accordance with at least one aspect of this disclosure.

Figure 76:
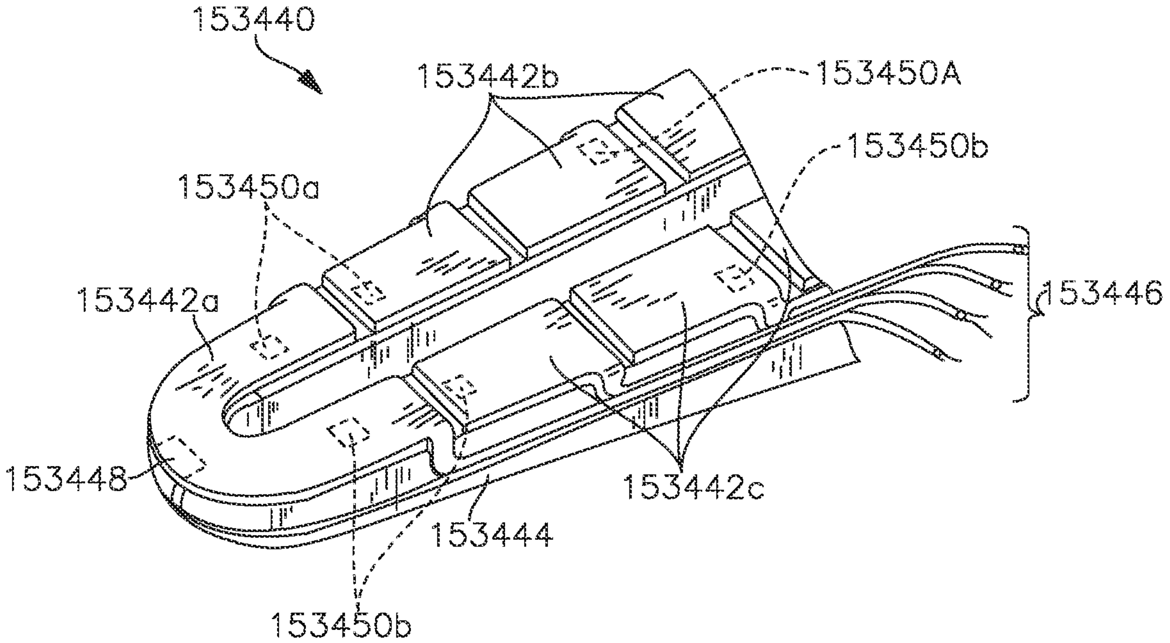

FIG. 76 illustrates one aspect of a segmented flexible circuit configured to mount to a jaw member of an end effector, in accordance with at least one aspect of this disclosure.

Figure 77:
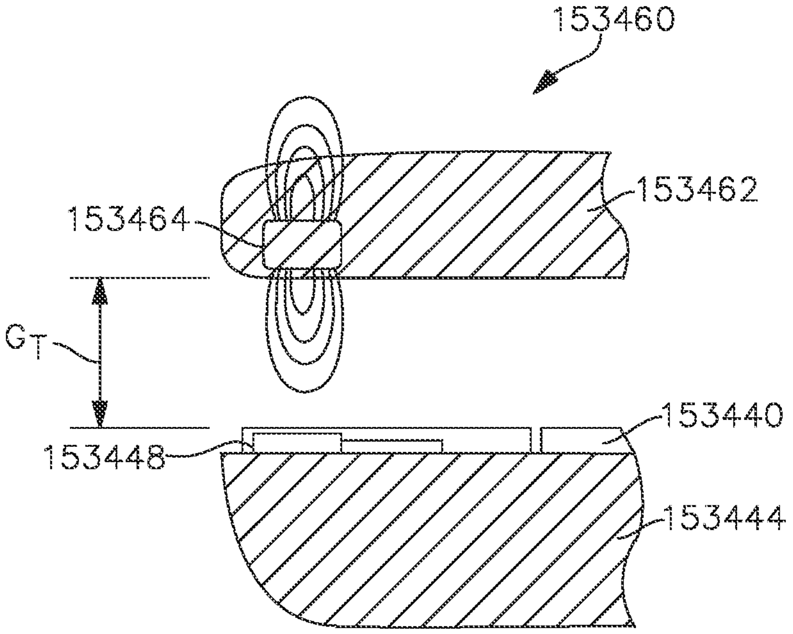

FIG. 77 illustrates one aspect of an end effector configured to measure a tissue gap GT, in accordance with at least one aspect of this disclosure.

Figure 78:
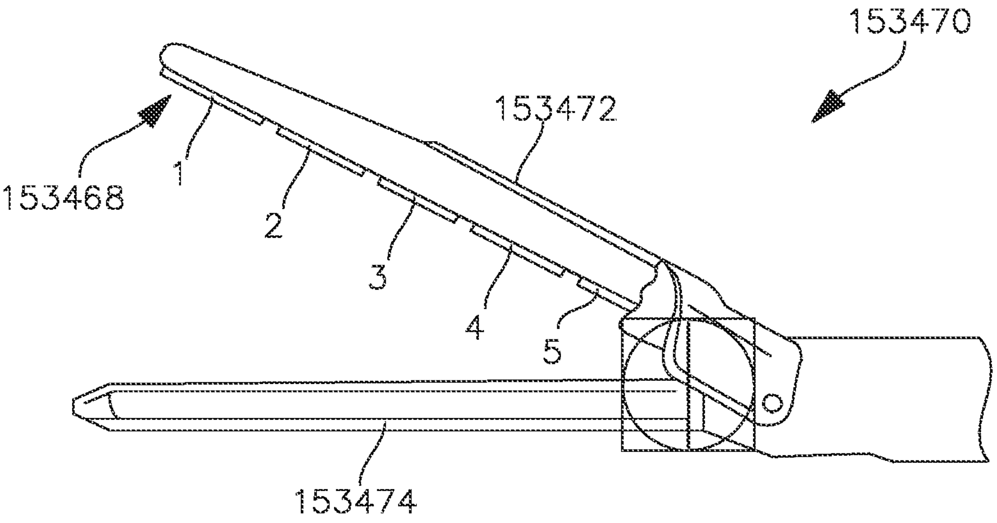

FIG. 78 illustrates one aspect of an end effector comprising segmented flexible circuit, in accordance with at least one aspect of this present disclosure.

Figure 79:
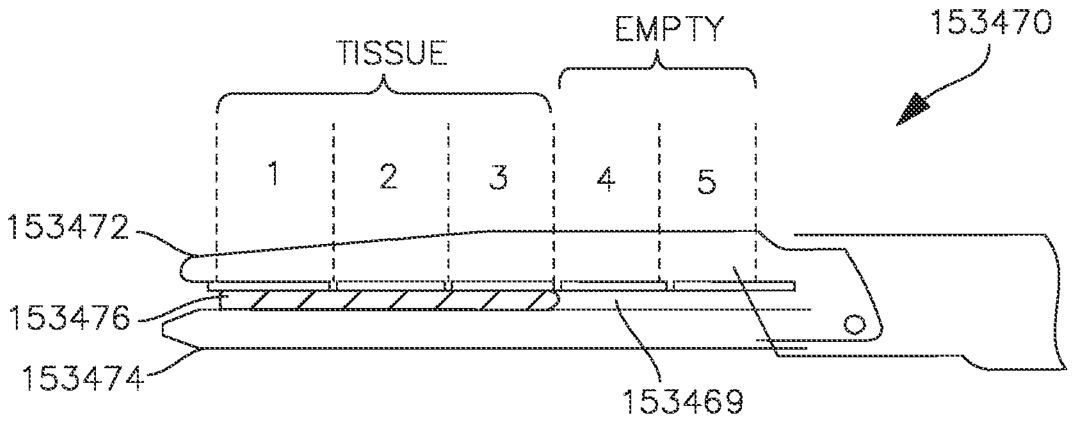

FIG. 79 illustrates the end effector shown in FIG. 78 with the jaw member clamping tissue between the jaw member and the staple cartridge, in accordance with at least one aspect of this disclosure.

Figure 80:
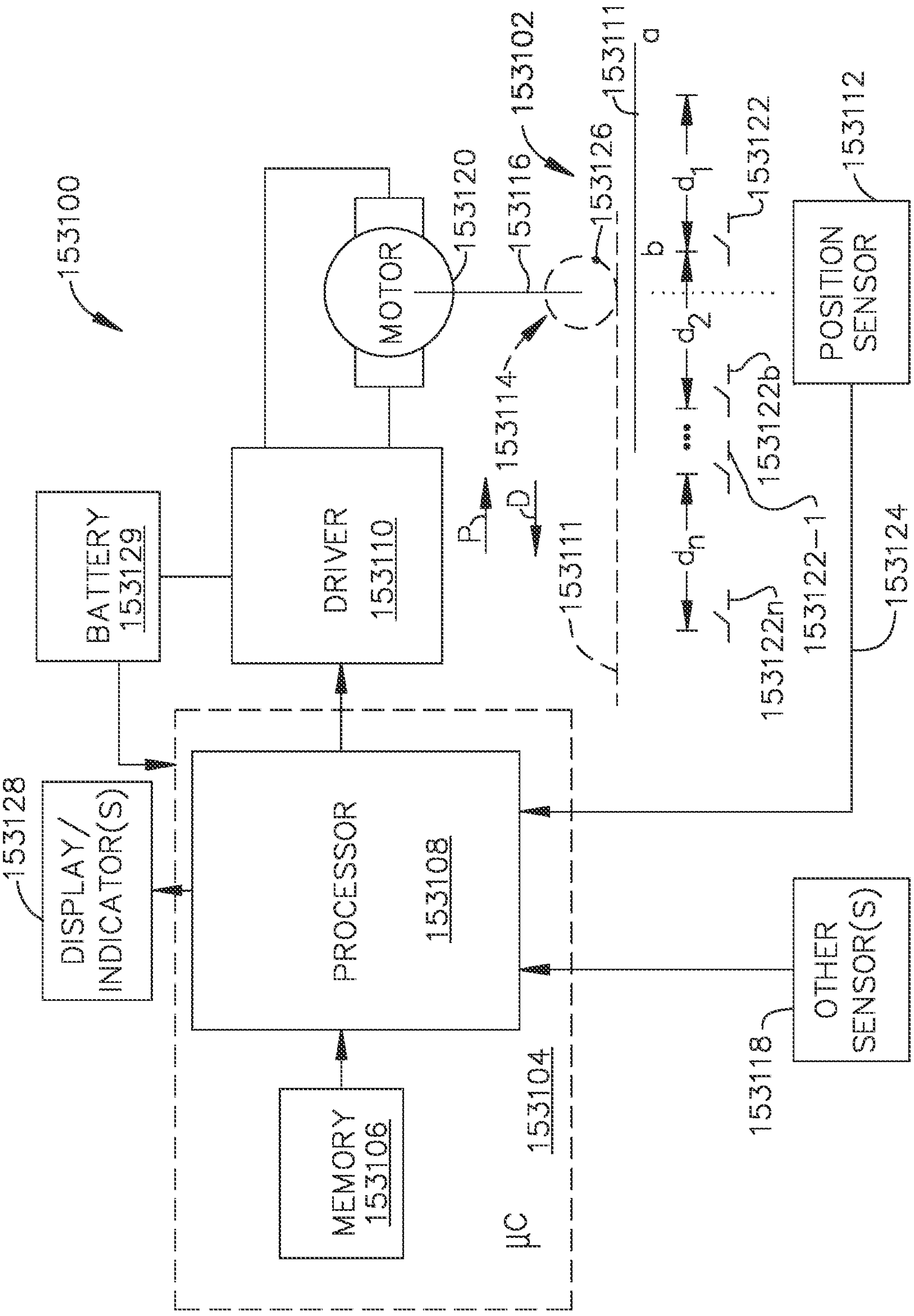

FIG. 80 is a diagram of an absolute positioning system of a surgical instrument where the absolute positioning system comprises a controlled motor drive circuit arrangement comprising a sensor arrangement, in accordance with at least one aspect of this disclosure.

Figure 81:
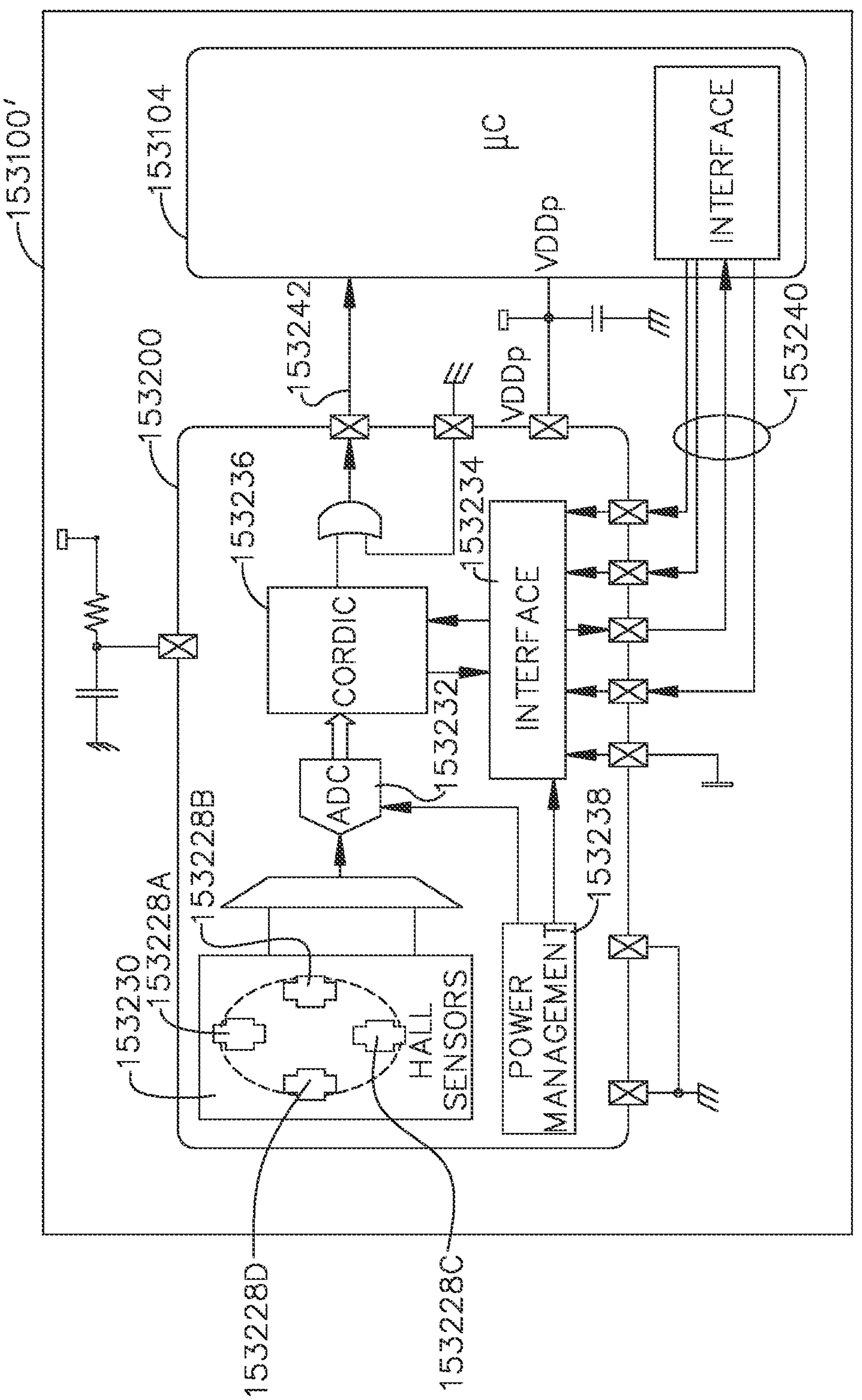

FIG. 81 is a diagram of a position sensor comprising a magnetic rotary absolute positioning system, in accordance with at least one aspect of this disclosure.

Figure 82:
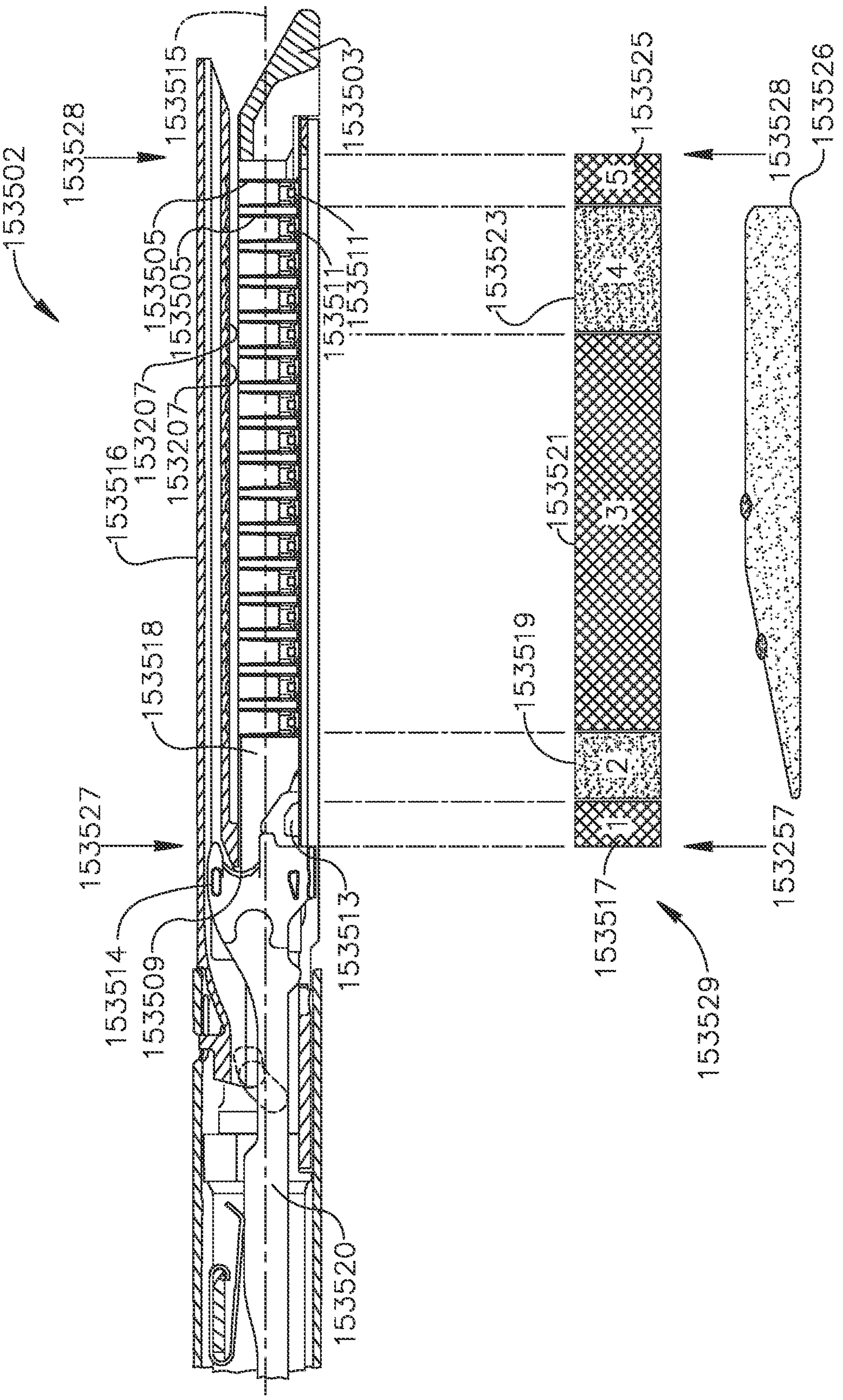

FIG. 82 is a section view of an end effector of a surgical instrument showing a firing member stroke relative to tissue grasped within the end effector, in accordance with at least one aspect of this disclosure.

Figure 83:
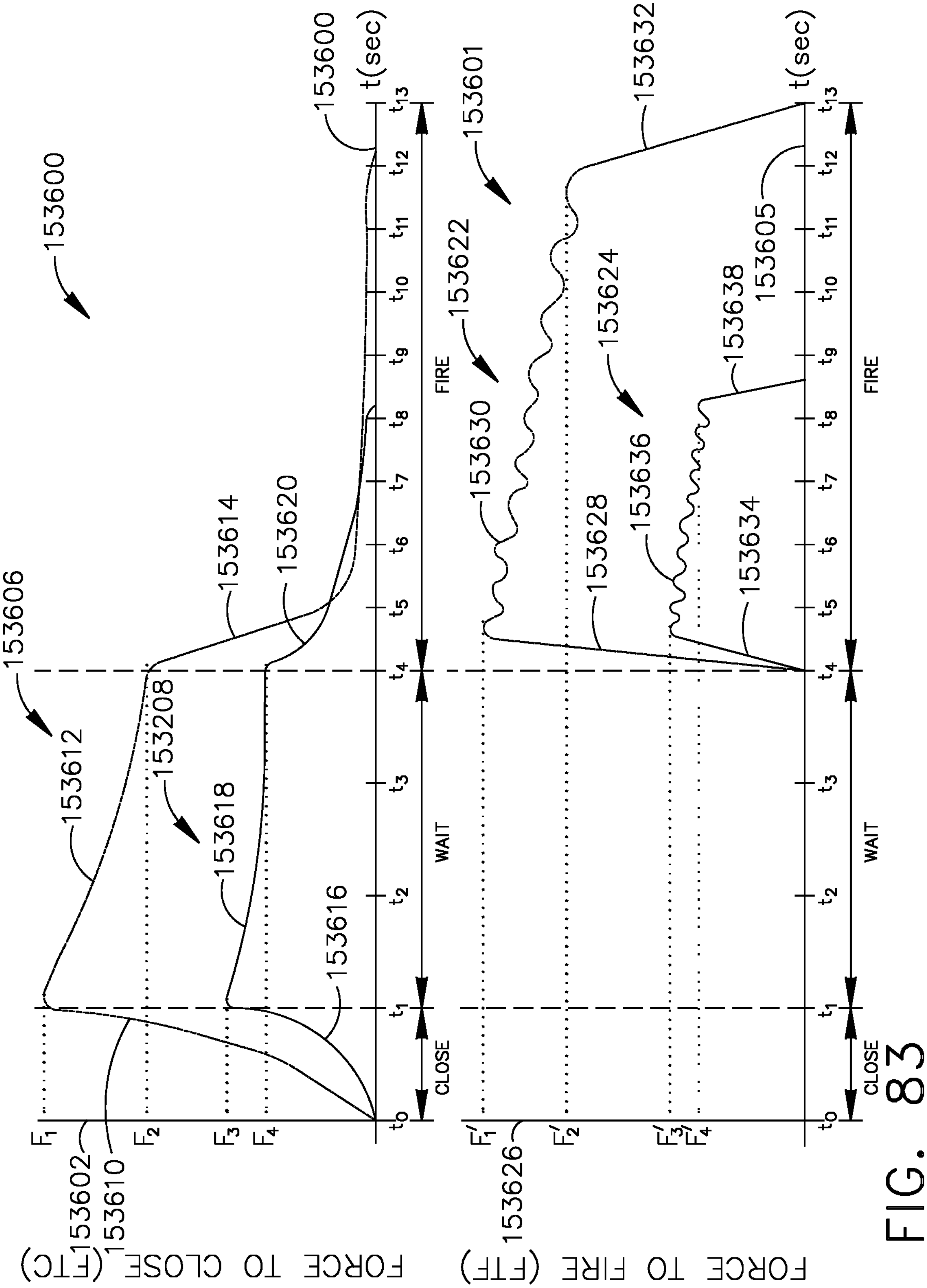

FIG. 83 is a first graph of two closure force (FTC) plots depicting the force applied to a closure member to close on thick and thin tissue during a closure phase and a second graph of two firing force (FTF) plots depicting the force applied to a firing member to fire through thick and thin tissue during a firing phase.

Figure 84:
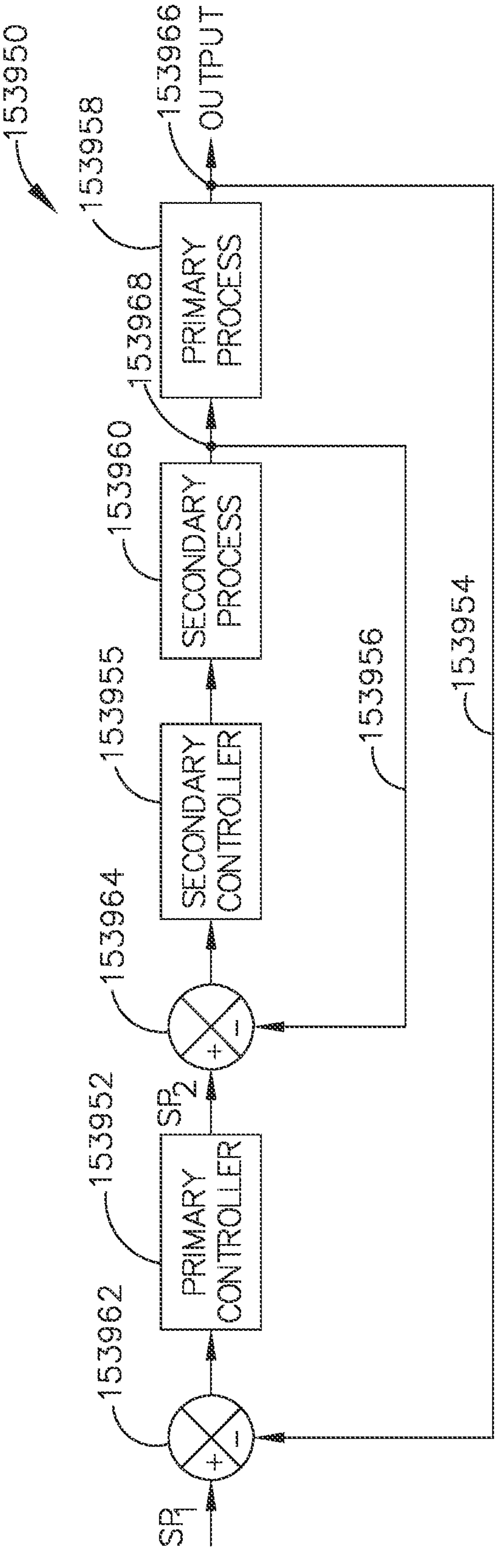

FIG. 84 is a graph of a control system configured to provide progressive closure of a closure member during a firing stroke when the firing member advances distally and couples into a clamp arm to lower the closure force load on the closure member at a desired rate and decrease the firing force load on the firing member, in accordance with at least one aspect of this disclosure.

Figure 85:
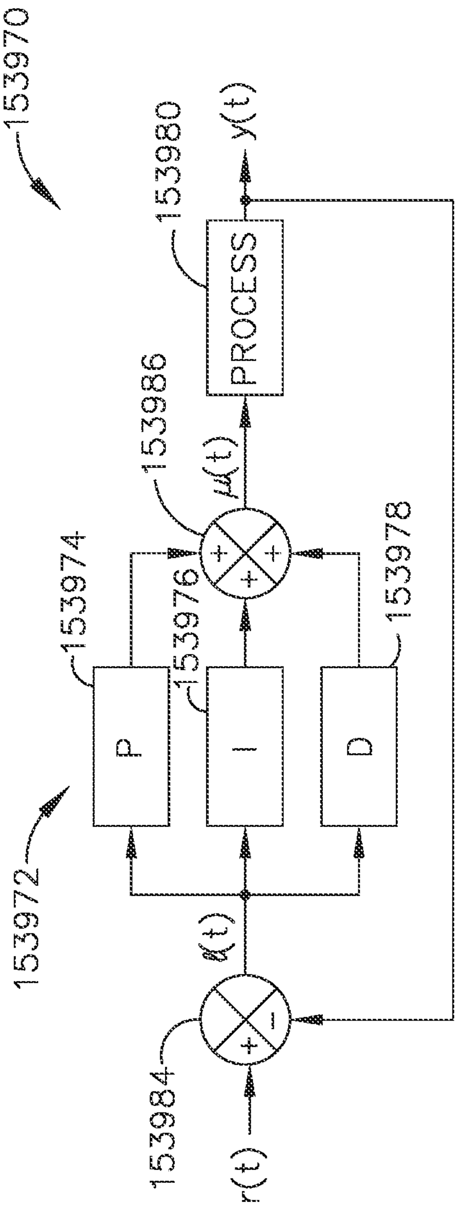

FIG. 85 illustrates a proportional-integral-derivative (PID) controller feedback control system, in accordance with at least one aspect of this disclosure.

Figure 86:
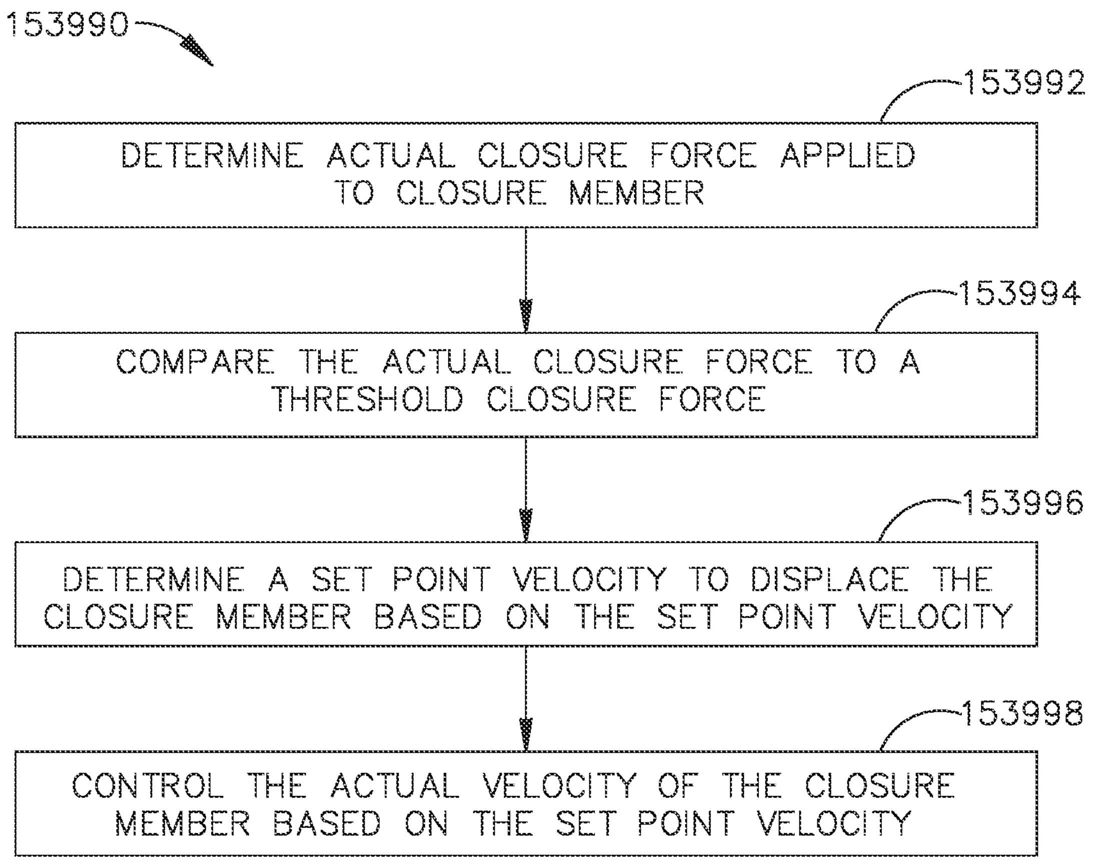

FIG. 86 is a logic flow diagram depicting a process of a control program or a logic configuration for determining the velocity of a closure member, in accordance with at least one aspect of this disclosure.

Figure 87:
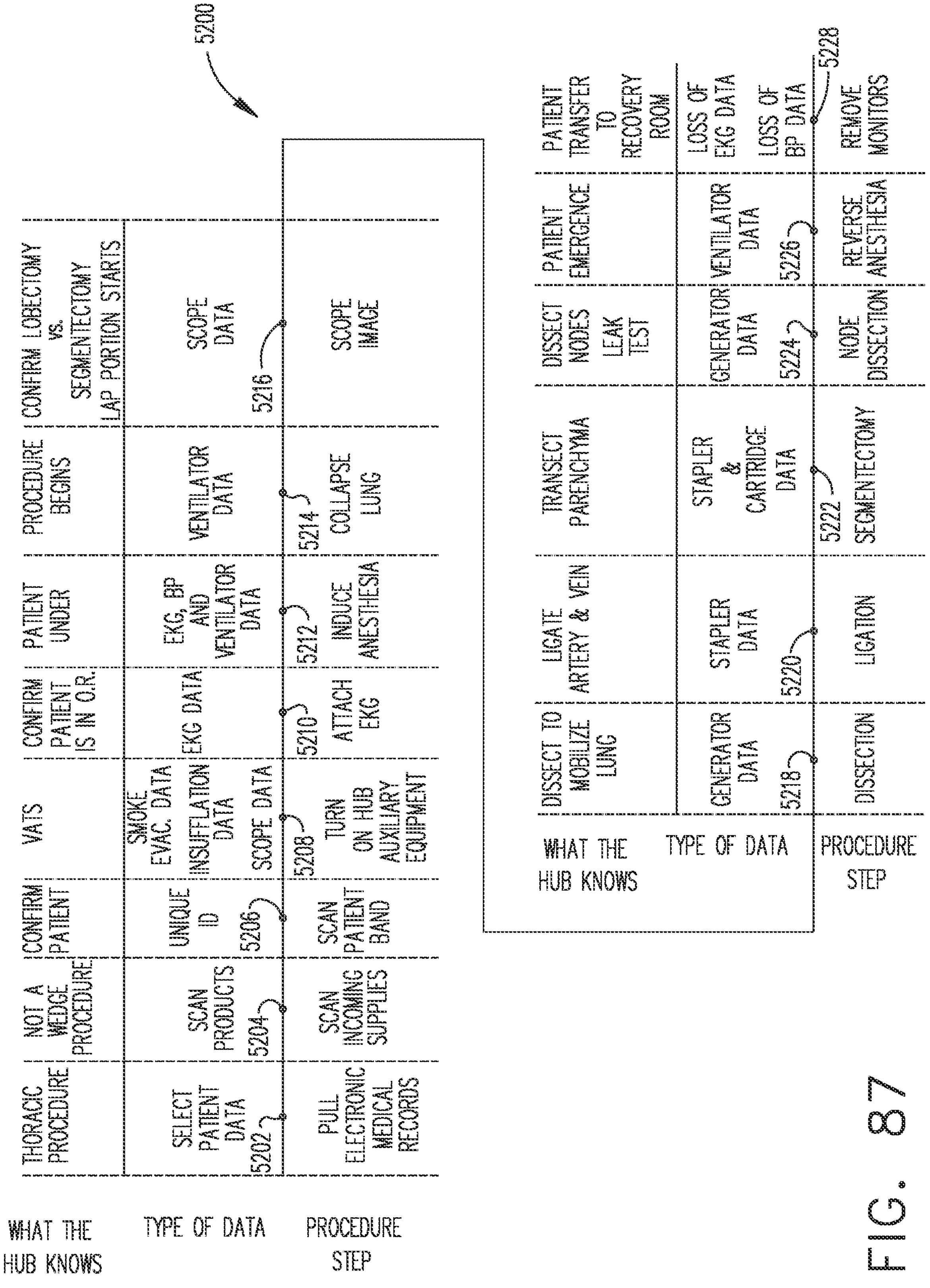

FIG. 87 is a timeline depicting situational awareness of a surgical hub, in accordance with at least one aspect of the present disclosure.

Figure 88:
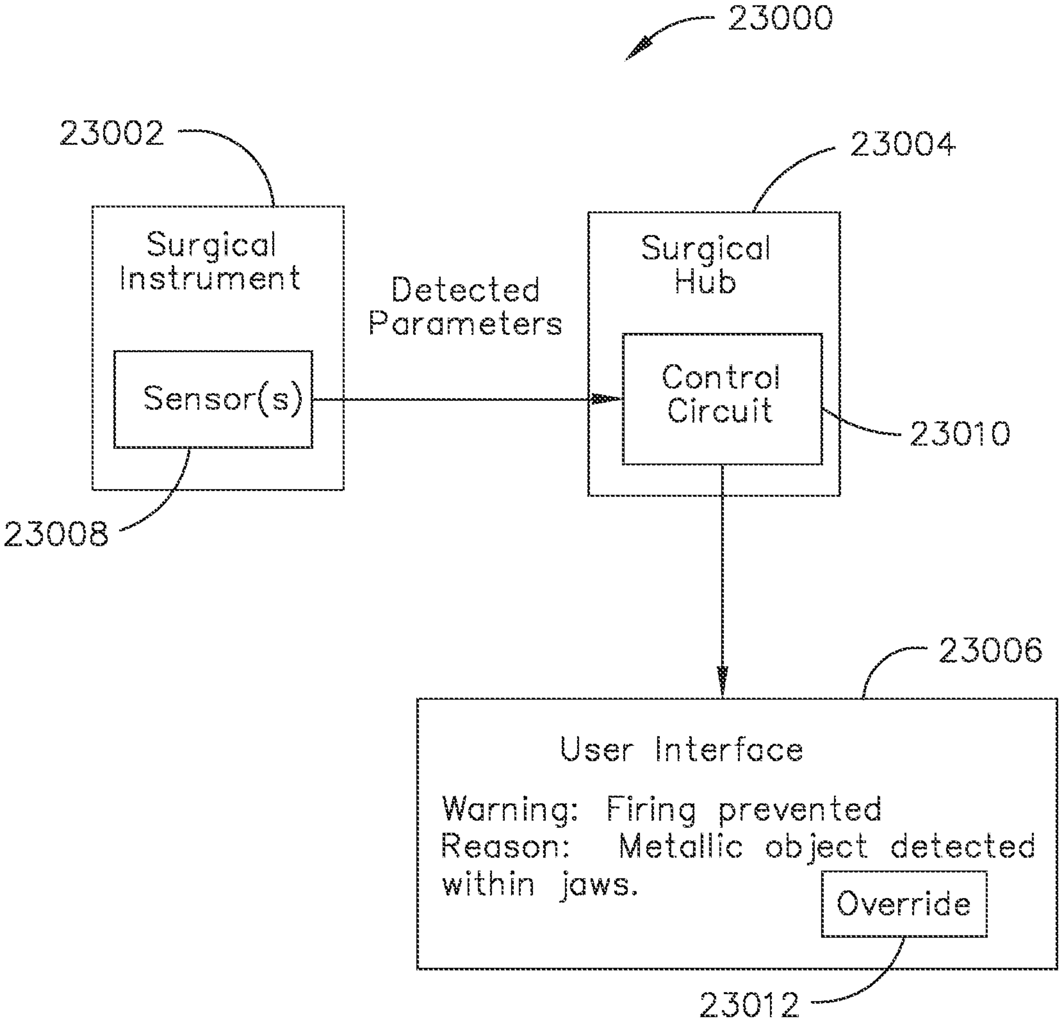

FIG. 88 illustrates a block diagram of a surgical system configured to control a surgical function, in accordance with at least one aspect of the present disclosure.

Figure 89:
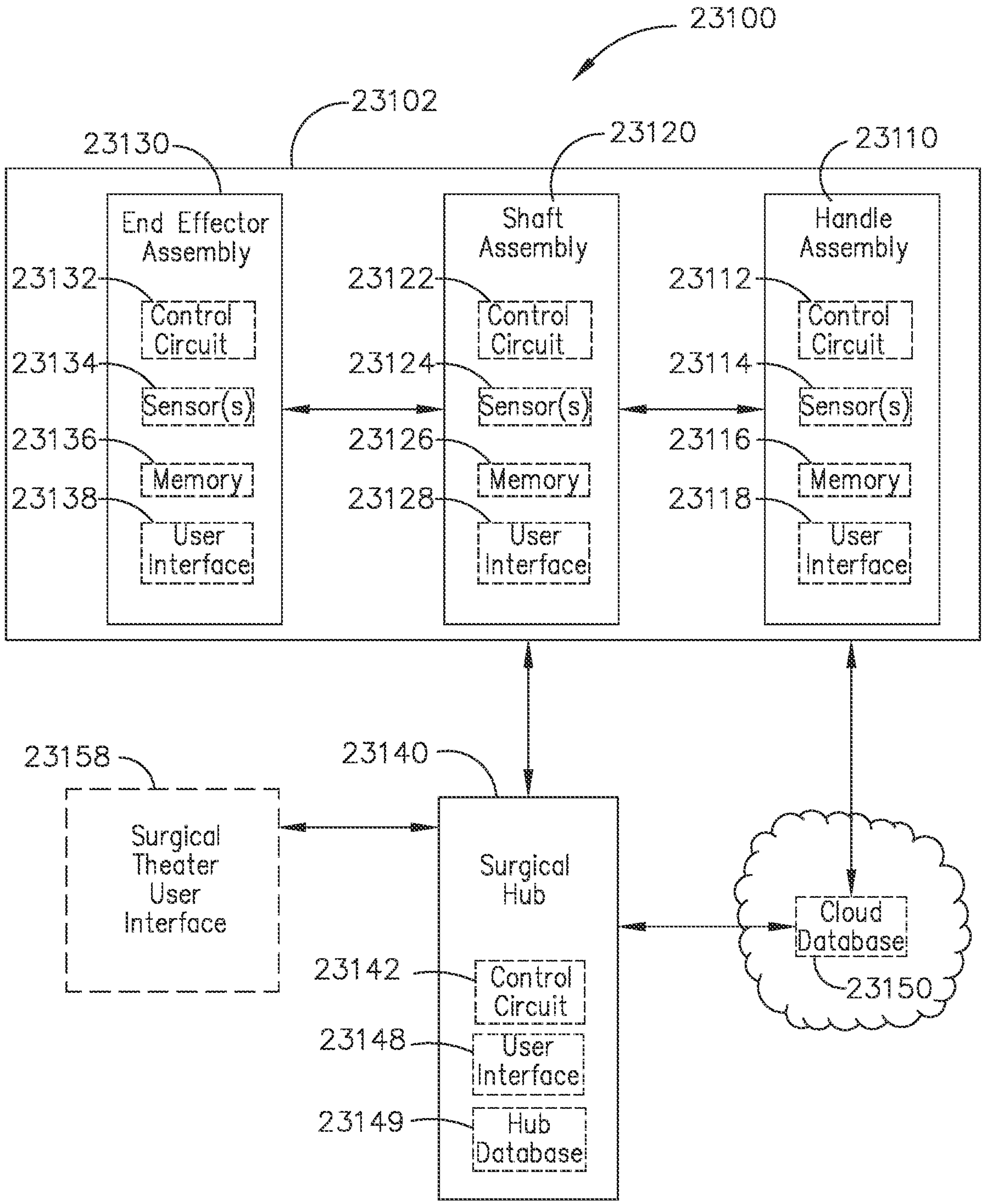

FIG. 89 illustrates a block diagram of a situationally aware surgical system configured to control a surgical function, in accordance with at least one aspect of the present disclosure.

Figure 90:
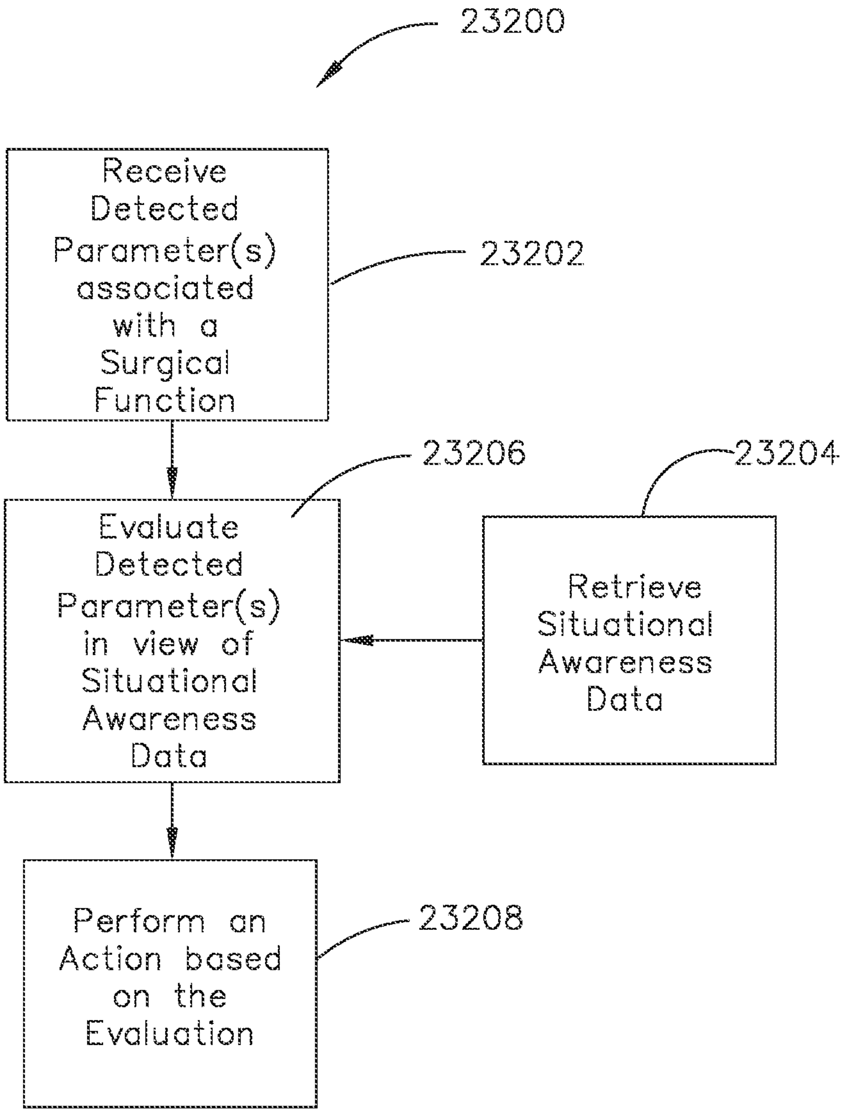

FIG. 90 is a logic flow diagram depicting a situational awareness based algorithm for controlling a surgical function, in accordance with at least one aspect of the present disclosure.

Figure 91:
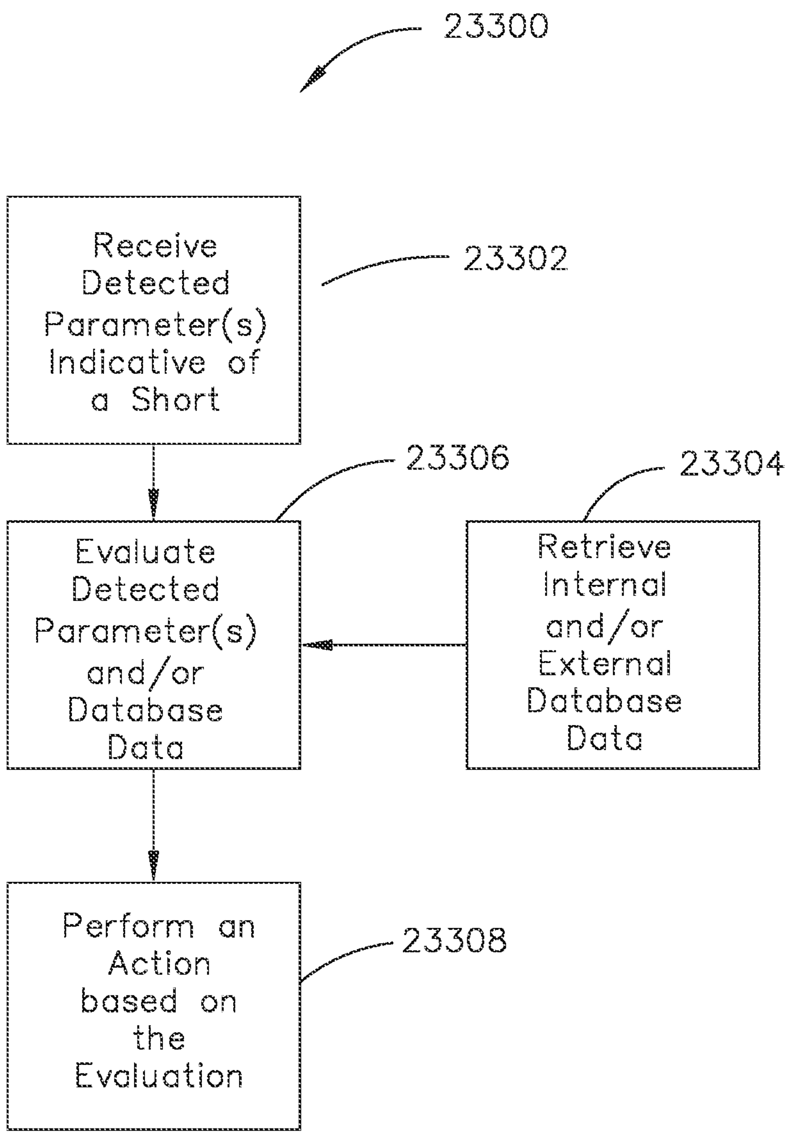

FIG. 91 is a logic flow diagram depicting an algorithm for controlling a surgical function, in accordance with at least one aspect of the present disclosure.

Figure 92:
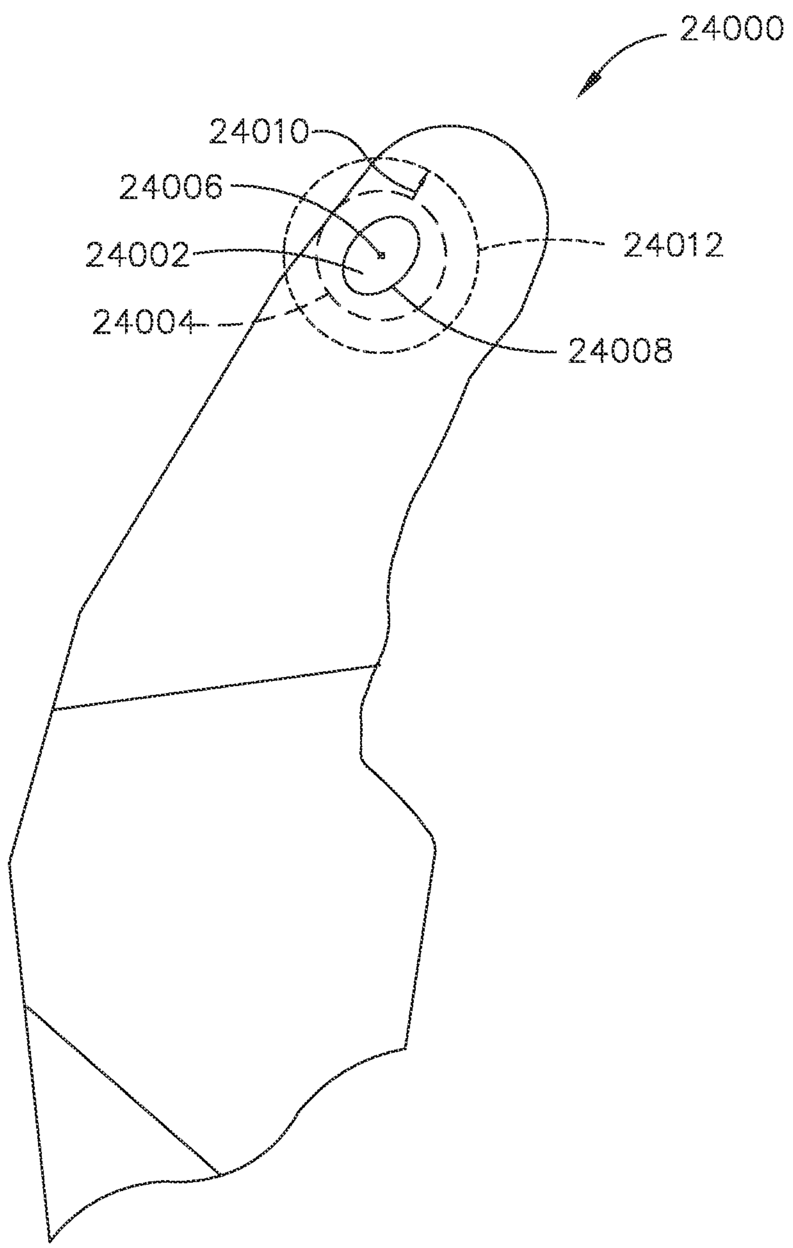

FIG. 92 illustrates a portion of patient tissue comprising a tumor as well as surgical margins defined with respect to the tumor, in accordance with at least one aspect of the present disclosure.

Figure 93:
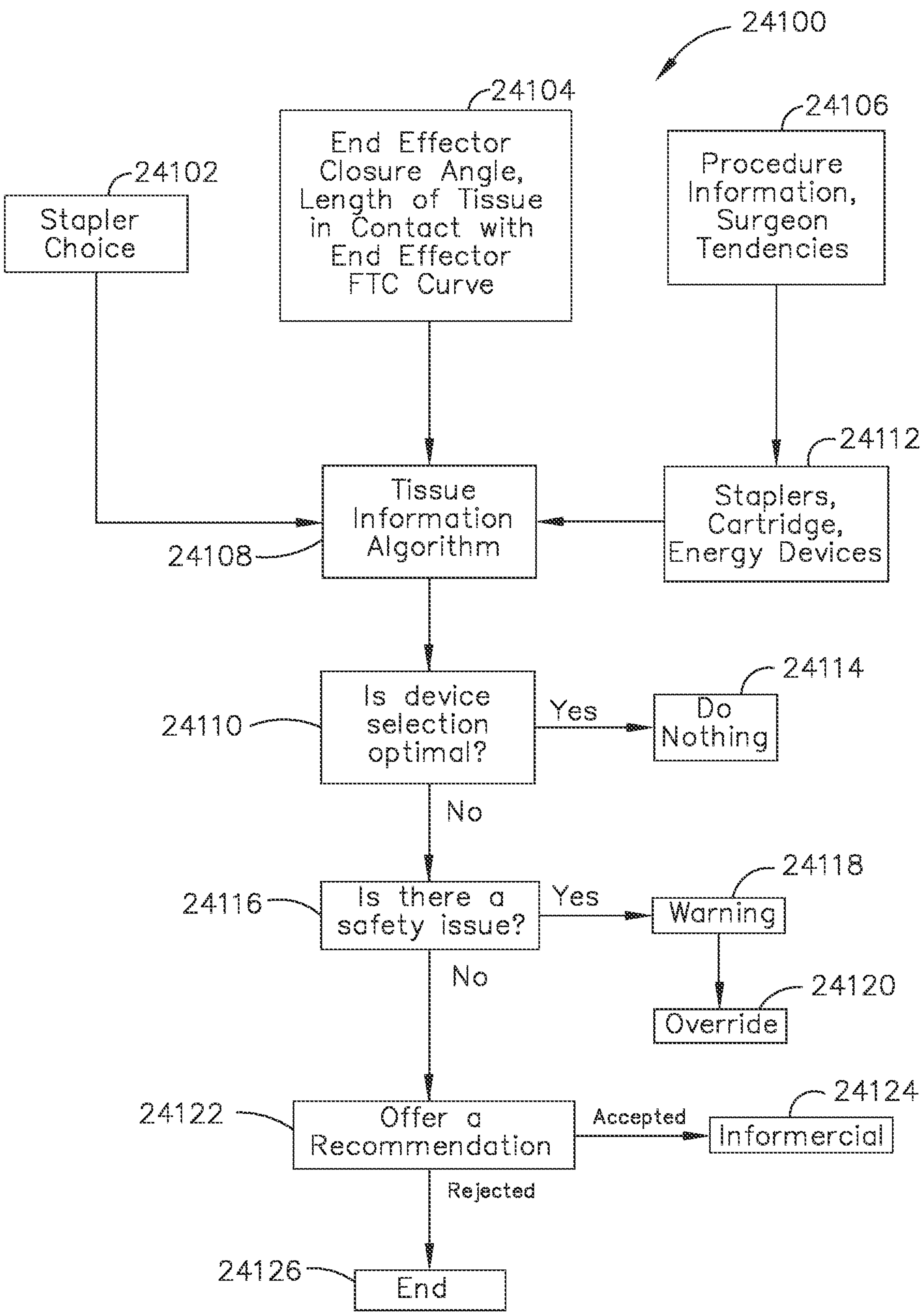

FIG. 93 is a logic flow diagram depicting a process of a control program or a logic configuration for addressing device selection concerns, in accordance with at least one aspect of the present disclosure.

Figure 94:
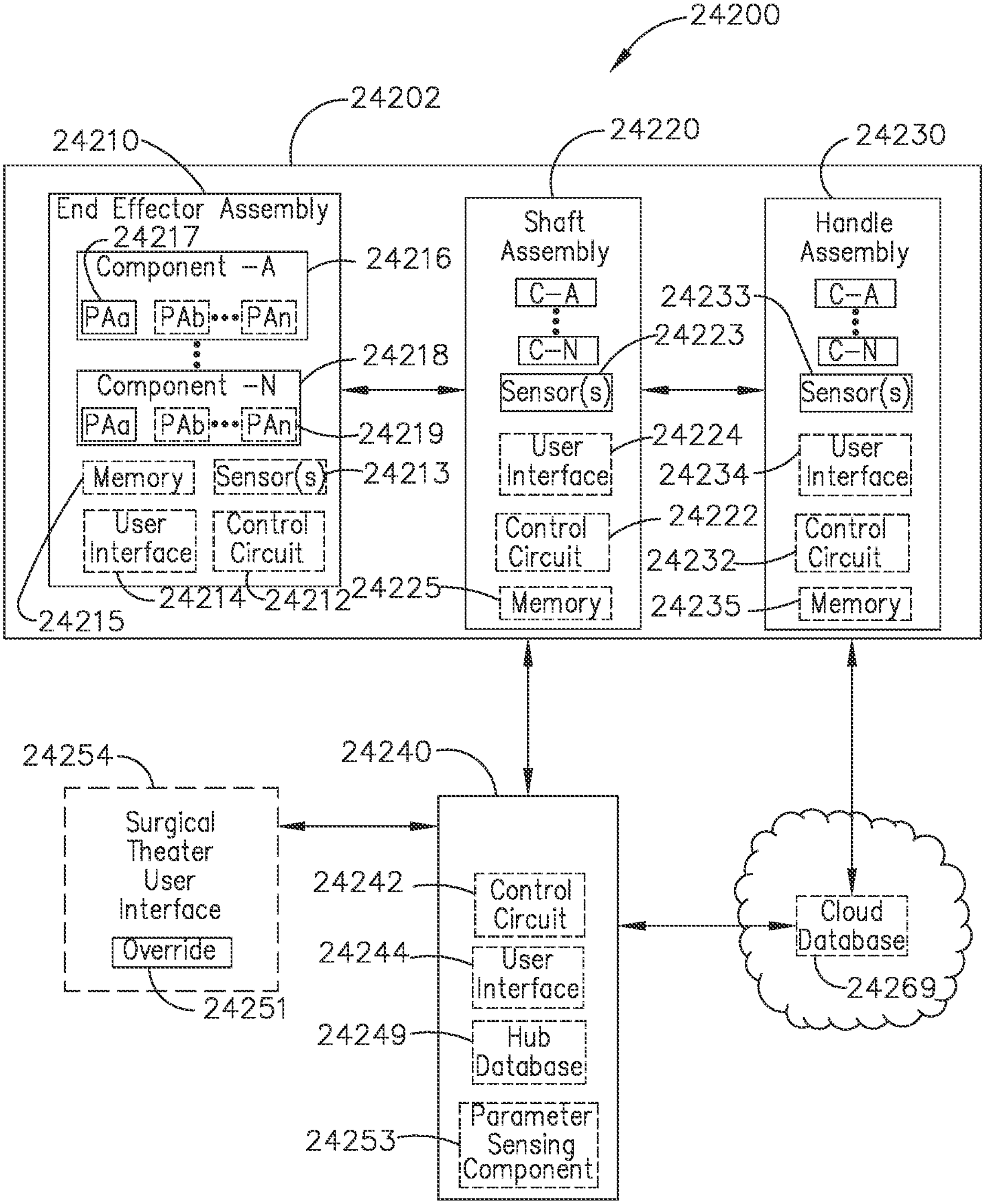

FIG. 94 illustrates a block diagram of a surgical system configured to determine the appropriateness of a surgical instrument based on device parameters and sensed parameters, in accordance with at least one aspect of the present disclosure.

Figure 95:
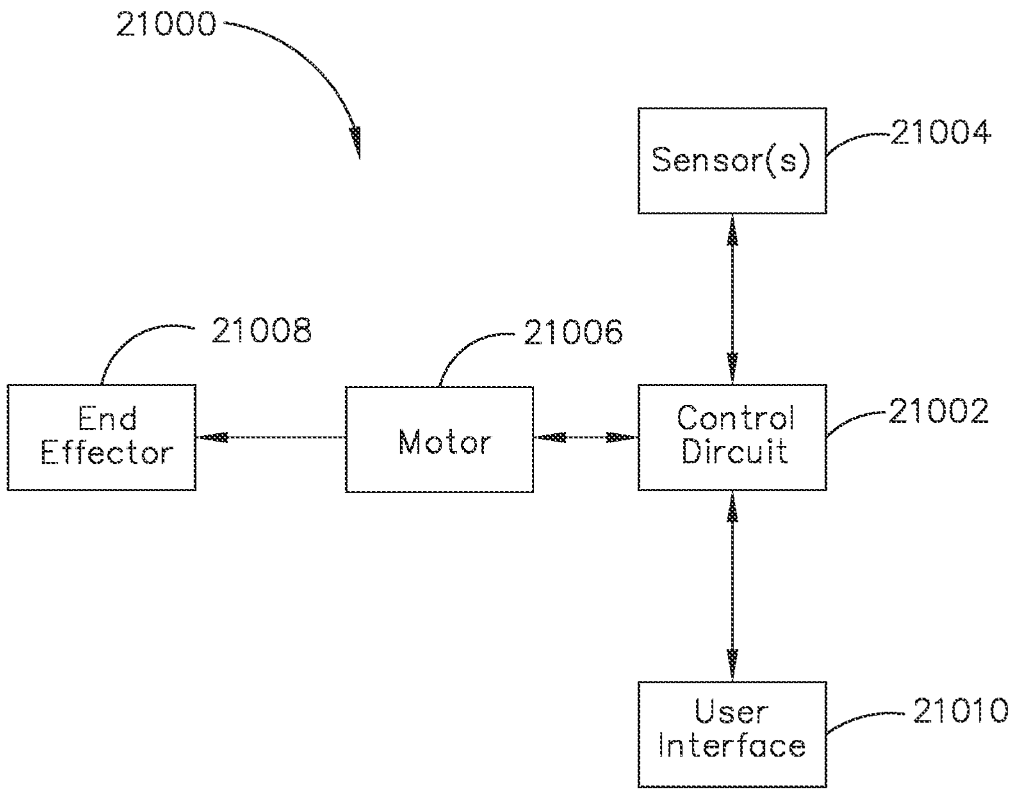

FIG. 95 illustrates a block diagram of a surgical instrument, in accordance with at least one aspect of the present disclosure.

Figure 96:
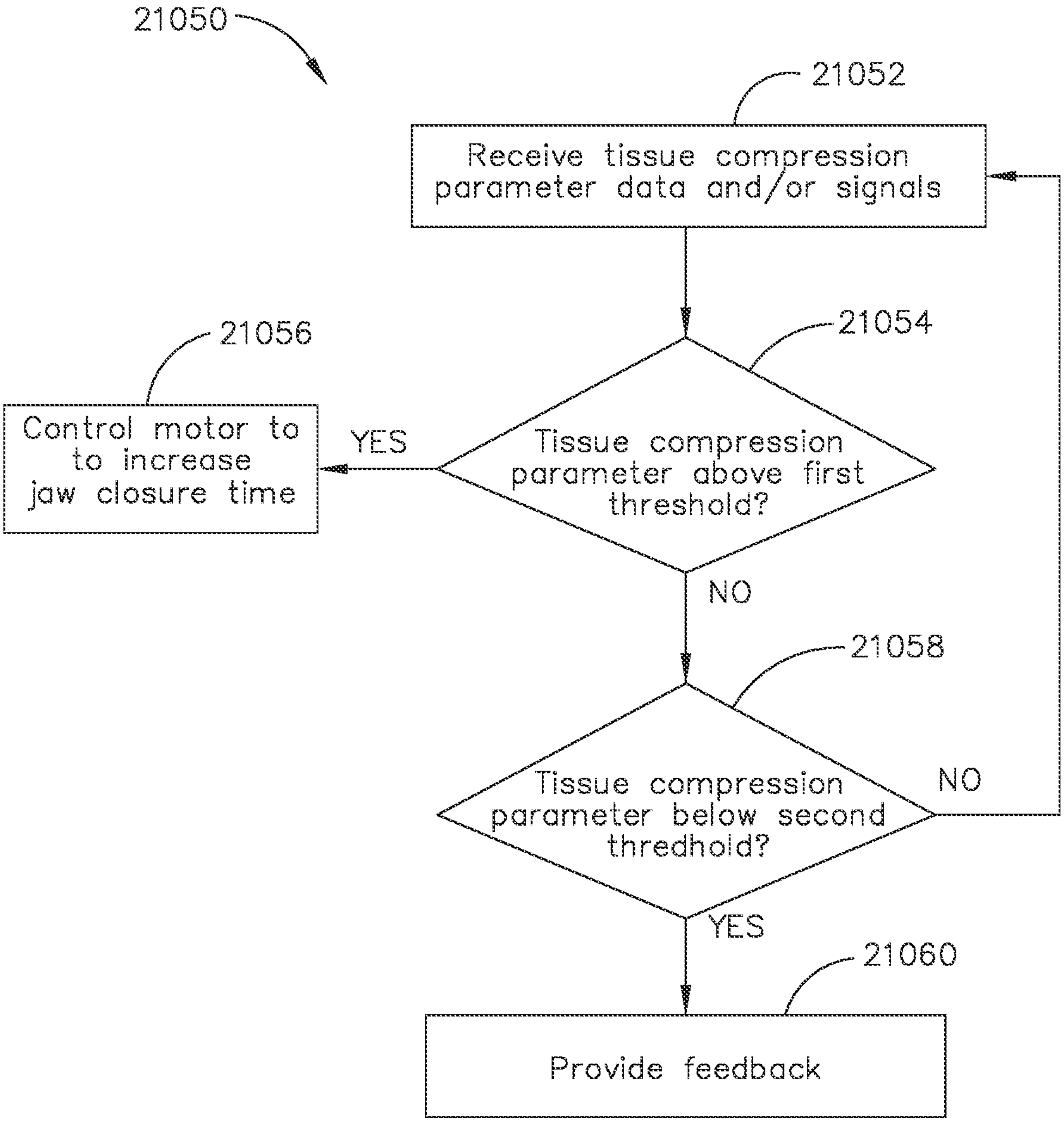

FIG. 96 illustrates a logic flow diagram of a process for controlling a surgical instrument according to the integrity of the clamped tissue, in accordance with at least one aspect of the present disclosure.

Figure 97:
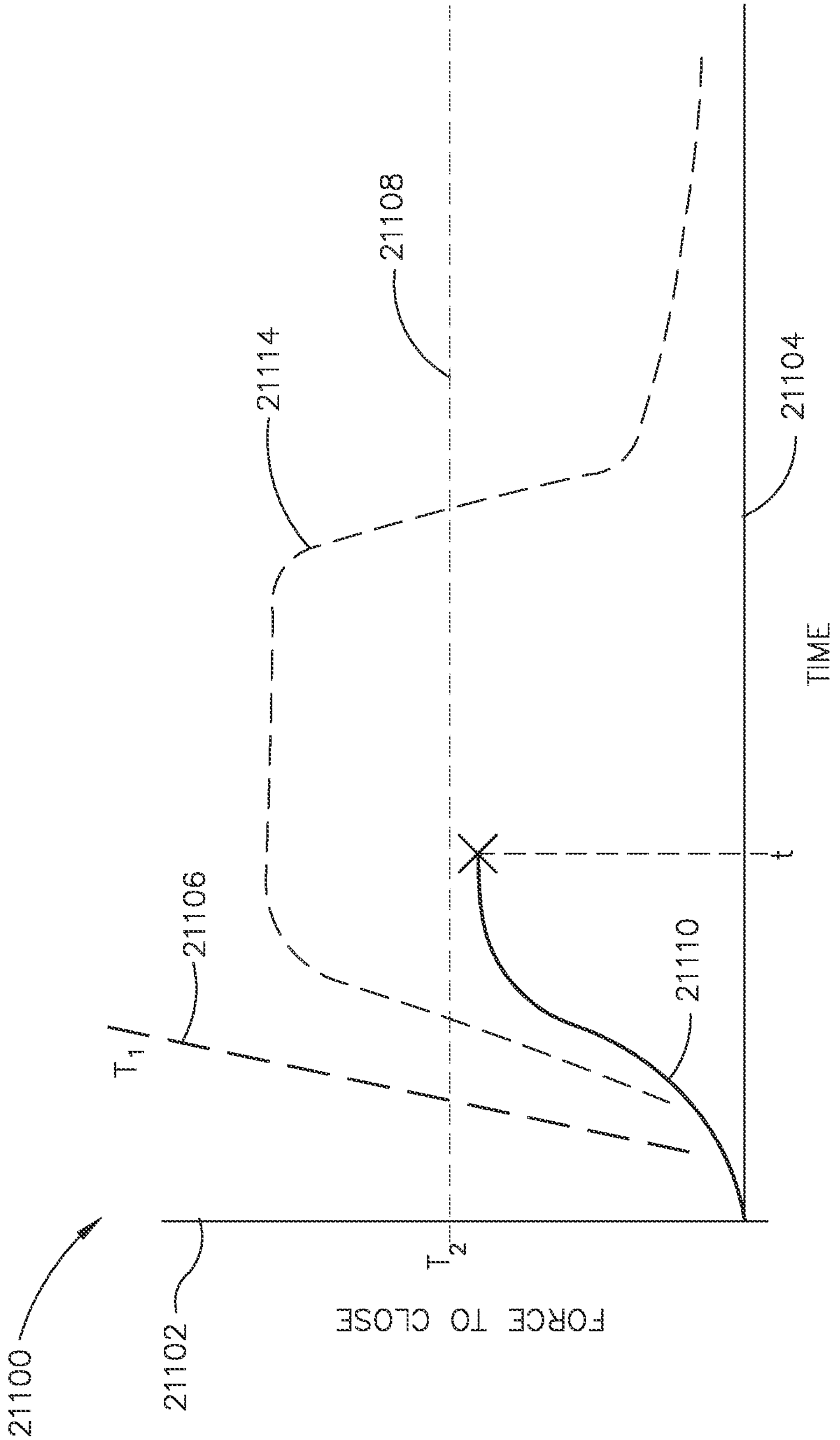

FIG. 97 illustrates a first graph depicting end effector force to close verse time for illustrative firings of a surgical instrument, in accordance with at least one aspect of the present disclosure.

Figure 98:
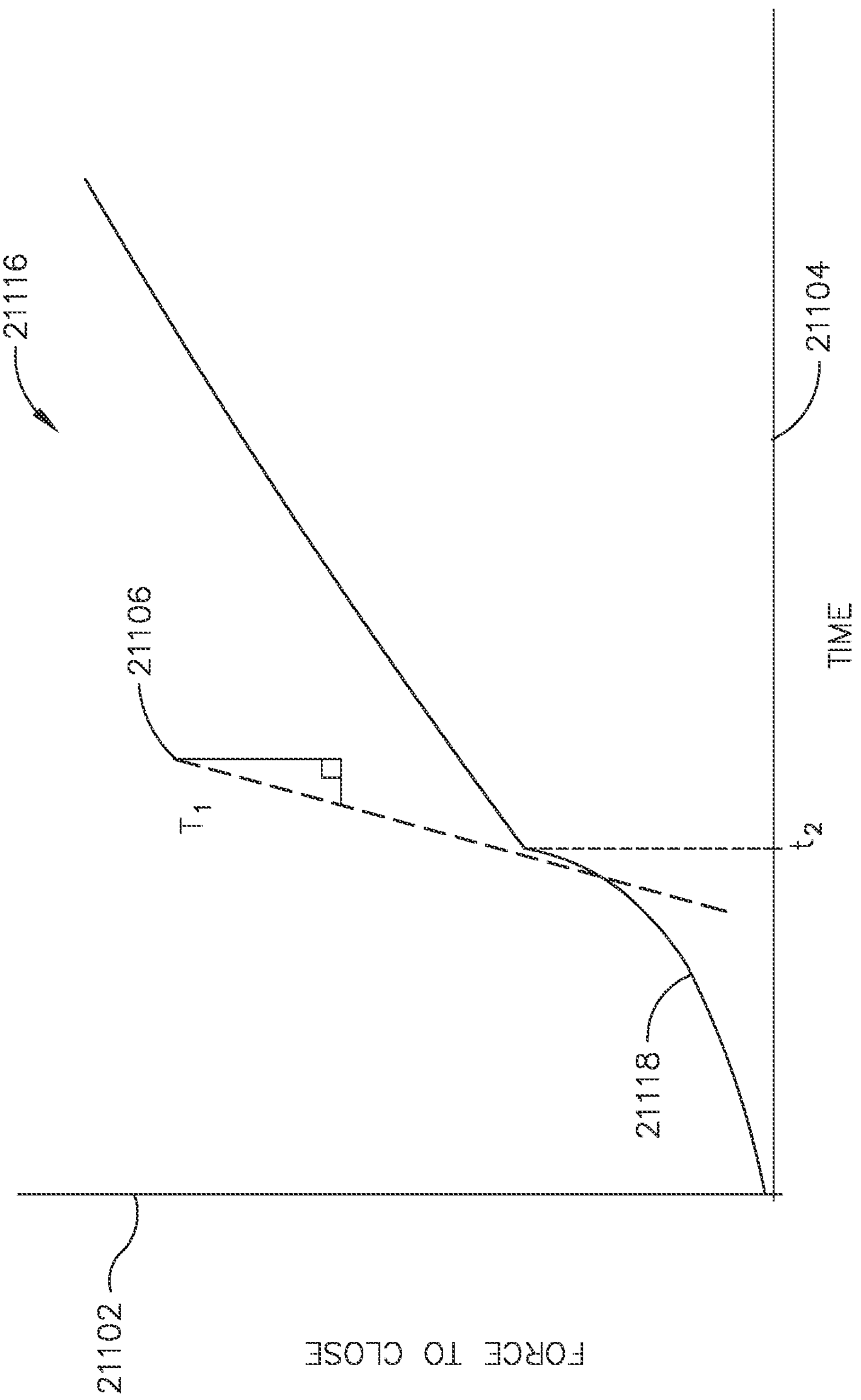

FIG. 98 illustrates a second graph depicting end effector force to close verse time for an illustrative firing of a surgical instrument, in accordance with at least one aspect of the present disclosure.

Figure 99:
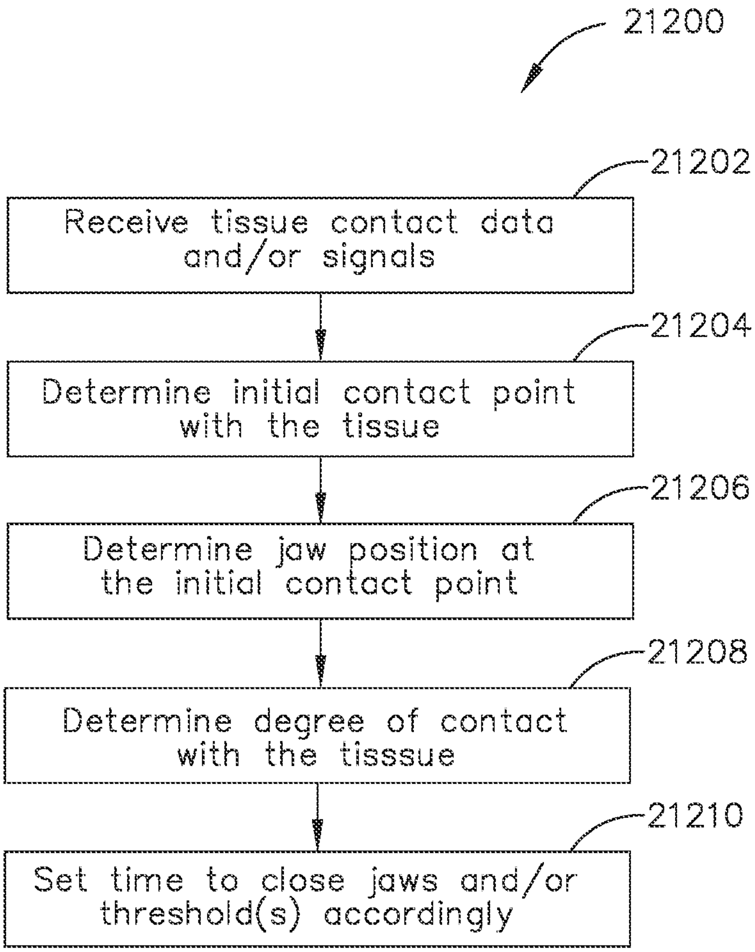

FIG. 99 illustrates a logic flow diagram of a process for controlling a surgical instrument according to the physiological type of the clamped tissue, in accordance with at least one aspect of the present disclosure.

Figure 100A:
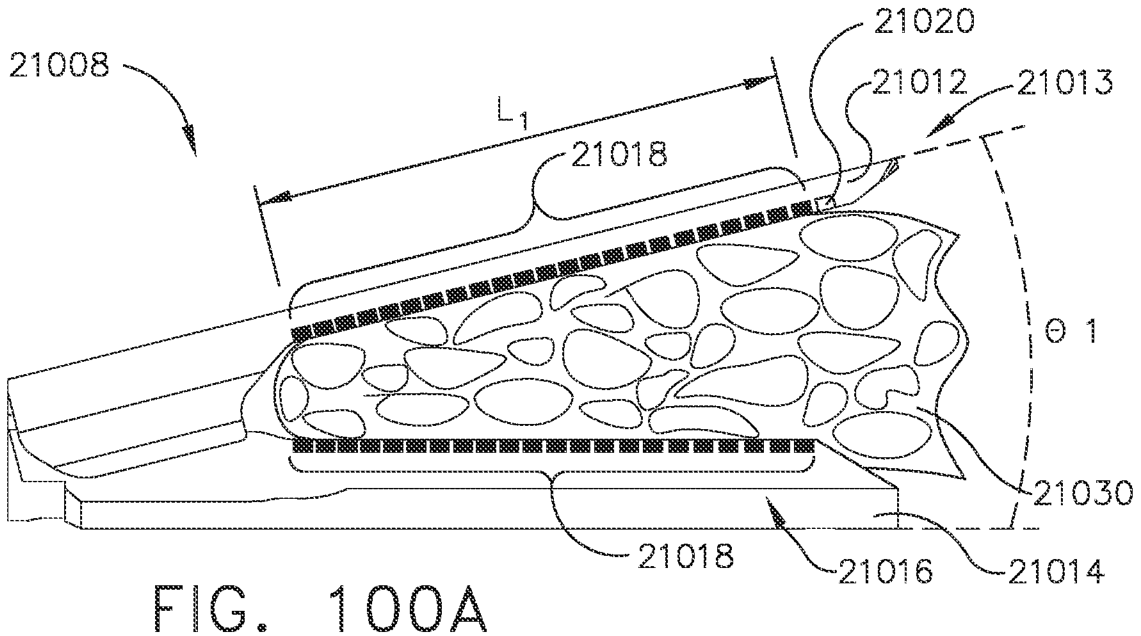

FIG. 100A illustrates a side elevational view of an end effector grasping parenchyma, wherein the end effector is at the initial contact position with the parenchyma, in accordance with at least one aspect of the present disclosure.

Figure 100B:
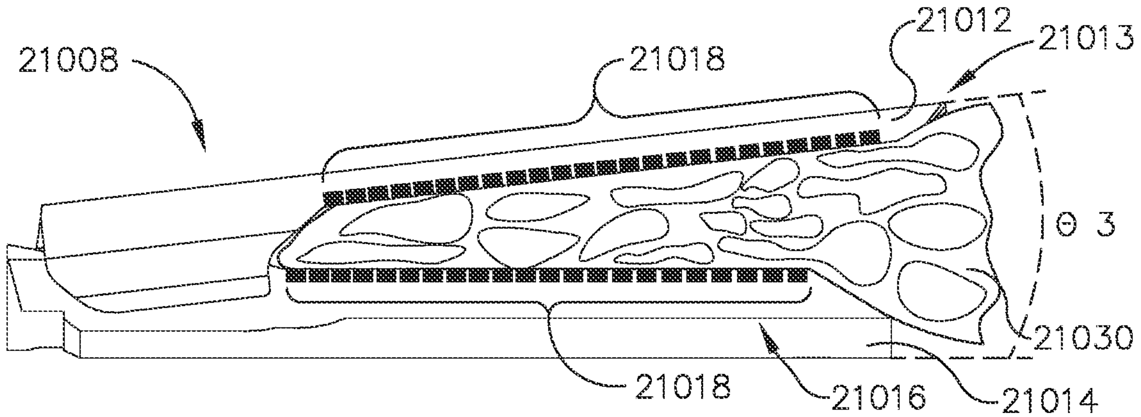

FIG. 100B illustrates a side elevational view of an end effector grasping parenchyma, wherein the end effector is closed, in accordance with at least one aspect of the present disclosure.

Figure 101A:
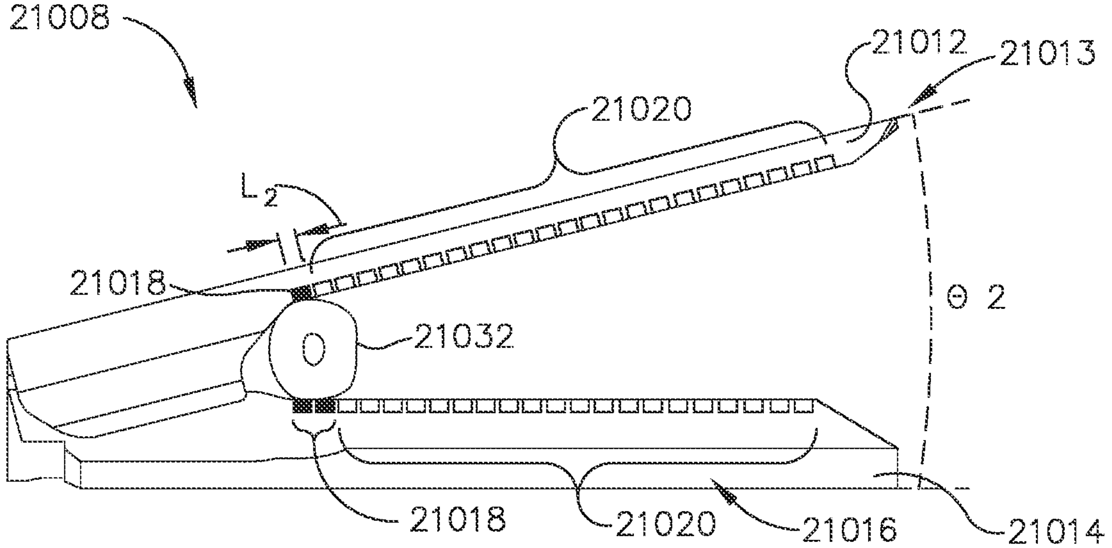

FIG. 101A illustrates a side elevational view of an end effector grasping a vessel, wherein the end effector is at the initial contact position with the vessel, in accordance with at least one aspect of the present disclosure.

Figure 101B:
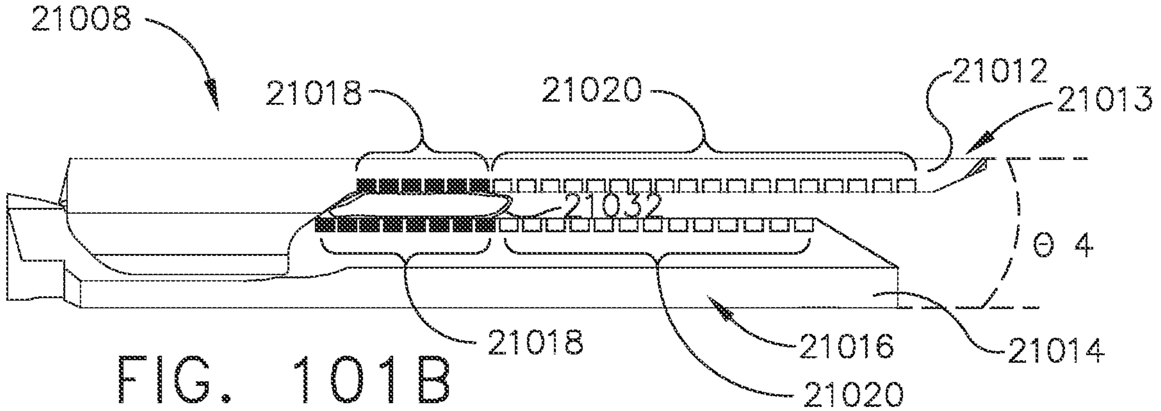

FIG. 101B illustrates a side elevational view of an end effector grasping a vessel, wherein the end effector is closed, in accordance with at least one aspect of the present disclosure.

Figure 102:
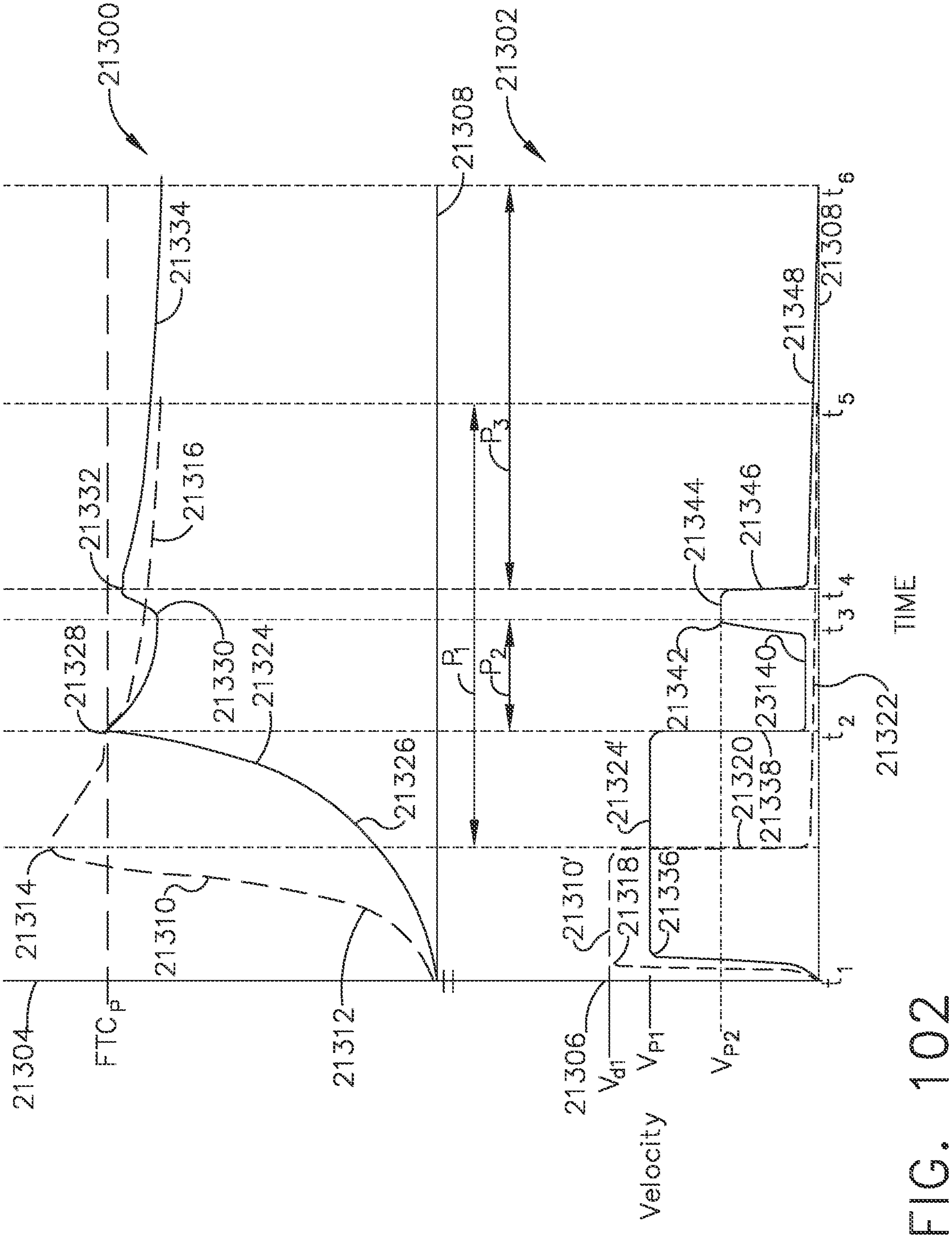

FIG. 102 illustrates a first graph and a second graph depicting end effector force to close and closure velocity, respectively, verse time for illustrative firings of a surgical instrument grasping parenchyma, in accordance with at least one aspect of the present disclosure.

Figure 103:
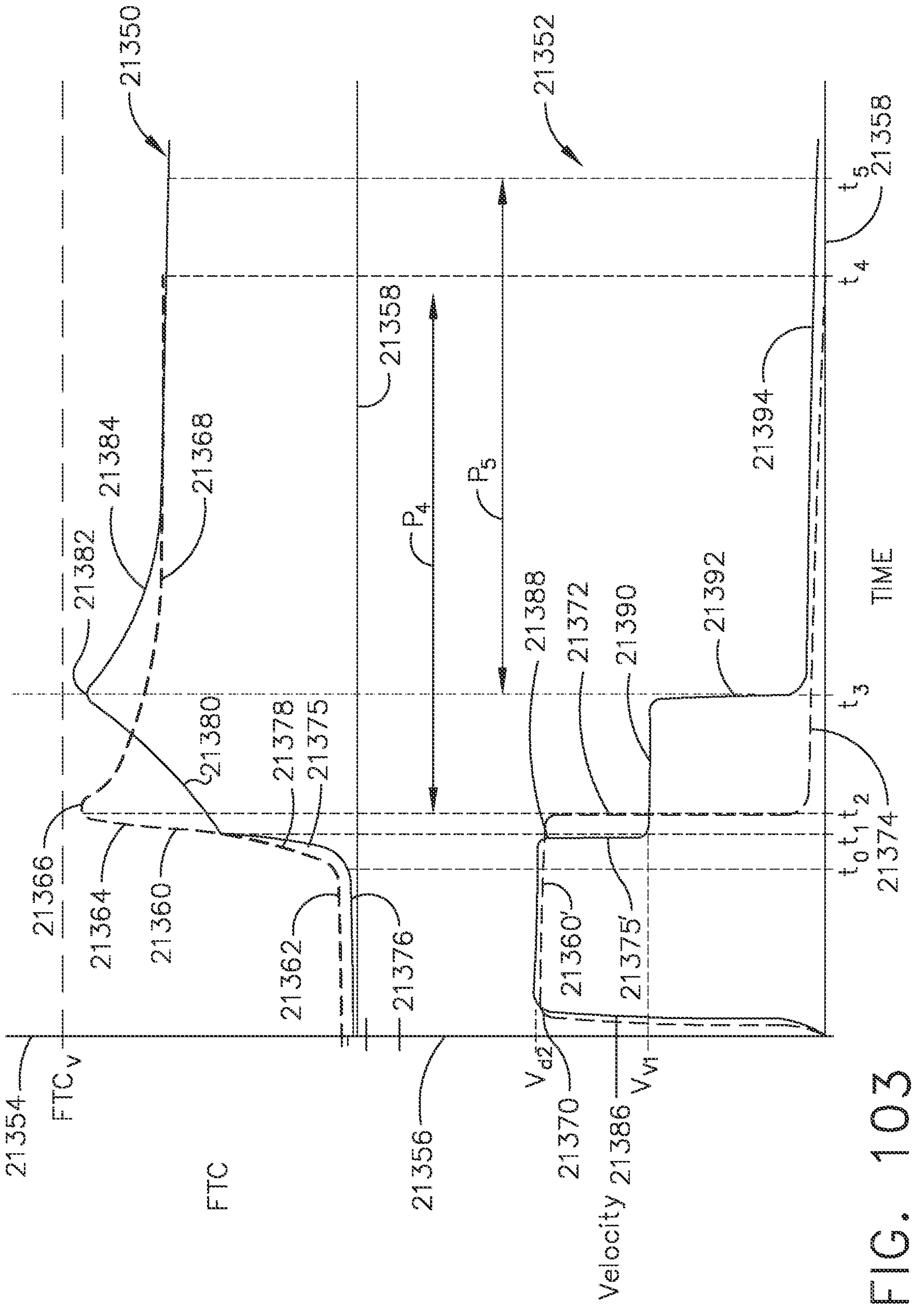

FIG. 103 illustrates a third graph and a fourth graph depicting end effector force to close and closure velocity, respectively, verse time for illustrative firings of a surgical instrument grasping a vessel, in accordance with at least one aspect of the present disclosure.

Figure 104:
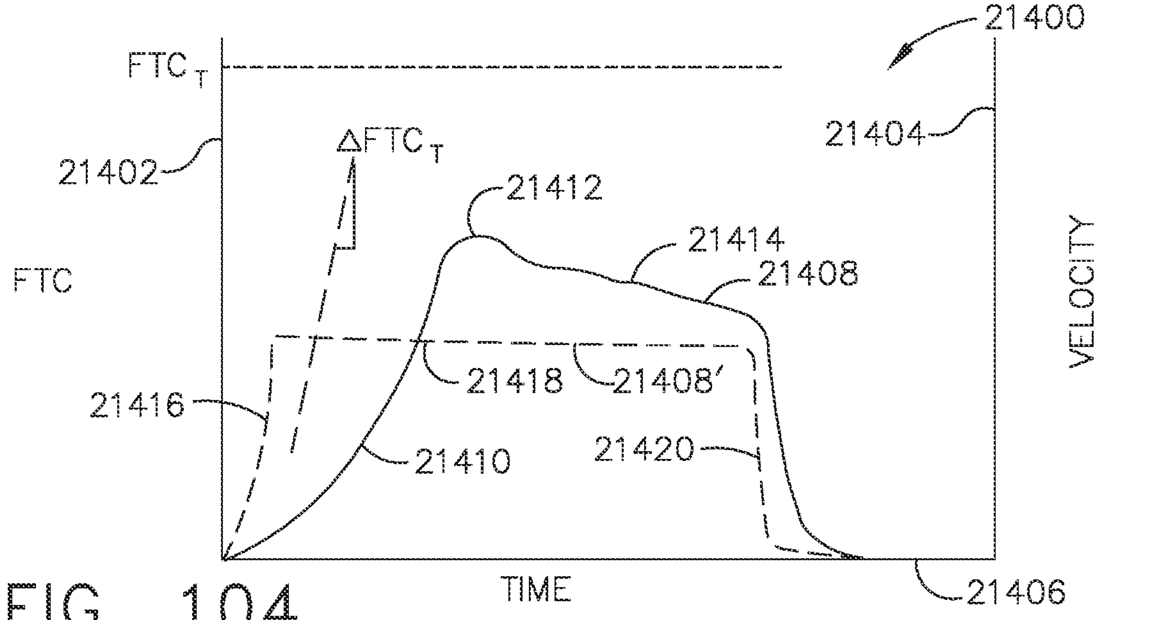

FIG. 104 illustrates a fifth graph depicting end effector force to close and closure velocity verse time for an illustrative firing of a surgical instrument, in accordance with at least one aspect of the present disclosure.

Figure 105:
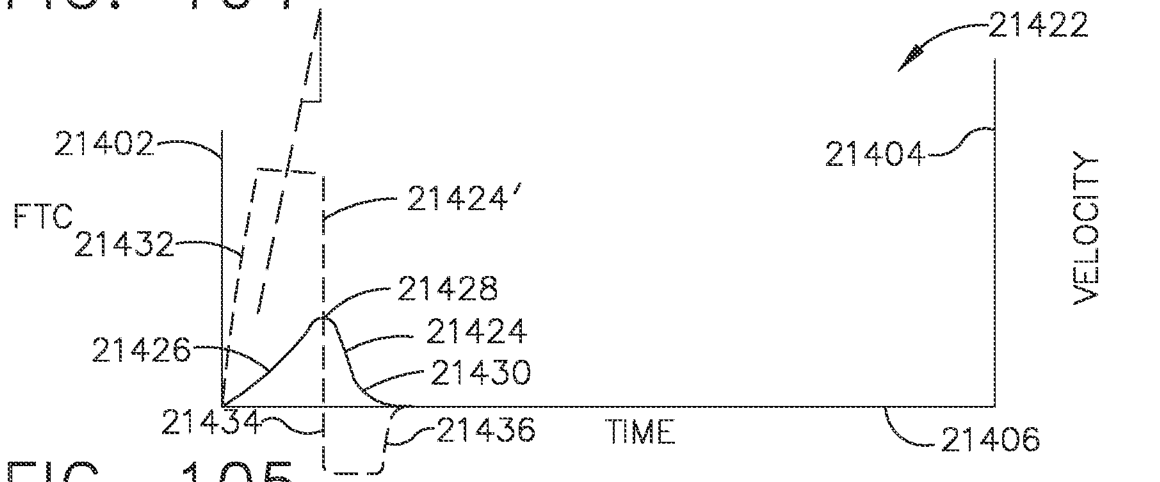

FIG. 105 illustrates a fifth graph depicting end effector force to close and closure velocity verse time for an illustrative firing of a surgical instrument, in accordance with at least one aspect of the present disclosure.

Figure 106:
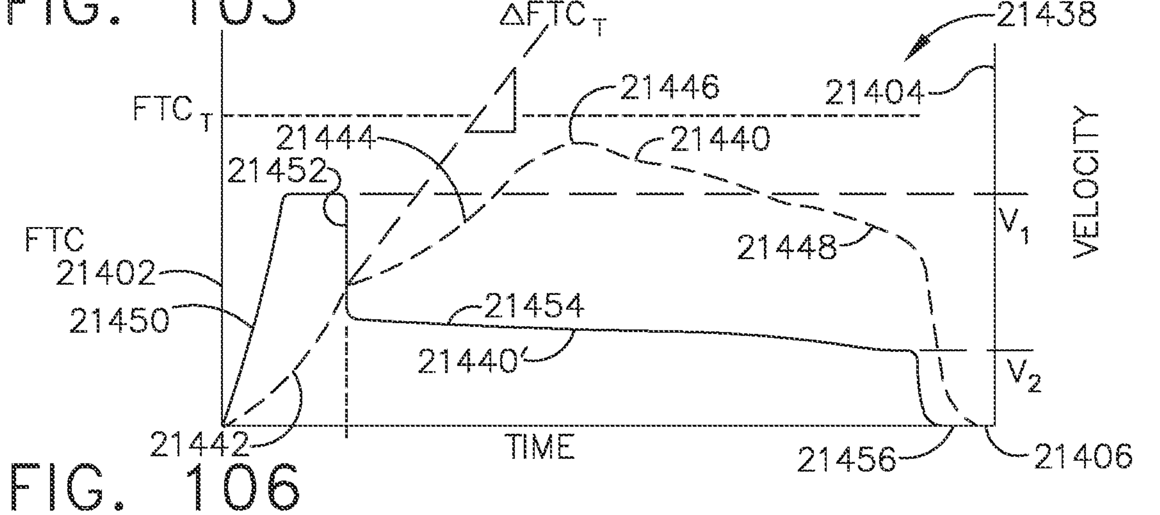

FIG. 106 illustrates a fifth graph depicting end effector force to close and closure velocity verse time for an illustrative firing of a surgical instrument, in accordance with at least one aspect of the present disclosure.

Figure 107:
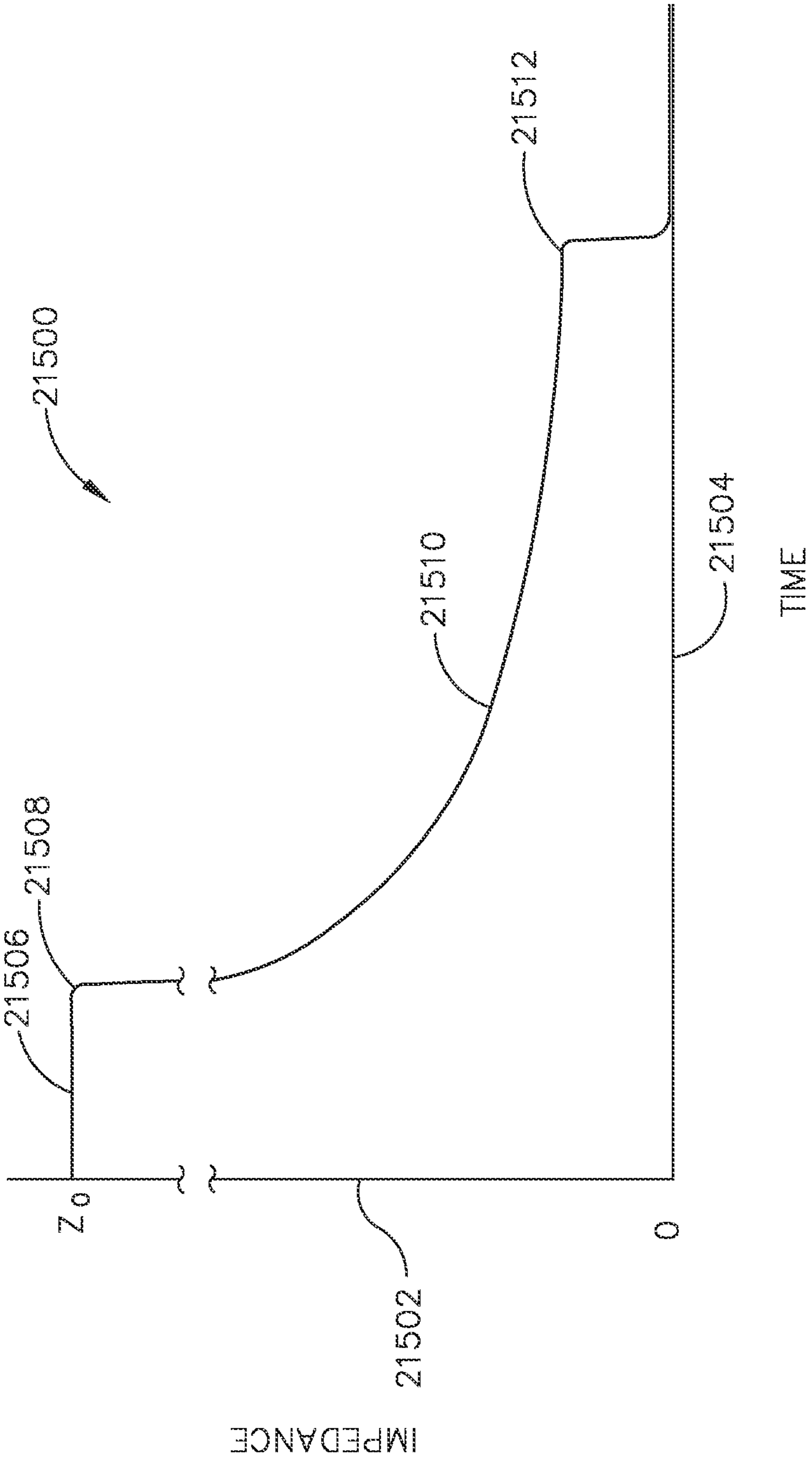

FIG. 107 illustrates a graph depicting impedance verse time to determine when the jaws of a surgical instrument contact tissue and/or staples, in accordance with at least one aspect of the present disclosure.

Figure 108:
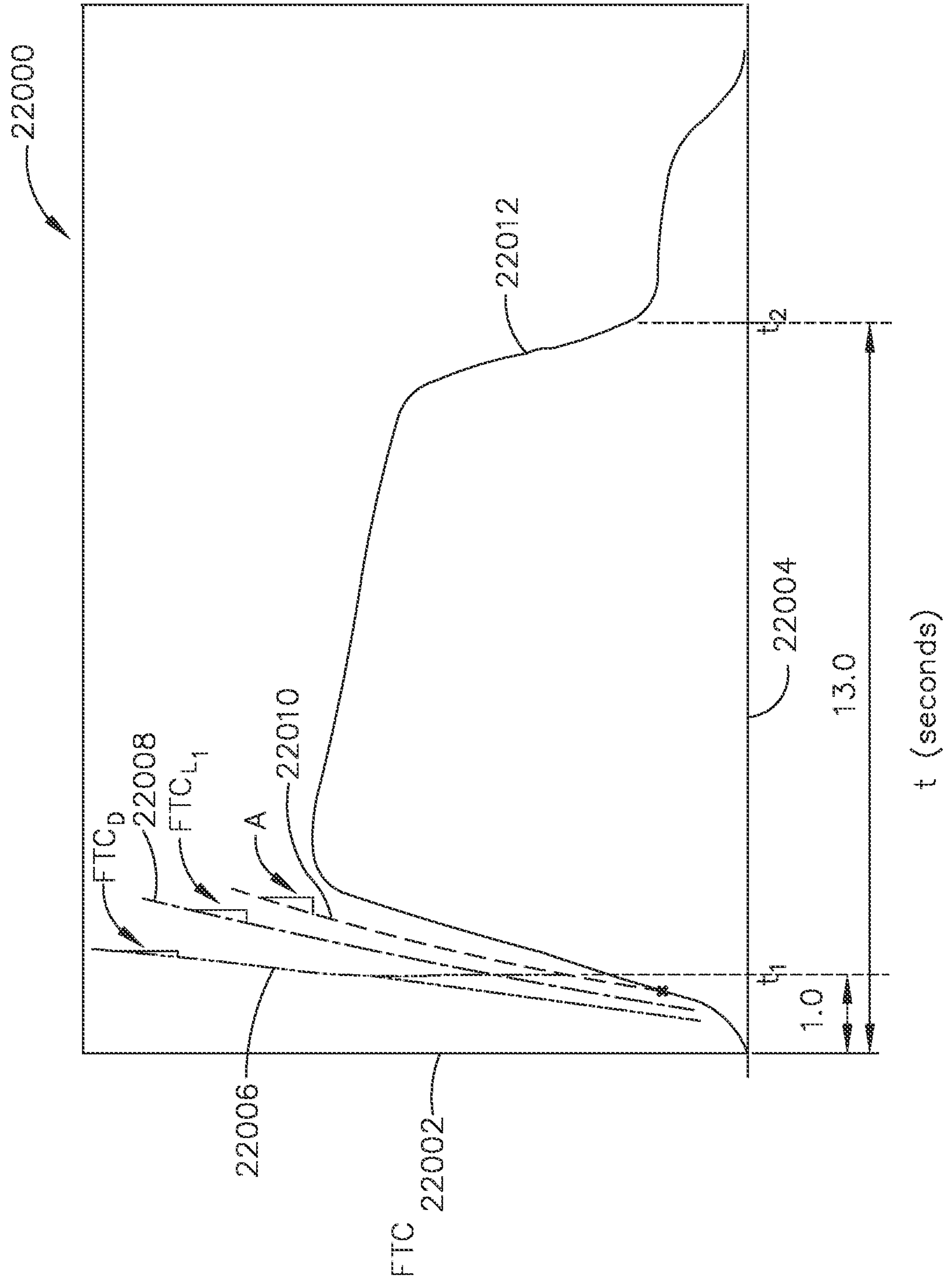

FIG. 108 illustrates a first graph depicting various tissue closure thresholds for controlling end effector closure, in accordance with at least one aspect of the present disclosure.

Figure 109:
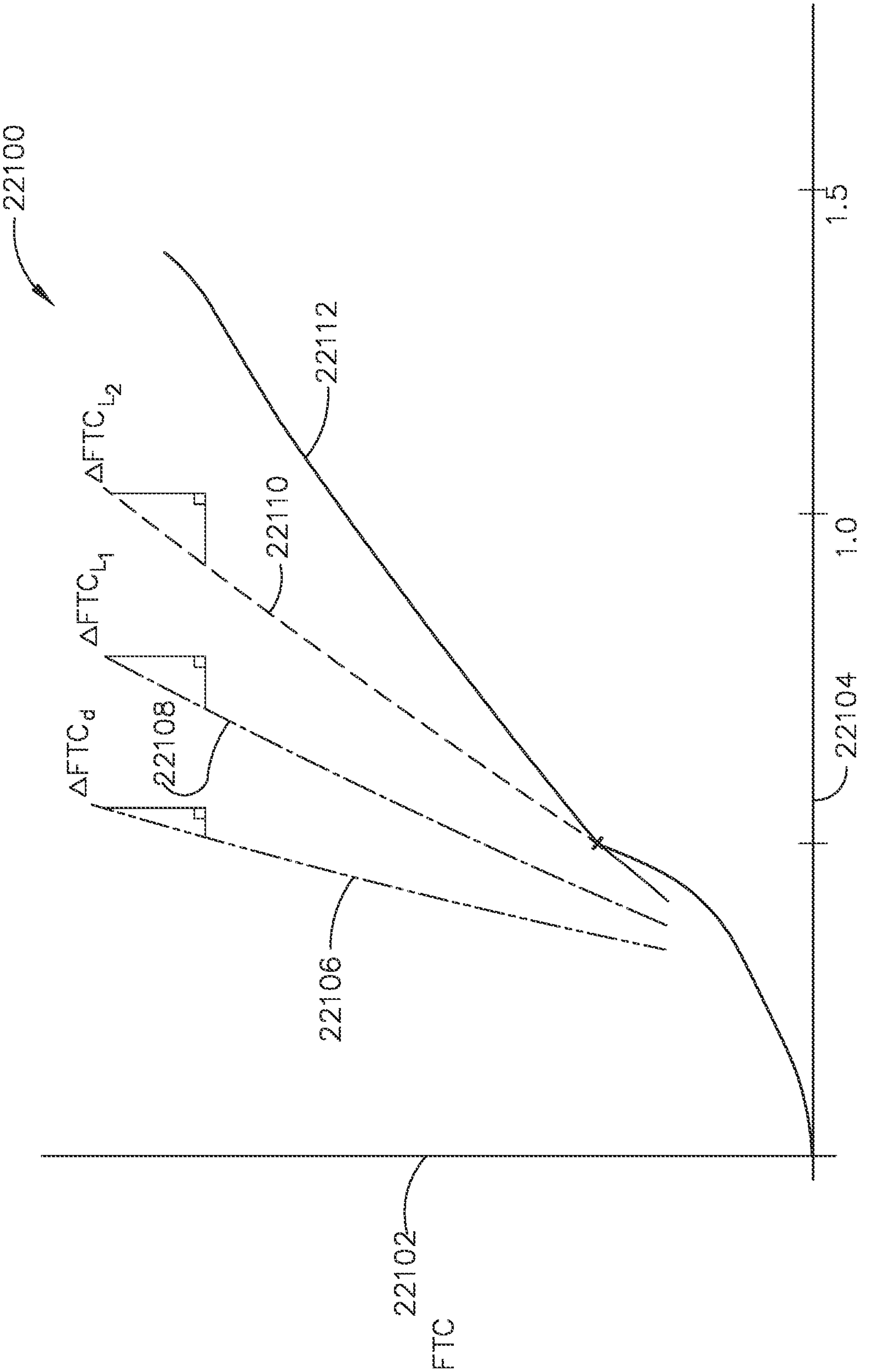

FIG. 109 illustrates a second graph depicting various tissue closure thresholds for controlling end effector closure, in accordance with at least one aspect of the present disclosure.

Figure 110:
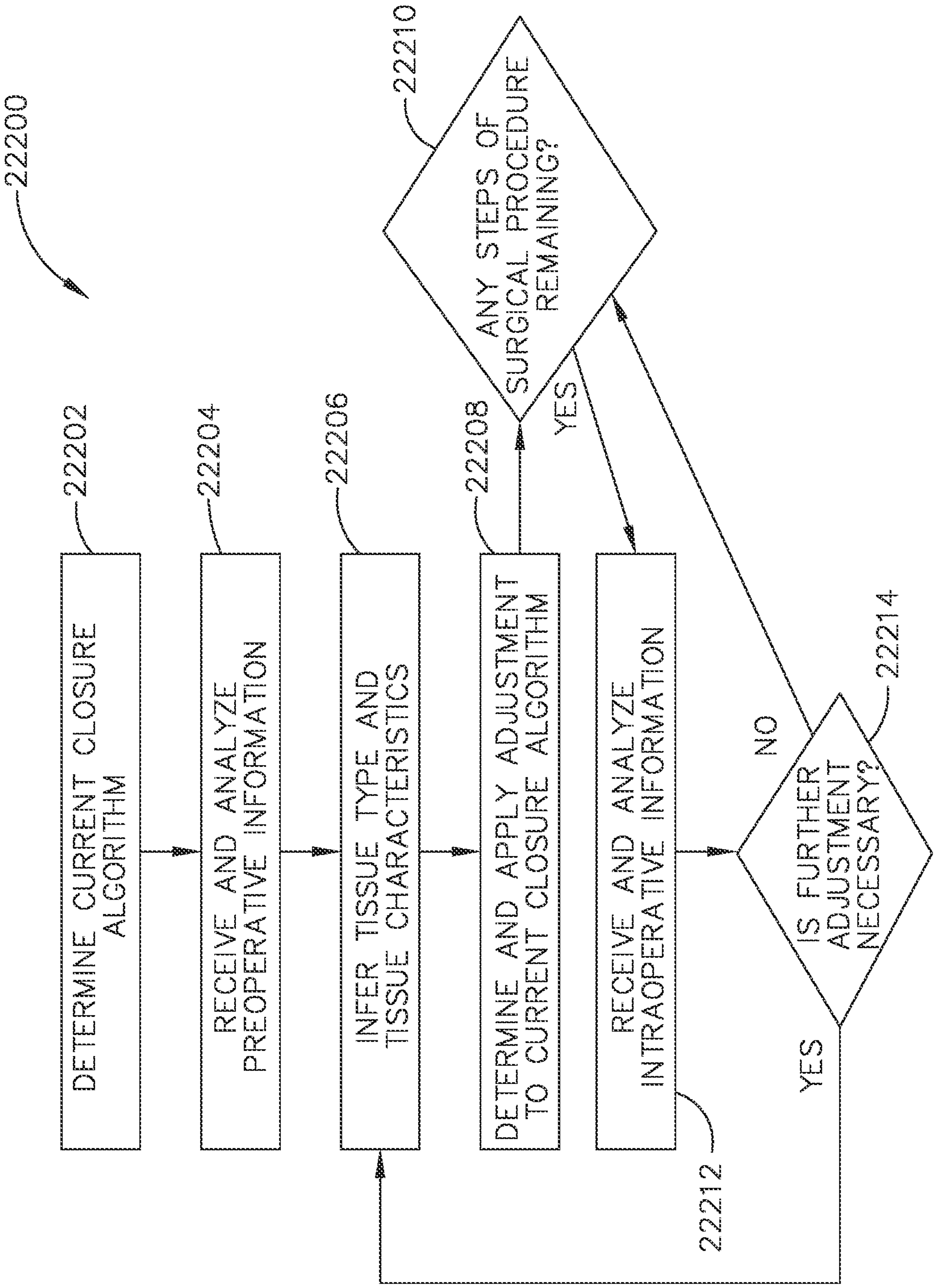

FIG. 110 is a logic flow diagram depicting a process of a control program or a logic configuration for adjusting a closure rate algorithm, in accordance with at least one aspect of the present disclosure.

Figure 111:
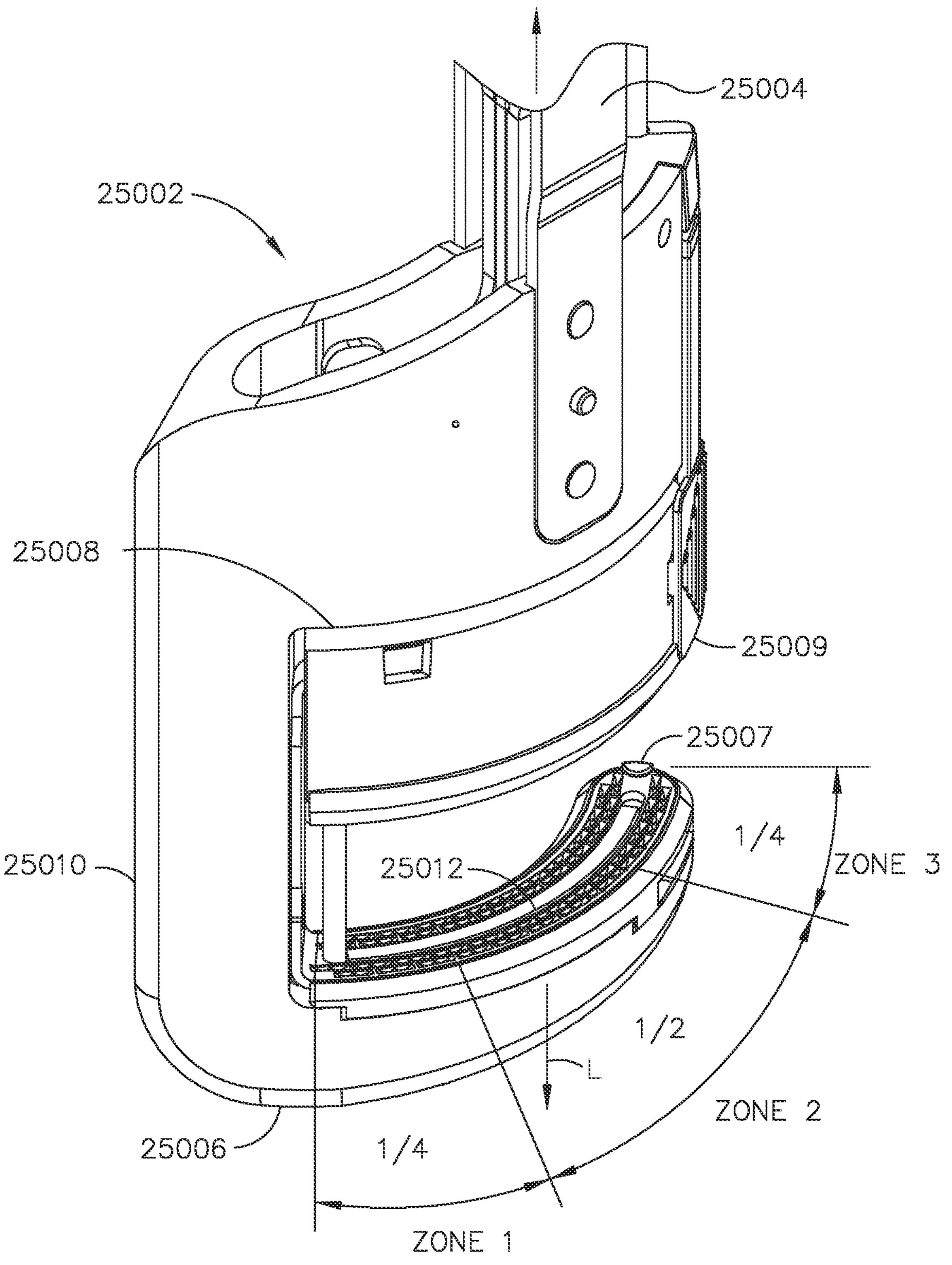

FIG. 111 illustrates a perspective view of an end effector of a curved surgical stapling and cutting instrument including predetermined zones, in accordance with at least one aspect of the present disclosure.

Figure 112:
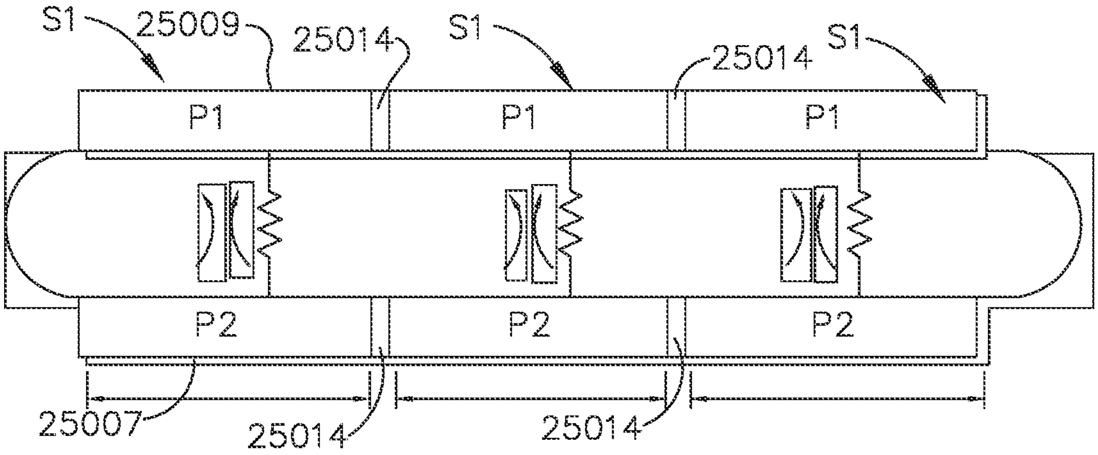

FIG. 112 illustrates a straightened partial cross-sectional of the end effector of the curved surgical stapling and cutting instrument of FIG. 111 with tissue grasped by the end effector, in accordance with at least one aspect of the present disclosure.

Figure 113:
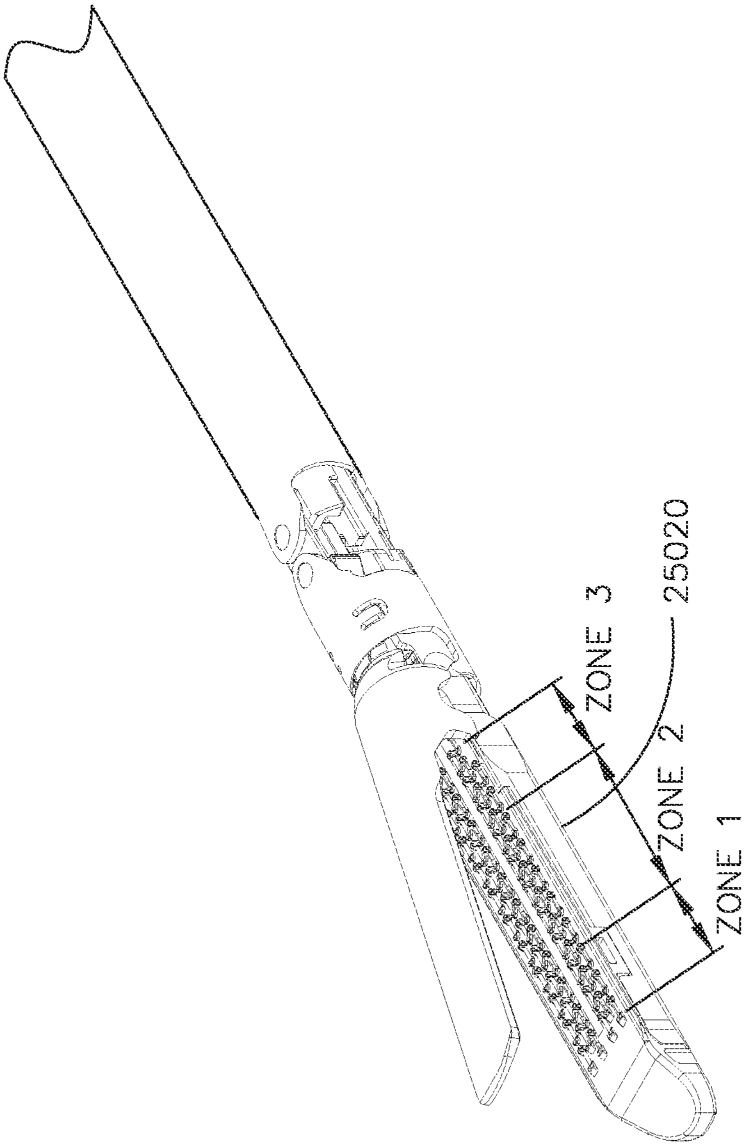

FIG. 113 illustrates a perspective view of an end effector of a surgical stapling and cutting instrument including predetermined zones, in accordance with at least one aspect of the present disclosure, in accordance with at least one aspect of the present disclosure.

Figure 114:
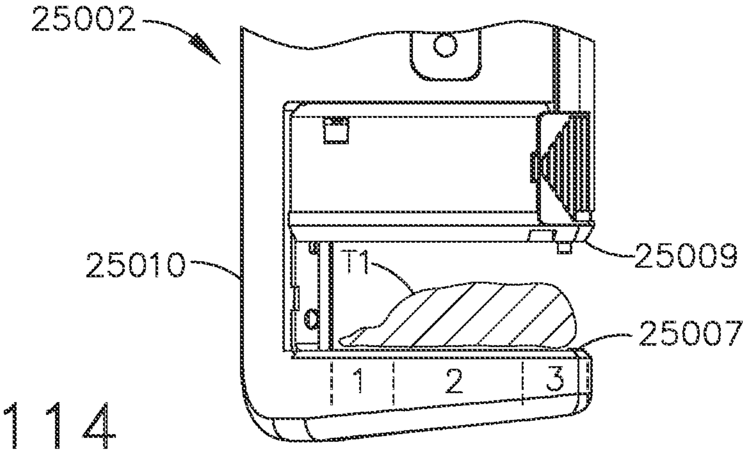

FIG. 114 illustrates a straightened partial cross-sectional of the end effector of the curved surgical stapling and cutting instrument of FIG. 111 with a tissue disposed between jaws of the end effector, in accordance with at least one aspect of the present disclosure.

Figure 115:
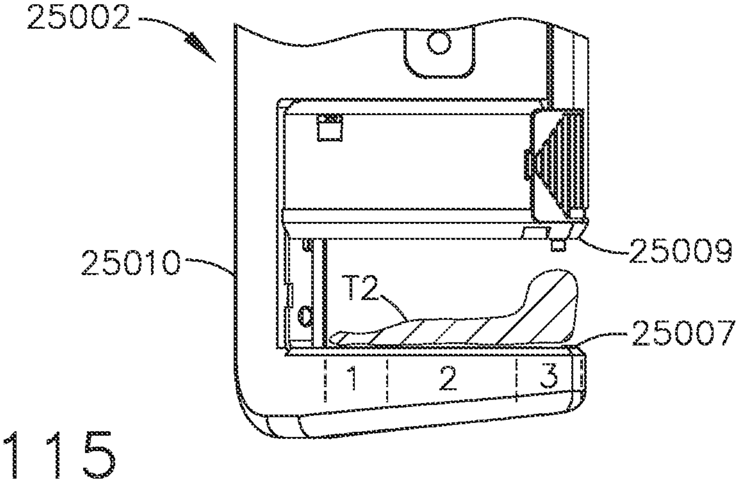

FIG. 115 illustrates a straightened partial cross-sectional of the end effector of the curved surgical stapling and cutting instrument of FIG. 111 with a tissue disposed between jaws of the end effector, in accordance with at least one aspect of the present disclosure.

Figure 116:
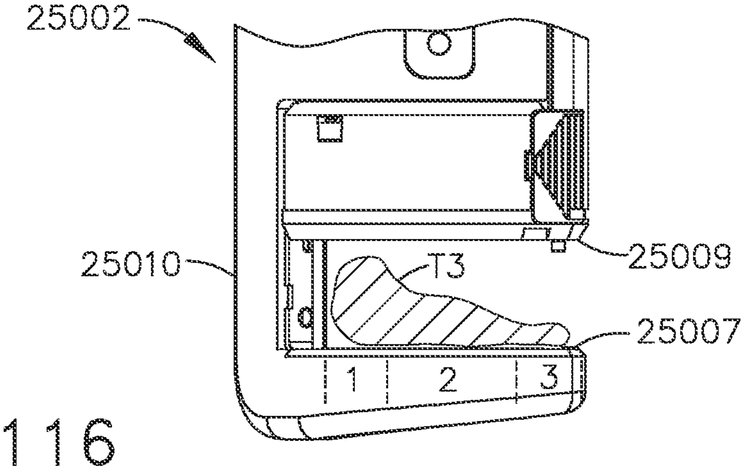

FIG. 116 illustrates a straightened partial cross-sectional of the end effector of the curved surgical stapling and cutting instrument of FIG. 111 with a tissue disposed between jaws of the end effector, in accordance with at least one aspect of the present disclosure.

Figure 117:
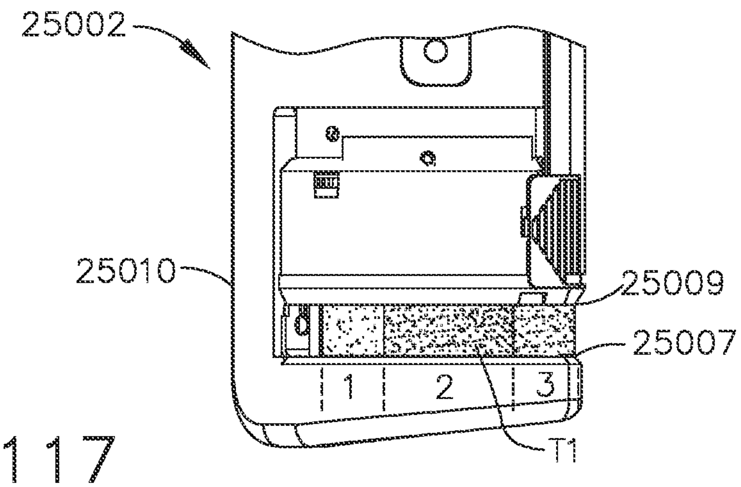

FIG. 117 illustrates the tissue of FIG. 114 being grasped by the end effector of FIG. 111, in accordance with at least one aspect of the present disclosure.

Figure 118:
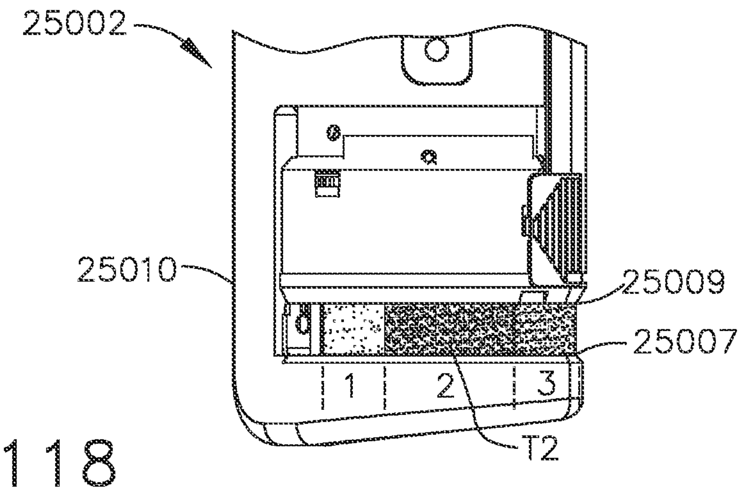

FIG. 118 illustrates the tissue of FIG. 115 being grasped by the end effector of FIG. 111, in accordance with at least one aspect of the present disclosure.

Figure 119:
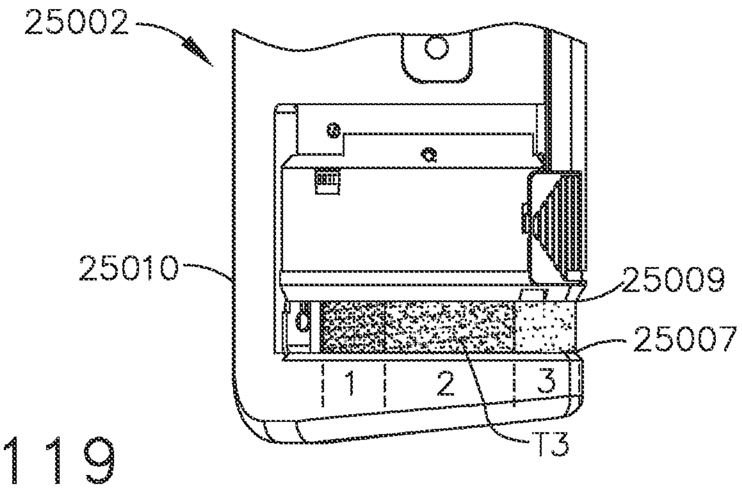

FIG. 119 illustrates the tissue of FIG. 116 being grasped by the end effector of FIG. 111, in accordance with at least one aspect of the present disclosure.

Figure 120:
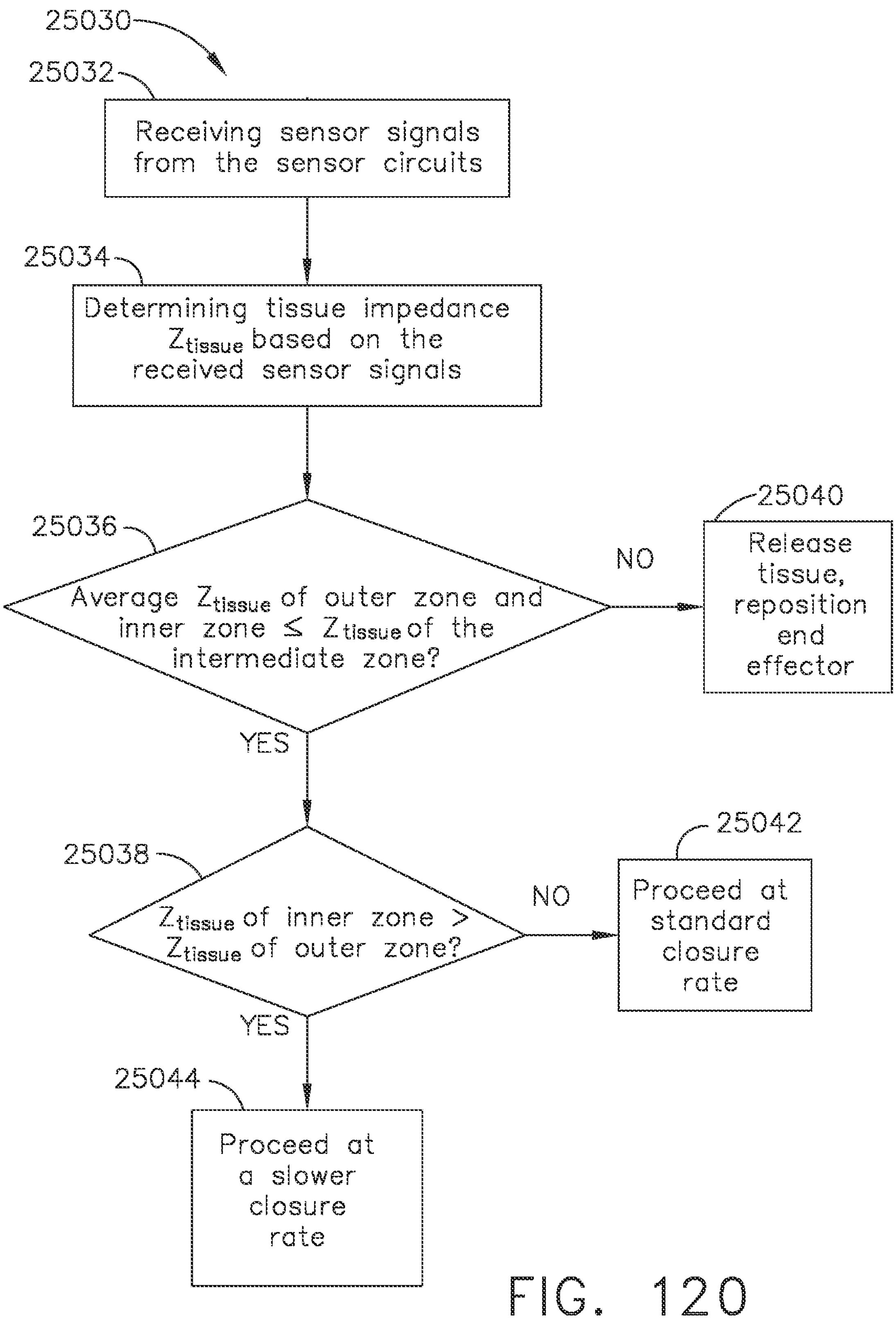

FIG. 120 illustrates a logic flow diagram of a process depicting a control program or a logic configuration for identifying irregularities in tissue distribution within an end effector of a surgical instrument, in accordance with at least one aspect of the present disclosure.

Figure 121:
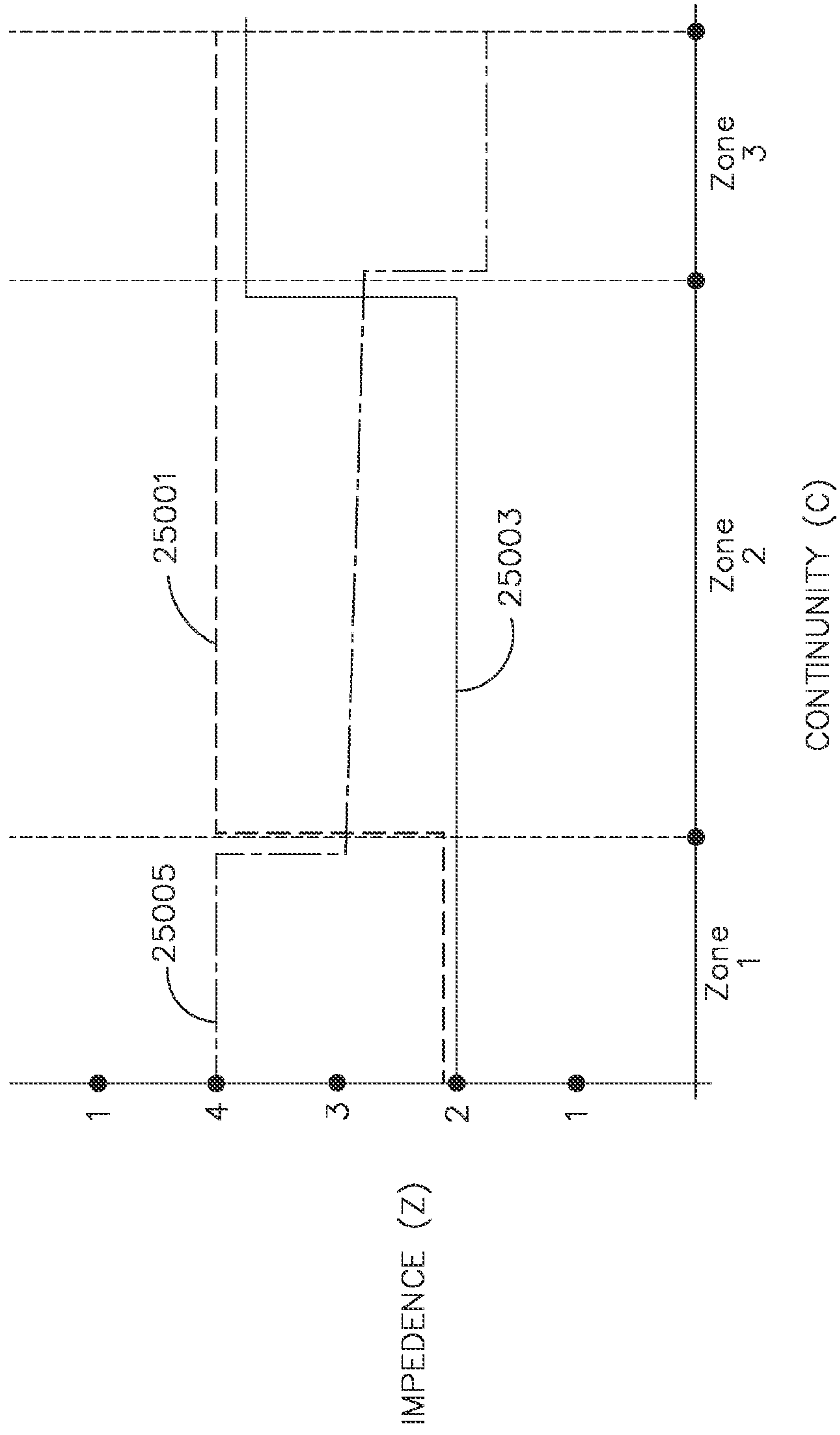

FIG. 121 is a graph representing tissue impedance measurements at the three predetermined of the end effector of FIG. 111 over time, in accordance with at least one aspect of the present disclosure.

Figure 122:
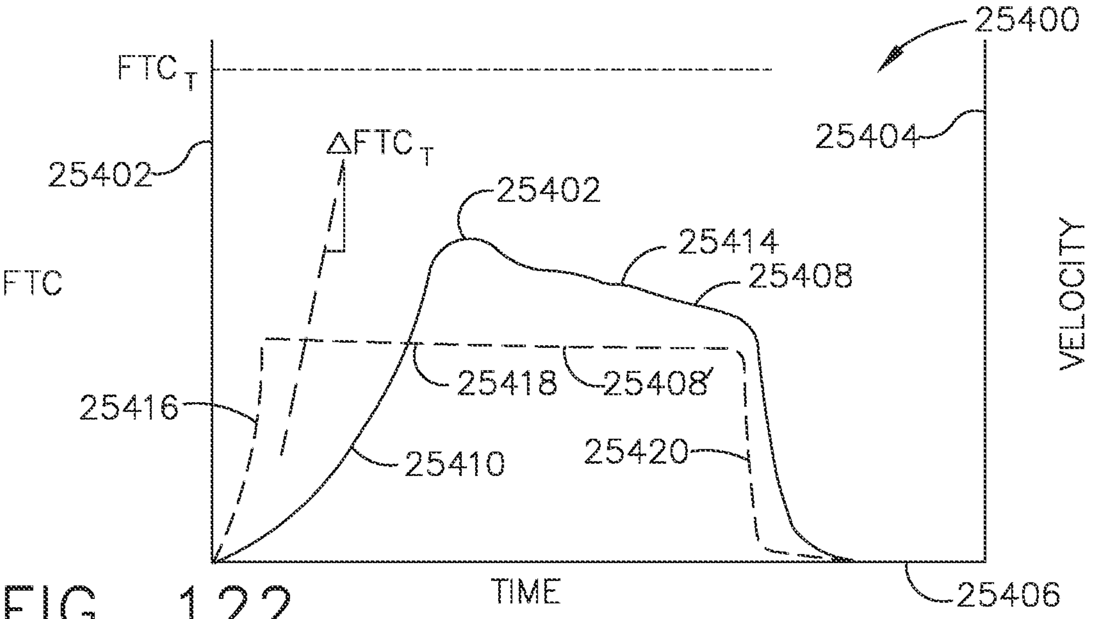

FIG. 122 is a graph representing Force-To-Close the end effector of FIG. 111 around the tissue of FIG. 114 and motor speed of a motor effecting the end effector closure plotted against time, in accordance with at least one aspect of the present disclosure.

Figure 123:
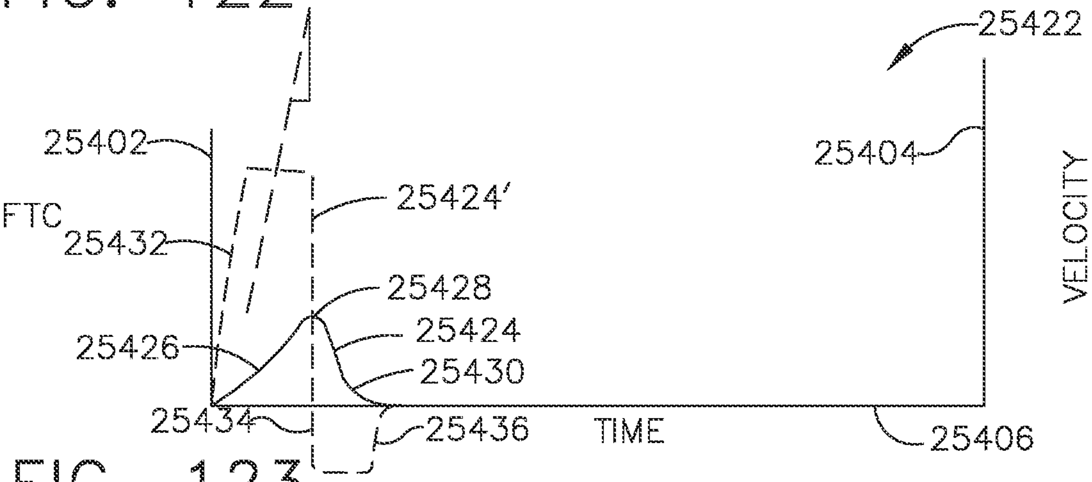

FIG. 123 is a graph representing Force-To-Close the end effector of FIG. 111 around the tissue of FIG. 115 and motor speed of a motor effecting the end effector closure plotted against time, in accordance with at least one aspect of the present disclosure.

Figure 124:
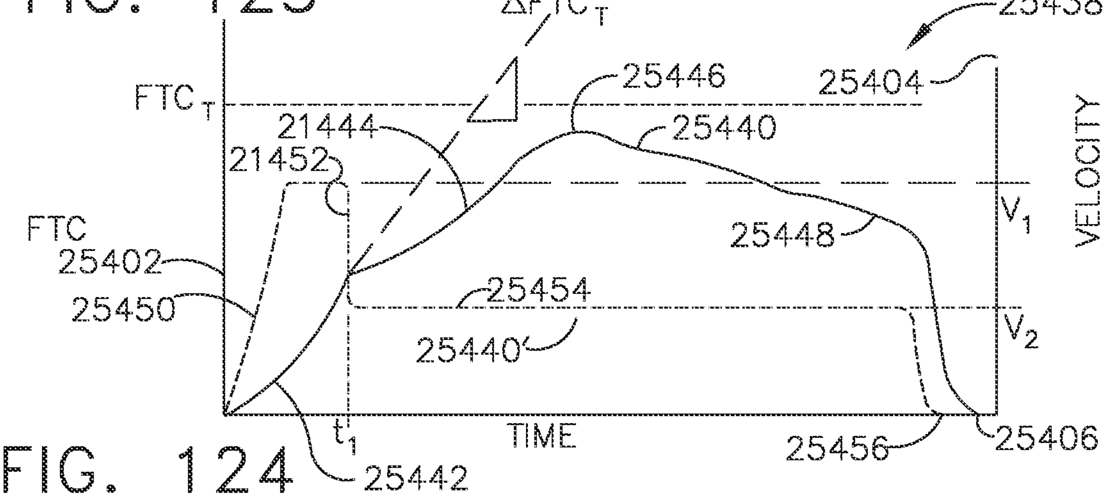

FIG. 124 is a graph representing Force-To-Close the end effector of FIG. 111 around the tissue of FIG. 116 and motor speed of a motor effecting the end effector closure plotted against time, in accordance with at least one aspect of the present disclosure.

Figure 125:
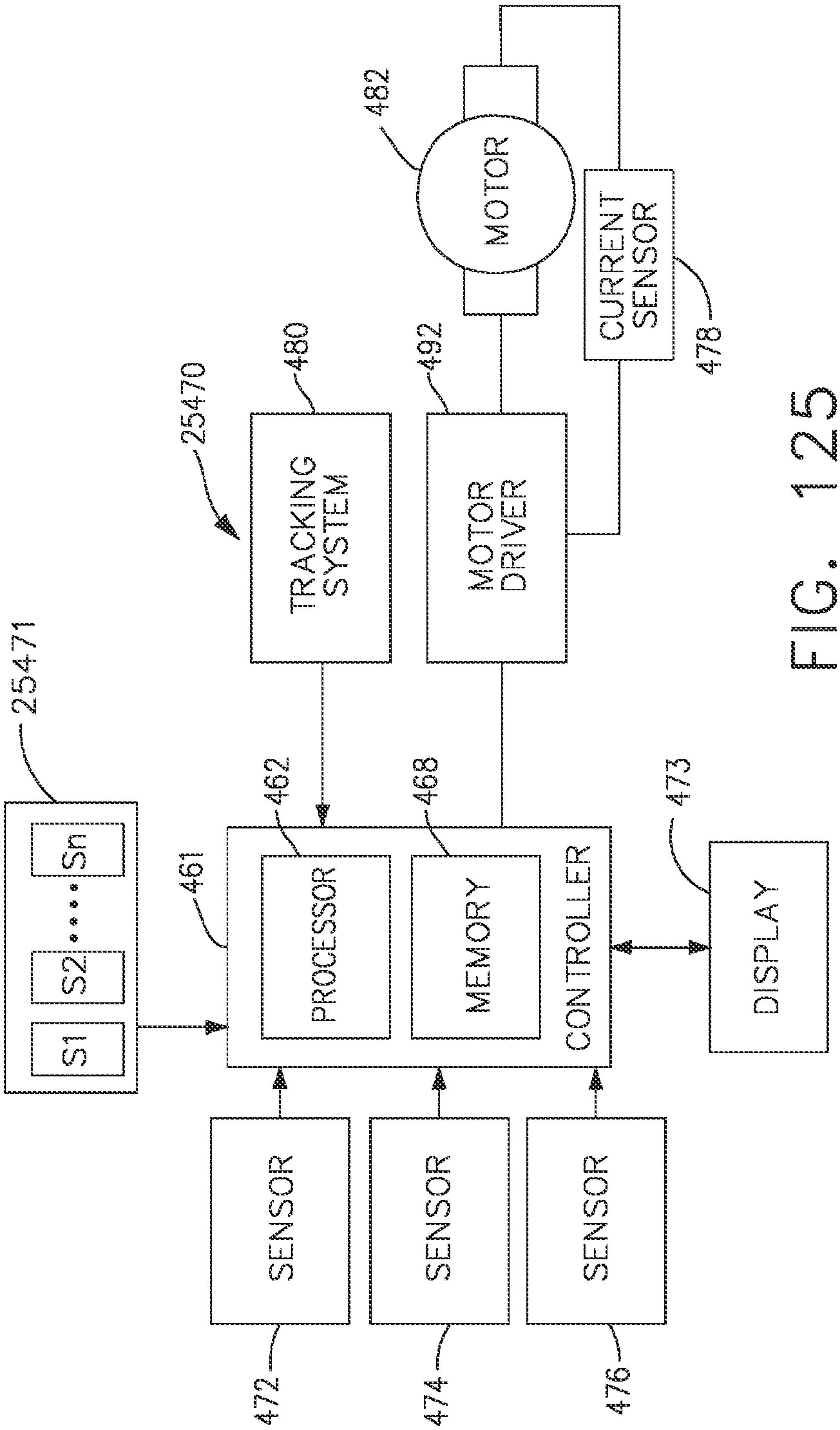

FIG. 125 illustrates a control system of a surgical instrument, in accordance with at least one aspect of the present disclosure.

Figure 126:
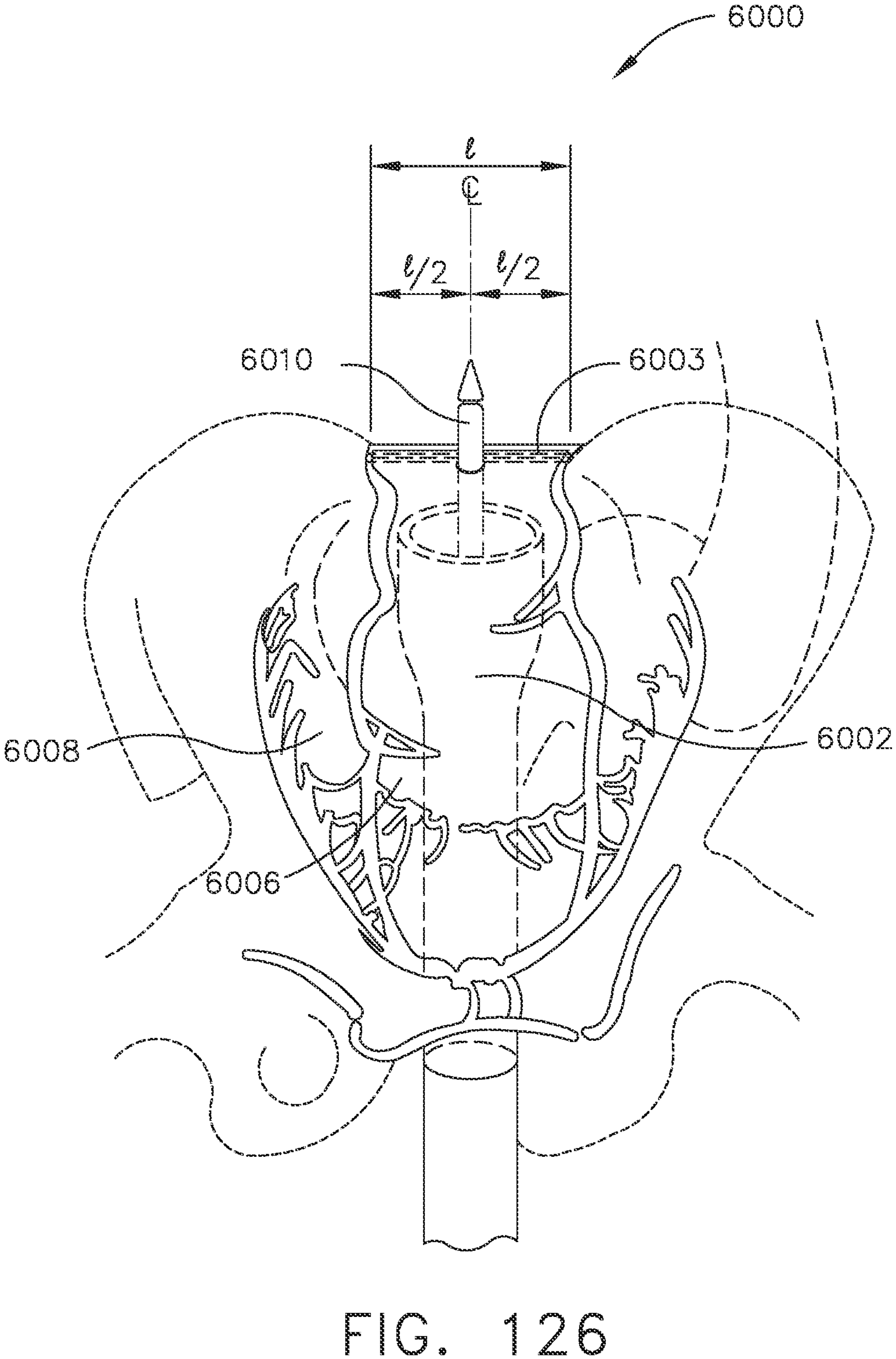

FIG. 126 illustrates a diagram of a surgical instrument centered on a linear staple transection line using the benefit of centering tools and techniques described in connection with FIGS. 127-129, in accordance with at least one aspect of the present disclosure.

Figures 127, 128, 129:
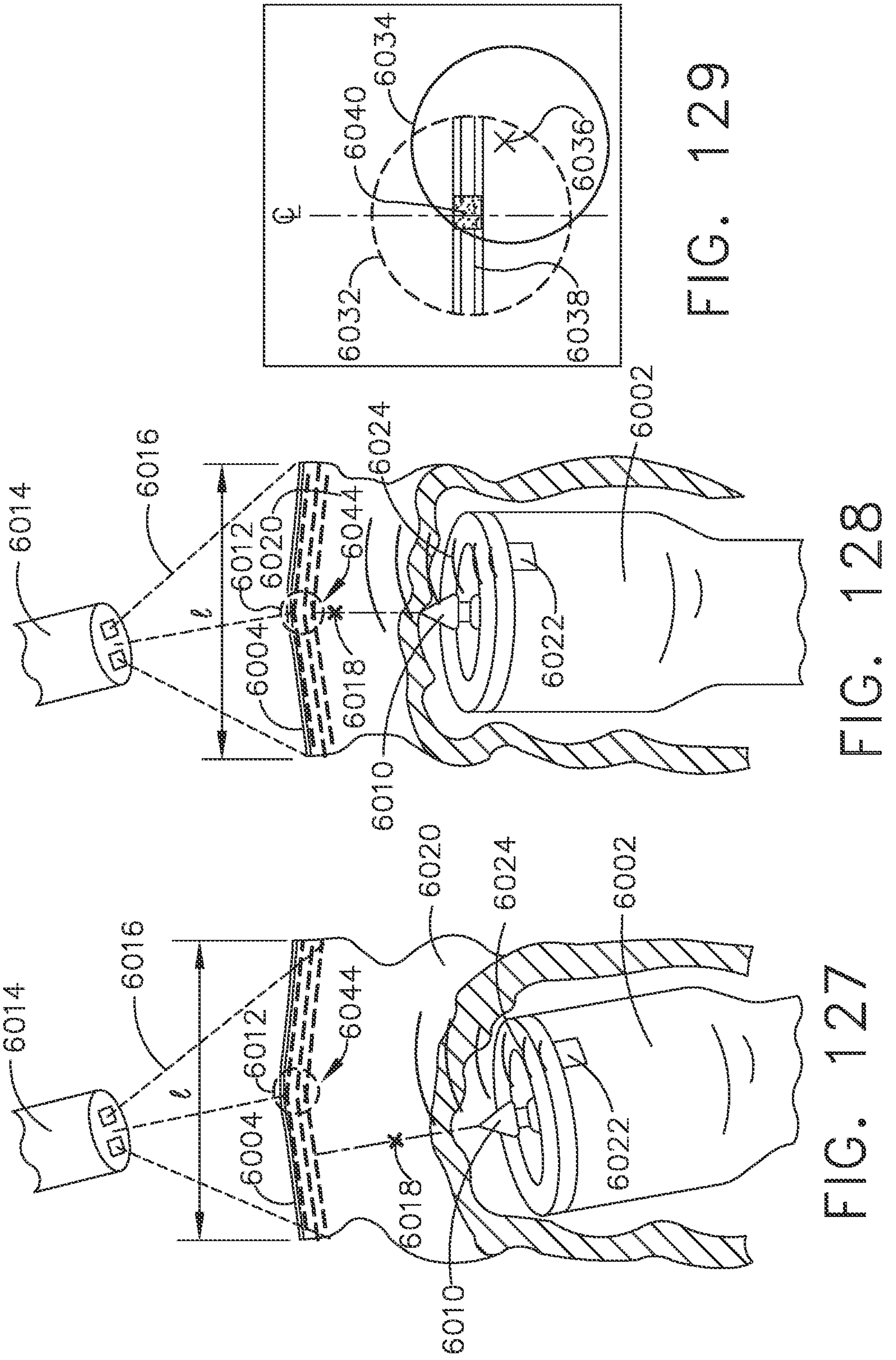

FIGS. 127-129 illustrate a process of aligning an anvil trocar of a circular stapler to a staple overlap portion of a linear staple line created by a double-stapling technique, in accordance with at least one aspect of the present disclosure, where:

FIG. 127 illustrates an anvil trocar of a circular stapler that is not aligned with a staple overlap portion of a linear staple line created by a double-stapling technique;

FIG. 128 illustrates an anvil trocar of a circular stapler that is aligned with the center of the staple overlap portion of the linear staple line created by a double-stapling technique; and FIG. 129 illustrates a centering tool displayed on a surgical hub display showing a staple overlap portion of a linear staple line created by a double-stapling technique to be cut out by a circular stapler, where the anvil trocar is not aligned with the staple overlap portion of the double staple line as shown in FIG. 127.

Figure 131:
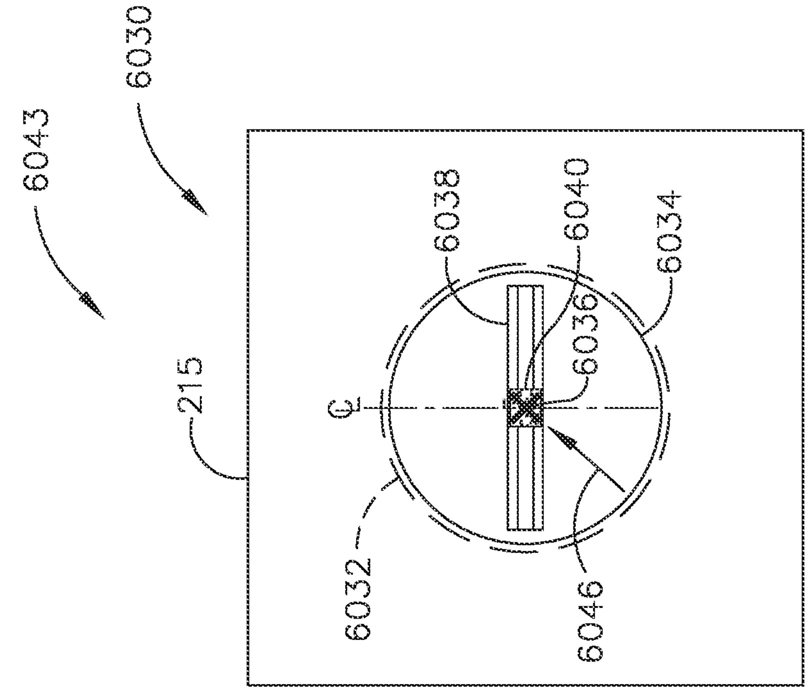
Figure 130:
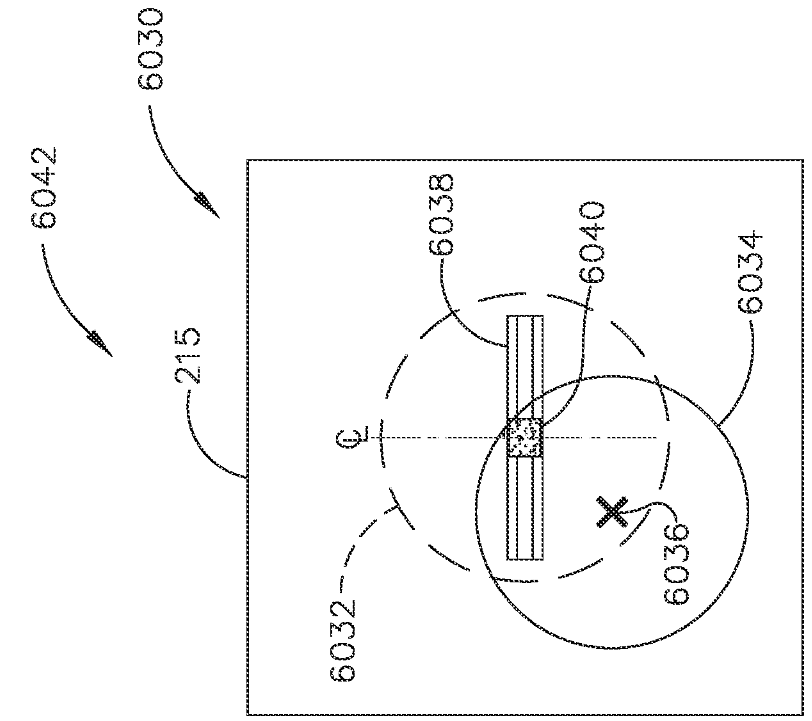

FIGS. 130 and 131 illustrate a before image and an after image of a centering tool, in accordance with at least one aspect of the present disclosure, where:

FIG. 130 illustrates an image of a projected cut path of an anvil trocar and circular knife before alignment with the target alignment ring circumscribing the image of the linear staple line over the image of the staple overlap portion presented on a surgical hub display;

FIG. 131 illustrates an image of a projected cut path of an anvil trocar and circular knife after alignment with the target alignment ring circumscribing the image of the linear staple line over the image of the staple overlap portion presented on a surgical hub display.

Figure 134:
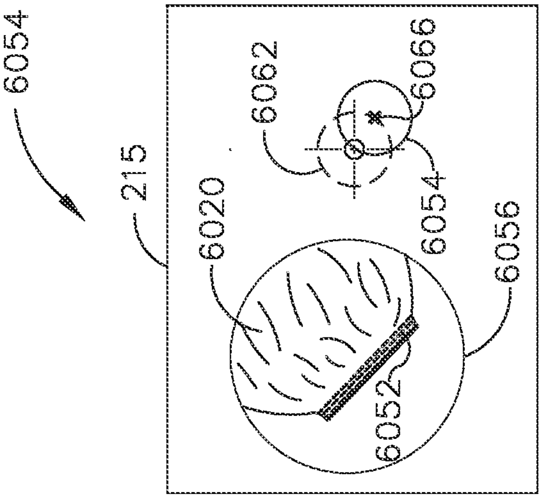
Figure 133:
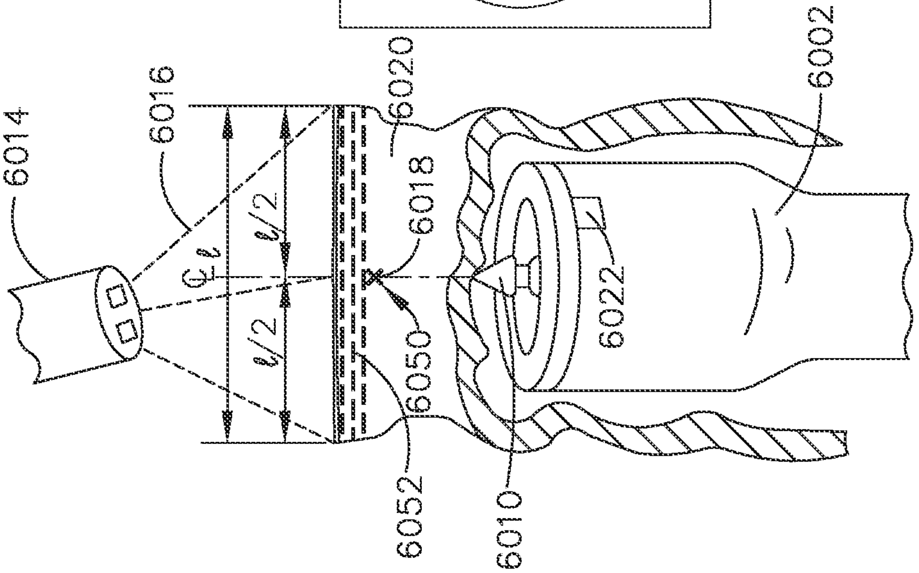
Figure 132:
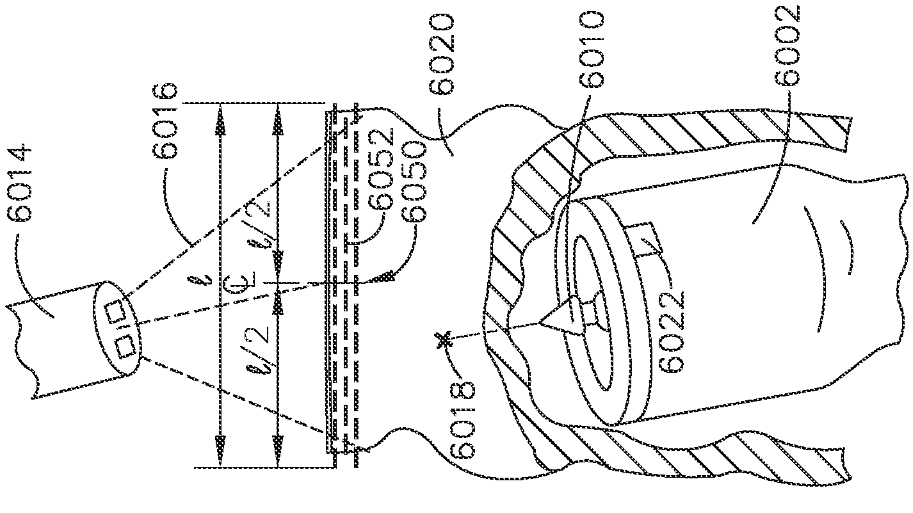

FIGS. 132-134 illustrate a process of aligning an anvil trocar of a circular stapler to a center of a linear staple line, in accordance with at least one aspect of the present disclosure, where:

FIG. 132 illustrates the anvil trocar out of alignment with the center of the linear staple line;

FIG. 133 illustrates the anvil trocar in alignment with the center of the linear staple line;

FIG. 134 illustrates a centering tool displayed on a surgical hub display of a linear staple line, where the anvil trocar is not aligned with the staple overlap portion of the double staple line as shown in FIG. 132.

Figure 135:
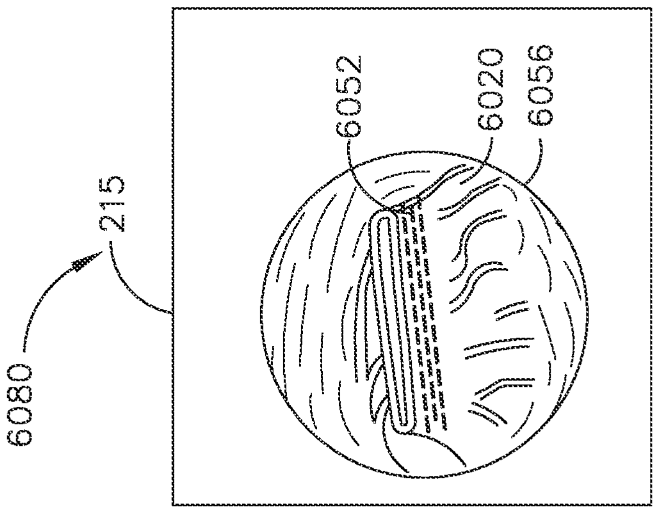

FIG. 135 is an image of a standard reticle field view of a linear staple line transection of a surgical as viewed through a laparoscope displayed on the surgical hub display, in accordance with at least one aspect of the present disclosure.

Figure 136:
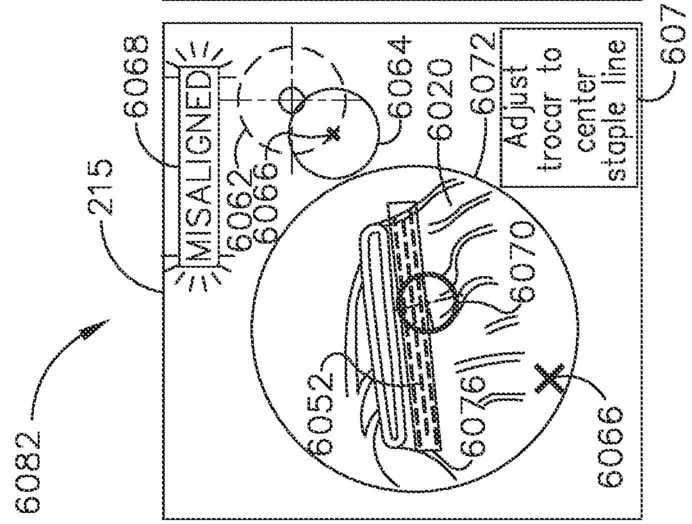

FIG. 136 is an image of a laser-assisted reticle field of view of the surgical site shown in FIG. 135 before the anvil trocar and circular knife of the circular stapler are aligned to the center of the linear staple line, in accordance with at least one aspect of the present disclosure.

Figure 137:
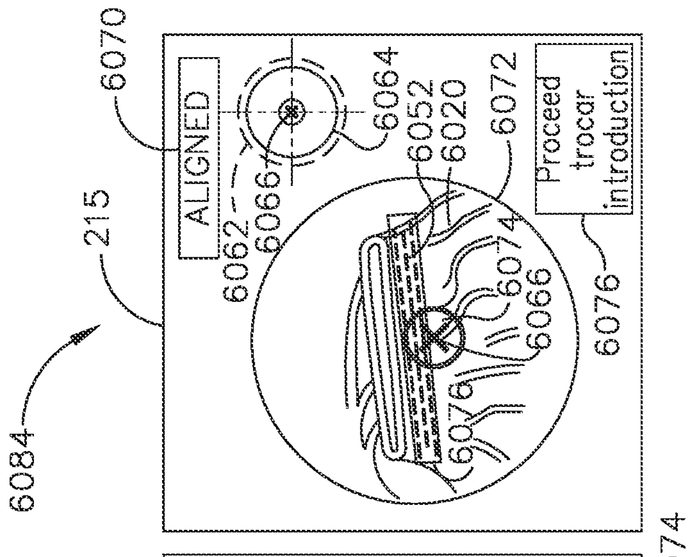

FIG. 137 is an image of a laser-assisted reticle field of view of the surgical site shown in FIG. 136 after the anvil trocar and circular knife of the circular stapler are aligned to the center of the linear staple line, in accordance with at least one aspect of the present disclosure.

Figure 138:
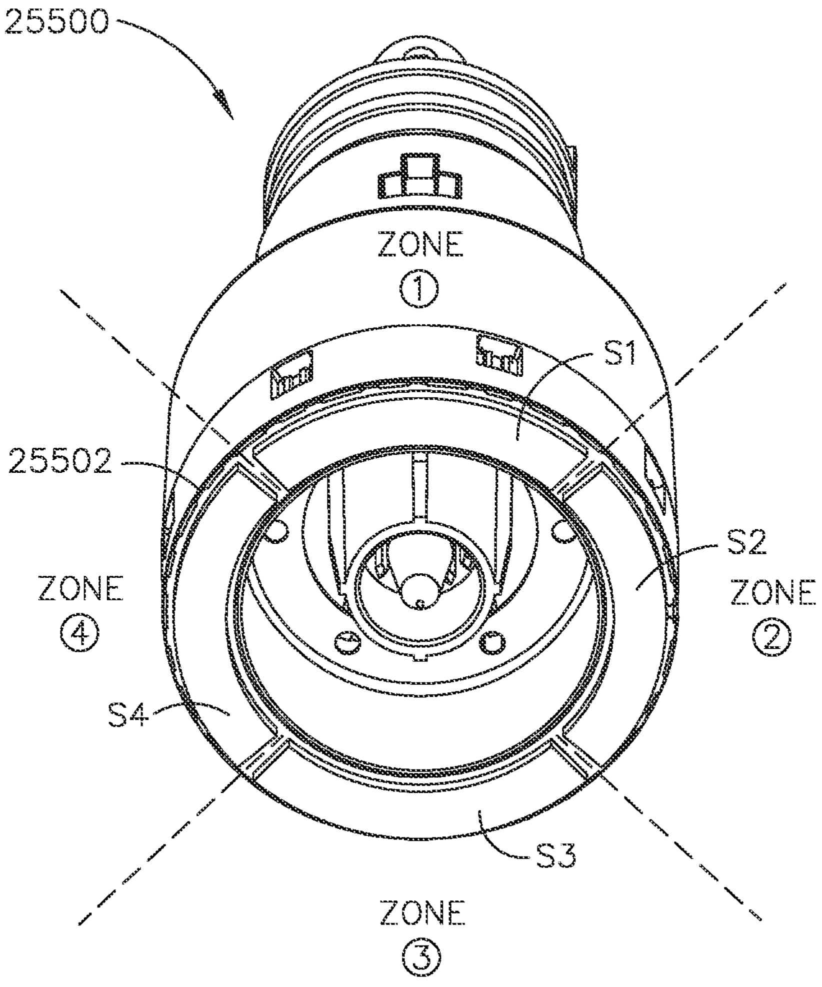

FIG. 138 illustrates a partial perspective view of a circular stapler showing a circular stapler trocar including a staple cartridge, which has four predetermined zones, in accordance with at least one aspect of the present disclosure.

Figure 139:
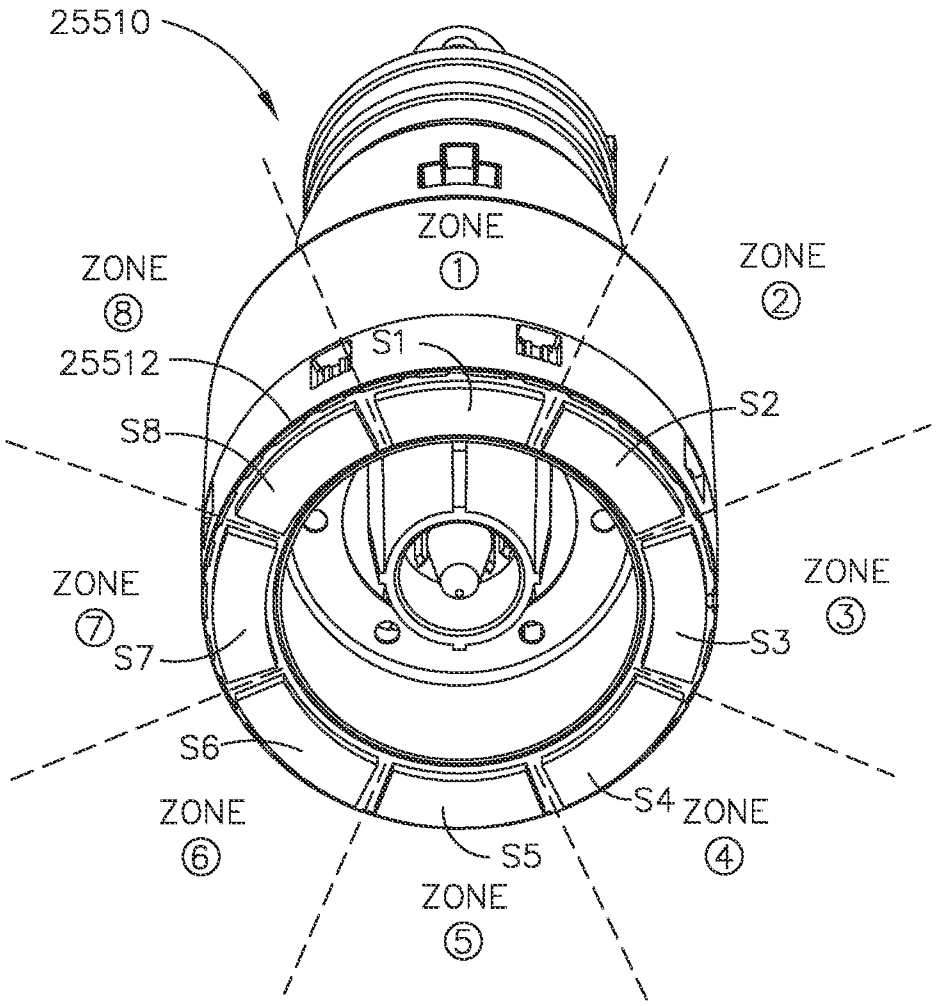

FIG. 139 illustrates a partial perspective view of a circular stapler showing a circular stapler trocar including a staple cartridge, which has eight predetermined zones, in accordance with at least one aspect of the present disclosure.

Figure 140:
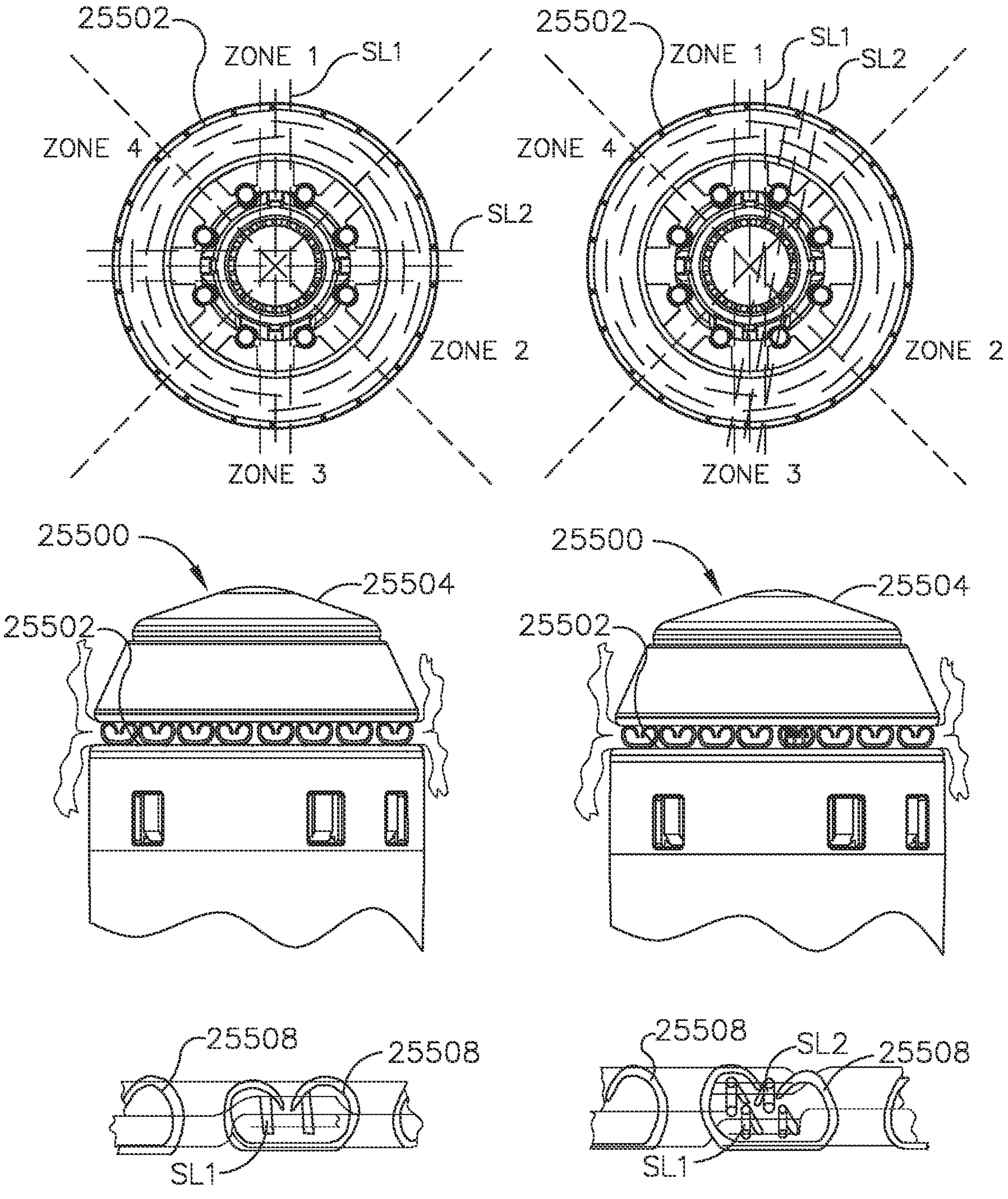

FIG. 140 illustrates, on the left, two tissues including previously deployed staples properly disposed onto the staple cartridge of FIG. 138, and on the right, two tissues including previously deployed staples properly disposed onto the staple cartridge of FIG. 138, in accordance with at least one aspect of the present disclosure.

Figure 141:
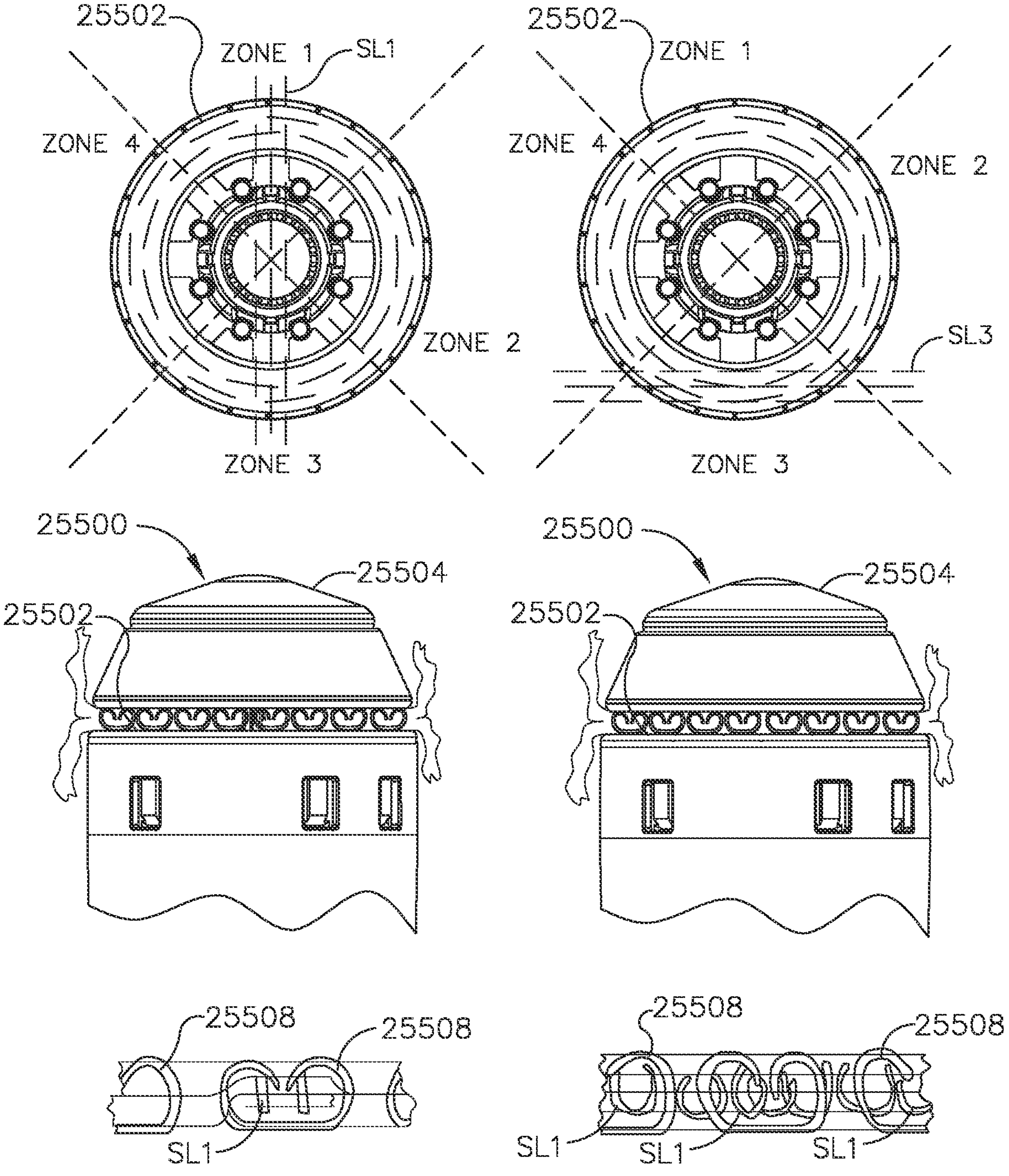

FIG. 141 illustrates, on the left, a tissue including previously deployed staples properly disposed onto the staple cartridge of FIG. 138, and on the right, a tissue including previously deployed staples properly disposed onto the staple cartridge of FIG. 138, in accordance with at least one aspect of the present disclosure.

Figure 142:
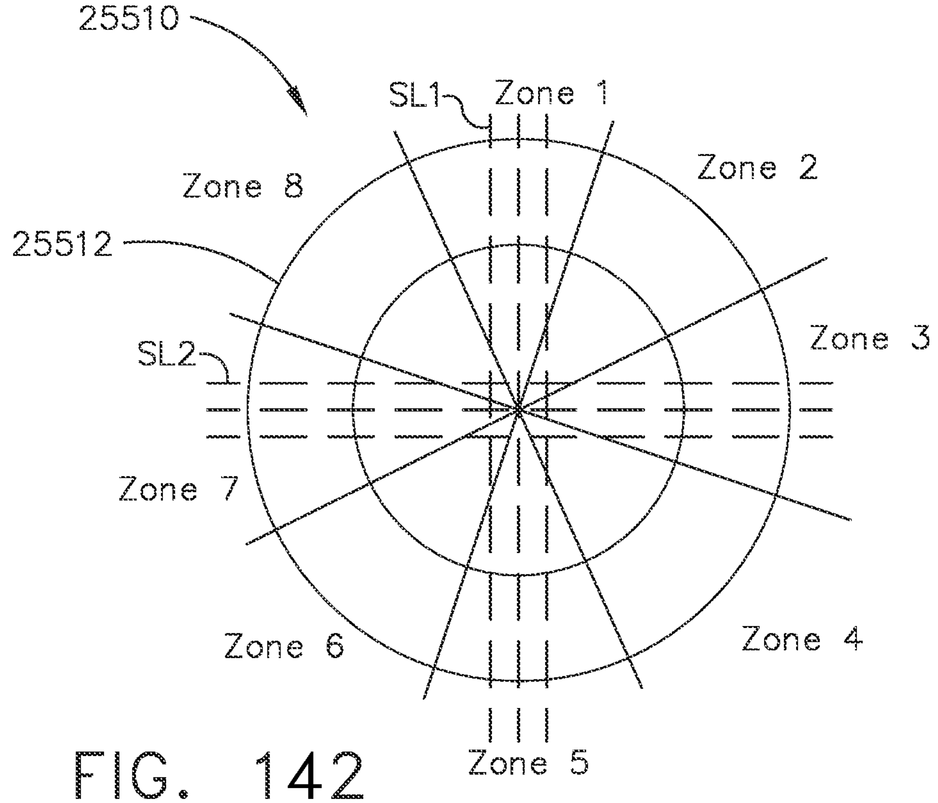

FIG. 142 illustrates two tissues including previously deployed staples properly disposed onto the staple cartridge of FIG. 139, in accordance with at least one aspect of the present disclosure.

Figure 143:
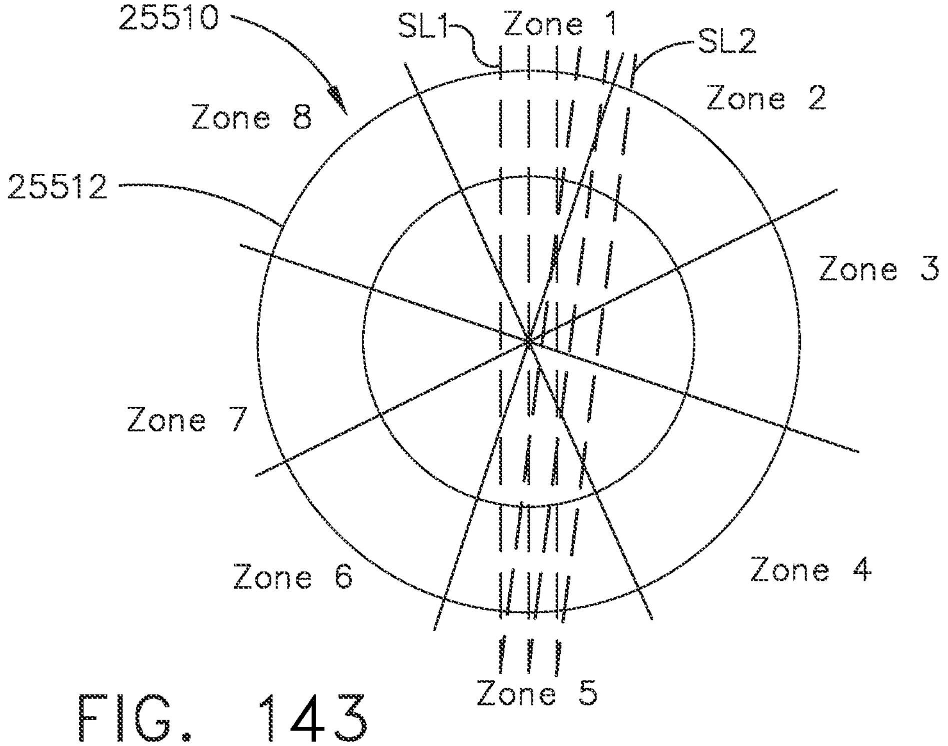

FIG. 143 illustrates two tissues including previously deployed staples improperly disposed onto the staple cartridge of FIG. 139, in accordance with at least one aspect of the present disclosure.

Figure 144:
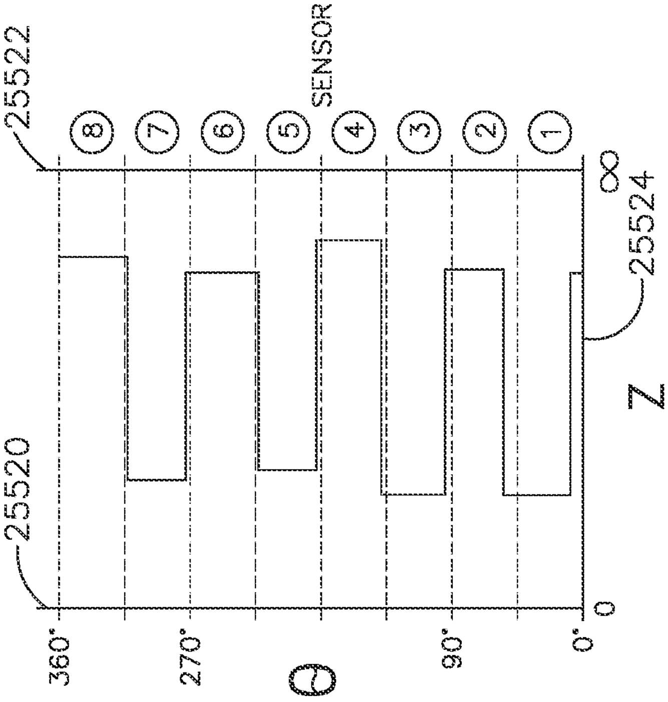

FIG. 144 is a graph depicting a tissue impedance signature of the properly disposed tissues of FIG. 142, in accordance with at least one aspect of the present disclosure.

Figure 145:
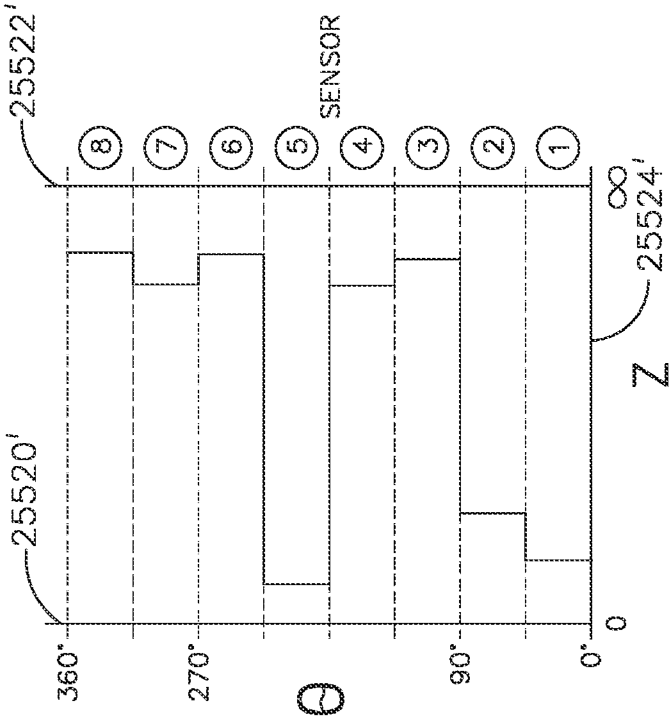

FIG. 145 is a graph depicting a tissue impedance signature of the improperly disposed tissues of FIG. 143, in accordance with at least one aspect of the present disclosure.

Figure 146:
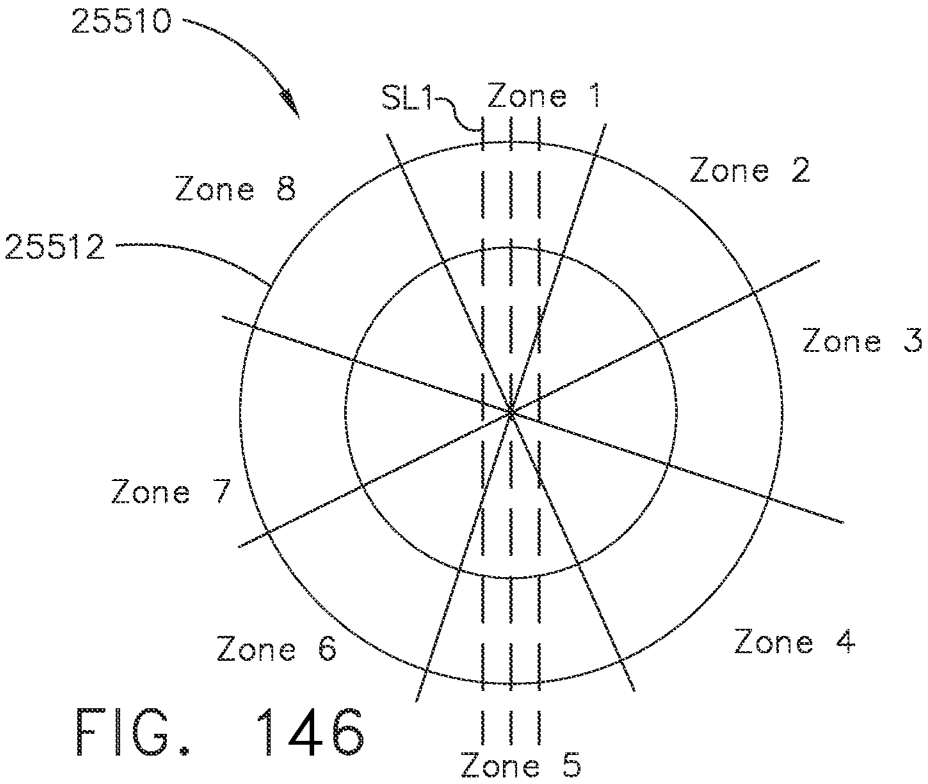

FIG. 146 illustrates a tissue including previously deployed staples properly disposed onto the staple cartridge of FIG. 139, in accordance with at least one aspect of the present disclosure.

Figure 147:
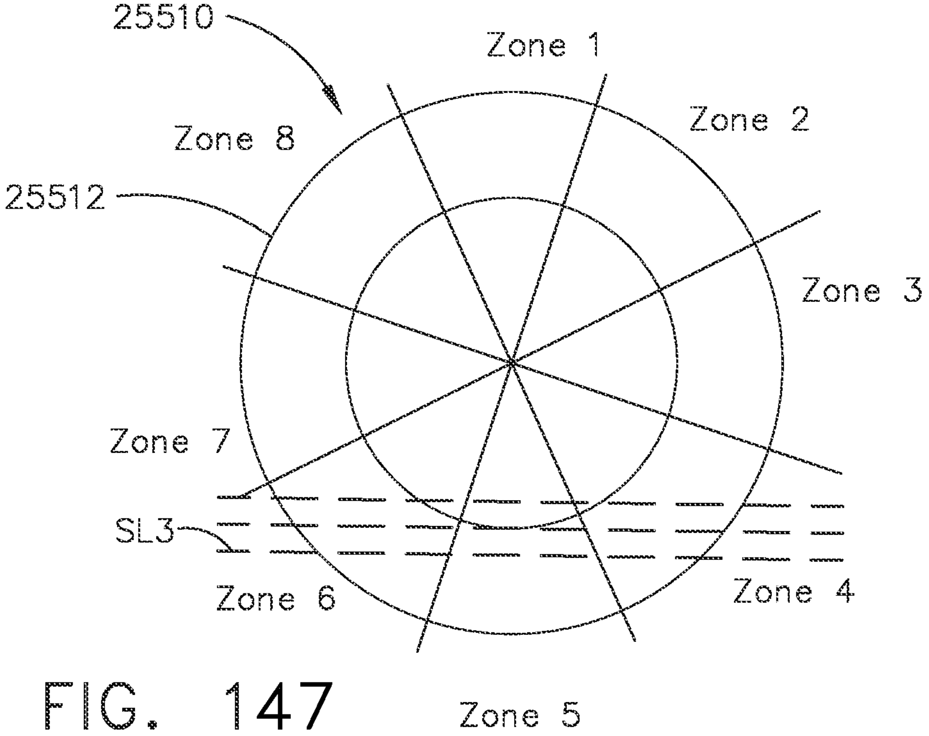

FIG. 147 illustrates a tissue including previously deployed staples improperly disposed onto the staple cartridge of FIG. 139, in accordance with at least one aspect of the present disclosure.

Figure 148:
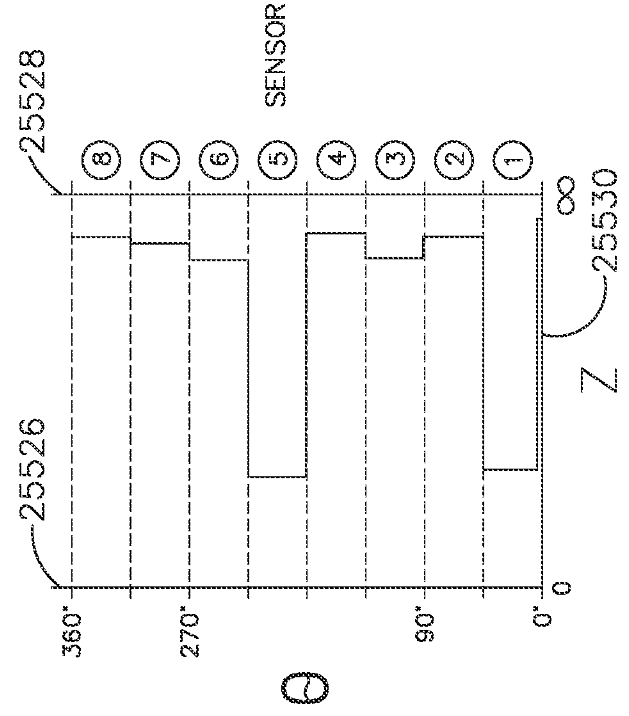

FIG. 148 is a graph depicting a tissue impedance signature of the properly disposed tissue of FIG. 146, in accordance with at least one aspect of the present disclosure.

Figure 149:
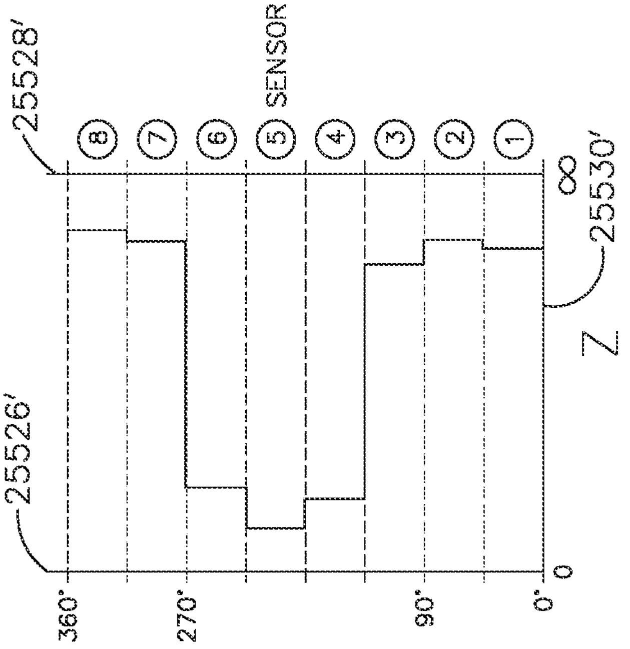

FIG. 149 is a graph depicting a tissue impedance signature of the improperly disposed tissue of FIG. 147, in accordance with at least one aspect of the present disclosure.

Figure 150:
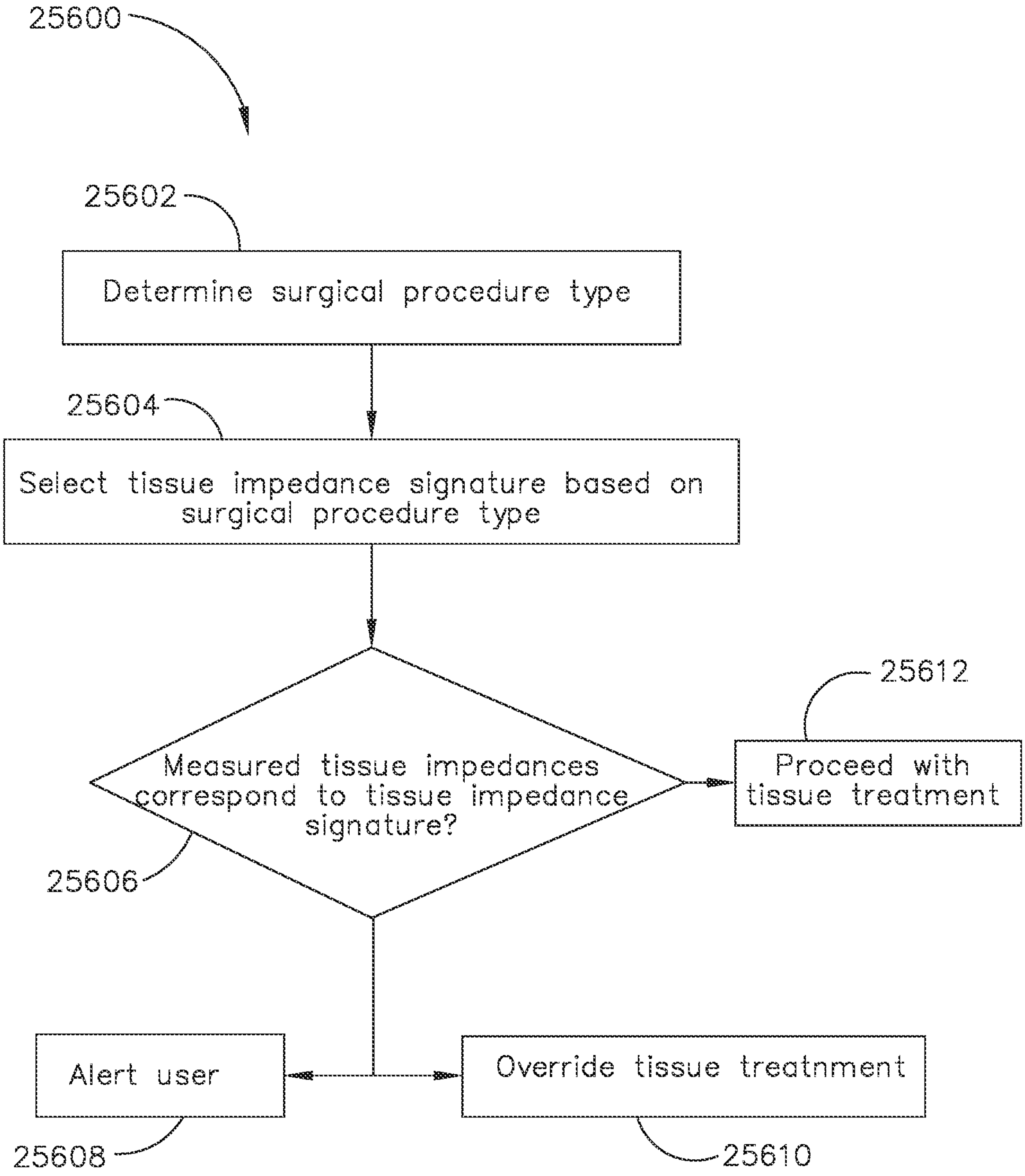

FIG. 150 illustrates a logic flow diagram of a process depicting a control program or a logic configuration for properly positioning a previously-stapled tissue within an end effector, in accordance with at least one aspect of the present disclosure.

Figure 151:
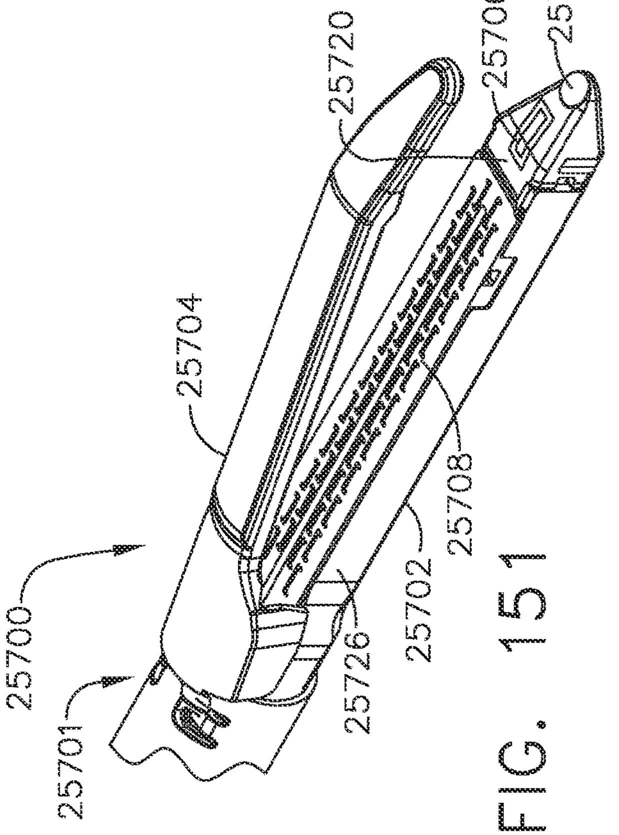

FIG. 151 illustrates an end effector extending from a shaft of a surgical instrument in an open configuration, in accordance with at least one aspect of the present disclosure.

Figure 152:
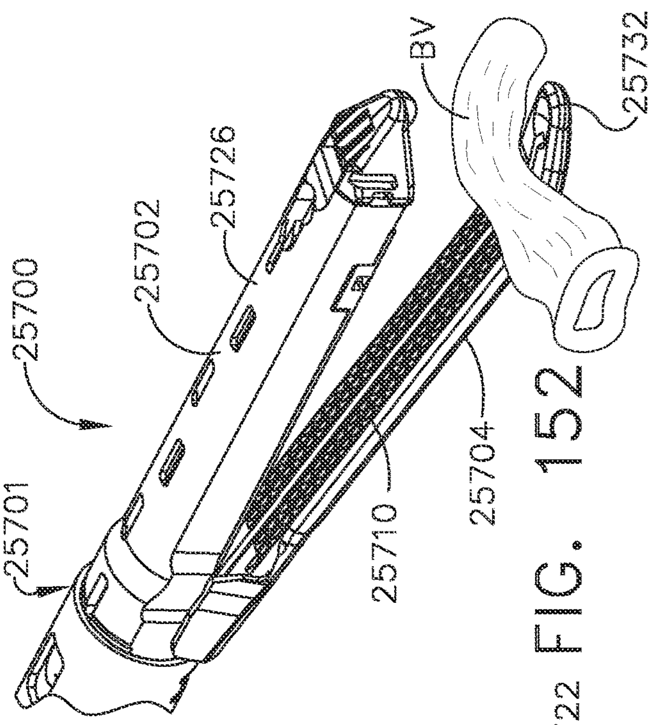

FIG. 152 illustrates the end effector of FIG. 151 with a blood vessel (BV) extending between the jaws of the end effector, in accordance with at least one aspect of the present disclosure.

Figure 153:
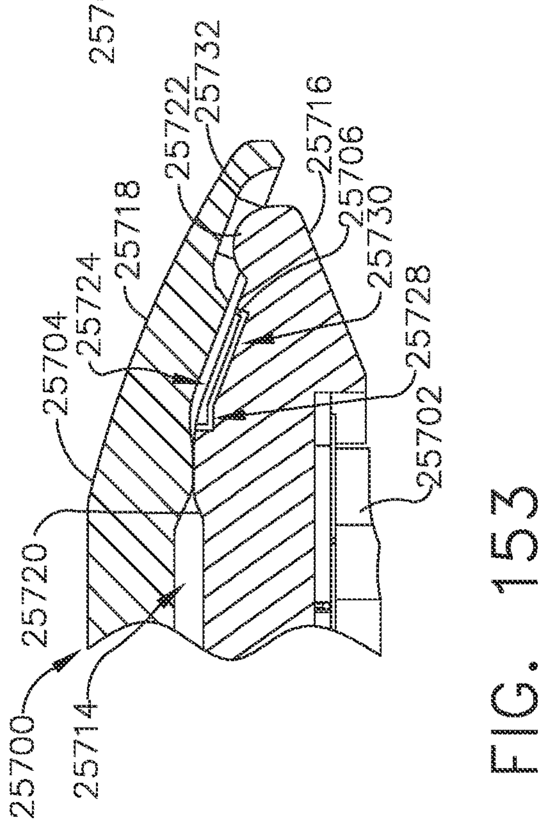

FIG. 153 illustrates the end effector of FIG. 151 in a closed configuration without tissue, in accordance with at least one aspect of the present disclosure.

Figure 154:
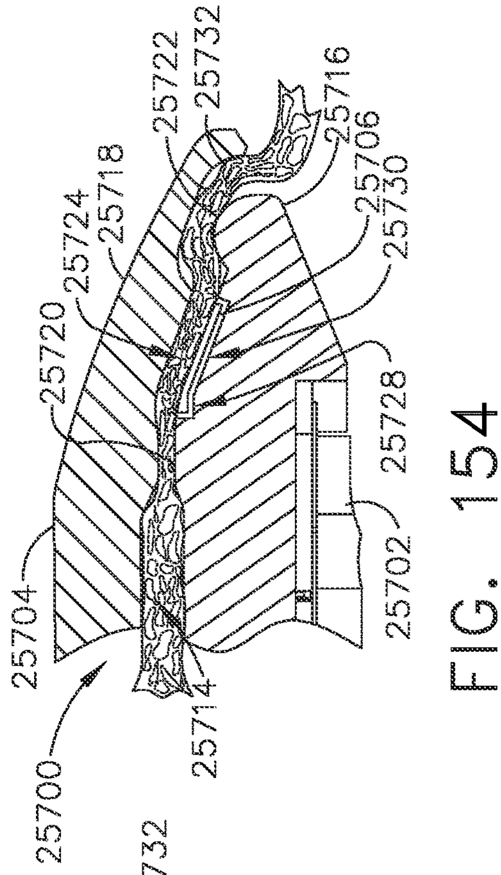

FIG. 154 illustrates the end effector of FIG. 151 with tissue grasped between the jaws of the end effector, in accordance with at least one aspect of the present disclosure.

Figure 155:
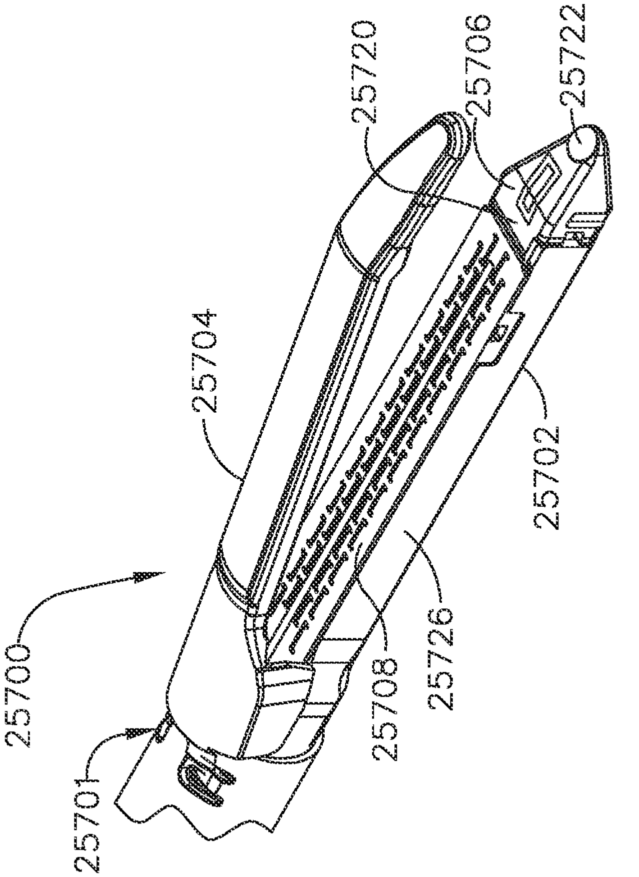

FIG. 155 illustrates an end effector extending from a shaft of a surgical instrument in an open configuration, in accordance with at least one aspect of the present disclosure.

Figure 156:
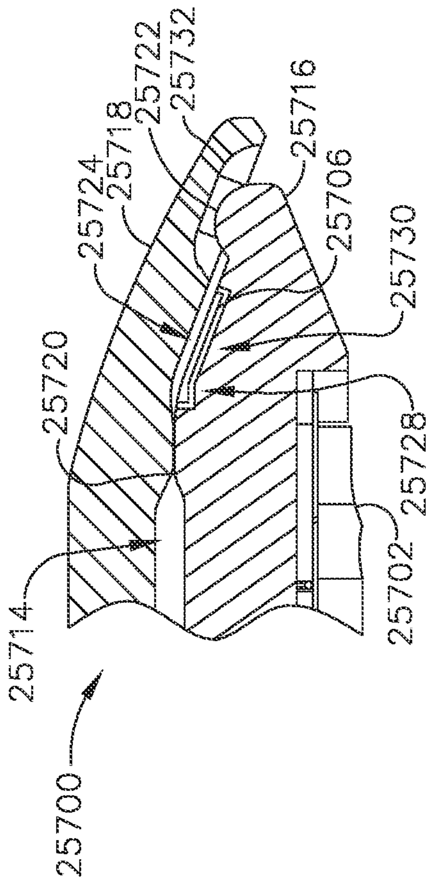

FIG. 156 illustrates the end effector of FIG. 151 in a closed configuration without tissue, in accordance with at least one aspect of the present disclosure.

Figure 157:
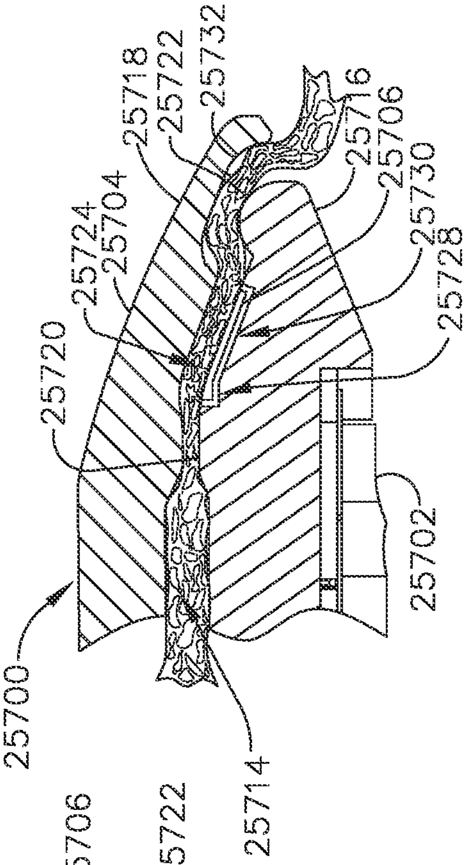

FIG. 157 illustrates the end effector of FIG. 151 with tissue grasped between the jaws of the end effector, in accordance with at least one aspect of the present disclosure.

Figure 158:
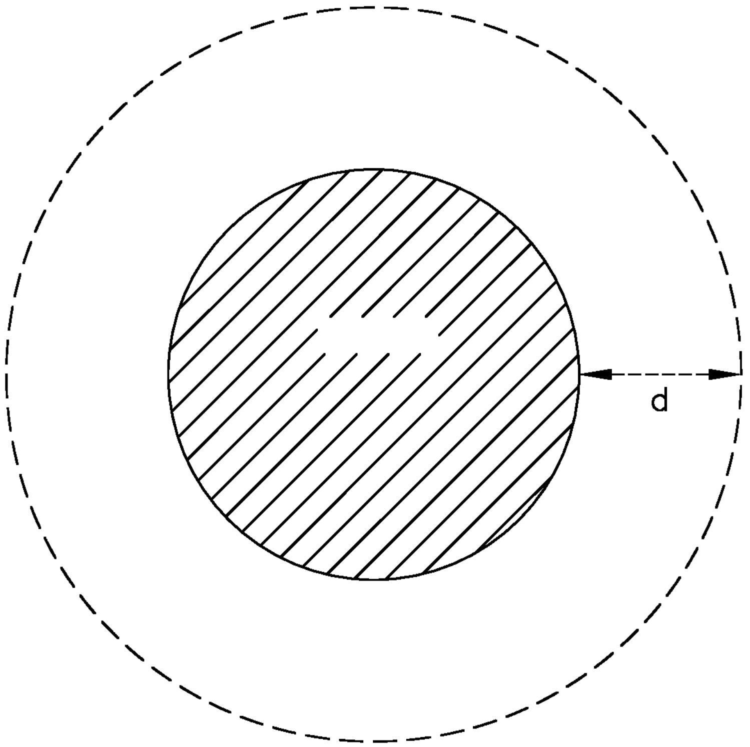

FIG. 158 illustrates a tumor surrounded by healthy tissue, and a clear margin defined in the healthy tissue, in accordance with at least one aspect of the present disclosure.

Figure 159:
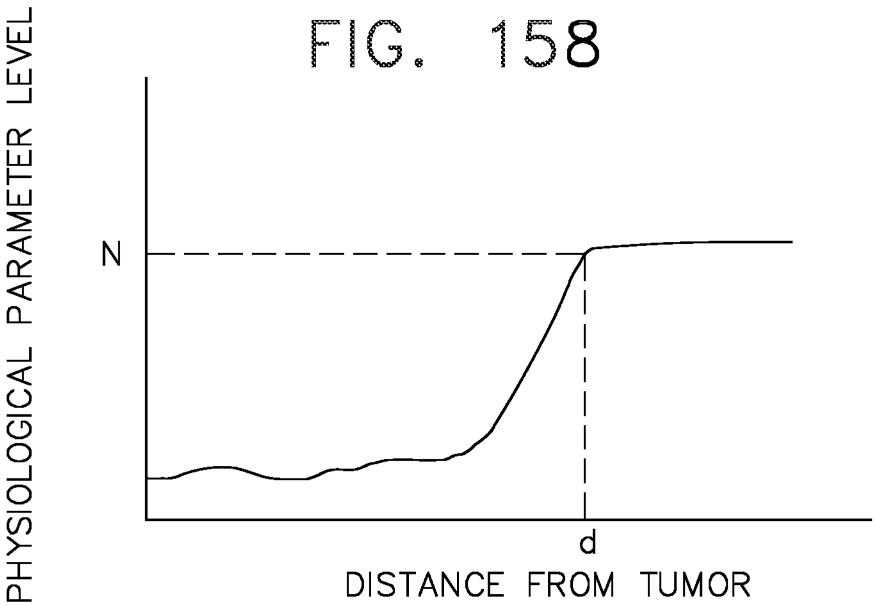

FIG. 159 is a graph illustrating of a physiological parameter of tissue plotted against distance from a tumor, in accordance with at least one aspect of the present disclosure.

Figure 160:
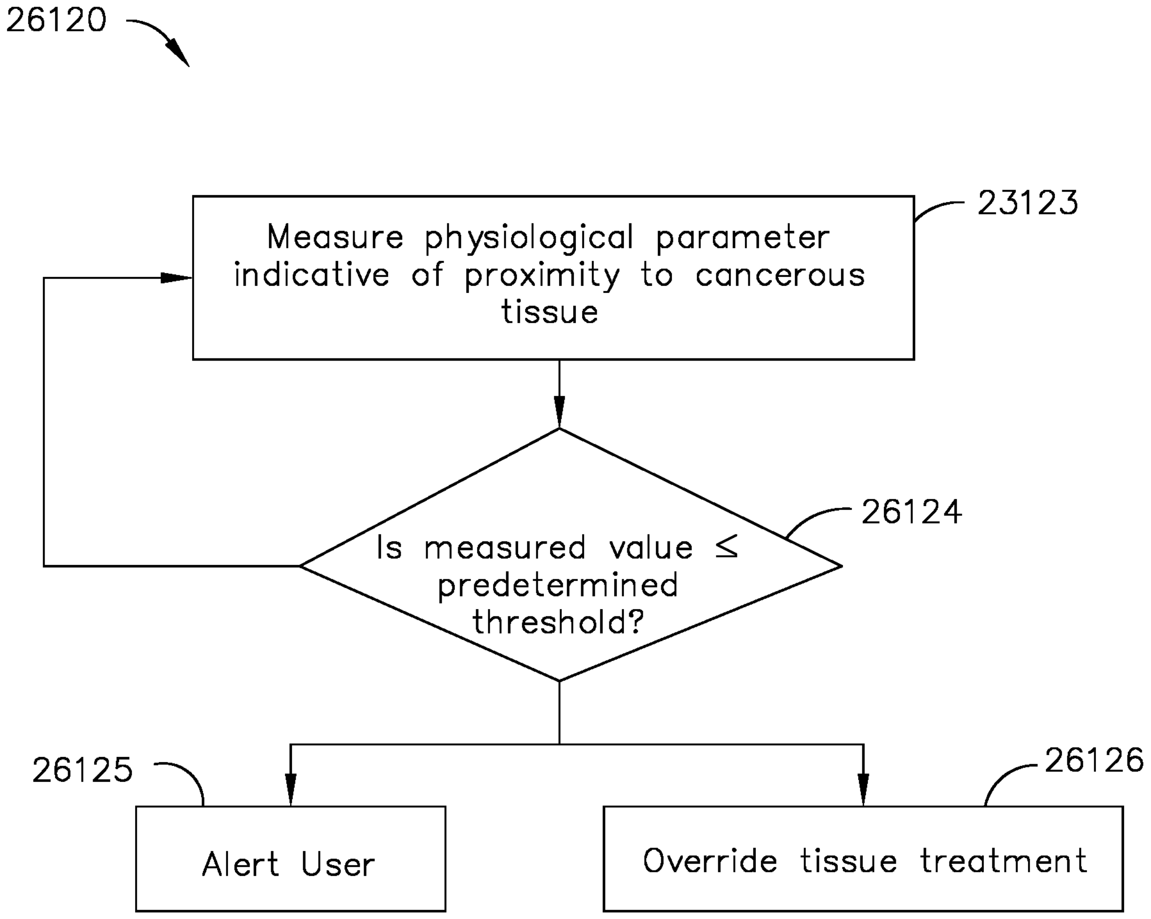

FIG. 160 is a logic flow diagram of a process depicting a control program or a logic configuration for assessing proximity of an end effector of a surgical instrument to cancerous tissue, in accordance with at least one aspect of the present disclosure.

Figure 161:
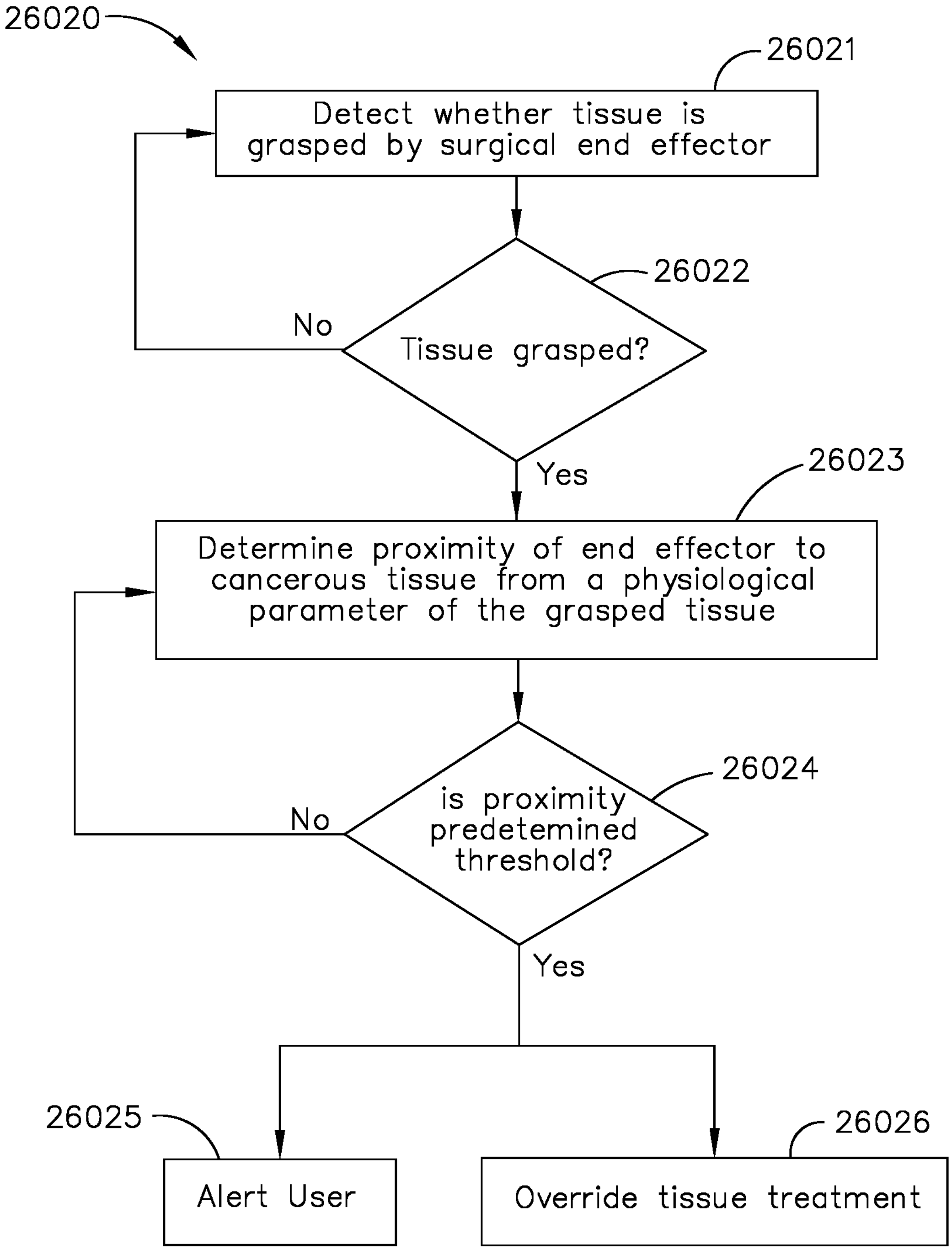

FIG. 161 illustrates a logic flow diagram of a process depicting a control program or a logic configuration for assessing proximity of an end effector to cancerous tissue, in accordance with at least one aspect of the present disclosure.

Figure 162:
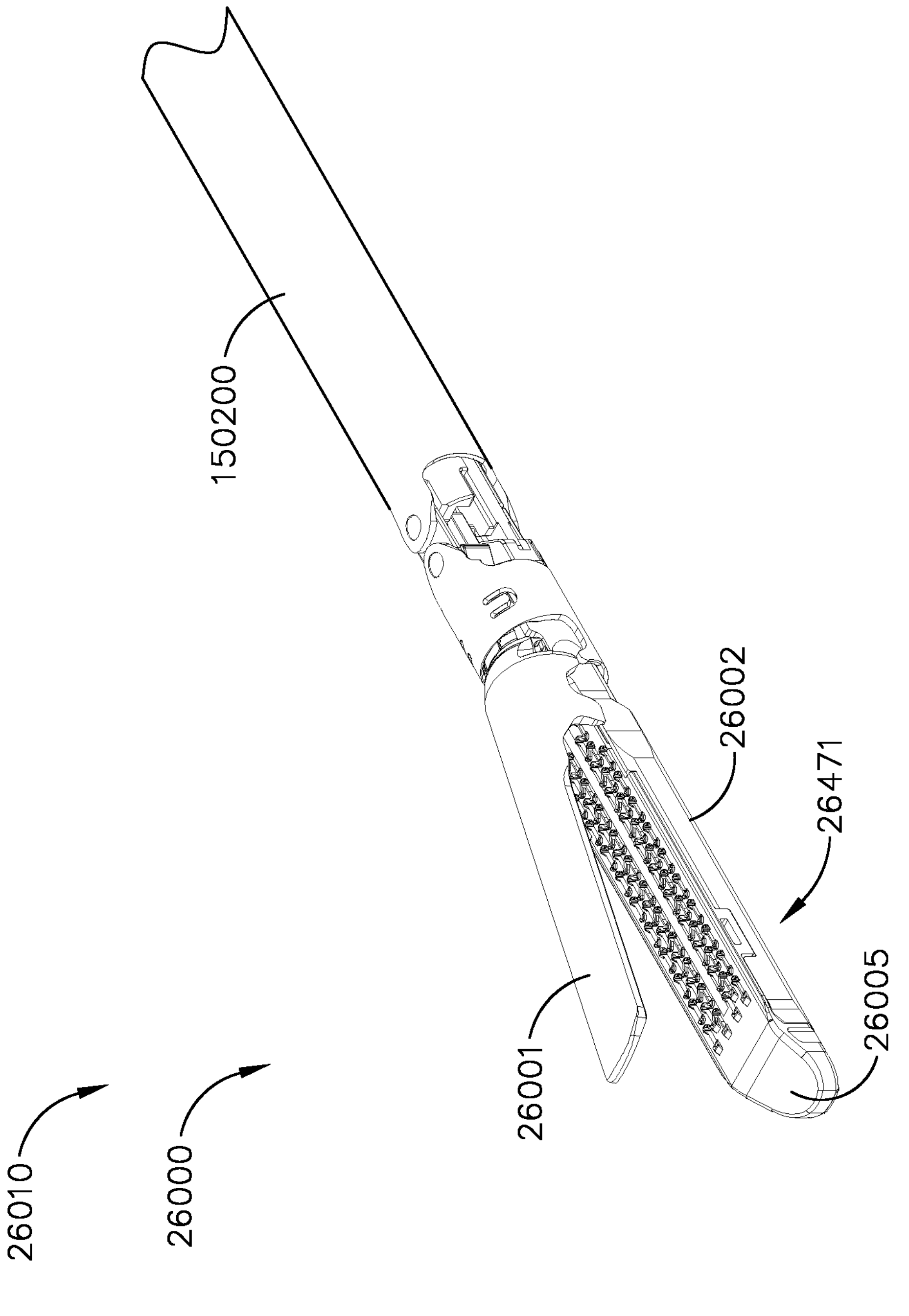

FIG. 162 illustrates an end effector of a surgical instrument, in accordance with at least one aspect of the present disclosure.

Figure 163:
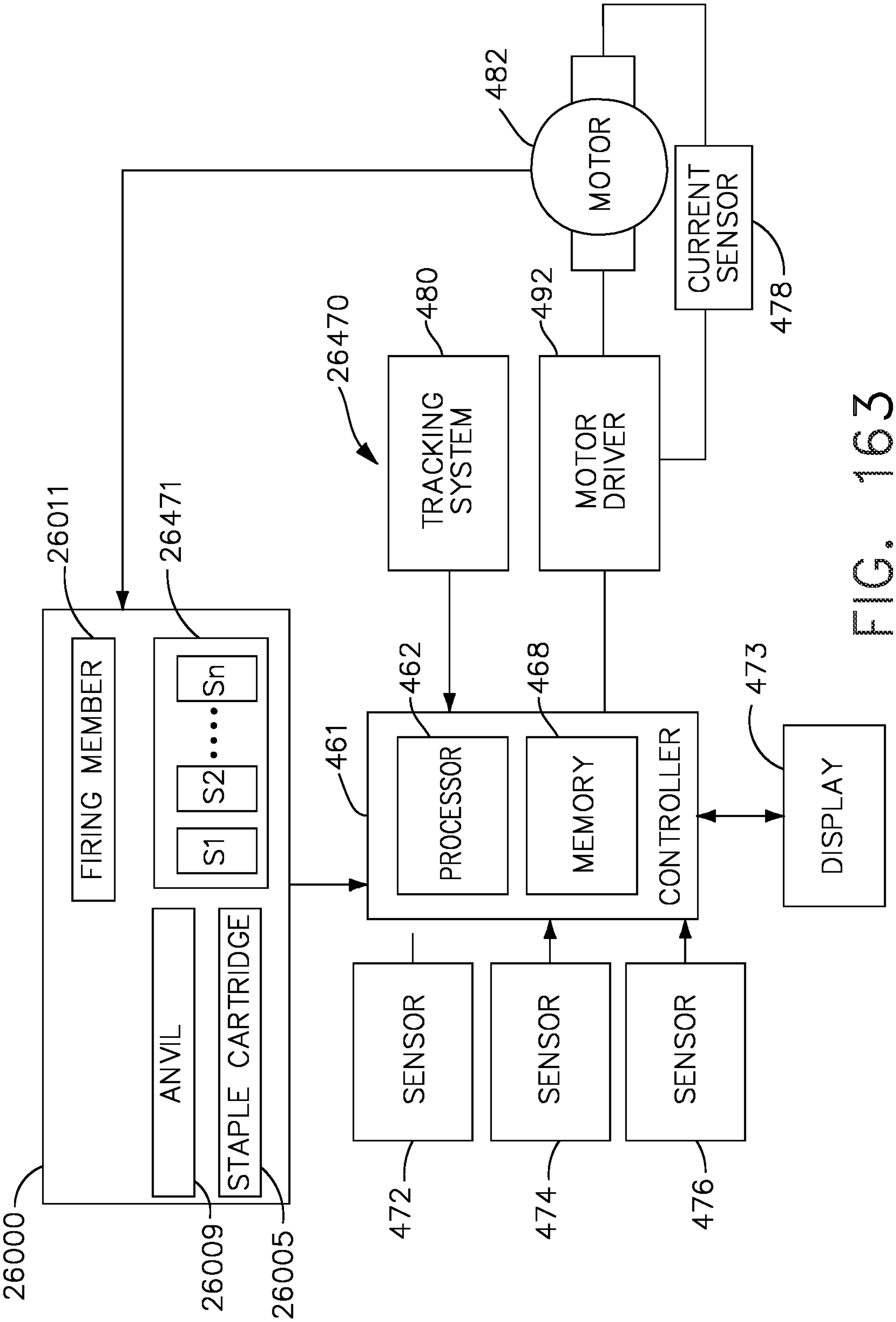

FIG. 163 illustrates a control system of a surgical instrument, in accordance with at least one aspect of the present disclosure.

Figures 164, 165:
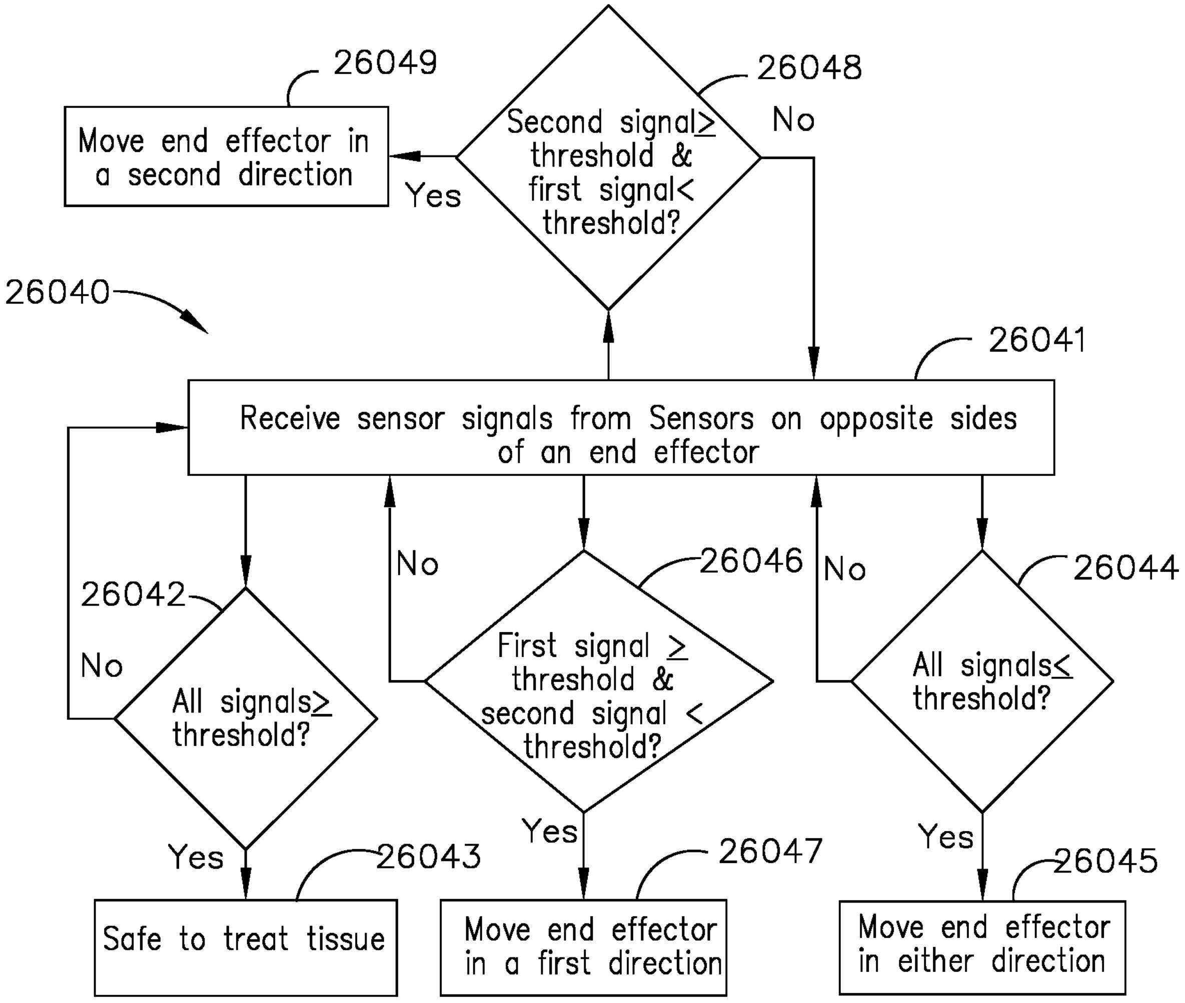

FIG. 164 illustrates a proximity index correlating a sensor signal to proximity from an end effector, in accordance with at least one aspect of the present disclosure.

FIG. 165 illustrates a logic flow diagram of a process depicting a control program or a logic configuration for determining the direction at which cancerous tissue is located with respect to an end effector, in accordance with at least one aspect of the present disclosure.

Figure 166:
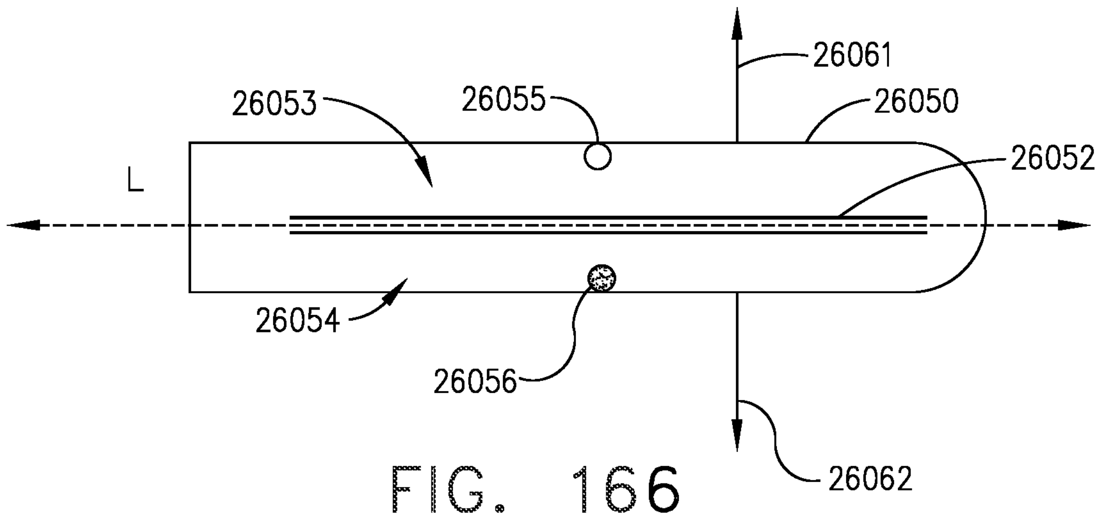

FIG. 166 illustrates a top view of an end effector of a surgical instrument, in accordance with at least one aspect of the present disclosure.

Figure 167:
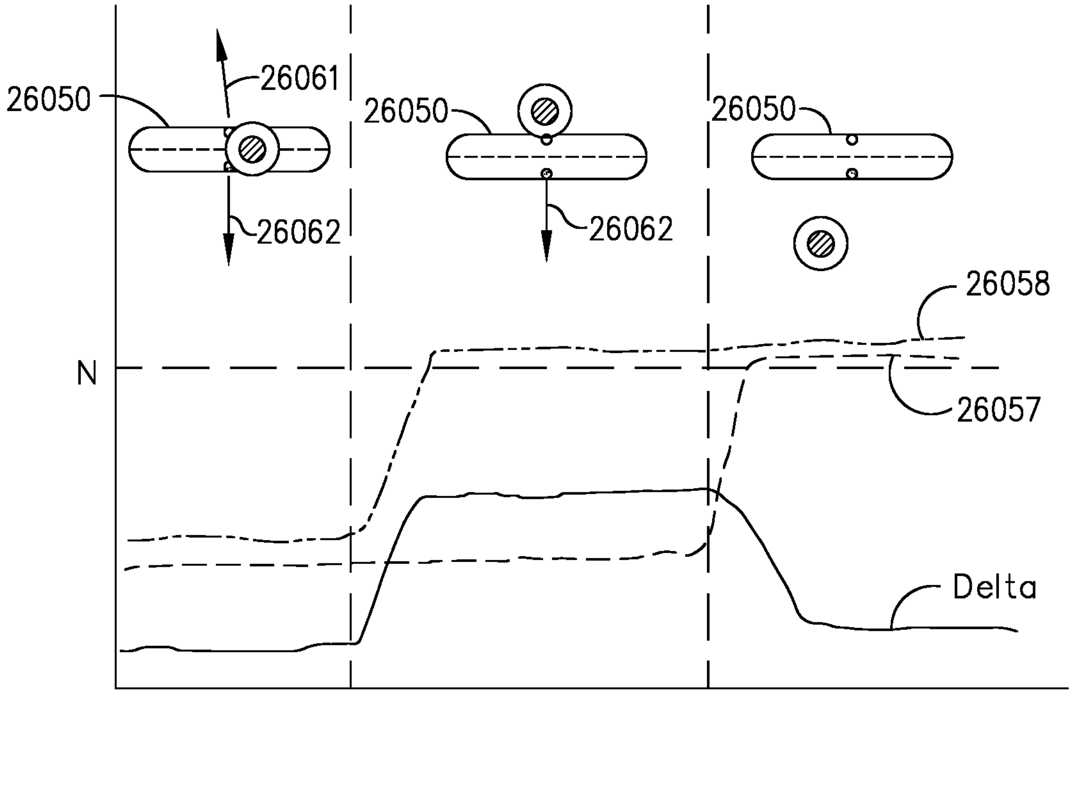

FIG. 167 is a graph illustrating sensor signals representing a physiological parameter of tissue plotted against time, in accordance with at least one aspect of the present disclosure.

Figure 168:
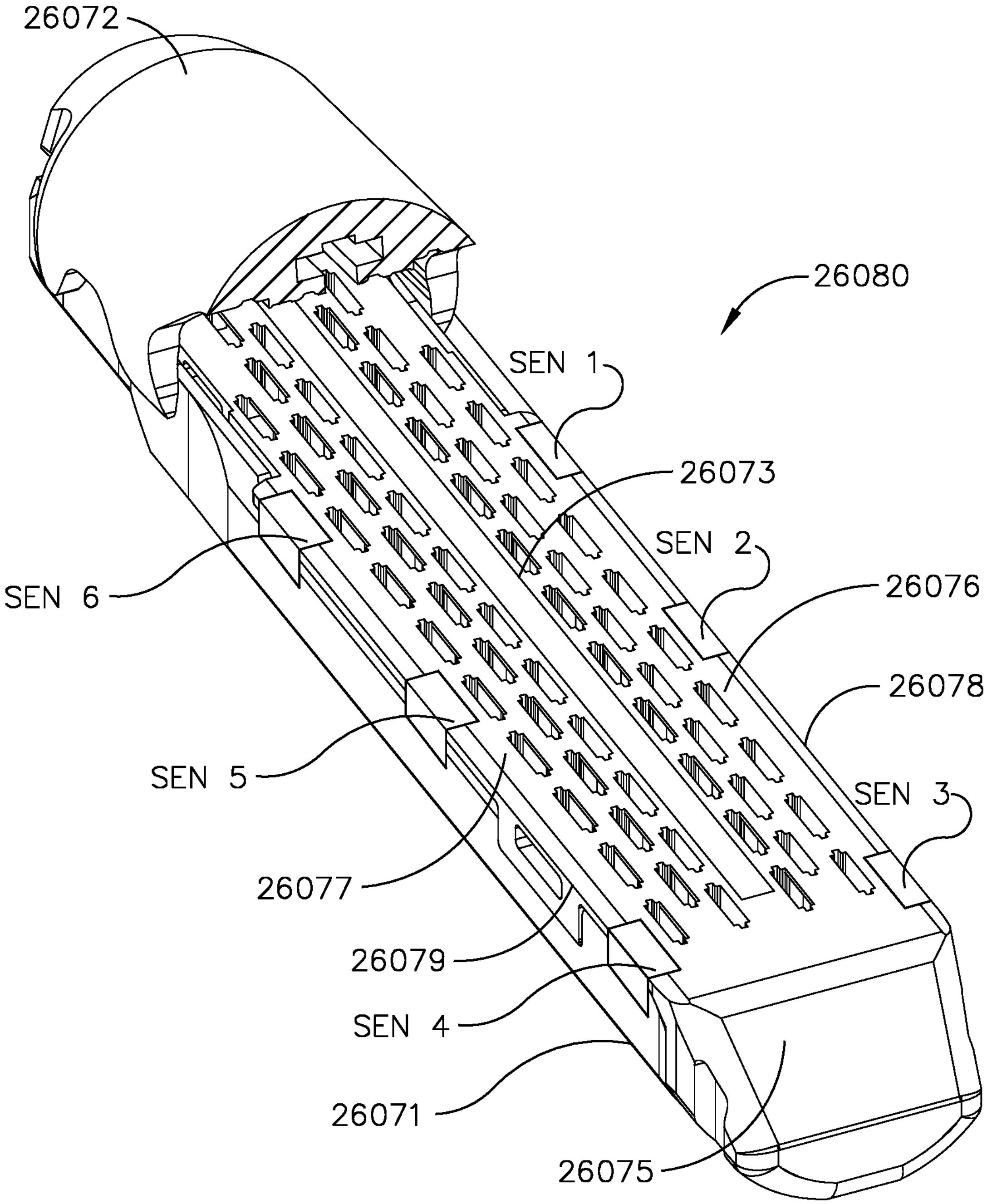

FIG. 168 illustrates a partial view of an end effector of a surgical instrument, in accordance with at least one aspect of the present disclosure.

Figure 169:
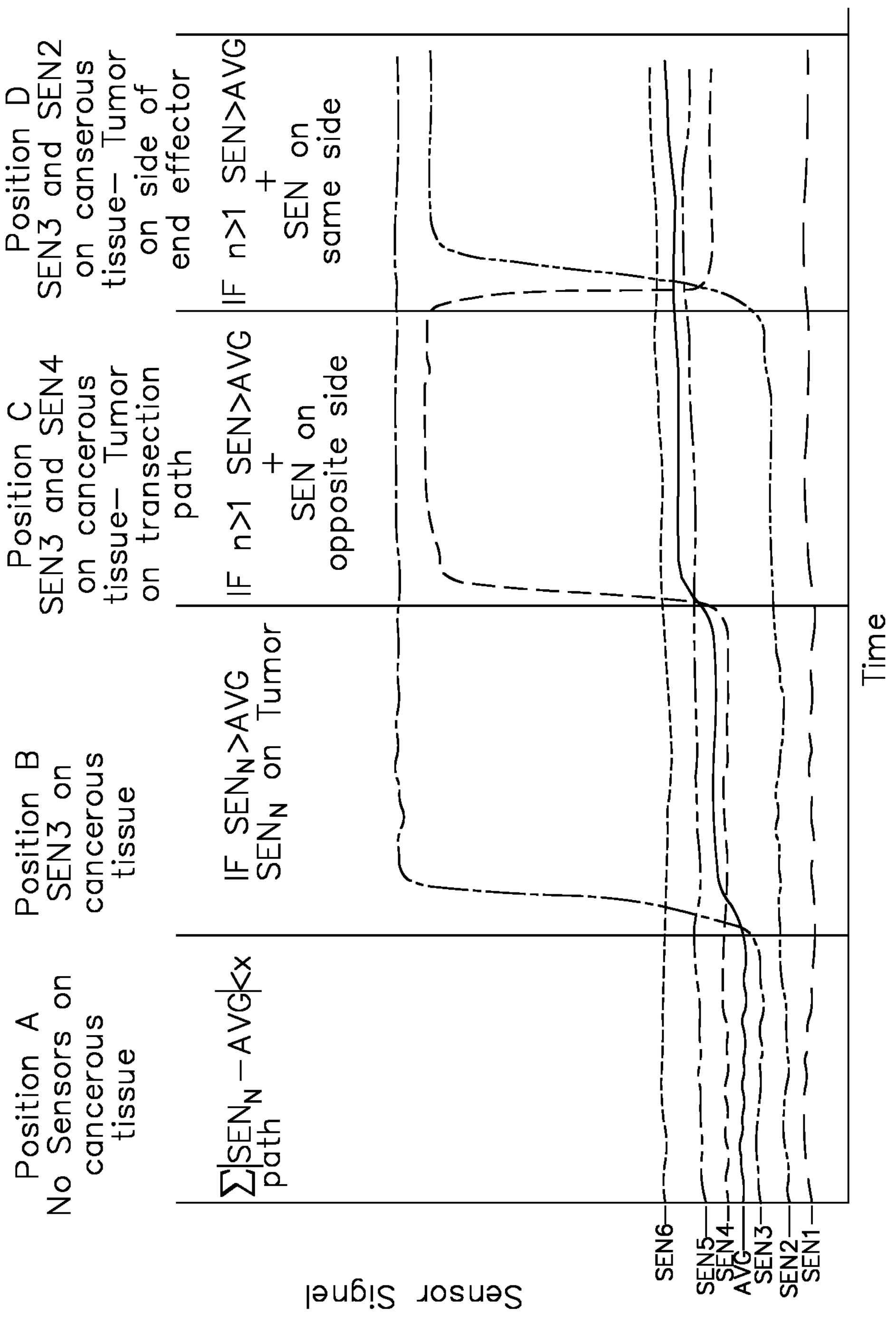

FIG. 169 is a graph illustrating sensor signals representing a physiological parameter of tissue plotted against time, in accordance with at least one aspect of the present disclosure.

Figure 170:
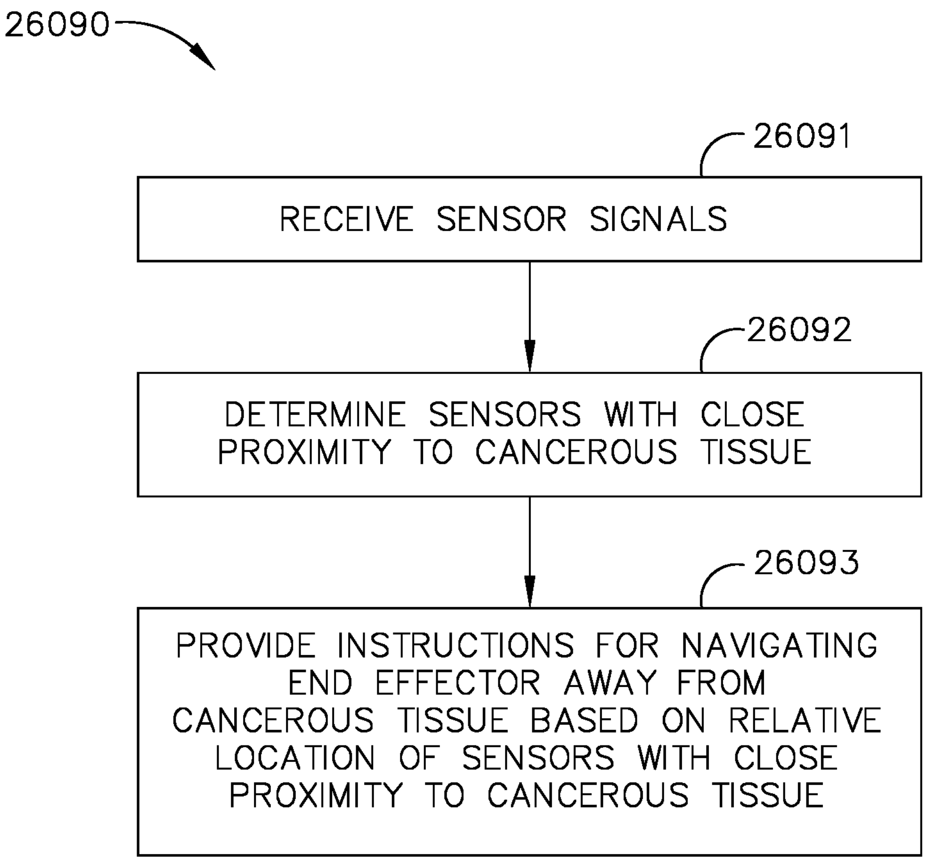

FIG. 170 is a logic flow diagram of a process depicting a control program or a logic configuration for providing instructions for navigating an end effector with respect to cancerous tissue, in accordance with at least one aspect of the present disclosure.

Figure 171:
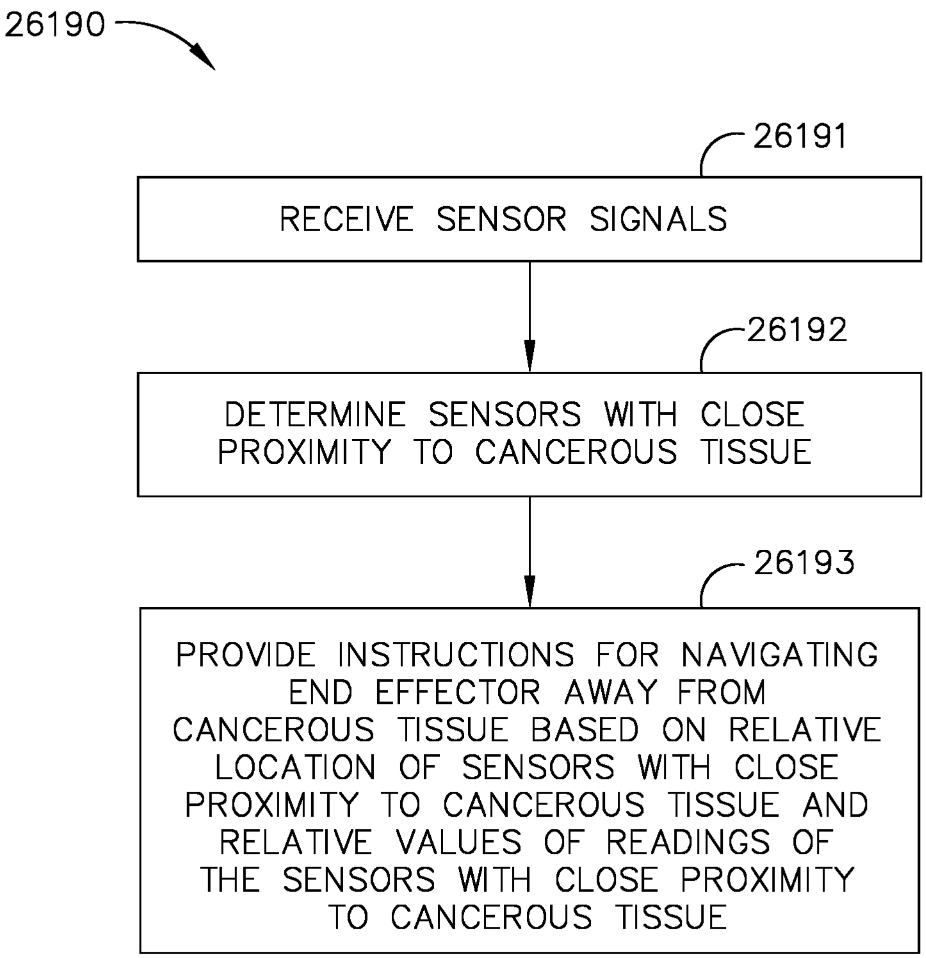

FIG. 171 is a logic flow diagram of a process depicting a control program or a logic configuration for providing instructions for navigating an end effector with respect to cancerous tissue, in accordance with at least one aspect of the present disclosure.

Figure 172:
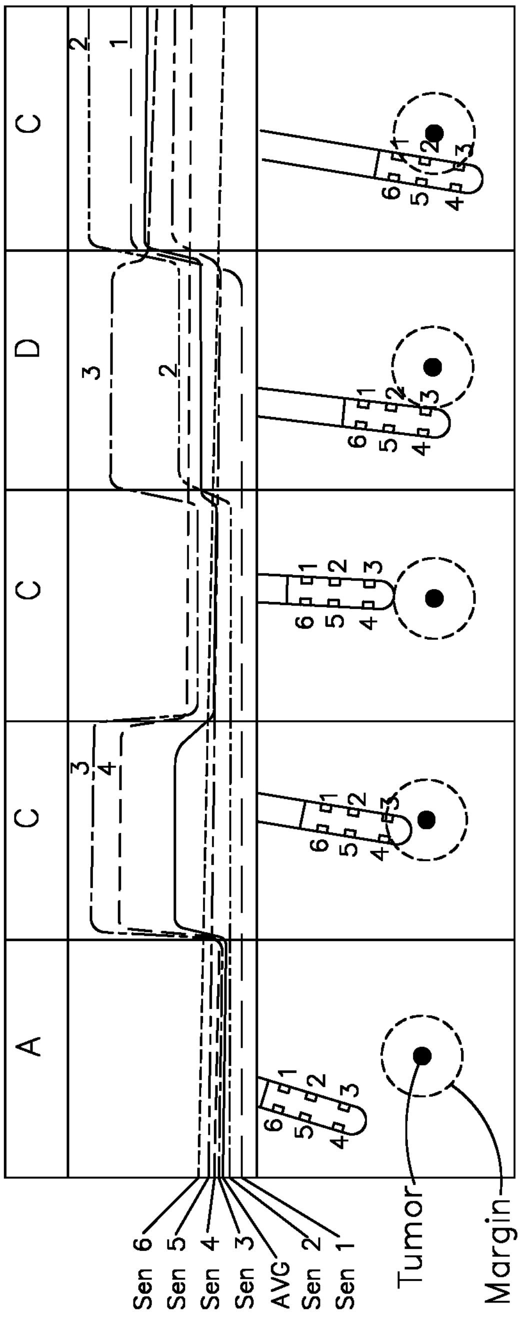

FIG. 172 is a graph illustrating sensor signals representing a physiological parameter of tissue plotted against time, in accordance with at least one aspect of the present disclosure.

Figure 173:
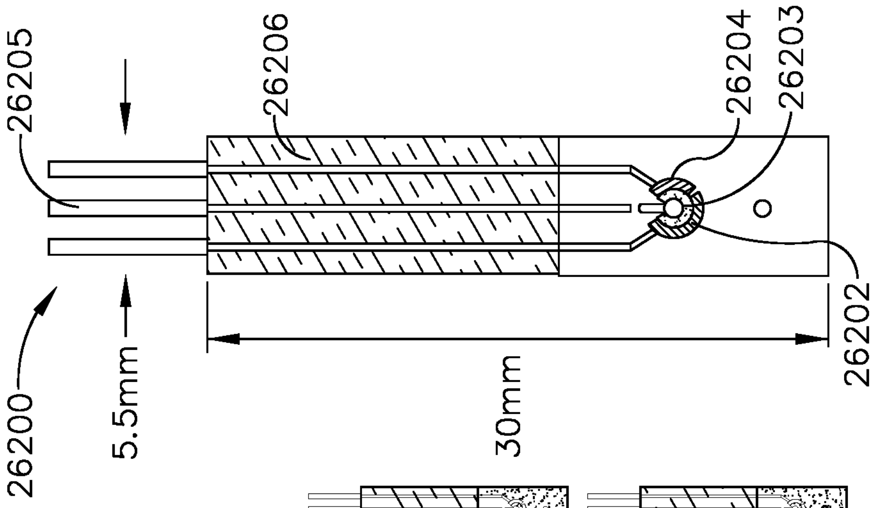

FIG. 173 illustrates a glucose sensor, in accordance with at least one aspect of the present disclosure.

Figure 174:
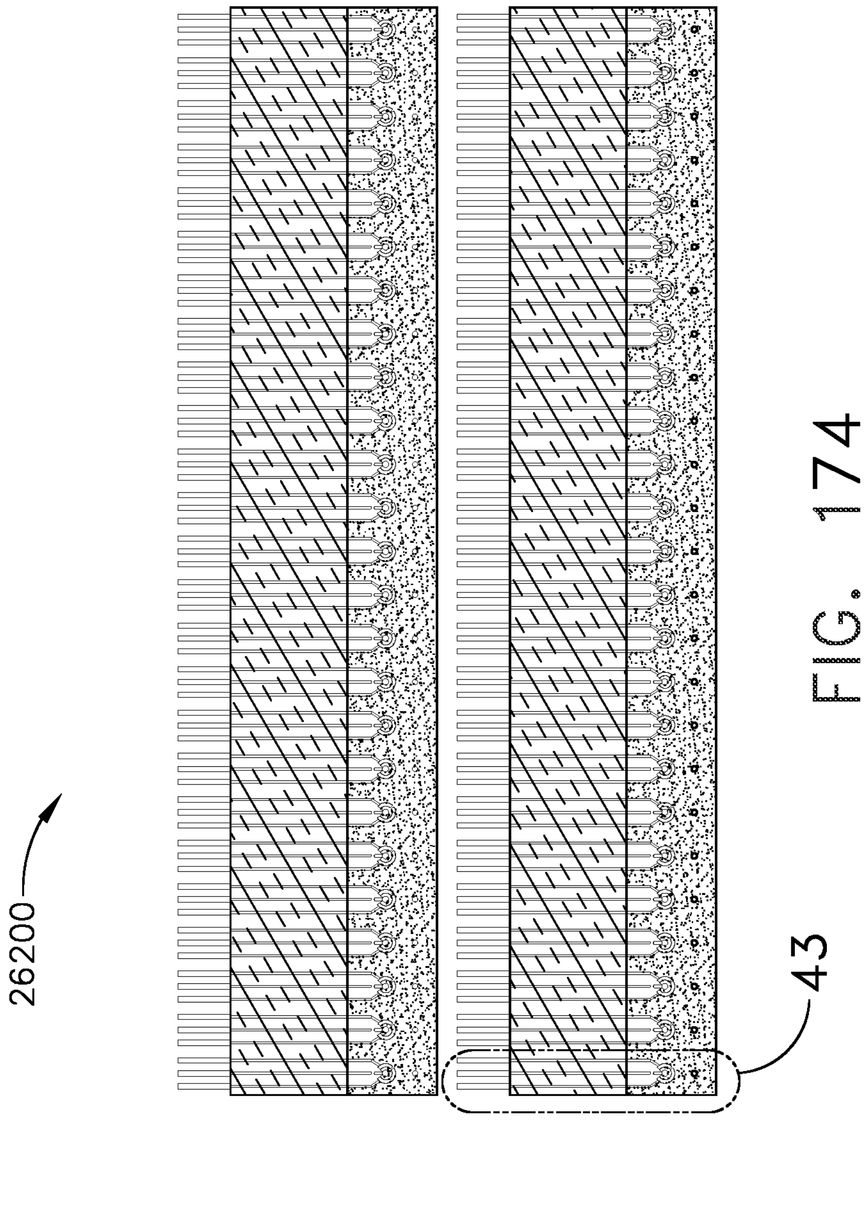

FIG. 174 illustrates an expanded view of the glucose sensor of FIG. 173.

Figure 175:
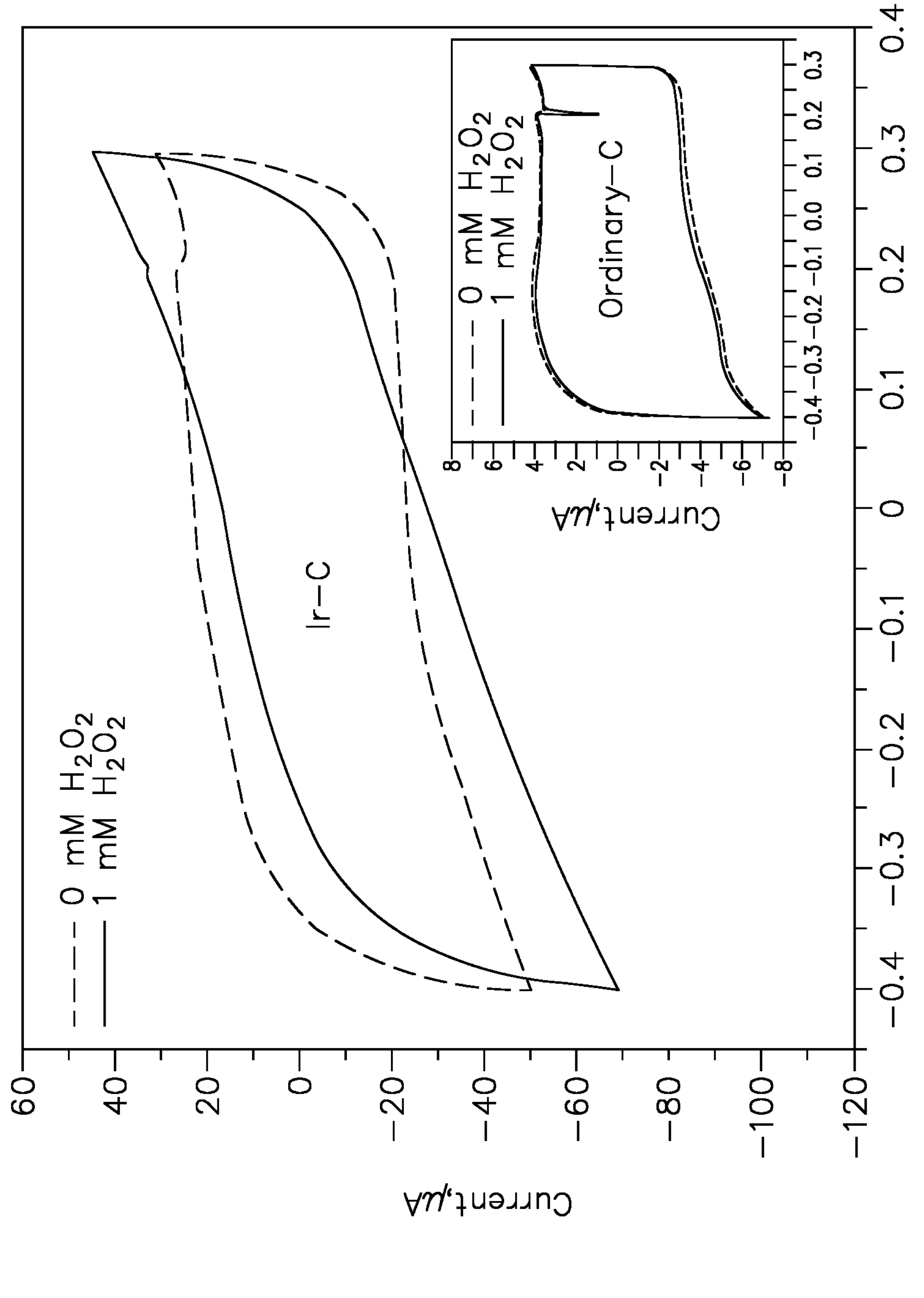

FIG. 175 is a graph illustrating Current plotted against Potential, in accordance with at least one aspect of the present disclosure.

Figure 176:
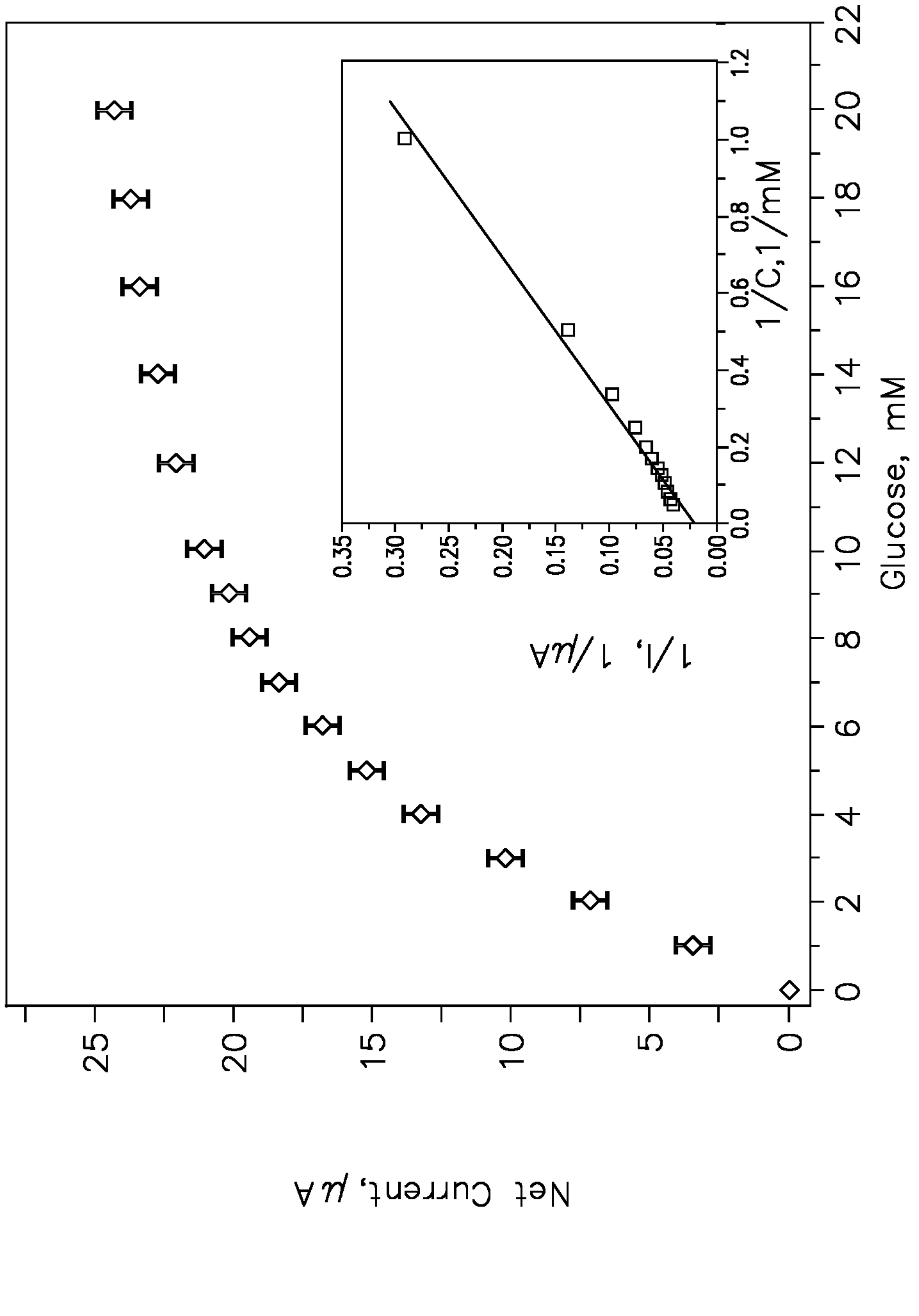

FIG. 176 is a graph illustrating Net Current plotted against Glucose level, in accordance with at least one aspect of the present disclosure.

Figure 177:
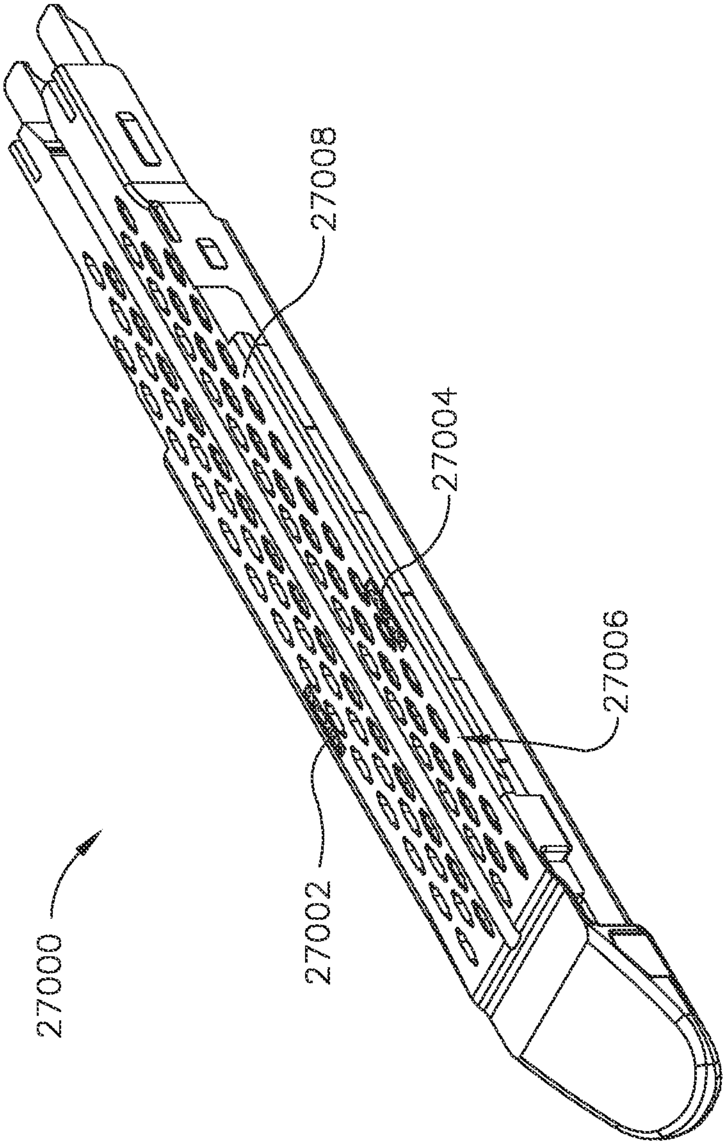

FIG. 177 illustrates a perspective view of a staple cartridge including an active element and a sensor, in accordance with at least one aspect of the present disclosure.

Figure 178:
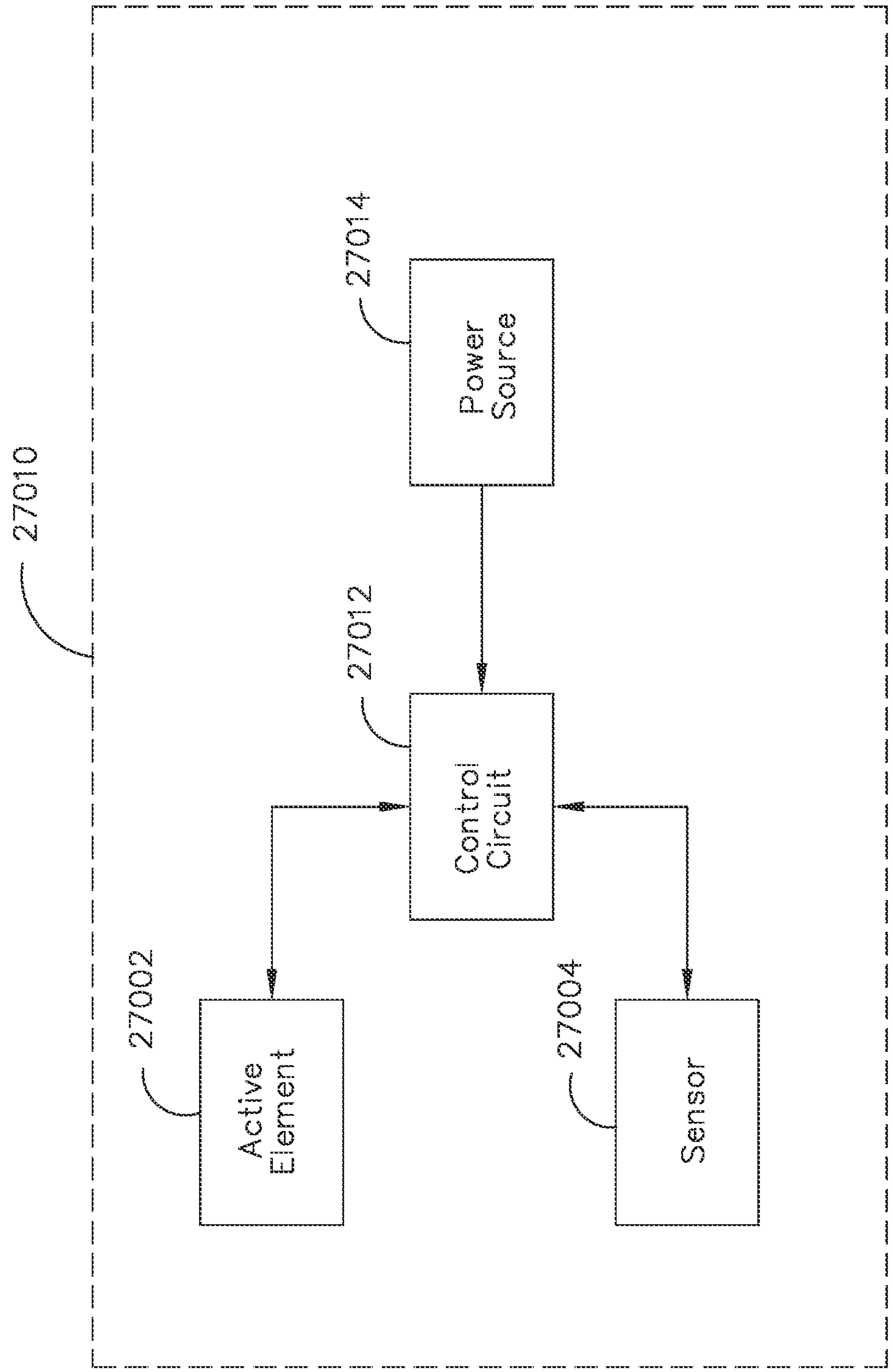

FIG. 178 illustrates a block diagram of an active sensor assembly, in accordance with at least one aspect of the present disclosure.

Figure 179:
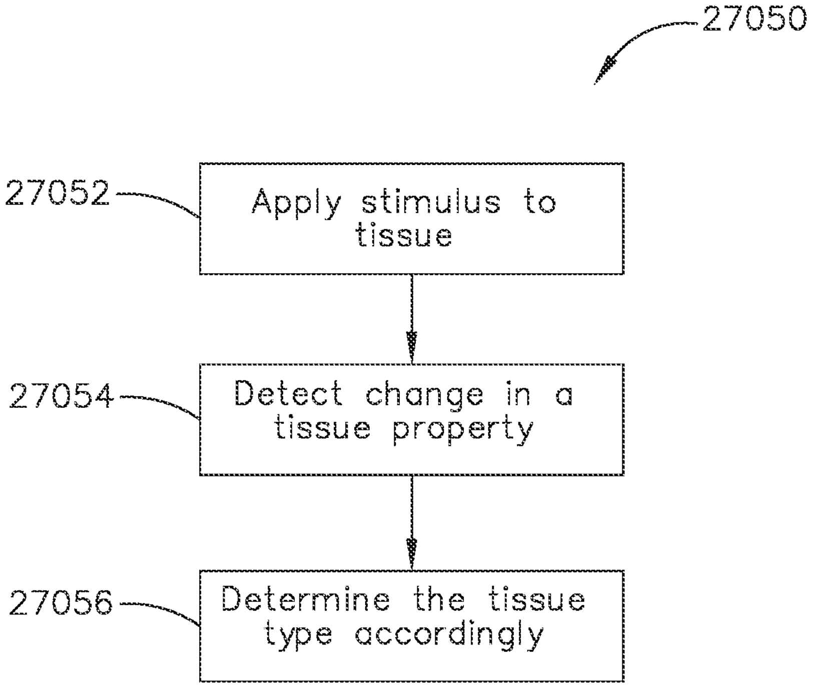

FIG. 179 illustrates a logic flow diagram of a process for determining a tissue type, in accordance with at least one aspect of the present disclosure.

Figure 180:
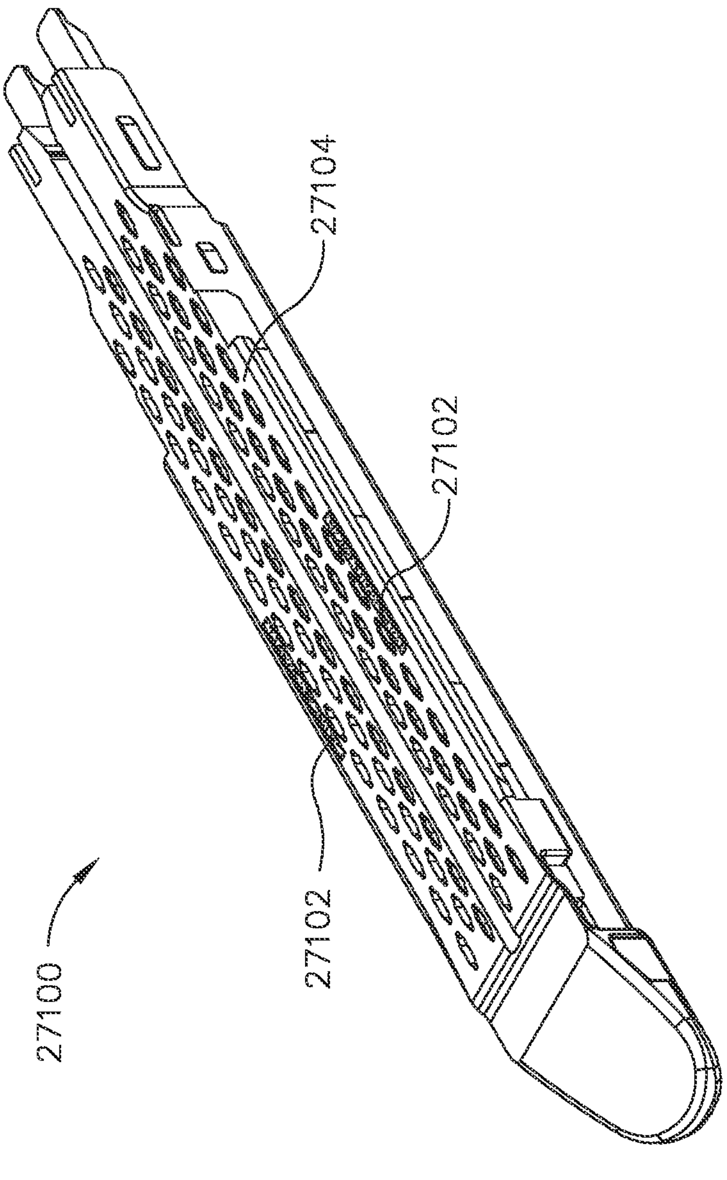

FIG. 180 illustrates a perspective view of a cartridge including hydrophobic areas, in accordance with at least one aspect of the present disclosure.

Figure 181:
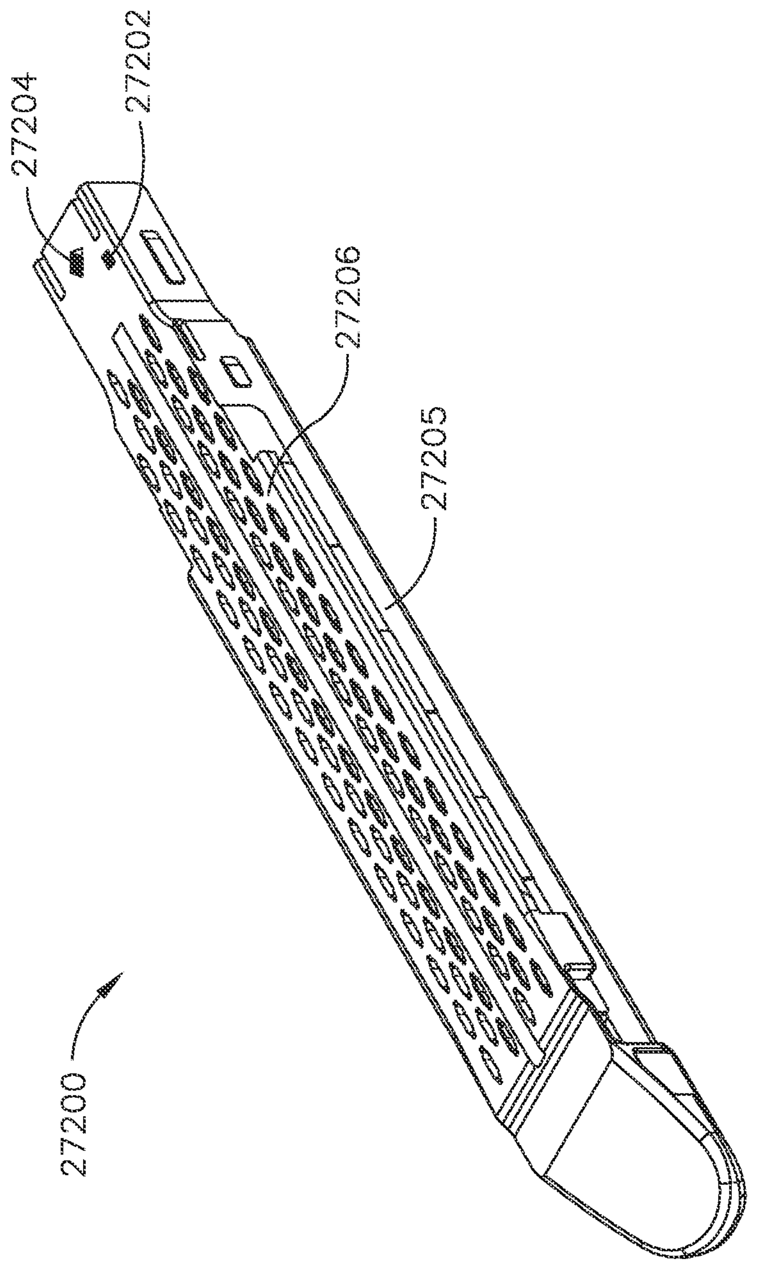

FIG. 181 illustrates a perspective view of a cartridge including a pair of data elements, in accordance with at least one aspect of the present disclosure.

Figure 182:
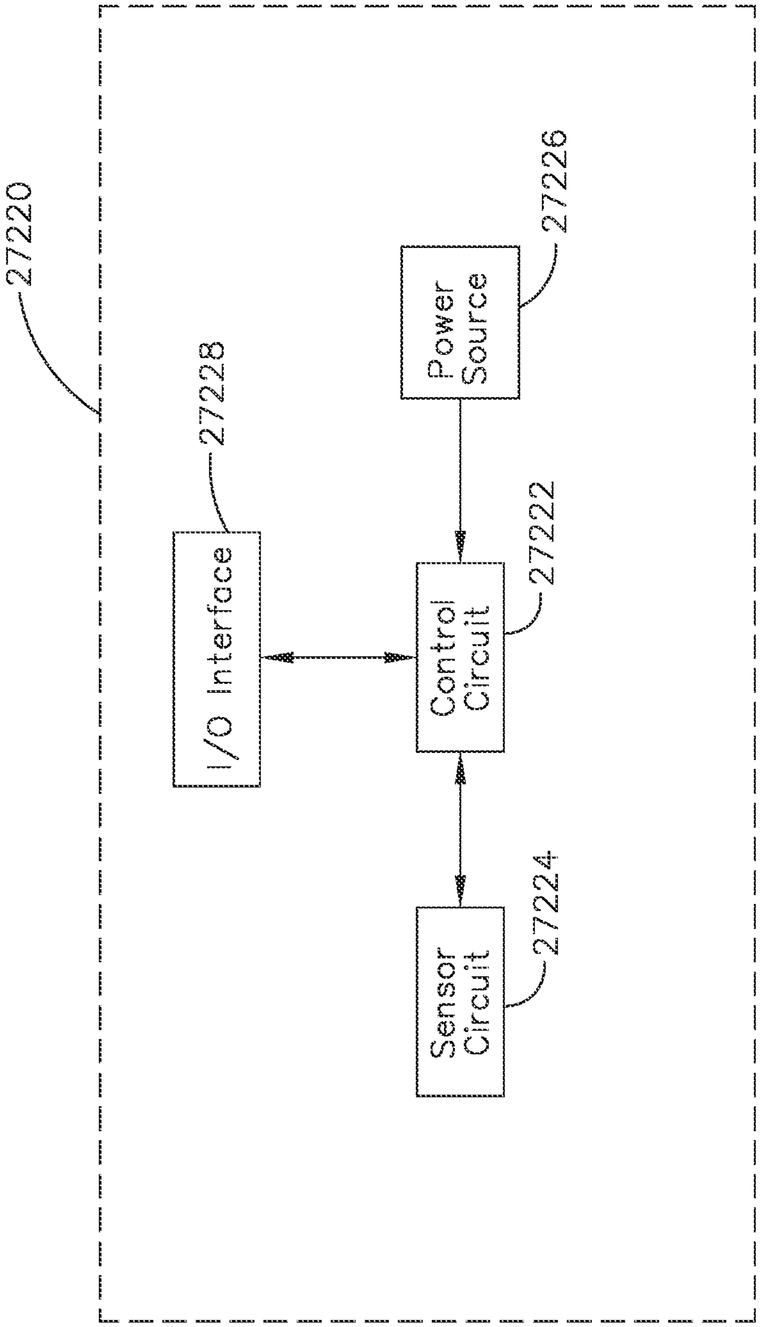

FIG. 182 illustrates a block diagram of a sensor assembly for detecting and/or receiving data from data elements associated with a cartridge, in accordance with at least one aspect of the present disclosure.

Figure 183:
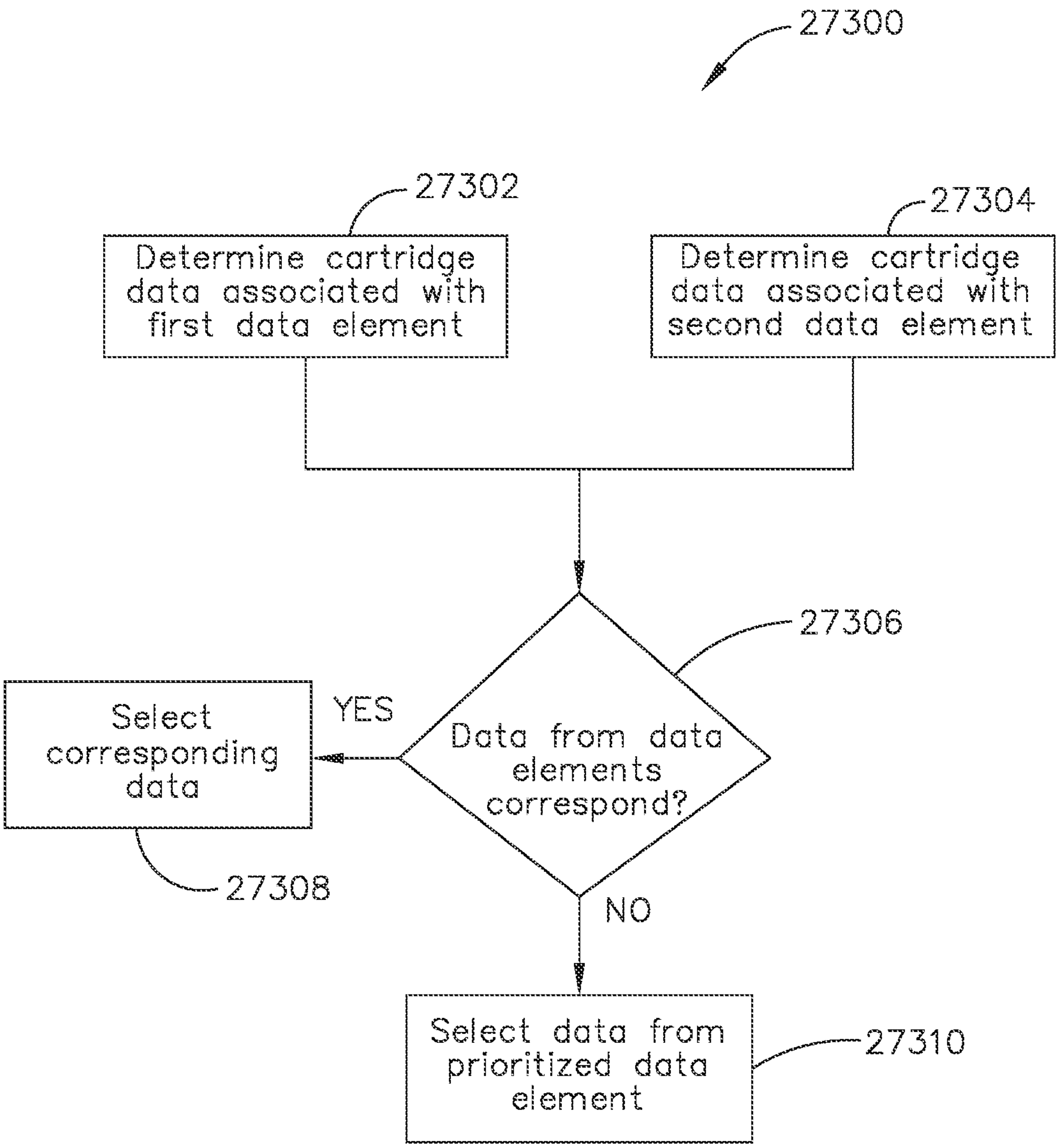

FIG. 183 illustrates a logic flow diagram of a process for resolving data identification conflicts, in accordance with at least one aspect of the present disclosure.

Figure 184:
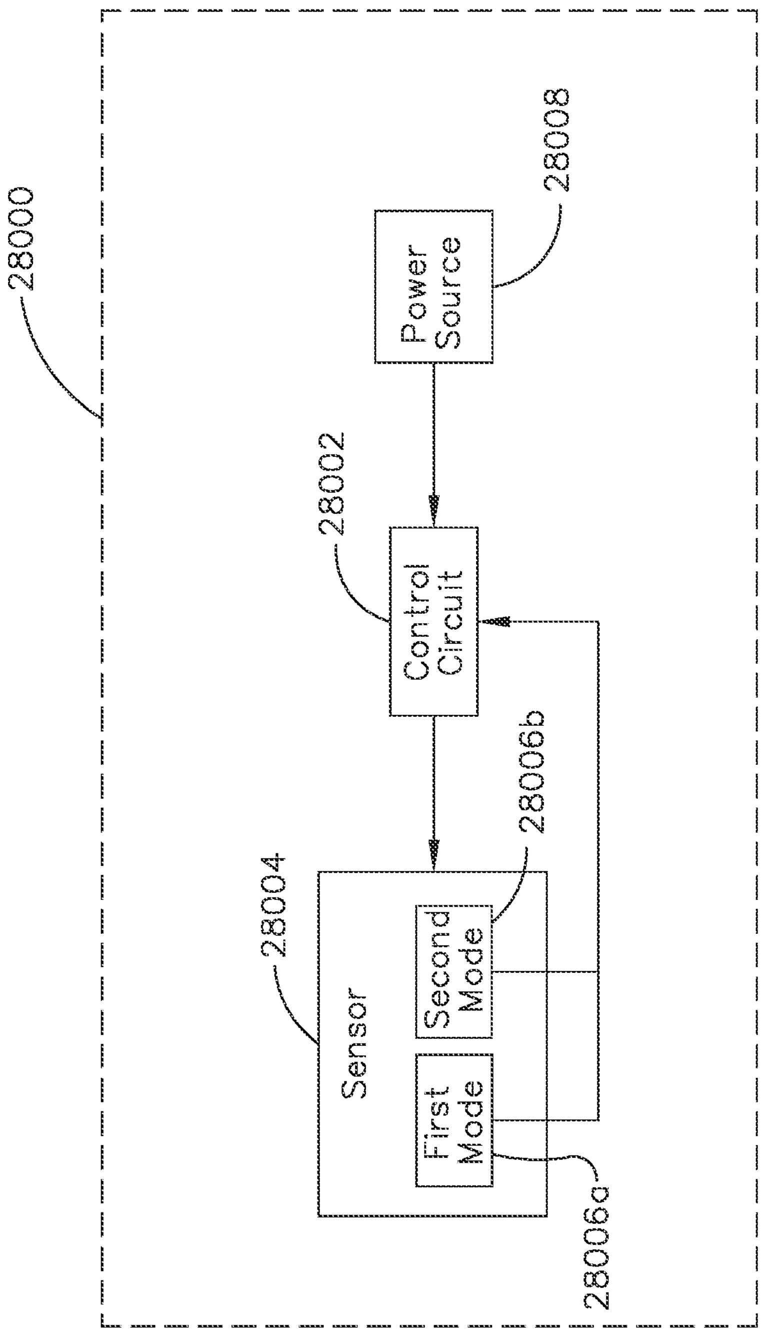

FIG. 184 illustrates a block diagram of a circuit including a variable output sensor, in accordance with at least one aspect of the present disclosure.

Figure 185:
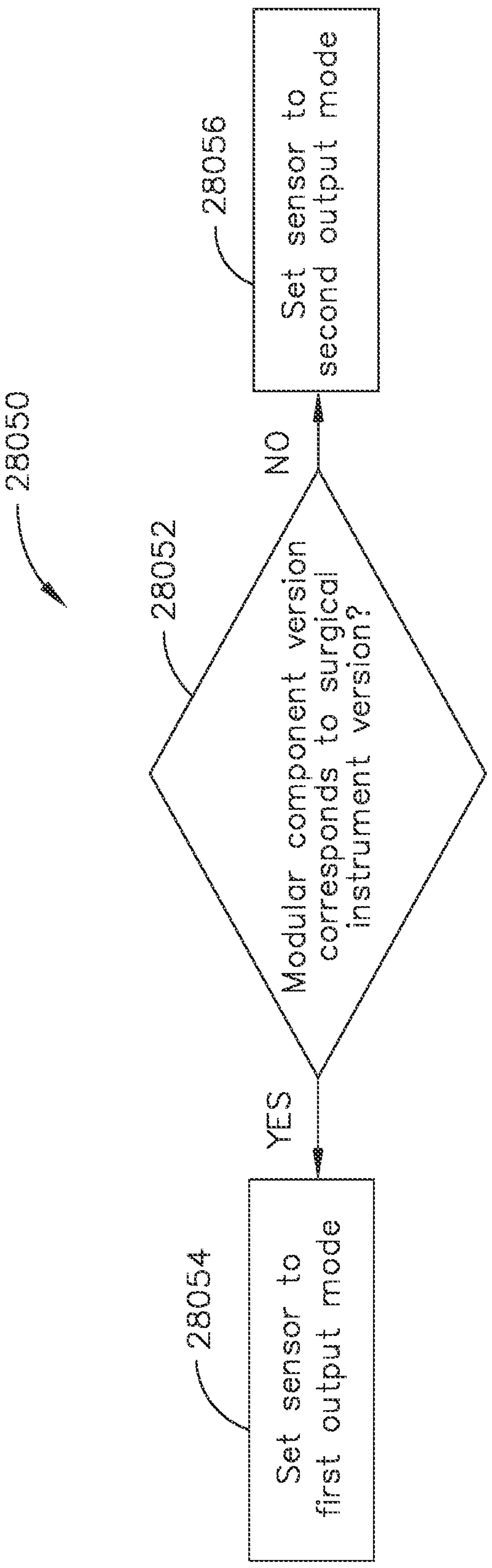

FIG. 185 illustrates a logic flow diagram of a process for controlling an output mode of a sensor, in accordance with at least one aspect of the present disclosure.

Figure 186:
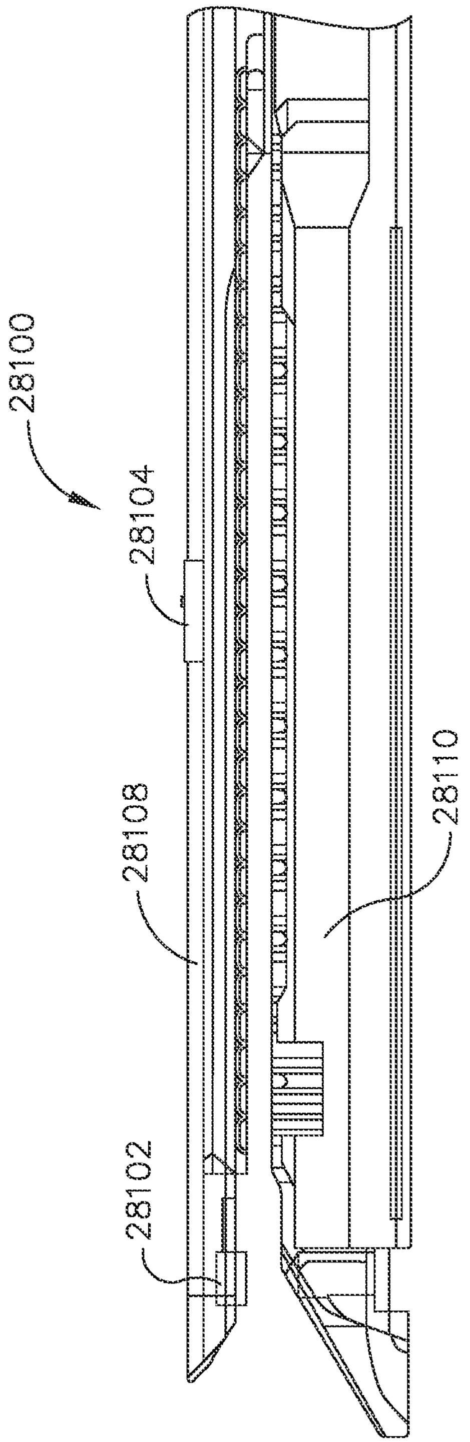

FIG. 186 illustrates an end effector comprising a first sensor and a second sensor, in accordance with at least one aspect of the present disclosure.

Figure 187:
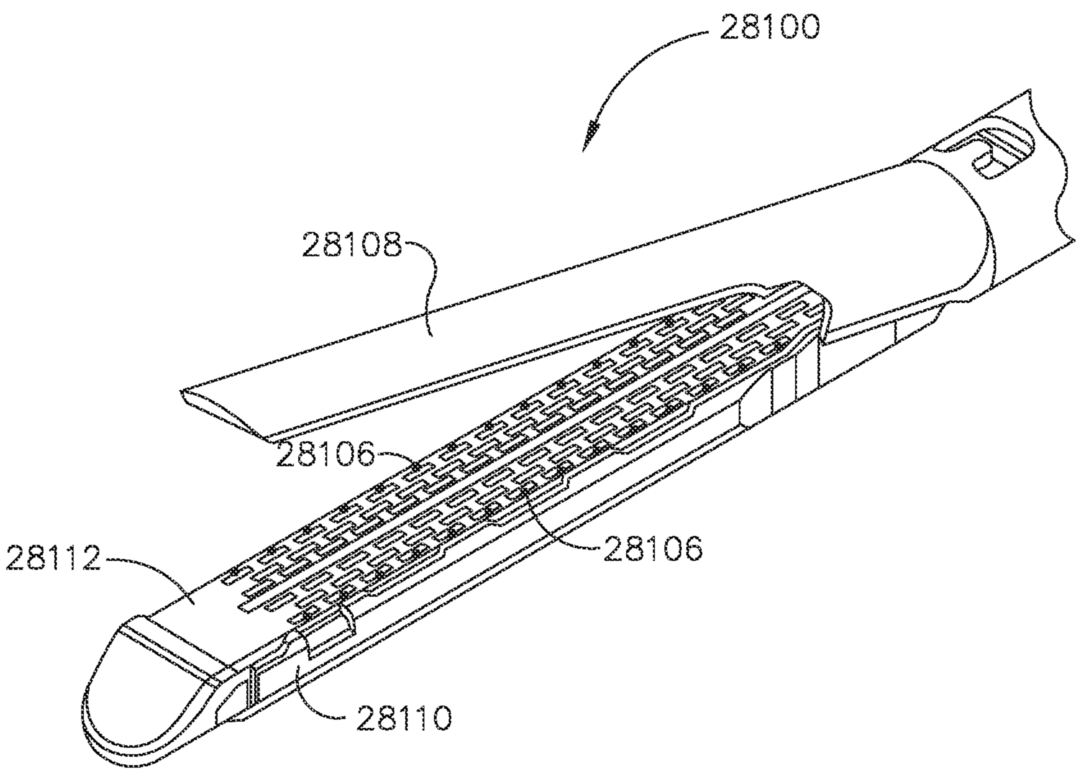

FIG. 187 illustrates a perspective view of an end effector, with the anvil in an open position, including a plurality of light sources arranged between the proximal end and the distal end of the staple cartridge on either side of the cartridge deck, in accordance with at least one aspect of the present disclosure.

DESCRIPTION

Applicant of the present application owns the following U.S. Patent Applications, filed on Dec. 4, 2018, the disclosure of each of which is herein incorporated by reference in its entirety:

- U.S. patent application Ser. No. 16/209,385, titled METHOD OF HUB COMMUNICATION, PROCESSING, STORAGE AND DISPLAY, now U.S. Patent Application Publication No. 2019/0200844;
- U.S. patent application Ser. No. 16/209,395, titled METHOD OF HUB COMMUNICATION, now U.S. Patent Application Publication No. 2019/0201136;
- U.S. patent application Ser. No. 16/209,403, titled METHOD OF CLOUD BASED DATA ANALYTICS FOR USE WITH THE HUB, now U.S. Patent Application Publication No. 2019/0206569;
- U.S. patent application Ser. No. 16/209,407, titled METHOD OF ROBOTIC HUB COMMUNICATION, DETECTION, AND CONTROL, now U.S. Patent Application Publication No. 2019/0201137;
- U.S. patent application Ser. No. 16/209,416, titled METHOD OF HUB COMMUNICATION, PROCESSING, DISPLAY, AND CLOUD ANALYTICS, now U.S. Patent Application Publication No. 2019/0206562;
- U.S. patent application Ser. No. 16/209,427, titled METHOD OF USING REINFORCED FLEXIBLE CIRCUITS WITH MULTIPLE SENSORS TO OPTIMIZE PERFORMANCE OF RADIO FREQUENCY DEVICES, now U.S. Patent Application Publication No. 2019/0208641;
- U.S. patent application Ser. No. 16/209,433, titled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB, now U.S. Patent Application Publication No. 2019/0201594;
- U.S. patent application Ser. No. 16/209,447, titled METHOD FOR SMOKE EVACUATION FOR SURGICAL HUB, now U.S. Patent Application Publication No. 2019/0201045;
- U.S. patent application Ser. No. 16/209,453, titled METHOD FOR CONTROLLING SMART ENERGY DEVICES, now U.S. Patent Application Publication No. 2019/0201046;
- U.S. patent application Ser. No. 16/209,458, titled METHOD FOR SMART ENERGY DEVICE INFRASTRUCTURE, now U.S. Patent Application Publication No. 2019/0201047;
- U.S. patent application Ser. No. 16/209,465, titled METHOD FOR ADAPTIVE CONTROL SCHEMES FOR SURGICAL NETWORK CONTROL AND INTERACTION, now U.S. Patent Application Publication No. 2019/0206563;
- U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, now U.S. Patent Application Publication No. 2019-0104919;
- U.S. patent application Ser. No. 16/209,490, titled METHOD FOR FACILITY DATA COLLECTION AND INTERPRETATION, now U.S. Patent Application Publication No. 2019/0206564; and
- U.S. patent application Ser. No. 16/209,491, titled METHOD FOR CIRCULAR STAPLER CONTROL ALGORITHM ADJUSTMENT BASED ON SITUATIONAL AWARENESS, now U.S. Patent Application Publication No. 2019/0200998.

Applicant of the present application owns the following U.S. Patent Applications, filed on Nov. 6, 2018, the disclosure of each of which is herein incorporated by reference in its entirety:

- U.S. patent application Ser. No. 16/182,224, titled SURGICAL NETWORK, INSTRUMENT, AND CLOUD RESPONSES BASED ON VALIDATION OF RECEIVED DATASET AND AUTHENTICATION OF ITS SOURCE AND INTEGRITY;
- U.S. patent application Ser. No. 16/182,230, titled SURGICAL SYSTEM FOR PRESENTING INFORMATION INTERPRETED FROM EXTERNAL DATA;
- U.S. patent application Ser. No. 16/182,233, titled SURGICAL SYSTEMS WITH AUTONOMOUSLY ADJUSTABLE CONTROL PROGRAMS;
- U.S. patent application Ser. No. 16/182,239, titled ADJUSTMENT OF DEVICE CONTROL PROGRAMS BASED ON STRATIFIED CONTEXTUAL DATA IN ADDITION TO THE DATA;
- U.S. patent application Ser. No. 16/182,243, titled SURGICAL HUB AND MODULAR DEVICE RESPONSE ADJUSTMENT BASED ON SITUATIONAL AWARENESS;

U.S. patent application Ser. No. 16/182,248, titled DETECTION AND ESCALATION OF SECURITY RESPONSES OF SURGICAL INSTRUMENTS TO INCREASING SEVERITY THREATS;

U.S. patent application Ser. No. 16/182,251, titled INTERACTIVE SURGICAL SYSTEM;

U.S. patent application Ser. No. 16/182,260, titled AUTOMATED DATA SCALING, ALIGNMENT, AND ORGANIZING BASED ON PREDEFINED PARAMETERS WITHIN SURGICAL NETWORKS;

U.S. patent application Ser. No. 16/182,267, titled SENSING THE PATIENT POSITION AND CONTACT UTILIZING THE MONO-POLAR RETURN PAD ELECTRODE TO PROVIDE SITUATIONAL AWARENESS TO THE HUB;

U.S. patent application Ser. No. 16/182,249, titled POWERED SURGICAL TOOL WITH PREDEFINED ADJUSTABLE CONTROL ALGORITHM FOR CONTROLLING END EFFECTOR PARAMETER;

U.S. patent application Ser. No. 16/182,246, titled ADJUSTMENTS BASED ON AIRBORNE PARTICLE PROPERTIES;

U.S. patent application Ser. No. 16/182,256, titled ADJUSTMENT OF A SURGICAL DEVICE FUNCTION BASED ON SITUATIONAL AWARENESS;

U.S. patent application Ser. No. 16/182,242, titled REAL-TIME ANALYSIS OF COMPREHENSIVE COST OF ALL INSTRUMENTATION USED IN SURGERY UTILIZING DATA FLUIDITY TO TRACK INSTRUMENTS THROUGH STOCKING AND IN-HOUSE PROCESSES;

U.S. patent application Ser. No. 16/182,255, titled USAGE AND TECHNIQUE ANALYSIS OF SURGEON/STAFF PERFORMANCE AGAINST A BASELINE TO OPTIMIZE DEVICE UTILIZATION AND PERFORMANCE FOR BOTH CURRENT AND FUTURE PROCEDURES;

U.S. patent application Ser. No. 16/182,269, titled IMAGE CAPTURING OF THE AREAS OUTSIDE THE ABDOMEN TO IMPROVE PLACEMENT AND CONTROL OF A SURGICAL DEVICE IN USE;

U.S. patent application Ser. No. 16/182,278, titled COMMUNICATION OF DATA WHERE A SURGICAL NETWORK IS USING CONTEXT OF THE DATA AND REQUIREMENTS OF A RECEIVING SYSTEM/USER TO INFLUENCE INCLUSION OR LINKAGE OF DATA AND METADATA TO ESTABLISH CONTINUITY;

U.S. patent application Ser. No. 16/182,290, titled SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION;

U.S. patent application Ser. No. 16/182,232, titled CONTROL OF A SURGICAL SYSTEM THROUGH A SURGICAL BARRIER;

U.S. patent application Ser. No. 16/182,227, titled SURGICAL NETWORK DETERMINATION OF PRIORITIZATION OF COMMUNICATION, INTERACTION, OR PROCESSING BASED ON SYSTEM OR DEVICE NEEDS;

U.S. patent application Ser. No. 16/182,231, titled WIRELESS PAIRING OF A SURGICAL DEVICE WITH ANOTHER DEVICE WITHIN A STERILE SURGICAL FIELD BASED ON THE USAGE AND SITUATIONAL AWARENESS OF DEVICES;

U.S. patent application Ser. No. 16/182,229, titled ADJUSTMENT OF STAPLE HEIGHT OF AT LEAST ONE ROW OF STAPLES BASED ON THE SENSED TISSUE THICKNESS OR FORCE IN CLOSING;

U.S. patent application Ser. No. 16/182,234, titled STAPLING DEVICE WITH BOTH COMPULSORY AND DISCRETIONARY LOCKOUTS BASED ON SENSED PARAMETERS;

U.S. patent application Ser. No. 16/182,240, titled POWERED STAPLING DEVICE CONFIGURED TO ADJUST FORCE, ADVANCEMENT SPEED, AND OVERALL STROKE OF CUTTING MEMBER BASED ON SENSED PARAMETER OF FIRING OR CLAMPING;

U.S. patent application Ser. No. 16/182,235, titled VARIATION OF RADIO FREQUENCY AND ULTRASONIC POWER LEVEL IN COOPERATION WITH VARYING CLAMP ARM PRESSURE TO ACHIEVE PREDEFINED HEAT FLUX OR POWER APPLIED TO TISSUE; and U.S. patent application Ser. No. 16/182,238, titled ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION.

Applicant of the present application owns the following U.S. Patent Applications that were filed on Oct. 26, 2018, the disclosure of each of which is herein incorporated by reference in its entirety:

U.S. patent application Ser. No. 16/172,303, titled METHOD FOR OPERATING A POWERED ARTICULATING MULTI-CLIP APPLIER;

U.S. patent application Ser. No. 16/172,130, titled CLIP APPLIER COMPRISING INTERCHANGEABLE CLIP RELOADS;

U.S. patent application Ser. No. 16/172,066, titled CLIP APPLIER COMPRISING A MOVABLE CLIP MAGAZINE;

U.S. patent application Ser. No. 16/172,078, titled CLIP APPLIER COMPRISING A ROTATABLE CLIP MAGAZINE;

U.S. patent application Ser. No. 16/172,087, titled CLIP APPLIER COMPRISING CLIP ADVANCING SYSTEMS;

U.S. patent application Ser. No. 16/172,094, titled CLIP APPLIER COMPRISING A CLIP CRIMPING SYSTEM;

U.S. patent application Ser. No. 16/172,128, titled CLIP APPLIER COMPRISING A RECIPROCATING CLIP ADVANCING MEMBER;

U.S. patent application Ser. No. 16/172,168, titled CLIP APPLIER COMPRISING A MOTOR CONTROLLER;

U.S. patent application Ser. No. 16/172,164, titled SURGICAL SYSTEM COMPRISING A SURGICAL TOOL AND A SURGICAL HUB;

U.S. patent application Ser. No. 16/172,328, titled METHOD OF HUB COMMUNICATION WITH SURGICAL INSTRUMENT SYSTEMS;

U.S. patent application Ser. No. 16/172,280, titled METHOD FOR PRODUCING A SURGICAL INSTRUMENT COMPRISING A SMART ELECTRICAL SYSTEM;

U.S. patent application Ser. No. 16/172,219, titled METHOD OF HUB COMMUNICATION WITH SURGICAL INSTRUMENT SYSTEMS;

U.S. patent application Ser. No. 16/172,248, titled METHOD OF HUB COMMUNICATION WITH SURGICAL INSTRUMENT SYSTEMS;

U.S. patent application Ser. No. 16/172,198, titled METHOD OF HUB COMMUNICATION WITH SURGICAL INSTRUMENT SYSTEMS; and U.S. patent application Ser. No. 16/172,155, titled METHOD OF HUB COMMUNICATION WITH SURGICAL INSTRUMENT SYSTEMS.

Applicant of the present application owns the following U.S. Patent Applications, filed on Aug. 28, 2018, the disclosure of each of which is herein incorporated by reference in its entirety:

U.S. patent application Ser. No. 16/115,214, titled ESTIMATING STATE OF ULTRASONIC END EFFECTOR AND CONTROL SYSTEM THEREFOR;

U.S. patent application Ser. No. 16/115,205, titled TEMPERATURE CONTROL OF ULTRASONIC END EFFECTOR AND CONTROL SYSTEM THEREFOR;

U.S. patent application Ser. No. 16/115,233, titled RADIO FREQUENCY ENERGY DEVICE FOR DELIVERING COMBINED ELECTRICAL SIGNALS;

U.S. patent application Ser. No. 16/115,208, titled CONTROLLING AN ULTRASONIC SURGICAL INSTRUMENT ACCORDING TO TISSUE LOCATION;

U.S. patent application Ser. No. 16/115,220, titled CONTROLLING ACTIVATION OF AN ULTRASONIC SURGICAL INSTRUMENT ACCORDING TO THE PRESENCE OF TISSUE;

U.S. patent application Ser. No. 16/115,232, titled DETERMINING TISSUE COMPOSITION VIA AN ULTRASONIC SYSTEM;

U.S. patent application Ser. No. 16/115,239, titled DETERMINING THE STATE OF AN ULTRASONIC ELECTROMECHANICAL SYSTEM ACCORDING TO FREQUENCY SHIFT;

U.S. patent application Ser. No. 16/115,247, titled DETERMINING THE STATE OF AN ULTRASONIC END EFFECTOR;

U.S. patent application Ser. No. 16/115,211, titled SITUATIONAL AWARENESS OF ELECTROSURGICAL SYSTEMS;

U.S. patent application Ser. No. 16/115,226, titled MECHANISMS FOR CONTROLLING DIFFERENT ELECTROMECHANICAL SYSTEMS OF AN ELECTROSURGICAL INSTRUMENT;

U.S. patent application Ser. No. 16/115,240, titled DETECTION OF END EFFECTOR EMERSION IN LIQUID;

U.S. patent application Ser. No. 16/115,249, titled INTERRUPTION OF ENERGY DUE TO INADVERTENT CAPACITIVE COUPLING;

U.S. patent application Ser. No. 16/115,256, titled INCREASING RADIO FREQUENCY TO CREATE PAD-LESS MONOPOLAR LOOP;

U.S. patent application Ser. No. 16/115,223, titled BIPOLAR COMBINATION DEVICE THAT AUTOMATICALLY ADJUSTS PRESSURE BASED ON ENERGY MODALITY; and U.S. patent application Ser. No. 16/115,238, titled ACTIVATION OF ENERGY DEVICES.

Applicant of the present application owns the following U.S. Patent Applications, filed on Aug. 24, 2018, the disclosure of each of which is herein incorporated by reference in its entirety:

U.S. patent application Ser. No. 16/112,129, titled SURGICAL SUTURING INSTRUMENT CONFIGURED TO MANIPULATE TISSUE USING MECHANICAL AND ELECTRICAL POWER;

U.S. patent application Ser. No. 16/112,155, titled SURGICAL SUTURING INSTRUMENT COMPRISING A CAPTURE WIDTH WHICH IS LARGER THAN TROCAR DIAMETER;

U.S. patent application Ser. No. 16/112,168, titled SURGICAL SUTURING INSTRUMENT COMPRISING A NON-CIRCULAR NEEDLE;

U.S. patent application Ser. No. 16/112,180, titled ELECTRICAL POWER OUTPUT CONTROL BASED ON MECHANICAL FORCES;

U.S. patent application Ser. No. 16/112,193, titled REACTIVE ALGORITHM FOR SURGICAL SYSTEM;

U.S. patent application Ser. No. 16/112,099, titled SURGICAL INSTRUMENT COMPRISING AN ADAPTIVE ELECTRICAL SYSTEM;

U.S. patent application Ser. No. 16/112,112, titled CONTROL SYSTEM ARRANGEMENTS FOR A MODULAR SURGICAL INSTRUMENT;

U.S. patent application Ser. No. 16/112,119, titled ADAPTIVE CONTROL PROGRAMS FOR A SURGICAL SYSTEM COMPRISING MORE THAN ONE TYPE OF CARTRIDGE;

U.S. patent application Ser. No. 16/112,097, titled SURGICAL INSTRUMENT SYSTEMS COMPRISING BATTERY ARRANGEMENTS;

U.S. patent application Ser. No. 16/112,109, titled SURGICAL INSTRUMENT SYSTEMS COMPRISING HANDLE ARRANGEMENTS;

U.S. patent application Ser. No. 16/112,114, titled SURGICAL INSTRUMENT SYSTEMS COMPRISING FEEDBACK MECHANISMS;

U.S. patent application Ser. No. 16/112,117, titled SURGICAL INSTRUMENT SYSTEMS COMPRISING LOCKOUT MECHANISMS;

U.S. patent application Ser. No. 16/112,095, titled SURGICAL INSTRUMENTS COMPRISING A LOCKABLE END EFFECTOR SOCKET;

U.S. patent application Ser. No. 16/112,121, titled SURGICAL INSTRUMENTS COMPRISING A SHIFTING MECHANISM;

U.S. patent application Ser. No. 16/112,151, titled SURGICAL INSTRUMENTS COMPRISING A SYSTEM FOR ARTICULATION AND ROTATION COMPENSATION;

U.S. patent application Ser. No. 16/112,154, titled SURGICAL INSTRUMENTS COMPRISING A BIASED SHIFTING MECHANISM;

U.S. patent application Ser. No. 16/112,226, titled SURGICAL INSTRUMENTS COMPRISING AN ARTICULATION DRIVE THAT PROVIDES FOR HIGH ARTICULATION ANGLES;

U.S. patent application Ser. No. 16/112,062, titled SURGICAL DISSECTORS AND MANUFACTURING TECHNIQUES;

U.S. patent application Ser. No. 16/112,098, titled SURGICAL DISSECTORS CONFIGURED TO APPLY MECHANICAL AND ELECTRICAL ENERGY;

U.S. patent application Ser. No. 16/112,237, titled SURGICAL CLIP APPLIER CONFIGURED TO STORE CLIPS IN A STORED STATE;

U.S. patent application Ser. No. 16/112,245, titled SURGICAL CLIP APPLIER COMPRISING AN EMPTY CLIP CARTRIDGE LOCKOUT;

- U.S. patent application Ser. No. 16/112,249, titled SURGICAL CLIP APPLIER COMPRISING AN AUTOMATIC CLIP FEEDING SYSTEM;
- U.S. patent application Ser. No. 16/112,253, titled SURGICAL CLIP APPLIER COMPRISING ADAPTIVE FIRING CONTROL; and
- U.S. patent application Ser. No. 16/112,257, titled SURGICAL CLIP APPLIER COMPRISING ADAPTIVE CONTROL IN RESPONSE TO A STRAIN GAUGE CIRCUIT.

Applicant of the present application owns the following U.S. Patent Applications, filed on Jun. 29, 2018, the disclosure of each of which is herein incorporated by reference in its entirety:

- U.S. patent application Ser. No. 16/024,090, titled CAPACITIVE COUPLED RETURN PATH PAD WITH SEPARABLE ARRAY ELEMENTS;
- U.S. patent application Ser. No. 16/024,057, titled CONTROLLING A SURGICAL INSTRUMENT ACCORDING TO SENSED CLOSURE PARAMETERS;
- U.S. patent application Ser. No. 16/024,067, titled SYSTEMS FOR ADJUSTING END EFFECTOR PARAMETERS BASED ON PERIOPERATIVE INFORMATION;
- U.S. patent application Ser. No. 16/024,075, titled SAFETY SYSTEMS FOR SMART POWERED SURGICAL STAPLING;
- U.S. patent application Ser. No. 16/024,083, titled SAFETY SYSTEMS FOR SMART POWERED SURGICAL STAPLING;
- U.S. patent application Ser. No. 16/024,094, titled SURGICAL SYSTEMS FOR DETECTING END EFFECTOR TISSUE DISTRIBUTION IRREGULARITIES;
- U.S. patent application Ser. No. 16/024,138, titled SYSTEMS FOR DETECTING PROXIMITY OF SURGICAL END EFFECTOR TO CANCEROUS TISSUE;
- U.S. patent application Ser. No. 16/024,150, titled SURGICAL INSTRUMENT CARTRIDGE SENSOR ASSEMBLIES;
- U.S. patent application Ser. No. 16/024,160, titled VARIABLE OUTPUT CARTRIDGE SENSOR ASSEMBLY;
- U.S. patent application Ser. No. 16/024,124, titled SURGICAL INSTRUMENT HAVING A FLEXIBLE ELECTRODE;
- U.S. patent application Ser. No. 16/024,132, titled SURGICAL INSTRUMENT HAVING A FLEXIBLE CIRCUIT;
- U.S. patent application Ser. No. 16/024,141, titled SURGICAL INSTRUMENT WITH A TISSUE MARKING ASSEMBLY;
- U.S. patent application Ser. No. 16/024,162, titled SURGICAL SYSTEMS WITH PRIORITIZED DATA TRANSMISSION CAPABILITIES;
- U.S. patent application Ser. No. 16/024,066, titled SURGICAL EVACUATION SENSING AND MOTOR CONTROL;
- U.S. patent application Ser. No. 16/024,096, titled SURGICAL EVACUATION SENSOR ARRANGEMENTS;
- U.S. patent application Ser. No. 16/024,116, titled SURGICAL EVACUATION FLOW PATHS;
- U.S. patent application Ser. No. 16/024,149, titled SURGICAL EVACUATION SENSING AND GENERATOR CONTROL;
- U.S. patent application Ser. No. 16/024,180, titled SURGICAL EVACUATION SENSING AND DISPLAY;
- U.S. patent application Ser. No. 16/024,245, titled COMMUNICATION OF SMOKE EVACUATION SYSTEM PARAMETERS TO HUB OR CLOUD IN SMOKE EVACUATION MODULE FOR INTERACTIVE SURGICAL PLATFORM;
- U.S. patent application Ser. No. 16/024,258, titled SMOKE EVACUATION SYSTEM INCLUDING A SEGMENTED CONTROL CIRCUIT FOR INTERACTIVE SURGICAL PLATFORM;
- U.S. patent application Ser. No. 16/024,265, titled SURGICAL EVACUATION SYSTEM WITH A COMMUNICATION CIRCUIT FOR COMMUNICATION BETWEEN A FILTER AND A SMOKE EVACUATION DEVICE; and
- U.S. patent application Ser. No. 16/024,273, titled DUAL IN-SERIES LARGE AND SMALL DROPLET FILTERS.

Applicant of the present application owns the following U.S. Patent Applications, filed on Mar. 29, 2018, the disclosure of each of which is herein incorporated by reference in its entirety:

- U.S. patent application Ser. No. 15/940,641, titled INTERACTIVE SURGICAL SYSTEMS WITH ENCRYPTED COMMUNICATION CAPABILITIES;
- U.S. patent application Ser. No. 15/940,648, titled INTERACTIVE SURGICAL SYSTEMS WITH CONDITION HANDLING OF DEVICES AND DATA CAPABILITIES;
- U.S. patent application Ser. No. 15/940,656, titled SURGICAL HUB COORDINATION OF CONTROL AND COMMUNICATION OF OPERATING ROOM DEVICES;
- U.S. patent application Ser. No. 15/940,666, titled SPATIAL AWARENESS OF SURGICAL HUBS IN OPERATING ROOMS;
- U.S. patent application Ser. No. 15/940,670, titled COOPERATIVE UTILIZATION OF DATA DERIVED FROM SECONDARY SOURCES BY INTELLIGENT SURGICAL HUBS;
- U.S. patent application Ser. No. 15/940,677, titled SURGICAL HUB CONTROL ARRANGEMENTS;
- U.S. patent application Ser. No. 15/940,632, titled DATA STRIPPING METHOD TO INTERROGATE PATIENT RECORDS AND CREATE ANONYMIZED RECORD;
- U.S. patent application Ser. No. 15/940,640, titled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS;
- U.S. patent application Ser. No. 15/940,645, titled SELF DESCRIBING DATA PACKETS GENERATED AT AN ISSUING INSTRUMENT;
- U.S. patent application Ser. No. 15/940,649, titled DATA PAIRING TO INTERCONNECT A DEVICE MEASURED PARAMETER WITH AN OUTCOME;
- U.S. patent application Ser. No. 15/940,654, titled SURGICAL HUB SITUATIONAL AWARENESS;
- U.S. patent application Ser. No. 15/940,663, titled SURGICAL SYSTEM DISTRIBUTED PROCESSING;
- U.S. patent application Ser. No. 15/940,668, titled AGGREGATION AND REPORTING OF SURGICAL HUB DATA;

U.S. patent application Ser. No. 15/940,671, titled SURGICAL HUB SPATIAL AWARENESS TO DETERMINE DEVICES IN OPERATING THEATER;

U.S. patent application Ser. No. 15/940,686, titled DISPLAY OF ALIGNMENT OF STAPLE CARTRIDGE TO PRIOR LINEAR STAPLE LINE;

U.S. patent application Ser. No. 15/940,700, titled STERILE FIELD INTERACTIVE CONTROL DISPLAYS;

U.S. patent application Ser. No. 15/940,629, titled COMPUTER IMPLEMENTED INTERACTIVE SURGICAL SYSTEMS;

U.S. patent application Ser. No. 15/940,704, titled USE OF LASER LIGHT AND RED-GREEN-BLUE COLORATION TO DETERMINE PROPERTIES OF BACK SCATTERED LIGHT;

U.S. patent application Ser. No. 15/940,722, titled CHARACTERIZATION OF TISSUE IRREGULARITIES THROUGH THE USE OF MONO-CHROMATIC LIGHT REFRACTIVITY;

U.S. patent application Ser. No. 15/940,742, titled DUAL CMOS ARRAY IMAGING;

U.S. patent application Ser. No. 15/940,636, titled ADAPTIVE CONTROL PROGRAM UPDATES FOR SURGICAL DEVICES;

U.S. patent application Ser. No. 15/940,653, titled ADAPTIVE CONTROL PROGRAM UPDATES FOR SURGICAL HUBS;

U.S. patent application Ser. No. 15/940,660, titled CLOUD-BASED MEDICAL ANALYTICS FOR CUSTOMIZATION AND RECOMMENDATIONS TO A USER;

U.S. patent application Ser. No. 15/940,679, titled CLOUD-BASED MEDICAL ANALYTICS FOR LINKING OF LOCAL USAGE TRENDS WITH THE RESOURCE ACQUISITION BEHAVIORS OF LARGER DATA SET;

U.S. patent application Ser. No. 15/940,694, titled CLOUD-BASED MEDICAL ANALYTICS FOR MEDICAL FACILITY SEGMENTED INDIVIDUALIZATION OF INSTRUMENT FUNCTION;

U.S. patent application Ser. No. 15/940,634, titled CLOUD-BASED MEDICAL ANALYTICS FOR SECURITY AND AUTHENTICATION TRENDS AND REACTIVE MEASURES;

U.S. patent application Ser. No. 15/940,706, titled DATA HANDLING AND PRIORITIZATION IN A CLOUD ANALYTICS NETWORK;

U.S. patent application Ser. No. 15/940,675, titled CLOUD INTERFACE FOR COUPLED SURGICAL DEVICES;

U.S. patent application Ser. No. 15/940,627, titled DRIVE ARRANGEMENTS FOR ROBOT-ASSISTED SURGICAL PLATFORMS;

U.S. patent application Ser. No. 15/940,637, titled COMMUNICATION ARRANGEMENTS FOR ROBOT-ASSISTED SURGICAL PLATFORMS;

U.S. patent application Ser. No. 15/940,642, titled CONTROLS FOR ROBOT-ASSISTED SURGICAL PLATFORMS;

U.S. patent application Ser. No. 15/940,676, titled AUTOMATIC TOOL ADJUSTMENTS FOR ROBOT-ASSISTED SURGICAL PLATFORMS;

U.S. patent application Ser. No. 15/940,680, titled CONTROLLERS FOR ROBOT-ASSISTED SURGICAL PLATFORMS;

U.S. patent application Ser. No. 15/940,683, titled COOPERATIVE SURGICAL ACTIONS FOR ROBOT-ASSISTED SURGICAL PLATFORMS;

U.S. patent application Ser. No. 15/940,690, titled DISPLAY ARRANGEMENTS FOR ROBOT-ASSISTED SURGICAL PLATFORMS; and U.S. patent application Ser. No. 15/940,711, titled SENSING ARRANGEMENTS FOR ROBOT-ASSISTED SURGICAL PLATFORMS.

Applicant of the present application owns the following U.S. Provisional Patent Applications, filed on Mar. 8, 2018, the disclosure of each of which is herein incorporated by reference in its entirety:

U.S. Provisional Patent Application No. 62/640,417, titled TEMPERATURE CONTROL IN ULTRASONIC DEVICE AND CONTROL SYSTEM THEREFOR; and U.S. Provisional Patent Application No. 62/640,415, titled ESTIMATING STATE OF ULTRASONIC END EFFECTOR AND CONTROL SYSTEM THEREFOR.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Certain exemplary aspects will now be described to provide an overall understanding of the principles of the structure, function, manufacture, and use of the devices and methods disclosed herein. One or more examples of these aspects are illustrated in the accompanying drawings. Those of ordinary skill in the art will understand that the devices and methods specifically described herein and illustrated in the accompanying drawings are non-limiting exemplary aspects and that the scope of the various aspects is defined solely by the claims. The features illustrated or described in connection with one exemplary aspect may be combined with the features of other aspects. Such modifications and variations are intended to be included within the scope of the claims.

Figure 1:
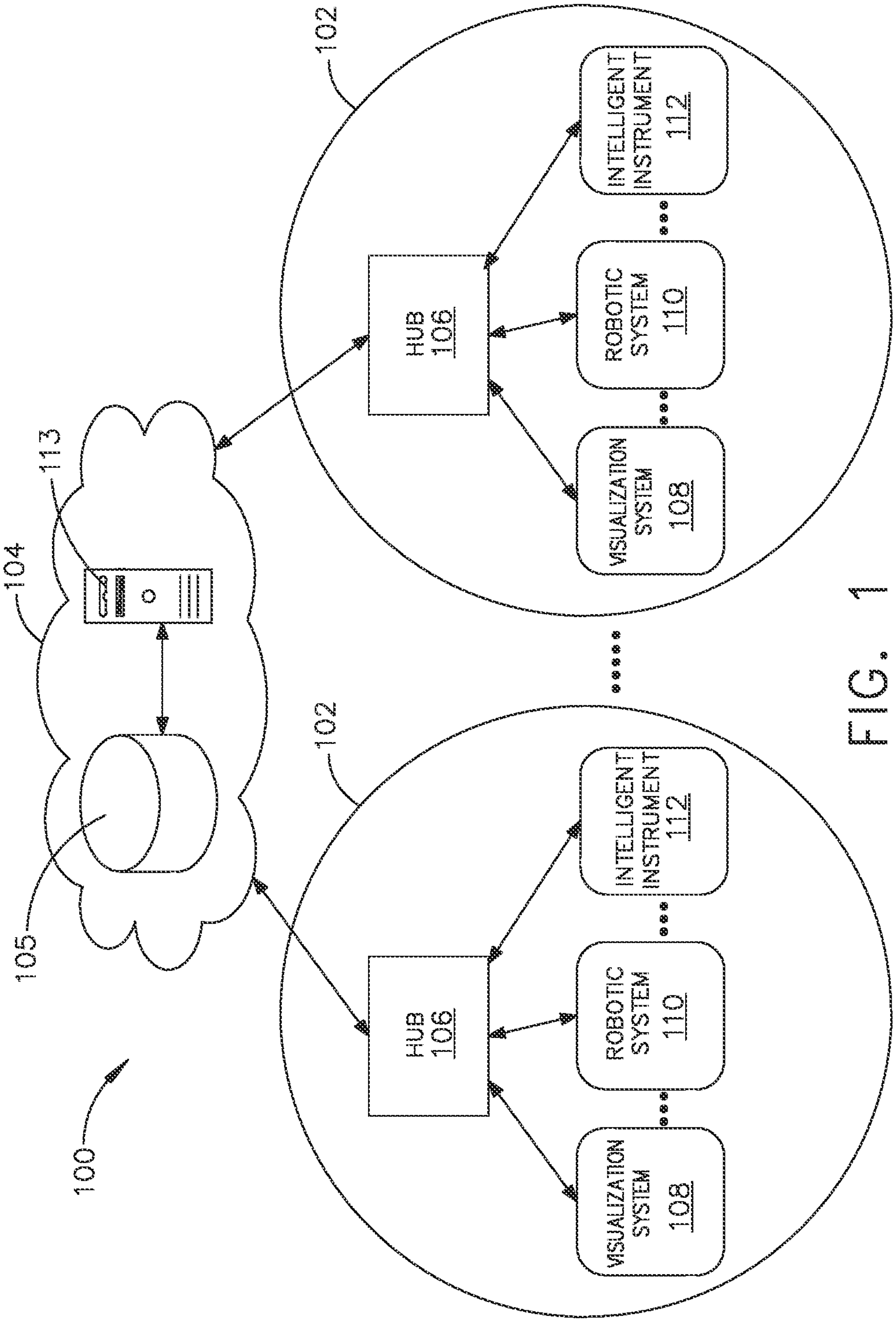
FIG. 1 is a block diagram of a computer-implemented interactive surgical system, in accordance with at least one aspect of the present disclosure.

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 3:
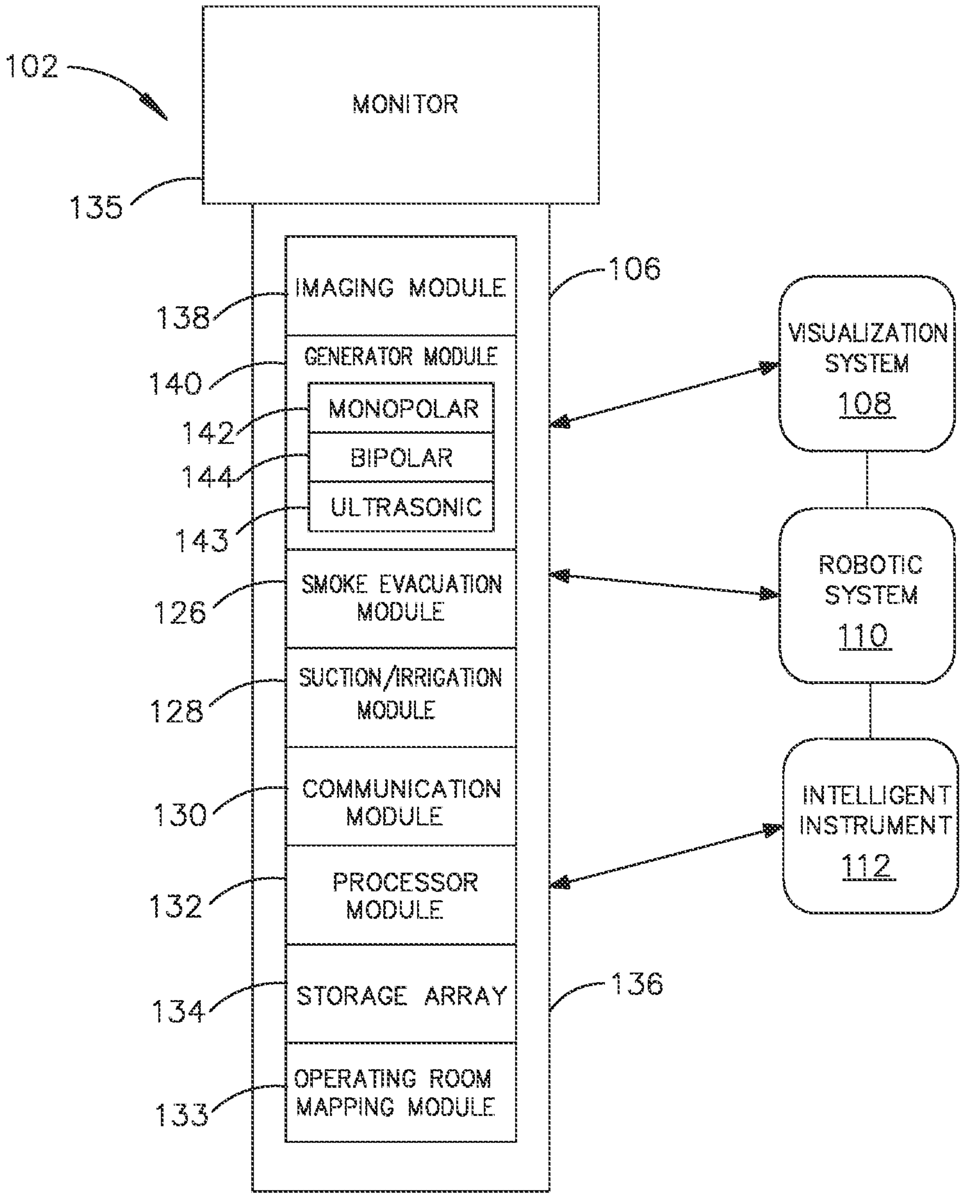
FIG. 3 is a surgical hub paired with a visualization system, a robotic system, and an intelligent instrument, in accordance with at least one aspect of the present disclosure.

FIG. 3 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngoneproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Figure 2:
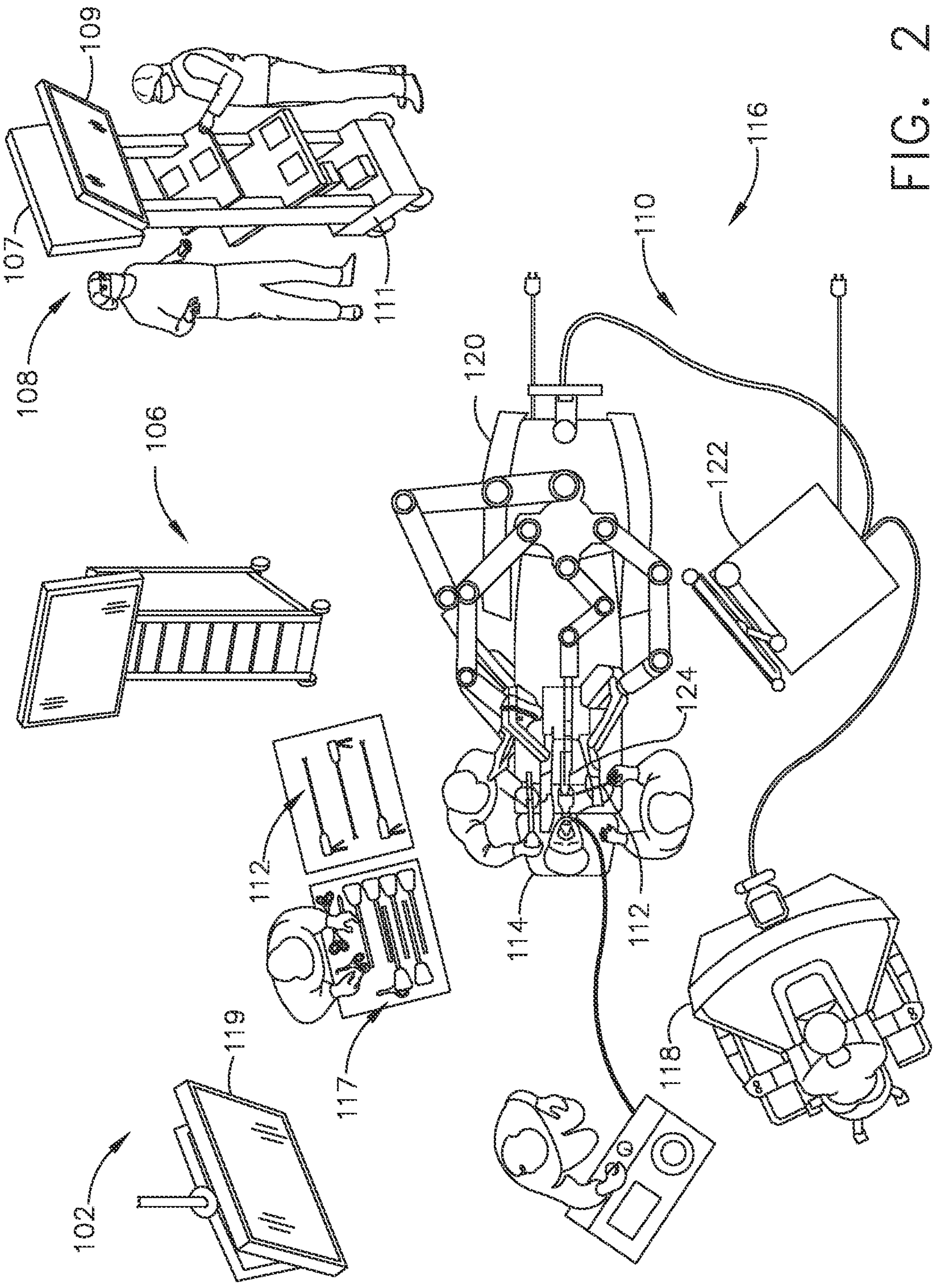
FIG. 2 is a surgical system being used to perform a surgical procedure in an operating room, in accordance with at least one aspect of the present disclosure.

In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No.

62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, and a storage array 134. In certain aspects, as illustrated in FIG. 3, the hub 106 further includes a smoke evacuation module 126 and/or a suction/irrigation module 128.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts.

Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Figure 5:
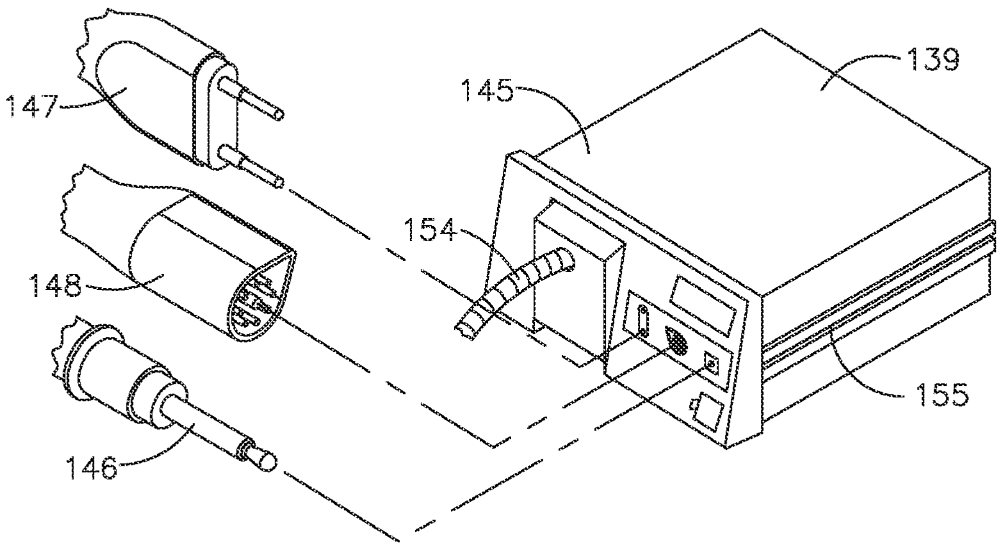
FIG. 5 is a perspective view of a combo generator module with bipolar, ultrasonic, and monopolar contacts and a smoke evacuation component, in accordance with at least one aspect of the present disclosure.

Referring to FIGS. 3-7, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. As illustrated in FIG. 5, the generator module 140 can be a generator module with integrated monopolar, bipolar, and ultrasonic components supported in a single housing unit 139 slidably insertable into the hub modular enclosure 136. As illustrated in FIG. 5, the generator module 140 can be configured to connect to a monopolar device 146, a bipolar device 147, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128 and interactive communication therebetween.

Figure 4:
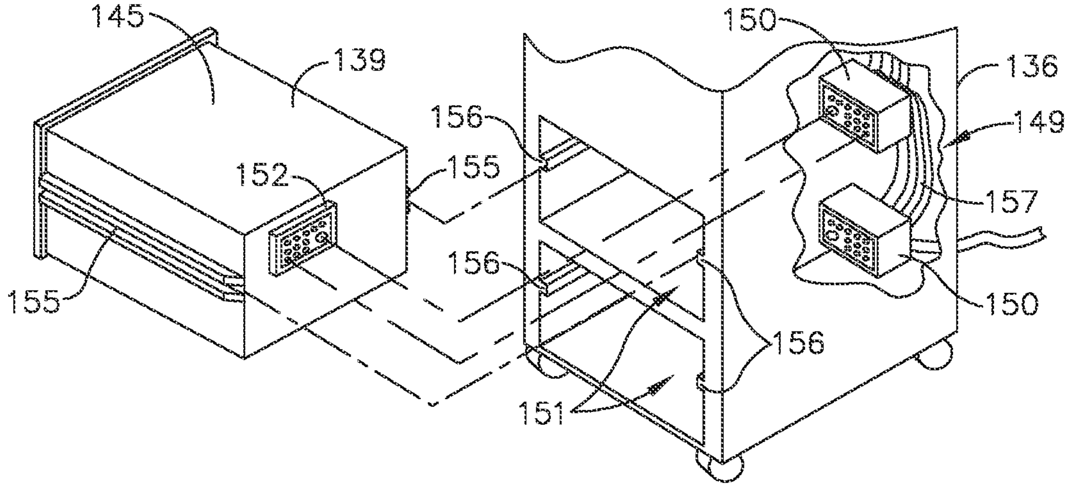
FIG. 4 is a partial perspective view of a surgical hub enclosure, and of a combo generator module slidably receivable in a drawer of the surgical hub enclosure, in accordance with at least one aspect of the present disclosure.

In one aspect, the hub modular enclosure 136 includes docking stations, or drawers, 151, herein also referred to as drawers, which are configured to slidably receive the modules 140, 126, 128. FIG. 4 illustrates a partial perspective view of a surgical hub enclosure 136, and a combo generator module 145 slidably receivable in a docking station 151 of the surgical hub enclosure 136. A docking port 152 with power and data contacts on a rear side of the combo generator module 145 is configured to engage a corresponding docking port 150 with power and data contacts of a corresponding docking station 151 of the hub modular enclosure 136 as the combo generator module 145 is slid into position within the corresponding docking station 151 of the hub module enclosure 136. In one aspect, the combo generator module 145 includes a bipolar, ultrasonic, and monopolar module and a smoke evacuation module integrated together into a single housing unit 139, as illustrated in FIG. 5.

In various aspects, the smoke evacuation module 126 includes a fluid line 154 that conveys captured/collected smoke and/or fluid away from a surgical site and to, for example, the smoke evacuation module 126. Vacuum suction originating from the smoke evacuation module 126 can draw the smoke into an opening of a utility conduit at the surgical site. The utility conduit, coupled to the fluid line, can be in the form of a flexible tube terminating at the smoke evacuation module 126. The utility conduit and the fluid line define a fluid path extending toward the smoke evacuation module 126 that is received in the hub enclosure 136.

In various aspects, the suction/irrigation module 128 is coupled to a surgical tool comprising an aspiration fluid line and a suction fluid line. In one example, the aspiration and suction fluid lines are in the form of flexible tubes extending from the surgical site toward the suction/irrigation module 128. One or more drive systems can be configured to cause irrigation and aspiration of fluids to and from the surgical site.

In one aspect, the surgical tool includes a shaft having an end effector at a distal end thereof and at least one energy treatment associated with the end effector, an aspiration tube, and an irrigation tube. The aspiration tube can have an inlet port at a distal end thereof and the aspiration tube extends through the shaft. Similarly, an irrigation tube can extend through the shaft and can have an inlet port in proximity to the energy deliver implement. The energy deliver implement is configured to deliver ultrasonic and/or RF energy to the surgical site and is coupled to the generator module 140 by a cable extending initially through the shaft.

The irrigation tube can be in fluid communication with a fluid source, and the aspiration tube can be in fluid communication with a vacuum source. The fluid source and/or the vacuum source can be housed in the suction/irrigation module 128. In one example, the fluid source and/or the vacuum source can be housed in the hub enclosure 136 separately from the suction/irrigation module 128. In such example, a fluid interface can be configured to connect the suction/irrigation module 128 to the fluid source and/or the vacuum source.

In one aspect, the modules 140, 126, 128 and/or their corresponding docking stations on the hub modular enclosure 136 may include alignment features that are configured to align the docking ports of the modules into engagement with their counterparts in the docking stations of the hub modular enclosure 136. For example, as illustrated in FIG. 4, the combo generator module 145 includes side brackets 155 that are configured to slidably engage with corresponding brackets 156 of the corresponding docking station 151 of the hub modular enclosure 136. The brackets cooperate to guide the docking port contacts of the combo generator module 145 into an electrical engagement with the docking port contacts of the hub modular enclosure 136.

In some aspects, the drawers 151 of the hub modular enclosure 136 are the same, or substantially the same size, and the modules are adjusted in size to be received in the drawers 151. For example, the side brackets 155 and/or 156 can be larger or smaller depending on the size of the module. In other aspects, the drawers 151 are different in size and are each designed to accommodate a particular module.

Furthermore, the contacts of a particular module can be keyed for engagement with the contacts of a particular drawer to avoid inserting a module into a drawer with mismatching contacts.

As illustrated in FIG. 4, the docking port 150 of one drawer 151 can be coupled to the docking port 150 of another drawer 151 through a communications link 157 to facilitate an interactive communication between the modules housed in the hub modular enclosure 136. The docking ports 150 of the hub modular enclosure 136 may alternatively, or additionally, facilitate a wireless interactive communication between the modules housed in the hub modular enclosure 136. Any suitable wireless communication can be employed, such as for example Air Titan-Bluetooth.

Figure 6:
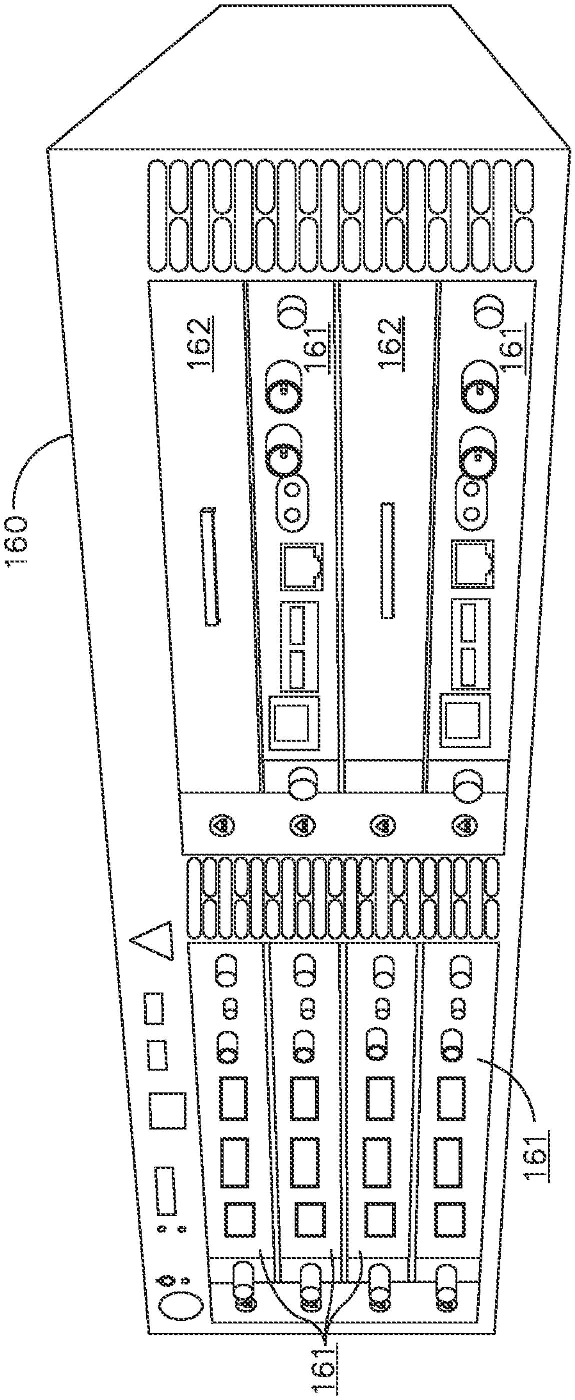
FIG. 6 illustrates individual power bus attachments for a plurality of lateral docking ports of a lateral modular housing configured to receive a plurality of modules, in accordance with at least one aspect of the present disclosure.

FIG. 6 illustrates individual power bus attachments for a plurality of lateral docking ports of a lateral modular housing 160 configured to receive a plurality of modules of a surgical hub 206. The lateral modular housing 160 is configured to laterally receive and interconnect the modules 161. The modules 161 are slidably inserted into docking stations 162 of lateral modular housing 160, which includes a backplane for interconnecting the modules 161. As illustrated in FIG. 6, the modules 161 are arranged laterally in the lateral modular housing 160. Alternatively, the modules 161 may be arranged vertically in a lateral modular housing.

Figure 7:
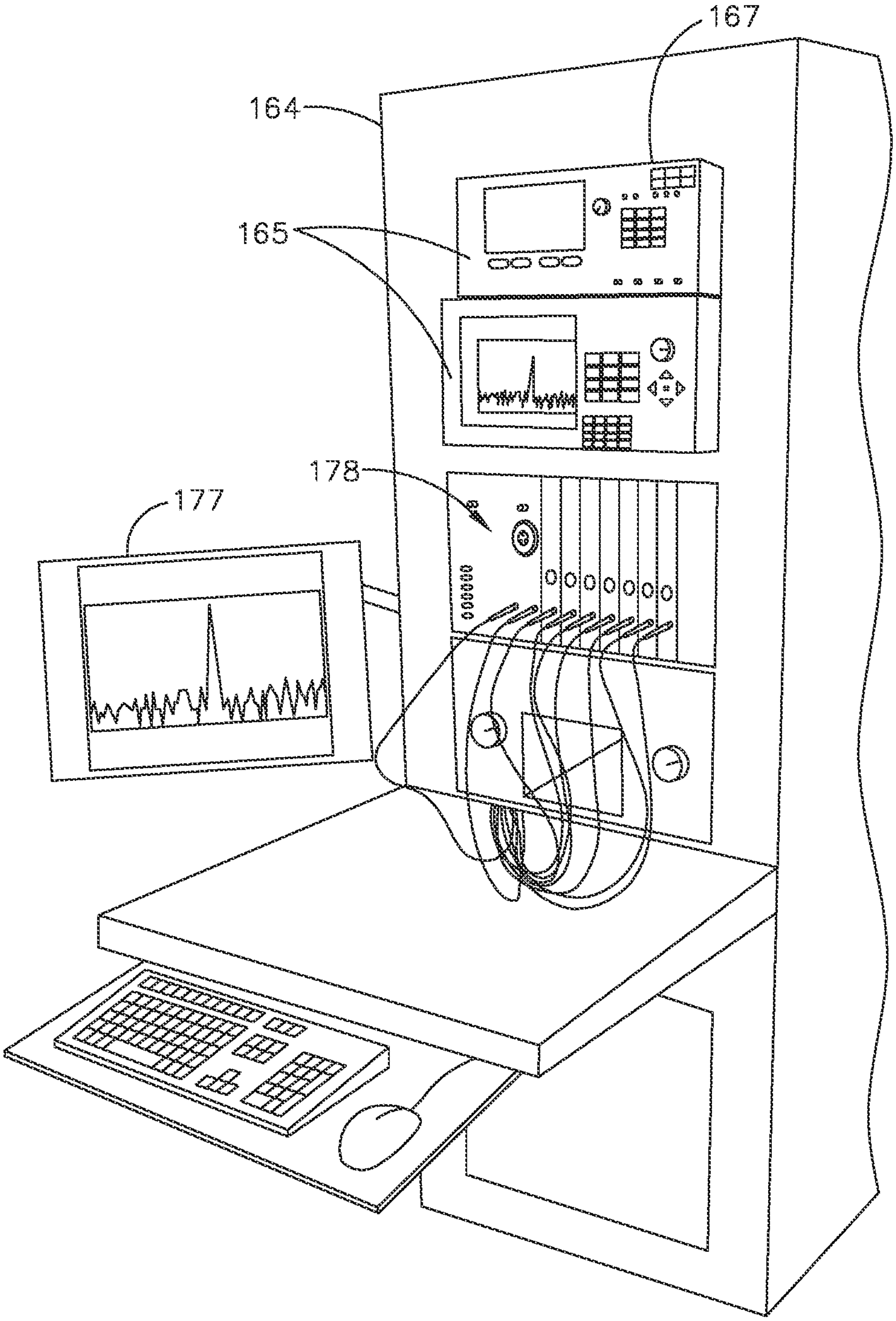
FIG. 7 illustrates a vertical modular housing configured to receive a plurality of modules, in accordance with at least one aspect of the present disclosure.

FIG. 7 illustrates a vertical modular housing 164 configured to receive a plurality of modules 165 of the surgical hub 106. The modules 165 are slidably inserted into docking stations, or drawers, 167 of vertical modular housing 164, which includes a backplane for interconnecting the modules 165. Although the drawers 167 of the vertical modular housing 164 are arranged vertically, in certain instances, a vertical modular housing 164 may include drawers that are arranged laterally. Furthermore, the modules 165 may interact with one another through the docking ports of the vertical modular housing 164. In the example of FIG. 7, a display 177 is provided for displaying data relevant to the operation of the modules 165. In addition, the vertical modular housing 164 includes a master module 178 housing a plurality of sub-modules that are slidably received in the master module 178.

In various aspects, the imaging module 138 comprises an integrated video processor and a modular light source and is adapted for use with various imaging devices. In one aspect, the imaging device is comprised of a modular housing that can be assembled with a light source module and a camera module. The housing can be a disposable housing. In at least one example, the disposable housing is removably coupled to a reusable controller, a light source module, and a camera module. The light source module and/or the camera module can be selectively chosen depending on the type of surgical procedure. In one aspect, the camera module comprises a CCD sensor. In another aspect, the camera module comprises a CMOS sensor. In another aspect, the camera module is configured for scanned beam imaging. Likewise, the light source module can be configured to deliver a white light or a different light, depending on the surgical procedure.

During a surgical procedure, removing a surgical device from the surgical field and replacing it with another surgical device that includes a different camera or a different light source can be inefficient. Temporarily losing sight of the surgical field may lead to undesirable consequences. The module imaging device of the present disclosure is configured to permit the replacement of a light source module or a camera module midstream during a surgical procedure, without having to remove the imaging device from the surgical field.

In one aspect, the imaging device comprises a tubular housing that includes a plurality of channels. A first channel is configured to slidably receive the camera module, which can be configured for a snap-fit engagement with the first channel. A second channel is configured to slidably receive the light source module, which can be configured for a snap-fit engagement with the second channel. In another example, the camera module and/or the light source module can be rotated into a final position within their respective channels. A threaded engagement can be employed in lieu of the snap-fit engagement.

In various examples, multiple imaging devices are placed at different positions in the surgical field to provide multiple views. The imaging module 138 can be configured to switch between the imaging devices to provide an optimal view. In various aspects, the imaging module 138 can be configured to integrate the images from the different imaging device.

Various image processors and imaging devices suitable for use with the present disclosure are described in U.S. Pat. No. 7,995,045, titled COMBINED SBI AND CONVENTIONAL IMAGE PROCESSOR, which issued on Aug. 9, 2011, which is herein incorporated by reference in its entirety. In addition, U.S. Pat. No. 7,982,776, titled SBI MOTION ARTIFACT REMOVAL APPARATUS AND METHOD, which issued on Jul. 19, 2011, which is herein incorporated by reference in its entirety, describes various systems for removing motion artifacts from image data. Such systems can be integrated with the imaging module 138. Furthermore, U.S. Patent Application Publication No. 2011/0306840, titled CONTROLLABLE MAGNETIC SOURCE TO FIXTURE INTRACORPOREAL APPARATUS, which published on Dec. 15, 2011, and U.S. Patent Application Publication No. 2014/0243597, titled SYSTEM FOR PERFORMING A MINIMALLY INVASIVE SURGICAL PROCEDURE, which published on Aug. 28, 2014, the disclosure of each of which is herein incorporated by reference in its entirety.

Figure 8:
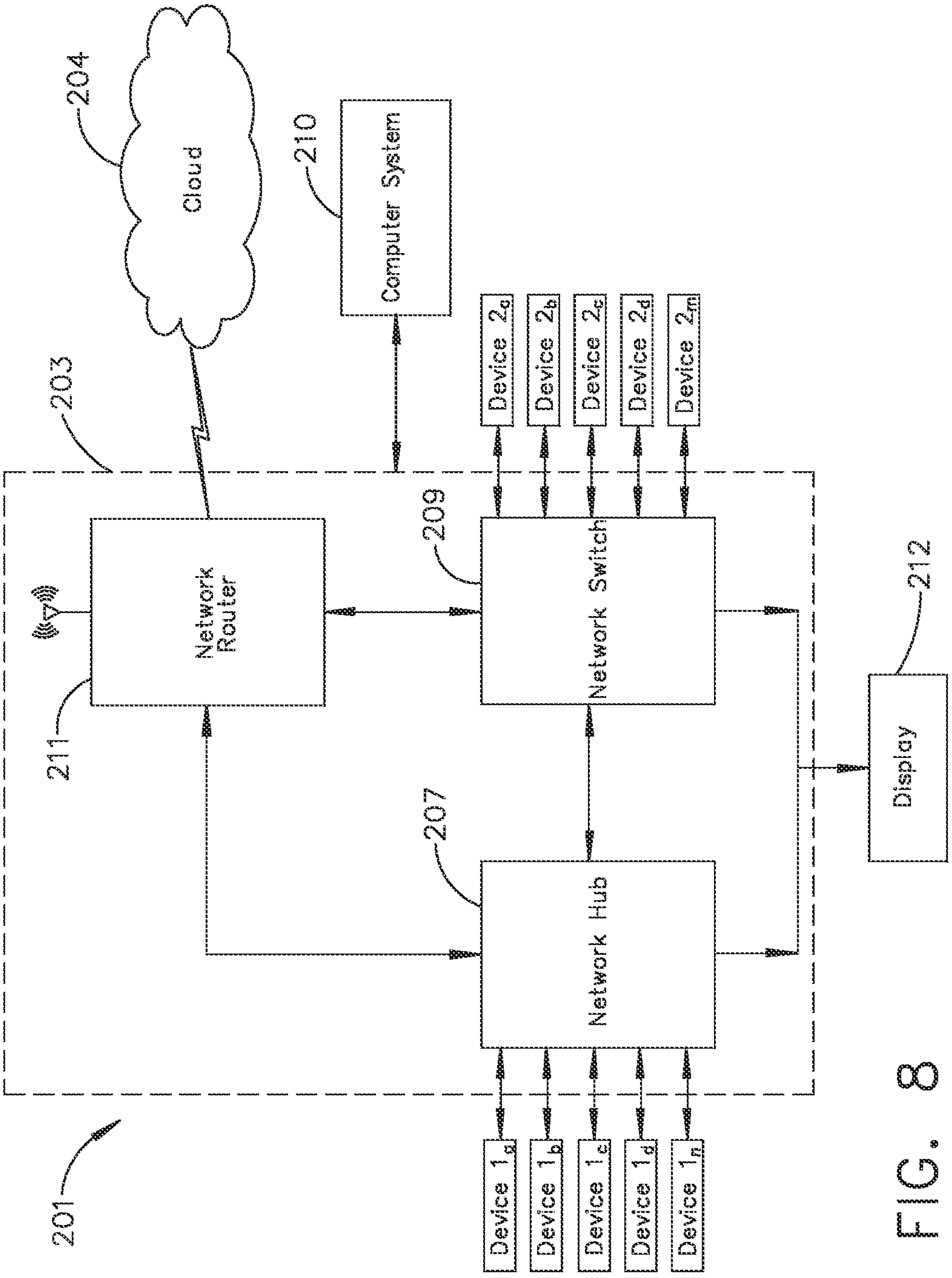
FIG. 8 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 8 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1*a*-1*n* located in the operating theater may be coupled to the modular communication hub 203. The network hub 207 and/or the network switch 209 may be coupled to a network router 211 to connect the devices 1*a*-into the cloud 204 or the local computer system 210. Data associated with the devices 1*a*-1*n* may be transferred to cloud-based computers via the router for remote data processing and manipulation. Data associated with the devices 1*a*-1*n* may also be transferred to the local computer system 210 for local data processing and manipulation. Modular devices 2*a*-2*m* located in the same operating theater also may be coupled to a network switch 209. The network switch 209 may be coupled to the network hub 207 and/or the network router 211 to connect to the devices 2*a*-2*m* to the cloud 204. Data associated with the devices 2*a*-2*n* may be transferred to the cloud 204 via the network router 211 for data processing and manipulation. Data associated with the devices 2*a*-2*m* may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1*a*-1*n*/2*a*-2*m*. The local computer system 210 also may be contained in a modular control tower. The modular communication hub 203 is connected to a display 212 to display images obtained by some of the devices 1*a*-1*n*/2*a*-2*m*, for example during surgical procedures. In various aspects, the devices 1*a*-1*n*/2*a*-2*m* may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1*a*-1*n*/2*a*-2*m* to the cloud. Any one of or all of the devices 1*a*-1*n*/2*a*-2*m* coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1*a*-1*n*/2*a*-2*m* located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1*a*-1*n*/2*a*-2*m*, the surgical data network provides improved surgical outcomes, reduced costs, and improved patient satisfaction. At least some of the devices 1*a*-1*n*/2*a*-2*m* may be employed to view tissue states to assess leaks or perfusion of sealed tissue after a tissue sealing and cutting procedure. At least some of the devices 1*a*-1*n*/2*a*-2*m* may be employed to identify pathology, such as the effects of diseases, using the cloud-based computing to examine data including images of samples of body tissue for diagnostic purposes. This includes localization and margin confirmation of tissue and phenotypes. At least some of the devices 1*a*-1*n*/2*a*-2*m* may be employed to identify anatomical structures of the body using a variety of sensors integrated with imaging devices and techniques such as overlaying images captured by multiple imaging devices. The data gathered by the devices 1*a*-1*n*/2*a*-2*m*, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1*a*-1*n* may be connected to the modular communication hub 203 over a wired channel or a wireless channel depending on the configuration of the devices 1*a*-1*n* to a network hub. The network hub 207 may be implemented, in one aspect, as a local network broadcast device that works on the physical layer of the Open System Interconnection (OSI) model. The network hub provides connectivity to the devices 1*a*-1*n* located in the same operating theater network. The network hub 207 collects data in the form of packets and sends them to the router in half duplex mode. The network hub 207 does not store any media access control/Internet Protocol (MAC/IP) to transfer the device data. Only one of the devices 1*a*-1*n* can send data at a time through the network hub 207. The network hub 207 has no routing tables or intelligence regarding where to send information and broadcasts all network data across each connection and to a remote server 213 (FIG. 9) over the cloud 204. The network hub 207 can detect basic network errors such as collisions, but having all information broadcast to multiple ports can be a security risk and cause bottlenecks.

In another implementation, the operating theater devices 2*a*-2*m* may be connected to a network switch 209 over a wired channel or a wireless channel. The network switch 209 works in the data link layer of the OSI model. The network switch 209 is a multicast device for connecting the devices 2*a*-2*m* located in the same operating theater to the network. The network switch 209 sends data in the form of frames to the network router 211 and works in full duplex mode. Multiple devices 2*a*-2*m* can send data at the same time through the network switch 209. The network switch 209 stores and uses MAC addresses of the devices 2*a*-2*m* to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1*a*-1*n*/2*a*-2*m*. The network router 211 may be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1*a*-1*n* and devices 2*a*-2*m* located in the operating theater.

In other examples, the operating theater devices 1*a*-1*n*/2*a*-2*m* may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices 1*a*-1*n*/2*a*-2*m* may communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1*a*-1*n*/2*a*-2*m* and handles a data type known as frames. Frames carry the data generated by the devices 1*a*-1*n*/2*a*-2*m*. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices 1*a*-1*n*/2*a*-2*m*.

Figure 9:
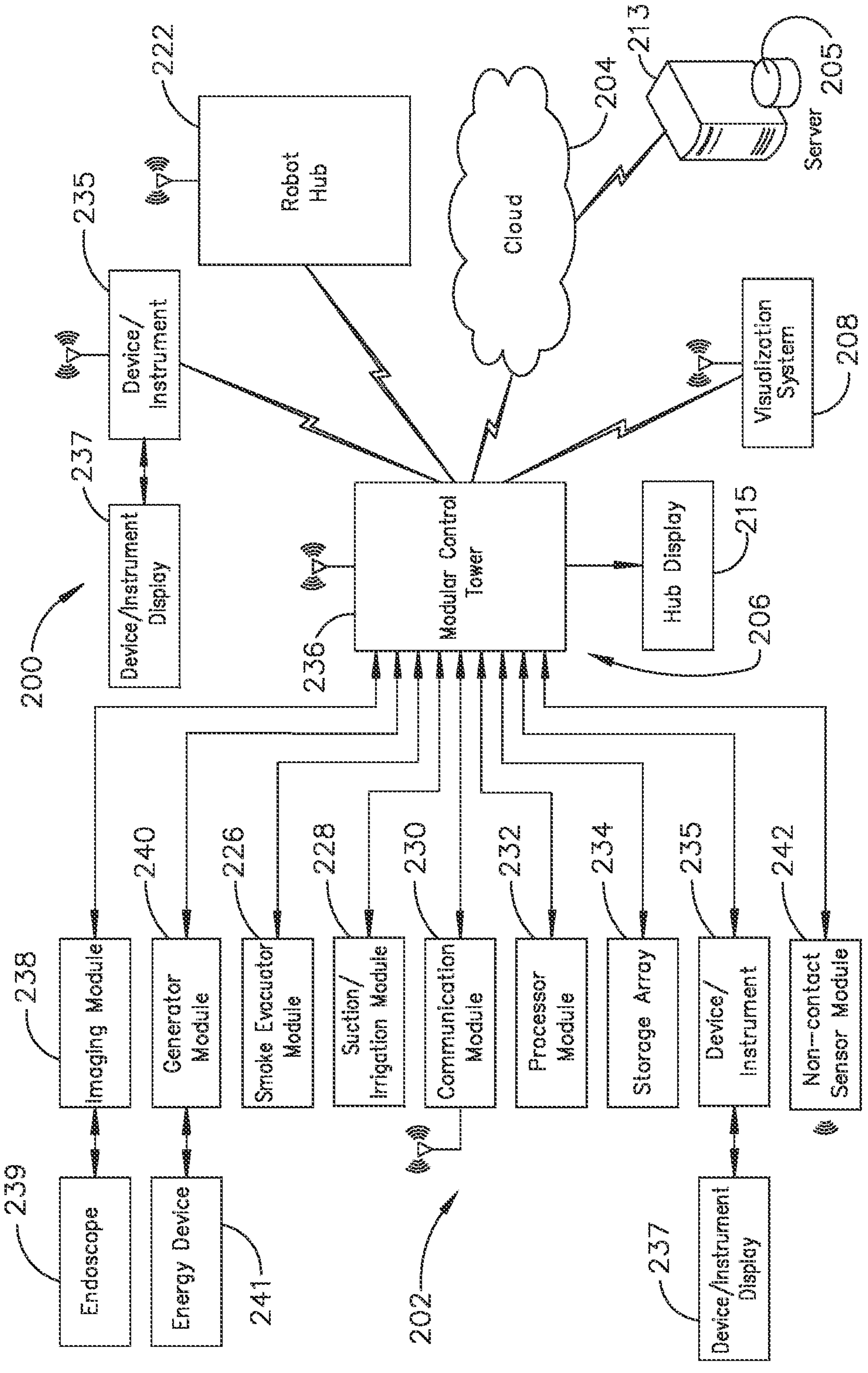
FIG. 9 illustrates a computer-implemented interactive surgical system, in accordance with at least one aspect of the present disclosure.
Figure 10:
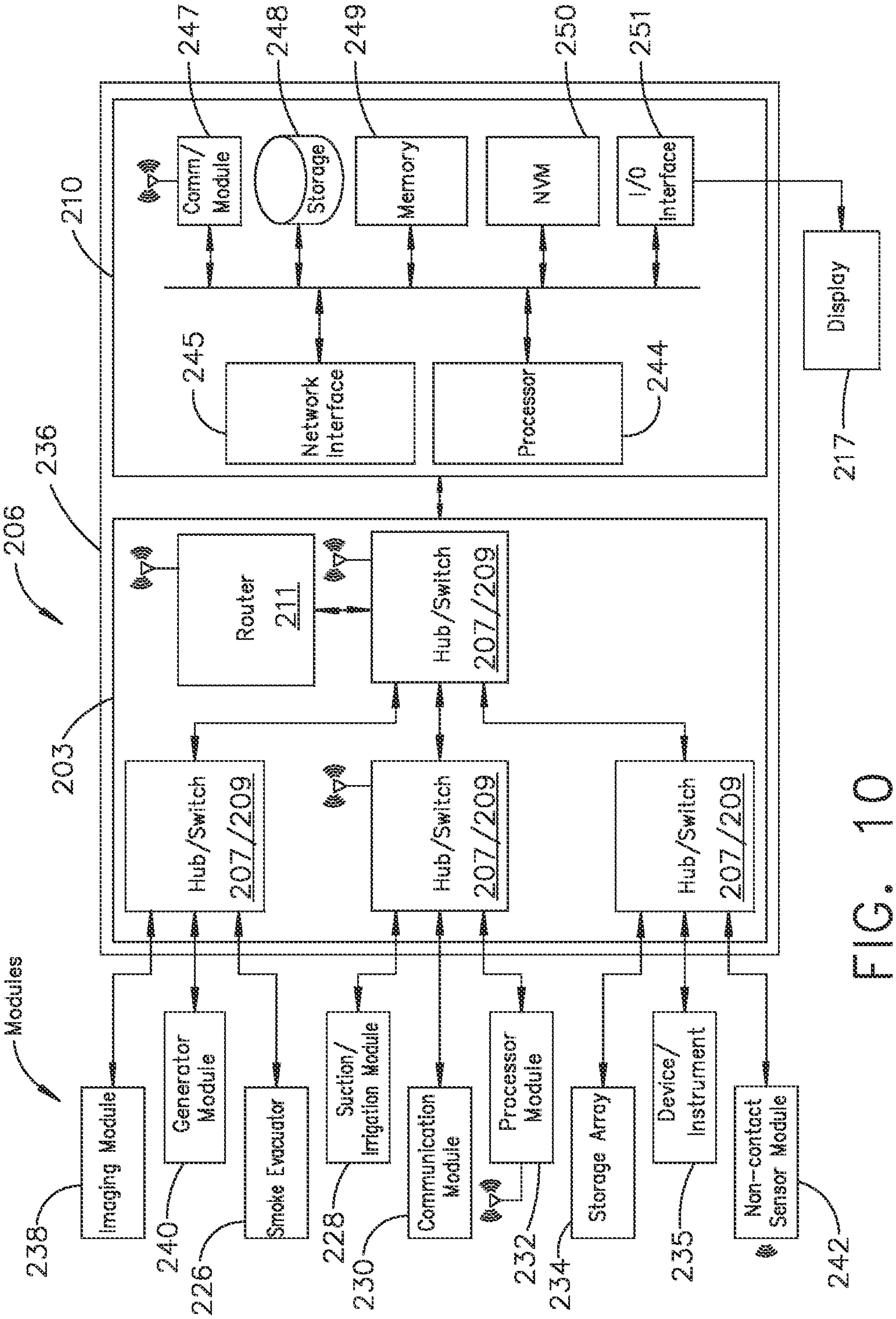
FIG. 10 illustrates a surgical hub comprising a plurality of modules coupled to the modular control tower, in accordance with at least one aspect of the present disclosure.

FIG. 9 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 10, the modular control tower 236 comprises a modular communication hub 203 coupled to a computer system 210. As illustrated in the example of FIG. 9, the modular control tower 236 is coupled to an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 10 illustrates a surgical hub 206 comprising a plurality of modules coupled to the modular control tower 236. The modular control tower 236 comprises a modular communication hub 203, e.g., a network connectivity device, and a computer system 210 to provide local processing, visualization, and imaging, for example. As shown in FIG. 10, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 10, each of the network hubs/switches in the modular communication hub 203 includes three downstream ports and one upstream port. The upstream network hub/switch is connected to a processor to provide a communication connection to the cloud computing resources and a local display 217. Communication to the cloud 204 may be made either through a wired or a wireless communication channel.

The surgical hub 206 employs a non-contact sensor module 242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 comprises a processor 244 and a network interface 245. The processor 244 is coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 210 through input device(s) coupled to the I/O interface 251. The input devices include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus. It should be noted that other devices and/or systems of devices, such as remote computer(s), provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system.

For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 10, the imaging module 238 and/or visualization system 208, and/or the processor module 232 of FIGS. 9-10, may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) refers to the hardware/software employed to connect the network interface to the bus. While the communication connection is shown for illustrative clarity inside the computer system, it can also be external to the computer system 210. The hardware/software necessary for connection to the network interface includes, for illustrative purposes only, internal and external technologies such as modems, including regular telephone-grade modems, cable modems, and DSL modems, ISDN adapters, and Ethernet cards.

Figure 11:
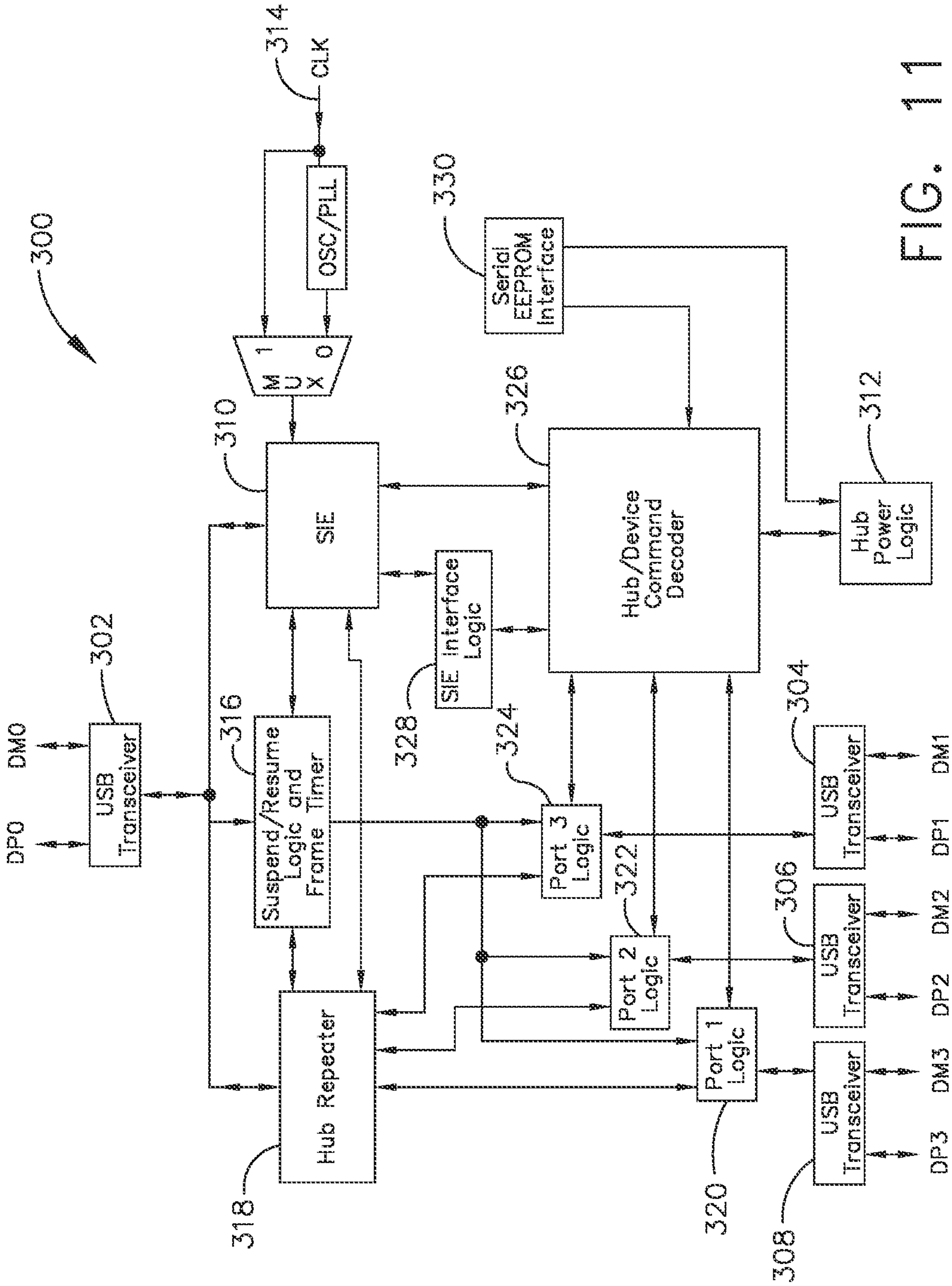
FIG. 11 illustrates one aspect of a Universal Serial Bus (USB) network hub device, in accordance with at least one aspect of the present disclosure.

FIG. 11 illustrates a functional block diagram of one aspect of a USB network hub 300 device, in accordance with at least one aspect of the present disclosure. In the illustrated aspect, the USB network hub device 300 employs a TUSB2036 integrated circuit hub by Texas Instruments. The USB network hub 300 is a CMOS device that provides an upstream USB transceiver port 302 and up to three downstream USB transceiver ports 304, 306, 308 in compliance with the USB 2.0 specification. The upstream USB transceiver port 302 is a differential root data port comprising a differential data minus (DM0) input paired with a differential data plus (DP0) input. The three downstream USB transceiver ports 304, 306, 308 are differential data ports where each port includes differential data plus (DP1-DP3) outputs paired with differential data minus (DM1-DM3) outputs.

The USB network hub 300 device is implemented with a digital state machine instead of a microcontroller, and no firmware programming is required. Fully compliant USB transceivers are integrated into the circuit for the upstream USB transceiver port 302 and all downstream USB transceiver ports 304, 306, 308. The downstream USB transceiver ports 304, 306, 308 support both full-speed and low-speed devices by automatically setting the slew rate according to the speed of the device attached to the ports. The USB network hub 300 device may be configured either in bus-powered or self-powered mode and includes a hub power logic 312 to manage power.

The USB network hub 300 device includes a serial interface engine 310 (SIE). The SIE 310 is the front end of the USB network hub 300 hardware and handles most of the protocol described in chapter 8 of the USB specification. The SIE 310 typically comprehends signaling up to the transaction level. The functions that it handles could include: packet recognition, transaction sequencing, SOP, EOP, RESET, and RESUME signal detection/generation, clock/data separation, non-return-to-zero invert (NRZI) data encoding/decoding and bit-stuffing, CRC generation and checking (token and data), packet ID (PID) generation and checking/decoding, and/or serial-parallel/parallel-serial conversion.

The 310 receives a clock input 314 and is coupled to a suspend/resume logic and frame timer 316 circuit and a hub repeater circuit 318 to control communication between the upstream USB transceiver port 302 and the downstream USB transceiver ports 304, 306, 308 through port logic circuits 320, 322, 324. The SIE 310 is coupled to a command decoder 326 via interface logic to control commands from a serial EEPROM via a serial EEPROM interface 330.

In various aspects, the USB network hub 300 can connect 127 functions configured in up to six logical layers (tiers) to a single computer. Further, the USB network hub 300 can connect to all peripherals using a standardized four-wire cable that provides both communication and power distribution. The power configurations are bus-powered and self-powered modes. The USB network hub 300 may be configured to support four modes of power management: a bus-powered hub, with either individual-port power management or ganged-port power management, and the self-powered hub, with either individual-port power management or ganged-port power management. In one aspect, using a USB cable, the USB network hub 300, the upstream USB transceiver port 302 is plugged into a USB host controller, and the downstream USB transceiver ports 304, 306, 308 are exposed for connecting USB compatible devices, and so forth.

Surgical Instrument Hardware

Figure 12:
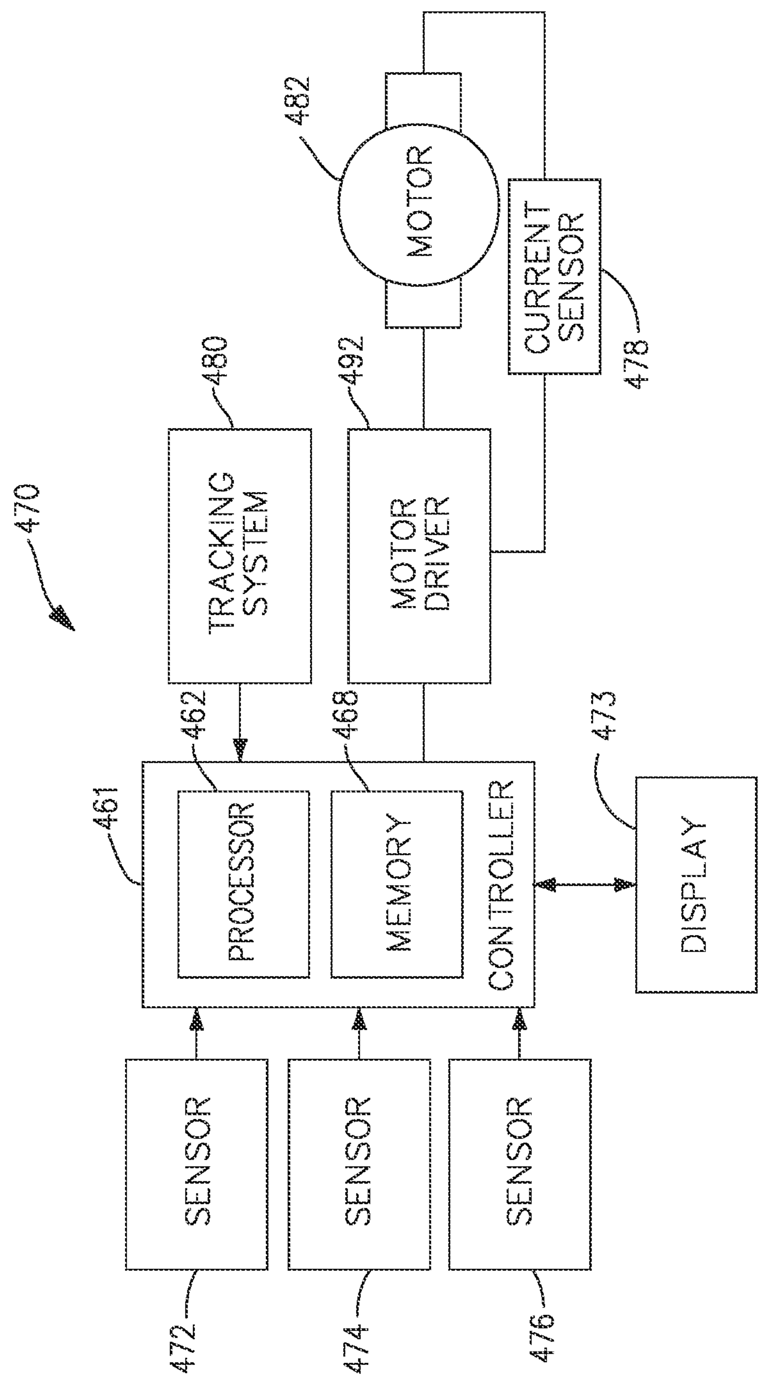
FIG. 12 illustrates a logic diagram of a control system of a surgical instrument or tool, in accordance with at least one aspect of the present disclosure.

FIG. 12 illustrates a logic diagram of a control system 470 of a surgical instrument or tool in accordance with one or more aspects of the present disclosure. The system 470 comprises a control circuit. The control circuit includes a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive the I-beam knife element. A tracking system 480 is configured to determine the position of the longitudinally movable displacement member. The position information is provided to the processor 462, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 473 displays a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife and articulation systems. In one aspect, the microcontroller 461 includes a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

In one aspect, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In other arrangements, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 492 may be an A3941 available from Allegro Microsystems, Inc. The A3941 492 is a full-bridge controller for use with external N-channel power metal-oxide semiconductor field-effect transistors (MOSFETs) specifically designed for inductive loads, such as brush DC motors. The driver 492 comprises a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 comprises a controlled motor drive circuit arrangement comprising a position sensor 472, in accordance with at least one aspect of this disclosure. The position sensor 472 for an absolute positioning system provides a unique position signal corresponding to the location of a displacement member. In one aspect, the displacement member represents a longitudinally movable drive member comprising a rack of drive teeth for meshing engagement with a corresponding drive gear of a gear reducer assembly. In other aspects, the displacement member represents the firing member, which could be adapted and configured to include a rack of drive teeth. In yet another aspect, the displacement member represents a firing bar or the I-beam, each of which can be adapted and configured to include a rack of drive teeth. Accordingly, as used herein, the term displacement member is used generically to refer to any movable member of the surgical instrument or tool such as the drive member, the firing member, the firing bar, the I-beam, or any element that can be displaced. In one aspect, the longitudinally movable drive member is coupled to the firing member, the firing bar, and the I-beam. Accordingly, the absolute positioning system can, in effect, track the linear displacement of the I-beam by tracking the linear displacement of the longitudinally movable drive member. In various other aspects, the displacement member may be coupled to any position sensor 472 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable firing member, firing bar, I-beam, or combinations thereof.

A single revolution of the sensor element associated with the position sensor 472 is equivalent to a longitudinal linear displacement d1 of the of the displacement member, where d1 is the longitudinal linear distance that the displacement member moves from point “a” to point “b” after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches are fed back to the microcontroller 461 that applies logic to determine a unique position signal corresponding to the longitudinal linear displacement d1+d2+ . . . dn of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system comprises a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 is a low-voltage and low-power component and includes four Hall-effect elements in an area of the position sensor 472 that is located above a magnet. A high-resolution ADC and a smart power management controller are also provided on the chip. A coordinate rotation digital computer (CORDIC) processor, also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface, such as a serial peripheral interface (SPI) interface, to the microcontroller 461. The position sensor 472 provides 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, is configured to measure one or more parameters of the end effector, such as, for example, the amplitude of the strain exerted on the anvil during a clamping operation, which can be indicative of the closure forces applied to the anvil. The measured strain is converted to a digital signal and provided to the processor 462. Alternatively, or in addition to the sensor 474, a sensor 476, such as, for example, a load sensor, can measure the closure force applied by the closure drive system to the anvil. The sensor 476, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also includes a sharpened cutting edge that can be used to sever tissue as the I-beam is advanced distally by the firing bar. Alternatively, a current sensor 478 can be employed to measure the current drawn by the motor 482. The force required to advance the firing member can correspond to the current drawn by the motor 482, for example. The measured force is converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector comprises a strain gauge sensor 474, such as, for example, a micro-strain gauge, that is configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain is converted to a digital signal and provided to a processor 462 of the microcontroller 461. A load sensor 476 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub as shown in FIGS. 8-11.

Figure 13:
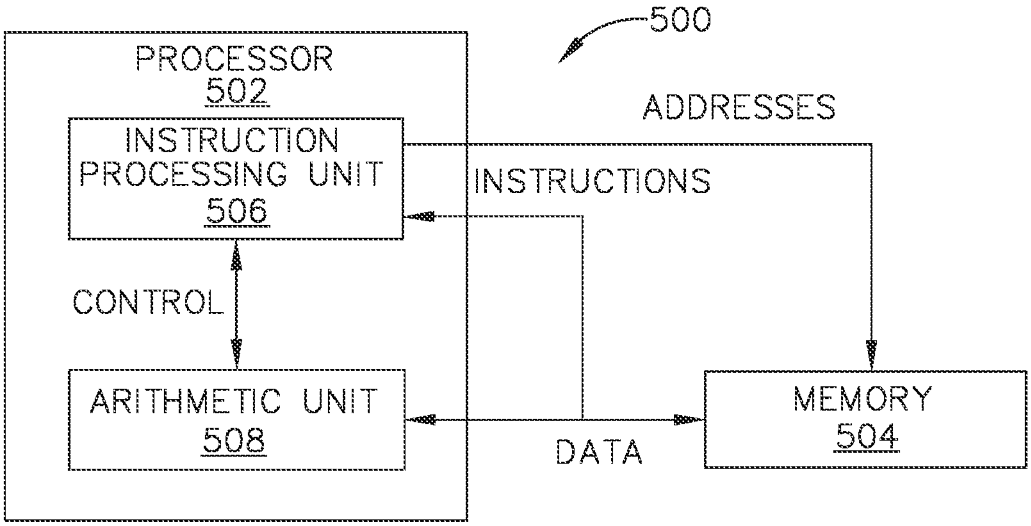
FIG. 13 illustrates a control circuit configured to control aspects of the surgical instrument or tool, in accordance with at least one aspect of the present disclosure.

FIG. 13 illustrates a control circuit 500 configured to control aspects of the surgical instrument or tool, in accordance with at least one aspect of this disclosure. The control circuit 500 can be configured to implement various processes described herein. The control circuit 500 may comprise a microcontroller comprising one or more processors 502 (e.g., microprocessor, microcontroller) coupled to at least one memory circuit 504. The memory circuit 504 stores machine-executable instructions that, when executed by the processor 502, cause the processor 502 to execute machine instructions to implement various processes described herein. The processor 502 may be any one of a number of single-core or multicore processors known in the art. The memory circuit 504 may comprise volatile and non-volatile storage media. The processor 502 may include an instruction processing unit 506 and an arithmetic unit 508. The instruction processing unit may be configured to receive instructions from the memory circuit 504 of this disclosure.

Figure 14:
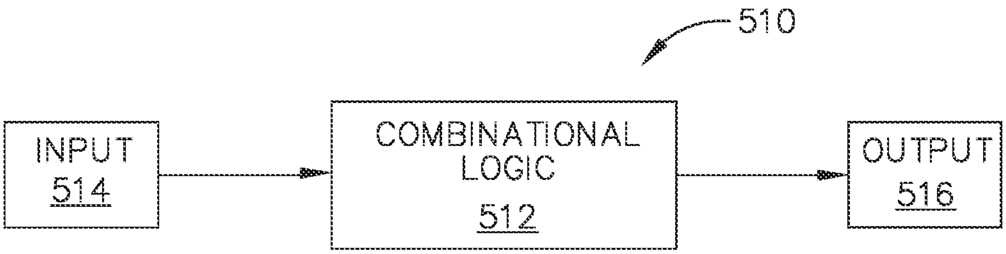
FIG. 14 illustrates a combinational logic circuit configured to control aspects of the surgical instrument or tool, in accordance with at least one aspect of the present disclosure.

FIG. 14 illustrates a combinational logic circuit 510 configured to control aspects of the surgical instrument or tool, in accordance with at least one aspect of this disclosure. The combinational logic circuit 510 can be configured to implement various processes described herein. The combinational logic circuit 510 may comprise a finite state machine comprising a combinational logic 512 configured to receive data associated with the surgical instrument or tool at an input 514, process the data by the combinational logic 512, and provide an output 516.

Figure 15:
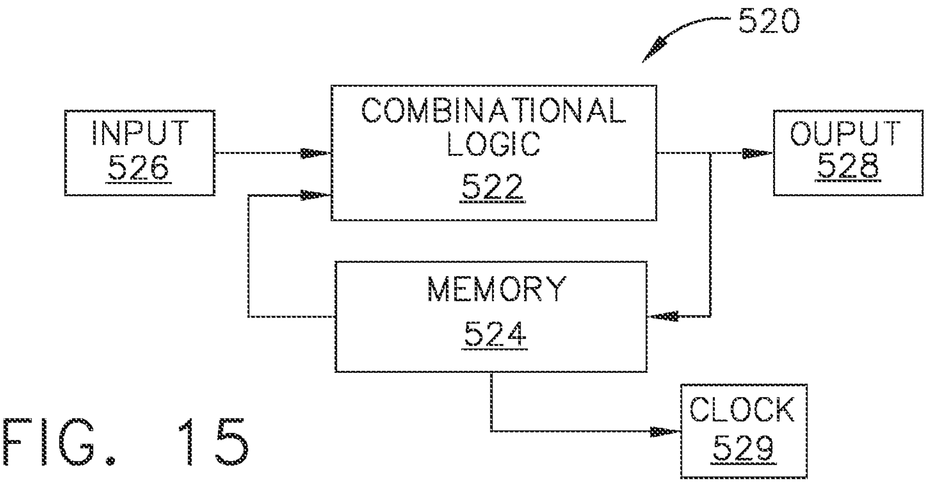
FIG. 15 illustrates a sequential logic circuit configured to control aspects of the surgical instrument or tool, in accordance with at least one aspect of the present disclosure.

FIG. 15 illustrates a sequential logic circuit 520 configured to control aspects of the surgical instrument or tool, in accordance with at least one aspect of this disclosure. The sequential logic circuit 520 or the combinational logic 522 can be configured to implement various processes described herein. The sequential logic circuit 520 may comprise a finite state machine. The sequential logic circuit 520 may comprise a combinational logic 522, at least one memory circuit 524, and a clock 529, for example. The at least one memory circuit 524 can store a current state of the finite state machine. In certain instances, the sequential logic circuit 520 may be synchronous or asynchronous. The combinational logic 522 is configured to receive data associated with the surgical instrument or tool from an input 526, process the data by the combinational logic 522, and provide an output 528. In other aspects, the circuit may comprise a combination of a processor (e.g., processor 502, FIG. 13) and a finite state machine to implement various processes herein. In other aspects, the finite state machine may comprise a combination of a combinational logic circuit (e.g., combinational logic circuit 510, FIG. 14) and the sequential logic circuit 520.

Figure 16:
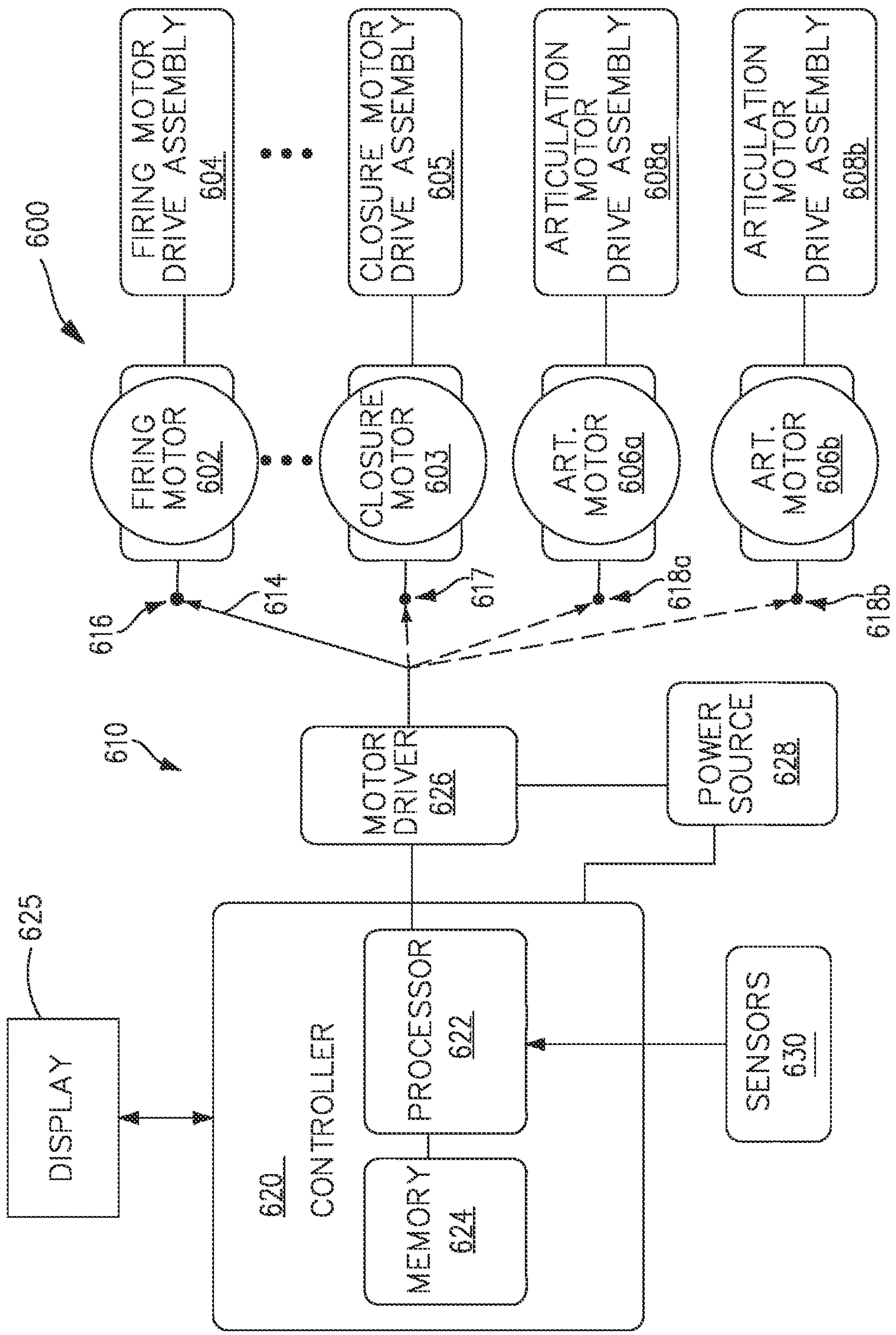
FIG. 16 illustrates a surgical instrument or tool comprising a plurality of motors which can be activated to perform various functions, in accordance with at least one aspect of the present disclosure.

FIG. 16 illustrates a surgical instrument or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the I-beam element. In certain instances, the firing motions generated by the motor 602 may cause the staples to be deployed from the staple cartridge into tissue captured by the end effector and/or the cutting edge of the I-beam element to be advanced to cut the captured tissue, for example. The I-beam element may be retracted by reversing the direction of the motor 602.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors **606*a*, 606*b*, for example. The motors 606*a*, 606*b* may be operably coupled to respective articulation motor drive assemblies 608*a*, 608*b*, which can be configured to transmit articulation motions generated by the motors 606*a*, 606*b*** to the end effector. In certain instances, the articulation motions may cause the end effector to articulate relative to the shaft, for example.

As described above, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors **606*a*, 606*b* can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602** to cause the closure tube and the I-beam element to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors **606*a*, 606*b* and operable engagement with either the firing motor 602 or the closure motor 603. In at least one example, as illustrated in FIG. 16, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618***a*, the switch 614 may electrically couple the common control module 610 to the first articulation motor 606*a*; and in a fourth position 618*b*, the switch 614 may electrically couple the common control module 610 to the second articulation motor 606*b*, for example. In certain instances, separate common control modules 610 can be electrically coupled to the firing motor 602, the closure motor 603, and the articulations motor 606*a*, 606*b* at the same time. In certain instances, the switch 614 may be a mechanical switch, an electromechanical switch, a solid-state switch, or any suitable switching mechanism.

Each of the motors 602, 603, 606*a*, 606*b* may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 16, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 622 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606*a*, 606*b*. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the I-beam of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618*a*, 618*b*.

Figure 17:
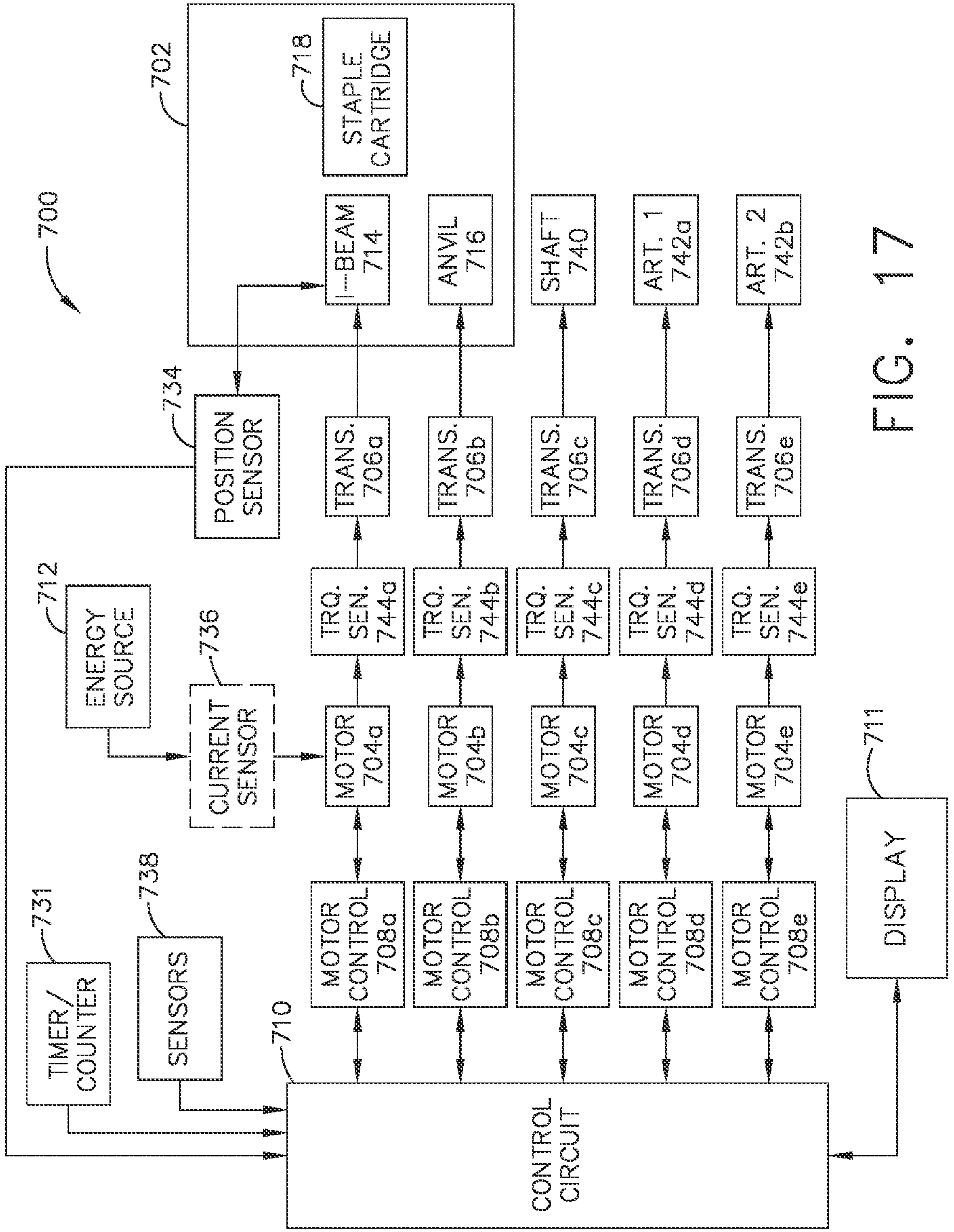
FIG. 17 is a schematic diagram of a robotic surgical instrument configured to operate a surgical tool described herein, in accordance with at least one aspect of the present disclosure.

FIG. 17 is a schematic diagram of a robotic surgical instrument 700 configured to operate a surgical tool described herein, in accordance with at least one aspect of this disclosure. The robotic surgical instrument 700 may be programmed or configured to control distal/proximal translation of a displacement member, distal/proximal displacement of a closure tube, shaft rotation, and articulation, either with single or multiple articulation drive links. In one aspect, the surgical instrument 700 may be programmed or configured to individually control a firing member, a closure member, a shaft member, and/or one or more articulation members. The surgical instrument 700 comprises a control circuit 710 configured to control motor-driven firing members, closure members, shaft members, and/or one or more articulation members.

In one aspect, the robotic surgical instrument 700 comprises a control circuit 710 configured to control an anvil 716 and an I-beam 714 (including a sharp cutting edge) portion of an end effector 702, a removable staple cartridge 718, a shaft 740, and one or more articulation members 742*a*, 742*b* via a plurality of motors 704*a*-704*e*. A position sensor 734 may be configured to provide position feedback of the I-beam 714 to the control circuit 710. Other sensors 738 may be configured to provide feedback to the control circuit 710. A timer/counter 731 provides timing and counting information to the control circuit 710. An energy source 712 may be provided to operate the motors 704*a*-704*e*, and a current sensor 736 provides motor current feedback to the control circuit 710. The motors 704*a*-704*e* can be operated individually by the control circuit 710 in an open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the I-beam 714 as determined by the position sensor 734 with the output of the timer/counter 731 such that the control circuit 710 can determine the position of the I-beam 714 at a specific time (t) relative to a starting position or the time (t) when the I-beam 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the anvil 716. Other control programs control the rotation of the shaft 740 and the articulation members 742*a*, 742*b*.

In one aspect, the control circuit 710 may generate motor set point signals. The motor set point signals may be provided to various motor controllers 708*a*-708*e*. The motor controllers 708*a*-708*e* may comprise one or more circuits configured to provide motor drive signals to the motors 704*a*-704*e* to drive the motors 704*a*-704*e* as described herein. In some examples, the motors 704*a*-704*e* may be brushed DC electric motors. For example, the velocity of the motors 704*a*-704*e* may be proportional to the respective motor drive signals. In some examples, the motors 704*a*-704*e* may be brushless DC electric motors, and the respective motor drive signals may comprise a PWM signal provided to one or more stator windings of the motors 704*a*-704*e*. Also, in some examples, the motor controllers 708*a*-708*e* may be omitted and the control circuit 710 may generate the motor drive signals directly.

In one aspect, the control circuit 710 may initially operate each of the motors 704*a*-704*e* in an open-loop configuration for a first open-loop portion of a stroke of the displacement member. Based on the response of the robotic surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704*a*-704*e* during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704*a*-704*e* based on translation data describing a position of the displacement member in a closed-loop manner to translate the displacement member at a constant velocity.

In one aspect, the motors 704*a*-704*e* may receive power from an energy source 712. The energy source 712 may be a DC power supply driven by a main alternating current power source, a battery, a super capacitor, or any other suitable energy source. The motors 704*a*-704*e* may be mechanically coupled to individual movable mechanical elements such as the I-beam 714, anvil 716, shaft 740, articulation 742*a*, and articulation 742*b* via respective transmissions 706*a*-706*e*. The transmissions 706*a*-706*e* may include one or more gears or other linkage components to couple the motors 704*a*-704*e* to movable mechanical elements. A position sensor 734 may sense a position of the I-beam 714. The position sensor 734 may be or include any type of sensor that is capable of generating position data that indicate a position of the I-beam 714. In some examples, the position sensor 734 may include an encoder configured to provide a series of pulses to the control circuit 710 as the I-beam 714 translates distally and proximally. The control circuit 710 may track the pulses to determine the position of the I-beam 714. Other suitable position sensors may be used, including, for example, a proximity sensor. Other types of position sensors may provide other signals indicating motion of the I-beam 714. Also, in some examples, the position sensor 734 may be omitted. Where any of the motors 704*a*-704*e* is a stepper motor, the control circuit 710 may track the position of the I-beam 714 by aggregating the number and direction of steps that the motor 704 has been instructed to execute. The position sensor 734 may be located in the end effector 702 or at any other portion of the instrument. The outputs of each of the motors 704*a*-704*e* include a torque sensor 744*a*-744*e* to sense force and have an encoder to sense rotation of the drive shaft.

In one aspect, the control circuit 710 is configured to drive a firing member such as the I-beam 714 portion of the end effector 702. The control circuit 710 provides a motor set point to a motor control 708*a*, which provides a drive signal to the motor 704*a*. The output shaft of the motor 704*a* is coupled to a torque sensor 744*a*. The torque sensor 744*a* is coupled to a transmission 706*a* which is coupled to the I-beam 714. The transmission 706*a* comprises movable mechanical elements such as rotating elements and a firing member to control the movement of the I-beam 714 distally and proximally along a longitudinal axis of the end effector 702. In one aspect, the motor 704*a* may be coupled to the knife gear assembly, which includes a knife gear reduction set that includes a first knife drive gear and a second knife drive gear. A torque sensor 744*a* provides a firing force feedback signal to the control circuit 710. The firing force signal represents the force required to fire or displace the I-beam 714. A position sensor 734 may be configured to provide the position of the I-beam 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708*a*. In response to the firing signal, the motor 704*a* may drive the firing member distally along the longitudinal axis of the end effector 702 from a proximal stroke start position to a stroke end position distal to the stroke start position. As the firing member translates distally, an I-beam 714, with a cutting element positioned at a distal end, advances distally to cut tissue located between the staple cartridge 718 and the anvil 716.

In one aspect, the control circuit 710 is configured to drive a closure member such as the anvil 716 portion of the end effector 702. The control circuit 710 provides a motor set point to a motor control 708*b*, which provides a drive signal to the motor 704*b*. The output shaft of the motor 704*b* is coupled to a torque sensor 744*b*. The torque sensor 744*b* is coupled to a transmission 706*b* which is coupled to the anvil 716. The transmission 706*b* comprises movable mechanical elements such as rotating elements and a closure member to control the movement of the anvil 716 from the open and closed positions. In one aspect, the motor 704*b* is coupled to a closure gear assembly, which includes a closure reduction gear set that is supported in meshing engagement with the closure spur gear. The torque sensor 744*b* provides a closure force feedback signal to the control circuit 710. The closure force feedback signal represents the closure force applied to the anvil 716. The position sensor 734 may be configured to provide the position of the closure member as a feedback signal to the control circuit 710. Additional sensors 738 in the end effector 702 may provide the closure force feedback signal to the control circuit 710. The pivotable anvil 716 is positioned opposite the staple cartridge 718. When ready to use, the control circuit 710 may provide a closure signal to the motor control 708*b*. In response to the closure signal, the motor 704*b* advances a closure member to grasp tissue between the anvil 716 and the staple cartridge 718.

In one aspect, the control circuit 710 is configured to rotate a shaft member such as the shaft 740 to rotate the end effector 702. The control circuit 710 provides a motor set point to a motor control 708*c*, which provides a drive signal to the motor 704*c*. The output shaft of the motor 704*c* is coupled to a torque sensor 744*c*. The torque sensor 744*c* is coupled to a transmission 706*c* which is coupled to the shaft 740. The transmission 706*c* comprises movable mechanical elements such as rotating elements to control the rotation of the shaft 740 clockwise or counterclockwise up to and over 360°. In one aspect, the motor 704*c* is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744*c* provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738 such as a shaft encoder may provide the rotational position of the shaft 740 to the control circuit 710.

In one aspect, the control circuit 710 is configured to articulate the end effector 702. The control circuit 710 provides a motor set point to a motor control 708*d*, which provides a drive signal to the motor 704*d*. The output shaft of the motor 704*d* is coupled to a torque sensor 744*d*. The torque sensor 744*d* is coupled to a transmission 706*d* which is coupled to an articulation member 742*a*. The transmission 706*d* comprises movable mechanical elements such as articulation elements to control the articulation of the end effector 702±65°. In one aspect, the motor 704*d* is coupled to an articulation nut, which is rotatably journaled on the proximal end portion of the distal spine portion and is rotatably driven thereon by an articulation gear assembly. The torque sensor 744*d* provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742*a*, 742*b*. These articulation members 742*a*, 742*b* are driven by separate disks on the robot interface (the rack) which are driven by the two motors 708*d*, 708*e*. When the separate firing motor 704*a* is provided, each of articulation links 742*a*, 742*b* can be antagonistically driven with respect to the other link in order to provide a resistive holding motion and a load to the head when it is not moving and to provide an articulation motion as the head is articulated. The articulation members 742*a*, 742*b* attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704*a*-704*e* may comprise a brushed DC motor with a gearbox and mechanical links to a firing member, closure member, or articulation member. Another example includes electric motors 704*a*-704*e* that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704*a*-704*e*. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effector 702 and adapted to operate with the robotic surgical instrument 700 to measure the various derived parameters such as the gap distance versus time, tissue compression versus time, and anvil strain versus time. The sensors 738 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 702. The sensors 738 may include one or more sensors. The sensors 738 may be located on the staple cartridge 718 deck to determine tissue location using segmented electrodes. The torque sensors 744*a*-744*e* may be configured to sense force such as firing force, closure force, and/or articulation force, among others. Accordingly, the control circuit 710 can sense (1) the closure load experienced by the distal closure tube and its position, (2) the firing member at the rack and its position, (3) what portion of the staple cartridge 718 has tissue on it, and (4) the load and position on both articulation rods.

In one aspect, the one or more sensors 738 may comprise a strain gauge, such as a micro-strain gauge, configured to measure the magnitude of the strain in the anvil 716 during a clamped condition. The strain gauge provides an electrical signal whose amplitude varies with the magnitude of the strain. The sensors 738 may comprise a pressure sensor configured to detect a pressure generated by the presence of compressed tissue between the anvil 716 and the staple cartridge 718. The sensors 738 may be configured to detect impedance of a tissue section located between the anvil 716 and the staple cartridge 718 that is indicative of the thickness and/or fullness of tissue located therebetween.

In one aspect, the sensors 738 may be implemented as one or more limit switches, electromechanical devices, solid-state switches, Hall-effect devices, magneto-resistive (MR) devices, giant magneto-resistive (GMR) devices, magnetometers, among others. In other implementations, the sensors 738 may be implemented as solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the anvil 716 by the closure drive system. For example, one or more sensors 738 can be at an interaction point between the closure tube and the anvil 716 to detect the closure forces applied by the closure tube to the anvil 716. The forces exerted on the anvil 716 can be representative of the tissue compression experienced by the tissue section captured between the anvil 716 and the staple cartridge 718. The one or more sensors 738 can be positioned at various interaction points along the closure drive system to detect the closure forces applied to the anvil 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the anvil 716.

In one aspect, a current sensor 736 can be employed to measure the current drawn by each of the motors 704*a*-704*e*. The force required to advance any of the movable mechanical elements such as the I-beam 714 corresponds to the current drawn by one of the motors 704*a*-704*e*. The force is converted to a digital signal and provided to the control circuit 710. The control circuit 710 can be configured to simulate the response of the actual system of the instrument in the software of the controller. A displacement member can be actuated to move an I-beam 714 in the end effector 702 at or near a target velocity. The robotic surgical instrument 700 can include a feedback controller, which can be one of any feedback controllers, including, but not limited to a PID, a state feedback, a linear-quadratic (LQR), and/or an adaptive controller, for example. The robotic surgical instrument 700 can include a power source to convert the signal from the feedback controller into a physical input such as case voltage, PWM voltage, frequency modulated voltage, current, torque, and/or force, for example. Additional details are disclosed in U.S. patent application Ser. No. 15/636,829, titled CLOSED LOOP VELOCITY CONTROL TECHNIQUES FOR ROBOTIC SURGICAL INSTRUMENT, filed Jun. 29, 2017, which is herein incorporated by reference in its entirety.

Figure 18:
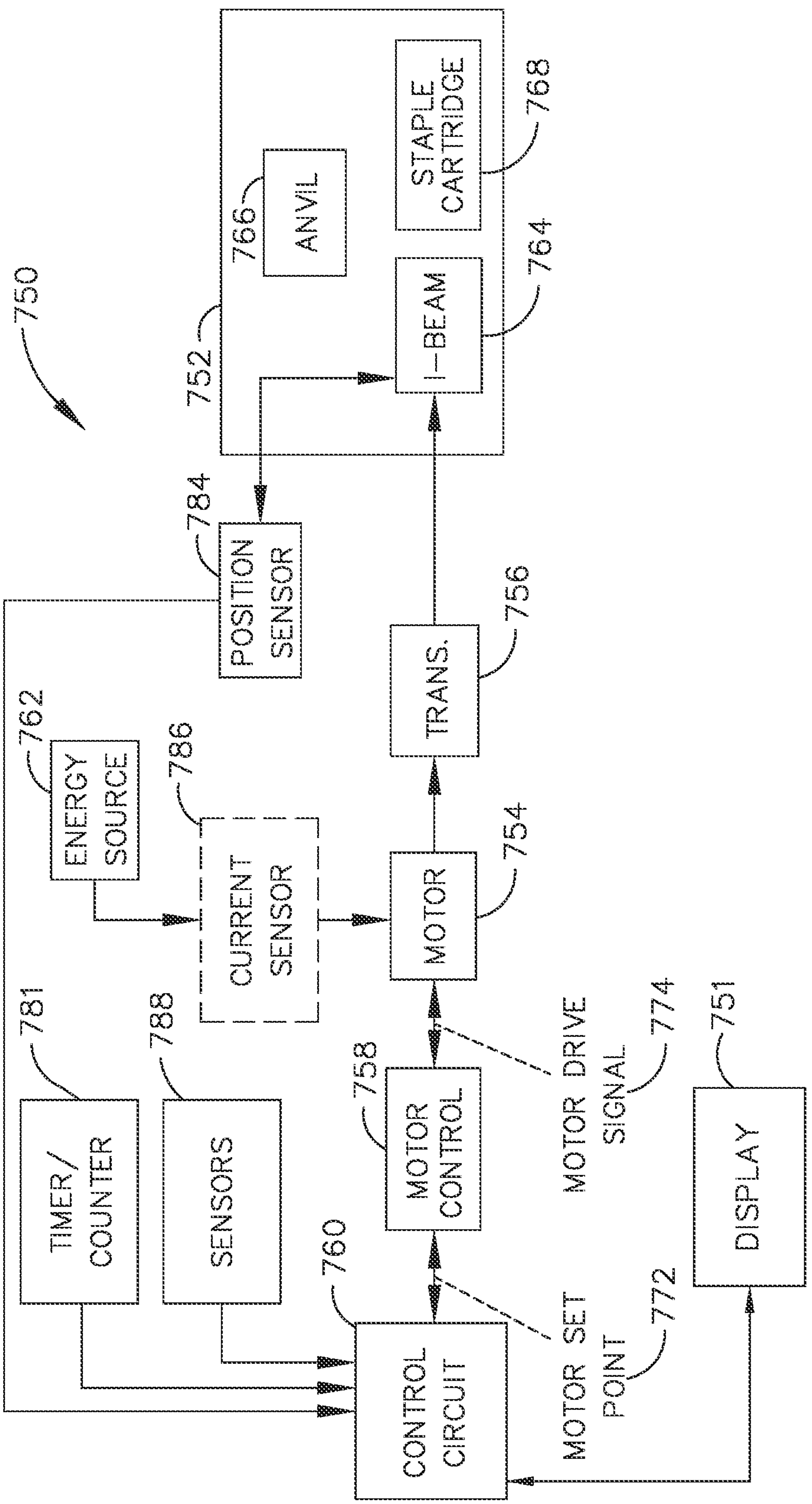
FIG. 18 illustrates a block diagram of a surgical instrument programmed to control the distal translation of a displacement member, in accordance with at least one aspect of the present disclosure.

FIG. 18 illustrates a block diagram of a surgical instrument 750 programmed to control the distal translation of a displacement member, in accordance with at least one aspect of this disclosure. In one aspect, the surgical instrument 750 is programmed to control the distal translation of a displacement member such as the I-beam 764. The surgical instrument 750 comprises an end effector 752 that may comprise an anvil 766, an I-beam 764 (including a sharp cutting edge), and a removable staple cartridge 768.

The position, movement, displacement, and/or translation of a linear displacement member, such as the I-beam 764, can be measured by an absolute positioning system, sensor arrangement, and position sensor 784. Because the I-beam 764 is coupled to a longitudinally movable drive member, the position of the I-beam 764 can be determined by measuring the position of the longitudinally movable drive member employing the position sensor 784. Accordingly, in the following description, the position, displacement, and/or translation of the I-beam 764 can be achieved by the position sensor 784 as described herein. A control circuit 760 may be programmed to control the translation of the displacement member, such as the I-beam 764. The control circuit 760, in some examples, may comprise one or more microcontrollers, microprocessors, or other suitable processors for executing instructions that cause the processor or processors to control the displacement member, e.g., the I-beam 764, in the manner described. In one aspect, a timer/counter 781 provides an output signal, such as the elapsed time or a digital count, to the control circuit 760 to correlate the position of the I-beam 764 as determined by the position sensor 784 with the output of the timer/counter 781 such that the control circuit 760 can determine the position of the I-beam 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the I-beam 764 via a transmission 756. The transmission 756 may include one or more gears or other linkage components to couple the motor 754 to the I-beam 764. A position sensor 784 may sense a position of the I-beam 764. The position sensor 784 may be or include any type of sensor that is capable of generating position data that indicate a position of the I-beam 764. In some examples, the position sensor 784 may include an encoder configured to provide a series of pulses to the control circuit 760 as the I-beam 764 translates distally and proximally. The control circuit 760 may track the pulses to determine the position of the I-beam 764. Other suitable position sensors may be used, including, for example, a proximity sensor. Other types of position sensors may provide other signals indicating motion of the I-beam 764. Also, in some examples, the position sensor 784 may be omitted. Where the motor 754 is a stepper motor, the control circuit 760 may track the position of the I-beam 764 by aggregating the number and direction of steps that the motor 754 has been instructed to execute. The position sensor 784 may be located in the end effector 752 or at any other portion of the instrument.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by a closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the I-beam 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move an I-beam 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or I-beam 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical stapling and cutting implements. For example, a motor 754 may drive a displacement member distally and proximally along a longitudinal axis of the end effector 752. The end effector 752 may comprise a pivotable anvil 766 and, when configured for use, a staple cartridge 768 positioned opposite the anvil 766. A clinician may grasp tissue between the anvil 766 and the staple cartridge 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, an I-beam 764 with a cutting element positioned at a distal end, may cut the tissue between the staple cartridge 768 and the anvil 766.

In various examples, the surgical instrument 750 may comprise a control circuit 760 programmed to control the distal translation of the displacement member, such as the I-beam 764, for example, based on one or more tissue conditions. The control circuit 760 may be programmed to sense tissue conditions, such as thickness, either directly or indirectly, as described herein. The control circuit 760 may be programmed to select a firing control program based on tissue conditions. A firing control program may describe the distal motion of the displacement member. Different firing control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, titled SYSTEM AND METHODS FOR CONTROLLING A DISPLAY OF A SURGICAL INSTRUMENT, filed Sep. 29, 2017, which is herein incorporated by reference in its entirety.

Figure 19:
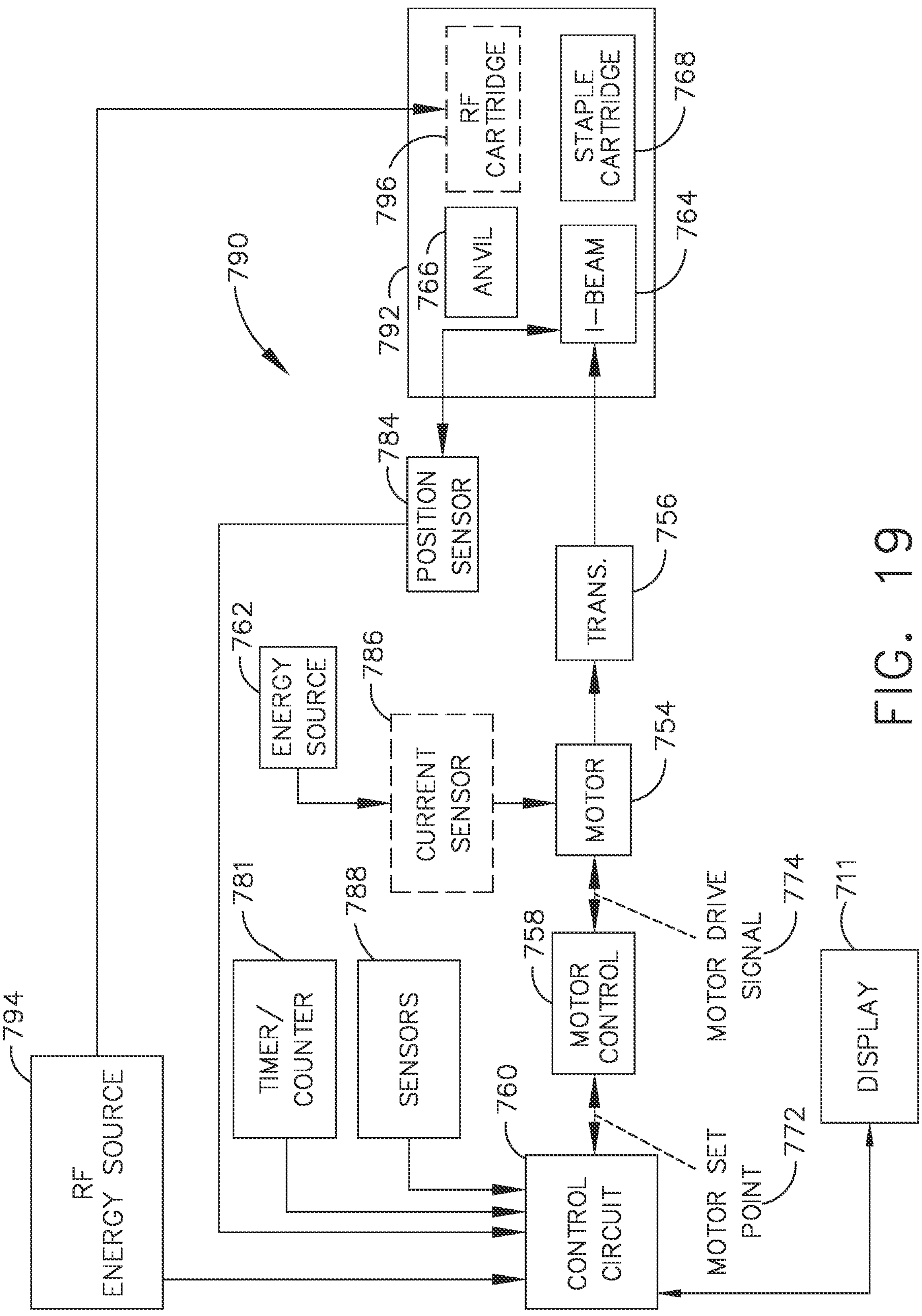
FIG. 19 is a schematic diagram of a surgical instrument configured to control various functions, in accordance with at least one aspect of the present disclosure.

FIG. 19 is a schematic diagram of a surgical instrument 790 configured to control various functions, in accordance with at least one aspect of this disclosure. In one aspect, the surgical instrument 790 is programmed to control distal translation of a displacement member such as the I-beam 764. The surgical instrument 790 comprises an end effector 792 that may comprise an anvil 766, an I-beam 764, and a removable staple cartridge 768 which may be interchanged with an RF cartridge 796 (shown in dashed line).

In one aspect, sensors 788 may be implemented as a limit switch, electromechanical device, solid-state switches, Hall-effect devices, MR devices, GMR devices, magnetometers, among others. In other implementations, the sensors 638 may be solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 788 may include electrical conductorless switches, ultrasonic switches, accelerometers, and inertial sensors, among others.

In one aspect, the position sensor 784 may be implemented as an absolute positioning system comprising a magnetic rotary absolute positioning system implemented as an AS5055EQFT single-chip magnetic rotary position sensor available from Austria Microsystems, AG. The position sensor 784 may interface with the control circuit 760 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the I-beam 764 may be implemented as a knife member comprising a knife body that operably supports a tissue cutting blade thereon and may further include anvil engagement tabs or features and channel engagement features or a foot. In one aspect, the staple cartridge 768 may be implemented as a standard (mechanical) surgical fastener cartridge. In one aspect, the RF cartridge 796 may be implemented as an RF cartridge. These and other sensors arrangements are described in commonly owned U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety.

The position, movement, displacement, and/or translation of a linear displacement member, such as the I-beam 764, can be measured by an absolute positioning system, sensor arrangement, and position sensor represented as position sensor 784. Because the I-beam 764 is coupled to the longitudinally movable drive member, the position of the I-beam 764 can be determined by measuring the position of the longitudinally movable drive member employing the position sensor 784. Accordingly, in the following description, the position, displacement, and/or translation of the I-beam 764 can be achieved by the position sensor 784 as described herein. A control circuit 760 may be programmed to control the translation of the displacement member, such as the I-beam 764, as described herein. The control circuit 760, in some examples, may comprise one or more microcontrollers, microprocessors, or other suitable processors for executing instructions that cause the processor or processors to control the displacement member, e.g., the I-beam 764, in the manner described. In one aspect, a timer/counter 781 provides an output signal, such as the elapsed time or a digital count, to the control circuit 760 to correlate the position of the I-beam 764 as determined by the position sensor 784 with the output of the timer/counter 781 such that the control circuit 760 can determine the position of the I-beam 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the I-beam 764 via a transmission 756. The transmission 756 may include one or more gears or other linkage components to couple the motor 754 to the I-beam 764. A position sensor 784 may sense a position of the I-beam 764. The position sensor 784 may be or include any type of sensor that is capable of generating position data that indicate a position of the I-beam 764. In some examples, the position sensor 784 may include an encoder configured to provide a series of pulses to the control circuit 760 as the I-beam 764 translates distally and proximally. The control circuit 760 may track the pulses to determine the position of the I-beam 764. Other suitable position sensors may be used, including, for example, a proximity sensor. Other types of position sensors may provide other signals indicating motion of the I-beam 764. Also, in some examples, the position sensor 784 may be omitted. Where the motor 754 is a stepper motor, the control circuit 760 may track the position of the I-beam 764 by aggregating the number and direction of steps that the motor has been instructed to execute. The position sensor 784 may be located in the end effector 792 or at any other portion of the instrument.

The control circuit 760 may be in communication with one or more sensors 788. The sensors 788 may be positioned on the end effector 792 and adapted to operate with the surgical instrument 790 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 792. The sensors 788 may include one or more sensors.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by the closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor portion of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the I-beam 764 corresponds to the current drawn by the motor 754. The force is converted to a digital signal and provided to the control circuit 760.

An RF energy source 794 is coupled to the end effector 792 and is applied to the RF cartridge 796 when the RF cartridge 796 is loaded in the end effector 792 in place of the staple cartridge 768. The control circuit 760 controls the delivery of the RF energy to the RF cartridge 796.

Additional details are disclosed in U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, filed Jun. 28, 2017, which is herein incorporated by reference in its entirety.

Figure 20:
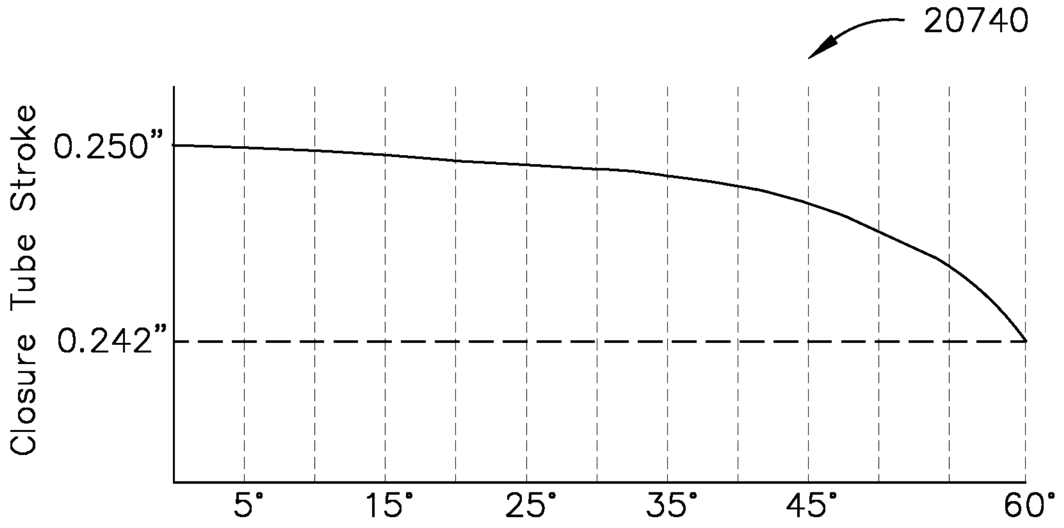
FIG. 20 is a stroke length graph showing an example of a control system modifying the stroke length of a clamping assembly based on the articulation angle.

FIG. 20 illustrates a stroke length graph 20740 showing how a control system can modify the stroke length of a closure tube assembly based on the articulation angle θ. Such modifying of the stroke length includes shortening the stroke length to a compensated stroke length (e.g., defined along the y-axis) as the articulation angle θ increases (e.g., defined along the x-axis). The compensated stroke length defines a length of travel of the closure tube assembly in the distal direction to close the jaws of an end effector, which is dependent upon the articulation angle θ and prevents overtravel of the closure tube assembly causing damage to the surgical device.

For example, as shown in the stroke length graph 20740, the stroke length of the closure tube assembly to close the jaws is approximately 0.250 inches when the end effector is not articulated, and the compensated stroke length is approximately 0.242 inches when the articulation angle θ is approximately 60 degrees. Such measurements are provided as examples only and can include any of a variety of angles and corresponding stroke lengths and compensated stroke lengths without departing from the scope of this disclosure. Furthermore, the relationship between the articulation angles θ and compensated stroke lengths is non-linear and the rate at which the compensated stroke length shortens increases as the articulation angle increases. For example, the decrease in compensated stroke lengths between 45 degrees and 60 degrees articulation is greater than the decrease in compensated stroke lengths between zero degrees and 15 degrees articulation. Although with this approach the control system is adjusting the stroke length based on the articulation angle θ to prevent damage to the surgical device (e.g., jamming the distal end of the closure tube assembly in a distal position), the distal closure tube is still allowed to advance during articulation, thereby potentially at least partly closing the jaws.

Figure 21:
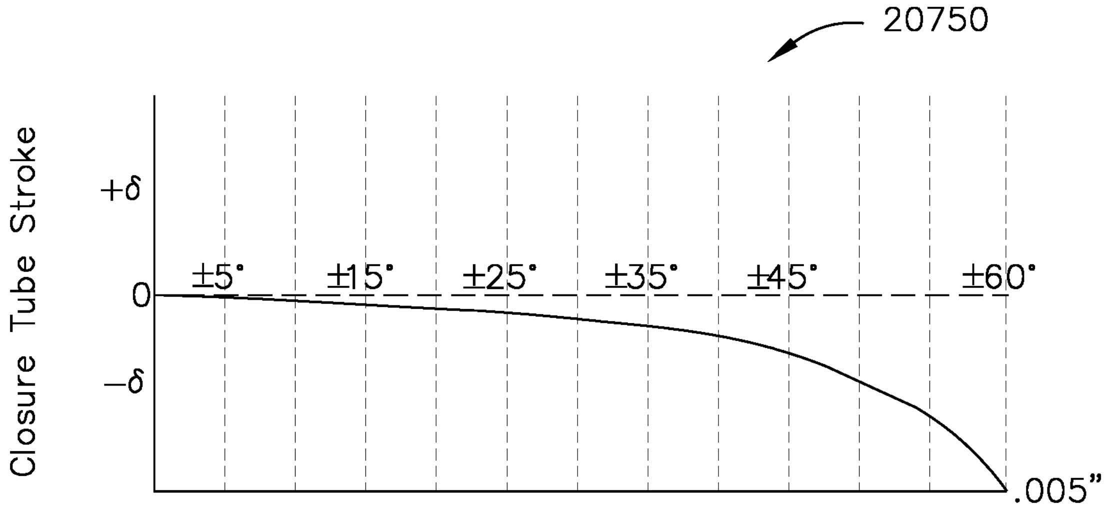
FIG. 21 is a closure tube assembly positioning graph showing an example of a control system modifying a longitudinal position of the closure tube assembly based on the articulation angle.

FIG. 21 illustrates a closure tube assembly positioning graph 20750 showing one aspect in which a control system modifies a longitudinal position of a closure tube assembly based on the articulation angle θ. Such modifying of the longitudinal position of the closure tube assembly includes proximally retracting the closure tube assembly by a compensation distance (e.g., defined along the y-axis) as the end effector articulates and based on the articulation angle θ (e.g., defined along the x-axis). The compensation distance that the closure tube assembly is proximally retracted prevents distal advancement of the distal closure tube thereby maintaining the jaws in the open position during articulation. By proximally retracting the closure tube assembly by the compensation distance during articulation, the closure tube assembly can travel the stroke length starting form the proximally retracted position to close the jaws upon activation of the closure assembly.

For example, as shown in the closure tube assembly positioning graph 20750, the compensation distance when the end effector is not articulated is zero and the compensation distance when the articulation angle θ is approximately 60 degrees is approximately 0.008 inches. In this example, the closure tube assembly is retracted by a 0.008 inch compensation distance during articulation. As such, to close the jaws, the closure tube assembly can advance the stoke length starting from this retracted position. Such measurements are provided for example purposes only and can include any of a variety of angles and corresponding compensation distances without departing from the scope of the disclosure. As shown in FIG. 21, the relationship between the articulation angle θ and the compensation distance is non-linear and the rate at which the compensation distance lengthens increases as the articulation angle θ increases. For example, the increase in compensation distance between 45 degrees and 60 degrees is greater than the increase in compensation distance between zero degrees and 15 degrees.

Figure 22:
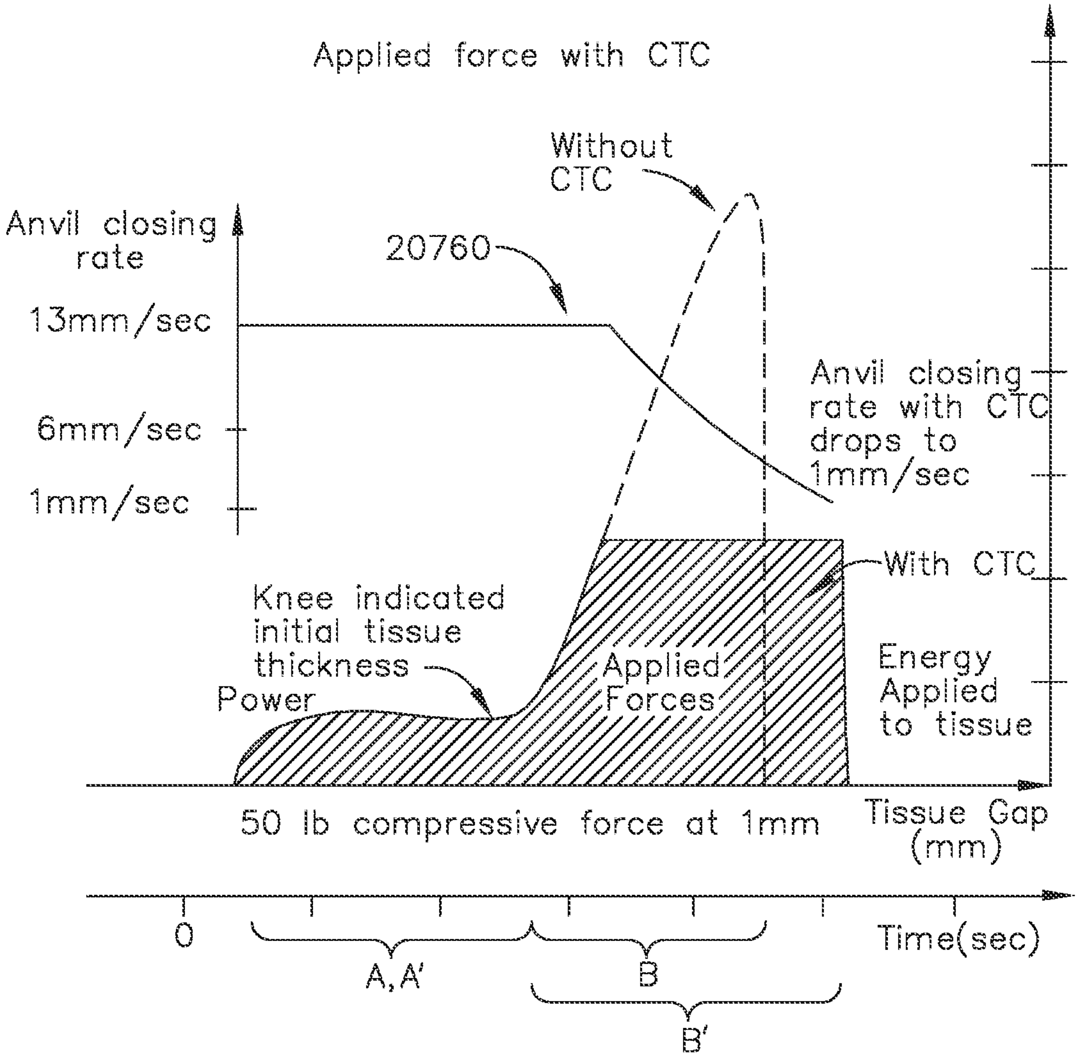
FIG. 22 is a comparison of a stapling method utilizing controlled tissue compression versus a stapling method without controlled tissue compression.

When clamping patient tissue, forces exerted through the clamping device, e.g., a linear stapler, and the tissue may reach an unacceptably high level. For example, when a constant closure rate is employed, the force may become high enough to cause excess trauma to the clamped tissue and may cause deformation in the clamping device such that an acceptable tissue gap is not maintained across the stapling path. FIG. 22 is a graph illustrating the power applied to tissue during compression at a constant anvil closure rate (i.e.; without controlled tissue compression (CTC)) vs. the power applied to tissue during compression with a variable anvil closure rate (i.e.; with CTC). The closure rate may be adjusted to control tissue compression so that the power imparted into the tissue remains constant over a portion of the compression. The peak power imparted into the tissue according to FIG. 22 is much lower when a variable anvil closure rate is utilized. Based on the imparted power, the force exerted by the surgical device (or a parameter related to or proportional to the force) may be calculated. In this regard, the power may be limited such that the force exerted through the surgical device, e.g., through the jaws of a linear stapler, do not exceed a yield force or pressure that results in splaying of the jaws such that the tissue gap is not within an acceptable range along the entire stapling length when in the fully closed position. For example, the jaws should be parallel or close enough to parallel that the tissue gap remains within the acceptable or target range for all staple positions along the entire length of the jaws. Further, the limitation of the exerted power avoids, or at least minimizes, trauma or damage to tissue.

In FIG. 22, the total energy exerted in the method without CTC is the same as the total energy exerted in the method with CTC, i.e., the areas under the power curves of FIG. 22 are the same or substantially the same. The difference in the power profiles utilized is, however, substantial, as the peak power is much lower in the example with CTC as compared to the example without CTC.

The limiting of power is achieved in the example with CTC by slowing the closing rate, as illustrated by line 20760. It is noted that the compression time B' is longer than the closing time B. As illustrated in FIG. 22, a device and method that provides a constant closure rate (i.e.; without CTC) achieves the same 50 lb of compressive force at the same 1 mm tissue gap as the device and method that provides a variable closure rate (i.e.; with CTC). While the device and method that provide for a constant closure rate may achieve the compressive force at the desired tissue gap in a shorter time period as compared with a device and method using a variable closure rate, this results in the spike in power applied to the tissue, as shown in FIG. 22. In contrast, the example aspect illustrated with CTC begins slowing the rate of closure to limit the amount of power applied to the tissue below a certain level. By limiting the power applied to the tissue, tissue trauma may be minimized with respect to the system and method that does not use CTC.

FIG. 22 and additional exemplifications are further described in U.S. Pat. No. 8,499,992, filed Jun. 1, 2012, titled DEVICE AND METHOD FOR CONTROLLING COMPRESSION OF TISSUE, which issued Aug. 6, 2013, the entire disclosure of which is incorporated by reference herein.

In some aspects, a control system can include a plurality of predefined force thresholds that assist the control system in determining a position of an E-beam and/or articulation angle of a firing shaft and appropriately controlling at least one motor based on such determination. For example, the force thresholds can change depending on a length of travel of the firing bar configured to translate the firing shaft, and such force thresholds can be compared to a measured torsional force of the one or more motors in communication with the control system. Comparison of the measured torsional forces against the force thresholds can provide a dependable way for the control system to determine a location of the E-beam and/or articulation of the end effector. This can allow the control system to appropriately control the one or more motors (e.g., reduce or stop torsional loads) to ensure proper firing of the firing assembly and articulation of the end effector, as well as prevent against damage to the system, as will be described in greater detail below.

Figure 23:
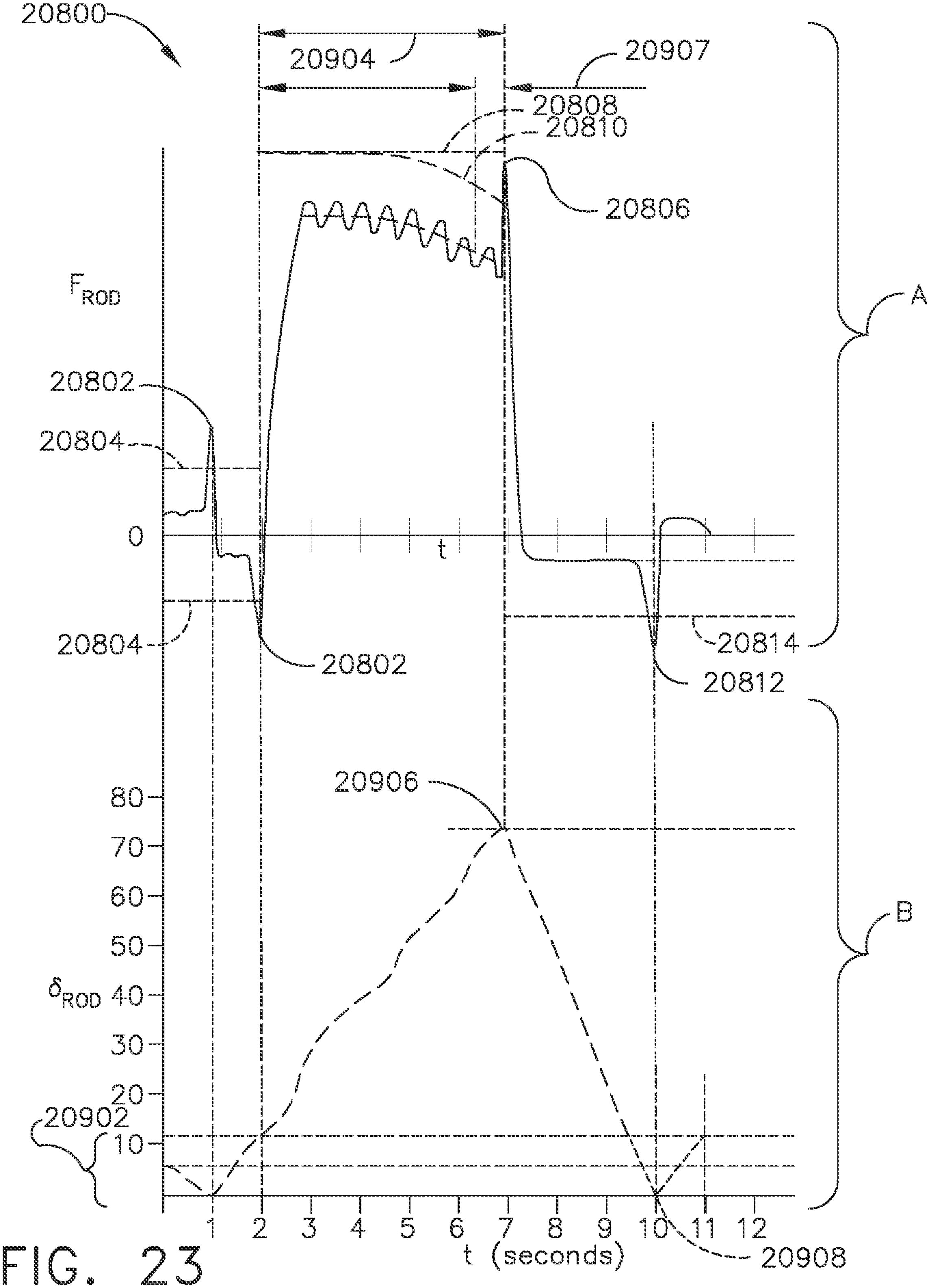
FIG. 23 is a force graph shown in section A and a related displacement graph shown in section B, where the force graph and the displacement graph have an x-axis defining time, a y-axis of the displacement graph defines a travel displacement of a firing rod, and a y-axis of the force graph defines a sensed torsional force on a motor that is configured to advance the firing rod.

FIG. 23 illustrates a force and displacement graph 20800 including measured forces in section A that are related to measured displacements in section B. Both section A and B have an x-axis defining time (e.g., seconds). The y-axis of section B defines a travel displacement (e.g., in millimeters) of a firing rod and the y-axis of section A defines a force applied to the firing bar to thereby advance the firing shaft. As shown in section A, travel of the firing bar within a first articulation range 20902 (e.g., a first approximately 12 mm of travel) causes the end effector to articulate. For example, at the 12 mm displacement position the end effector is fully articulated to the right and is mechanically unable to articulate further. As a result of being at full articulation the torsional force on the motor will increase and the control system can sense an articulation force peak 20802 that exceeds a predefined articulation threshold 20804, as shown in section A. The control system can include more than one predefined articulation threshold 20804 for sensing more than one max articulation direction (e.g., left articulation and right articulation). After the control system detects an articulation force peak 20802 that exceeds the predetermined articulation threshold 20804, the control system can reduce or stop actuation of the motor thereby protecting at least the motor from damage.

After the firing bar advances past the articulation range 20902, a shifting mechanism within the surgical stapler can cause further distal travel of the firing bar to cause distal travel of the firing shaft. For example, as shown in section B, travel between approximately 12 mm and 70 mm of travel displacement can cause the E-beam to advance along a firing stroke 20904 and cut tissue captured between the jaws, however, other lengths of travel are within the scope of this disclosure. In this example, a maximum firing stroke position 20906 of the E-beam occurs at 70 mm travel. At this point, the E-beam or knife abuts a distal end of the cartridge or jaw thereby increasing torsional forces on the motor and causing a knife travel force peak 20806, as shown in section A, to be sensed by the control system. As shown in section A, the control system can include a motor threshold 20808 and an end of knife travel threshold 20810 that branches off from the motor threshold 20808 and decreases (e.g., non-linearly) as the E-beam approaches the maximum firing stroke position 20906.

The control system can be configured to monitor the sensed motor torsional force during at least the last part of distal travel 20907 (e.g., last 10 percent of the firing stroke 904) of the E-beam before reaching the maximum firing stroke position 20906. While monitoring along such last part of distal travel 20907, the control system can cause the motor to reduce torsional forces to thereby reduce the load on the E-beam. This can protect damage to the surgical stapler, including the E-beam, by reducing loads on the E-beam as the E-beam approaches the maximum firing stroke position 20906 thereby reducing impact of the E-beam against the distal end of the cartridge or jaw. As mentioned above, such impact can cause a knife travel force peak 20806, which can exceed the knife travel threshold 20810 but not the motor threshold 20808 thereby not damaging the motor. As such, the control system can stop actuation of the motor after the knife travel force peak 20806 exceeds the knife travel threshold 20810 and before the knife travel force peak 20806 exceeds the motor threshold 20808 thereby protecting the motor from damage. Furthermore, the increasing reduction in the knife travel threshold 20810 prevents the control system from preliminarily thinking that the E-beam has reached the maximum firing stroke position 20906.

After the control system has detected a knife travel force peak 20806 exceeding the knife travel threshold 20810, the control system can confirm a position of the E-beam (e.g., at 70 mm displacement and/or at end of firing stroke 20904) and can retract the firing bar based on such known displacement position to reset the E-beam in a most proximal position 20908 (e.g., 0 mm displacement). At the most proximal position 20908, a knife retraction force peak 20812 that exceeds a predefined knife retraction threshold 20814, as shown in section A, can be sensed by the control system. At this point, the control system can recalibrate, if needed, and associate the position of the E-beam as being in a home position where subsequent advancement of the firing rod in the distal direction (e.g., approximately 12 mm in length) will cause the shifter to disengage the E-beam from the firing bar. Once disengaged, firing bar travel within the articulation range 20902 will again cause articulation of the end effector.

As such, the control system can sense torsional forces on the motor controlling travel of the firing bar and compare such sensed torsional forces against a plurality of thresholds to determine a position of the E-beam or angle of articulation of the end effector and thereby appropriately control the motor to prevent damage to the motor, as well as confirm positioning of the firing bar and/or E-beam.

As described supra, tissue contact or pressure sensors determine when the jaw members initially come into contact with the tissue "T". This enables a surgeon to determine the initial thickness of the tissue "T" and/or the thickness of the tissue "T" prior to clamping. In any of the surgical instrument aspects described above, as seen in FIG. 24, contact of the jaw members with tissue "T" closes a sensing circuit "SC" that is otherwise open, by establishing contacting with a pair of opposed plates "P1, P2" provided on the jaw members. The contact sensors may also include sensitive force transducers that determine the amount of force being applied to the sensor, which may be assumed to be the same amount of force being applied to the tissue "T". Such force being applied to the tissue, may then be translated into an amount of tissue compression. The force sensors measure the amount of compression a tissue is under and provide a surgeon with information about the force applied to the tissue "T". Excessive tissue compression may have a negative impact on the tissue "T" being operated on. For example, excessive compression of tissue "T" may result in tissue necrosis and, in certain procedures, staple line failure. Information regarding the pressure being applied to tissue "T" enables a surgeon to better determine that excessive pressure is not being applied to tissue "T".

Any of the contact sensors disclosed herein may include, and are not limited to, electrical contacts placed on an inner surface of a jaw which, when in contact with tissue, close a sensing circuit that is otherwise open. The contact sensors may also include sensitive force transducers that detect when the tissue being clamped first resists compression. Force transducers may include, and are not limited to, piezoelectric elements, piezoresistive elements, metal film or semiconductor strain gauges, inductive pressure sensors, capacitive pressure sensors, and potentiometric pressure transducers that use bourbon tubes, capsules or bellows to drive a wiper arm on a resistive element.

In an aspect, any one of the aforementioned surgical instruments may include one or more piezoelectric elements to detect a change in pressure occurring on the jaw members. Piezoelectric elements are bi-directional transducers which convert stress into an electrical potential. Elements may consist of metallized quartz or ceramics. In operation, when stress is applied to the crystals there is a change in the charge distribution of the material resulting in a generation of voltage across the material. Piezoelectric elements may be used to indicate when any one or both of the jaw members makes contact with the tissue "T" and the amount of pressure exerted on the tissue "T" after contact is established.

In an aspect, any one of the aforementioned surgical instruments may include or be provided with one or more metallic strain gauges placed within or upon a portion of the body thereof. Metallic strain gauges operate on the principle that the resistance of the material depends upon length, width and thickness. Accordingly, when the material of the metallic strain gauge undergoes strain the resistance of the material changes. Thus, a resistor made of this material incorporated into a circuit will convert strain to a change in an electrical signal. Desirably, the strain gauge may be placed on the surgical instruments such that pressure applied to the tissue effects the strain gauge.

Alternatively, in another aspect, one or more semiconductor strain gauges may be used in a similar manner as the metallic strain gauge described above, although the mode of transduction differs. In operation, when a crystal lattice structure of the semiconductor strain gauge is deformed, as a result of an applied stress, the resistance of the material changes. This phenomenon is referred to as the piezoresistive effect.

In yet another aspect, any one of the aforementioned surgical instruments may include or be provided with one or more inductive pressure sensors to transduce pressure or force into motion of inductive elements relative to each other. This motion of the inductive elements relative to one another alters the overall inductance or inductive coupling. Capacitive pressure transducers similarly transduce pressure or force into motion of capacitive elements relative to each other altering the overall capacitance.

In still another aspect, any one of the aforementioned surgical instruments may include or be provided with one or more capacitive pressure transducers to transduce pressure or force into motion of capacitive elements relative to each other altering an overall capacitance.

In an aspect, any one of the aforementioned surgical instruments may include or be provided with one or more mechanical pressure transducers to transduce pressure or force into motion. In use, a motion of a mechanical element is used to deflect a pointer or dial on a gauge. This movement of the pointer or dial may be representative of the pressure or force applied to the tissue "T". Examples of mechanical elements include and are not limited to bourbon tubes, capsules or bellows. By way of example, mechanical elements may be coupled with other measuring and/or sensing elements, such as a potentiometer pressure transducer. In this example the mechanical element is coupled with a wiper on the variable resistor. In use, pressure or force may be transduced into mechanical motion which deflects the wiper on the potentiometer thus changing the resistance to reflect the applied pressure or force.

The combination of the above aspects, in particular the combination of the gap and tissue contact sensors, provides the surgeon with feedback information and/or real-time information regarding the condition of the operative site and/or target tissue "T". For example, information regarding the initial thickness of the tissue "T" may guide the surgeon in selecting an appropriate staple size, information regarding the clamped thickness of the tissue "T" may let the surgeon know if the selected staple will form properly, information relating to the initial thickness and clamped thickness of the tissue "T" may be used to determine the amount of compression or strain on the tissue "T", and information relating to the strain on the tissue "T" may be used this strain to avoid compressing tissue to excessive strain values and/or stapling into tissue that has undergone excessive strain.

Additionally, force sensors may be used to provide the surgeon with the amount of pressure applied to the tissue. The surgeon may use this information to avoid applying excessive pressure on the tissue "T" or stapling into tissue "T" which has experienced excessive strain.

Figure 24:
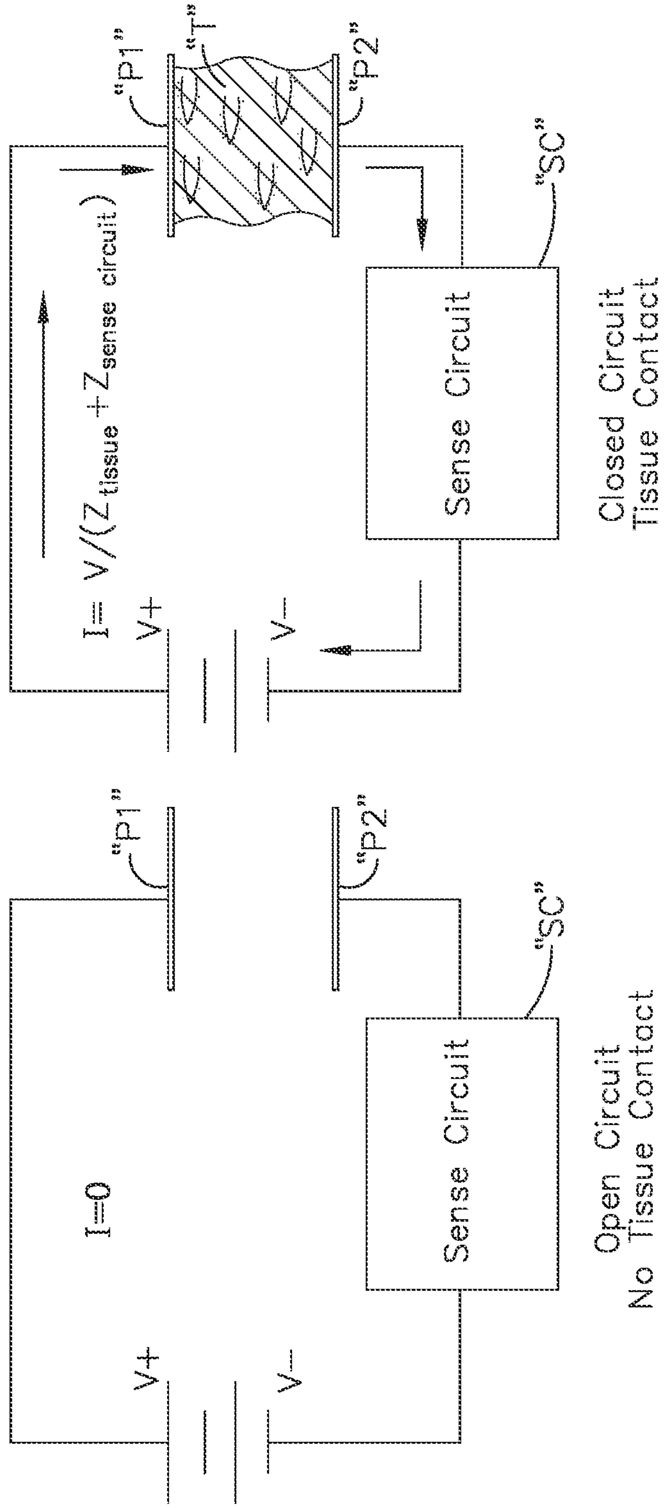
FIG. 24 is a schematic illustration of a tissue contact circuit showing the completion of the circuit upon contact with tissue a pair of spaced apart contact plates.

FIG. 24 and additional exemplifications are further described in U.S. Pat. No. 8,181,839, filed Jun. 27, 2011, titled SURGICAL INSTRUMENT EMPLOYING SENSORS, which issued May 5, 2012, the entire disclosure of which is incorporated by reference herein.

Certain aspects are shown and described to provide an understanding of the structure, function, manufacture, and use of the disclosed devices and methods. Features shown or described in one example may be combined with features of other examples and modifications and variations are within the scope of this disclosure.

The terms "proximal" and "distal" are relative to a clinician manipulating the handle of the surgical instrument where "proximal" refers to the portion closer to the clinician and "distal" refers to the portion located further from the clinician. For expediency, spatial terms "vertical," "horizontal," "up," and "down" used with respect to the drawings are not intended to be limiting and/or absolute, because surgical instruments can used in many orientations and positions.

Example devices and methods are provided for performing laparoscopic and minimally invasive surgical procedures. Such devices and methods, however, can be used in other surgical procedures and applications including open surgical procedures, for example. The surgical instruments can be inserted into a through a natural orifice or through an incision or puncture hole formed in tissue. The working portions or end effector portions of the instruments can be inserted directly into the body or through an access device that has a working channel through which the end effector and elongated shaft of the surgical instrument can be advanced.

FIGS. 25 to 28 depict a motor-driven surgical instrument 150010 for cutting and fastening that may or may not be reused. In the illustrated examples, the surgical instrument 150010 includes a housing 150012 that comprises a handle assembly 150014 that is configured to be grasped, manipulated, and actuated by the clinician. The housing 150012 is configured for operable attachment to an interchangeable shaft assembly 150200 that has an end effector 150300 operably coupled thereto that is configured to perform one or more surgical tasks or procedures. In accordance with the present disclosure, various forms of interchangeable shaft assemblies may be effectively employed in connection with robotically controlled surgical systems. The term "housing" may encompass a housing or similar portion of a robotic system that houses or otherwise operably supports at least one drive system configured to generate and apply at least one control motion that could be used to actuate interchangeable shaft assemblies. The term "frame" may refer to a portion of a handheld surgical instrument. The term "frame" also may represent a portion of a robotically controlled surgical instrument and/or a portion of the robotic system that may be used to operably control a surgical instrument. Interchangeable shaft assemblies may be employed with various robotic systems, instruments, components, and methods disclosed in U.S. Pat. No. 9,072,535, titled SURGICAL STAPLING INSTRUMENTS WITH ROTATABLE STAPLE DEPLOYMENT ARRANGEMENTS, which is herein incorporated by reference in its entirety.

Figure 25:
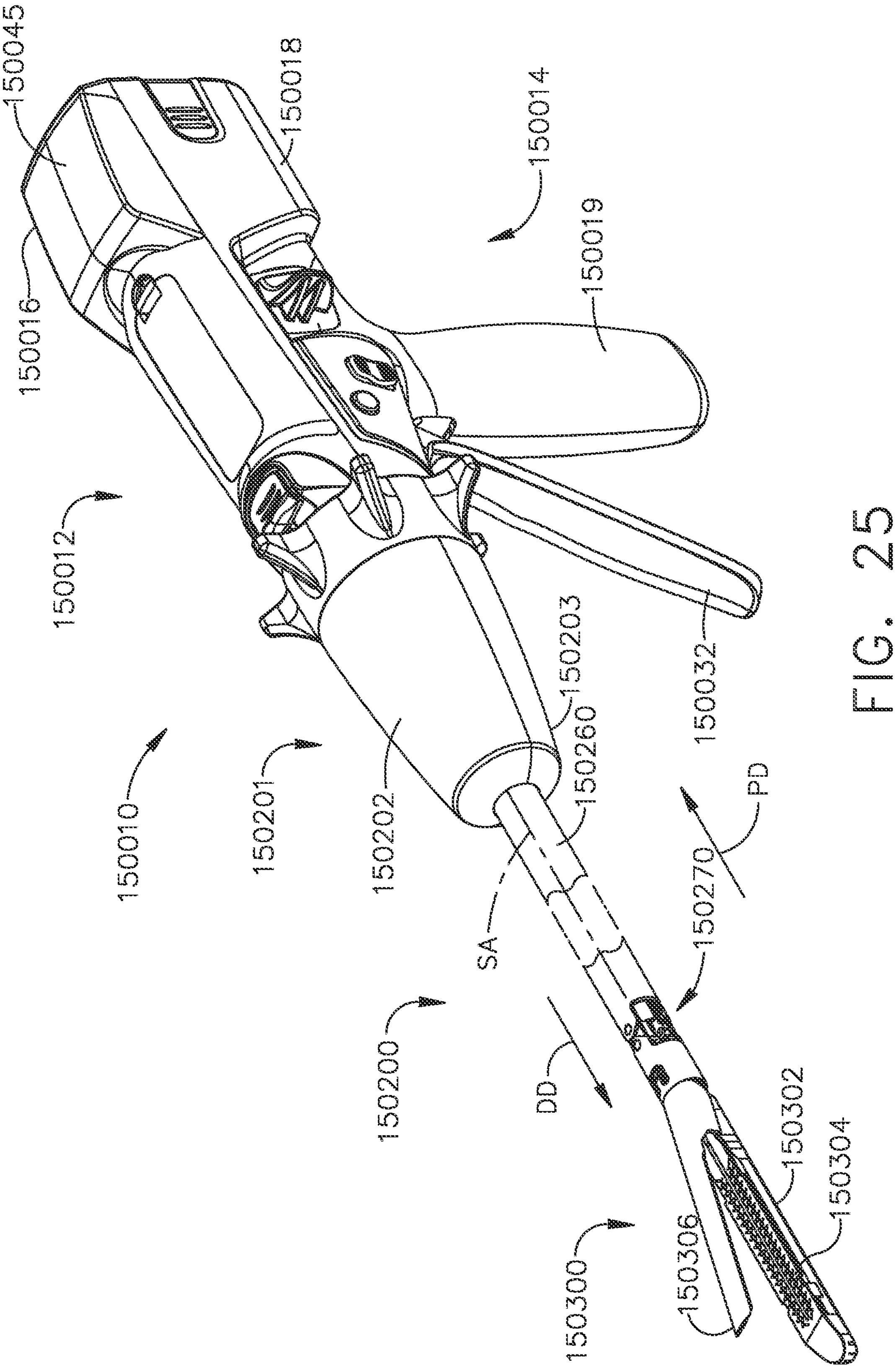
FIG. 25 is a perspective view of a surgical instrument that has an interchangeable shaft assembly operably coupled thereto, in accordance with at least one aspect of this disclosure.

FIG. 25 is a perspective view of a surgical instrument 150010 that has an interchangeable shaft assembly 150200 operably coupled thereto, in accordance with at least one aspect of this disclosure. The housing 150012 includes an end effector 150300 that comprises a surgical cutting and fastening device configured to operably support a surgical staple cartridge 150304 therein. The housing 150012 may be configured for use in connection with interchangeable shaft assemblies that include end effectors that are adapted to support different sizes and types of staple cartridges, have different shaft lengths, sizes, and types. The housing 150012 may be employed with a variety of interchangeable shaft assemblies, including assemblies configured to apply other motions and forms of energy such as, radio frequency (RF) energy, ultrasonic energy, and/or motion to end effector arrangements adapted for use in connection with various surgical applications and procedures. The end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

The handle assembly 150014 may comprise a pair of interconnectable handle housing segments 150016, 150018 interconnected by screws, snap features, adhesive, etc. The handle housing segments 150016, 150018 cooperate to form a pistol grip portion 150019 that can be gripped and manipulated by the clinician. The handle assembly 150014 operably supports a plurality of drive systems configured to generate and apply control motions to corresponding portions of the interchangeable shaft assembly that is operably attached thereto. A display may be provided below a cover 150045.

Figure 26:
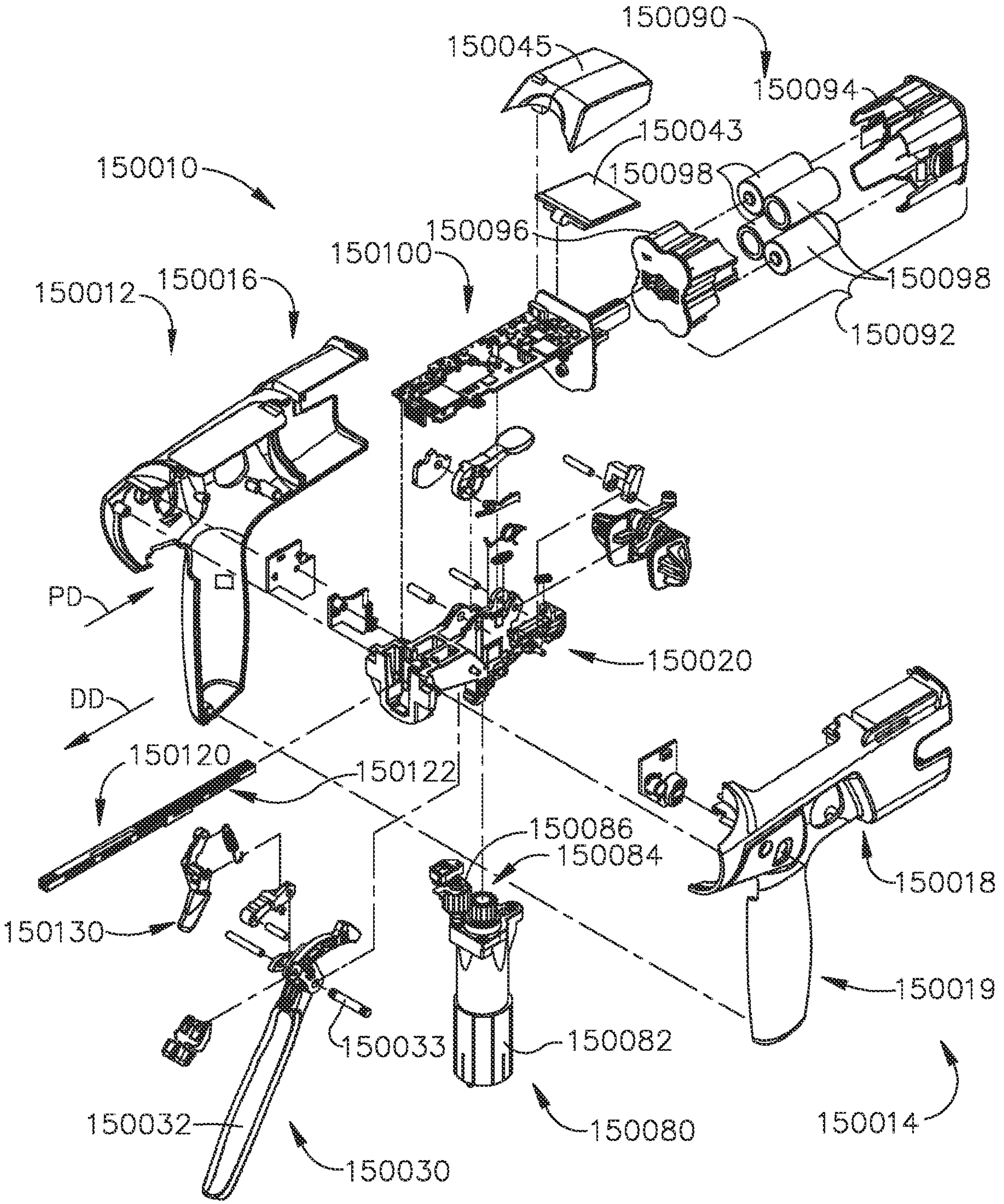
FIG. 26 is an exploded assembly view of a portion of the surgical instrument of FIG. 25, in accordance with at least one aspect of this disclosure.

FIG. 26 is an exploded assembly view of a portion of the surgical instrument 150010 of FIG. 25, in accordance with at least one aspect of this disclosure. The handle assembly 150014 may include a frame 150020 that operably supports a plurality of drive systems. The frame 150020 can operably support a "first" or closure drive system 150030, which can apply closing and opening motions to the interchangeable shaft assembly 150200. The closure drive system 150030 may include an actuator such as a closure trigger 150032 pivotally supported by the frame 150020. The closure trigger 150032 is pivotally coupled to the handle assembly 150014 by a pivot pin 150033 to enable the closure trigger 150032 to be manipulated by a clinician. When the clinician grips the pistol grip portion 150019 of the handle assembly 150014, the closure trigger 150032 can pivot from a starting or "unactuated" position to an "actuated" position and more particularly to a fully compressed or fully actuated position.

The handle assembly 150014 and the frame 150020 may operably support a firing drive system 150080 configured to apply firing motions to corresponding portions of the interchangeable shaft assembly attached thereto. The firing drive system 150080 may employ an electric motor 150082 located in the pistol grip portion 150019 of the handle assembly 150014. The electric motor 150082 may be a DC brushed motor having a maximum rotational speed of approximately 25,000 RPM, for example. In other arrangements, the motor may include a brushless motor, a cordless motor, a synchronous motor, a stepper motor, or any other suitable electric motor. The electric motor 150082 may be powered by a power source 150090 that may comprise a removable power pack 150092. The removable power pack 150092 may comprise a proximal housing portion 150094 configured to attach to a distal housing portion 150096. The proximal housing portion 150094 and the distal housing portion 150096 are configured to operably support a plurality of batteries 150098 therein. Batteries 150098 may each comprise, for example, a Lithium Ion (LI) or other suitable battery. The distal housing portion 150096 is configured for removable operable attachment to a control circuit board 150100, which is operably coupled to the electric motor 150082. Several batteries 150098 connected in series may power the surgical instrument 150010. The power source 150090 may be replaceable and/or rechargeable. A display 150043, which is located below the cover 150045, is electrically coupled to the control circuit board 150100. The cover 150045 may be removed to expose the display 150043.

The electric motor 150082 can include a rotatable shaft (not shown) that operably interfaces with a gear reducer assembly 150084 mounted in meshing engagement with a set, or rack, of drive teeth 150122 on a longitudinally movable drive member 150120. The longitudinally movable drive member 150120 has a rack of drive teeth 150122 formed thereon for meshing engagement with a corresponding drive gear 150086 of the gear reducer assembly 150084.

In use, a voltage polarity provided by the power source 150090 can operate the electric motor 150082 in a clockwise direction wherein the voltage polarity applied to the electric motor by the battery can be reversed in order to operate the electric motor 150082 in a counter-clockwise direction. When the electric motor 150082 is rotated in one direction, the longitudinally movable drive member 150120 will be axially driven in the distal direction "DD." When the electric motor 150082 is driven in the opposite rotary direction, the longitudinally movable drive member 150120 will be axially driven in a proximal direction "PD." The handle assembly 150014 can include a switch that can be configured to reverse the polarity applied to the electric motor 150082 by the power source 150090. The handle assembly 150014 may include a sensor configured to detect the position of the longitudinally movable drive member 150120 and/or the direction in which the longitudinally movable drive member 150120 is being moved.

Actuation of the electric motor 150082 can be controlled by a firing trigger 150130 that is pivotally supported on the handle assembly 150014. The firing trigger 150130 may be pivoted between an unactuated position and an actuated position.

Turning back to FIG. 25, the interchangeable shaft assembly 150200 includes an end effector 150300 comprising an elongated channel 150302 configured to operably support a surgical staple cartridge 150304 therein. The end effector 150300 may include an anvil 150306 that is pivotally supported relative to the elongated channel 150302. The interchangeable shaft assembly 150200 may include an articulation joint 150270. Construction and operation of the end effector 150300 and the articulation joint 150270 are set forth in U.S. Patent Application Publication No. 2014/0263541, titled ARTICULATABLE SURGICAL INSTRUMENT COMPRISING AN ARTICULATION LOCK, which is herein incorporated by reference in its entirety. The interchangeable shaft assembly 150200 may include a proximal housing or nozzle 150201 comprised of nozzle portions 150202, 150203. The interchangeable shaft assembly 150200 may include a closure tube 150260 extending along a shaft axis SA that can be utilized to close and/or open the anvil 150306 of the end effector 150300.

Turning back to FIG. 25, the closure tube 150260 is translated distally (direction "DD") to close the anvil 150306, for example, in response to the actuation of the closure trigger 150032 in the manner described in the aforementioned reference U.S. Patent Application Publication No. 2014/0263541. The anvil 150306 is opened by proximally translating the closure tube 150260. In the anvil-open position, the closure tube 150260 is moved to its proximal position.

Figure 27:
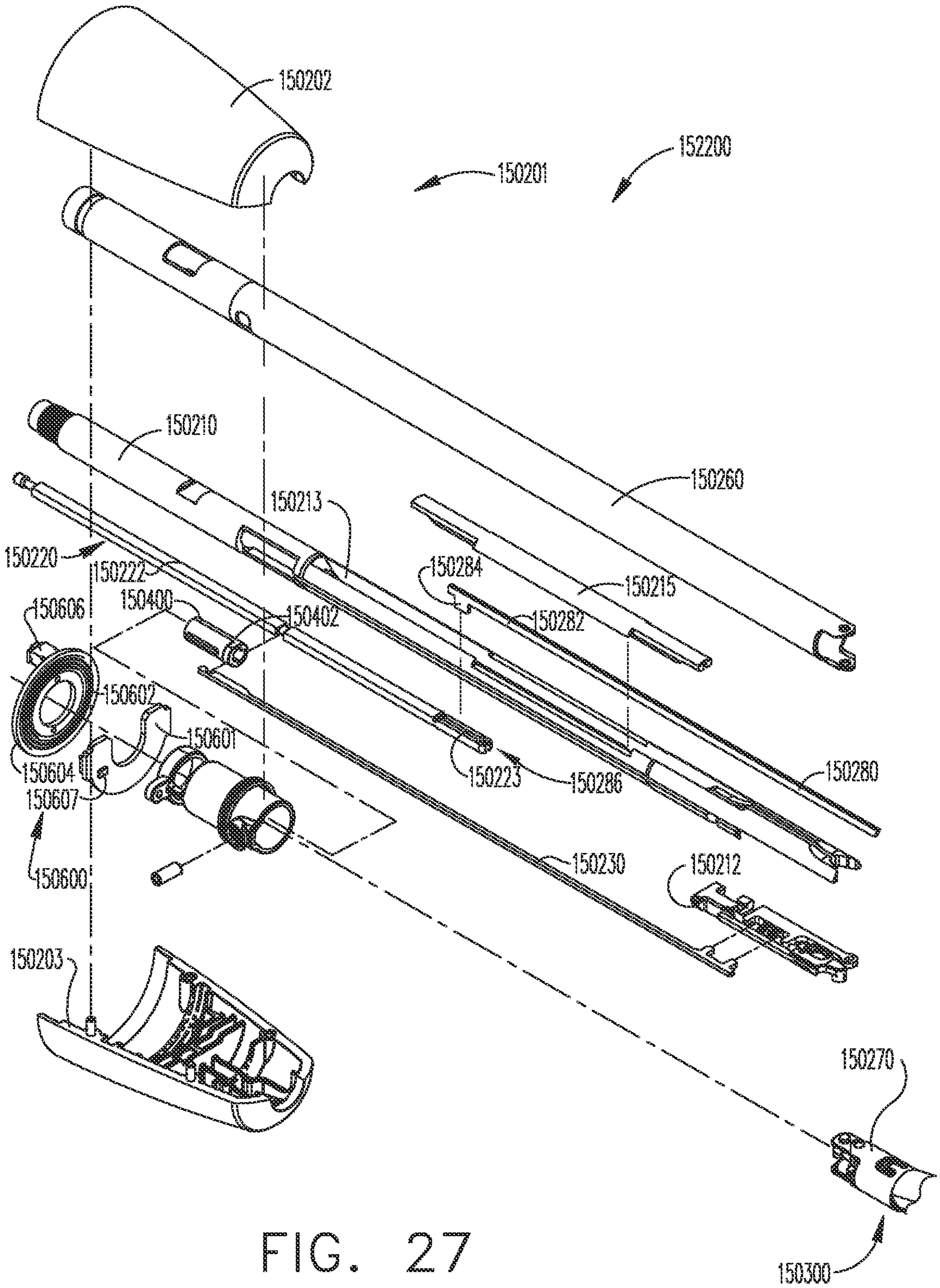
FIG. 27 is an exploded assembly view of portions of the interchangeable shaft assembly, in accordance with at least one aspect of this disclosure.

FIG. 27 is another exploded assembly view of portions of the interchangeable shaft assembly 150200, in accordance with at least one aspect of this disclosure. The interchangeable shaft assembly 150200 may include a firing member 150220 supported for axial travel within the spine 150210. The firing member 150220 includes an intermediate firing shaft 150222 configured to attach to a distal cutting portion or knife bar 150280. The firing member 150220 may be referred to as a "second shaft" or a "second shaft assembly". The intermediate firing shaft 150222 may include a longitudinal slot 150223 in a distal end configured to receive a tab 150284 on the proximal end 150282 of the knife bar 150280. The longitudinal slot 150223 and the proximal end 150282 may be configured to permit relative movement there between and can comprise a slip joint 150286. The slip joint 150286 can permit the intermediate firing shaft 150222 of the firing member 150220 to articulate the end effector 150300 about the articulation joint 150270 without moving, or at least substantially moving, the knife bar 150280. Once the end effector 150300 has been suitably oriented, the intermediate firing shaft 150222 can be advanced distally until a proximal sidewall of the longitudinal slot 150223 contacts the tab 150284 to advance the knife bar 150280 and fire the staple cartridge positioned within the channel 150302. The spine 150210 has an elongated opening or window 150213 therein to facilitate assembly and insertion of the intermediate firing shaft 150222 into the spine 150210. Once the intermediate firing shaft 150222 has been inserted therein, a top frame segment 150215 may be engaged with the shaft frame 150212 to enclose the intermediate firing shaft 150222 and knife bar 150280 therein. Operation of the firing member 150220 may be found in U.S. Patent Application Publication No. 2014/0263541. A spine 150210 can be configured to slidably support a firing member 150220 and the closure tube 150260 that extends around the spine 150210. The spine 150210 may slidably support an articulation driver 150230.

The interchangeable shaft assembly 150200 can include a clutch assembly 150400 configured to selectively and releasably couple the articulation driver 150230 to the firing member 150220. The clutch assembly 150400 includes a lock collar, or lock sleeve 150402, positioned around the firing member 150220 wherein the lock sleeve 150402 can be rotated between an engaged position in which the lock sleeve 150402 couples the articulation driver 150230 to the firing member 150220 and a disengaged position in which the articulation driver 150230 is not operably coupled to the firing member 150220. When the lock sleeve 150402 is in the engaged position, distal movement of the firing member 150220 can move the articulation driver 150230 distally and, correspondingly, proximal movement of the firing member 150220 can move the articulation driver 150230 proximally. When the lock sleeve 150402 is in the disengaged position, movement of the firing member 150220 is not transmitted to the articulation driver 150230 and, as a result, the firing member 150220 can move independently of the articulation driver 150230. The nozzle 150201 may be employed to operably engage and disengage the articulation drive system with the firing drive system in the various manners described in U.S. Patent Application Publication No. 2014/0263541.

The interchangeable shaft assembly 150200 can comprise a slip ring assembly 150600 which can be configured to conduct electrical power to and/or from the end effector 150300 and/or communicate signals to and/or from the end effector 150300, for example. The slip ring assembly 150600 can comprise a proximal connector flange 150604 and a distal connector flange 150601 positioned within a slot defined in the nozzle portions 150202, 150203. The proximal connector flange 150604 can comprise a first face and the distal connector flange 150601 can comprise a second face positioned adjacent to and movable relative to the first face. The distal connector flange 150601 can rotate relative to the proximal connector flange 150604 about the shaft axis SA-SA (FIG. 25). The proximal connector flange 150604 can comprise a plurality of concentric, or at least substantially concentric, conductors 150602 defined in the first face thereof. A connector 150607 can be mounted on the proximal side of the distal connector flange 150601 and may have a plurality of contacts wherein each contact corresponds to and is in electrical contact with one of the conductors 150602. Such an arrangement permits relative rotation between the proximal connector flange 150604 and the distal connector flange while maintaining electrical contact there between. The proximal connector flange 150604 can include an electrical connector 150606 that can place the conductors 150602 in signal communication with a shaft circuit board, for example. In at least one instance, a wiring harness comprising a plurality of conductors can extend between the electrical connector 150606 and the shaft circuit board. The electrical connector 150606 may extend proximally through a connector opening defined in the chassis mounting flange. U.S. Patent Application Publication No. 2014/0263551, titled STAPLE CARTRIDGE TISSUE THICKNESS SENSOR SYSTEM, is incorporated herein by reference in its entirety. U.S. Patent Application Publication No. 2014/0263552, titled STAPLE CARTRIDGE TISSUE THICKNESS SENSOR SYSTEM, is incorporated by reference in its entirety. Further details regarding slip ring assembly 150600 may be found in U.S. Patent Application Publication No. 2014/0263541.

The interchangeable shaft assembly 150200 can include a proximal portion fixably mounted to the handle assembly 150014 and a distal portion that is rotatable about a longitudinal axis. The rotatable distal shaft portion can be rotated relative to the proximal portion about the slip ring assembly 150600. The distal connector flange 150601 of the slip ring assembly 150600 can be positioned within the rotatable distal shaft portion.

Figure 28:
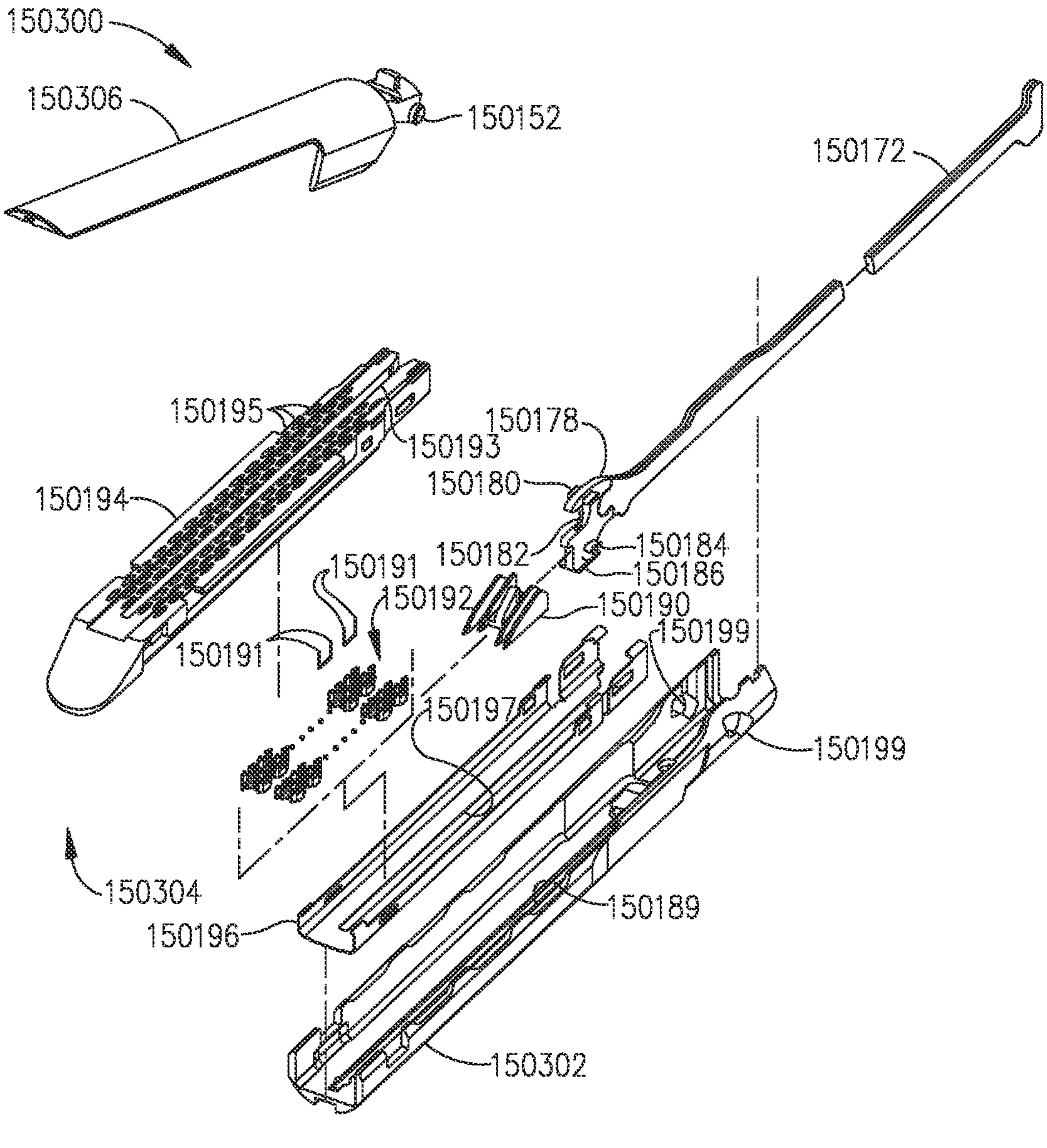
FIG. 28 is an exploded view of an end effector of the surgical instrument of FIG. 25, in accordance with at least one aspect of this disclosure.

FIG. 28 is an exploded view of one aspect of an end effector 150300 of the surgical instrument 150010 of FIG. 25, in accordance with at least one aspect of this disclosure. The end effector 150300 may include the anvil 150306 and the surgical staple cartridge 150304. The anvil 150306 may be coupled to an elongated channel 150302. Apertures 150199 can be defined in the elongated channel 150302 to receive pins 150152 extending from the anvil 150306 to allow the anvil 150306 to pivot from an open position to a closed position relative to the elongated channel 150302 and surgical staple cartridge 150304. A firing bar 150172 is configured to longitudinally translate into the end effector 150300. The firing bar 150172 may be constructed from one solid section, or may include a laminate material comprising a stack of steel plates. The firing bar 150172 comprises an I-beam 150178 and a cutting edge 150182 at a distal end thereof. A distally projecting end of the firing bar 150172 can be attached to the I-beam 150178 to assist in spacing the anvil 150306 from a surgical staple cartridge 150304 positioned in the elongated channel 150302 when the anvil 150306 is in a closed position. The I-beam 150178 may include a sharpened cutting edge 150182 to sever tissue as the I-beam 150178 is advanced distally by the firing bar 150172. In operation, the I-beam 150178 may, or fire, the surgical staple cartridge 150304. The surgical staple cartridge 150304 can include a molded cartridge body 150194 that holds a plurality of staples 150191 resting upon staple drivers 150192 within respective upwardly open staple cavities 150195. A wedge sled 150190 is driven distally by the I-beam 150178, sliding upon a cartridge tray 150196 of the surgical staple cartridge 150304. The wedge sled 150190 upwardly cams the staple drivers 150192 to force out the staples 150191 into deforming contact with the anvil 150306 while the cutting edge 150182 of the I-beam 150178 severs clamped tissue.

The I-beam 150178 can include upper pins 150180 that engage the anvil 150306 during firing. The I-beam 150178 may include middle pins 150184 and a bottom foot 150186 to engage portions of the cartridge body 150194, cartridge tray 150196, and elongated channel 150302. When a surgical staple cartridge 150304 is positioned within the elongated channel 150302, a slot 150193 defined in the cartridge body 150194 can be aligned with a longitudinal slot 150197 defined in the cartridge tray 150196 and a slot 150189 defined in the elongated channel 150302. In use, the I-beam 150178 can slide through the aligned longitudinal slots 150193, 150197, and 150189 wherein, as indicated in FIG. 28, the bottom foot 150186 of the I-beam 150178 can engage a groove running along the bottom surface of elongated channel 150302 along the length of slot 150189, the middle pins 150184 can engage the top surfaces of cartridge tray 150196 along the length of longitudinal slot 150197, and the upper pins 150180 can engage the anvil 150306. The I-beam 150178 can space, or limit the relative movement between, the anvil 150306 and the surgical staple cartridge 150304 as the firing bar 150172 is advanced distally to fire the staples from the surgical staple cartridge 150304 and/or incise the tissue captured between the anvil 150306 and the surgical staple cartridge 150304. The firing bar 150172 and the I-beam 150178 can be retracted proximally allowing the anvil 150306 to be opened to release the two stapled and severed tissue portions.

Figure 29A:
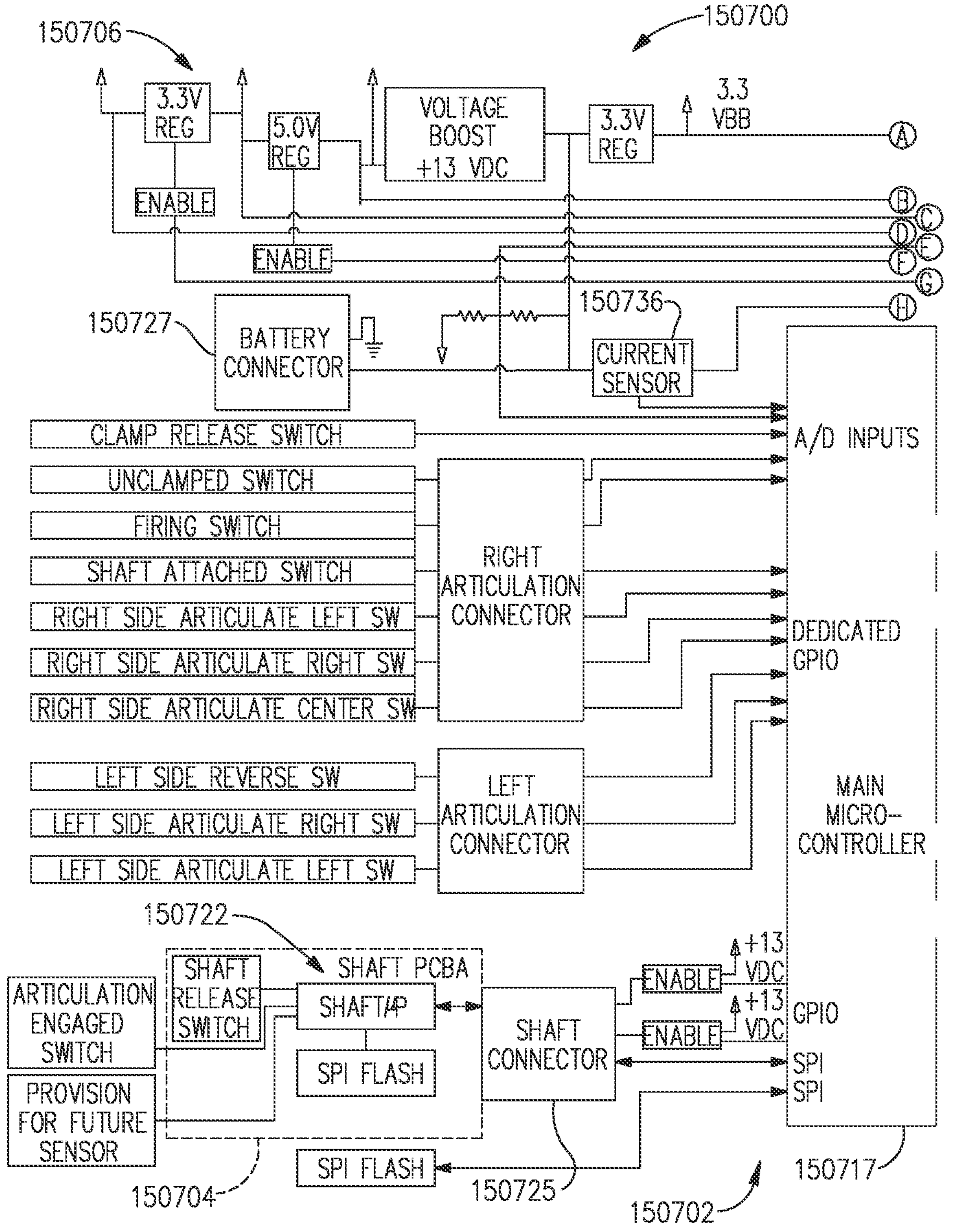
FIG. 29A is a block diagram of a control circuit of the surgical instrument of FIG. 25 spanning two drawing sheets, in accordance with at least one aspect of this disclosure.
Figure 29B:
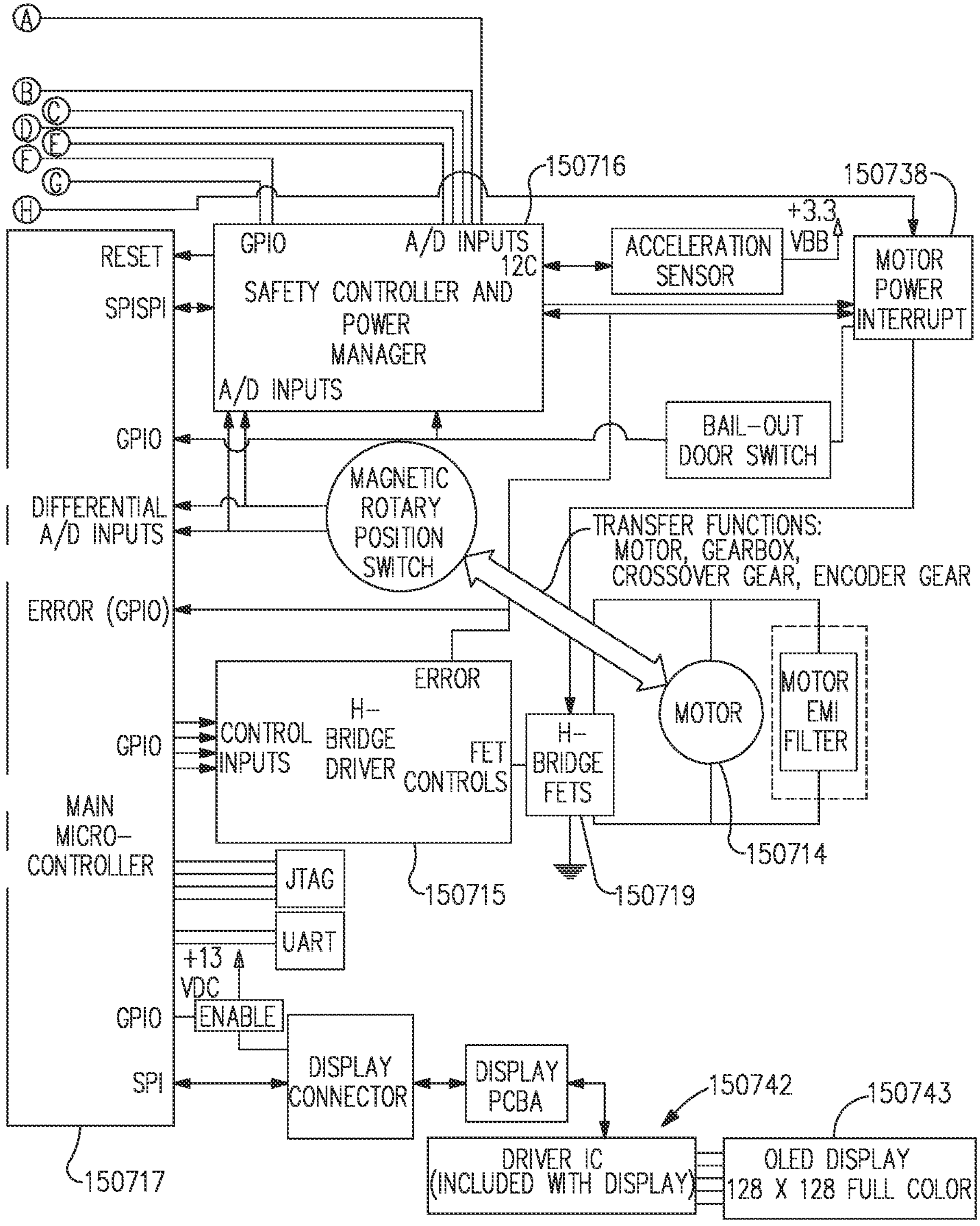
FIG. 29B is a block diagram of a control circuit of the surgical instrument of FIG. 25 spanning two drawing sheets, in accordance with at least one aspect of this disclosure.

FIGS. 29A and 29B is a block diagram of a control circuit 150700 of the surgical instrument 150010 of FIG. 25 spanning two drawing sheets, in accordance with at least one aspect of this disclosure. Referring primarily to FIGS. 29A and 29B, a handle assembly 150702 may include a motor 150714 which can be controlled by a motor driver 150715 and can be employed by the firing system of the surgical instrument 150010. In various forms, the motor 150714 may be a DC brushed driving motor having a maximum rotational speed of approximately 25,000 RPM. In other arrangements, the motor 150714 may include a brushless motor, a cordless motor, a synchronous motor, a stepper motor, or any other suitable electric motor. The motor driver 150715 may comprise an H-Bridge driver comprising field-effect transistors (FETs) 150719, for example. The motor 150714 can be powered by the power assembly 150706 releasably mounted to the handle assembly 150200 for supplying control power to the surgical instrument 150010. The power assembly 150706 may comprise a battery which may include a number of battery cells connected in series that can be used as the power source to power the surgical instrument 150010. In certain circumstances, the battery cells of the power assembly 150706 may be replaceable and/or rechargeable. In at least one example, the battery cells can be Lithium-Ion batteries which can be separably couplable to the power assembly 150706.

The shaft assembly 150704 may include a shaft assembly controller 150722 which can communicate with a safety controller and power management controller 150716 through an interface while the shaft assembly 150704 and the power assembly 150706 are coupled to the handle assembly 150702. For example, the interface may comprise a first interface portion 150725 which may include one or more electric connectors for coupling engagement with corresponding shaft assembly electric connectors and a second interface portion 150727 which may include one or more electric connectors for coupling engagement with corresponding power assembly electric connectors to permit electrical communication between the shaft assembly controller 150722 and the power management controller 150716 while the shaft assembly 150704 and the power assembly 150706 are coupled to the handle assembly 150702. One or more communication signals can be transmitted through the interface to communicate one or more of the power requirements of the attached interchangeable shaft assembly 150704 to the power management controller 150716. In response, the power management controller may modulate the power output of the battery of the power assembly 150706, as described below in greater detail, in accordance with the power requirements of the attached shaft assembly 150704. The connectors may comprise switches which can be activated after mechanical coupling engagement of the handle assembly 150702 to the shaft assembly 150704 and/or to the power assembly 150706 to allow electrical communication between the shaft assembly controller 150722 and the power management controller 150716.

The interface can facilitate transmission of the one or more communication signals between the power management controller 150716 and the shaft assembly controller 150722 by routing such communication signals through a main controller 150717 residing in the handle assembly 150702, for example. In other circumstances, the interface can facilitate a direct line of communication between the power management controller 150716 and the shaft assembly controller 150722 through the handle assembly 150702 while the shaft assembly 150704 and the power assembly 150706 are coupled to the handle assembly 150702.

The main controller 150717 may be any single core or multicore processor such as those known under the trade name ARM Cortex by Texas Instruments. In one aspect, the main controller 150717 may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

The safety controller may be a safety controller platform comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The power assembly 150706 may include a power management circuit which may comprise the power management controller 150716, a power modulator 150738, and a current sense circuit 150736. The power management circuit can be configured to modulate power output of the battery based on the power requirements of the shaft assembly 150704 while the shaft assembly 150704 and the power assembly 150706 are coupled to the handle assembly 150702.

The power management controller 150716 can be programmed to control the power modulator 150738 of the power output of the power assembly 150706 and the current sense circuit 150736 can be employed to monitor power output of the power assembly 150706 to provide feedback to the power management controller 150716 about the power output of the battery so that the power management controller 150716 may adjust the power output of the power assembly 150706 to maintain a desired output. The power management controller 150716 and/or the shaft assembly controller 150722 each may comprise one or more processors and/or memory units which may store a number of software modules.

The surgical instrument 150010 (FIGS. 25 to 28) may comprise an output device 150742 which may include devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). In certain circumstances, the output device 150742 may comprise a display 150743 which may be included in the handle assembly 150702. The shaft assembly controller 150722 and/or the power management controller 150716 can provide feedback to a user of the surgical instrument 150010 through the output device 150742. The interface can be configured to connect the shaft assembly controller 150722 and/or the power management controller 150716 to the output device 150742. The output device 150742 can instead be integrated with the power assembly 150706. In such circumstances, communication between the output device 150742 and the shaft assembly controller 150722 may be accomplished through the interface while the shaft assembly 150704 is coupled to the handle assembly 150702.

The control circuit 150700 comprises circuit segments configured to control operations of the powered surgical instrument 150010. A safety controller segment (Segment 1) comprises a safety controller and the main controller 150717 segment (Segment 2). The safety controller and/or the main controller 150717 are configured to interact with one or more additional circuit segments such as an acceleration segment, a display segment, a shaft segment, an encoder segment, a motor segment, and a power segment. Each of the circuit segments may be coupled to the safety controller and/or the main controller 150717. The main controller 150717 is also coupled to a flash memory. The main controller 150717 also comprises a serial communication interface. The main controller 150717 comprises a plurality of inputs coupled to, for example, one or more circuit segments, a battery, and/or a plurality of switches. The segmented circuit may be implemented by any suitable circuit, such as, for example, a printed circuit board assembly (PCBA) within the powered surgical instrument 150010. It should be understood that the term processor as used herein includes any microprocessor, processors, controller, controllers, or other basic computing device that incorporates the functions of a computer's central processing unit (CPU) on an integrated circuit or at most a few integrated circuits. The main controller 150717 is a multipurpose, programmable device that accepts digital data as input, processes it according to instructions stored in its memory, and provides results as output. It is an example of sequential digital logic, as it has internal memory. The control circuit 150700 can be configured to implement one or more of the processes described herein.

The acceleration segment (Segment 3) comprises an accelerometer. The accelerometer is configured to detect movement or acceleration of the powered surgical instrument 150010. Input from the accelerometer may be used to transition to and from a sleep mode, identify an orientation of the powered surgical instrument, and/or identify when the surgical instrument has been dropped. In some examples, the acceleration segment is coupled to the safety controller and/or the main controller 150717.

The display segment (Segment 4) comprises a display connector coupled to the main controller 150717. The display connector couples the main controller 150717 to a display through one or more integrated circuit drivers of the display. The integrated circuit drivers of the display may be integrated with the display and/or may be located separately from the display. The display may comprise any suitable display, such as, for example, an organic light-emitting diode (OLED) display, a liquid-crystal display (LCD), and/or any other suitable display. In some examples, the display segment is coupled to the safety controller.

The shaft segment (Segment 5) comprises controls for an interchangeable shaft assembly 150200 (FIGS. 25 and 27) coupled to the surgical instrument 150010 (FIGS. 25 to 28) and/or one or more controls for an end effector 150300 coupled to the interchangeable shaft assembly 150200. The shaft segment comprises a shaft connector configured to couple the main controller 150717 to a shaft PCBA. The shaft PCBA comprises a low-power microcontroller with a ferroelectric random access memory (FRAM), an articulation switch, a shaft release Hall effect switch, and a shaft PCBA EEPROM. The shaft PCBA EEPROM comprises one or more parameters, routines, and/or programs specific to the interchangeable shaft assembly 150200 and/or the shaft PCBA. The shaft PCBA may be coupled to the interchangeable shaft assembly 150200 and/or integral with the surgical instrument 150010. In some examples, the shaft segment comprises a second shaft EEPROM. The second shaft EEPROM comprises a plurality of algorithms, routines, parameters, and/or other data corresponding to one or more shaft assemblies 150200 and/or end effectors 150300 that may be interfaced with the powered surgical instrument 150010.

The position encoder segment (Segment 6) comprises one or more magnetic angle rotary position encoders. The one or more magnetic angle rotary position encoders are configured to identify the rotational position of the motor 150714, an interchangeable shaft assembly 150200 (FIGS. 25 and 27), and/or an end effector 150300 of the surgical instrument 150010 (FIGS. 25 to 28). In some examples, the magnetic angle rotary position encoders may be coupled to the safety controller and/or the main controller 150717.

The motor circuit segment (Segment 7) comprises a motor 150714 configured to control movements of the powered surgical instrument 150010 (FIGS. 25 to 28). The motor 150714 is coupled to the main microcontroller processor 150717 by an H-bridge driver comprising one or more H-bridge field-effect transistors (FETs) and a motor controller. The H-bridge driver is also coupled to the safety controller. A motor current sensor is coupled in series with the motor to measure the current draw of the motor. The motor current sensor is in signal communication with the main controller 150717 and/or the safety controller. In some examples, the motor 150714 is coupled to a motor electromagnetic interference (EMI) filter.

The motor controller controls a first motor flag and a second motor flag to indicate the status and position of the motor 150714 to the main controller 150717. The main controller 150717 provides a pulse-width modulation (PWM) high signal, a PWM low signal, a direction signal, a synchronize signal, and a motor reset signal to the motor controller through a buffer. The power segment is configured to provide a segment voltage to each of the circuit segments.

The power segment (Segment 8) comprises a battery coupled to the safety controller, the main controller 150717, and additional circuit segments. The battery is coupled to the segmented circuit by a battery connector and a current sensor. The current sensor is configured to measure the total current draw of the segmented circuit. In some examples, one or more voltage converters are configured to provide predetermined voltage values to one or more circuit segments. For example, in some examples, the segmented circuit may comprise 3.3V voltage converters and/or 5V voltage converters. A boost converter is configured to provide a boost voltage up to a predetermined amount, such as, for example, up to 13V. The boost converter is configured to provide additional voltage and/or current during power intensive operations and prevent brownout or low-power conditions.

A plurality of switches are coupled to the safety controller and/or the main controller 150717. The switches may be configured to control operations of the surgical instrument 150010 (FIGS. 25 to 28), of the segmented circuit, and/or indicate a status of the surgical instrument 150010. A bail-out door switch and Hall effect switch for bailout are configured to indicate the status of a bail-out door. A plurality of articulation switches, such as, for example, a left side articulation left switch, a left side articulation right switch, a left side articulation center switch, a right side articulation left switch, a right side articulation right switch, and a right side articulation center switch are configured to control articulation of an interchangeable shaft assembly 150200 (FIGS. 25 and 27) and/or the end effector 150300 (FIGS. 25 and 28). A left side reverse switch and a right side reverse switch are coupled to the main controller 150717. The left side switches comprising the left side articulation left switch, the left side articulation right switch, the left side articulation center switch, and the left side reverse switch are coupled to the main controller 150717 by a left flex connector. The right side switches comprising the right side articulation left switch, the right side articulation right switch, the right side articulation center switch, and the right side reverse switch are coupled to the main controller 150717 by a right flex connector. A firing switch, a clamp release switch, and a shaft engaged switch are coupled to the main controller 150717.

Any suitable mechanical, electromechanical, or solid state switches may be employed to implement the plurality of switches, in any combination. For example, the switches may be limit switches operated by the motion of components associated with the surgical instrument 150010 (FIGS. 25 to 28) or the presence of an object. Such switches may be employed to control various functions associated with the surgical instrument 150010. A limit switch is an electromechanical device that consists of an actuator mechanically linked to a set of contacts. When an object comes into contact with the actuator, the device operates the contacts to make or break an electrical connection. Limit switches are used in a variety of applications and environments because of their ruggedness, ease of installation, and reliability of operation. They can determine the presence or absence, passing, positioning, and end of travel of an object. In other implementations, the switches may be solid state switches that operate under the influence of a magnetic field such as Hall-effect devices, magneto-resistive (MR) devices, giant magneto-resistive (GMR) devices, magnetometers, among others. In other implementations, the switches may be solid state switches that operate under the influence of light, such as optical sensors, infrared sensors, ultraviolet sensors, among others. Still, the switches may be solid state devices such as transistors (e.g., FET, Junction-FET, metal-oxide semiconductor-FET (MOSFET), bipolar, and the like). Other switches may include wireless switches, ultrasonic switches, accelerometers, inertial sensors, among others.

Figure 30:
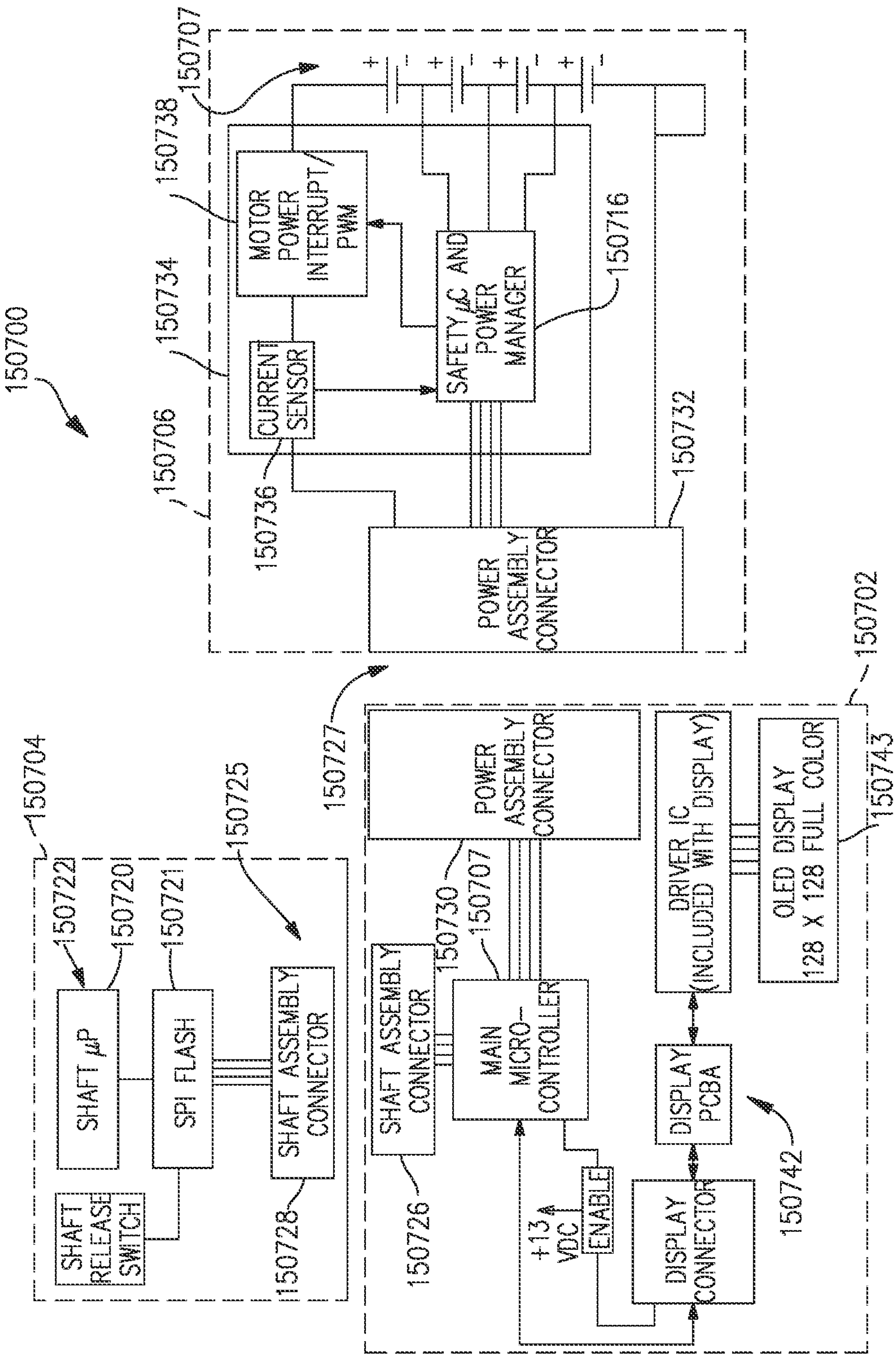
FIG. 30 is a block diagram of the control circuit of the surgical instrument of FIG. 25 illustrating interfaces between the handle assembly, the power assembly, and the handle assembly and the interchangeable shaft assembly, in accordance with at least one aspect of this disclosure.

FIG. 30 is another block diagram of the control circuit 150700 of the surgical instrument of FIG. 25 illustrating interfaces between the handle assembly 150702 and the power assembly 150706 and between the handle assembly 150702 and the interchangeable shaft assembly 150704, in accordance with at least one aspect of this disclosure. The handle assembly 150702 may comprise a main controller 150717, a shaft assembly connector 150726 and a power assembly connector 150730. The power assembly 150706 may include a power assembly connector 150732, a power management circuit 150734 that may comprise the power management controller 150716, a power modulator 150738, and a current sense circuit 150736. The shaft assembly connectors 150730, 150732 form an interface 150727. The power management circuit 150734 can be configured to modulate power output of the battery 150707 based on the power requirements of the interchangeable shaft assembly 150704 while the interchangeable shaft assembly 150704 and the power assembly 150706 are coupled to the handle assembly 150702. The power management controller 150716 can be programmed to control the power modulator 150738 of the power output of the power assembly 150706 and the current sense circuit 150736 can be employed to monitor power output of the power assembly 150706 to provide feedback to the power management controller 150716 about the power output of the battery 150707 so that the power management controller 150716 may adjust the power output of the power assembly 150706 to maintain a desired output. The shaft assembly 150704 comprises a shaft processor 150720 coupled to a non-volatile memory 150721 and shaft assembly connector 150728 to electrically couple the shaft assembly 150704 to the handle assembly 150702. The shaft assembly connectors 150726, 150728 form interface 150725. The main controller 150717, the shaft processor 150720, and/or the power management controller 150716 can be configured to implement one or more of the processes described herein.

The surgical instrument 150010 (FIGS. 25 to 28) may comprise an output device 150742 to a sensory feedback to a user. Such devices may comprise visual feedback devices (e.g., an LCD display screen, LED indicators), audio feedback devices (e.g., a speaker, a buzzer), or tactile feedback devices (e.g., haptic actuators). In certain circumstances, the output device 150742 may comprise a display 150743 that may be included in the handle assembly 150702. The shaft assembly controller 150722 and/or the power management controller 150716 can provide feedback to a user of the surgical instrument 150010 through the output device 150742. The interface 150727 can be configured to connect the shaft assembly controller 150722 and/or the power management controller 150716 to the output device 150742. The output device 150742 can be integrated with the power assembly 150706. Communication between the output device 150742 and the shaft assembly controller 150722 may be accomplished through the interface 150725 while the interchangeable shaft assembly 150704 is coupled to the handle assembly 150702. Having described a control circuit 150700 (FIGS. 29A and 29B and 6) for controlling the operation of the surgical instrument 150010 (FIGS. 25 to 28), the disclosure now turns to various configurations of the surgical instrument 150010 (FIGS. 25 to 28) and control circuit 150700.

Figure 31:
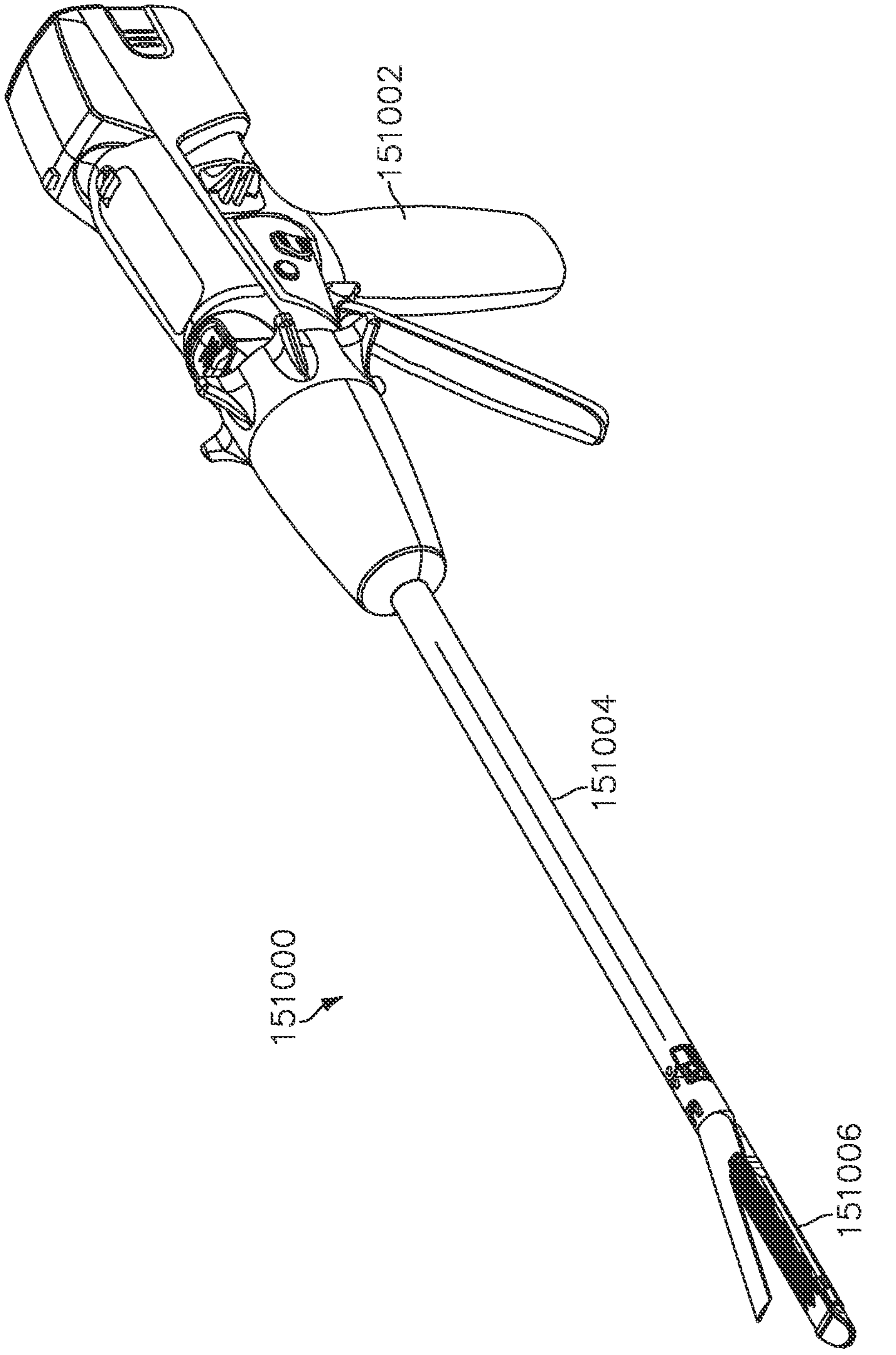
FIG. 31 depicts an example medical device that can include one or more aspects of the present disclosure.
Figure 32:
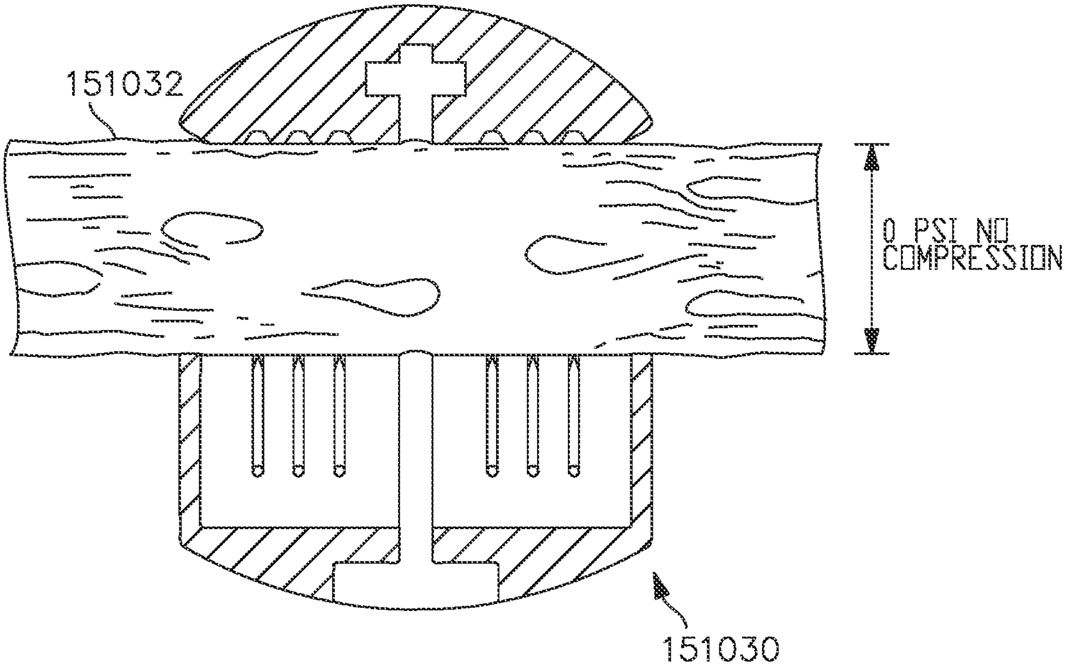
FIG. 32 depicts an example end-effector of a medical device surrounding tissue in accordance with one or more aspects of the present disclosure.
Figure 33:
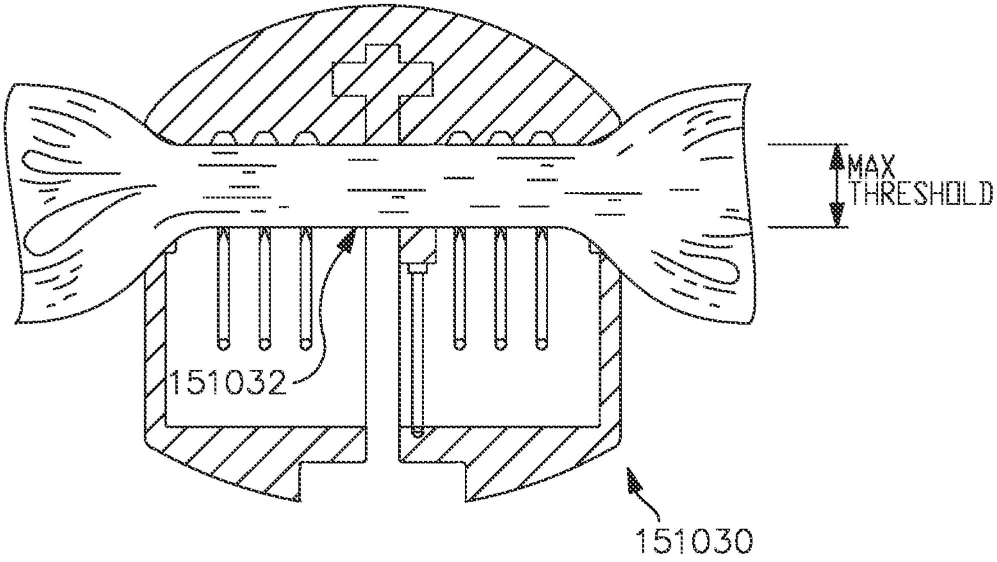
FIG. 33 depicts an example end-effector of a medical device compressing tissue in accordance with one or more aspects of the present disclosure.

Referring to FIG. 31, a surgical stapler 151000 may include a handle component 151002, a shaft component 151004, and an end-effector component 151006. The surgical stapler 151000 is similarly constructed and equipped as the motor-driven surgical cutting and fastening instrument 150010 described in connection with FIG. 25. Accordingly, for conciseness and clarity the details of operation and construction will not be repeated here. The end-effector 151006 may be used to compress, cut, or staple tissue. Referring now to FIG. 32, an end-effector 151030 may be positioned by a physician to surround tissue 151032 prior to compression, cutting, or stapling. As shown in FIG. 32, no compression may be applied to the tissue while preparing to use the end-effector. Referring now to FIG. 33, by engaging the handle (e.g., handle 151002) of the surgical stapler, the physician may use the end-effector 151030 to compress the tissue 151032. In one aspect, the tissue 151032 may be compressed to its maximum threshold, as shown in FIG. 33.

Figure 34:
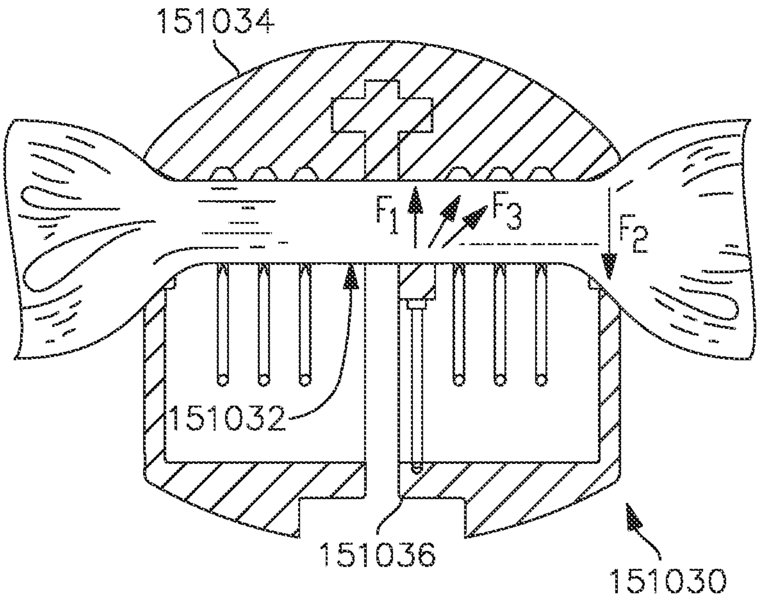
FIG. 34 depicts example forces exerted by an end-effector of a medical device compressing tissue in accordance with one or more aspects of the present disclosure.

Referring to FIG. 34, various forces may be applied to the tissue 151032 by the end-effector 151030. For example, vertical forces F1 and F2 may be applied by the anvil 151034 and the channel frame 151036 of the end-effector 151030 as tissue 151032 is compressed between the two. Referring now to FIG. 35, various diagonal and/or lateral forces also may be applied to the tissue 151032 when compressed by the end-effector 151030. For example, force F3 may be applied. For the purposes of operating a medical device such as surgical stapler 151000, it may be desirable to sense or calculate the various forms of compression being applied to the tissue by the end-effector. For example, knowledge of vertical or lateral compression may allow the end-effector to more precisely or accurately apply a staple operation or may inform the operator of the surgical stapler such that the surgical stapler can be used more properly or safely.

The compression through tissue 151032 may be determined from an impedance of tissue 151032. At various levels of compression, the impedance Z of tissue 151032 may increase or decrease. By applying a voltage V and a current I to the tissue 151032, the impedance Z of the tissue 151032 may be determined at various levels of compression. For example, impedance Z may be calculated by dividing the applied voltage V by the current I.

Referring now to FIG. 36, in one aspect, an RF electrode 151038 may be positioned on the end-effector 151030 (e.g., on a staple cartridge, knife, or channel frame of the end-effector 151030). Further, an electrical contact 151040 may be positioned on the anvil 151034 of the end-effector 151030. In one aspect, the electrical contact may be positioned on the channel frame of the end-effector. As the tissue 151032 is compressed between the anvil 151034 and, for example, the channel frame 151036 of the end-effector 151030, an impedance Z of the tissue 151032 changes. The vertical tissue compression 151042 caused by the end-effector 151030 may be measured as a function of the impedance Z of the tissue 151032.

Referring now to FIG. 37, in one aspect, an electrical contact 151044 may be positioned on an opposite end of the anvil 151034 of the end-effector 151030 as the RF electrode 151038 is positioned. As the tissue 151032 is compressed between the anvil 151034 and, for example, the channel frame 151036 of the end-effector 151030, an impedance Z of the tissue 151032 changes. The lateral tissue compression 151046 caused by the end-effector 151030 may be measured as a function of the impedance Z of the tissue 151032.

Referring now to FIG. 38, in one aspect, electrical contact 151050 may be positioned on the anvil 151034 and electrical contact 151052 may be positioned on an opposite end of the end-effector 151030 at channel frame 151036. RF electrode 151048 may be positioned laterally to the central to the end-effector 151030. As the tissue 151032 is compressed between the anvil 151034 and, for example, the channel frame 151036 of the end-effector 151030, an impedance Z of the tissue 151032 changes. The lateral compression or angular compressions 151054 and 151056 on either side of the RF electrode 151048 may be caused by the end-effector 151030 and may be measured as a function of different impedances Z of the tissue 151032, based on the relative positioning of the RF electrode 151048 and electrical contacts 151050 and 151052.

Referring now to FIG. 39, a frequency generator 151222 may receive power or current from a power source and may supply one or more RF signals to one or more RF electrodes 151224. As discussed above, the one or more RF electrodes may be positioned at various locations or components on an end-effector or surgical stapler, such as a staple cartridge or channel frame. One or more electrical contacts, such as electrical contacts 151226 or 151228 may be positioned on a channel frame or an anvil of an end-effector. Further, one or more filters, such as filters 151230 or 151232 may be communicatively coupled to the electrical contacts 151226 or 151228. The filters 151230 and 151232 may filter one or more RF signals supplied by the frequency generator 151222 before joining a single return path 151234. A voltage V and a current I associated with the one or more RF signals may be used to calculate an impedance Z associated with a tissue that may be compressed and/or communicatively coupled between the one or more RF electrodes 151224 and the electrical contacts 151226 or 151228.

Referring still to FIG. 39, various components of the tissue compression sensor system described herein may be located in a handle 151236 of a surgical stapler. For example, as shown in circuit diagram 151220*a*, frequency generator 151222 may be located in the handle 151236 and receives power from power source 151221. Also, current I1 and current I2 may be measured on a return path corresponding to electrical contacts 151228 and 151226. Using a voltage V applied between the supply and return paths, impedances Z1 and Z2 may be calculated. Z1 may correspond to an impedance of a tissue compressed and/or communicatively coupled between one or more of RF electrodes 151224 and electrical contact 151228. Further, Z2 may correspond to an impedance of a tissue compressed and/or communicatively coupled between one or more of RF electrodes 151224 and electrical contact 151226. Applying the formulas Z1=V/I1 and Z2=V/I2, impedances Z1 and Z2 corresponding to different compression levels of a tissue compressed by an end-effector may be calculated.

Referring now to FIG. 40, one or more aspects of the present disclosure are described in circuit diagram 151250. In an implementation, a power source at a handle 151252 of a surgical stapler may provide power to a frequency generator 151254. The frequency generator 151254 may generate one or more RF signals. The one or more RF signals may be multiplexed or overlaid at a multiplexer 151256, which may be in a shaft 151258 of the surgical stapler. In this way, two or more RF signals may be overlaid (or, e.g., nested or modulated together) and transmitted to the end-effector. The one or more RF signals may energize one or more RF electrodes 151260 at an end-effector 151262 (e.g., positioned in a staple cartridge) of the surgical stapler. A tissue (not shown) may be compressed and/or communicatively coupled between the one or more of RF electrodes 151260 and one or more electrical contacts. For example, the tissue may be compressed and/or communicatively coupled between the one or more RF electrodes 151260 and the electrical contact 151264 positioned in a channel frame of the end-effector 151262 or the electrical contact 151266 positioned in an anvil of the end-effector 151262. A filter 151268 may be communicatively coupled to the electrical contact 151264 and a filter 151270 may be communicatively coupled to the electrical contact 151266.

A voltage V and a current I associated with the one or more RF signals may be used to calculate an impedance Z associated with a tissue that may be compressed between the staple cartridge (and communicatively coupled to one or more RF electrodes 151260) and the channel frame or anvil (and communicatively coupled to one or more of electrical contacts 151264 or 151266).

In one aspect, various components of the tissue compression sensor system described herein may be located in a shaft 151258 of the surgical stapler. For example, as shown in circuit diagram 151250 (and in addition to the frequency generator 151254), an impedance calculator 151272, a controller 151274, a non-volatile memory 151276, and a communication channel 151278 may be located in the shaft 151258. In one example, the frequency generator 151254, impedance calculator 151272, controller 151274, non-volatile memory 151276, and communication channel 151278 may be positioned on a circuit board in the shaft 151258.

The two or more RF signals may be returned on a common path via the electrical contacts. Further, the two or more RF signals may be filtered prior to the joining of the RF signals on the common path to differentiate separate tissue impedances represented by the two or more RF signals. Current I1 and current I2 may be measured on a return path corresponding to electrical contacts 151264 and 151266. Using a voltage V applied between the supply and return paths, impedances Z1 and Z2 may be calculated. Z1 may correspond to an impedance of a tissue compressed and/or communicatively coupled between one or more of RF electrodes 151260 and electrical contact 151264. Further, Z2 may correspond to an impedance of the tissue compressed and/or communicatively coupled between one or more of RF electrodes 151260 and electrical contact 151266. Applying the formulas Z1=V/I1 and Z2=V/I2, impedances Z1 and Z2 corresponding to different compressions of a tissue compressed by an end-effector 151262 may be calculated. In example, the impedances Z1 and Z2 may be calculated by the impedance calculator 151272. The impedances Z1 and Z2 may be used to calculate various compression levels of the tissue.

Referring now to FIG. 41, a frequency graph 151290 is shown. The frequency graph 151290 shows a frequency modulation to nest two RF signals. The two RF signals may be nested before reaching RF electrodes at an end-effector as described above. For example, an RF signal with Frequency 1 and an RF signal with Frequency 2 may be nested together. Referring now to FIG. 42, the resulting nested RF signal is shown in frequency graph 151300. The compound signal shown in frequency graph 151300 includes the two RF signals of frequency graph 151290 compounded. Referring now to FIG. 43, a frequency graph 151400 is shown. Frequency graph 151400 shows the RF signals with Frequencies 1 and 2 after being filtered (by, e.g., filters 151268 and 151270). The resulting RF signals can be used to make separate impedance calculations or measurements on a return path, as described above.

In one aspect, filters 151268 and 151270 may be High Q filters such that the filter range may be narrow (e.g., Q=10). Q may be defined by the Center frequency (Wo)/Bandwidth (BW) where Q=Wo/BW. In one example, Frequency 1 may be 150 kHz and Frequency 2 may be 300 kHz. A viable impedance measurement range may be 100 kHz-20 MHz. In various examples, other sophisticated techniques, such as correlation, quadrature detection, etc., may be used to separate the RF signals.

Using one or more of the techniques and features described herein, a single energized electrode on a staple cartridge or an isolated knife of an end-effector may be used to make multiple tissue compression measurements simultaneously. If two or more RF signals are overlaid or multiplexed (or nested or modulated), they may be transmitted down a single power side of the end-effector and may return on either the channel frame or the anvil of the end-effector. If a filter were built into the anvil and channel contacts before they join a common return path, the tissue impedance represented by both paths could be differentiated. This may provide a measure of vertical tissue vs lateral tissue compression. This approach also may provide proximal and distal tissue compression depending on placement of the filters and location of the metallic return paths. A frequency generator and signal processor may be located on one or more chips on a circuit board or a sub board (which may already exist in a surgical stapler).

In one aspect, the present disclosure provides an instrument 150010 (described in connection with FIGS. 25-30) configured with various sensing systems. Accordingly, for conciseness and clarity the details of operation and construction will not be repeated here. In one aspect, the sensing system includes a viscoelasticity/rate of change sensing system to monitor knife acceleration, rate of change of impedance, and rate of change of tissue contact. In one example, the rate of change of knife acceleration can be used as a measure of for tissue type. In another example, the rate of change of impedance can be measures with a pulse sensor ad can be employed as a measure for compressibility. Finally, the rate of change of tissue contact can be measured with a sensor based on knife firing rate to measure tissue flow.

The rate of change of a sensed parameter or stated otherwise, how much time is necessary for a tissue parameter to reach an asymptotic steady state value, is a separate measurement in itself and may be more valuable than the sensed parameter it was derived from. To enhance measurement of tissue parameters such as waiting a predetermined amount of time before making a measurement, the present disclosure provides a novel technique for employing the derivate of the measure such as the rate of change of the tissue parameter.

The derivative technique or rate of change measure becomes most useful with the understanding that there is no single measurement that can be employed alone to dramatically improve staple formation. It is the combination of multiple measurements that make the measurements valid. In the case of tissue gap it is helpful to know how much of the jaw is covered with tissue to make the gap measure relevant. Rate of change measures of impedance may be combined with strain measurements in the anvil to relate force and compression applied to the tissue grasped between the jaw members of the end effector such as the anvil and the staple cartridge. The rate of change measure can be employed by the endosurgical device to determine the tissue type and not merely the tissue compression. Although stomach and lung tissue sometimes have similar thicknesses, and even similar compressive properties when the lung tissue is calcified, an instrument may be able to distinguish these tissue types by employing a combination of measurements such as gap, compression, force applied, tissue contact area, and rate of change of compression or rate of change of gap. If any of these measurements were used alone, it may be difficult for the endosurgical device to distinguish one tissue type form another. Rate of change of compression also may be helpful to enable the device to determine if the tissue is "normal" or if some abnormality exists. Measuring not only how much time has passed but the variation of the sensor signals and determining the derivative of the signal would provide another measurement to enable the endosurgical device to measure the signal. Rate of change information also may be employed in determining when a steady state has been achieved to signal the next step in a process. For example, after clamping the tissue between the jaw members of the end effector such as the anvil and the staple cartridge, when tissue compression reaches a steady state (e.g., about 15 seconds), an indicator or trigger to start firing the device can be enabled.

Also provided herein are methods, devices, and systems for time dependent evaluation of sensor data to determine stability, creep, and viscoelastic characteristics of tissue during surgical instrument operation. A surgical instrument, such as the stapler illustrated in FIG. 25, can include a variety of sensors for measuring operational parameters, such as jaw gap size or distance, firing current, tissue compression, the amount of the jaw that is covered by tissue, anvil strain, and trigger force, to name a few. These sensed measurements are important for automatic control of the surgical instrument and for providing feedback to the clinician.

The examples shown in connection with FIGS. 30-49 may be employed to measure the various derived parameters such as gap distance versus time, tissue compression versus time, and anvil strain versus time. Motor current may be monitored employing a current sensor in series with the battery 2308.

Turning now to FIG. 44, a motor-driven surgical cutting and fastening instrument 151310 is depicted that may or may not be reused. The motor-driven surgical cutting and fastening instrument 151310 is similarly constructed and equipped as the motor-driven surgical cutting and fastening instrument 150010 described in connection with FIGS. 25-30. In the example illustrated in FIG. 44, the instrument 151310 includes a housing 151312 that comprises a handle assembly 151314 that is configured to be grasped, manipulated and actuated by the clinician. The housing 151312 is configured for operable attachment to an interchangeable shaft assembly 151500 that has a surgical end effector 151600 operably coupled thereto that is configured to perform one or more surgical tasks or procedures. Since the motor-driven surgical cutting and fastening instrument 151310 is similarly constructed and equipped as the motor-driven surgical cutting and fastening instrument 150010 described in connection with FIGS. 25-30, for conciseness and clarity the details of operation and construction will not be repeated here.

The housing 151312 depicted in FIG. 44 is shown in connection with an interchangeable shaft assembly 151500 that includes an end effector 151600 that comprises a surgical cutting and fastening device that is configured to operably support a surgical staple cartridge 151304 therein. The housing 151312 may be configured for use in connection with interchangeable shaft assemblies that include end effectors that are adapted to support different sizes and types of staple cartridges, have different shaft lengths, sizes, and types, etc. In addition, the housing 151312 also may be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

FIG. 44 illustrates the surgical instrument 151310 with an interchangeable shaft assembly 151500 operably coupled thereto. In the illustrated arrangement, the handle housing forms a pistol grip portion 151319 that can be gripped and manipulated by the clinician. The handle assembly 151314 operably supports a plurality of drive systems therein that are configured to generate and apply various control motions to corresponding portions of the interchangeable shaft assembly that is operably attached thereto. Trigger 151332 is operably associated with the pistol grip for controlling various of these control motions.

With continued reference to FIG. 44, the interchangeable shaft assembly 151500 includes a surgical end effector 151600 that comprises an elongated channel 151302 that is configured to operably support a staple cartridge 151304 therein. The end effector 151600 may further include an anvil 151306 that is pivotally supported relative to the elongated channel 151302.

The inventors have discovered that derived parameters can be even more useful for controlling a surgical instrument, such as the instrument illustrated in FIG. 44, than the sensed parameter(s) upon which the derived parameter is based. Non-limiting examples of derived parameters include the rate of change of a sensed parameter (e.g., jaw gap distance) and how much time elapses before a tissue parameter reaches an asymptotic steady state value (e.g., 15 seconds). Derived parameters, such as rate of change, are particularly useful because they dramatically improve measurement accuracy and also provide information not otherwise evident directly from sensed parameters. For example, impedance (i.e., tissue compression) rate of change can be combined with strain in the anvil to relate compression and force, which enables the microcontroller to determine the tissue type and not merely the amount of tissue compression. This example is illustrative only, and any derived parameters can be combined with one or more sensed parameters to provide more accurate information about tissue types (e.g., stomach vs. lung), tissue health (calcified vs. normal), and operational status of the surgical device (e.g., clamping complete). Different tissues have unique viscoelastic properties and unique rates of change, making these and other parameters discussed herein useful indicia for monitoring and automatically adjusting a surgical procedure.

Figure 46:
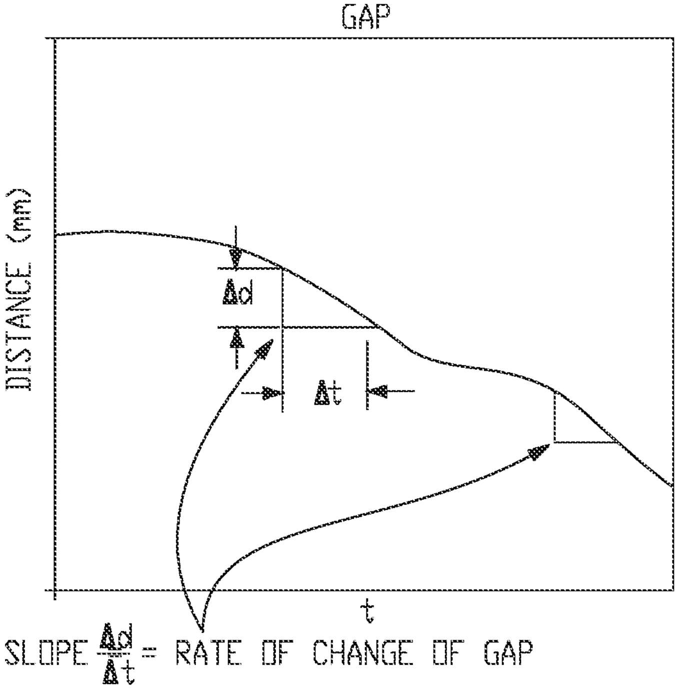

FIG. 46 is an illustrative graph showing gap distance overtime, where the gap is the space between the jaws being occupied by clamped tissue. The vertical (y) axis is distance and the horizontal (x) axis is time. Specifically, referring to FIGS. 44 and 45, the gap distance 151340 is the distance between the anvil 151306 and the elongated channel 151302 of the end effector. In the open jaw position, at time zero, the gap 151340 between the anvil 151306 and the elongated member is at its maximum distance. The width of the gap 151340 decreases as the anvil 151306 closes, such as during tissue clamping. The gap distance rate of change can vary because tissue has non-uniform resiliency. For example, certain tissue types may initially show rapid compression, resulting in a faster rate of change. However, as tissue is continually compressed, the viscoelastic properties of the tissue can cause the rate of change to decrease until the tissue cannot be compressed further, at which point the gap distance will remain substantially constant. The gap decreases over time as the tissue is squeezed between the anvil 151306 and the staple cartridge 151304 of the end effector 151340. The one or more sensors described in connection with FIGS. 31 to 43 such as, for example, a magnetic field sensor, a strain gauge, a pressure sensor, a force sensor, an inductive sensor such as, for example, an eddy current sensor, a resistive sensor, a capacitive sensor, an optical sensor, and/or any other suitable sensor, may be adapted and configured to measure the gap distance “d” between the anvil 151306 and the staple cartridge 151304 over time “t” as represented graphically in FIG. 46. The rate of change of the gap distance “d” over time “t” is the Slope of the curve shown in FIG. 46, where Slope=$\Delta d/\Delta t$.

Figure 47:
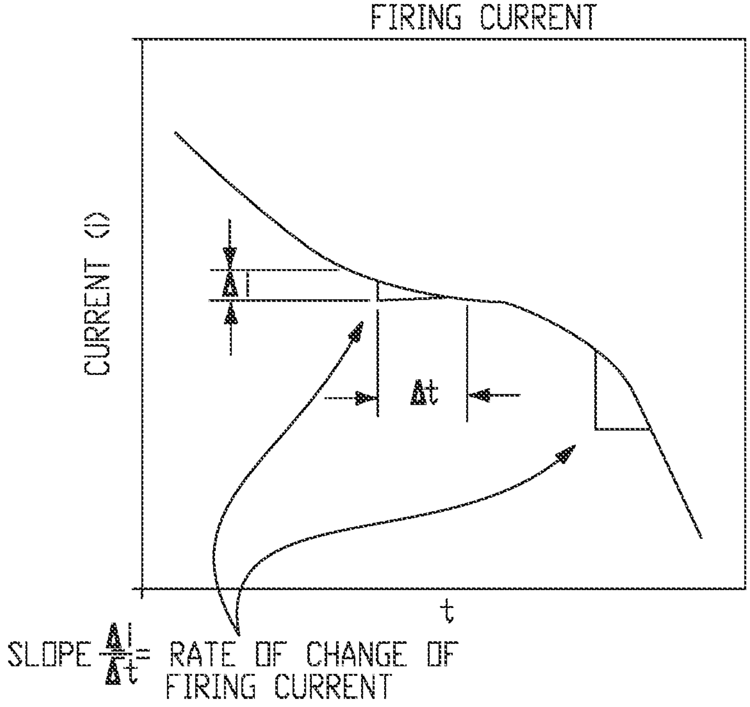

FIG. 47 is an illustrative graph showing firing current of the end effector jaws. The vertical (y) axis is current and the horizontal (x) axis is time. As discussed herein, the surgical instrument and/or the microcontroller, as shown and described in connection with FIG. 25, thereof can include a current sensor that detects the current utilized during various operations, such as clamping, cutting, and/or stapling tissue. For example, when tissue resistance increases, the instrument’s electric motor can require more current to clamp, cut, and/or staple the tissue. Similarly, if resistance is lower, the electric motor can require less current to clamp, cut, and/or staple the tissue. As a result, firing current can be used as an approximation of tissue resistance. The sensed current can be used alone or more preferably in conjunction with other measurements to provide feedback about the target tissue. Referring still to FIG. 47, during some operations, such as stapling, firing current initially is high at time zero but decreases over time. During other device operations, current may increase over time if the motor draws more current to overcome increasing mechanical load. In addition, the rate of change of firing current is can be used as an indicator that the tissue is transitioning from one state to another state. Accordingly, firing current and, in particular, the rate of change of firing current can be used to monitor device operation. The firing current decreases over time as the knife cuts through the tissue. The rate of change of firing current can vary if the tissue being cut provides more or less resistance due to tissue properties or sharpness of the knife 151305 (FIG. 45). As the cutting conditions vary, the work being done by the motor varies and hence will vary the firing current over time. A current sensor may be may be employed to measure the firing current over time while the knife 151305 is firing as represented graphically in FIG. 47. For example, the motor current may be monitored employing a current sensor. The current sensors may be adapted and configured to measure the motor firing current "i" over time "t" as represented graphically in FIG. 47. The rate of change of the firing current "i" over time "t" is the Slope of the curve shown in FIG. 47, where Slope=Δi/Δt.

FIG. 48 is an illustrative graph of impedance over time. The vertical (y) axis is impedance and the horizontal (x) axis is time. At time zero, impedance is low but increases over time as tissue pressure increases under manipulation (e.g., clamping and stapling). The rate of change varies over time as because as the tissue between the anvil 151306 and the staple cartridge 151304 of the end effector 151340 is severed by the knife or is sealed using RF energy between electrodes located between the anvil 151306 and the staple cartridge 151304 of the end effector 151340. For example, as the tissue is cut the electrical impedance increases and reaches infinity when the tissue is completely severed by the knife. Also, if the end effector 151340 includes electrodes coupled to an RF energy source, the electrical impedance of the tissue increases as energy is delivered through the tissue between the anvil 151306 and the staple cartridge 151304 of the end effector 151340. The electrical impedance increase as the energy through the tissue dries out the tissue by vaporizing moistures in the tissue. Eventually, when a suitable amount of energy is delivered to the tissue, the impedance increases to a very high value or infinity when the tissue is severed. In addition, as illustrated in FIG. 48, different tissues can have unique compression properties, such as rate of compression, that distinguish tissues. The tissue impedance can be measured by driving a sub-therapeutic RF current through the tissue grasped between the first and second jaw members 9014, 9016. One or more electrodes can be positioned on either or both the anvil 151306 and the staple cartridge 151304. The tissue compression/impedance of the tissue between the anvil 151306 and the staple cartridge 151304 can be measured over time as represented graphically in FIG. 48. The sensors described in connection with FIGS. 31 to 43 such as, for example, a magnetic field sensor, a strain gauge, a pressure sensor, a force sensor, an inductive sensor such as, for example, an eddy current sensor, a resistive sensor, a capacitive sensor, an optical sensor, and/or any other suitable sensor, may be adapted and configured to measure tissue compression/impedance. The sensors may be adapted and configured to measure tissue impedance "Z" over time "t" as represented graphically in FIG. 48.

FIG. 49 is an illustrative graph of anvil 151306 (FIGS. 44, 45) strain overtime. The vertical (y) axis is strain and the horizontal (x) axis is time. During stapling, for example, anvil 151306 strain initially is high but decreases as the tissue reaches a steady state and exerts less pressure on the anvil 151306. The rate of change of anvil 151306 strain can be measured by a pressure sensor or strain gauge positioned on either or both the anvil 151306 and the staple cartridge 151304 (FIGS. 44, 45) to measure the pressure or strain applied to the tissue grasped between the anvil 151306 and the staple cartridge 151304. The anvil 151306 strain can be measured over time as represented graphically in FIG. 49. The rate of change of strain "S" over time "t" is the Slope of the curve shown in FIG. 49, where Slope=ΔS/Δt.

FIG. 50 is an illustrative graph of trigger force over time. The vertical (y) axis is trigger force and the horizontal (x) axis is time. In certain examples, trigger force is progressive, to provide the clinician tactile feedback. Thus, at time zero, trigger 151320 (FIG. 44) pressure may be at its lowest and trigger pressure may increase until completion of an operation (e.g., clamping, cutting, or stapling). The rate of change trigger force can be measured by a pressure sensor or strain gauge positioned on the trigger 151302 of the handle 151319 of the instrument 151310 (FIG. 44) to measure the force required to drive the knife 151305 (FIG. 45) through the tissue grasped between the anvil 151306 and the staple cartridge 151304. The trigger 151332 force can be measured over time as represented graphically in FIG. 50. The rate of change of strain trigger force "F" over time "t" is the Slope of the curve shown in FIG. 50, where Slope=ΔF/Δt.

For example, stomach and lung tissue can be differentiated even though these tissue can have similar thicknesses, and can have similar compressive properties if the lung tissue is calcified. Stomach and lung tissues can be distinguished by analyzing jaw gap distance, tissue compression, force applied, tissue contact area, compression rate of change, and jaw gap rate of change. For example, FIG. 51 shows a graph of tissue pressure "P" versus tissue displacement for various tissues. The vertical (y) axis is tissue pressure and the horizontal (x) axis is tissue displacement. When tissue pressure reaches a predetermined threshold, such as 50-100 pounds per square inch (psi), the amount of tissue displacement as well as the rate of tissue displacement before reaching the threshold can be used to differentiate tissues. For instance, blood vessel tissue reaches the predetermined pressure threshold with less tissue displacement and with a faster rate of change than colon, lung, or stomach tissue. In addition, the rate of change (tissue pressure over displacement) for blood vessel tissue is nearly asymptotic at a threshold of 50-100 psi, whereas the rate of change for colon, lung, and stomach is not asymptotic at a threshold of 50-100 psi. As will be appreciated, any pressure threshold can be used such as, for example, between 1 and 1000 psi, more preferably between 10 and 500 psi, and more preferably still between 50 and 100 psi. In addition, multiple thresholds or progressive thresholds can be used to provide further resolution of tissue types that have similar viscoelastic properties.

Compression rate of change also can enable the microcontroller to determine if the tissue is "normal" or if some abnormality exists, such as calcification. For example, referring to FIG. 52, compression of calcified lung tissue follows a different curve than compression of normal lung tissue. Tissue displacement and rate of change of tissue displacement therefore can be used to diagnose and/or differentiate calcified lung tissue from normal lung tissue.

In addition, certain sensed measurements may benefit from additional sensory input. For example, in the case of jaw gap, knowing how much of the jaw is covered with tissue can make the gap measurement more useful and accurate. If a small portion of the jaw is covered in tissue, tissue compression may appear to be less than if the entire jaw is covered in tissue. Thus, the amount of jaw coverage can be taken into account by the microcontroller when analyzing tissue compression and other sensed parameters.

In certain circumstances, elapsed time also can be an important parameter. Measuring how much time has passed, together with sensed parameters, and derivative parameters (e.g., rate of change) provides further useful information. For example, if jaw gap rate of change remains constant after a set period of time (e.g., 5 seconds), then the parameter may have reached its asymptotic value.

Rate of change information also is useful in determining when a steady state has been achieved, thus signaling a next step in a process. For example, during clamping, when tissue compression reaches a steady state—e.g., no significant rate of change occurs after a set period of time—the microcontroller can send a signal to the display alerting the clinician to start the next step in the operation, such as staple firing. Alternatively, the microcontroller can be programmed to automatically start the next stage of operation (e.g., staple firing) once a steady state is reached.

Similarly, impedance rate of change can be combined with strain in the anvil to relate force and compression. The rate of change would allow the device to determine the tissue type rather than merely measure the compression value. For example, stomach and lung sometimes have similar thicknesses, and even similar compressive properties if the lung is calcified.

The combination of one or more sensed parameters with derived parameters provides more reliable and accurate assessment of tissue types and tissue health, and allows for better device monitoring, control, and clinician feedback.

FIG. 53 illustrates one embodiment of an end effector 152000 comprising a first sensor 152008*a* and a second sensor 152008*b*. The end effector 152000 is similar to the end effector 150300 described above. The end effector 152000 comprises a first jaw member, or anvil, 152002 pivotally coupled to a second jaw member 152004. The second jaw member 152004 is configured to receive a staple cartridge 152006 therein. The staple cartridge 152006 comprises a plurality of staples (not shown). The plurality of staples is deployable from the staple cartridge 152006 during a surgical operation. The end effector 152000 comprises a first sensor 152008*a*. The first sensor 152008*a* is configured to measure one or more parameters of the end effector 152000. For example, in one embodiment, the first sensor 152008*a* is configured to measure the gap 152010 between the anvil 152002 and the second jaw member 152004. The first sensor 152008*a* may comprise, for example, a Hall effect sensor configured to detect a magnetic field generated by a magnet 152012 embedded in the second jaw member 152004 and/or the staple cartridge 152006. As another example, in one embodiment, the first sensor 152008*a* is configured to measure one or more forces exerted on the anvil 152002 by the second jaw member 152004 and/or tissue clamped between the anvil 152002 and the second jaw member 152004.

The end effector 152000 comprises a second sensor 152008*b*. The second sensor 152008*b* is configured to measure one or more parameters of the end effector 152000. For example, in various embodiments, the second sensor 152008*b* may comprise a strain gauge configured to measure the magnitude of the strain in the anvil 152002 during a clamped condition. The strain gauge provides an electrical signal whose amplitude varies with the magnitude of the strain. In various embodiments, the first sensor 152008*a* and/or the second sensor 152008*b* may comprise, for example, a magnetic sensor such as, for example, a Hall effect sensor, a strain gauge, a pressure sensor, a force sensor, an inductive sensor such as, for example, an eddy current sensor, a resistive sensor, a capacitive sensor, an optical sensor, and/or any other suitable sensor for measuring one or more parameters of the end effector 152000. The first sensor 152008*a* and the second sensor 152008*b* may be arranged in a series configuration and/or a parallel configuration. In a series configuration, the second sensor 152008*b* may be configured to directly affect the output of the first sensor 152008*a*. In a parallel configuration, the second sensor 152008*b* may be configured to indirectly affect the output of the first sensor 152008*a*.

In one embodiment, the one or more parameters measured by the first sensor 152008*a* are related to the one or more parameters measured by the second sensor 152008*b*. For example, in one embodiment, the first sensor 152008*a* is configured to measure the gap 152010 between the anvil 152002 and the second jaw member 152004. The gap 152010 is representative of the thickness and/or compressibility of a tissue section clamped between the anvil 152002 and the staple cartridge 152006. The first sensor 152008*a* may comprise, for example, a Hall effect sensor configured to detect a magnetic field generated by the magnet 152012 coupled to the second jaw member 152004 and/or the staple cartridge 152006. Measuring at a single location accurately describes the compressed tissue thickness for a calibrated full bit of tissue, but may provide inaccurate results when a partial bite of tissue is placed between the anvil 152002 and the second jaw member 152004. A partial bite of tissue, either a proximal partial bite or a distal partial bite, changes the clamping geometry of the anvil 152002.

In some embodiments, the second sensor 152008*b* is configured to detect one or more parameters indicative of a type of tissue bite, for example, a full bite, a partial proximal bite, and/or a partial distal bite. The measurement of the second sensor 152008*b* may be used to adjust the measurement of the first sensor 152008*a* to accurately represent a proximal or distal positioned partial bite's true compressed tissue thickness. For example, in one embodiment, the second sensor 152008*b* comprises a strain gauge, such as, for example, a micro-strain gauge, configured to monitor the amplitude of the strain in the anvil during a clamped condition. The amplitude of the strain of the anvil 152002 is used to modify the output of the first sensor 152008*a*, for example, a Hall effect sensor, to accurately represent a proximal or distal positioned partial bite's true compressed tissue thickness. The first sensor 152008*a* and the second sensor 152008*b* may be measured in real-time during a clamping operation. Real-time measurement allows time based information to be analyzed, for example, by a primary processor (e.g., processor 462 (FIG. 12), for example), and used to select one or more algorithms and/or look-up tables to recognize tissue characteristics and clamping positioning to dynamically adjust tissue thickness measurements.

In some embodiments, the thickness measurement of the first sensor 152008*a* may be provided to an output device of a surgical instrument 150010 coupled to the end effector 152000. For example, in one embodiment, the end effector 152000 is coupled to the surgical instrument 150010 comprising a display (e.g., display 473 (FIG. 12), for example). The measurement of the first sensor 152008*a* is provided to a processor, for example, the primary processor. The primary processor adjusts the measurement of the first sensor 152008*a* based on the measurement of the second sensor 152008*b* to reflect the true tissue thickness of a tissue section clamped between the anvil 152002 and the staple cartridge 152006. The primary processor outputs the adjusted tissue thickness measurement and an indication of full or partial bite to the display. An operator may determine whether or not to deploy the staples in the staple cartridge 152006 based on the displayed values.

In some embodiments, the first sensor 152008*a* and the second sensor 152008*b* may be located in different environments, such as, for example, the first sensor 152008*a* being located within a patient at a treatment site and the second sensor 152008*b* being located externally to the patient. The second sensor 152008*b* may be configured to calibrate and/or modify the output of the first sensor 152008*a*. The first sensor 152008*a* and/or the second sensor 152008*b* may comprise, for example, an environmental sensor. Environmental sensors may comprise, for example, temperature sensors, humidity sensors, pressure sensors, and/or any other suitable environmental sensor.

FIG. 54 is a logic diagram illustrating one embodiment of a process 152020 for adjusting the measurement of a first sensor 152008*a* based on input from a second sensor 152008*b*. A first signal 152022*a* is captured by the first sensor 152008*a*. The first signal 152022*a* may be conditioned based on one or more predetermined parameters, such as, for example, a smoothing function, a look-up table, and/or any other suitable conditioning parameters. A second signal 152022*b* is captured by the second sensor 152008*b*. The second signal 152022*b* may be conditioned based on one or more predetermined conditioning parameters. The first signal 152022*a* and the second signal 152022*b* are provided to a processor, such as, for example, the primary processor. The processor adjusts the measurement of the first sensor 152008*a*, as represented by the first signal 152022*a*, based on the second signal 152022*b* from the second sensor. For example, in one embodiment, the first sensor 152008*a* comprises a Hall effect sensor and the second sensor 152008*b* comprises a strain gauge. The distance measurement of the first sensor 152008*a* is adjusted by the amplitude of the strain measured by the second sensor 152008*b* to determine the fullness of the bite of tissue in the end effector 152000. The adjusted measurement is displayed 152026 to an operator by, for example, a display embedded in the surgical instrument 150010.

FIG. 55 is a logic diagram illustrating one embodiment of a process 152030 for determining a look-up table for a first sensor 152008*a* based on the input from a second sensor 152008*b*. The first sensor 152008*a* captures a signal 152022*a* indicative of one or more parameters of the end effector 152000. The first signal 152022*a* may be conditioned based on one or more predetermined parameters, such as, for example, a smoothing function, a look-up table, and/or any other suitable conditioning parameters. A second signal 152022*b* is captured by the second sensor 152008*b*. The second signal 152022*b* may be conditioned based on one or more predetermined conditioning parameters. The first signal 152022*a* and the second signal 152022*b* are provided to a processor, such as, for example, the primary processor. The processor selects a look-up table from one or more available look-up tables 152034*a*, 152034*b* based on the value of the second signal. The selected look-up table is used to convert the first signal into a thickness measurement of the tissue located between the anvil 152002 and the staple cartridge 152006. The adjusted measurement is displayed 152026 to an operator by, for example, a display embedded in the surgical instrument 150010.

FIG. 56 is a logic diagram illustrating one embodiment of a process 152040 for calibrating a first sensor 152008*a* in response to an input from a second sensor 152008*b*. The first sensor 152008*a* is configured to capture a signal 152022*a* indicative of one or more parameters of the end effector 152000. The first signal 152022*a* may be conditioned based on one or more predetermined parameters, such as, for example, a smoothing function, a look-up table, and/or any other suitable conditioning parameters. A second signal 152022*b* is captured by the second sensor 152008*b*. The second signal 152022*b* may be conditioned based on one or more predetermined conditioning parameters. The first signal 152022*a* and the second signal 152022*b* are provided to a processor, such as, for example, the primary processor. The primary processor calibrates 152042 the first signal 152022*a* in response to the second signal 152022*b*. The first signal 152022*a* is calibrated 152042 to reflect the fullness of the bite of tissue in the end effector 152000. The calibrated signal is displayed 152026 to an operator by, for example, a display embedded in the surgical instrument 150010.

FIG. 57 is a logic diagram illustrating one embodiment of a process 152050 for determining and displaying the thickness of a tissue section clamped between the anvil 152002 and the staple cartridge 152006 of the end effector 152000. The process 152050 comprises obtaining a Hall effect voltage 152052, for example, through a Hall effect sensor located at the distal tip of the anvil 152002. The Hall effect voltage 152052 is provided to an analog to digital convertor 152054 and converted into a digital signal. The digital signal is provided to a processor, such as, for example, the primary processor. The primary processor calibrates 152056 the curve input of the Hall effect voltage 152052 signal. A strain gauge 152058, such as, for example, a micro-strain gauge, is configured to measure one or more parameters of the end effector 152000, such as, for example, the amplitude of the strain exerted on the anvil 152002 during a clamping operation. The measured strain is converted 152060 to a digital signal and provided to the processor, such as, for example, the primary processor. The primary processor uses one or more algorithms and/or lookup tables to adjust the Hall effect voltage 152052 in response to the strain measured by the strain gauge 152058 to reflect the true thickness and fullness of the bite of tissue clamped by the anvil 152002 and the staple cartridge 152006. The adjusted thickness is displayed 152026 to an operator by, for example, a display embedded in the surgical instrument 150010.

In some embodiments, the surgical instrument can further comprise a load cell or sensor 152082. The load sensor 152082 can be located, for instance, in the shaft assembly 150200, described above, or in the housing 150012, also described above. FIG. 58 is a logic diagram illustrating one embodiment of a process 152070 for determining and displaying the thickness of a tissue section clamped between the anvil 152002 and the staple cartridge 152006 of the end effector 152000. The process comprises obtaining a Hall effect voltage 152072, for example, through a Hall effect sensor located at the distal tip of the anvil 152002. The Hall effect voltage 152072 is provided to an analog to digital convertor 152074 and converted into a digital signal. The digital signal is provided to a processor, such as, for example, the primary processor. The primary processor calibrates 152076 the curve input of the Hall effect voltage 152072 signal. A strain gauge 152078, such as, for example, a micro-strain gauge, is configured to measure one or more parameters of the end effector 152000, such as, for example, the amplitude of the strain exerted on the anvil 152002 during a clamping operation. The measured strain is converted 152080 to a digital signal and provided to the processor, such as, for example, the primary processor. The load sensor 152082 measures the clamping force of the anvil 152002 against the staple cartridge 152006. The measured clamping force is converted 152084 to a digital signal and provided to the processor, such as for example, the primary processor. The primary processor uses one or more algorithms and/or lookup tables to adjust the Hall effect voltage 152072 in response to the strain measured by the strain gauge 152078 and the clamping force measured by the load sensor 152082 to reflect the true thickness and fullness of the bite of tissue clamped by the anvil 152002 and the staple cartridge 152006. The adjusted thickness is displayed 152026 to an operator by, for example, a display embedded in the surgical instrument 150010.

FIG. 59 is a graph 152090 illustrating an adjusted Hall effect thickness measurement 152092 compared to an unmodified Hall effect thickness measurement 152094. As shown in FIG. 59, the unmodified Hall effect thickness measurement 152094 indicates a thicker tissue measurement, as the single sensor is unable to compensate for partial distal/proximal bites that result in incorrect thickness measurements. The adjusted thickness measurement 152092 is generated by, for example, the process 152050 illustrated in FIG. 57. The adjusted Hall effect thickness measurement 152092 is calibrated based on input from one or more additional sensors, such as, for example, a strain gauge. The adjusted Hall effect thickness 152092 reflects the true thickness of the tissue located between an anvil 152002 and a staple cartridge 152006.

FIG. 60 illustrates one embodiment of an end effector 152100 comprising a first sensor **152108*a* and a second sensor 152108*b*. The end effector 152100 is similar to the end effector 152000 illustrated in FIG. 53. The end effector 152100 comprises a first jaw member, or anvil, 152102 pivotally coupled to a second jaw member 152104. The second jaw member 152104 is configured to receive a staple cartridge 152106 therein. The end effector 152100 comprises a first sensor 152108*a* coupled to the anvil 152102. The first sensor 152108*a* is configured to measure one or more parameters of the end effector 152100, such as, for example, the gap 152110 between the anvil 152102 and the staple cartridge 152106. The gap 152110 may correspond to, for example, a thickness of tissue clamped between the anvil 152102 and the staple cartridge 152106. The first sensor 152108*a* may comprise any suitable sensor for measuring one or more parameters of the end effector. For example, in various embodiments, the first sensor 152108*a*** may comprise a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

In some embodiments, the end effector 152100 comprises a second sensor **152108*b*. The second sensor 152108*b* is coupled to second jaw member 152104 and/or the staple cartridge 152106. The second sensor 152108*b* is configured to detect one or more parameters of the end effector 152100. For example, in some embodiments, the second sensor 152108*b* is configured to detect one or more instrument conditions such as, for example, a color of the staple cartridge 152106 coupled to the second jaw member 152104, a length of the staple cartridge 152106, a clamping condition of the end effector 152100, the number of uses/number of remaining uses of the end effector 152100 and/or the staple cartridge 152106, and/or any other suitable instrument condition. The second sensor 152108*b*** may comprise any suitable sensor for detecting one or more instrument conditions, such as, for example, a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

The end effector 152100 may be used in conjunction with any of the processes shown in FIGS. 54 to 57. For example, in one embodiment, input from the second sensor **152108*b* may be used to calibrate the input of the first sensor 152108*a*. The second sensor 152108*b* may be configured to detect one or more parameters of the staple cartridge 152106, such as, for example, the color and/or length of the staple cartridge 152106. The detected parameters, such as the color and/or the length of the staple cartridge 152106, may correspond to one or more properties of the cartridge, such as, for example, the height of the cartridge deck, the thickness of tissue useable/optimal for the staple cartridge, and/or the pattern of the staples in the staple cartridge 152106. The known parameters of the staple cartridge 152106 may be used to adjust the thickness measurement provided by the first sensor 152108*a*. For example, if the staple cartridge 152106 has a higher deck height, the thickness measurement provided by the first sensor 152108*a* may be reduced to compensate for the added deck height. The adjusted thickness may be displayed to an operator, for example, through a display coupled to the surgical instrument 150010**.

FIG. 61 illustrates one embodiment of an end effector 152150 comprising a first sensor 152158 and a plurality of second sensors **152160*a*, 152160*b*. The end effector 152150 comprises a first jaw member, or anvil, 152152 and a second jaw member 152154. The second jaw member 152154 is configured to receive a staple cartridge 152156. The anvil 152152 is pivotally moveable with respect to the second jaw member 152154 to clamp tissue between the anvil 152152 and the staple cartridge 152156. The anvil comprises a first sensor 152158. The first sensor 152158 is configured to detect one or more parameters of the end effector 152150, such as, for example, the gap 152110 between the anvil 152152 and the staple cartridge 152156. The gap 152110 may correspond to, for example, a thickness of tissue clamped between the anvil 152152 and the staple cartridge 152156. The first sensor 152158 may comprise any suitable sensor for measuring one or more parameters of the end effector. For example, in various embodiments, the first sensor 152158** may comprise a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

In some embodiments, the end effector 152150 comprises a plurality of secondary sensors **152160*a*, 152160*b*. The secondary sensors 152160*a*, 152160*b* are configured to detect one or more parameters of the end effector 152150. For example, in some embodiments, the secondary sensors 152160*a*, 152160*b* are configured to measure an amplitude of strain exerted on the anvil 152152 during a clamping procedure. In various embodiments, the secondary sensors 152160*a*, 152160*b* may comprise a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor. The secondary sensors 152160*a*, 152160*b* may be configured to measure one or more identical parameters at different locations of the anvil 152152, different parameters at identical locations on the anvil 152152, and/or different parameters at different locations on the anvil 152152**.

FIG. 62 is a logic diagram illustrating one embodiment of a process 152170 for adjusting a measurement of a first sensor 152158 in response to a plurality of secondary sensors **152160*a*, 152160*b*. In one embodiment, a Hall effect voltage is obtained 152172, for example, by a Hall effect sensor. The Hall effect voltage is converted 152174 by an analog to digital convertor. The converted Hall effect voltage signal is calibrated 152176. The calibrated curve represents the thickness of a tissue section located between the anvil 152152 and the staple cartridge 152156. A plurality of secondary measurements are obtained 152178***a*, 152178*b* by a plurality of secondary sensors, such as, for example, a plurality of strain gauges. The input of the strain gauges is converted 152180*a*, 152180*b* into one or more digital signals, for example, by a plurality of electronic μStrain conversion circuits. The calibrated Hall effect voltage and the plurality of secondary measurements are provided to a processor, such as, for example, the primary processor. The primary processor utilizes the secondary measurements to adjust 152182 the Hall effect voltage, for example, by applying an algorithm and/or utilizing one or more look-up tables. The adjusted Hall effect voltage represents the true thickness and fullness of the bite of tissue clamped by the anvil 152152 and the staple cartridge 152156. The adjusted thickness is displayed 152026 to an operator by, for example, a display embedded in the surgical instrument 150010.

FIG. 63 illustrates one embodiment of a circuit 152190 configured to convert signals from the first sensor 152158 and the plurality of secondary sensors 152160*a*, 152160*b* into digital signals receivable by a processor, such as, for example, the primary processor. The circuit 152190 comprises an analog-to-digital convertor 152194. In some embodiments, the analog-to-digital convertor 152194 comprises a 4-channel, 18-bit analog to digital convertor. Those skilled in the art will recognize that the analog-to-digital convertor 152194 may comprise any suitable number of channels and/or bits to convert one or more inputs from analog to digital signals. The circuit 152190 comprises one or more level shifting resistors 152196 configured to receive an input from the first sensor 152158, such as, for example, a Hall effect sensor. The level shifting resistors 152196 adjust the input from the first sensor, shifting the value to a higher or lower voltage depending on the input. The level shifting resistors 152196 provide the level-shifted input from the first sensor 152158 to the analog-to-digital convertor.

In some embodiments, a plurality of secondary sensors 152160*a*, 152160*b* are coupled to a plurality of bridges 152192*a*, 152192*b* within the circuit 152190. The plurality of bridges 152192*a*, 152192*b* may provide filtering of the input from the plurality of secondary sensors 152160*a*, 152160*b*. After filtering the input signals, the plurality of bridges 152192*a*, 152192*b* provide the inputs from the plurality of secondary sensors 152160*a*, 152160*b* to the analog-to-digital convertor 152194. In some embodiments, a switch 152198 coupled to one or more level shifting resistors may be coupled to the analog-to-digital convertor 152194. The switch 152198 is configured to calibrate one or more of the input signals, such as, for example, an input from a Hall effect sensor. The switch 152198 may be engaged to provide one or more level shifting signals to adjust the input of one or more of the sensors, such as, for example, to calibrate the input of a Hall effect sensor. In some embodiments, the adjustment is not necessary, and the switch 152198 is left in the open position to decouple the level shifting resistors. The switch 152198 is coupled to the analog-to-digital convertor 152194. The analog-to-digital convertor 152194 provides an output to one or more processors, such as, for example, the primary processor. The primary processor calculates one or more parameters of the end effector 152150 based on the input from the analog-to-digital convertor 152194. For example, in one embodiment, the primary processor calculates a thickness of tissue located between the anvil 152152 and the staple cartridge 152156 based on input from one or more sensors 152158, 152160*a*, 152160*b*.

FIG. 64 illustrates one embodiment of an end effector 152200 comprising a plurality of sensors 152208*a*-152208*d*. The end effector 152200 comprises an anvil 152202 pivotally coupled to a second jaw member 152204. The second jaw member 152204 is configured to receive a staple cartridge 152206 therein. The anvil 152202 comprises a plurality of sensors 152208*a*-152208*d* thereon. The plurality of sensors 152208*a*-152208*d* is configured to detect one or more parameters of the end effector 152200, such as, for example, the anvil 152202. The plurality of sensors 152208*a*-152208*d* may comprise one or more identical sensors and/or different sensors. The plurality of sensors 152208*a*-152208*d* may comprise, for example, magnetic sensors, such as a Hall effect sensor, strain gauges, pressure sensors, inductive sensors, such as an eddy current sensor, resistive sensors, capacitive sensors, optical sensors, and/or any other suitable sensors or combination thereof. For example, in one embodiment, the plurality of sensors 152208*a*-152208*d* may comprise a plurality of strain gauges.

In one embodiment, the plurality of sensors 152208*a*-152208*d* allows a robust tissue thickness sensing process to be implemented. By detecting various parameters along the length of the anvil 152202, the plurality of sensors 152208*a*-152208*d* allow a surgical instrument, such as, for example, the surgical instrument 150010, to calculate the tissue thickness in the jaws regardless of the bite, for example, a partial or full bite. In some embodiments, the plurality of sensors 152208*a*-152208*d* comprises a plurality of strain gauges. The plurality of strain gauges is configured to measure the strain at various points on the anvil 152202. The amplitude and/or the slope of the strain at each of the various points on the anvil 152202 can be used to determine the thickness of tissue in between the anvil 152202 and the staple cartridge 152206. The plurality of strain gauges may be configured to optimize maximum amplitude and/or slope differences based on clamping dynamics to determine thickness, tissue placement, and/or material properties of the tissue. Time based monitoring of the plurality of sensors 152208*a*-152208*d* during clamping allows a processor, such as, for example, the primary processor, to utilize algorithms and look-up tables to recognize tissue characteristics and clamping positions and dynamically adjust the end effector 152200 and/or tissue clamped between the anvil 152202 and the staple cartridge 152206.

FIG. 65 is a logic diagram illustrating one embodiment of a process 152220 for determining one or more tissue properties based on a plurality of sensors 152208*a*-152208*d*. In one embodiment, a plurality of sensors 152208*a*-152208*d* generate 152222*a*-152222*d* a plurality of signals indicative of one or more parameters of the end effector 152200. The plurality of generated signals is converted 152224*a*-152224*d* to digital signals and provided to a processor. For example, in one embodiment comprising a plurality of strain gauges, a plurality of electronic μStrain (micro-strain) conversion circuits convert 152224*a*-152224*d* the strain gauge signals to digital signals. The digital signals are provided to a processor, such as, for example, the primary processor. The primary processor determines 152226 one or more tissue characteristics based on the plurality of signals. The processor may determine the one or more tissue characteristics by applying an algorithm and/or a look-up table. The one or more tissue characteristics are displayed 152026 to an operator, for example, by a display embedded in the surgical instrument 150010.

FIG. 66 illustrates one embodiment of an end effector 152250 comprising a plurality of sensors **152260*a*-152260*d* coupled to a second jaw member 3254. The end effector 152250 comprises an anvil 152252 pivotally coupled to a second jaw member 152254. The anvil 152252 is moveable relative to the second jaw member 152254 to clamp one or more materials, such as, for example, a tissue section 152264, therebetween. The second jaw member 152254 is configured to receive a staple cartridge 152256. A first sensor 152258 is coupled to the anvil 152252. The first sensor is configured to detect one or more parameters of the end effector 152150, such as, for example, the gap 152110 between the anvil 152252 and the staple cartridge 152256. The gap 152110 may correspond to, for example, a thickness of tissue clamped between the anvil 152252 and the staple cartridge 152256. The first sensor 152258 may comprise any suitable sensor for measuring one or more parameters of the end effector. For example, in various embodiments, the first sensor 152258** may comprise a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

A plurality of secondary sensors **152260*a*-152260*d* is coupled to the second jaw member 152254. The plurality of secondary sensors 152260*a*-152260*d* may be formed integrally with the second jaw member 152254 and/or the staple cartridge 152256. For example, in one embodiment, the plurality of secondary sensors 152260*a*-152260*d* is disposed on an outer row of the staple cartridge 152256 (see FIG. 67). The plurality of secondary sensors 152260*a*-152260*d* are configured to detect one or more parameters of the end effector 152250 and/or a tissue section 152264 clamped between the anvil 152252 and the staple cartridge 152256. The plurality of secondary sensors 152260*a*-152260*d* may comprise any suitable sensors for detecting one or more parameters of the end effector 152250 and/or the tissue section 152264, such as, for example, magnetic sensors, such as a Hall effect sensor, strain gauges, pressure sensors, inductive sensors, such as an eddy current sensor, resistive sensors, capacitive sensors, optical sensors, and/or any other suitable sensors or combination thereof. The plurality of secondary sensors 152260*a*-152260*d*** may comprise identical sensors and/or different sensors.

In some embodiments, the plurality of secondary sensors **152260*a*-152260*d* comprises dual purpose sensors and tissue stabilizing elements. The plurality of secondary sensors 152260*a*-152260*d* comprise electrodes and/or sensing geometries configured to create a stabilized tissue condition when the plurality of secondary sensors 152260*a*-152260*d* are engaged with a tissue section 152264, such as, for example, during a clamping operation. In some embodiments, one or more of the plurality of secondary sensors 152260*a*-152260*d* may be replaced with non-sensing tissue stabilizing elements. The secondary sensors 152260*a*-152260*d*** create a stabilized tissue condition by controlling tissue flow, staple formation, and/or other tissue conditions during a clamping, stapling, and/or other treatment process.

FIG. 67 illustrates one embodiment of a staple cartridge 152270 comprising a plurality of sensors **152272*a*-152272*h* formed integrally therein. The staple cartridge 152270 comprises a plurality of rows containing a plurality of holes for storing staples therein. One or more of the holes in the outer row 152278 are replaced with one of the plurality of sensors 152272*a*-152272*h*. A cut-away section is shown to illustrate a sensor 152272*f* coupled to a sensor wire 152276*b*. The sensor wires 152276*a*, 152276*b* may comprise a plurality of wires for coupling the plurality of sensors 152272*a*-152272*h* to one or more circuits of a surgical instrument, such as, for example, the surgical instrument 150010. In some embodiments, one or more of the plurality of sensors 152272*a*-152272*h* comprise dual purpose sensor and tissue stabilizing elements having electrodes and/or sensing geometries configured to provide tissue stabilization. In some embodiments, the plurality of sensors 152272*a*-152272*h* may be replaced with and/or co-populated with a plurality of tissue stabilizing elements. Tissue stabilization may be provided by, for example, controlling tissue flow and/or staple formation during a clamping and/or stapling process. The plurality of sensors 152272*a*-152272*h* provide signals to one or more circuits of the surgical instrument 150010** to enhance feedback of stapling performance and/or tissue thickness sensing.

FIG. 68 is a logic diagram illustrating one embodiment of a process 152280 for determining one or more parameters of a tissue section 152264 clamped within an end effector, such as, for example, the end effector 152250 illustrated in FIG. 66. In one embodiment, a first sensor 152258 is configured to detect one or more parameters of the end effector 152250 and/or a tissue section 152264 located between the anvil 152252 and the staple cartridge 152256. A first signal is generated 152282 by the first sensors 152258. The first signal is indicative of the one or more parameters detected by the first sensor 152258. One or more secondary sensors 152260 are configured to detect one or more parameters of the end effector 152250 and/or the tissue section 152264. The secondary sensors 152260 may be configured to detect the same parameters, additional parameters, or different parameters as the first sensor 152258. Secondary signals 152284 are generated by the secondary sensors 152260. The secondary signals 152284 are indicative of the one or more parameters detected by the secondary sensors 152260. The first signal and the secondary signals are provided to a processor, such as, for example, the primary processor. The processor adjusts 152286 the first signal generated by the first sensor 152258 based on input generated by the secondary sensors 152260. The adjusted signal may be indicative of, for example, the true thickness of a tissue section 152264 and the fullness of the bite. The adjusted signal is displayed 152026 to an operator by, for example, a display embedded in the surgical instrument 150010.

FIG. 69 illustrates one embodiment of an end effector 152300 comprising a plurality of redundant sensors **152308*a*, 152308*b*. The end effector 152300 comprises a first jaw member, or anvil, 152302 pivotally coupled to a second jaw member 152304. The second jaw member 152304 is configured to receive a staple cartridge 152306 therein. The anvil 152302 is moveable with respect to the staple cartridge 152306 to grasp a material, such as, for example, a tissue section, between the anvil 152302 and the staple cartridge 152306. A plurality of sensors 152308*a*, 152308*b* is coupled to the anvil. The plurality of sensors 152308*a*, 152308*b* are configured to detect one or more parameters of the end effector 152300 and/or a tissue section located between the anvil 152302 and the staple cartridge 152306. In some embodiments, the plurality of sensors 152308*a*, 152308*b* are configured to detect a gap 152310 between the anvil 152302 and the staple cartridge 152306. The gap 152310 may correspond to, for example, the thickness of tissue located between the anvil 152302 and the staple cartridge 152306. The plurality of sensors 152308***a*, 152308*b* may detect the gap 152310 by, for example, detecting a magnetic field generated by a magnet 152312 coupled to the second jaw member 152304.

In some embodiments, the plurality of sensors 152308*a*, 152308*b* comprise redundant sensors. The redundant sensors are configured to detect the same properties of the end effector 152300 and/or a tissue section located between the anvil 152302 and the staple cartridge 152306. The redundant sensors may comprise, for example, Hall effect sensors configured to detect the gap 152310 between the anvil 152302 and the staple cartridge 152306. The redundant sensors provide signals representative of one or more parameters allowing a processor, such as, for example, the primary processor, to evaluate the multiple inputs and determine the most reliable input. In some embodiments, the redundant sensors are used to reduce noise, false signals, and/or drift. Each of the redundant sensors may be measured in real-time during clamping, allowing time-based information to be analyzed and algorithms and/or look-up tables to recognize tissue characteristics and clamping positioning dynamically. The input of one or more of the redundant sensors may be adjusted and/or selected to identify the true tissue thickness and bite of a tissue section located between the anvil 152302 and the staple cartridge 152306.

FIG. 70 is a logic diagram illustrating one embodiment of a process 152320 for selecting the most reliable output from a plurality of redundant sensors, such as, for example, the plurality of sensors 152308*a*, 152308*b* illustrated in FIG. 69. In one embodiment, a first signal is generated by a first sensor 152308*a*. The first signal is converted 152322*a* by an analog-to-digital convertor. One or more additional signals are generated by one or more redundant sensors 152308*b*. The one or more additional signals are converted 152322*b* by an analog-to-digital convertor. The converted signals are provided to a processor, such as, for example, the primary processor. The primary processor evaluates 152324 the redundant inputs to determine the most reliable output. The most reliable output may be selected based on one or more parameters, such as, for example, algorithms, look-up tables, input from additional sensors, and/or instrument conditions. After selecting the most reliable output, the processor may adjust the output based on one or more additional sensors to reflect, for example, the true thickness and bite of a tissue section located between the anvil 152302 and the staple cartridge 152306. The adjusted most reliable output is displayed 152026 to an operator by, for example, a display embedded in the surgical instrument 150010.

FIG. 71 illustrates one embodiment of an end effector 152350 comprising a sensor 152358 comprising a specific sampling rate to limit or eliminate false signals. The end effector 152350 comprises a first jaw member, or anvil, 152352 pivotably coupled to a second jaw member 152354. The second jaw member 152354 is configured to receive a staple cartridge 152356 therein. The staple cartridge 152356 contains a plurality of staples that may be delivered to a tissue section located between the anvil 152352 and the staple cartridge 152356. A sensor 152358 is coupled to the anvil 152352. The sensor 152358 is configured to detect one or more parameters of the end effector 152350, such as, for example, the gap 152364 between the anvil 152352 and the staple cartridge 152356. The gap 152364 may correspond to the thickness of a material, such as, for example, a tissue section, and/or the fullness of a bite of material located between the anvil 152352 and the staple cartridge 152356. The sensor 152358 may comprise any suitable sensor for detecting one or more parameters of the end effector 152350, such as, for example, a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

In one embodiment, the sensor 152358 comprises a magnetic sensor configured to detect a magnetic field generated by an electromagnetic source 152360 coupled to the second jaw member 152354 and/or the staple cartridge 152356. The electromagnetic source 152360 generates a magnetic field detected by the sensor 152358. The strength of the detected magnetic field may correspond to, for example, the thickness and/or fullness of a bite of tissue located between the anvil 152352 and the staple cartridge 152356. In some embodiments, the electromagnetic source 152360 generates a signal at a known frequency, such as, for example, 1 MHz. In other embodiments, the signal generated by the electromagnetic source 152360 may be adjustable based on, for example, the type of staple cartridge 152356 installed in the second jaw member 152354, one or more additional sensor, an algorithm, and/or one or more parameters.

In one embodiment, a signal processor 152362 is coupled to the end effector 152350, such as, for example, the anvil 152352. The signal processor 152362 is configured to process the signal generated by the sensor 152358 to eliminate false signals and to boost the input from the sensor 152358. In some embodiments, the signal processor 152362 may be located separately from the end effector 152350, such as, for example, in the handle 150014 of the surgical instrument 150010. In some embodiments, the signal processor 152362 is formed integrally with and/or comprises an algorithm executed by a general processor, such as, for example, the primary processor. The signal processor 152362 is configured to process the signal from the sensor 152358 at a frequency substantially equal to the frequency of the signal generated by the electromagnetic source 152360. For example, in one embodiment, the electromagnetic source 152360 generates a signal at a frequency of 1 MHz. The signal is detected by the sensor 152358. The sensor 152358 generates a signal indicative of the detected magnetic field which is provided to the signal processor 152362. The signal is processed by the signal processor 152362 at a frequency of 1 MHz to eliminate false signals. The processed signal is provided to a processor, such as, for example, the primary processor. The primary processor correlates the received signal to one or more parameters of the end effector 152350, such as, for example, the gap 152364 between the anvil 152352 and the staple cartridge 152356.

FIG. 72 is a logic diagram illustrating one embodiment of a process 152370 for generating a thickness measurement for a tissue section located between an anvil and a staple cartridge of an end effector, such as, for example, the end effector 152350 illustrated in FIG. 71. In one embodiment of the process 152370, a signal is generated 152372 by a modulated electromagnetic source 152360. The generated signal may comprise, for example, a 1 MHz signal. A magnetic sensor 152358 is configured to detect 152374 the signal generated by the electromagnetic source 152360. The magnetic sensor 152358 generates a signal indicative of the detected magnetic field and provides the signal to a signal processor 152362. The signal processor 152362 processes 152376 the signal to remove noise, false signals, and/or to boost the signal. The processed signal is provided to an analog-to-digital convertor for conversion 152378 to a digital signal. The digital signal may be calibrated 152380, for example, by application of a calibration curve input algorithm and/or look-up table. The signal processing 152376, conversion 152378, and calibration 152380 may be performed by one or more circuits. The calibrated signal is displayed 152026 to a user by, for example, a display formed integrally with the surgical instrument 150010.

FIGS. 73 and 74 illustrate one embodiment of an end effector 152400 comprising a sensor 152408 for identifying staple cartridges 152406 of different types. The end effector 152400 comprises a first jaw member or anvil 152402, pivotally coupled to a second jaw member or elongated channel 152404. The elongated channel 152404 is configured to operably support a staple cartridge 152406 therein. The end effector 152400 further comprises a sensor 152408 located in the proximal area. The sensor 152408 can be any of an optical sensor, a magnetic sensor, an electrical sensor, or any other suitable sensor.

The sensor 152408 can be operable to detect a property of the staple cartridge 152406 and thereby identify the staple cartridge 152406 type. FIG. 74 illustrates an example where the sensor 152408 is an optical emitter and detector 152410. The body of the staple cartridge 152406 can be different colors, such that the color identifies the staple cartridge 152406 type. An optical emitter and detector 152410 can be operable to interrogate the color of the staple cartridge 152406 body. In the illustrated example, the optical emitter and detector 152410 can detect white 152412 by receiving reflected light in the red, green, and blue spectrums in equal intensity. The optical emitter and detector 152410 can detect red 152414 by receiving very little reflected light in the green and blue spectrums while receiving light in the red spectrum in greater intensity.

Alternately or additionally, the optical emitter and detector 152410, or another suitable sensor 152408, can interrogate and identify some other symbol or marking on the staple cartridge 152406. The symbol or marking can be any one of a barcode, a shape or character, a color-coded emblem, or any other suitable marking. The information read by the sensor 152408 can be communicated to a microcontroller in the surgical device 150010, such as for instance a microcontroller (e.g., microcontroller 461 (FIG. 12), for example). The microcontroller can be configured to communicate information about the staple cartridge 152406 to the operator of the instrument. For instance, the identified staple cartridge 152406 may not be appropriate for a given application; in such case, the operator of the instrument can be informed, and/or a function of the instrument s inappropriate. In such instance, the microcontroller can optionally be configured to disable a function of surgical instrument can be disabled. Alternatively or additionally, the microcontroller can be configured to inform the operator of the surgical instrument 150010 of the parameters of the identified staple cartridge 152406 type, such as for instance the length of the staple cartridge 152406, or information about the staples, such as the height and length.

FIG. 75 illustrates one aspect of a segmented flexible circuit 153430 configured to fixedly attach to a jaw member 153434 of an end effector. The segmented flexible circuit 153430 comprises a distal segment 153432*a* and lateral segments 153432*b*, 153432*c* that include individually addressable sensors to provide local tissue presence detection. The segments 153432*a*, 153432*b*, 153432*c* are individually addressable to detect tissue and to measure tissue parameters based on individual sensors located within each of the segments 153432*a*, 153432*b*, 153432*c*. The segments 153432*a*, 153432*b*, 153432*c* of the segmented flexible circuit 153430 are mounted to the jaw member 153434 and are electrically coupled to an energy source such as an electrical circuit via electrical conductive elements 153436. A Hall effect sensor 153438, or any suitable magnetic sensor, is located on a distal end of the jaw member 153434. The Hall effect sensor 153438 operates in conjunction with a magnet to provide a measurement of an aperture defined by the jaw member 153434, which otherwise may be referred to as a tissue gap, as shown with particularity in FIG. 77. The segmented flexible circuit 153430 may be employed to measure tissue thickness, force, displacement, compression, tissue impedance, and tissue location within an end effector.

FIG. 76 illustrates one aspect of a segmented flexible circuit 153440 configured to mount to a jaw member 153444 of an end effector. The segmented flexible circuit 153440 comprises a distal segment 153442*a* and lateral segments 153442*b*, 153442*c* that include individually addressable sensors for tissue control. The segments 153442*a*, 153442*b*, 153442*c* are individually addressable to treat tissue and to read individual sensors located within each of the segments 153442*a*, 153442*b*, 153442*c*. The segments 153442*a*, 153442*b*, 153442*c* of the segmented flexible circuit 153440 are mounted to the jaw member 153444 and are electrically coupled to an energy source, via electrical conductive elements 153446. A Hall effect sensor 153448, or other suitable magnetic sensor, is provided on a distal end of the jaw member 153444. The Hall effect sensor 153448 operates in conjunction with a magnet to provide a measurement of an aperture defined by the jaw member 153444 of the end effector or tissue gap as shown with particularity in FIG. 77. In addition, a plurality of lateral asymmetric temperature sensors 153450*a*, 153450*b* are mounted on or formally integrally with the segmented flexible circuit 153440 to provide tissue temperature feedback to the control circuit. The segmented flexible circuit 153440 may be employed to measure tissue thickness, force, displacement, compression, tissue impedance, and tissue location within an end effector.

FIG. 77 illustrates one aspect of an end effector 153460 configured to measure a tissue gap GT. The end effector 153460 comprises a jaw member 153462 and a jaw member 153444. The flexible circuit 153440 as described in FIG. 76 is mounted to the jaw member 153444. The flexible circuit 153440 comprises a Hall effect sensor 153448 that operates with a magnet 153464 mounted to the jaw member 153462 to measure the tissue gap GT. This technique can be employed to measure the aperture defined between the jaw member 153444 and the jaw member 153462. The jaw member 153462 may be a staple cartridge.

FIG. 78 illustrates one aspect of an end effector 153470 comprising a segmented flexible circuit 153468. The end effector 153470 comprises a jaw member 153472 and a staple cartridge 153474. The segmented flexible circuit 153468 is mounted to the jaw member 153472. Each of the sensors disposed within the segments 1-5 are configured to detect the presence of tissue positioned between the jaw member 153472 and the staple cartridge 153474 and represent tissue zones 1-5. In the configuration shown in FIG. 78, the end effector 153470 is shown in an open position ready to receive or grasp tissue between the jaw member 153472 and the staple cartridge 153474. The segmented flexible circuit 153468 may be employed to measure tissue thickness, force, displacement, compression, tissue impedance, and tissue location within the end effector 153470.

FIG. 79 illustrates the end effector 153470 shown in FIG. 78 with the jaw member 153472 clamping tissue 153476 between the jaw members 153472, e.g., the anvil and the staple cartridge. As shown in FIG. 79, the tissue 153476 is positioned between segments 1-3 and represents tissue zones 1-3. Accordingly, tissue 153476 is detected by the sensors in segments 1-3 and the absence of tissue (empty) is detected in section 153469 by segments 4-5. The information regarding the presence and absence of tissue 153476 positioned within certain segments 1-3 and 4-5, respectively, is communicated to a control circuit as described herein via interface circuits, for example. The control circuit is configured to detect tissue located in segments 1-3. It will be appreciated that the segments 1-5 may contain any suitable temperature, force/pressure, and/or Hall effect magnetic sensors to measure tissue parameters of tissue located within certain segments 1-5 and electrodes to deliver energy to tissue located in certain segments 1-5. The segmented flexible circuit 153468 may be employed to measure tissue thickness, force, displacement, compression, tissue impedance, and tissue location within the end effector 153470.

FIG. 80 is a diagram of an absolute positioning system 153100 that can be used with a surgical instrument or system in accordance with the present disclosure. The absolute positioning system 153100 comprises a controlled motor drive circuit arrangement comprising a sensor arrangement 153102, in accordance with at least one aspect of this disclosure. The sensor arrangement 153102 for an absolute positioning system 153100 provides a unique position signal corresponding to the location of a displacement member 153111. In one aspect the displacement member 153111 represents the longitudinally movable drive member coupled to the cutting instrument or knife (e.g., a cutting instrument, an I-beam, and/or I-beam 153514 (FIG. 82)). In other aspects, the displacement member 153111 represents a firing member coupled to the cutting instrument or knife, which could be adapted and configured to include a rack of drive teeth. In yet another aspect, the displacement member 153111 represents a firing bar or an I-beam, each of which can be adapted and configured to include a rack of drive teeth.

Accordingly, as used herein, the term displacement member is used generically to refer to any movable member of a surgical instrument or system as described herein, such as a drive member, firing member, firing bar, cutting instrument, knife, and/or I-beam, or any element that can be displaced. Accordingly, the absolute positioning system 153100 can, in effect, track the displacement of the cutting instrument I-beam 153514 (FIG. 82) by tracking the displacement of a longitudinally movable drive member. In various other aspects, the displacement member 153111 may be coupled to any sensor suitable for measuring displacement. Thus, a longitudinally movable drive member, firing member, the firing bar, or I-beam, or combinations thereof, may be coupled to any suitable displacement sensor. Displacement sensors may include contact or non-contact displacement sensors. Displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable linearly arranged Hall effect sensors, an optical sensing system comprising a movable light source and a series of linearly arranged photo diodes or photo detectors, or an optical sensing system comprising a fixed light source and a series of movable linearly arranged photo diodes or photo detectors, or any combination thereof.

An electric motor 153120 can include a rotatable shaft 153116 that operably interfaces with a gear assembly 153114 that is mounted in meshing engagement with a set, or rack, of drive teeth on the displacement member 153111. A sensor element 153126 may be operably coupled to the gear assembly 153114 such that a single revolution of the sensor element 153126 corresponds to some linear longitudinal translation of the displacement member 153111. An arrangement of gearing and sensors 153118 can be connected to the linear actuator via a rack and pinion arrangement or a rotary actuator via a spur gear or other connection. A power source 153129 supplies power to the absolute positioning system 153100 and an output indicator 153128 may display the output of the absolute positioning system 153100.

A single revolution of the sensor element 153126 associated with the position sensor 153112 is equivalent to a longitudinal displacement $d_1$ of the of the displacement member 153111, where $d_1$ is the longitudinal distance that the displacement member 153111 moves from point "a" to point "b" after a single revolution of the sensor element 153126 coupled to the displacement member 153111. The sensor arrangement 153102 may be connected via a gear reduction that results in the position sensor 153112 completing one or more revolutions for the full stroke of the displacement member 153111. The position sensor 153112 may complete multiple revolutions for the full stroke of the displacement member 153111.

A series of switches 153122*a*-153122*n*, where n is an integer greater than one, may be employed alone or in combination with gear reduction to provide a unique position signal for more than one revolution of the position sensor 153112. The state of the switches 153122*a*-153122*n* are fed back to a controller 153110 that applies logic to determine a unique position signal corresponding to the longitudinal displacement $d_1+d_2+\ldots d_n$ of the displacement member 153111. The output 153124 of the position sensor 153112 is provided to the controller 153110. The position sensor 153112 of the sensor arrangement 153102 may comprise a magnetic sensor, an analog rotary sensor like a potentiometer, an array of analog Hall-effect elements, which output a unique combination of position signals or values. The controller 153110 may be contained within a master controller or may be contained within a tool mounting portion housing of a surgical instrument or system in accordance with the present disclosure.

The absolute positioning system 153100 provides an absolute position of the displacement member 153111 upon power up of the surgical instrument or system without retracting or advancing the displacement member 153111 to a reset (zero or home) position as may be required with conventional rotary encoders that merely count the number of steps forwards or backwards that the motor 153120 has taken to infer the position of a device actuator, drive bar, knife, and the like.

The controller 153110 may be programmed to perform various functions such as precise control over the speed and position of the knife and articulation systems. In one aspect, the controller 153110 includes a processor 153108 and a memory 153106. The electric motor 153120 may be a brushed DC motor with a gearbox and mechanical links to an articulation or knife system. In one aspect, a motor driver 153110 may be an A3941 available from Allegro Microsystems, Inc. Other motor drivers may be readily substituted for use in the absolute positioning system 153100.

The controller 153110 may be programmed to provide precise control over the speed and position of the displacement member 153111 and articulation systems. The controller 153110 may be configured to compute a response in the software of the controller 153110. The computed response is compared to a measured response of the actual system to obtain an "observed" response, which is used for actual feedback decisions. The observed response is a favorable, tuned, value that balances the smooth, continuous nature of the simulated response with the measured response, which can detect outside influences on the system.

The absolute positioning system 153100 may comprise and/or be programmed to implement a feedback controller, such as a PID, state feedback, and adaptive controller. A power source 153129 converts the signal from the feedback controller into a physical input to the system, in this case voltage. Other examples include pulse width modulation (PWM) of the voltage, current, and force. Other sensor(s) 153118 may be provided to measure physical parameters of the physical system in addition to position measured by the position sensor 153112. In a digital signal processing system, absolute positioning system 153100 is coupled to a digital data acquisition system where the output of the absolute positioning system 153100 will have finite resolution and sampling frequency. The absolute positioning system 153100 may comprise a compare and combine circuit to combine a computed response with a measured response using algorithms such as weighted average and theoretical control loop that drives the computed response towards the measured response. The computed response of the physical system takes into account properties like mass, inertial, viscous friction, inductance resistance, etc., to predict what the states and outputs of the physical system will be by knowing the input.

The motor driver 153110 may be an A3941 available from Allegro Microsystems, Inc. The A3941 driver 153110 is a full-bridge controller for use with external N-channel power metal oxide semiconductor field effect transistors (MOSFETs) specifically designed for inductive loads, such as brush DC motors. The driver 153110 comprises a unique charge pump regulator provides full (>10 V) gate drive for battery voltages down to 7 V and allows the A3941 to operate with a reduced gate drive, down to 5.5 V. A bootstrap capacitor may be employed to provide the above-battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor adjustable dead time. Integrated diagnostics provide indication of undervoltage, overtemperature, and power bridge faults, and can be configured to protect the power MOSFETs under most short circuit conditions. Other motor drivers may be readily substituted for use in the absolute positioning system 153100.

FIG. 81 is a diagram of a position sensor 153200 for an absolute positioning system 153100' comprising a magnetic rotary absolute positioning system, in accordance with at least one aspect of this disclosure. The absolute positioning system 153100' is similar in many respects to the absolute positioning system 153100. The position sensor 153200 may be implemented as an AS5055EQFT single-chip magnetic rotary position sensor available from Austria Microsystems, AG. The position sensor 153200 is interfaced with the controller 153110 to provide the absolute positioning system 153100'. The position sensor 153200 is a low-voltage and low-power component and includes four Hall-effect elements 153228A, 153228B, 153228C, 153228D in an area 153230 of the position sensor 153200 that is located above a magnet positioned on a rotating element associated with a displacement member such as, for example, a knife drive gear and/or a closure drive gear such that the displacement of a firing member and/or a closure member can be precisely tracked. A high-resolution ADC 153232 and a smart power management controller 153238 are also provided on the chip. A CORDIC processor 153236 (for Coordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface such as an SPI interface 153234 to the controller 153110. The position sensor 153200 provides 12 or 14 bits of resolution. The position sensor 153200 may be an AS5055 chip provided in a small QFN 16-pin 4×4×0.85 mm package.

The Hall-effect elements 153228A, 153228B, 153228C, 153228D are located directly above the rotating magnet. The Hall-effect is a well-known effect and for expediency will not be described in detail herein, however, generally, the Hall-effect produces a voltage difference (the Hall voltage) across an electrical conductor transverse to an electric current in the conductor and a magnetic field perpendicular to the current. A Hall coefficient is defined as the ratio of the induced electric field to the product of the current density and the applied magnetic field. It is a characteristic of the material from which the conductor is made, since its value depends on the type, number, and properties of the charge carriers that constitute the current. In the AS5055 position sensor 153200, the Hall-effect elements 153228A, 153228B, 153228C, 153228D are capable producing a voltage signal that is indicative of the absolute position of the magnet in terms of the angle over a single revolution of the magnet. This value of the angle, which is unique position signal, is calculated by the CORDIC processor 153236 is stored onboard the AS5055 position sensor 153200 in a register or memory. The value of the angle that is indicative of the position of the magnet over one revolution is provided to the controller 153110 in a variety of techniques, e.g., upon power up or upon request by the controller 153110.

The AS5055 position sensor 153200 requires only a few external components to operate when connected to the controller 153110. Six wires are needed for a simple application using a single power supply: two wires for power and four wires 153240 for the SPI interface 153234 with the controller 153110. A seventh connection can be added in order to send an interrupt to the controller 153110 to inform that a new valid angle can be read. Upon power-up, the AS5055 position sensor 153200 performs a full power-up sequence including one angle measurement. The completion of this cycle is indicated as an INT output 153242, and the angle value is stored in an internal register. Once this output is set, the AS5055 position sensor 153200 suspends to sleep mode. The controller 153110 can respond to the INT request at the INT output 153242 by reading the angle value from the AS5055 position sensor 153200 over the SPI interface 153234. Once the angle value is read by the controller 153110, the INT output 153242 is cleared again. Sending a "read angle" command by the SPI interface 153234 by the controller 153110 to the position sensor 153200 also automatically powers up the chip and starts another angle measurement. As soon as the controller 153110 has completed reading of the angle value, the INT output 153242 is cleared and a new result is stored in the angle register. The completion of the angle measurement is again indicated by setting the INT output 153242 and a corresponding flag in the status register.

Due to the measurement principle of the AS5055 position sensor 153200, only a single angle measurement is performed in very short time (~600 μs) after each power-up sequence. As soon as the measurement of one angle is completed, the AS5055 position sensor 153200 suspends to power-down state. An on-chip filtering of the angle value by digital averaging is not implemented, as this would require more than one angle measurement and, consequently, a longer power-up time that is not desired in low-power applications. The angle jitter can be reduced by averaging of several angle samples in the controller 153110. For example, an averaging of four samples reduces the jitter by 6 dB (50%).

FIG. 82 is a section view of an end effector 153502 showing an I-beam 153514 firing stroke relative to tissue 153526 grasped within the end effector 153502, in accordance with at least one aspect of this disclosure. The end effector 153502 is configured to operate with any of the surgical instruments or systems in accordance with the present disclosure. The end effector 153502 comprises an anvil 153516 and an elongated channel 153503 with a staple cartridge 153518 positioned in the elongated channel 153503. A firing bar 153520 is translatable distally and proximally along a longitudinal axis 153515 of the end effector 153502. When the end effector 153502 is not articulated, the end effector 153502 is in line with the shaft of the instrument. An I-beam 153514 comprising a cutting edge 153509 is illustrated at a distal portion of the firing bar 153520. A wedge sled 153513 is positioned in the staple cartridge 153518. As the I-beam 153514 translates distally, the cutting edge 153509 contacts and may cut tissue 153526 positioned between the anvil 153516 and the staple cartridge 153518. Also, the I-beam 153514 contacts the wedge sled 153513 and pushes it distally, causing the wedge sled 153513 to contact staple drivers 153511. The staple drivers 153511 may be driven up into staples 153505, causing the staples 153505 to advance through tissue and into pockets 153507 defined in the anvil 153516, which shape the staples 153505.

An example I-beam 153514 firing stroke is illustrated by a chart 153529 aligned with the end effector 153502. Example tissue 153526 is also shown aligned with the end effector 153502. The firing member stroke may comprise a stroke begin position 153527 and a stroke end position 153528. During an I-beam 153514 firing stroke, the I-beam 153514 may be advanced distally from the stroke begin position 153527 to the stroke end position 153528. The I-beam 153514 is shown at one example location of a stroke begin position 153527. The I-beam 153514 firing member stroke chart 153529 illustrates five firing member stroke regions 153517, 153519, 153521, 153523, 153525. In a first firing stroke region 153517, the I-beam 153514 may begin to advance distally. In the first firing stroke region 153517, the I-beam 153514 may contact the wedge sled 153513 and begin to move it distally. While in the first region, however, the cutting edge 153509 may not contact tissue and the wedge sled 153513 may not contact a staple driver 153511. After static friction is overcome, the force to drive the I-beam 153514 in the first region 153517 may be substantially constant.

In the second firing member stroke region 153519, the cutting edge 153509 may begin to contact and cut tissue 153526. Also, the wedge sled 153513 may begin to contact staple drivers 153511 to drive staples 153505. Force to drive the I-beam 153514 may begin to ramp up. As shown, tissue encountered initially may be compressed and/or thinner because of the way that the anvil 153516 pivots relative to the staple cartridge 153518. In the third firing member stroke region 153521, the cutting edge 153509 may continuously contact and cut tissue 153526 and the wedge sled 153513 may repeatedly contact staple drivers 153511. Force to drive the I-beam 153514 may plateau in the third region 153521. By the fourth firing stroke region 153523, force to drive the I-beam 153514 may begin to decline. For example, tissue in the portion of the end effector 153502 corresponding to the fourth firing region 153523 may be less compressed than tissue closer to the pivot point of the anvil 153516, requiring less force to cut. Also, the cutting edge 153509 and wedge sled 153513 may reach the end of the tissue 153526 while in the fourth region 153523. When the I-beam 153514 reaches the fifth region 153525, the tissue 153526 may be completely severed. The wedge sled 153513 may contact one or more staple drivers 153511 at or near the end of the tissue. Force to advance the I-beam 153514 through the fifth region 153525 may be reduced and, in some examples, may be similar to the force to drive the I-beam 153514 in the first region 153517. At the conclusion of the firing member stroke, the I-beam 153514 may reach the stroke end position 153528. The positioning of firing member stroke regions 153517, 153519, 153521, 153523, 153525 in FIG. 82 is just one example. In some examples, different regions may begin at different positions along the end effector longitudinal axis 153515, for example, based on the positioning of tissue between the anvil 153516 and the staple cartridge 153518.

As discussed above and with reference now to FIGS. 80 to 82, the electric motor 153120 positioned within a master controller of the surgical instrument and can be utilized to advance and/or retract the firing system of the shaft assembly, including the I-beam 153514, relative to the end effector 153502 of the shaft assembly in order to staple and/or incise tissue captured within the end effector 153502. The I-beam 153514 may be advanced or retracted at a desired speed, or within a range of desired speeds. The controller 153110 may be configured to control the speed of the I-beam 153514. The controller 153110 may be configured to predict the speed of the I-beam 153514 based on various parameters of the power supplied to the electric motor 153120, such as voltage and/or current, for example, and/or other operating parameters of the electric motor 153120 or external influences. The controller 153110 may be configured to predict the current speed of the I-beam 153514 based on the previous values of the current and/or voltage supplied to the electric motor 153120, and/or previous states of the system like velocity, acceleration, and/or position. The controller 153110 may be configured to sense the speed of the I-beam 153514 utilizing the absolute positioning sensor system described herein. The controller can be configured to compare the predicted speed of the I-beam 153514 and the sensed speed of the I-beam 153514 to determine whether the power to the electric motor 153120 should be increased in order to increase the speed of the I-beam 153514 and/or decreased in order to decrease the speed of the I-beam 153514.

Force acting on the I-beam 153514 may be determined using various techniques. The I-beam 153514 force may be determined by measuring the motor 153120 current, where the motor 153120 current is based on the load experienced by the I-beam 153514 as it advances distally. The I-beam 153514 force may be determined by positioning a strain gauge on the drive member, the firing member, I-beam 153514, the firing bar, and/or on a proximal end of the cutting edge 153509. The I-beam 153514 force may be determined by monitoring the actual position of the I-beam 153514 moving at an expected velocity based on the current set velocity of the motor 153120 after a predetermined elapsed period $T_1$ and comparing the actual position of the I-beam 153514 relative to the expected position of the I-beam 153514 based on the current set velocity of the motor 153120 at the end of the period $T_1$. Thus, if the actual position of the I-beam 153514 is less than the expected position of the I-beam 153514, the force on the I-beam 153514 is greater than a nominal force. Conversely, if the actual position of the I-beam 153514 is greater than the expected position of the I-beam 153514, the force on the I-beam 153514 is less than the nominal force. The difference between the actual and expected positions of the I-beam 153514 is proportional to the deviation of the force on the I-beam 153514 from the nominal force.

Prior to turning to a description of closed loop control techniques of the closure tube and firing member, the description turns briefly to FIG. 83. FIG. 83 is a graph 153600 depicting two closure force (FTC) plots 153606, 153608 depicting the force applied to a closure member to close on thick and thin tissue during a closure phase and a graph depicting two firing force (FTF) plots 153622, 153624 depicting the force applied to a firing member to fire through thick and thin tissue during a firing phase. Referring to FIG. 83, the graph 153600 depicts an example of the force applied to thick and thin tissue during a closure stroke to close the end effector 153502 relative to tissue grasped between the anvil 153516 and the staple cartridge 153518, where the closure force is plotted as a function of time. The closure force plots 153606, 153608 are plotted on two axes. A vertical axis 153602 indicates the closure force (FTC) the end effector 153502 in Newtons (N). A horizontal axis 153604 indicates time in seconds and labeled $t_0$ to $t_{13}$ for clarity of description. The first closure force plot 153606 is an example of the force applied to thick tissue during a closure stroke to close the end effector 153502 relative to tissue grasped between the anvil 153516 and the staple cartridge 153518 and a second plot 153608 is an example of the force applied to thin tissue during a closure stroke to close the end effector 153502 relative to tissue grasped between the anvil 153516 and the staple cartridge 153518. The first and second closure force plots 153606, 153608 are divided into three phases, a close stroke (CLOSE), a waiting period (WAIT), and a firing stroke (FIRE). During the closure stroke, a closure tube is translated distally (direction "DD") to move the anvil 153516, for example, relative to the staple cartridge 153518 in response to the actuation of the closure stroke by a closure motor. In other instances, the closure stroke involves moving the staple cartridge 153518 relative to an anvil 153516 in response to the actuation of the closure motor and in other instances the closure stroke involves moving the staple cartridge 153518 and the anvil 153516 in response to the actuation of the closure motor. With reference to the first closure force plot 153606, during the closure stroke the closure force 153610 increases from 0 up to a maximum force $F_1$ from time $t_0$ to $t_1$. With reference to the second closure force graph 153608, during the closure stroke the closure force 153616 increases from 0 up to a maximum force $F_3$ from time $t_0$ to $t_1$. The relative difference between the maximum forces $F_1$ and $F_3$ is due to the difference in closure force necessary for thick tissue relative to thin tissue, where greater force is required to close the anvil onto thick tissue versus thin tissue.

The first and second closure force plots 153606, 153608 indicate that the closure force in the end effector 153502 increases during an initial clamping time period ending at a time ($t_1$). The closure force reaches a maximum force ($F_1$, $F_3$) at the time ($t_1$). The initial clamping time period can be about one second, for example. A waiting period can be applied prior to initiating a firing stroke. The waiting period allows fluid egress from tissue compressed by the end effector 153502, which reduces the thickness of the compressed tissue yielding a smaller gap between the anvil 153516 and the staple cartridge 153518 and a reduced closure force at the end of the waiting period. With reference to the first closure force plot 153606, there is a nominal drop in closure force 153612 from $F_1$ to $F_2$ during the waiting period between $t_1$ to $t_4$. Similarly, with reference to the second closure force plot 153608, the closure force 153618 drops nominally from $F_3$ to $F_4$ during the waiting period between $t_1$ to $t_4$. In some examples, a waiting period ($t_1$ to $t_4$) selected from a range of about 10 seconds to about 20 seconds is typically employed. In the example first and second closure force plots 153606, 153608, a period of time of about 15 seconds is employed. The waiting period is followed by the firing stroke, which typically lasts a period of time selected from a range of about 3 seconds, for example, to about 5 seconds, for example. The closure force decreases as the I-beam 153514 is advanced relative to the end effector through the firing stroke. As indicated by the closure force 153614, 153620 of the first and second closure force plots 153606, 153608, respectively, the closure force 153614, 153620 exerted on the closure tube drops precipitously from about time $t_4$ to about time $t_5$. Time $t_4$ represents the moment where the I-beam 153514 couples into the anvil 153516 and begins to take over the closing load. Accordingly, the closure force decreases as the firing force increases as shown by the first and second firing force plots 153622, 153624.

FIG. 83 also depicts a graph 153601 of first and second firing force plots 153622, 153624 that plot the force applied to advance the I-beam 153514 during the firing stroke of a surgical instrument or system in accordance with the present disclosure. The firing force plots 153622, 153624 are plotted on two axes. A vertical axis 153626 indicates the firing force, in Newtons (N), applied to advance the I-beam 153514 during the firing stroke. The I-beam 153514 is configured to advance a knife or cutting element and motivate drivers to deploy staples during the firing stroke. A horizontal axis 153605 indicates the time in seconds on the same time scale as the horizontal axis 153604 of the upper graph 153600.

As previously described, the closure tube force drops precipitously from time $t_4$ to about time $t_5$, which represents the moment the I-beam 153514 couples into the anvil 153516 and begins to take load and the closure force decreases as the firing force increases as shown by the first and second firing force plots 153622, 153624. The I-beam 153514 is advanced from the stroke begin position at time $t_4$ to the stroke end positions between $t_8$ and $t_9$ for the firing force plot 153624 for thin tissue and at $t_{13}$ for the firing force plot 153622 for thick tissue. As the I-beam 153514 is advanced distally during the firing stroke, the closure assembly surrenders control of the staple cartridge 153518 and the anvil 153516 to the firing assembly, which causes the firing force to increase and the closure force to decrease.

In the thick tissue firing force plot 153622, during the firing period (FIRE) the plot 153622 is divided into three distinct segments. A first segment 153628 indicates the firing force as it increases from 0 at $t_4$ to a peak force $F_1'$ just prior to $t_5$. The first segment 153628 is the firing force during the initial phase of the firing stroke where the I-beam 153514 advances distally from the top of the closure ramp until the I-beam 153514 contacts tissue. A second segment 153630 indicates the firing force during a second phase of the firing stroke where the I-beam 153514 is advancing distally deploying staples and cutting the tissue. During the second phase of the firing stroke the firing force drops from $F_1'$ to $F_2'$ at about $t_{12}$. A third segment 153632 indicates the firing force during the third and final phase of the firing stroke where the I-beam 153514 leaves the tissue and advances to the end of stroke in a tissue free zone. During the third phase of the firing stroke the firing force drops to from $F_2$' to zero (0) at about $t_{13}$ where the I-beam 153514 reaches the end of stroke. In summary, during the firing stroke, the firing force rises dramatically as the I-beam 153514 enters a tissue zone, decrease steadily in the tissue zone during the stapling and cutting operation, and drops dramatically as the I-beam 153514 exits the tissue zone and enters a tissue free zone at the end of stroke.

The thin tissue firing force plot 153624 follows a similar pattern as the thick tissue firing force plot 153622. Thus, during the first phase of the firing stroke the firing force 153634 increases dramatically from 0 to $F_3$' at about $t_5$. During the second phase of the firing stroke, the firing force 153636 drops steadily from $F_3$' to $F_4$' at about $t_8$. During the final phase of the firing stroke the firing force 153638 drops dramatically from $F'_4$ to 0 between $t_8$ and $t_9$.

To overcome the precipitous drop in closure force from time $t_4$ to about time $t_5$, which represents the moment the I-beam 153514 couples into the anvil 153516 and begins to take load and the closure force decreases as the firing force increases, as shown by the first and second firing force plots 153622, 153624, the closure tube may be advanced distally while the firing member such as the I-beam 153514 is advancing distally. The closure tube is represented as a transmission element that applies a closure force to the anvil 153516. As described herein, a control circuit applies motor set points to the motor control which applies a motor control signal to the motor to drive the transmission element and advance the closure tube distally to apply a closing force to the anvil 153516. A torque sensor coupled to an output shaft of the motor can be used to measure the force applied to the closure tube. In other aspects, the closure force can be measured with a strain gauge, load cell, or other suitable force sensor.

FIG. 84 is a diagram of a control system 153950 configured to provide progressive closure of a closure member (e.g., a closure tube) when the firing member (e.g., I-beam 153514) advances distally and couples into a clamp arm (e.g., anvil 153516) to lower the closure force load on the closure member at a desired rate and decrease the firing force load on the firing member, in accordance with at least one aspect of this disclosure. In one aspect, the control system 153950 may be implemented as a nested PID feedback controller. A PID controller is a control loop feedback mechanism (controller) to continuously calculate an error value as the difference between a desired set point and a measured process variable and applies a correction based on proportional, integral, and derivative terms (sometimes denoted P, I, and D respectively). The nested PID controller feedback control system 153950 includes a primary controller 153952, in a primary (outer) feedback loop 153954 and a secondary controller 153955 in a secondary (inner) feedback loop 153956.

The primary controller 153952 may be a PID controller 153972 as shown in FIG. 84, and the secondary controller 153955 also may be a PID controller 153972 as shown in FIG. 85. The primary controller 153952 controls a primary process 153958 and the secondary controller 153955 controls a secondary process 153960. The output 153966 of the primary process 153958 (OUTPUT) is subtracted from a primary set point $SP_1$ by a first summer 153962. The first summer 153962 produces a single sum output signal which is applied to the primary controller 153952. The output of the primary controller 153952 is the secondary set point $SP_2$. The output 153968 of the secondary process 153960 is subtracted from the secondary set point $SP_2$ by a second summer 153964.

In the context of controlling the displacement of the closure tube, the control system 153950 may be configured such that the primary set point $SP_1$ is a desired closure force value and the primary controller 153952 is configured to receive the closure force from the torque sensor coupled to the output of the closure motor and determine a set point $SP_2$ motor velocity for the closure motor. In other aspects, the closure force may be measured with strain gauges, load cells, or other suitable force sensors. The closure motor velocity set point $SP_2$ is compared to the actual velocity of the closure tube, which is determined by the secondary controller 153955. The actual velocity of the closure tube may be measured by comparing the displacement of the closure tube with the position sensor and measuring elapsed time with the timer/counter. Other techniques, such as linear or rotary encoders may be employed to measure displacement of the closure tube. The output 153968 of the secondary process 153960 is the actual velocity of the closure tube. This closure tube velocity output 153968 is provided to the primary process 153958 which determines the force acting on the closure tube and is fed back to the adder 153962, which subtracts the measured closure force from the primary set point $SP_1$. The primary set point $SP_1$ may be an upper threshold or a lower threshold. Based on the output of the adder 153962, the primary controller 153952 controls the velocity and direction of the closure tube motor as described herein. The secondary controller 153955 controls the velocity of the closure motor based on the actual velocity of closure tube measured by the secondary process 153960 and the secondary set point $SP_2$, which is based on a comparison of the actual firing force and the firing force upper and lower thresholds.

FIG. 85 illustrates a PID feedback control system 153970, in accordance with at least one aspect of this disclosure. The primary controller 153952 or the secondary controller 153955, or both, may be implemented as a PID controller 153972. In one aspect, the PID controller 153972 may comprise a proportional element 153974 (P), an integral element 153976 (I), and a derivative element 153978 (D). The outputs of the P, I, D elements 153974, 153976, 153978 are summed by a summer 153986, which provides the control variable u(t) to the process 153980. The output of the process 153980 is the process variable y(t). The summer 153984 calculates the difference between a desired set point r(t) and a measured process variable y(t). The PID controller 153972 continuously calculates an error value e(t) (e.g., difference between closure force threshold and measured closure force) as the difference between a desired set point r(t) (e.g., closure force threshold) and a measured process variable y(t) (e.g., velocity and direction of closure tube) and applies a correction based on the proportional, integral, and derivative terms calculated by the proportional element 153974 (P), integral element 153976 (I), and derivative element 153978 (D), respectively. The PID controller 153972 attempts to minimize the error e(t) over time by adjustment of the control variable u(t) (e.g., velocity and direction of the closure tube).

In accordance with the PID algorithm, the "P" element 153974 accounts for present values of the error. For example, if the error is large and positive, the control output will also be large and positive. In accordance with the present disclosure, the error term e(t) is the different between the desired closure force and the measured closure force of the closure tube. The "I" element 153976 accounts for past values of the error. For example, if the current output is not sufficiently strong, the integral of the error will accumulate over time, and the controller will respond by applying a stronger action. The "D" element 153978 accounts for possible future trends of the error, based on its current rate of change. For example, continuing the P example above, when the large positive control output succeeds in bringing the error closer to zero, it also puts the process on a path to large negative error in the near future. In this case, the derivative turns negative and the D module reduces the strength of the action to prevent this overshoot.

It will be appreciated that other variables and set points may be monitored and controlled in accordance with the feedback control systems 153950, 153970. For example, the adaptive closure member velocity control algorithm described herein may measure at least two of the following parameters: firing member stroke location, firing member load, displacement of cutting element, velocity of cutting element, closure tube stroke location, closure tube load, among others.

FIG. 86 is a logic flow diagram depicting a process 153990 of a control program or a logic configuration for determining the velocity of a closure member, in accordance with at least one aspect of this disclosure. A control circuit of a surgical instrument or system in accordance with the present disclosure is configured to determine 153992 the actual closure force of a closure member. The control circuit compares 153994 the actual closure force to a threshold closure force and determines 153996 a set point velocity to displace the closure member based on the comparison. The control circuit controls 153998 the actual velocity of the closure member based on the set point velocity.

With reference now also to FIGS. 84 and 85, in one aspect, the control circuit comprises a proportional, integral, and derivative (PID) feedback control system 153950, 153970. The PID feedback control system 153950, 153970 comprises a primary PID feedback loop 153954 and a secondary PID feedback loop 153956. The primary feedback loop 153954 determines a first error between the actual closure force of the closure member and a threshold closure force $SP_1$ and sets the closure member velocity set point $SP_2$ based on the first error. The secondary feedback loop 153956 determines a second error between the actual velocity of the closure member and the set point velocity of the closure member an sets the closure member velocity based on the second error.

In one aspect, the threshold closure force $SP_1$ comprises an upper threshold and a lower threshold. The set point velocity $SP_2$ is configured to advance the closure member distally when the actual closure force is less than the lower threshold and the set point velocity is configured to retract the closure member proximally when the actual closure force is greater than the lower threshold. In one aspect, the set point velocity is configured to hold the closure member in place when the actual closure force is between the upper and lower thresholds.

In one aspect, the control system further comprises a force sensor (e.g., any of sensors 472, 474, 476 (FIG. 12), for example) coupled to the control circuit. The force sensor is configured measure the closure force. In one aspect, the force sensor comprises a torque sensor coupled to an output shaft of a motor coupled to the closure member. In one aspect, the force sensor comprises a strain gauge coupled to the closure member. In one aspect, the force sensor comprises a load cell coupled to the closure member. In one aspect, the control system comprises a position sensor coupled to the closure member, wherein the position sensor is configured to measure the position of the closure member.

In one aspect, the control system comprises a first motor configured to couple to the closure member and the control circuit is configured to advance the closure member during at least a portion of a firing stroke.

The functions or processes 153990 described herein may be executed by any of the processing circuits described herein. Aspects of the motorized surgical instrument may be practiced without the specific details disclosed herein. Some aspects have been shown as block diagrams rather than detail.

Parts of this disclosure may be presented in terms of instructions that operate on data stored in a computer memory. An algorithm refers to a self-consistent sequence of steps leading to a desired result, where a "step" refers to a manipulation of physical quantities which may take the form of electrical or magnetic signals capable of being stored, transferred, combined, compared, and otherwise manipulated. These signals may be referred to as bits, values, elements, symbols, characters, terms, numbers. These and similar terms may be associated with the appropriate physical quantities and are merely convenient labels applied to these quantities.

Generally, aspects described herein which can be implemented, individually and/or collectively, by a wide range of hardware, software, firmware, or any combination thereof can be viewed as being composed of various types of "electrical circuitry." Consequently, "electrical circuitry" includes electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer or processor configured by a computer program which at least partially carries out processes and/or devices described herein, electrical circuitry forming a memory device (e.g., forms of random access memory), and/or electrical circuitry forming a communications device (e.g., a modem, communications switch, or optical-electrical equipment). These aspects may be implemented in analog or digital form, or combinations thereof.

The foregoing description has set forth aspects of devices and/or processes via the use of block diagrams, flowcharts, and/or examples, which may contain one or more functions and/or operation. Each function and/or operation within such block diagrams, flowcharts, or examples can be implemented, individually and/or collectively, by a wide range of hardware, software, firmware, or virtually any combination thereof. In one aspect, several portions of the subject matter described herein may be implemented via Application Specific Integrated Circuits (ASICs), Field Programmable Gate Arrays (FPGAs), digital signal processors (DSPs), Programmable Logic Devices (PLDs), circuits, registers and/or software components, e.g., programs, subroutines, logic and/or combinations of hardware and software components. Logic gates, or other integrated formats. Some aspects disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

The mechanisms of the disclosed subject matter are capable of being distributed as a program product in a variety of forms, and that an illustrative aspect of the subject matter described herein applies regardless of the particular type of signal bearing medium used to actually carry out the distribution. Examples of a signal bearing medium include the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.).

The foregoing description of these aspects has been presented for purposes of illustration and description. It is not intended to be exhaustive or limiting to the precise form disclosed. Modifications or variations are possible in light of the above teachings. These aspects were chosen and described in order to illustrate principles and practical application to thereby enable one of ordinary skill in the art to utilize the aspects and with modifications as are suited to the particular use contemplated. It is intended that the claims submitted herewith define the overall scope.

Situational Awareness

Situational awareness is the ability of some aspects of a surgical system to determine or infer information related to a surgical procedure from data received from databases and/or instruments. The information can include the type of procedure being undertaken, the type of tissue being operated on, or the body cavity that is the subject of the procedure. With the contextual information related to the surgical procedure, the surgical system can, for example, improve the manner in which it controls the modular devices (e.g. a robotic arm and/or robotic surgical tool) that are connected to it and provide contextualized information or suggestions to the surgeon during the course of the surgical procedure.

Referring now to FIG. 87, a timeline 5200 depicting situational awareness of a hub, such as the surgical hub 106 or 206, for example, is depicted. The timeline 5200 is an illustrative surgical procedure and the contextual information that the surgical hub 106, 206 can derive from the data received from the data sources at each step in the surgical procedure. The timeline 5200 depicts the typical steps that would be taken by the nurses, surgeons, and other medical personnel during the course of a lung segmentectomy procedure, beginning with setting up the operating theater and ending with transferring the patient to a post-operative recovery room.

The situationally aware surgical hub 106, 206 receives data from the data sources throughout the course of the surgical procedure, including data generated each time medical personnel utilize a modular device that is paired with the surgical hub 106, 206. The surgical hub 106, 206 can receive this data from the paired modular devices and other data sources and continually derive inferences (i.e., contextual information) about the ongoing procedure as new data is received, such as which step of the procedure is being performed at any given time. The situational awareness system of the surgical hub 106, 206 is able to, for example, record data pertaining to the procedure for generating reports, verify the steps being taken by the medical personnel, provide data or prompts (e.g., via a display screen) that may be pertinent for the particular procedural step, adjust modular devices based on the context (e.g., activate monitors, adjust the field of view (FOV) of the medical imaging device, or change the energy level of an ultrasonic surgical instrument or RF electrosurgical instrument), and take any other such action described above.

As the first step 5202 in this illustrative procedure, the hospital staff members retrieve the patient's EMR from the hospital's EMR database. Based on select patient data in the EMR, the surgical hub 106, 206 determines that the procedure to be performed is a thoracic procedure.

Second step 5204, the staff members scan the incoming medical supplies for the procedure. The surgical hub 106, 206 cross-references the scanned supplies with a list of supplies that are utilized in various types of procedures and confirms that the mix of supplies corresponds to a thoracic procedure. Further, the surgical hub 106, 206 is also able to determine that the procedure is not a wedge procedure (because the incoming supplies either lack certain supplies that are necessary for a thoracic wedge procedure or do not otherwise correspond to a thoracic wedge procedure).

Third step 5206, the medical personnel scan the patient band via a scanner that is communicably connected to the surgical hub 106, 206. The surgical hub 106, 206 can then confirm the patient's identity based on the scanned data.

Fourth step 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices can automatically pair with the surgical hub 106, 206 that is located within a particular vicinity of the modular devices as part of their initialization process. The surgical hub 106, 206 can then derive contextual information about the surgical procedure by detecting the types of modular devices that pair with it during this pre-operative or initialization phase. In this particular example, the surgical hub 106, 206 determines that the surgical procedure is a VATS procedure based on this particular combination of paired modular devices. Based on the combination of the data from the patient's EMR, the list of medical supplies to be used in the procedure, and the type of modular devices that connect to the hub, the surgical hub 106, 206 can generally infer the specific procedure that the surgical team will be performing. Once the surgical hub 106, 206 knows what specific procedure is being performed, the surgical hub 106, 206 can then retrieve the steps of that procedure from a memory or from the cloud and then cross-reference the data it subsequently receives from the connected data sources (e.g., modular devices and patient monitoring devices) to infer what step of the surgical procedure the surgical team is performing.

Fifth step 5210, the staff members attach the EKG electrodes and other patient monitoring devices to the patient. The EKG electrodes and other patient monitoring devices are able to pair with the surgical hub 106, 206. As the surgical hub 106, 206 begins receiving data from the patient monitoring devices, the surgical hub 106, 206 thus confirms that the patient is in the operating theater.

Sixth step 5212, the medical personnel induce anesthesia in the patient. The surgical hub 106, 206 can infer that the patient is under anesthesia based on data from the modular devices and/or patient monitoring devices, including EKG data, blood pressure data, ventilator data, or combinations thereof, for example. Upon completion of the sixth step

5212, the pre-operative portion of the lung segmentectomy procedure is completed and the operative portion begins.

Seventh step 5214, the patient's lung that is being operated on is collapsed (while ventilation is switched to the contralateral lung). The surgical hub 106, 206 can infer from the ventilator data that the patient's lung has been collapsed, for example. The surgical hub 106, 206 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure.

Eighth step 5216, the medical imaging device (e.g., a scope) is inserted and video from the medical imaging device is initiated. The surgical hub 106, 206 receives the medical imaging device data (i.e., video or image data) through its connection to the medical imaging device. Upon receipt of the medical imaging device data, the surgical hub 106, 206 can determine that the laparoscopic portion of the surgical procedure has commenced. Further, the surgical hub 106, 206 can determine that the particular procedure being performed is a segmentectomy, as opposed to a lobectomy (note that a wedge procedure has already been discounted by the surgical hub 106, 206 based on data received at the second step 5204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 106, 206), and monitoring the types of visualization devices utilized. For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device, the surgical hub 106, 206 can thereby determine the specific type of surgical procedure being performed and/or the technique being used for a particular type of surgical procedure.

Ninth step 5218, the surgical team begins the dissection step of the procedure. The surgical hub 106, 206 can infer that the surgeon is in the process of dissecting to mobilize the patient's lung because it receives data from the RF or ultrasonic generator indicating that an energy instrument is being fired. The surgical hub 106, 206 can cross-reference the received data with the retrieved steps of the surgical procedure to determine that an energy instrument being fired at this point in the process (i.e., after the completion of the previously discussed steps of the procedure) corresponds to the dissection step. In certain instances, the energy instrument can be an energy tool mounted to a robotic arm of a robotic surgical system.

Tenth step 5220, the surgical team proceeds to the ligation step of the procedure. The surgical hub 106, 206 can infer that the surgeon is ligating arteries and veins because it receives data from the surgical stapling and cutting instrument indicating that the instrument is being fired. Similarly to the prior step, the surgical hub 106, 206 can derive this inference by cross-referencing the receipt of data from the surgical stapling and cutting instrument with the retrieved steps in the process. In certain instances, the surgical instrument can be a surgical tool mounted to a robotic arm of a robotic surgical system.

Eleventh step 5222, the segmentectomy portion of the procedure is performed. The surgical hub 106, 206 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 106, 206 to infer that the segmentectomy portion of the procedure is being performed.

Twelfth step 5224, the node dissection step is then performed. The surgical hub 106, 206 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 106, 206 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Moreover, in certain instances, robotic tools can be utilized for one or more steps in a surgical procedure and/or handheld surgical instruments can be utilized for one or more steps in the surgical procedure. The surgeon(s) can alternate between robotic tools and handheld surgical instruments and/or can use the devices concurrently, for example. Upon completion of the twelfth step 5224, the incisions are closed up and the post-operative portion of the procedure begins.

Thirteenth step 5226, the patient's anesthesia is reversed. The surgical hub 106, 206 can infer that the patient is emerging from the anesthesia based on the ventilator data (i.e., the patient's breathing rate begins increasing), for example.

Lastly, the fourteenth step 5228 is that the medical personnel remove the various patient monitoring devices from the patient. The surgical hub 106, 206 can thus infer that the patient is being transferred to a recovery room when the hub loses EKG, BP, and other data from the patient monitoring devices. As can be seen from the description of this illustrative procedure, the surgical hub 106, 206 can determine or infer when each step of a given surgical procedure is taking place according to data received from the various data sources that are communicably coupled to the surgical hub 106, 206.

Situational awareness is further described in U.S. Provisional Patent Application Ser. No. 62/611,341, titled INTERACTIVE SURGICAL PLATFORM, filed Dec. 28, 2017, which is incorporated by reference herein in its entirety. In certain instances, operation of a robotic surgical system, including the various robotic surgical systems disclosed herein, for example, can be controlled by the hub 106, 206 based on its situational awareness and/or feedback from the components thereof and/or based on information from the cloud 104.

Safety Systems for Smart Powered Surgical Stapling

Various aspects of the present disclosure are directed to improved safety systems capable of adapting, controlling, and/or tuning internal drive operations of a surgical instrument in response to tissue parameters detected via one or more than one sensor of the surgical instrument. In accordance with at least one aspect, a force detected, via one or more than one sensor, at the jaws of an end effector may be of a magnitude that prohibits one or more than one subsequent/further functionality of the end effector from being performed. According to another aspect, a metallic object may be detected, via one or more than one sensor, as within the jaws of the end effector that prohibits one or more than one subsequent/further functionality of the end effector from being performed. FIG. 88 illustrates a surgical system 23000 comprising a surgical instrument 23002, a surgical hub 23004, and a user interface 23006. In such an aspect, the surgical instrument 23002 may comprise one or more than one sensor 23008 and parameters detected by the one or more than one sensor 23008 of the surgical instrument 23002 may be transmitted/communicated (e.g., wirelessly) to a control circuit 23010 of the surgical hub 23004. Further, in such an aspect, the surgical hub 23004 may be configured to determine whether a surgical function (e.g., dissect, clamp, coagulate, staple, cut, rotate, articulate, etc.) associated with a component (e.g., end effector, shaft, etc.) of the surgical instrument 23002 may be performed safely based on the parameters detected by the one or more than one sensor 23008 of the surgical instrument 23002. Notably, in such an aspect, the surgical hub 23004 may be configured to transmit/communicate a result(s) (i.e., a warning associated with the surgical function, a reason the surgical function is prevented, etc.) associated with that determination to the user interface 23006. Further, according to various aspects, various user interfaces disclosed herein may comprise a selectable user interface feature (e.g., override element 23012) to proceed with the surgical function despite any warnings and/or reasons supporting prevention. Notably, in such aspects, such a user interface feature (e.g., override element 23012) may not be displayed (e.g., performing the surgical function may endanger the patient).

Referring to FIG. 89, according to various aspects of the present disclosure, a surgical system 23100 may comprise a control circuit (23112, 23122, 23132 and/or 23142, e.g., in phantom to show optional location(s)), a user interface (23118, 23128, 23138, 23148 and/or 23158, e.g., in phantom to show optional locations), and a surgical instrument 23102 including, for example, a handle assembly 23110, a shaft assembly 23120, and an end effector assembly 23130. In such aspects, the control circuit may be integrated into one or more than one component (e.g., the handle assembly 23110, the shaft assembly 23120, and/or the end effector assembly 23130, etc.) of the surgical instrument 23102 (e.g., 23112, 23122, and/or 23132) and/or integrated into a surgical hub 23140 (e.g., 23142) paired (e.g., wirelessly) with the surgical instrument 23102. Notably, according to various aspects, the surgical instrument 23102 and/or the surgical hub 23140 may be a situationally aware surgical instrument and/or a situationally aware surgical hub. Situational awareness refers to the ability of a surgical system, e.g., 23100, to determine or infer information related to a surgical procedure from data received from databases (e.g., historical data associated with a surgical procedure, e.g., 23149 and/or 23150) and/or surgical instruments (e.g., sensor data during a surgical procedure). For example, the determined or inferred information can include the type of procedure being undertaken, the type of tissue being operated on, the body cavity that is the subject of the procedure, etc. Based on such contextual information related to the surgical procedure, the surgical system can, for example, control a paired surgical instrument 23102 or a component thereof (e.g., 23110, 23120, and/or 23130) and/or provide contextualized information or suggestions to a surgeon throughout the course of the surgical procedure (e.g., via user interface 23118, 23128, 23138, 23148 and/or 23158). Additional details regarding situational awareness can be found, for example, above under the heading "Situational Awareness."

Also in FIG. 89, according to one aspect, a situationally aware surgical hub 23140 is paired (e.g., wirelessly) with a surgical instrument 23102 being utilized to perform a surgical procedure. In such an aspect, the surgical instrument 23102 may comprise an end effector assembly 23130, including a first jaw, a second jaw pivotably coupled to the first jaw, and a sensor 23134 configured to detect a parameter associated with a function (e.g., dissect, clamp, coagulate, cut, staple, etc.) of the end effector assembly 23130 and to transmit the detected parameter to a control circuit 23142 of the surgical hub 23140.

Further, in such an aspect, the surgical instrument 23102 may further comprise a shaft assembly 23120 including a sensor 23124 configured to detect a parameter associated with a function (e.g., rotation, articulation, etc.) of the shaft assembly 23120 and to transmit the detected parameter to the control circuit 23142 of the surgical hub 23140. Notably, it should be appreciated that a sensor, as referenced herein and in other disclosed aspects, may comprise a plurality of sensors configured to detect a plurality of parameters associated with a plurality of end effector assembly and/or shaft assembly functions. As such, further, in such an aspect, the surgical hub control circuit 23142 may be configured to receive detected parameters (e.g., sensor data) from such sensors 23134 and/or 23124 throughout the course of the surgical procedure.

A detected parameter can be received each time an associated end effector assembly 23130 function (e.g., dissection, clamping, coagulation, cutting, stapling, etc.) and/or an associated shaft assembly 23120 function (e.g., rotating, articulating, etc.) is performed. The surgical hub control circuit 23142 may be further configured to receive data from an internal database (e.g., a surgical hub database 23149) and/or an external database (e.g., from a cloud database 23150) throughout the course of the surgical procedure. According to various aspects, the data received from the internal and/or external databases may comprise procedural data (e.g., steps to perform the surgical procedure) and/or historical data (e.g., data indicating expected parameters based on historical data associated with the surgical procedure).

In various aspects, the procedural data may comprise current/recognized standard-of-care procedures for the surgical procedure and the historical data may comprise preferred/ideal parameters and/or preferred/ideal parameter ranges based on historical data associated with the surgical procedure (e.g., system-defined constraints). Based on the received data (e.g., sensor data, internal and/or external data, etc.), the surgical hub control circuit 23142 may be configured to continually derive inferences (e.g., contextual information) about the ongoing surgical procedure. Namely, the situationally aware surgical hub may be configured to, for example, record data pertaining to the surgical procedure for generating reports, verify the steps being taken by the surgeon to perform the surgical procedure, provide data or prompts (e.g., via a user interface associated with the surgical hub and/or the surgical instrument, e.g., 23148, 23158, 23118, 23128, and/or 23138) that may be pertinent for a particular procedural step, control a surgical instrument function, etc. According to various aspects, the situationally aware surgical hub 23140 may (e.g., after an initial surgical function of the end effector assembly 23130 or the shaft assembly 23120 is performed) infer a next surgical function to be performed based on procedural data received from an internal database 23149 and/or an external database 23150.

Further, in such an aspect, the situationally aware surgical hub 23140 may evaluate detected parameters (e.g., received from sensors 23134 and/or 23124 in response to the initial surgical function) based on historical data received from the internal database 23149 and/or the external database 23150 (e.g., preferred/ideal parameters). Here, if the detected parameters do not exceed the preferred/ideal parameters and/or are within respective preferred/ideal parameter ranges, the situationally aware surgical hub 23140 may permit the next surgical function to be performed and/or not prevent/control the next surgical function from being performed. Alternatively, if the detected parameters do exceed the preferred/ideal parameters and/or are not within respective preferred/ideal parameter ranges, the situationally aware surgical hub 23140 may proactively prevent the next surgical function from being performed.

According to another aspect of the present disclosure, the situationally aware surgical hub 23140 may receive a communication (e.g., from a component, e.g., 23130 and/or 23120, of the surgical instrument 23102) that a particular surgical function is being attempted/requested/actuated. In such an aspect, the situationally aware surgical hub 23140 may compare that particular surgical function to an inferred next surgical function to ensure that current/recognized standard-of-care procedures are being adhered to. If so, the situationally aware surgical hub 23140 may then evaluate detected parameters (e.g., as described) before permitting that particular surgical function to proceed (as described). If not, the situationally aware surgical hub 23140 may prevent that particular surgical function from being performed or prevent that particular surgical function from being performed until an override is received (e.g., via a user interface 23, 158, 23148, 23138, 23128 and/or 23118, see, e.g., FIG. 88, selectable user interface element 23012). In such an aspect, if the override is received, the situationally aware surgical hub 23140 may then evaluate detected parameters before permitting that particular surgical function to proceed (as described).

Referring again to FIG. 89, according to another aspect, a situationally aware surgical instrument 23102 may be utilized to perform a surgical procedure. In such an aspect, the surgical instrument 23102 may comprise a handle assembly 23110, a shaft assembly 23120, and an end effector assembly 23130. The end effector assembly 23130 may include a first jaw, a second jaw pivotably coupled to the first jaw, and a sensor 23134 configured to detect a parameter associated with a function (e.g., dissect, clamp, coagulate, cut, staple, etc.) of the end effector assembly 23130 and to transmit the detected parameter to a control circuit (23112, 23122, 23132 and/or 23142, e.g., in phantom to show optional location(s)).

For example, in such an aspect, the detected parameter may be transmitted to a control circuit 23132 of the end effector assembly 23130. Here, the end effector assembly control circuit 23132 may be configured to receive detected parameters (e.g., sensor data) from the sensor 23134 throughout the course of the surgical procedure. A detected parameter can be received each time an associated end effector assembly 23130 function (e.g., dissection, clamping, coagulation, cutting, stapling, etc.) is performed.

The end effector assembly 23130 may be further configured to receive data from an internal database (e.g., end effector memory 23136) and/or an external database (e.g., from a cloud database 23150 via a surgical hub 23140, from a surgical hub database 23149, etc.) throughout the course of the surgical procedure. According to various aspects, the data received from the internal and/or external databases may comprise staple cartridge data (e.g., sizes and/or types of staples associated with a staple cartridge positioned in the end effector assembly) and/or historical data (e.g., data indicating expected tissues and/or types of tissues to be stapled with those sizes and/or types of staples based on historical data). In various aspects, the received data may comprise preferred/ideal parameters and/or preferred/ideal parameter ranges associated with those sizes and/or types of staples or those expected tissues and/or tissue types, based on historical data (e.g., system-defined constraints). Based on the received data (e.g., sensor data, internal and/or external data, etc.), the end effector control circuit 23132 may be configured to continually derive inferences (e.g., contextual information) about the ongoing surgical procedure. Notably, according to an alternative aspect, the sensor 23134 of the end effector assembly 23130 may transmit the detected parameter to a control circuit (e.g., 23112 and/or 23122) associated with another surgical instrument 23102 component, for example, the handle assembly 23110 and/or the shaft assembly 23120. In such an aspect, that other surgical instrument component control circuit (e.g., 23112 and/or 23122) may be similarly configured to perform the various aspects of the end effector control circuit 23132 as described above. Furthermore, according to various aspects, the shaft assembly 23120 of the surgical instrument 23102 may include a sensor 23124 configured to detect a parameter associated with a function (e.g., rotation, articulation, etc.) of the shaft assembly 23120 and to transmit the detected parameter to a control circuit (e.g., 23112) similarly configured to perform the various aspects of the end effector control circuit 23132 as described above. In end, the situationally aware surgical instrument 23102 may be configured to, for example, alert its user of a discrepancy (e.g., via a user interface 23138 of the end effector assembly 23130, via a user interface (e.g., 23128 and/or 23118) of another surgical instrument 23102 component, for example, the shaft assembly 23120 and/or the handle assembly 23110, and/or via a user interface 23148 and/or 23158 associated with a surgical hub 23140 coupled to the surgical instrument 23102). For example, the discrepancy may include that a detected parameter exceeds a preferred/ideal parameter and/or a preferred/ideal parameter range associated with those sizes and/or types of staples or those expected tissues and/or tissue types. As a further example, the situationally aware surgical instrument 23102 may be configured to control a surgical instrument 23102 function based on the discrepancy. In accordance with at least one aspect, the situationally aware surgical instrument 23102 may prevent a surgical function based on a discrepancy.

Situationally Aware Functionality Control

As highlighted herein, various aspects of the present disclosure pertain to a surgical instrument performing a function (e.g., clamping), detecting a parameter associated with that function, using situational awareness aspects to assess, via a control circuit, whether that detected parameter is below or exceeds a predefined parameter (e.g., considered ideal/preferred) or is below or exceeds a predefined range (e.g., considered normal) for that parameter, and performing an action (i.e., stop a function(s), alert the user, inform the user of possible causes, etc.) in response to the detected parameter being outside the predefined parameter and/or predefined parameter/range. For example, FIG. 90 illustrates an algorithm 23200 to implement such aspects wherein a control circuit receives a detected parameter(s) associated with a surgical function performed by a surgical instrument 23202 and retrieves situational awareness data from an internal and/or external database 23204. The control circuit then evaluates the detected parameter(s) in view of the situational awareness data 23206 and performs an action based on the evaluation 23208.

According to various aspects of the present disclosure, a force detected (e.g., via one or more than one sensor) at the jaws of an end effector assembly may be of a magnitude that prohibits one or more than one subsequent/further functionality of the end effector assembly from being performed. For example, referring back to FIG. 12, the force may be detected via sensors 474, 476, and/or 478. In such an aspect, sensor 474 may be a strain gauge coupled to the end effector wherein the strain gauge is configured to measure the magnitude/amplitude of strain on a jaw(s) of the end effector, which is indicative of closure forces being applied to the jaw(s). Further, in such an aspect, sensor 476 may be a load sensor configured to measure a closure force applied to the jaws by a closure drive system. Yet further, in such an aspect, sensor 478 may be a current sensor configured to measure a current drawn by the motor, which correlates to a closure force applied to the jaws. In addition to or as a further example, referring back to FIG. 17, the force may be detected via sensors **744*a* and/or 744*b*. In such an aspect, sensor 744*a* and/or 744*b*** may be a torque sensor configured to provide a firing force feedback signal representing the closure force being applied to the jaws by a closure drive system.

In one aspect, referring back to FIG. 58, a load sensor 152082 (e.g., positioned in the shaft assembly or the handle assembly) may be configured to detect a load, after attachment of the shaft assembly to the handle assembly. In such an aspect, the detected load may exceed a predefined load and/or a predefined load range. In such an aspect, referring to FIG. 89, for example, a control circuit associated with the surgical instrument (e.g., integrated in a component of the surgical instrument 23132, 23122, and/or 23112 or a coupled surgical hub 23142) may assess that detected load and determine, using situational awareness (e.g., based on historical data), that the shaft assembly and/or the end effector assembly is/must be damaged. In such an aspect, the control circuit may be configured to record a unique identifier associated with the shaft assembly 23120 and/or the end effector assembly 23130 and designate that unique identifier as prohibited from further use and/or attachment to the handle assembly 23110.

In another aspect, referring to FIG. 89, for example, a control circuit associated with the surgical instrument (e.g., integrated in a component of the surgical instrument 23132, 23122, and/or 23112 or a coupled surgical hub 23142) may be configured to assess a force detected/sensed at the jaws (e.g., via one or more than one sensor as described) and determine to prevent a firing function/cycle of the end effector assembly. In particular, the control circuit may determine, using situational awareness (e.g., based on historical data), that the force detected/sensed at the jaws (e.g., detected before a firing function/cycle commences) exceeds a predefined force and/or a predefined force range. In such an aspect, the control circuit may be configured to prevent the firing function/cycle from commencing. Further, in such an aspect, referring again to FIG. 89, the control circuit may be configured to alert the user (e.g., via a user interface of a component of the surgical instrument 23138, 23128, and/or 23118 and/or a user interface associated with a surgical hub 23148 and/or 23158) that the firing function/cycle cannot be performed and/or inform the user of possible causes (e.g., so that the user can attempt to reduce the force detected/sensed at the jaws). According to various aspects, the control circuit may be configured to permit the firing function/cycle to commence if the force detected/sensed at the jaws is reduced to the predefined force and/or within the predefined force range.

In another aspect, referring to FIG. 89, for example, a control circuit associated with the surgical instrument (e.g., integrated in a component of the surgical instrument 23132, 23122, and/or 23112 or a coupled surgical hub 23142) may assess a force detected/sensed at the jaws (e.g., via one or more than one sensor, e.g., a load sensor, a torque sensor, etc., as described) and initially determine to permit a firing function/cycle of the end effector assembly. However, after commencing the firing function/cycle, the control circuit may determine, using situational awareness (e.g., based on historical data), that a force-to-fire (e.g., detected during the firing function/cycle) exceeds a predefined force-to-fire and/or a predefined force-to-fire range. In such an aspect, the control circuit may be configured to stop the firing function/cycle (e.g., prevent the firing function/cycle from continuing). Further, in such an aspect, referring again to FIG. 89, the control circuit may be configured to provide an alert to the surgeon (e.g., via a user interface of a component of the surgical instrument 23138, 23128, and/or 23118 and/or a user interface associated with a surgical hub 23148 and/or 23158) regarding the exceeded force-to-fire or force-to-fire range. According to various aspects, the control circuit may be further configured to receive an override command (e.g., via the user interface(s), see, e.g., FIG. 88, selectable user interface element 23012) to permit the firing function/cycle to continue. In such an aspect, the control circuit may determine, using situational awareness (e.g., based on historical data), that a second force-to-fire (e.g., detected during the continued firing function/cycle) exceeds a second predefined force-to-fire and/or a second predefined force-to-fire range (e.g., higher thresholds). In such an aspect, the control circuit may be configured to again stop the firing function/cycle, alert the surgeon, and/or receive an override command as described.

In another aspect, referring to FIG. 89, for example, a control circuit associated with the surgical instrument (e.g., integrated in a component of the surgical instrument 23132, 23122, and/or 23112 or a coupled surgical hub 23142) may assess a force detected/sensed at the jaws (e.g., via one or more than one sensor as described). In addition, the control circuit may further assess a force detected/sensed within the shaft assembly (i.e., via one or more than one sensor as described). Here, according to various aspects, the control circuit may cross-reference the force detected/sensed at the jaws and/or the force detected/sensed within the shaft assembly with the surgical procedure being performed. According to such an aspect, the control circuit may determine, using situational awareness (e.g., based on procedural and/or historical data), that the force detected/sensed within the shaft assembly exceeds a predefined shaft force and/or a predefined shaft force range. In one example, the shaft assembly may comprise a specialty shaft assembly configured for use with a particular tissue type in a particular surgical procedure. In such an aspect, the control circuit may determine, using situational awareness (e.g., based on procedural and/or historical data), that the force detected/sensed within the specialty shaft assembly is too high (e.g., exceeds the predefined shaft force and/or the predefined shaft force range associated with the specialty shaft assembly) and/or that the force detected/sensed at the jaws is not a predefined force and/or within an predefined range (e.g., an expected force historically associated with the surgical procedure being performed). In such an aspect, the control circuit may be configured to stop a firing function/cycle (e.g., prevent the firing function/cycle from commencing and/or continuing). Further, in such an aspect, referring again to FIG. 89, the control circuit may be configured to provide an alert to the surgeon (e.g., via a user interface of a component of the surgical instrument 23138, 23128, and/or 23118 and/or a user interface associated with a surgical hub 23148 and/or 23158) regarding the exceeded shaft force and/or shaft force range. In various aspects, the alert may inform the surgeon to consider detaching the specialty shaft assembly, e.g., 23120, from the handle assembly 23110 and attaching another shaft assembly (e.g., a regular reload configured for the forces detected/sensed and the tissue being encountered) to the handle assembly 23110. In such an aspect, the control circuit may be configured to permit the firing function/cycle to commence and/or continue when an appropriate shaft assembly is attached.

In another aspect, referring to FIG. 89, for example, a control circuit associated with the surgical instrument (e.g., integrated in a component of the surgical instrument 23132, 23122, and/or 23112 or a coupled surgical hub 23142) may assess a force detected/sensed at the jaws (e.g., via one or more than one sensor as described) during a surgical procedure. According to such an aspect, the control circuit may determine, using situational awareness (e.g., based on procedural and/or historical data), that a tissue creep wait time is below a predefined creep wait time and/or predefined creep wait time range associated with a particular thickness and a particular tissue being clamped during the surgical procedure. Stated differently, in light of FIGS. 83 and 84 herein, an initial force-to-close may have decayed and reached creep stability at a lower force-to-close quicker than expected. In such an aspect, the control circuit may be configured to stop a firing function/cycle (e.g., prevent the firing function/cycle from commencing and/or continuing). Further, in such an aspect, referring again to FIG. 89, the control circuit may be configured to provide an alert to the surgeon (e.g., via a user interface of a component of the surgical instrument 23138, 23128 and/or 23118 and/or a user interface associated with a surgical hub 23148 and/or 23158) regarding the abbreviated creep wait time. In various aspects, the alert may inform the surgeon to consider detaching the end effector assembly, e.g., 23130 from the handle assembly and attaching another end effector assembly (e.g., an end effector assembly configured to treat tissue having the detected creep wait time) to the handle assembly 23110. In such an aspect, the control circuit may be configured to permit the firing function/cycle to commence and/or continue when an appropriate end effector assembly is attached.

In another aspect, referring to FIG. 89, for example, a control circuit associated with the surgical instrument (e.g., integrated in a component of the surgical instrument 23132, 23122, and/or 23112 or a coupled surgical hub 23142) may assess a force detected/sensed at the jaws (e.g., via one or more than one sensor as described). In addition, the control circuit may further assess a position detected/sensed for an articulation member (i.e., via one or more than one sensor). For example, referring back to FIG. 12, the position may be detected/sensed by sensor 472 coupled to the articulation member. In one aspect, sensor 472 may be a position sensor configured to measure linear displacement wherein a single rotation of a sensor element corresponds to a specific linear displacement of the articulation member. In another example, referring back to FIG. 17, the positon may be detected/sensed by position sensor 734 located in the end effector. Here, position sensor 734 may be a proximity sensor or a sensor configured to provide a series of pulses trackable by the control circuit to determine a positon of the articulation member. Here, according to various aspects, the control circuit may cross-reference the force detected/sensed at the jaws and/or the position detected/sensed for the articulation member with the surgical procedure being performed. According to such an aspect, the control circuit may determine, using situational awareness (e.g., based on procedural and/or historical data), that the position detected/sensed for the articulation member indicates that the articulation member has advanced (e.g., within the shaft assembly) beyond a predetermined advancement position and/or a predetermined advancement position range. In various aspects, the predetermined advancement position and/or the predetermined advancement position range may be correlated to the force-to-close detected/sensed at the jaws. In such an aspect, with the designated predetermined advancement position exceeded, the control circuit may be configured to stop a firing function/cycle (e.g., prevent the firing function/cycle from commencing and/or continuing). Further, in such an aspect, referring again to FIG. 89, the control circuit may be configured to provide an alert to the surgeon (e.g., via a user interface of a component of the surgical instrument 23138, 23128 and/or 23118 and/or a user interface associated with a surgical hub 23148 and/or 23158) regarding the exceeded advancement position and/or advancement position range. In various aspects, the alert may inform the surgeon to consider retracting the articulation member to the predetermined advancement position and/or within the predetermined advancement position range. Here, in one example, the predetermined advancement position and/or predetermined advancement position range may have historically realized desired and/or successful firing functions/cycles for the corresponding force-to close. In such an aspect, the control circuit may be configured to permit the firing function/cycle to commence and/or continue when an appropriate advancement position is achieved.

In another aspect, referring to FIG. 89, for example, a control circuit associated with the surgical instrument (e.g., integrated in a component of the surgical instrument 23132, 23122, and/or 23112 or a coupled surgical hub 23142) may assess a force detected/sensed at the jaws (e.g., via one or more than one sensor as described) during a surgical procedure. According to such an aspect, the control circuit may determine, using situational awareness (e.g., based on procedural and/or historical data), that a force-to-close is above a predefined force-to-close and/or predefined force-to-close range associated with a particular tissue being clamped during the surgical procedure. Stated differently, in light of FIGS. 83 and 84 herein, the detected/sensed force-to-close is higher than expected to permit a firing function/cycle to proceed. In such an aspect, the control circuit may be configured to stop a firing function/cycle (e.g., prevent the firing function/cycle from commencing and/or continuing). Further, in such an aspect, referring again to FIG. 89, the control circuit may be configured to provide an alert to the surgeon (e.g., via a user interface of a component of the surgical instrument 23138, 23128, and/or 23118 and/or a user interface associated with a surgical hub 23148 and/or 23158) regarding the elevated force-to-close. In various aspects, the alert may inform the surgeon to consider adjusting a firing motor speed. In one example, if the particular tissue is stiff tissue, the alert may suggest that the surgeon adjust the firing motor speed down to avoid tearing the stiff tissue. In such an aspect, the downward adjustment may be based on historical data associated with the surgical procedure being performed. In another example, if the particular tissue is squishy tissue of weak shear strength, the alert may suggest that the surgeon adjust the firing motor speed up to ensure that the tissue is properly clamped. In such an aspect, the upward adjustment may be based on historical data associated with the surgical procedure being performed. In such aspects, the control circuit may be configured to permit the firing function/cycle to commence and/or continue when an appropriate firing motor speed is set.

In another aspect, referring to FIG. 89, for example, a control circuit associated with the surgical instrument (e.g., integrated in a component of the surgical instrument 23132, 23122, and/or 23112 or a coupled surgical hub 23142) may assess a force detected/sensed at the jaws (e.g., via one or more than one sensor as described) during a surgical procedure. According to such an aspect, the control circuit may determine, using situational awareness (e.g., based on procedural and/or historical data), that a cyclic force on the firing system is above a predefined cyclic force and/or predefined cyclic force range during the surgical procedure. Stated differently, the detected/sensed cyclic force is higher than expected and may be indicative of impending motor failure based on historical data. In such an aspect, the control circuit may be configured to stop a firing function/cycle (e.g., prevent the firing function/cycle from commencing and/or continuing advancement). Further, in such an aspect, referring again to FIG. 89, the control circuit may be configured to provide an alert to the surgeon (e.g., via a user interface of a component of the surgical instrument 23138, 23128, and/or 23118 and/or a user interface associated with a surgical hub 23148 and/or 23158) regarding the elevated cyclic force and possible motor failure. According to various aspects, the control circuit may be further configured to receive an override command (e.g., via the user interface, see, e.g., FIG. 88, selectable user interface element 23012) to permit the firing function/cycle to continue. In such an aspect, the control circuit may continue to monitor whether the cyclic force on the firing system is above the predefined cyclic force and/or predefined cyclic force range during the surgical procedure. In such an aspect, the control circuit may be configured to again stop the firing function/cycle, alert the surgeon, and/or receive an override command as described.

According to another aspect of the present disclosure, referring to FIG. 89, for example, a control circuit associated with the surgical instrument (e.g., integrated in a component of the surgical instrument 23132, 23122, and/or 23112 or a coupled surgical hub 23142) may assess a force detected/sensed at the jaws (e.g., via one or more than one sensor as described). In addition, the control circuit may further assess a force/torque to articulate the end effector assembly 23130. In such an aspect, the articulation force/torque may be detected via one or more than one sensor (e.g., a force sensor associated with an articulation member, a torque sensor associated with the articulation member, a current sensor associated with a motor configured to drive the articulation member, etc.). For example, referring back to FIG. 17, the articulation force/torque may be detected/sensed by torque sensors **744*d* and/or 744*e* coupled to an articulation drive system. In addition to and/or alternatively, referring again to FIG. 17, the articulation force/torque may be correlated to a current drawn by motors 704*d* and/or 704*e* as measured by sensor 736. Here, according to various aspects, the control circuit may cross-reference the force detected/sensed at the jaws and/or the articulation force/toque detected for the articulation member with the surgical procedure being performed. According to such an aspect, the control circuit may determine, using situational awareness (e.g., based on procedural and/or historical data), that the articulation force/torque detected for the articulation member exceeds a predefined articulation force/torque and/or a predefined articulation force/torque range. In various aspects, the predefined articulation force/torque and/or the predefined articulation force/torque range may be correlated to the force detected/sensed at the jaws. In such an aspect, with a designated articulation force/torque exceeded, the control circuit may be configured to stop articulations of the end effector assembly (e.g., to prevent articulations from continuing). Further, in such an aspect, referring again to FIG. 89, the control circuit may be configured to provide an alert to the surgeon (e.g., via a user interface of a component of the surgical instrument 23138, 23128, and/or 23118 and/or a user interface associated with a surgical hub 23148 and/or 23158) regarding the exceeded articulation force/torque and/or articulation force/torque range. According to various aspects, the control circuit may be further configured to receive an override command (e.g., via the user interface, see, e.g., FIG. 88, selectable user interface element 23012**) to permit the articulating to continue. In such an aspect, the control circuit may continue to monitor whether the articulation force/torque is above the predefined articulation force/torque and/or the predefined articulation force/torque range during the surgical procedure. In such an aspect, the control circuit may be configured to again stop the articulating, alert the surgeon, and/or receive an override command as described.

According to yet another aspect of the present disclosure, referring to FIG. 89, for example, a control circuit associated with the surgical instrument (e.g., integrated in a component of the surgical instrument 23132, 23122, and/or 23112 or a coupled surgical hub 23142) may assess a force detected/sensed at the jaws (e.g., via one or more than one sensor as described). In addition, the control circuit may further assess a force/torque to rotate the shaft assembly 23120 (e.g., shaft member). In such an aspect, the rotation force/torque may be detected via one or more than one sensor (e.g., a force sensor associated with a rotation/shaft member, a torque sensor associated with the rotation/shaft member, a current sensor associated with a motor configured to rotate the rotation/shaft member, etc.). For example, referring back to FIG. 17, the rotation force/torque may be detected/sensed by torque sensor 744*c* coupled to a rotation/shaft member drive system. In addition to and/or alternatively, referring again to FIG. 17, the rotation force/torque may be correlated to a current drawn by motor 704*c* as measured by sensor 736. Here, according to various aspects, the control circuit may cross-reference the force detected/sensed at the jaws and/or the rotation force/toque detected for the rotation/shaft member with the surgical procedure being performed. According to such an aspect, the control circuit may determine, using situational awareness (e.g., based on procedural and/or historical data), that the rotation force/torque detected for the rotation/shaft member exceeds a predefined rotation force/torque and/or a predefined rotation force/torque range. In various aspects, the predefined rotation force/torque and/or the predefined rotation force/torque range may be correlated to the force detected/sensed at the jaws. In other aspects, the predefined rotation force/torque and/or the predefined rotation force/torque range may correspond to a force/torsion the rotation/shaft member itself is able to withstand. In such an aspect, with a designated rotation force/torque exceeded, the control circuit may be configured to stop rotation of the shaft assembly (e.g., to prevent rotations of the rotation/shaft member from continuing). Further, in such an aspect, referring again to FIG. 89, the control circuit may be configured to provide an alert to the surgeon (e.g., via a user interface of a component of the surgical instrument 23138, 23128, and/or 23118 and/or a user interface associated with a surgical hub 23148 and/or 23158) regarding the exceeded rotation force/torque and/or rotation force/torque range. According to various aspects, the control circuit may be further configured to receive an override command (e.g., via the user interface, see, e.g., FIG. 88, selectable user interface element 23012) to permit the rotating to continue. In such an aspect, the control circuit may continue to monitor whether the rotation force/torque is above the predefined rotation force/torque and/or the predefined rotation force/torque range during the surgical procedure. In such an aspect, the control circuit may be configured to again stop the rotating, alert the surgeon, and/or receive an override command as described.

According to yet another aspect of the present disclosure, referring to FIG. 89, for example, a control circuit associated with the surgical instrument (e.g., integrated in a component of the surgical instrument 23132, 23122, and/or 23112 or a coupled surgical hub 23142) may be configured to assess an opening force detected/sensed at the jaws (e.g., via one or more than one sensor as described) and determine to prevent the jaws from opening. In particular, the control circuit may determine, using situational awareness (e.g., based on historical data), that the opening force detected/sensed at the jaws exceeds a predefined opening force and/or a predefined opening force range. In such an aspect, the control circuit may be configured to maintain the jaws in a clamped or partially clamped position. Further, in such an aspect, referring again to FIG. 89, the control circuit may be configured to alert the user (e.g., via a user interface of a component of the surgical instrument 23138, 23128, and/or 23118 and/or a user interface associated with a surgical hub 23148 and/or 23158) that the jaws cannot be opened and/or inform the user of possible causes (e.g., so that the user can attempt to reduce the opening force detected/sensed at the jaws). According to various aspects, the control circuit may be configured to permit the jaws to open if the opening force detected/sensed at the jaws is reduced to the predefined opening force and/or within the predefined opening force range.

Short Detection and Functionality Control

According to various other aspects of the present disclosure, the functionality of a surgical instrument may be controlled based on one or more than one sensor configured to detect a short. Namely, if a metallic object is detected within the jaws, at least one surgical instrument function/actuation (e.g., cutting, coagulation, etc.) may me prevented/prohibited. For example, FIG. 91 illustrates an algorithm 23300 to implement such aspects wherein a control circuit receives a detected parameter(s) indicative of a short 23302. The control circuit may also retrieve internal and/or external database data 23304. The control circuit then evaluates the detected parameter(s) and/or the database data 23306 and performs an action based on the evaluation 23308.

Referring again to FIG. 89, according to aspects of the present disclosure, a surgical system 23100 may comprise a control circuit (23112, 23122, 23132, and/or 23142, e.g., in phantom to show optional location(s)), a user interface (23118, 23128, 23138, 23148, and/or 23158, e.g., in phantom to show optional locations), and a surgical instrument 23100, including, for example, a handle assembly 23110, a shaft assembly 23120, and an end effector assembly 23130. In such aspects, the control circuit may be integrated into one or more than one component (e.g., the handle assembly 23110, the shaft assembly 23120, and/or end effector assembly 23130, etc.) of the surgical instrument 23102 (e.g., 23112, 23122, and/or 23132) and/or integrated into a surgical hub 23140 (e.g., 23142) paired (e.g., wirelessly) with the surgical instrument 23102. In such aspects, the end effector assembly 23130 may include a first jaw, a second jaw pivotably coupled to the first jaw, and a sensor 23134 configured to detect a parameter associated with a function (e.g., dissect, clamp, coagulate, cut, staple, etc.) of the end effector assembly 23130 and to transmit the detected parameter to the control circuit (e.g., 23112, 23122, 23132, and/or 23142). In various aspects, the first jaw may comprise an anvil and the second jaw may comprise an elongated channel configured to receive a staple cartridge. Further, in such an aspect, the surgical instrument 23102 may further comprise a shaft assembly 23120, including a sensor 23124 configured to detect a parameter associated with a function (e.g., rotation, articulation, etc.) of the shaft assembly 23120 and to transmit the detected parameter to the control circuit (e.g., 23112, 23122, 23132, and/or 23142). In such aspects, the control circuit may be configured to receive detected parameters (e.g., sensor data) from such sensors, e.g., 23134 and/or 23124, throughout the course of a surgical procedure. A detected parameter can be received each time an associated end effector assembly 23130 function (e.g., dissection, clamping, coagulation, cutting, stapling, etc.) and/or an associated shaft assembly 23120 function (e.g., rotating, articulating, etc.) is performed. The control circuit may be further configured to receive data from an internal database (e.g., in memory of a component of the surgical instrument 23136, 23126, and/or 23116 or a surgical hub database 23149) and/or an external database (e.g., from a surgical hub database 23149, a cloud database 23150, etc.) throughout the course of the surgical procedure. According to various aspects, the data received from the internal and/or external databases may comprise procedural data (e.g., steps to perform the surgical procedure) and/or historical data (e.g., data indicating expected parameters based on historical data associated with the surgical procedure). In various aspects, the procedural data may comprise current/recognized standard-of-care procedures for the surgical procedure and the historical data may comprise preferred/ideal parameters and/or preferred/ideal parameter ranges based on historical data associated with the surgical procedure (e.g., system-defined constraints). Based on the received data (e.g., sensor data, internal and/or external data, etc.), the control circuit (e.g., 23112, 23122, 23132, and/or 23142) may be configured to continually derive inferences (e.g., contextual information) about the ongoing procedure. Namely, the surgical instrument may be configured to, for example, record data pertaining to the surgical procedure for generating reports, verify the steps being taken by the surgeon to perform the surgical procedure, provide data or prompts (e.g., via a user interface associated with the surgical hub 23148 and/or 23158 and/or the surgical instrument 23138, 23128, and/or 23118) that may be pertinent for a particular procedural step, control a surgical instrument 23102 function, etc.

Referring back to FIG. 89, in one aspect, during and/or after clamping targeted tissue between the jaws of the end effector assembly, the control circuit (23112, 23122, 23132, and/or 23142) may be configured to, before permitting a subsequent function (e.g., firing, coagulation, etc.), check for continuity between the jaws. Here, according to various aspects, the surgical instrument may comprise an electrosurgical instrument comprising an electrode in at least one of the jaws (e.g., integrated with the anvil and/or the staple cartridge). In such aspects, if a short exists between the electrodes, it may be difficult to treat tissue grasped between the jaws with electrosurgical energy (e.g., RF energy). In one example, a conductive object (e.g., a clip, a staple, metal element, etc.) between the electrodes may result in continuity between the jaws. In another example, if a sufficient gap does not exist between the jaws (e.g., after clamping the targeted tissue) the electrodes may touch resulting in continuity between the jaws. Referring back to FIG. 53, for example, in one aspect of the present disclosure sensor 152008*a* is configured to measure a gap between the end effector jaws. In such an aspect, sensor 152008*a* of the first jaw may comprise a Hall-effect sensor configured to detect a magnetic field generated by magnet 152012 of the second jaw to measure the gap between the first jaw and the second jaw. Notably, the gap may be representative of the thickness of tissue clamped between the first jaw and the second jaw. Here, if continuity exists between the jaws, an undesired surgical outcome may result (e.g., incomplete tissue treatment, excessive heating of the conductive object, etc.).

According to one aspect (e.g., bipolar mode), the first jaw may comprise an anvil and the second jaw may comprise an elongated channel configured to receive a staple cartridge, such as is depicted in FIG. 25. In one example, the staple cartridge may comprise an active electrode to deliver electrosurgical energy (e.g., RF energy) to the grasped tissue and at least a portion of the anvil may act as a return electrode. In another example, the anvil may comprise an active electrode to deliver electrosurgical energy (e.g., RF energy) to the grasped tissue and at least a portion of the elongated channel may act as a return electrode. According to another aspect (e.g., monopolar mode), the first jaw may comprise an anvil and the second jaw may comprise an elongated channel configured to receive a staple cartridge. In one example, the staple cartridge may comprise an active electrode to deliver electrosurgical energy (e.g., RF energy) to the grasped tissue and a return electrode (e.g., grounding pad) may be separately located on the patient's body. In another example, the anvil may comprise an active electrode to deliver electrosurgical energy (e.g., RF energy) to the grasped tissue and a return electrode (e.g., grounding pad) may be separately located on the patient's body. Various configurations for detecting short circuits are described in U.S. Pat. No. 9,554,854, titled DETECTING SHORT CIRCUITS IN ELECTROSURGICAL MEDICAL DEVICES, the entire disclosure of which is incorporated herein by reference.

Referring again to FIG. 89, according to various aspects, the control circuit (23112, 23122, 23132, and/or 23142) may be configured to check for continuity in numerous ways. In one aspect, a generator producing the electrosurgical energy and/or a sensor, e.g., 23134, integrated in the surgical instrument may be configured to detect when impedance between the electrodes falls below a threshold value for a threshold time period (i.e., impedance drop indicative of a short). Here, referring back to FIG. 48, sensor, e.g., 23134, may be configured to measure impedance over time. In one example, when the electrodes encounter a line of conducting staples, the current may spike, while impedance and voltage drop sharply. In another example, continuity may present as a current sink with minimal changes in voltage. Various alternate methods for checking continuity/detecting a short, such as those described in U.S. Pat. No. 9,554,854, titled DETECTING SHORT CIRCUITS IN ELECTROSURGICAL MEDICAL DEVICES, are expressly incorporated herein by reference (e.g., comparing impedance values at different positions within a pulse of a series of pulses).

In such aspects, if continuity is detected, a conductive object (e.g., a clip, a staple, a staple line, metal element, etc.) may be present/exposed in the tissue grasped between the jaws. Notably, such a conductive object may be from the current surgical procedure and/or a previous surgical procedure. In such an aspect, the control circuit may be configured to provide an alert to the surgeon (e.g., via a user interface of a component of the surgical instrument 23138, 23128, and/or 23118 and/or a user interface associated with a surgical hub 23148 and/or 23158) regarding the detection of the conductive object. For example, the alert may suggest that the surgeon reposition the end effector assembly 23130 such that the electrodes are not in contact with any conductive object and/or remove the conductive object causing the short. According to various aspects, the control circuit may be further configured to receive an override command (e.g., via the user interface, see, e.g., FIG. 88, selectable user interface element 23012) to permit the subsequent function (e.g., cutting, coagulation, etc.) despite the detection of the conductive object (e.g., clip, staple, staple line, metal element, etc.).

According to one aspect, the control circuit (23112, 23122, 23132, and/or 23142) may be configured to check for continuity to avoid transecting clips. In such an aspect, after a short being detected, the control circuit may be configured to provide an alert to the surgeon (e.g., via a user interface of a component of the surgical instrument 23138, 23128, and/or 23118 and/or a user interface associated with a surgical hub 23148 and/or 23158) regarding the detection of a conductive object between the jaws. In one aspect, the surgeon may adjust the sensitivity of the control circuit via a user interface (e.g., an interactive user interface element on the surgical instrument, the surgical hub, a generator, etc.). In such an aspect, based on the adjustment, the control circuit may be configured to prevent firing if a conductive object is detected between the jaws.

Referring again to FIG. 89, according to another aspect, the control circuit 23142 may be integrated into a surgical hub 23140 paired (e.g., wirelessly) with the electrosurgical instrument 23102. In such an aspect, the surgical hub 23140 may be preloaded with surgeon/user settings regarding the detection of a conductive object between the jaws. In one example, a surgeon/user setting comprises preventing firing if a conductive object is detected between the jaws. In another example, a surgeon/user setting comprises alerting before permitting firing if a conductive object is detected between the jaws. In yet another aspect, a surgeon/user setting comprises permitting surgeon/user override of an alert. In yet another aspect, a surgeon/user setting comprises a temporary reset permitting the surgeon/user to remedy the situation (e.g., move the jaws, remove the conductive object) before again checking for continuity.

Referring again to FIG. 89, according to yet another aspect, the control circuit (23112, 23122, 23132, and/or 23142) may be configured to check for continuity to deliberately cross a staple line. Here, in some surgical procedures, it may be beneficial to have crossing staple lines to ensure a contiguous transection (e.g., lung resections, especially wedges from multiple angles, sleeve procedures, etc.). In such an aspect, after continuity is detected, the control circuit may be configured to provide an alert (e.g., audible and/or visual cue) to the surgeon (e.g., via a user interface of a component of the surgical instrument 23138, 23128, and/or 23118 and/or a user interface associated with a surgical hub 23148 and/or 23158) regarding the detection of a conductive object (e.g., existing staple line) between the jaws.

Referring again to FIG. 89, according to other aspects, the control circuit (23112, 23122, 23132, and/or 23142) may be configured to receive data from an internal database (e.g., in memory of a component of the surgical instrument 23136, 23126, and/or 23116 or a surgical hub database 23149) and/or an external database (e.g., from a surgical hub database 23149, a cloud database 23150, etc.) throughout the course of the surgical procedure. According to various aspects, the data received from the internal and/or external databases may comprise surgical history data (e.g., data regarding previous surgical procedures performed on the patient, data regarding the current surgical procedure, etc.). In one example, the surgical history data may indicate that staples were used in a previous surgery and/or where the staples were used and the current surgical procedure data may indicate whether a clip applier has been used to apply clips. Based on the received data (e.g., surgical history data, etc.), the control circuit (23112, 23122, 23132, and/or 23142) may be configured to continually derive inferences (e.g., contextual information) about the ongoing procedure. Namely, the surgical instrument 23120 may be situationally aware and may be configured to, for example, infer/determine that a detected continuity may be a staple line from a previous surgical procedure or a clip from the current surgical procedure. As another example, if the patient has never had a surgical procedure performed, a clip applier has not been used in the current surgical procedure, and a staple cartridge has been fired in the current surgical procedure, the control circuit may be configured to infer/determine that the conductive object detected between the jaws is a previous staple line. As yet another example, if the patient has never had a surgical procedure performed, a clip applier has been used in the current procedure, and no staple cartridge has yet been fired in the current surgical procedure, the control circuit may be configured to infer/determine that the conductive object detected between the jaws is a clip.

Safety Systems for Smart Powered Surgical Stapling

Safety Systems for Assessing Operational Parameters

Various aspects of the present disclosure are directed to improved safety systems capable of adapting, controlling, and/or tuning internal drive operations of a surgical instrument in response to tissue parameters detected via one or more than one sensors of the surgical instrument. More specifically, various aspects are directed to sensing and indicating an appropriateness of current device parameters to sensed tissue parameters.

For example, sensed tissue parameters may include a type of the tissue, a thickness of the tissue, a stiffness of the tissue, a position of the tissue on a patient's anatomy, vascularization of the tissue, etc., and current device parameters may include cartridge color, cartridge type, adjuncts, clamp load, gap, firing rate, etc. As such, according to aspects of the present disclosure, physiologic sensing may indicate an inappropriate use of a device or a component thereof and/or an inappropriate positioning of the device.

In one example, an inappropriate use of a surgical instrument or a component thereof and/or an improper positioning of the surgical instrument may be determined, via an associated control circuit, based on physiologic sensing detected via one or more than one sensor at the jaws of the end effector. In such an example, after the determined inappropriate use and/or the determined improper positioning, the associated control circuit may prevent one or more than one functionality (e.g., stapling) of the end effector from being performed. Further, in such an example, the associated control circuit may permit the one or more than one functionality of the end effector if the associated control circuit determines that the surgical instrument or the component thereof and/or the positioning of the surgical instrument has been rectified (e.g., improper staple cartridge replaced, surgical instrument repositioned, etc.) or an override has been received (e.g., via a user interface on the surgical instrument, on a surgical hub coupled to the surgical instrument, in the surgical theater, etc.).

Referring to FIG. 94, according to various aspects of the present disclosure, a surgical system 24200 may comprise a control circuit (24212, 24222, 24232, and/or 24242, e.g., in phantom to show optional location(s)), a user interface (24214, 24224, 22234, 24244, and/or 24254, e.g., in phantom to show optional location(s)), and a surgical instrument 24202. The surgical instrument 24202 includes a plurality of components, such as Component-A 24216 to Component-N 24218 of the end effector assembly 24210, and similarly, in abbreviated form for purposes of illustration, Component-A (C-A) to Component-N (C-N) of the shaft assembly 24220 and the handle assembly 24230, respectively. In various aspects, each component of the surgical instrument 24202 can comprise at least one device parameter. For example, Component-A 24216 of the end effector assembly 24210 can include parameters PAa-PAn 24217, Component-N 24218 of the end effector assembly 24210 can include parameters PNa-PNn 24219, and so on. As another example, each of C-A to C-N of the shaft assembly 24220 and each of C-A to C-N of the handle assembly 24230 can similarly include at least one device parameter. Each component can be configured to transmit its respective device parameter(s) to the control circuit. The surgical instrument 24202 further includes a sensor (24213, 24223, and/or 24233) configured to detect a tissue parameter associated with a function of the surgical instrument and transmit the detected tissue parameter to the control circuit. The control circuit may be configured to analyze the detected tissue parameter in cooperation with each respective device parameter based on system-defined constraints.

Referring again to FIG. 94, the control circuit 24212, 24222, and/or 24232 (e.g., shown as an element of the end effector assembly 24210, the shaft assembly 24220, and the handle assembly 24230, respectively) may, in various aspects, be integrated into one or more than one of the plurality of components (e.g., a handle of the handle assembly 24230, a shaft of the shaft assembly 24220, an end effector of the end effector assembly 24210, a staple cartridge of the end effector assembly, etc.) of the surgical instrument 24202 or integrated into a surgical hub 24240 (e.g., 24242) paired (e.g., wirelessly) with the surgical instrument 24202. Similarly, the sensor(s) 24213, 24223, and/or 24233; the user interface 24214, 24224, and/or 24234; and the memory 24215, 24225, and/or 24235 (e.g., shown as elements of the end effector assembly 24210, the shaft assembly 24220, and the handle assembly 24230, respectively) may, in various aspects, be integrated into one or more than one of the plurality of components. Notably, according to various aspects, the surgical instrument 24202 and/or the surgical hub 24240 may be a situationally aware surgical instrument and/or a situationally aware surgical hub. Situational awareness refers to the ability of a surgical system (e.g., 24200) to determine or infer information related to a surgical procedure from data received from databases (e.g., historical data associated with a surgical procedure) and/or surgical instruments (e.g., sensor data during a surgical procedure). For example, the determined or inferred information can include the type of procedure being undertaken, the type of tissue being operated on, the body cavity that is the subject of the procedure, etc. Based on such contextual information related to the surgical procedure, the surgical system can, for example, control a paired surgical instrument or a component thereof and/or provide contextualized information or suggestions to a surgeon throughout the course of the surgical procedure.

According to one aspect, a situationally aware surgical hub (e.g., 24240) is paired (e.g., wirelessly) with a surgical instrument 24202 being utilized to perform a surgical procedure. In such an aspect, the surgical instrument 24202 may comprise a plurality of components, including an end effector (e.g., Component-A 24216). The end effector 24216 may comprise a first jaw, a second jaw pivotably coupled to the first jaw, a cutting blade, and an integrated sensor 24213 configured to detect a tissue parameter associated with a function (e.g., dissect, clamp, coagulate, cut, staple, etc.) of the end effector 24216, and transmit the detected tissue parameter to a control circuit 24242 of the surgical hub 24240. Each of the plurality of components of the surgical instrument 24202 (e.g., Component-N 24218, e.g., a staple cartridge, etc.), including the end effector 24216, is also configured to transmit its respective device parameter(s) (e.g., 24219 and 24217, respectively) to the surgical hub 24240. Notably, it should be appreciated that a sensor (e.g., 24213), as referenced herein and in other disclosed aspects, may comprise a plurality of sensors configured to detect a plurality tissue parameters associated with a plurality of end effector 24216 functions. As such, further, in such an aspect, the surgical hub control circuit 24242 may be configured to receive such parameter data (e.g., detected tissue parameter(s), device parameter of each component including the end effector, etc.) throughout the course of the surgical procedure. A detected tissue parameter may be received each time an associated end effector function (e.g., dissection, clamping, coagulation, cutting, stapling, etc.) is to be performed. The surgical hub control circuit 24242 may be further configured to receive data from an internal database (e.g., a surgical hub database 24249) and/or an external database (e.g., from a cloud database 24269) throughout the course of the surgical procedure. According to various aspects, the data received from the internal 24249 and/or external databases 24269 may comprise procedural data (e.g., steps to perform the surgical procedure, data indicating respective device parameters associated with the surgical procedure) and/or historical data (e.g., data indicating expected tissue parameters based on historical data associated with the surgical procedure, a patient's surgical history data, etc.). In various aspects, the procedural data may comprise current/recognized standard-of-care procedures for the surgical procedure, and the historical data may comprise preferred/ideal tissue parameters and/or preferred/ideal tissue parameter ranges for each received device parameter based on historical data associated with the surgical procedure (e.g., system-defined constraints). Based on the received data (e.g., parameter data, internal and/or external data, etc.), the surgical hub control circuit 24242 may be configured to continually derive inferences (e.g., contextual information) about the ongoing surgical procedure. Namely, the situationally aware surgical hub may be configured to, for example, record data pertaining to the surgical procedure for generating reports, verify the steps being taken by the surgeon to perform the surgical procedure, provide data or prompts (e.g., via a user interface associated with the surgical hub 24244 and/or 24254 and/or the surgical instrument 24214, 24224, and/or 24234) that may be pertinent for a particular procedural step, control a surgical instrument function, etc.

According to another aspect, a situationally aware surgical instrument (e.g., 24202) may be utilized to perform a surgical procedure. In such an aspect, as described herein, the surgical instrument 24202 may comprise a plurality of components, including an end effector 24216. The end effector may comprise a first jaw, a second jaw pivotably coupled to the first jaw, a cutting blade, and an integrated sensor 24213 configured to detect a tissue parameter associated with a function (e.g., dissect, clamp, coagulate, cut, staple, etc.) of the end effector 24216, and transmit the detected tissue parameter to a control circuit. Notably, in such an aspect, the detected tissue parameter may be transmitted to an integrated control circuit 24212 of the end effector 24216. Each of the plurality of components of the surgical instrument (e.g., Component-N 24218, e.g., the staple cartridge, etc.), including the end effector 24216, is configured to transmit its respective device parameter(s) to the integrated end effector control circuit 24212. In such an aspect, the integrated end effector control circuit 24212 may be configured to receive such parameter data (e.g., detected tissue parameter(s), device parameter(s) of each component, including the end effector) throughout the course of the surgical procedure. A detected tissue parameter may be received each time an associated end effector function (e.g., dissection, clamping, coagulation, cutting, stapling, etc.) is to be performed. The integrated end effector control circuit 24212 may be further configured to receive data from an internal database (e.g., end effector memory 24215) and/or an external database (e.g., from a cloud database 24269 via a surgical hub 24240, from a surgical hub database 24249, etc.) throughout the course of the surgical procedure. According to various aspects, the data received from the internal and/or external databases may comprise staple cartridge data (e.g., sizes and/or types of staples associated with a staple cartridge (e.g., 24218) for which a device parameter(s) has been received by the end effector control circuit 24212) and/or historical data (e.g., data indicating expected tissues and/or types of tissues to be stapled with those sizes and/or types of staples based on historical data). In various aspects, the internal and/or external data may comprise preferred/ideal tissue parameters and/or preferred/ideal tissue parameter ranges for each received device parameter based on historical data associated with the surgical procedure (e.g., system-defined constraints). In one example, the internal and/or external data may comprise preferred/ideal tissue parameters and/or preferred/ideal tissue parameter ranges for expected tissues and/or tissue types or for the sizes and/or types of staples associated with the device parameter of the staple cartridge (e.g., 24218) based on historical data (e.g., system-defined constraints). Based on the received data (e.g., parameter data, internal and/or external data, etc.), the end effector control circuit 24212 may be configured to continually derive inferences (e.g., contextual information) about the ongoing procedure. Notably, according to an alternative aspect, the integrated sensor 24213 of the end effector 24216 may transmit the detected tissue parameter(s) to a control circuit (e.g., 24222 and/or 24232) associated with another surgical instrument component, for example, a handle of the handle assembly 24230. In such an aspect, that other surgical instrument component control circuit (e.g., 24222 and/or 24232) may be similarly configured to perform the various aspects of the end effector control circuit 24212 as described above. In end, the situationally aware surgical instrument (e.g., 24202) may be configured to, for example, alert its user (e.g., via a user interface of the end effector 24214, via a user interface of another surgical instrument component 24224 and/or 24234, for example, the handle of the handle assembly 24230, or via a user interface 24244 associated with a surgical hub 24240 coupled to the surgical instrument 24202) of a discrepancy. For example, the discrepancy may include that a detected tissue parameter exceeds a preferred/ideal tissue parameter and/or a preferred/ideal tissue parameter range associated with those sizes and/or types of staples or those expected tissues and/or tissue types. As a further example, the situationally aware surgical instrument (e.g., 24202) may be configured to control a surgical instrument function based on the discrepancy. In accordance with at least one aspect, the situationally aware surgical instrument (e.g., 24202) may prevent a surgical function based on a discrepancy.

Inappropriate Device Placement

According to various aspects of the present disclosure, physiologic sensing (e.g., detected via one or more than one sensor) may indicate device placement concerns. More specifically, according to such aspects, a physiologic incompatibility may be present within/between a first jaw and a second jaw of an end effector (e.g., after clamping) and further functionality (e.g., coagulation, cutting, stapling, etc.) of the end effector may be prohibited/prevented.

According to various aspects, a surgical procedure may comprise the resection of target tissue (e.g., a tumor). Referring to FIG. 92, for example, a portion of patient tissue 24000 may comprise a tumor 24002. In such an aspect, a surgical margin 24004 may be defined around the tumor 24002. Notably, during a surgical procedure, it is ideal to avoid and/or minimize the resection of healthy tissue surrounding a tumor. However, to ensure complete removal of the tumor, current/recognized standard-of-care procedures associated with that surgical procedure may endorse the resection of a predetermined surgical margin defined by a distance surrounding the tumor and/or predetermined surgical margin range defined by a distance range surrounding the tumor. In one aspect, the endorsed surgical margin may be tumor-dependent (e.g., based on type of tumor, size of tumor, etc.). In another aspect, the endorsed surgical margin may depend on an extent of the tumor's micro-invasion into the surrounding tissue. In other aspects, the endorsed surgical margin may be correlated to improved long-term survival based on historical data associated with that tumor and/or that surgical procedure. In yet other aspects, an associated control circuit (e.g., in view of FIG. 94, in the surgical instrument, in a component of the surgical instrument 24212, 24222, 24232, in a surgical hub coupled to the surgical instrument 24242, etc.) may proactively adjust an endorsed surgical margin based on data received from an internal 24215, 24225, and/or 24235 and/or external database 24249 and/or 24269 (e.g., patient surgical history data, patient medical history data, standard-of-care procedures for recurrent tumors, etc. from the cloud, from a surgical hub, etc.). In such an aspect, referring back to FIG. 92, a normally endorsed surgical margin (e.g., 24004) may be altered by a determined amount/distance (e.g., 24010) to an adjusted surgical margin (e.g., 24012) based on such received data (e.g., that patient's surgical and/or medical history data may suggest that the tumor may have further micro-invaded the surrounding tissue, that patient may have already had an instance of a recurrent tumor, etc.)

Furthermore, in various aspects, after a target surgical margin (e.g., 24004 and/or 24012) is established for a surgical procedure, it may be difficult to efficiently and/or accurately identify and resect the tumor and/or its target surgical margin during a surgical procedure. Referring again to FIG. 94, according to various aspects of the present disclosure, an end effector (e.g., 24216) of a surgical instrument 24202 may comprise a first sensor (e.g., 24213) configured to measure a first signal and transmit the first signal to an associated control circuit (e.g., in the surgical instrument, in a component of the surgical instrument 24212, 24222, and/or 24232, in a surgical hub coupled to the surgical instrument 24242, etc.). In such an aspect, a second sensor configured to measure a second signal and transmit the second signal to the associated control circuit may be positioned on/within the tumor (see FIG. 92, e.g., 24006, a central position with respect to the tumor) prior to use of the surgical instrument to resect the tumor. Here, according to various aspects, the second sensor may be separate from the surgical instrument. In addition, and/or alternatively, in such an aspect, the second sensor may comprise a sensor positioned at a periphery of the tumor (see FIG. 92, e.g., 24008) prior to use of the surgical instrument to resect the tumor. According to another aspect, a plurality of second sensors may be positioned around the periphery of the tumor. Here, in such aspects, the control circuit may be configured to dynamically calculate a distance between the first sensor and the second sensor based on the first signal and the second signal. According to various aspects, the first sensor may be positioned at/near the cutting blade of the end effector. Further example methods for detecting a target surgical margin are described in U.S. Patent Application Publication No. 2016/0192960, titled SYSTEM AND METHOD FOR A TISSUE RESECTION MARGIN MEASUREMENT DEVICE, the entire disclosure of which is incorporated herein by reference.

In one example, if the second sensor is positioned on/within the tumor (e.g., at a central position, 24006), the control circuit may be further configured to determine a margin distance between the second sensor and the target surgical margin established for the surgical procedure. In such an example, the control circuit may compare the dynamically calculated distance (e.g., between the first sensor and the second sensor) to that determined margin distance to efficiently and accurately locate the end effector (e.g., cutting blade) at the target surgical margin (e.g., when the dynamically calculated distance is equal to or substantially equal to the determined margin distance, the end effector is properly positioned). The control circuit may be configured to utilize such a technique to efficiently and accurately locate the end effector (e.g., the cutting blade) around the target surgical margin (e.g., during resection).

In another example, if the second sensor is positioned at the periphery of the tumor or a plurality of second sensors are positioned around a periphery of the tumor, e.g., 24008, the control circuit may be further configured to determine a margin distance between the second sensor(s) and the target surgical margin established for the surgical procedure. In such an example, the control circuit may compare the dynamically calculated distance (e.g., between the first sensor and the second sensor) to that determined margin distance to efficiently and accurately locate the end effector (e.g., cutting blade) at the target surgical margin (e.g., when the dynamically calculated distance is equal to or substantially equal to the determined margin distance, the end effector is properly positioned). The control circuit may be configured to utilize such a technique to efficiently and accurately locate the end effector (e.g., the cutting blade) around the target surgical margin (e.g., during resection). Such an aspect may be beneficial when the tumor is abnormally shaped.

Referring again to FIG. 94, according to various aspects, the control circuit may be configured to inform the surgeon (e.g., in real time via a user interface on the surgical instrument 24214, 24224, and/or 24234, a user interface on a surgical hub coupled to the surgical instrument 24244, and/or a user interface in the surgical theater 24254, etc.) when the end effector (e.g., or the cutting blade thereof) is properly located/positioned with respect to the target surgical margin (e.g., 24004 and/or 24012). For example, the user interface may comprise at least one of i) a video image of the surgical site with a digital overlay indicating the target surgical margin for the surgeon to visually confirm that the end effector (e.g., 24216) is positioned at the target surgical margin and/or navigate the end effector (e.g., or the cutting blade thereof) with respect to the target surgical margin, ii) haptic feedback in the surgical instrument 24202 itself to indicate that the cutting blade of the end effector is positioned at the target surgical margin, and/or iii) auditory feedback to indicate that the cutting blade of the end effector is positioned at the target surgical margin.

Referring again to FIG. 94, according to further aspects, the control circuit may be configured to prevent the surgical instrument 24202 from firing if the end effector (e.g., cutting blade) is too close to and/or within a cancerous margin (e.g., inside the target surgical margin, to close to surrounding tissue micro-invaded by the tumor, etc.). According to such aspects, the control circuit may be further configured to receive an override command (e.g., via the user interface on the surgical instrument 24214, 24224 and/or 24234, a user interface on a surgical hub coupled to the surgical instrument 24244, and/or a user interface in the surgical theater 24254, etc.) to permit the firing to continue. In one example, such a user interface may comprise a user interface element selectable to permit the firing to continue, e.g., 24251. In such an aspect, the control circuit may continue to monitor the end effector (e.g., or the cutting blade thereof) with respect to the cancerous margin. Further, in such an aspect, the control circuit may be configured to again stop the firing, alert the surgeon, and/or receive an override command as described. According to other aspects, the control circuit may be configured to prevent firing until a reset event occurs (e.g., opening the jaws of the end effector and repositioning the jaws of the end effector with respect to the cancerous margin).

Referring again to FIG. 94, according to other aspects of the present disclosure, one or more than one sensor of a surgical system 24200 may detect blood flow through tissue clamped between/within a first jaw and a second jaw of an end effector (e.g., 24216). For example, a doppler imaging detector (e.g., integrated on the end effector 24213, coupled to a surgical hub, e.g., parameter sensing component 24253 comprising a doppler imaging detector, etc.) may be configured to locate and identify blood vessels not otherwise viewable at a surgical site (e.g., via red, green, and/or blue laser light) and a speckle contrast analysis may be performed to determine the amount and/or velocity of blood flow through such blood vessels. Notably, in one example, it may be desired to seal some blood vessels (e.g., associated with a tumor) but not seal others (e.g., associated with healthy tissues/organs). As such, an associated control circuit (e.g., in the surgical instrument, in a component of the surgical instrument 24212, 24, 222 and/or 24232, in a surgical hub coupled to the surgical instrument 24242, etc.) may be configured to prevent the surgical instrument 24202 from firing if blood flow exceeds a predetermined amount and/or velocity of blood flow. According to such aspects, the control circuit may be further configured to receive an override command (e.g., via the user interface on the surgical instrument 24214, 24224 and/or 24234, a user interface on a surgical hub coupled to the surgical instrument 24244, and/or a user interface in the surgical theater 24254, etc.) to permit the firing to continue (e.g., if the blood flow is associated with the tumor). In one example, such a user interface may comprise a user interface element selectable to permit the firing to continue, e.g., 24251. In such an aspect, the control circuit may continue to monitor clamped tissue for blood flow. Further, in such an aspect, the control circuit may be configured to again stop the firing, alert the surgeon, and/or receive an override command as described. According to other aspects, the control circuit may be configured to prevent firing until a reset event occurs (e.g., opening the jaws and repositioning the jaws of the end effector with respect to the blood vessel comprising a blood flow exceeding the predefined amount and/or velocity of blood flow).

Referring again to FIG. 94, according to other aspects of the present disclosure, one or more than one sensor of a surgical system 24200 may detect an increase in blood pressure concurrent with and/or immediately after the clamping of tissue between/within a first jaw and a second jaw of an end effector (e.g., 24216). For example, a blood pressure monitor (e.g., coupled to the surgical hub, e.g., parameter sensing component 24253 comprising a blood pressure monitor, etc.) may detect the increase in blood pressure contemporaneous to the clamping. According to various aspects, the surgical system 24200 is situationally aware and may infer that the detected increase in blood pressure has been caused by the clamping of the tissue between/within the jaws of the end effector. For example, a blood vessel comprising critical blood flow may have been captured between/within the jaws resulting in constricted blood flow. As such, according to various aspects, an associated control circuit (e.g., in the surgical instrument, in a component of the surgical instrument 24212, 24, 222 and/or 24232, in a surgical hub coupled to the surgical instrument 24242, etc.) may be configured to prevent a surgical instrument 24202 from firing if the blood pressure increase exceeds a predetermined amount and/or a predetermined range. According to such aspects, the control circuit may be further configured to receive an override command (e.g., via the user interface on the surgical instrument 24214, 24224 and/or 24234, a user interface on a surgical hub coupled to the surgical instrument 24244, and/or a user interface in the surgical theater 24254, etc.) to permit the firing to continue (e.g., surgeon observes that blood pressure has decreased while the tissue is still clamped, situationally aware surgical system attributes the blood pressure increase to another cause, etc.). In one example, such a user interface may comprise a user interface element selectable to permit the firing to continue, e.g., 24251. In such an aspect, the control circuit may continue to monitor the patient's blood pressure. Further, in such an aspect, the control circuit may be configured to again stop the firing, alert the surgeon, and/or receive an override command as described. According to other aspects, the control circuit may be configured to prevent firing until a reset event occurs (e.g., opening the jaws and repositioning the jaws of the end effector with respect to the clamped tissue).

Referring again to FIG. 94, according to other aspects of the present disclosure, one or more than one sensor of a surgical system may detect a substantial nerve bundle within tissue clamped between a first jaw and a second jaw of an end effector (e.g., 24216). For example a heart rate monitor (e.g., integrated on the end effector 24213, coupled to the surgical hub e.g., parameter sensing component 24253 comprising a hear rate monitor, etc.) may detect an increase in heart rate concurrent with and/or immediately after the clamping of tissue between/within the first jaw and the second jaw. According to various aspects, the surgical system 24200 is situationally aware and may infer that the detected increase in heart rate, in the context of data received from an internal 24215, 24225, 24235, 24249 and/or external database 24249 and/or 24269 (e.g., anatomical information associated with the surgical site of the surgical procedure being performed), has been caused by the clamping of the tissue between/within the jaws of the end effector. According to such aspects, an associated control circuit (e.g., in the surgical instrument, in a component of the surgical instrument 24212, 24, 222 and/or 24232, in a surgical hub coupled to the surgical instrument 24242, etc.) may be configured to prevent a surgical instrument 24202 from firing based on the inference. Further according to such aspects, the control circuit may be configured to receive an override command (e.g., via the user interface on the surgical instrument 24214, 24224 and/or 24234, a user interface on a surgical hub coupled to the surgical instrument 24244, and/or a user interface in the surgical theater 24254, etc.) to permit the firing to continue (e.g., surgeon observes that the patient's heart rate has decreased while the tissue is still clamped, situationally aware surgical system attributes the heart rate increase to another cause, etc.). In one example, such a user interface may comprise a user interface element selectable to permit the firing to continue, e.g., 24251. In such an aspect, the control circuit may continue to monitor the patient's heart rate. Further, in such an aspect, the control circuit may be configured to again stop the firing, alert the surgeon, and/or receive an override command as described. According to other aspects, the control circuit may be configured to prevent firing until a reset event occurs (e.g., opening the jaws and repositioning the jaws of the end effector with respect to the clamped tissue).

Referring again to FIG. 94, according to other aspects of the present disclosure, one or more than one sensor of a surgical system 24200 may detect that a surgical instrument 24202 is in contact with an energized device (e.g., an RF instrument/device). In one example, the surgical instrument and the energized device may be communicatively coupled to a surgical hub 24240 in the surgical system 24200. For example, referring back to FIG. 9, a device/instrument 235 as well as an energy device 241 may be coupled to a modular control tower 236 of a surgical hub 206. In such an example, either a generator 240 producing the electrosurgical energy for the energized device 241 and/or a sensor integrated in the energized device may be configured to detect when impedance, associated with the energized device, falls below a threshold value for a threshold time period (e.g., impedance drop indicative of a short). Similar to FIG. 48, an integrated sensor of the energized device may be configured to measure impedance over time. Various alternate methods for detecting a short, such as those described in U.S. Pat. No. 9,554,854, titled DETECTING SHORT CIRCUITS IN ELECTROSURGICAL MEDICAL DEVICES, are expressly incorporated herein by reference (e.g., comparing impedance values at different positions within a pulse of a series of pulses, etc.). According to various aspects, the surgical system 24200 is situationally aware and may infer that a detected short, in the context of data received from an internal 24215, 24225, 24235, 24249 and/or external database 24249 and/or 24269 (e.g., procedural data indicating that a step and/or the current step of the surgical procedure involves the use of a separate surgical instrument, e.g., an electrosurgical instrument/device), has been caused by the separate surgical instrument (e.g., a conductive surface of the surgical instrument may be in contact with the energized device causing the short). According to such aspects, an associated control circuit (e.g., in the surgical instrument, in a component of the surgical instrument 24212, 24, 222 and/or 24232, in the surgical hub coupled to the surgical instrument and the energized device 24242, etc.) may be configured to prevent the surgical instrument 24202 from firing based on the inference. If a short exists, it may be difficult to treat (e.g., coagulate) tissue with electrosurgical energy (e.g., RF energy) and an undesired surgical outcome may result (e.g., incomplete tissue treatment, excessive heating of the conductive object, etc.). In such a context, the control circuit may be configured to inform the surgeon (e.g., in real time via a user interface on the surgical instrument 24214, 24224 and/or 24234, a user interface on a surgical hub coupled to the surgical instrument 24244, and/or a user interface in the surgical theater 24254, etc.) that the short exists and that firing of the surgical instrument 24202 has been suspended. Further according to such aspects, the control circuit may be configured to receive an override command (e.g., via the user interface on the surgical instrument 24214, 24224 and/or 24234, a user interface on a surgical hub coupled to the surgical instrument 24244, and/or a user interface in the surgical theater 24254, etc.) to permit the firing to continue (e.g., surgeon verifies that no short exists, target tissue comprises a low impedance, etc.). In one example, such a user interface may comprise a user interface element selectable to permit the firing to continue, e.g., 24251. In such an aspect, the control circuit may continue to monitor for a short. Further, in such an aspect, the control circuit may be configured to again stop the firing, alert the surgeon, and/or receive an override command as described. According to other aspects, the control circuit may be configured to prevent firing until a reset event occurs (e.g., surgical instrument repositioned with respect to the energized device such that they are no longer in contact).

Inappropriate Device Selection/Proposed Use

According to various aspects of the present disclosure, physiologic sensing (e.g., detected via one or more than one sensor) may indicate surgical instrument/device selection concerns. More specifically, according to such aspects, a surgical device-tissue incompatibility may be present and further functionality (e.g., coagulation, cutting, stapling, etc.) of the end effector may be prohibited/prevented.

Referring yet again to FIG. 94, according to one aspect of the present disclosure, a control circuit (e.g., in a component of the surgical instrument 24212, 24, 222 and/or 24232, in a surgical hub coupled to the surgical instrument 24242, etc.) may be configured to provide a warning if a tissue specific stapler (e.g., vascular stapler) and any combination of sensed information (e.g., detected via the one or more than one sensor) suggests that the target tissue may be inappropriate (e.g., contra-indicated for) that tissue specific stapler.

FIG. 93 illustrates an example safety process 24100 for addressing device selection concerns according to various aspects of the present disclosure. In accordance with at least one aspect, the safety process 24100 may be executed/implemented (e.g., during a surgical procedure) by a control circuit associated with a situationally aware surgical hub (e.g., 24242 of FIG. 94) of a surgical system (e.g., 24200 of FIG. 94). According to other aspects, the safety process 24100 may be executed/implemented (e.g., during a surgical procedure) by a control circuit associated with a situationally aware surgical instrument (e.g., 24212, 24222 and/or 24232 of FIG. 94) of a surgical system (e.g., 24200 of FIG. 94).

Referring to FIG. 93, a tissue identification process 24108 may receive inputs comprising a device selection 24102 (e.g., a stapler choice, e.g., a stapler appropriate for parenchyma firings, a stapler appropriate for vascular firings, a stapler appropriate for bronchus firings, etc.), various device measures 24104 detected by the one or more than one sensor (e.g., end effector closure angle, length of tissue in contact with end effector, force to close/compress curve, etc.) and situationally aware information 24106 (e.g., procedure information, surgeon tendencies, etc.).

In view of FIG. 93, at device selection 24102, the control circuit executing/implementing the safety process 24100 may be configured to receive a device parameter from a selected stapler/device and/or device parameters associated with each component (e.g., staple cartridge) of the selected stapler/device to indicate the device selection. For example, device parameters associated with a staple cartridge may include a type of the cartridge, a color of the cartridge, adjuncts to the cartridge, a clamp load limit of the cartridge, a gap range for the cartridge, a firing rate for the cartridge, etc. According to one aspect, the device parameter(s) may be transmitted by the stapler/device to the control circuit upon coupling to the surgical system. According to alternative aspects, the device selection may be entered via a user interface (e.g., associated with a surgical hub and/or in the surgical theater, e.g., 24244 and/or 24254 of FIG. 94) and/or received from an internal and/or external database (e.g., data regarding surgical procedure being performed and/or surgical instruments available, e.g., 24249 and/or 24269 of FIG. 94).

Further in view of FIG. 93, the device measures 24104 may be detected via one or more than one sensor (e.g., as described in FIGS. 17, 18, 53, 78, etc. herein) associated with an end effector (e.g., Component-A, 24216 of FIG. 94) and/or other components of the surgical instrument (e.g., Component-N, 24218 of FIG. 94, e.g., a staple cartridge). For example, one or more than one tissue sensor may be positioned and configured to check for continuity and/or measure tissue impedance along the length of the end effector to assess a length of tissue in contact with the end effector (e.g., sensor(s) 738 of FIG. 17 to determine tissue location using segmented electrodes and/or measure tissue impedance, sensors 153468 of FIG. 78 to determine presence of tissue along length the end effector, etc.). As a further example, one or more than one sensor may be positioned and configured to detect/estimate the jaw/end effector closure angle (e.g., a displacement sensor, e.g., position sensor 734 of FIG. 17, to detect the displacement of a clamping actuator/drive member, gap sensor, e.g., sensor 152008*a* of FIG. 53, to detect a gap between a first jaw and a second jaw of the end effector, etc.). As a further example, one or more than one sensor may be positioned and configured to detect a force to compress/close tissue between the first jaw and the second jaw (e.g., force sensor, e.g., sensor 738 of FIG. 17 comprising a force sensor, on tissue surface of first jaw and/or second jaw to detect forces as tissue is clamped, sensor, e.g., current sensor 736 of FIG. 17, to detect current draw of drive member correlated to forces applied to tissue, torque sensor, e.g., 744*b* of FIG. 17, to measure a force to close, etc.). Various further aspects for detecting an end effector closure angle, a length of tissue in contact with the end effector, and a force to close/compress curve have been discussed elsewhere herein.

Next, in view of FIG. 93, the surgical awareness information 24106 may, in light of FIG. 94, be received via internal 24249 and/or external databases 24269 associated with a surgical hub 24242 and/or via internal 24215, 24225, 24235 and/or external databases 24249, 24269 associated with a surgical instrument 24202, etc.

Returning to FIG. 93, the tissue identification process 24108 is configured to determine a tissue type encountered by the surgical instrument (e.g., parenchyma, vessel, bronchus, etc.). In one example, the tissue identification process 24108 may determine that the tissue type is parenchyma based on various inputs (e.g., tissue contact detected along the length of the jaws when the jaws are fully open, closure vs. aperture curve suggests a tissue consistent with parenchyma, etc.). In another example, the tissue identification process 24108 may determine that the tissue type is a vessel (e.g., PA/PV) based on various inputs (e.g., tissue contact detected almost immediately during closure, tissue contact detected as only over a small area of the stapler and is detected as bounded on the distal side, initial detected closure forces suggest a tissue structure consistent with a vessel, etc.). In yet another example, the tissue identification process 24108 may determine that the tissue type is bronchus based on various inputs (e.g., tissue contact detected almost immediately during closure, tissue contact detected over a small area of the stapler and is detected as bounded on both distal and proximal sides, initial detected closure forces suggest a stiff tissue structure consistent with bronchus, etc.). According to various aspects, such tissue type determinations may be further based on tissue parameters comprising a thickness of the tissue, a stiffness of the tissue, a location of the tissue (e.g., with respect to the patient), and vascularization in the tissue detected by and/or derived from measurements taken via the one or more than one sensors described herein. Notably, the tissue identification process 24108 may further assess such initial tissue determinations in the context of the further inputs (e.g., stapler choice, surgical procedure information, surgeon tendencies, etc.) before arriving at a tissue identification output/result. Such a situational awareness ultimately results in the tissue identification output/result. Here, various aspects for identifying a tissue encountered have been further discussed elsewhere herein (e.g., thoracic surgery example, etc.).

Referring back to FIG. 93, the tissue identification output/result may be utilized to determine whether the selected stapler/device and/or each component of the selected stapler/device (e.g., staple cartridge, shaft, etc.) is optimal 24110 for the surgical procedure. In such an aspect, the control circuit may receive further information 24112 from internal and/or external databases (e.g., referring to FIG. 94, internal 24249 and/or external databases 24269 associated with a surgical hub 24242, internal 24215, 24225, 24235 and/or external databases 24249, 24269 associated with a surgical instrument 24202, etc.). More specifically, the further information 24112 may comprise other available staplers, other available energy devices, other stapler components (e.g., staple cartridges, shafts, etc.) available for use with the selected stapler/device, etc. In accordance with at least one aspect, availability may be subject to current inventory at the surgical location. Notably, the further information 24112 may also comprise device parameters associated with each other available stapler, each other available energy device, each other stapler component available for use with the selected stapler/device, etc.

According to various aspects, when assessing whether the selected stapler/device is optimal 24110, the control circuit executing/implementing the safety process 24100 may be configured to analyze each detected tissue parameter (e.g., detected via the one or more than one sensor described herein) in cooperation with each received device parameter associated with the selected stapler/device 24102 based on system-defined constraints. In addition, according to such aspects, the control circuit may be configured to analyze each detected tissue parameter (e.g., detected via the one or more than one sensor described herein) with the received device parameters associated with each other available stapler, each other available energy device, each other stapler component available for use with the selected stapler/device, etc., based on system-defined constraints. According to such aspects, the control circuit may be configured to determine whether one or more than one of the other available staplers, the other available energy devices, and/or the other stapler components available for use with the selected stapler/device are more optimal than the selected stapler/device 24102 and/or components of the selected stapler/device 24102 based on the detected tissue parameters.

In various aspects, a detected tissue parameter(s) may comprise, for example, a type of the tissue, a thickness of the tissue, a stiffness of the tissue, a location of the tissue, vascularization in the tissue, etc. and a received device parameter may comprise, for example, a type of staple cartridge, a color of the staple cartridge, adjuncts to the staple cartridge, a clamp load limit of the staple cartridge, a gap range for the staple cartridge, and a firing rate for the staple cartridge, etc. According to various aspects, a system-defined constraint (e.g., based on historical data and/or procedural data accessed in the situationally aware surgical system) may comprise preferred/ideal tissue parameters and/or preferred/ideal tissue parameter ranges for each received device parameter. For example, a preferred/ideal tissue thickness and/or preferred/ideal tissue thickness range may be associated with each staple cartridge color. In such an example, each staple cartridge color may indicate the types and/or sizes of staples in the staple cartridge. Here, a staple cartridge comprising short staples may not be optimal for thick tissue. According to further aspects, a system-defined constraint (e.g., based on historical data and/or procedural data accessed in the situationally aware surgical system) may comprise a preferred/ideal clamp load limit and/or preferred/ideal clamp load limit range for each detected tissue type. For example, each staple cartridge associated with its respective clamp load limit may indicate the types of tissue it can optimally staple. Here, various combinations of received device parameters (e.g., type of staple cartridge, color of the staple cartridge, adjuncts to the staple cartridge, clamp load limit of the staple cartridge, gap range for the staple cartridge, firing rate for the staple cartridge, etc.) and detected tissue parameters (e.g. type of the tissue, thickness of the tissue, stiffness of the tissue, location of the tissue, vascularization in the tissue, etc.) and established system defined constraints (e.g., associated with received device parameters and/or detected tissue parameters based on historical data and/or procedural data accessed in the situationally aware surgical system) are contemplated by the present disclosure.

Referring again to FIG. 93, if it is determined that the selected device 24102 is optimal, the control circuit executing/implementing the safety process 24100 may be configured to initially do nothing (e.g., recommend later) and/or document that the analysis was performed 24114. Instead, if it is determined that the selected device 24102 is not optimal, the control circuit may be configured to determine whether a safety issue exists 24116. According to various aspects, when assessing whether a safety issue exists with the selected stapler/device 24102, the control circuit may be configured to analyze each detected tissue parameter in cooperation with each received device parameter associated with the selected stapler/device 24102 based on system-defined constraints.

Similar to above, a detected tissue parameter may comprise, for example, a type of the tissue, a thickness of the tissue, a stiffness of the tissue, a location of the tissue, vascularization in the tissue, etc. and a received device parameter may comprise, for example, a type of staple cartridge, a color of the staple cartridge, adjuncts to the staple cartridge, a clamp load limit of the staple cartridge, a gap range for the staple cartridge, and a firing rate for the staple cartridge, etc. According to various aspects, a system-defined constraint (e.g., based on historical data and/or procedural data accessed in the situationally aware surgical system) may comprise preferred/ideal tissue parameters and/or preferred/ideal tissue parameter ranges for each received device parameter. For example, a preferred/ideal tissue thickness and/or preferred/ideal tissue thickness range may be associated with each staple cartridge color. In such an example, each staple cartridge color may indicate the types and/or sizes of staples in the staple cartridge. Here, continuing the example, if a received device parameter of the selected stapler/device 24102 comprises a staple cartridge color (e.g., indicating short staples) and the detected tissue parameter indicates a tissue thickness exceeding the preferred/ideal tissue thickness and/or the preferred/ideal tissue thickness range associated with the staple cartridge color of the selected stapler/device 24102, a safety issue exists with the selected stapler/device 24102. Utilizing an inappropriate staple cartridge may lead to less than satisfactory results and/or undesired results (e.g., failed stapling, oozing, bleeding, etc.). In such an instance, the control circuit may be configured to warn the surgeon 24118 (e.g., referring to FIG. 94, via a user interface on the selected stapler/device 24214, 24224 and/or 24234, via a user interface associated with the surgical hub 24244, via a user interface in the surgical theater 24254, etc.) of the safety issue. In such an aspect, the control circuit may be further configured to receive an override command 24120 (e.g., via the user interface on the selected stapler/device 24214, 24224 and/or 24234, via the user interface associated with the surgical hub 24244, via a user interface in the surgical theater 24254, etc.) to permit the surgical procedure to proceed. In one example, referring to FIG. 94, such a user interface may comprise a user interface element selectable to permit the procedure to continue, e.g., 24251. In an alternative aspect, in response to the warning, the surgeon may correct the noted safety issue (e.g., replacing the inappropriate staple cartridge with another staple cartridge) at which point the device selection safety process 24100 may be executed/implemented again.

Similar to above, according to further aspects, a system-defined constraint (e.g., based on historical data and/or procedural data accessed in the situationally aware surgical system) may comprise a preferred/ideal clamp load limit and/or preferred/ideal clamp load limit range for each detected tissue type. For example, each staple cartridge associated with its respective clamp load limit may indicate the types of tissue it can optimally staple. Here, continuing the example, if a received device parameter of the selected stapler/device 24102 comprises its staple cartridge clamp load limit and the tissue identified by the tissue identification process 24108 indicates a tissue type requiring a staple cartridge with a higher clamp load limit, a safety issue exists with the selected stapler/device 24102. Utilizing an inappropriate staple cartridge may lead to less than satisfactory results and/or undesired results (e.g., failed stapling, oozing, bleeding, etc.). In such an instance, the control circuit may be configured to warn the surgeon 24118 (e.g., referring to FIG. 94, via a user interface on the selected stapler/device 24214, 24224 and/or 24234, via a user interface associated with the surgical hub 24244, via a user interface in the surgical theater 24254, etc.) of the safety issue. In such an aspect, the control circuit may be further configured to receive an override command 24120 (e.g., via the user interface on the selected stapler/device 24214, 24224 and/or 24234, via the user interface associated with the surgical hub 24244, via a user interface in the surgical theater 24254, etc.) to permit the surgical procedure to proceed. In one example, referring to FIG. 94, such a user interface may comprise a user interface element selectable to permit the procedure to continue, e.g., 24251. In an alternative aspect, in response to the warning, the surgeon may correct the noted safety issue (e.g., replacing the inappropriate staple cartridge with another staple cartridge) at which point the device selection safety process 24100 may be executed/implemented again. Again, various combinations of received device parameters (e.g., type of staple cartridge, color of the staple cartridge, adjuncts to the staple cartridge, clamp load limit of the staple cartridge, gap range for the staple cartridge, firing rate for the staple cartridge, etc.) and detected tissue parameters (e.g. type of the tissue, thickness of the tissue, stiffness of the tissue, location of the tissue, vascularization in the tissue, etc.) and established system defined constraints (e.g., associated with received device parameters and/or detected tissue parameters based on historical data and/or procedural data accessed in the situationally aware surgical system) are contemplated by the present disclosure.

Referring back to FIG. 93, if it is determined that a safety issue does not exist with the selected stapler/device 24116, the control circuit executing/implementing the safety process 24100 may be configured to offer a recommendation to the surgeon 24122, in accordance with at least one aspect of the present disclosure, if another available stapler, another available energy device, and/or another stapler component (e.g., staple cartridge, shaft, etc. available for use with the selected stapler/device) 24112 is more optimal or optional, the control circuit may be configured to alert the surgeon (e.g., referring to FIG. 94, via a user interface on the selected stapler/device 24214, 24224 and/or 24234, via a user interface associated with the surgical hub 24244, via a user interface in the surgical theater 24254, etc.) of its availability and recommend its use in the current surgical procedure. In such an aspect, the control circuit may be further configured to receive an acceptance (e.g., via the user interface on the selected stapler/device 24214, 24224 and/or 24234, via the user interface associated with the surgical hub 24244, via a user interface in the surgical theater 24254, etc.) of the recommendation. Upon acceptance, the control circuit may be configured to present an infomercial 24124 regarding the other available stapler, the other available energy device, and/or the other stapler component (e.g., referring to FIG. 94, Components A to N, e.g., staple cartridge, shaft, etc. available for use with the selected stapler/device) 24112 that is more optimal. Upon rejection, the control circuit may be configured to end 24126 the device selection safety algorithm and/or execute a subsequent process.

According to various other aspects, although discussed specifically with respect to a stapler/device herein, the present disclosure should not be so limited. More specifically, the disclosed aspects similarly apply to other surgical instruments including energy devices (e.g. RF and/or ultrasonic surgical instruments) and/or their respective components and/or endoscopic devices and/or their respective components.

Controlling a Surgical Instrument According to Sensed Closure Parameters

Compression Rate to Determine Tissue Integrity

In various aspects, a surgical instrument can detect a variety of different variables or parameters associated with the closure of the jaws of the surgical instrument, which can in turn be utilized to adjust or affect various operational parameters that dictate how the surgical instrument functions. The rate at which the jaws of a surgical instrument are transitioned from the open position to the closed position to clamp tissue therebetween can be defined as the clamping rate or closure rate. In various aspects, the closure rate can be variable or constant during the course of an instance of the jaws closing. A threshold against which a particular parameter associated with the closure of the jaws is compared can be defined as a closure threshold.

Clamping tissue at an inappropriate closure rate or with inappropriate closure thresholds can result in damage to the tissue (e.g., the tissue can be torn due to the jaws applying too much force to the tissue) and/or operational failures by the surgical instrument (e.g., staples can be malformed due to the tissue not being fixedly held by the jaws as the staples are fired). Accordingly, in some aspects the surgical instrument is configured to detect the characteristics of the tissue being clamped by the surgical instrument and adjust the closure rate(s), closure threshold(s), and other operational parameters correspondingly. Further, each surgical procedure can involve multiple different tissue types and/or tissues with different characteristics. Accordingly, in some aspects the surgical instrument is configured to dynamically detect the tissue characteristics each time a tissue is clamped and adjust the closure rate(s), closure threshold(s), and other operational parameters correspondingly.

The present disclosure provides at least one solution, wherein a surgical instrument is configured to detect parameters associated with the compression of the tissue being clamped by the end effector. The surgical instrument can further be configured to differentiate between tissues exhibiting different integrities according to the detected tissue compression characteristics. The motor can then be controlled to affect the jaw closure rate and/or provide feedback to the user according to the integrity of the tissue. For example, the surgical instrument can be configured to decrease the closure rate of the jaws if the detected tissue compression characteristics indicate that the tissue is stiff and/or provide a suggestion to the user to utilize adjunct reinforcement if the tissue compression characteristics indicate that the tissue has low shear strength.

FIG. 95 illustrates a block diagram of a surgical instrument 21000, in accordance with at least one aspect of the present disclosure. In one aspect, a surgical instrument 21000 includes a control circuit 21002 coupled to a motor 21006, a user interface 21010, and a sensor(s) 21004. The motor 21006 is coupled to an end effector 21008 such that the motor 21006 causes the jaws (e.g., the anvil 150306 and/or channel 150302 of the surgical instrument 150010 depicted in FIG. 25) of the end effector 21008 to transition between a first or open configuration and a second or closed configuration, as is discussed with respect to FIG. 26, for example. The sensor(s) 21004 can be communicably coupled to the control circuit 21002 such that the control circuit 21002 receives data and/or signals therefrom. The control circuit 21002 can be communicably coupled to the motor 21006 such that the control circuit 21002 controls the operation of the motor 21006 according to, for example, data and/or signals received from the sensor(s) 21004. The user interface 21010 includes a device configured to provide feedback to a user of the surgical instrument, such as a display or a speaker.

In various aspects, the sensor(s) 21004 can be configured to detect the compression parameters of a tissue clamped at the end effector. In one aspect, the sensor(s) 21004 can be configured to detect the force to close (FTC) the jaws of the end effector 21008, i.e., the force exerted to transition the jaws from the open configuration to the closed configuration. For example, the sensor(s) 21004 can include a motor current sensor configured to detect the current drawn by the motor, such as is discussed with respect to FIG. 12, 18, or 19. For DC motors, the current drawn by the motor corresponds to the motor torque (e.g., the torque of the output shaft of the motor 21006), which is representative of the FTC the end effector 21008. The FTC the end effector 21008 corresponds to the tissue compression of the clamped tissue because it represents the force transmitted from the end effector 21008 to the clamped tissue as the end effector 21008 closes on the tissue. The more force that is being applied to the tissue, the more the tissue is being compressed. In another aspect, the sensor(s) 21004 includes a first electrode disposed on the end effector 21008 that is configured to receive an RF signal from a corresponding second electrode, such as is discussed with respect to FIGS. 36-38. The electrical impedance of a tissue can correspond to its tissue thickness, which can in turn correspond to the tissue compression of the clamped tissue. In yet another aspect, the sensor(s) 21004 include a force sensitive transducer that is configured to determine the amount of force being applied to the sensor(s) 21004, such as is discussed with respect to FIG. 24. Similarly to the discussion above with respect to FTC, the force detected by the transducer represents the force transmitted from the end effector 21008 to the clamped tissue as the end effector 21008 closes on the tissue. The more force that is being applied to the tissue, the more the tissue is being compressed. The user interface 21010 includes a device configured to provide feedback to a user of the surgical instrument, such as a display or a speaker. In still other aspects, the sensor(s) 21004 can include various combinations of the aforementioned sensors and other such sensors capable of detecting compression parameters associated with a tissue clamped at the end effector. For example, an end effector, such as the end effector 15200 depicted in FIG. 53, can include a first sensor 152008*a* that comprises a force sensitive transducer and a second sensor 152008*b* that comprises an impedance sensor.

The control circuit 21002 can be configured to adjust the closure rate of the jaws of the end effector 21008 to accommodate different tissue types. The control circuit 21002 can be configured to monitor the compression force exerted on the tissue (e.g., FTC) or another parameter associated with the compression of the tissue (e.g., tissue impedance) over an initial period of compression and, based on the rate of change of the tissue compression parameter, adjust the jaw closure rate or time accordingly. For example, it may be beneficial to lower the closure rate or increase the closure time for more viscoelastic tissues, rather than apply the total compressive force over a short period of time, as discussed above with respect to FIG. 22.

FIG. 96 illustrates a logic flow diagram of a process 21050 for controlling a surgical instrument according to the integrity of the clamped tissue, in accordance with at least one aspect of the present disclosure. In the following description of the process 21050, reference should also be made to FIG. 95. The illustrated process can be executed by, for example, the control circuit 21002 of the surgical instrument 21000. Accordingly, the control circuit 21002 executing the process receives 21052 data and/or signals (e.g., digital or analog) from the sensor(s) 21004 pertaining to a tissue compression parameter sensed thereby. In various aspects, the tissue compression parameter can include a parameter associated with a characteristic, type, property, and/or status of a tissue being operated on; a parameter associated with an internal operation and/or a property of the surgical instrument 21000; or a component thereof. In one aspect, the tissue compression parameter can include, for example, the FTC the end effector 21008. In another aspect, the tissue compression parameter can include, for example, the thickness of the clamped tissue. The control circuit 21002 can receive 21052 the data pertaining to a tissue compression parameter as one or more discrete values transmitted by the sensor(s) 21004, a signal transmitted by the sensor(s) 21004 that can then be correlated to associated value(s), and so on.

Accordingly, the control circuit 21002 determines how the value of the sensed tissue compression parameter compares to one or more thresholds and then generates a response accordingly. In one aspect, the control circuit 21002 determines 21054 the value of the sensed tissue compression parameter relative to a first threshold. For example, the control circuit 21002 can determine 21054 whether the sensed tissue compression parameter exceeds or is greater than a first or upper threshold. In one aspect, if the sensed tissue compression parameter exceeds the first threshold, then the process 21050 proceeds along the YES branch and the control circuit 21002 controls 21056 the motor 21006 to increase the length of time taken to close the jaws of the end effector 21008. The control circuit 21002 can control 21056 the motor 21006 to increase the jaw closure time by, for example, decreasing the rate at which the jaws are closed, increasing the length of time that the movement of the jaws is paused after the initial clamping of the tissue (i.e., the tissue creep wait time), or lowering the stabilization threshold to end the clamping phase. If the sensed tissue compression parameter does not exceed the first threshold, then the process 21050 proceeds along the NO branch and, in various aspects, the process 21050 can end or the process 21050 can continue and the control circuit 21002 can compare the value of the sensed tissue compression to one or more additional thresholds or continue receiving 21052 tissue parameter data and/or signals.

In another aspect, the control circuit 21002 further determines 21058 the value of the sensed tissue compression parameter relative to a second threshold. For example, the control circuit 21002 can determine 21058 whether the sensed tissue compression parameter is below or is less than a second or lower threshold. In one aspect, if the sensed tissue parameter is below the second threshold, then the process 21050 proceeds along the YES branch and the control circuit 21002 provides 21060 corresponding feedback via, for example, the user interface 21010. The provided 21060 feedback can include, for example, visual feedback provided via a display or audio feedback provided by a speaker. In one aspect, the feedback can suggest that the user take one or more corrective actions to ameliorate the situation resulting in the sensed tissue compression parameter being unexpectedly low. Such corrective action can include, for example, utilizing adjunct reinforcement (i.e., a tissue thickness compensator), such as is disclosed in U.S. Pat. No. 8,657,176, titled TISSUE THICKNESS COMPENSATOR FOR A SURGICAL STAPLER, which is hereby incorporated by reference herein. Adjunct reinforcement can, in various aspects, comprise a layer or series of layers of compressible material configured to adapt and/or apply an additional compressive force to the tissue captured between the anvil 150306 (FIG. 25) and the staple cartridge 150304 (FIG. 25).

The thresholds discussed above can include, for example, values for the parameter(s) sensed by the sensor(s) 21004 and/or derivatives of the parameter(s) sensed by the sensor (s) 21004 (e.g., the time rate change of a sensed parameter). In aspects where the tissue compression parameter includes FTC the end effector 21008, the first threshold can indicate the delineation above which the clamped tissue is considered stiff. Stiff tissue can be relatively prone to tearing, either due to the mechanical actions of the jaws on the tissue or, for lung tissue, during re-inflation. Further, the second threshold can indicate the delineation below which the clamped tissue is considered to have a weak shear strength (i.e., is squishy). Tissue having weak shear strength can be relatively difficult for the end effector 21008 to securely grasp or otherwise hold in place during stapling and/or firing of the cutting member (i.e., I-beam 150178 with cutting edge 150182).

It should be noted that although the steps of the particular example of the process 21050 in FIG. 96 are depicted as occurring in a particular order or sequence, such a depiction is solely for illustrative purposes and no particular sequence of the process 21050 is intended, unless a particular sequence of particular steps is explicitly necessary from the description hereabove. For example, in other aspects of the process 21050, the control circuit 21002 can determine 21058 whether the sensed tissue compression parameter is below a second or lower threshold, prior to determining 21054 whether the sensed tissue compression parameter exceeds a first or upper threshold.

FIG. 97 illustrates a first graph 21100 depicting end effector FTC 21104 verse time 21102 for illustrative firings of a surgical instrument 21000, in accordance with at least one aspect of the present disclosure. In the following description of the first graph 21100, reference should also be made to FIGS. 95-96. The first graph 21100 depicts a first firing 21110 and a second firing 21114, which are illustrative firings by a surgical instrument 21000 controlled by a control circuit 21002 executing the process 21050 described above with respect to FIG. 96. In this illustrative example, the first threshold 21106 includes a particular time rate change of the FTC (i.e., ΔFTC) and the second threshold 21108 includes a particular FTC. In various aspects, the thresholds 21106, 21108 can be fixed or predetermined values, defined with respect to one or more other variables, or programmed or set by a user of the surgical instrument 21000.

For the first firing 21110, the control circuit 21002 executing the process illustrated in FIG. 96 receives 21052 the tissue compression parameter data and/or signals and determines 21058 that the FTC falls below the second threshold 21108 at time $t_1$. Accordingly, the control circuit 21002 provides 21060 feedback to the user, including a suggestion for the user to take certain actions and/or indicate that the end effector 21008 is grasping tissue that has a low shear strength.

In one aspect, the provided 21060 feedback can include a suggestion that the user unclamp and re-fire the surgical instrument 21000 with a tissue compensator (e.g., a tissue compensator described in U.S. Pat. No. 8,657,176) applied to the end effector 21008 in order to reinforce and/or compensate for the low shear strength tissue. In one aspect, the control circuit 21002 can further be configured to cause the motor 21006 to stop closing the jaws of the end effector 21008 if the FTC is below the second threshold. In another aspect, the control circuit 21002 can be configured to provide a suggestion that the user stop closing the jaws of the end effector 21008 if the FTC is below the second threshold. The provided 21060 feedback can take a variety of forms, including, for example, a prompt displayed on an operating theater display 107, 109, 119 (FIG. 2) and/or a surgical instrument display, an audible message emitted via a speaker located in the operating theater and/or on the surgical instrument, haptic feedback via the surgical instrument, or combinations thereof.

For the second firing 21114 (which may be a firing utilizing a tissue compensator subsequent to the first firing 21110), the control circuit 21002 executing the process 21050 illustrated in FIG. 96 receives 21052 the tissue compression parameter data and/or signals and does not determine that the FTC falls below the second threshold or exceeds the first threshold at any point during the course of closing the end effector 21008. Accordingly, the control circuit 21002 does not affect the jaw closure rate, provide feedback to the user, or take any other such action.

FIG. 98 illustrates a second graph 21116 depicting end effector FTC 21102 verse time 21104 for an illustrative firing of a surgical instrument 21000, in accordance with at least one aspect of the present disclosure. In the following description of the second graph 21116, reference should also be made to FIGS. 95-96. The second graph 21116 depicts a third firing 21118, which is an illustrative firing by a surgical instrument 21000 controlled by a control circuit 21002 executing the process 21050 described above with respect to FIG. 96. In this illustrative example, the first threshold 21106 includes a particular time rate change of the FTC (i.e., ΔFTC).

For the third firing 21116, the control circuit 21002 executing the process illustrated in FIG. 96 receives 21052 the tissue compression parameter data and/or signals and determines 21058 that the ΔFTC exceeds the first threshold 21106 at time $t_2$. Accordingly, the control circuit 21002 controls 21056 the motor 21006 to increase the jaw closure time, such as by decreasing the jaw closure rate, which correspondingly lowers the rate at which the FTC 21102 increases. Increasing the jaw closure time can be beneficial to, e.g., avoid causing damage to stiff tissue by preventing a larger amount of force from being exerted on the tissue over a short period of time. In one aspect, the first threshold 21106 can include a default rate of change of the FTC ($\Delta FTC_D$), i.e., the default or baseline FTC rate for a surgical instrument 21000 absent any modifications to the FTC by a control algorithm according to tissue type and other such parameters. In this aspect, if the FTC experienced by the surgical instrument 21000 during a surgical procedure exceeds the $FTC_D$, then the control circuit 21002 executing the process 21050 can control 21056 the motor 21006 to increase the jaw closure time.

The time at which the control circuit 21002 executing the aforementioned algorithm or process determines compares the parameter sensed by the sensor(s) 21004 to one or more thresholds can include a discrete instance during the firing stroke of the surgical instrument 21000, a series of discrete instances during the firing stroke, and/or a continuous time interval during the firing stroke. The tissue compression parameter monitored by the control circuit 21002 and compared against a threshold can include, for example, a FTC value (e.g., the second threshold 21108 depicted in FIG. 97) or a ΔFTC value (e.g., the first threshold 21106 depicted in FIGS. 97-98).

In one aspect, the control circuit 21002 can be further configured to store data related to the firings of the surgical instrument 21000 and then optionally utilize the data from the previous firings to adjust an algorithm for determining the tissue integrity of a clamped tissue. For example, the data from the previous firings can be utilized to adjust the first and/or second thresholds of the process 21050 depicted in FIG. 96. In one aspect, the surgical instrument 21000 can be configured to pair with a surgical hub 106 (FIGS. 1-3) executing a situational awareness system, as described above under the heading "Situational Awareness" and described in U.S. patent application Ser. No. 15/940,654, titled SURGICAL HUB SITUATIONAL AWARENESS, filed Mar. 29, 2018, which is hereby incorporated by reference herein in its entirety. In this aspect, the situational awareness system can determine the type of tissue that is being operated on during the surgical procedure and adjust the algorithm for determining the tissue integrity of a clamped tissue accordingly. In another aspect, the surgical instrument 21000 can be configured to receive user input indicating the type of tissue that is being operated on and adjust the algorithm for determining tissue integrity accordingly. For example, the surgical instrument 21000 can be configured to adjust the first and/or second thresholds of the process 21050 depicted in FIG. 96 from default values according to the tissue type entered by the user.

The techniques described hereabove allow the surgical instrument 21000 to avoid damaging clamped tissue and prevent operational failures (e.g., malformed staples) resulting from jaw closure rates that are inappropriate or non-ideal for the particular characteristics of the tissue being operated on. Further, the techniques described hereabove improve the ability of the surgical instrument to respond appropriately to the characteristics of the tissues encountered during the course of a surgical procedure.

Tissue Initial Contact to Determine Tissue Type

Clamping tissue at an inappropriate closure rate or with inappropriate closure thresholds can result in damage to the tissue (e.g., the tissue can be torn due to the jaws applying too much force to the tissue) and/or operational failures by the surgical instrument (e.g., staples can be malformed due to the tissue not being fixedly held by the jaws as the staples are fired). Accordingly, in some aspects the surgical instrument is configured to detect the characteristics of the tissue being clamped by the surgical instrument and adjust the closure rate(s), closure threshold(s), and other operational parameters correspondingly. Further, each surgical procedure can involve multiple different tissue types and/or tissues with different characteristics. Accordingly, in some aspects the surgical instrument is configured to dynamically detect the tissue characteristics each time a tissue is clamped and adjust the closure rate(s), closure threshold(s), and other operational parameters correspondingly.

The present disclosure provides at least one solution, wherein a surgical instrument is configured characterize the tissue type of the tissue being clamped according to the degree of tissue contact against the surfaces of the jaws and the relative positions of the jaws at the initial point in contact with the tissue. The closure rate for the jaws and the threshold for adjusting the jaw closure rate can then be set to appropriate levels for the tissue type characterized by the detected degree of tissue contact and the detected position of the jaws. For example, the surgical instrument can be configured to differentiate between parenchyma and vessels because parenchyma contacts a greater degree of the surfaces of the jaws and the jaws at a larger angle at the point of initial contact as compared to vessels. The surgical instrument can then control the motor to affect the jaw closure rate and adjustment threshold accordingly for the detected tissue type.

Referring back to FIG. 95, in one aspect, a surgical instrument 21000 includes a control circuit 21002 coupled to a motor 21006, a user interface 21010, and sensor(s) 21004. The motor 21006 is coupled to an end effector 21008 such that the motor 21006 causes the jaws (e.g., the anvil 150306 and/or channel 150302 of the surgical instrument 150010 depicted in FIG. 25) of the end effector 21008 to transition between a first or open configuration and a second or closed configuration, as is discussed with respect to FIG. 26. The sensor(s) 21004 can be communicably coupled to the control circuit 21002 such that the control circuit 21002 receives data and/or signals therefrom. The control circuit 21002 can be communicably coupled to the motor 21006 such that the control circuit 21002 controls the operation of the motor 21006 according to, for example, data and/or signals received from the sensor(s) 21004.

In various aspects, the sensor(s) 21004 can be configured to detect physical contact of a tissue against the surface of the jaws of the end effector 21008. In one aspect, the sensor(s) 21004 can include one or more tissue contact sensors disposed along the tissue-contacting surfaces of the end effector 21008, such as the anvil and the cartridge or channel. The tissue contact sensors can include, for example, a plurality of sensors or segments of a segmented circuit arranged sequentially along the surfaces of the jaws that are each configured to determine whether tissue is positioned thereagainst, such as is discussed above with respect to FIGS. 75-79. In one aspect, the sensor(s) 21004 include a plurality of electrodes that are each configured to receive an RF signal from a corresponding electrode disposed on the opposing jaw, such as is discussed with respect to FIGS. 36-38. Accordingly, the control circuit 21002 can perform continuity tests along the length of the end effector 21008 to determine that tissue is present at the locations corresponding to each electrode that is able to receive the signal from its corresponding electrode (because a signal transmission medium, i.e., a tissue, must be situated therebetween for an electrode to receive the signal from its corresponding electrode). In another aspect, the sensor(s) 21004 include a plurality of force sensitive transducers that are each configured to determine the amount of force being applied to the sensor(s) 21004, such as is discussed with respect to FIG. 24. Accordingly, the control circuit 21002 can determine that tissue is present at the locations corresponding to each force sensitive transducer that is detecting a non-zero force thereagainst. In other aspects, the sensor(s) 21004 include a plurality of load cells, pressure sensors, and/or other sensors configured to detect physical contact thereagainst. Similarly to the discussion above with respect to the force sensitive transducer, the control circuit 21002 can determine that tissue is present at the locations corresponding to each load cell, pressure sensor, and/or other sensor that is detecting a non-zero force thereagainst. In yet another aspect, the sensor(s) 21004 include a current sensor that is configured to detect the amount of electrical current being drawn by the motor 21006, such as is discussed with respect to FIG. 12, 18, or 19. Accordingly, the control circuit 21002 can determine the point at which the jaws of the end effector 21008 initially contact the tissue according to when the current drawn by the motor 21006 increases to compensate for the increased clamp load experienced by the motor 21006 as the jaws contact tissue and begin exerting a clamping force thereagainst, such as is discussed with respect to FIG. 83 (i.e., FTC increases 153610, 153616 as the jaws clamp the tissue and FTC corresponds to motor current). The various aspects described hereabove can be utilized, either individually or in combination with other aspects, for determining the initial point of contact between the end effector 21008 and the tissue being clamped and/or the degree of contact between the tissue and the end effector 21008.

FIG. 99 illustrates a logic flow diagram of a process 21200 for controlling a surgical instrument according to the physiological type of the clamped tissue, in accordance with at least one aspect of the present disclosure. In the following description of the process 21200, reference should also be made to FIG. 95. The illustrated process can be executed by, for example, the control circuit 21002 of the surgical instrument 21000. Accordingly, the control circuit 21002 executing the illustrated process 21200 receives 21202 tissue contact data and/or signals from the sensor(s) 21004, such as the tissue contact sensors discussed above and depicted in FIGS. 100A-101B. The received 21202 tissue contact data and/or signals indicate whether tissue is contacting at least one of the sensors 21004. Accordingly, the control circuit 21002 can determine 21204 the initial point of contact between the end effector 21008 and the tissue being clamped. In one aspect, the control circuit 21002 determines 21204 when the initial tissue contact occurs by detecting when at least one of the sensors 21004 disposed on each of the jaws detects tissue contact thereagainst.

Accordingly, the control circuit 21002 determines 21206 the position of the jaws at the initial tissue contact point. In one aspect, the control circuit 21002 is communicably coupled to a Hall effect sensor disposed on one of the jaws of the end effector 21008 that is configured to detect the relative position of a corresponding magnetic element disposed on the opposing jaw, such as is discussed with respect to FIG. 77. The control circuit 21002 can thus determine 21206 the position of the jaws according to the sensed distance or gap therebetween. In another aspect, the control circuit 21002 is communicably coupled to a position sensor that is configured to detect the absolute or relative position of a closure tube that is configured to close the jaws as the closure tube is driven from a first or proximal position to a second or distal position, such as is discussed with respect to FIGS. 20-21 and 25. The control circuit 21002 can thus determine 21206 the position of the jaws according to the sensed position of the closure tube. In yet another aspect, the control circuit 21002 is communicably coupled to an angle sensor, such as a TLE5012B 360° angle sensor from Infineon Technologies, that is configured to detect the angle at which at least one of the jaws is oriented. The control circuit 21002 can thus determine 21206 the position of the jaws according to the sensed angle at which the jaw(s) are oriented.

Accordingly, the control circuit 21002 determines 21208 the degree of contact between the grasped tissue and the tissue-contacting surface(s) of the jaws. The degree of tissue contact can correspond to the number or ratio of the sensors 21004 that have detected the presence (or absence) of tissue, such as is discussed with respect to FIG. 79. In one aspect, the control circuit 21002 can determine the degree of tissue contact according to the ratio of the sensor(s) 21004 that have detected the presence of tissue to the sensor(s) 21004 that have not detected the presence of tissue.

Accordingly, the control circuit 21002 sets 21210 control parameters for the motor 21006 according to the determined 21206 position of the jaws and the determined 21208 degree of tissue contact. The motor control parameters can include, for example, the time to close the jaws and/or closure threshold(s). In one aspect, the control circuit 21002 can be configured to perform a runtime calculation and/or access a memory (e.g., a lookup table) to retrieve the motor control parameters (e.g., the jaw closure rate and closure threshold) associated with the particular position of the jaws and the particular degree of tissue contact sensed via the various sensors. In various aspects, the control circuit 21002 can control the motor 21006 to adjust the jaw closure time by, for example, adjusting the rate at which the jaws are transitioned from the open position to the closed position, adjusting the length of time that the jaws are paused after the initial clamping of the tissue (i.e., the tissue creep wait time), and/or adjusting the stabilization threshold that ends the clamping phase. In various aspects, the closure threshold(s) can include, for example, the maximum allowable FTC the end effector 21008 or rate of change for the FTC (i.e., ΔFTC) at which the control circuit 21002 stops the motor 21006 driving the closure of the jaws or takes other actions, as discussed above under the heading "Compression Rate to Determine Tissue Integrity." The control circuit 21002 can then control the motor 21206 according to the motor control parameters set 21210 by the process 21200.

The position of the jaws and the degree of contact with the tissue at the initial point of contact with the tissue corresponds to the thickness or geometry of the tissue being grasped, which in turn corresponds to the physiological type of the tissue. Thus, the control circuit 21002 can be configured to differentiate between tissue types and then set 21210 the control parameters for the motor 21006 accordingly. For example, the control circuit 21002 can be configured to determine whether parenchyma or vessel tissue has been grasped by the end effector 21008 and then set 21210 motor control parameters that are appropriate for the detected tissue type.

In some aspects, jaw closure rate can be selected for each tissue type to maintain the maximum FTC and/or ΔFTC under a particular closure threshold, which can likewise be selected for each tissue type. In one aspect, the control circuit 21002 can be configured to institute a minimum clamp rate so that the closure motion of the jaws is never permanently halted. In one aspect, the control circuit 21002 can be configured to control the maximum pause times to ensure that jaw closure progresses at least a default rate. In one aspect, the control circuit 21002 can be configured to halt the motor 21006 and/or provide feedback to the user when closure threshold(s) are exceeded or otherwise beached during user of the surgical instrument 21000.

It should be noted that although the steps of the particular example of the process 21200 in FIG. 99 are depicted as occurring in a particular order or sequence, such a depiction is solely for illustrative purposes and no particular sequence of the process 21200 is intended, unless a particular sequence of particular steps is explicitly necessary from the description hereabove. For example, in other aspects of the process 21200, the control circuit 21002 can determine 21208 the degree of tissue contact prior to determining 21206 the jaw position at the initial contact point.

FIGS. 100A-101B illustrate various side elevational views of an end effector 21008 grasping parenchyma 21030 and a vessel 21032, at both the initial contact positions with the tissue and the closed positions, in accordance with at least one aspect of the present disclosure. In the depicted aspect, the end effector 21008 includes a plurality of tissue contact sensors 21016 disposed along the tissue-contacting surfaces of the jaws, which include the anvil 21012 and the channel 21014. In other aspects, the tissue contact sensors 21016 can be disposed along a cartridge 150304 (FIG. 25), in addition to or in lieu of being disposed along the channel 21014 of the surgical instrument 21000. For brevity, the tissue contact sensors 21016 will be discussed as being disposed along the channel 21014 in the following description; however, it should be noted that the concepts discussed herein likewise apply to aspects where the tissue contact sensors 21016 are disposed along the cartridge 150304. The tissue contact sensors 21016 can include, for example, impedance sensors, load cells, force sensitive transducers, and combinations thereof, as discussed above. The tissue contact sensors 21016 can be delineated into activated sensors 21018 (i.e., sensors that are sensing the presence of tissue) and non-activated sensors 21020 (i.e., sensors that are not sensing the presence of tissue) during use of the surgical instrument 21000 in a surgical procedure.

FIGS. 100A and 101A illustrate the end effector's 21008 initial contact point with parenchyma 21030 and a vessel 21032, respectively. In one aspect, the initial contact point between the end effector 21008 and a tissue can be defined as the point at which there is at least one activated sensor 21018 on both the anvil 21012 and the channel 21014. As described above, tissue types can be differentiated according to the position of the jaws (i.e., the anvil 21012 and/or the channel 21014) and the degree of contact between the tissue and the jaws at the initial contact point with the tissue. For example, FIGS. 100A and 101A illustrate how parenchyma 21030 and a vessel 21032 can be differentiated based upon the proportion of activated sensors 21018 at the initial tissue contact point. Namely, clamping a vessel 21032 results in fewer activated sensors 21018 with respect to clamping parenchyma 21030. It should further be noted that the number of activated tissue sensors 21018 on the anvil 21012 and the channel 21014 need not be equal at the initial tissue contact point. As a further example, FIGS. 100A and 101A illustrate how parenchyma 21030 and a vessel 21032 can be differentiated based upon the angle at which the anvil 21012 is oriented with respect to the channel 21014 at the initial tissue contact point. Namely, the anvil 21012 is oriented at a first angle $\theta_1$ at the initial contact point with the parenchyma 21030 and at a second angle $\theta_2$ at the initial contact point with the vessel 21032. The differences between the proportion of activated sensors 21018 and the angle at which the anvil 21012 is oriented can be utilized either individually or in combination (e.g., by the process 21200 illustrated in FIG. 99) to characterize the physiological type of tissue that is being clamped and then set the appropriate jaw closure rate, closure thresholds, and other motor control parameters for the tissue type.

FIGS. 100B and 101B illustrate the point at which the end effector 21008 has fully clamped parenchyma 21030 and a vessel 21032, respectively. As can be seen, the change in the number or proportion of activated sensors 21018 and non-activated sensors 21020 as the end effector 21008 clamps the tissue can likewise be utilized to determine the tissue type and/or physical characteristics of the tissue, the degree to which the tissue is compressed and/or the distance between the anvil 21012 and the channel 21014, and various other parameters. For example, a vessel 21032 deforms much more than parenchyma 21030 when fully clamped, which results in a relatively larger change in the number of activated sensors 21018 as the end effector 21008 clamps the vessel 21032. In some aspects, a control circuit can execute a process to determine the tissue type (i.e., physiological tissue type or tissue having certain physical characteristics) according to the change or rate of change in the number of activated sensors 21018 as the end effector 21008 is clamped. In some aspects, a control circuit can execute a process to determine the degree to which the tissue is compressed and/or deformed according to the change or rate of change in the number of activated sensors 21018 as the end effector 21008 is clamped.

In some aspects where the surgical instrument 21000 includes a control circuit 21002 executing the process 21200 described above in FIG. 99, when the control circuit 21002 determines that the jaws 21013 have initially contacted the tissue, the control circuit 21002 can be configured to detect or measure the separation between the jaws $\theta$ and the length or degree of tissue contact between the tissue and the jaws L. The closure thresholds (e.g., the FTC threshold or ΔFTC threshold), initial closure speed, and adjusted closure speed(s) (i.e., the closure speed(s) at which the jaws 21013 are closed after a closure threshold is exceeded) can each be a function of $\theta$ and L. As depicted in FIGS. 100A-B, the jaw separation can be defined as $\theta_1$ and the degree of tissue contact can be defined as $L_1$ at the initial contact point with a first tissue (e.g., parenchyma 21030). As depicted in FIGS. 10A-B, the jaw separation can be defined as $\theta_2$ and the degree of tissue contact can be defined as $L_2$ at the initial contact point with a second tissue (e.g., a vessel 21032). Accordingly, in some aspects where $\theta_1>\theta_2$ and $L_1>L_2$, the parenchyma FTC threshold $FTC_p$>the vessel FTC threshold $FTC_v$; the parenchyma ΔFTC threshold $\Delta FTC_p$>the vessel slope threshold $\Delta FTC_v$; and the vessel initial closure speed $v_{V1}$>the parenchyma initial closure speed $v_{P1}$. The operational differences between these thresholds are discussed in further detail below with regards to FIGS. 102-103.

FIG. 102 illustrates a first graph 21300 and a second graph 21302 depicting end effector FTC 21304 and closure velocity 21306, respectively, verse time 21308 for illustrative firings of a surgical instrument 21000 grasping parenchyma 21030, in accordance with at least one aspect of the present disclosure. In the following description of the first graph 21300 and the second graph 21302, reference should also be made to FIGS. 95 and 99-100B. The illustrative firings described herein are for the purpose of demonstrating the concepts discussed above with respect to FIGS. 95 and 99-100B and should not be interpreted as limiting in any way.

A first firing of a surgical instrument 21000 can be represented by a first FTC curve 21310 and a corresponding first velocity curve 21310', which illustrate the change in FTC and closure velocity over time during the course of the first firing, respectively. The first firing can represent, for example, a default firing of the surgical instrument 21000 or a firing of the surgical instrument 21000 that does not include a control circuit 21002 executing the process 21200 depicted in FIG. 99. As firing of the surgical instrument 21000 is initiated, the control circuit 21002 controls the motor 21006 to begin driving the anvil 21014 from its open position, causing the closure velocity of the anvil 21012 to sharply increase 21318 to an initial or default closure velocity $v_{d1}$. As the anvil 21012 is driven from the open position, it makes contact with the clamped tissue that, for this particular firing, is parenchyma 21030. As the anvil 21012 contacts the tissue being clamped at time $t_0$, the FTC increases 21312 from an initial FTC (e.g., zero) to a peak 21314 at time $t_1$. At time $t_1$, the control circuit 21002 of the surgical instrument 21000 determines that the FTC has reached or exceeded a FTC threshold (which can be, for example, a default threshold independent of the tissue type) and controls the motor 21006 halt the movement of the anvil 21012, causing the closure velocity to drop 21320 to zero. The movement of the anvil 21012 can be paused for a duration $p_1$, during which time the closure velocity is maintained 21322 at zero. During the pause, the FTC gradually decreases 21316 as the clamped tissue relaxes.

A second firing of a surgical instrument 21000 can be represented by a second FTC curve 21324 and a corresponding first velocity curve 21324', which illustrate the change in FTC and closure velocity over time during the course of the second firing, respectively. In contrast to the first firing, the second firing can represent, for example, a firing of the surgical instrument 21000 that includes a control circuit 21002 executing the process depicted in FIG. 99. As firing of the surgical instrument 21000 is initiated, the control circuit 21002 controls the motor 21006 to begin driving the anvil 21014 from its open position, causing the closure velocity of the anvil 21014 to sharply increase 21336. Due to the relative thickness and/or geometry of the parenchyma 21030, the initial contact point between the tissue (i.e., parenchyma 21030) and the jaws 21013 occurs shortly after the anvil 21012 begins to be driven by the motor 21006; therefore, the control circuit 21002 executing the process 21200 depicted in FIG. 99 is able to nearly immediately determine that parenchyma 21030 is being clamped and correspondingly set the time to close the jaws, closure threshold(s), and other closure parameters at a relatively early point in the closure process. Accordingly, the control circuit 21002 controls the motor 21006 to cause the closure velocity of the anvil 21014 to sharply increase 21336 to an initial closure velocity $v_{p1}$ that is specific to parenchyma 21320 tissue.

As the anvil 21012 is driven from the open position, it makes contact with the clamped tissue that, for this particular firing, is parenchyma 21030. As the anvil 21012 contacts the tissue being clamped at time $t_0$, the FTC increases 21326 from an initial FTC (e.g., zero) to a first peak 21328 at time $t_2$. It should be noted that the FTC increases 21326 more slowly during the second firing as compared to the first firing because the control circuit 21002 executing the process 21200 selected a first or initial closure velocity $v_{p1}$ in the second firing that was appropriate for the type of tissue being clamped, which thereby reduces the amount of force exerted on the tissue as compared to an unmodified firing of the surgical instrument 21000. At time $t_2$, the control circuit 21002 of the surgical instrument 21000 determines that the FTC has reached or exceeded a FTC threshold $FTC_p$ (which had been set by the control circuit 21002 on or after to when the control circuit 21002 determined that parenchyma 21030 tissue was being clamped). The parenchyma FTC threshold $FTC_p$ can represent, for example, the maximum force that can be safely or desirably exerted on parenchyma 21030 tissue. Accordingly, the control circuit 21002 controls the motor 21006 to halt the movement of the anvil 21012, causing the closure velocity to drop 21338 to zero. The movement of the anvil 21012 can be paused for a duration $p_2$, during which time the closure velocity is maintained 21340 at zero. During the pause, the FTC gradually decreases 21330 as the clamped tissue relaxes. The pause duration $p_2$ can be equal to a default pause duration (e.g., $p_1$) or a closure parameter selected by the control circuit 21002 for parenchyma 21030 tissue.

After the pause duration $p_2$ has elapsed at time $t_3$, the control circuit 21002 re-engages the motor 21006 and resumes closing the anvil 21012. Accordingly, the closure velocity increases 21342 to a second closure velocity $v_{p2}$. In some aspects, after the parenchyma FTC threshold $FTC_p$ is first exceeded, the control circuit 21002 reduces the closure velocity at which the anvil 21012 is closed to a second closure velocity $v_{p2}$ that is specific to parenchyma 21030 tissue, wherein $v_{p2}<v_{p1}$. The control circuit 21002 can be configured to close the anvil 21012 at a lower velocity subsequent to the parenchyma FTC threshold $FTC_p$ being exceeded because that may indicate that the tissue is thicker, stiffer, or otherwise more resistant to the closure forces from the anvil 21012 than expected for the detected tissue type. Thus, it may be desirable to reduce the closure velocity to attempt to reduce the amount of closure forces subsequently exerted on the tissue being clamped.

As the anvil 21012 resumes closing at time $t_3$, the FTC once again begins increasing until it peaks 21332 at time $t_4$ and once again reaches or exceeds the parenchyma force threshold $FTC_p$. At time $t_4$, the control circuit 21002 of the surgical instrument 21000 determines that the FTC has reached or exceeded the FTC threshold $FTC_p$. Accordingly, the control circuit 21002 controls the motor 21006 halt the movement of the anvil 21012, causing the closure velocity to drop 21346 to zero. The movement of the anvil 21012 can be paused for a duration $p_3$, during which time the closure velocity is maintained 21348 at zero. During the pause, the FTC gradually decreases 21334 as the clamped tissue relaxes.

FIG. 103 illustrates a third graph 21350 and a fourth graph 21352 depicting end effector FTC 21354 and closure velocity 21356, respectively, verse time 21358 for illustrative firings of a surgical instrument 21000 grasping a vessel 21032, in accordance with at least one aspect of the present disclosure. In the following description of the third graph 21350 and the second graph 21352, reference should also be made to FIGS. 95, 99, 101A-B. The illustrative firings described herein are for the purpose of demonstrating the concepts discussed above with respect to FIGS. 95, 99, 101A-B and should not be interpreted as limiting in any way.

A third firing of a surgical instrument 21000 can be represented by a third FTC curve 21360 and a corresponding first velocity curve 21360', which illustrate the change in FTC and closure velocity over time during the course of the third firing, respectively. The third firing can represent, for example, a default firing of the surgical instrument 21000 or a firing of the surgical instrument 21000 that does not include a control circuit 21002 executing the process depicted in FIG. 99. As firing of the surgical instrument 21000 is initiated, the control circuit 21002 controls the motor 21006 to begin driving the anvil 21014 from its open position, causing the closure velocity of the anvil 21012 to sharply increase 21370 to an initial or default closure velocity $v_{d2}$. The initial closure velocity $v_{d2}$ may or may not be equal to the initial closure velocity $v_{d1}$ in FIG. 102. As the anvil 21012 is driven from the open position, it travels for a period of time before making contact with the clamped tissue that, for this particular firing, is a vessel 21032. It should be noted that this is in contrast to firings where the surgical instrument 21000 is clamping parenchyma 21030, as depicted in FIG. 102. As a vessel 21032 is relatively thin, the anvil 21012 generally must travel for a distance before making initial contact with the vessel 21032, whereas parenchyma 21032 is generally thicker than a vessel 21032 and thus the anvil 21012 generally nearly immediately makes initial contact with the vessel 21032. Therefore, the FTC is initially flat 21362 because the anvil 21012 travels for a period of time without contacting the tissue. Once the anvil 21012 contacts the tissue at time $t_0$, the FTC increases 21364 from an initial or flat 21376 FTC (e.g., zero) to a peak 21366 at time $t_2$. At time $t_2$, the control circuit 21002 of the surgical instrument 21000 determines that the FTC has reached or exceeded a FTC threshold (which can be, for example, a default threshold independent of the tissue type) and controls the motor 21006 halt the movement of the anvil 21012, causing the closure velocity to drop 21372 to zero. The movement of the anvil 21012 can be paused for a duration $p_4$, during which time the closure velocity is maintained 21374 at zero. During the pause, the FTC gradually decreases 21368 as the clamped tissue relaxes.

A fourth firing of a surgical instrument 21000 can be represented by a second FTC curve 21375 and a corresponding first velocity curve 21375', which illustrate the change in FTC and closure velocity over time during the course of the second firing, respectively. In contrast to the first firing, the fourth firing can represent, for example, a firing of the surgical instrument 21000 that includes a control circuit 21002 executing the process 21200 depicted in FIG. 99. As firing of the surgical instrument 21000 is initiated, the control circuit 21002 controls the motor 21006 to begin driving the anvil 21014 from its open position, causing the closure velocity of the anvil 21014 to sharply increase 21386. Due to the relative thinness and/or geometry of the vessel 21032 (compared to, for example, parenchyma 21030), the initial contact point between the tissue (i.e., the vessel 21032) and the jaws 21013 does not occur until after the anvil 21012 has been driven by the motor 21006 for a period of time; therefore, the control circuit 21002 executing the process 21200 depicted in FIG. 99 is not able to determine that a vessel 21032 is being clamped and correspondingly set the time to close the jaws, closure threshold(s), and other appropriate closure parameters until the closure process has been carried out for a period of time. Because the anvil 21012 does not contact the thinner tissue of the vessel 21032 for a period of time and thus the control circuit 21002 is accordingly not able to detect what type of tissue that is being clamped, the control circuit 21002 controls the motor 21006 to cause the closure velocity of the anvil 21014 to sharply increase 21386 to the default velocity $v_d$.

As the anvil 21012 is driven from the open position, the FTC is initially flat 21376 because the anvil 21012 travels for a period of time without contacting the tissue. Once the anvil 21012 contacts the tissue at time $t_0$, the FTC increases 21378 from an initial FTC (e.g., zero). After contacting the vessel 21032, the control circuit 21002 executing the process 21200 illustrated in FIG. 99 is able to determine that a vessel 21032 is being clamped and correspondingly set the time to close the jaws, closure threshold(s), and other closure parameters at that point in the closure process. At time $t_1$, the control circuit 21002 determines that the ΔFTC has reached or exceeded a ΔFTC threshold $\Delta FTC_v$ (which had been set by the control circuit 21002 on or after to when the control circuit 21002 determined that a vessel 21032 was being clamped). The vessel ΔFTC threshold $\Delta FTC_v$ can represent, for example, the maximum rate of change of force that can be safely or desirably exerted on a vessel 21032 tissue. Accordingly, the control circuit 21002 controls the motor 21006 to drop 21388 the closure velocity to a vessel closure velocity $v_{v1}$ that is specific to vessel 2032 tissue, wherein $v_v i < v_d$.

As the anvil 21012 advances at the lower vessel closure velocity $v_{v1}$, the FTC increases 21380 more slowly than previously until it peaks 21382 at time $t_3$. At time $t_3$, the control circuit 21002 determines that the FTC has reached or exceeded a FTC threshold FTC, (which had been set by the control circuit 21002 on or after to when the control circuit 21002 determined that a vessel 21032 was being clamped). The vessel FTC threshold FTC, can represent, for example, the maximum force that can be safely or desirably exerted on a vessel 21032 tissue. Accordingly, the control circuit 21002 controls the motor 21006 halt the movement of the anvil 21012, causing the closure velocity to drop 21932 to zero. The movement of the anvil 21012 can be paused for a duration $p_5$, during which time the closure velocity is maintained 21394 at zero. During the pause, the FTC gradually decreases 21384 as the clamped tissue relaxes. The pause duration $p_5$ can be equal to a default pause duration (e.g., $p_1$) or a closure parameter selected by the control circuit 21002 for vessel 21032 tissue.

In sum, FIGS. 102-103 highlights the different manners in which a surgical instrument 21000 functions with and without a control circuit 21002 executing the process 21200 illustrated in FIG. 99.

FIG. 104 illustrates a fifth graph 21400 depicting end effector FTC 21402 and closure velocity 21404 verse time 21406 for an illustrative firing of a surgical instrument, in accordance with at least one aspect of the present disclosure. In the following description of the fifth graph 21400, reference should also be made to FIGS. 95 and 99-101B. The illustrative firings described herein are for the purpose of demonstrating the concepts discussed above with respect to FIGS. 95 and 99-101B and should not be interpreted as limiting in any way.

A fifth firing of a surgical instrument 21000 can be represented by a fifth FTC curve 21408 and a corresponding fifth velocity curve 21408', which illustrate the change in FTC and closure velocity over time during the course of the fifth firing, respectively. The fifth firing can represent, for example, a firing of the surgical instrument 21000 that includes a control circuit 21002 executing the process depicted in FIG. 99. As firing of the surgical instrument 21000 is initiated, the control circuit 21002 controls the motor 21006 to begin driving the anvil 21014 from its open position, causing the closure velocity of the anvil 21014 to sharply increase 21416 until it plateaus 21418 at a particular closure velocity. As the anvil 21012 closes, the FTC increases 21410 until it peaks 21412 at a particular time. From the peak 21412, the FTC decreases 21414 until the tissue is fully clamped, at which point the control circuit 21002 controls the motor 21006 to halt the closure of the anvil 21012 and the closure velocity drops 21420 to zero.

The fifth firing thus represents a firing of the surgical instrument 21000 wherein none of the FTC threshold, the ΔFTC threshold, or any other closure threshold is reached or exceeded during closure of the jaws 21013. In other words, the fifth firing stays within all control parameters during the course of the jaws 21013 closing. Thus, the control circuit 21002 does not pause the anvil 21012, adjust the closure velocity of the anvil 21012, or take any other corrective action during the course of the jaws 21013 closing.

FIG. 105 illustrates a sixth graph 21422 depicting end effector FTC 21402 and closure velocity 21404 verse time 21406 for an illustrative firing of a surgical instrument, in accordance with at least one aspect of the present disclosure. In the following description of the sixth graph 21422, reference should also be made to FIGS. 95 and 99-101B. The illustrative firings described herein are for the purpose of demonstrating the concepts discussed above with respect to FIGS. 95 and 99-101B and should not be interpreted as limiting in any way.

A sixth firing of a surgical instrument 21000 can be represented by a sixth FTC curve 21424 and a corresponding sixth velocity curve 21424', which illustrate the change in FTC and closure velocity over time during the course of the sixth firing, respectively. The sixth firing can represent, for example, a firing of the surgical instrument 21000 that includes a control circuit 21002 executing the process 21200 depicted in FIG. 99. As firing of the surgical instrument 21000 is initiated, the control circuit 21002 controls the motor 21006 to begin driving the anvil 21014 from its open position, causing the closure velocity of the anvil 21014 to sharply increase 21432 until it reaches a particular closure velocity. As the anvil 21012 closes, the FTC increases 21426 until it peaks 21428 at a particular time. In this particular instance, the operator of the surgical instrument 21000 elects to open the jaws 21013 of the surgical instrument 21000 in order to readjust the tissue therein. Thus, the closure velocity drops 21434 until it reaches a negative closure velocity, indicating that the jaws 21013 are being opened in order to, for example, easily permit the tissue to be readjusted within the jaws 21013. The closure velocity then returns 21436 back to zero, the jaws 21013 stopped. Correspondingly, the FTC decreases 21430 to zero as the jaws 21013 are released from the tissue.

FIG. 106 illustrates a seventh graph 21438 depicting end effector FTC 21402 and closure velocity 21404 verse time 21406 for an illustrative firing of a surgical instrument, in accordance with at least one aspect of the present disclosure. In the following description of the seventh graph 21438, reference should also be made to FIGS. 95 and 99-101B. The illustrative firings described herein are for the purpose of demonstrating the concepts discussed above with respect to FIGS. 95 and 99-101B and should not be interpreted as limiting in any way.

A seventh firing of a surgical instrument 21000 can be represented by a seventh FTC curve 21440 and a corresponding seventh velocity curve 21440', which illustrate the change in FTC and closure velocity over time during the course of the seventh firing, respectively. The seventh firing can represent, for example, a firing of the surgical instrument 21000 that includes a control circuit 21002 executing the process 21200 depicted in FIG. 99. As firing of the surgical instrument 21000 is initiated, the control circuit 21002 controls the motor 21006 to begin driving the anvil 21014 from its open position, causing the closure velocity of the anvil 21014 to sharply increase 21450 to a first closure velocity $v_1$. As the anvil 21012 closes, the FTC increases 21442 until time $t_1$. At time $t_1$, the control circuit 21002 determines that the ΔFTC has reached or exceeded the ΔFTC threshold $\Delta FTC_T$, which can either be a default ΔFTC threshold or a ΔFTC threshold for a particular physiological tissue type detected by the control circuit 21002 according to the process 21200 depicted in FIG. 99. As another example, the $\Delta FTC_T$ can be set by another process being executed by the control circuit 21002 and/or another control circuit of the surgical instrument 2100 in response to other sensed parameters or according to another algorithm. For example, if the jaw closure is proceeding within the operational parameters of the process 21200 illustrated in FIG. 99, but another sensor and/or process of the surgical instrument 21000 determines that the tissue being clamped nonetheless deviates from the expected parameters in some manner (e.g., the tissue is thicker or thinner than expected for the given tissue type), then set the time to close the jaws 21013, the closure threshold(s), and other control parameters accordingly. In one example, a second sensor detects at time $t_1$ that the tissue is thinner than expected. Accordingly, the control circuit 21002 sets a new $\Delta FTC_T$ (which, in this example, is lower than the prior $\Delta FTC_T$), which the control circuit 21002 then determines is being reached or exceeded at that time $t_1$.

Accordingly, the control circuit 21002 controls the motor 21006 to drop 21452 the closure velocity of the anvil 21012 to a second closure velocity $v_2$, wherein $v_1 > v_2$. From $t_1$ onwards, the drop in the closure velocity results in the FTC increasing 21444 at a slower rate. The FTC increases 21444 until it peaks 21446 below the FTC threshold $FTC_T$ and then decreases thereafter. As the seventh firing remains within all closure parameters after $t_1$, the closure velocity is maintained 21454 at the second closure velocity $v_2$ until the tissue is fully clamped, at which point the control circuit 21002 controls the motor 21006 to halt the closure of the anvil 21012 and the closure velocity drops 21456 to zero.

FIG. 107 illustrates a graph 21500 depicting impedance 21502 verse time 21504 to determine when the jaws of a surgical instrument contact tissue and/or staples, in accordance with at least one aspect of the present disclosure. In the following description of the seventh graph 21438, reference should also be made to FIG. 95. As discussed above, the sensor(s) 21004 that are configured to detect the degree of compression of a tissue clamped by the end effector 21008 and/or are configured to detect the initial contact with a tissue can include, for example, impedance sensors. The impedance and/or rate of change of the impedance of the tissue, as detected by the impedance sensor(s), can be utilized to determine the state of the tissue being clamped. For example, if the detected impedance has plateaued 21506 at an impedance $Z_{OC}$ that indicates an open circuit condition, then a control circuit 21002 coupled to the impedance sensors can determine that the jaws are open and/or not contacting a tissue. As another example, when the detected impedance initially decreases 21508 from the open circuit impedance $Z_{OC}$, then a control circuit 21002 coupled to the impedance sensors can determine that initial contact with a tissue has been made. As another example, as the detected impedance decreases 21510 from the open circuit impedance $Z_{OC}$, the shape of the impedance curve verse time and/or the rate of change of the detected impedance can be utilized by a control circuit 21002 coupled to the impedance sensors to determine the rate of tissue compression and/or the degree to which the tissue is being compressed. As yet another example, if the detected impedance drops 21512 to zero, then a control circuit 21002 coupled to the impedance sensors can determine that the jaws of the end effector 21008 have contacted a staple, which shorts the impedance detecting system.

Systems for Adjusting End Effector Parameters Based on Preoperative Information

Aspects of the present disclosure are presented for adjusting the closure threshold and closure rate implemented by a closure control program executed by a control circuit of a surgical instrument, where the adjustment is made based on preoperative information. Adjusting closure thresholds may be one example of performing situational awareness by the computer-implemented interactive surgical system (including one or more surgical systems 102 and cloud based analytics medical system such as cloud 104, 204, which is referred to as cloud 104 for the sake of clarity). For example, closure thresholds can be adjusted to a patient specific closure threshold based on perioperative information received from the cloud 104 or determined by surgical hubs or surgical instruments. As used herein, perioperative information comprises preoperative, intraoperative information, and postoperative information.

Preoperative information refers to information received prior to performance of a surgical operation with a surgical instrument, while intraoperative information refers to information received during a surgical operation (e.g., while a step of the surgical operation is being performed). In particular, the computer-implemented interactive surgical system can determine or infer end effector closure parameters, such as an appropriate end effector closure threshold and closure rate algorithm, for particular handheld intelligent surgical instruments. Such inferences can be based on contextual information pertaining to a surgical procedure to be performed and pertaining to the corresponding patient. Contextual information can include or be determined based on perioperative information. The surgical instruments may be any suitable surgical instrument described in the present disclosure, such as surgical instrument 112, 600, 700, 750, 790, 150010. For the sake of clarity, surgical instrument 112 is referenced.

Perioperative information, such as perioperatively diagnosed diseases and treatments, may affect the properties or characteristics of tissue being treated by the surgical instrument 112. For example, a patient may have been previously diagnosed with cancer and have received radiation treatments to treat the cancer. Accordingly, this preoperative information would indicate that the patient's tissue may have an increased stiffness characteristic. However, the currently applied closure control program may not address this increased stiffness. Consequently, using the closure control program to perform a surgical procedure according to a general closure rate algorithm could result in unnecessary trauma or damage to tissue due to excessive compression of the patient's tissue. Additionally, during a surgical operation, intraoperative information may be analyzed, such as by identifying which tissue type of multiple potential types of tissue is being treated. Different types of tissue may also have different tissue characteristics such as tissue stiffness. Accordingly, changes in intraoperative information may be used for executing intraoperative adjustments alternatively or additionally to perioperative adjustments. In sum, closure control programs might not consider that different closure rate thresholds should be applied depending on perioperative information, such as the tissue type, surgical procedure being performed and surgical steps already performed.

It may be desirable for a surgical instrument to account for different tissue types and the various characteristics of such different tissue types when a surgical operation is performed with the surgical instrument 112. In particular, it may be desirable for the surgical instrument 112 to effectively determine the tissue type and characteristics of that tissue type prior to the clinician performing a surgical operation with the surgical instrument as well as during the performance of a surgical operation.

Accordingly, in some aspects, a cloud based analytics medical system (e.g., computer-implemented interactive surgical system 100) is provided in which perioperative information may be considered to determine the type of tissue to be treated and the characteristics of the treated tissue prior to treatment. For example, the surgical procedure to be performed and other patient information may be instances of preoperative information retrieved before the surgical procedure is performed. Previous performed steps of a surgical operation, other surgical history, and a change in tissue type are examples of intraoperative information that may be considered. In general, this perioperative information may be used in conjunction with sensor signals indicative of a closure parameter to determine, infer, or adjust parameters of an end effector (e.g., closure rate of change and closure threshold) of the surgical instrument 112. The end effector may be any end effector described in the present disclosure, such as end effector 702, 151600, 150300, 151340, 152000, 152100, 152150, 152200, 152300, 152350, 152400, 153460, 153470, 153502. For the sake of clarity, end effector 702 is referenced.

Analyzing perioperative information for closure rate related situational awareness could be achieved in a number of ways. Based on perioperative information, a control circuit such as control circuit 500, 710, 760, 150700 (discussed above with respect to FIG. 12, FIG. 15, FIG. 17, and FIGS. 29A-B) of a surgical instrument could adjust the closure rate of change and closure threshold inputs used in the selected closure control program. For the sake of clarity, control circuit 500 is referenced. The control circuit 500 could also select a different control program based on perioperative information. Additionally or alternatively, a surgical hub such as surgical hub 106, 206 (referred to as surgical hub 106 for the sake of clarity) may receive perioperative information from the cloud 104 or the surgical instrument 112. For example, the surgical hub 106 may receive a patient's electronic medical record (EMR) from the cloud 104 or initial tissue thickness measurements, which are determined based on tissue contact or pressure sensors (as shown in FIG. 24, for example) of the surgical instrument 112.

The surgical hub 106 may then analyze the received perioperative information. Based on this analysis, the surgical hub 106 could then transmit a signal to the surgical instrument 112 to adjust the closure rate of change and closure threshold inputs used in the selected closure control program. The surgical hub 106 could also instruct the surgical instrument 112 to select a different closure control program, such as by the control circuit selecting a different control program. The selection of a different control program can be based on a signal received from the hub 106 or by the surgical instrument 112 receiving an updated control program from the hub 106. The cloud 104 could also perform the analysis for adjusting the closure rate and maximum threshold used. In particular, the processors of the cloud 104 may analyze perioperative information to determine tissue type and characteristics for altering the inputs to a closure control program or selecting a different suitable closure control program to be executed by the surgical instrument, for example.

In this way, the surgical instrument 112 may be instructed by the cloud 104 (via the hub 106, for example) to apply a suitable closure rate algorithm and closure maximum threshold. The tissue type and characteristics may further be determined based on a sensor signal indicative of a closure parameter. Sensors may be tissue contact or pressure sensors, force sensors, motor current sensors, position sensors, load sensors, or other suitable sensors such as sensors 472, 474, 476, 630, 734, 736, 738, 744*a*-744*e*, 784, 788, 152408, 153102, 153112, 153118, 153126, 153200, 153438, 153448, 153450*a*, 153450*b*, 153474, described above. For the sake of clarity, sensor 474 is referenced. The sensor 474 is configured to transmit a sensor signal indicative of a parameter of the surgical instrument 112. Some types of perioperative information may be stored in the cloud 104 prior to determining tissue type and characteristics. For example, patient EMRs can be stored in the memory of the cloud 104 (e.g. cloud databases). In general, surgical instruments 112, hubs 106, or the cloud 104 can analyze perioperative information to determine tissue type and characteristics for situational awareness.

Accordingly, tissue type and characteristics determined based on perioperative information may be used to proactively adjust closure rate and maximum threshold used. That is, perioperative information may be used to predict more effective closure parameters (e.g., end effector 702 parameters) so that the closure control program applied by the surgical instrument 112 uses a closure rate and threshold that considers the patient specific tissue characteristics and type of the tissue being treated. Consequently, using the closure rate and threshold situational awareness as described herein may advantageously enable the surgical instrument 112 to apply an adjusted closure rate and threshold without over-compressing the tissue to be treated. Over-compression may be based on the first and second jaw members of the end effector 702. First and second jaw members may be first jaw member 152002, 152152, 152154 and second jaw member 152204, 152254, 152304, respectively, for example. The first and second jaw members may also refer to anvil 716, 766 and staple cartridge 718, 768. For the sake of clarity, the first jaw member is referred to as 152002 while the second jaw member is referred to as 152204. The first and second jaw members 152002, 152004 may define an end effector 702 aperture, which is defined as the distance between the first jaw member 152002 and second jaw member 152004.

Unnecessary tissue damage or trauma from over-compression may occur when the end effector 702 aperture is unnecessarily small, for example. Reducing or preventing such over-compression may be achieved by adjustment using perioperative information and/or sensor signals from sensors 474. Also, compression applied during initial closure parameter measurements, such as based on load sensor 474 (measuring closure force) and positioned sensor 474 (measuring position of first jaw member 152002 and second jaw member 152004) may be minimized. In general, sensors 474 may be configured to measure the closure force exerted by the end effector 702 of the surgical instrument 112. In addition to proactively inferring tissue characteristics and type from perioperative information, one or more of the surgical instrument 112, hub 106 and cloud 104 may use sensed measurements from the sensors 474 (as shown in FIG. 12) to verify or make further adjustments to applied closure force, closure rate, and closure threshold if necessary. Specifically, contact sensors can be used to determine undeformed tissue thickness. Also, the load sensor 474 in combination with the position sensor 474 may be used to determine tissue thickness based on applied closure force relative to the position of the first jaw member 152002 and second jaw member 152004, respectively. These verifications or further adjustments can be performed preoperatively or intraoperatively.

The closure parameter situational awareness may be continually performed. Thus, the clinician or surgeon may continually use perioperative information to adjust end effector 702 closure parameters (e.g., of a closure control program) as appropriate (e.g., as the steps of a surgical procedure are performed). For example, perioperative information could be used to adjust end effector 702 closure parameters when it is determined, based on clinician history (e.g., a surgeon's routine practice), that the next step of the surgical procedure being performed involves vascular tissue. In this situation, the situationally aware surgical instrument 112 may apply closure force with a constant closure rate of change. Such perioperative information may be used in conjunction with a sensor signal indicative of a closure parameter of the surgical instrument 112 to adjust end effector 702 closure parameters (e.g., closure rate of change and closure threshold of a control program). The perioperative information, such as intraoperative information, could indicate that the patient has previously been treated by radiation therapy.

Based on this information, the control circuit 500 may infer increased tissue stiffness, which is a tissue characteristic that can be considered throughout the steps of the surgical procedure. In one example, this increased tissue stiffness may be perioperative information used to supplement a sensor signal indicative of tissue thickness so that adjustment to a more appropriate end effector 702 closure parameter value may be achieved. The perioperative information may also indicate that the surgical procedure being applied is a lobectomy procedure, which could be determined from data stored in the cloud 104. Based on the knowledge of the lobectomy procedure, it may be determined that the possible tissue types to be treated (e.g., stapled) include blood vessels, bronchus tissue, and parenchyma tissue.

Accordingly, based on perioperative information, the specific tissue type and characteristics of the tissue currently being treated by the surgical instrument 112 may be predicted or inferred prior to beginning therapeutic treatment of tissue. For example, considering initial tissue thickness (measured when the tissue currently being treated first contacts the end effector 702) in conjunction with treatment, diagnosis, and patient information may enable an inference that previously irradiated parenchyma tissue is being treated. Because the type and characteristics of the tissue being treated can be contextually determined prior to commencing the surgical procedure, the closure control program implemented by the control circuit 500 of the surgical instrument 112 can be advantageously adjusted (e.g., by changing input parameters according to inferred tissue type or characteristics) or altered (e.g., by selecting a different control program) before therapeutic treatment begins. Specifically, the maximum tissue closure threshold may be decreased to address the stiffness and fragility of the irradiated parenchyma being treated. The maximum threshold could refer to a maximum closure force that may be applied or a maximum closure rate of change. Moreover, the closure algorithm of the closure control program could also be adjusted to apply a slower, more conservative closure rate based on identifying the irradiated parenchyma.

Also, it can be determined whether the surgical instrument 112 is an appropriate stapling surgical instrument 112 for the irradiated parenchyma, for example. If the perioperative information indicates that selected surgical instrument 112 is not suitable for its intended use, a warning may be generated. For example, if it can be inferred based on perioperative information that tissue currently being treated is bronchus tissue and an unsuitable vascular stapling surgical instrument 112 is selected, a warning would be generated to the clinician. In general, the surgical instrument 112 may generate an alert based on a determined, predicted or inferred inconsistency between the surgical instrument type, perioperative information, and the sensor signal. Furthermore, as discussed above, intraoperative information could also be used for adjustments during the overall surgical procedure. For example, the current step in an overall procedure operation could be treating stiff bronchus tissue, which would typically result in a slower closure rate. Further adjustments can also be made subsequent to an initial adjustment. Specifically, further adjustments could be made during operation, such as to adjust the slower closure rate to a faster closure rate when additional intraoperative information (e.g., sensed information) is analyzed and it is inferred that the force to close applied in the currently applied closure algorithm should be modified or adjusted. Such adjustments could also be made postoperatively in certain circumstances.

Therefore, closure rate and thresholds may be beneficially adjusted based on determined tissue type, tissue characteristics, and perioperative information prior to the commencement of or during therapeutic treatment. Accordingly, this adjustment may advantageously avoid or minimize tissue damage resulting from excessive strain and facilitate the proper formation of staples from a stapling surgical instrument 112.

FIGS. 108 and 109 are graphs 22000, 22100 illustrating various end effector closure threshold functions that may be used based on perioperative information and illustrating an adjusted end effector closure control algorithm, according to various aspects of the present disclosure. The graph 22100 is a zoomed in view of graph 22000. In FIGS. 108 and 109, the force to clamp or close (FTC), which can be understood as the clamping force applied to the end effector 702, is indicated on the y-axis 22002, 22102 of the graphs 22000, 22100. The time elapsed or spanning a surgical cycle is indicated on the x-axis 22004, 22104. The x-axis 22004 of FIG. 108 indicates that the cycle spans 13 seconds, for example. In contrast, the x-axis 22104 of FIG. 109 spans slightly less than 2 seconds. As shown in FIGS. 108, a default universal tissue closure threshold function (denoted as $FTC_d$ 22006) may be applied generally to controlling end effector 702 closures of surgical instruments 112 used in generic surgical procedures.

Other more conservative thresholds than the default $FTC_d$ 22006 are also shown on graphs 22000, 22100. However, less conservative thresholds could also be used. As represented by $FTC_{L1}$ 22008 and $FTC_{L2}$ 22010, the more conservative closure thresholds are employable to reduce closure force of the surgical instrument relative to the default closure force function. $FTC_L$ 22008 and $FTC_{L2}$ 22010 could be thresholds that are stored in a memory of the surgical instrument 112, hub 106, or cloud 104. Additionally or alternatively, $FTC_d$ 22006 could be dynamically adjusted at a suitable point during the surgical cycle. The dynamic adjustment could be performed by the control circuit 500, the corresponding hub 106, or the cloud 104. Also, the graphs 22000, 22100 indicate the corresponding slopes of the different closure threshold functions $FTC_d$, $FTC_{L1}$ and $FTC_{L2}$ 22006, 22008, 22010. Because the closure thresholds may change as a function of time in the corresponding surgical cycle, the slope of a closure threshold can be constant throughout or change as appropriate during the surgical cycle.

In other words, the instantaneous rate of change defined by the particular closure threshold function may be different between different ranges of time in the surgical cycle. For example, the particular closure threshold function may define a relatively slower rate of increase around the beginning of the surgical cycle and a relatively faster rate of increase around the middle of the surgical cycle. Closure threshold functions $\Delta FTC_d$, $\Delta FTC_{L1}$ and $\Delta FTC_{L2}$ 22106, 22108, 22110 are zoomed in views of functions $FTC_d$, $FTC_{L1}$ and $FTC_{L2}$ 22006, 22008, 22010 and illustrate the corresponding slopes of the closure threshold functions. In the aspect of FIG. 109, it can be seen that the slope is constant, although the slope could change as appropriate. The closure rate of change may be adjusted according to a selected closure threshold function. One example of adjustment is illustrated by the "x" in FIGS. 108 and 109 and is shown in larger size in the zoomed in view of graph 22100. In this example, the closure rate of change as represented by lines 22012, 22112 is adjusted such that they do not exceed $\Delta FTC_{L2}$ 22110.

In one aspect, a motor such as motor 482, 704*a*-704*e*, 754, 150082, 150714 of the surgical instrument 112 may move the first jaw member 152002 relative to the second jaw member 152004 of the end effector 702. For the sake of clarity, motor 482 is referenced. Motor 482 may move or close end effector 702 in accordance with the closure rate of change as represented by lines 22012, 22112 and with the selected closure threshold. To this end, the control circuit 500 may adjust a current drawn by the motor 482 to change the speed or torque of the motor 482 based on the selected threshold. For example, the graphs 22000, 22100 illustrate how the control circuit 500 may adjust the motor 482 at point "x" (as denoted on the graphs) such that the closure rate of change parameter of the surgical instrument 112 is changed to stay within the selected threshold $FTC_{L2}$ 22010. $FTC_{L2}$ 22010, which may be a patient specific threshold, may be selected and determined based on perioperative information.

The FTC thresholds 22006, 22008, 22010 depicted in graphs 22000, 22100 may be parameters of different or the same closure control programs executed by the control circuit 500. These closure control programs may be stored locally on the memory of the surgical instrument 112 or stored remotely on the hub 106 or cloud 104. In general, closure threshold functions define how closure thresholds change as a function of time in a cycle such that the instantaneously applicable closure threshold is indicated for any point of time during the cycle. Closure thresholds can define a maximum closure force that may be applied to close the end effector jaws or a maximum rate of change of closure force used, for example. FIG. 108 illustrates the use of thresholds as maximum rates of change of closure force used. At a selected point of time on the graphs 22000, 22100, the lines 22012, 22112 plotted against the time on x-axis 22004, 22104 and FTC on y-axis 22002, 22102 indicates the instantaneous force applied to close the jaws 152002, 152004 at that point in time.

As illustrated by line 22012, the force applied increases over time from time zero to time $t_1$, after which the rate of increase slows to zero and then to a rate of decreasing force. Shortly before time $t_2$, the rate of decrease is much steeper. After time $t_2$, the applied force to close the jaws begins to transition to a zero rate before again decreasing at a nonzero rate. As illustrated by line 22112 of graph 22100, the applied closure force to close the jaws 152002, 152004 is increasing between time zero to a time slightly before 0.5 seconds (shown on x-axis 22104). At the time corresponding to "x" on graph 22100, the control circuit 500 may adjust the motor 482 to adjust the selected closure algorithm such that rate of increase of the closure is decreased. In this way, the motor 482 can be controlled by the control circuit 500 to stay within the selected patient specific threshold $\Delta FTC_{L2}$ 22110. In addition, as shown in graph 22100, after the time corresponding to "x," the slower rate of increase of applied closure force becomes a constant rate.

In one aspect, the same overall amount of applied FTC may be applied during a surgical cycle. However, the force applied to close the end effector may be applied more gradually or immediately as appropriate. This is illustrated by the rate of change represented by closure rate of change lines such as lines 22012, 22112. Although FIG. 109 shows each of the three depicted thresholds $\Delta FTC_d$, $\Delta FTC_{L1}$ and $\Delta FTC_{L2}$ 22106, 22108, 22110 as zoomed in views of $FTC_d$, $FTC_{L1}$ and $FTC_{L2}$ 22006, 22008, 22010, in some aspects, $\Delta FTC_d$, $\Delta FTC_{L1}$ and $\Delta FTC_{L2}$ 22106, 22108, 22110 represent different closure threshold functions. In other words, the control circuit 500 may adjust from any one of thresholds $FTC_d$, $FTC_{L1}$ and $FTC_{L2}$ 22006, 22008, 22010 to thresholds $\Delta FTC_d$, $\Delta FTC_{L1}$ and $\Delta FTC_{L2}$ 22106, 22108, 22110, which would be different thresholds altogether in this situation.

As discussed above, it is possible for the slope of a closure threshold function to change during one surgical cycle. In such circumstances, the dynamic slope can be adjusted consistently or individually across the entire surgical cycle. In general, a closure threshold parameter adjustment could be achieved by changing the parameter of the current closure control program (e.g., by the control circuit 500 directly altering a closure threshold function being implemented by the control circuit 500) or switching to a new closure control program altogether. The switching or adjusting could be performed by the control circuit 500, hub 106, or cloud 104 based on perioperative information. For example, the control circuit 500 may switch from the current control program to a second closure control program received from the cloud 104. The second closure control program could also be transmitted from the cloud 104 to the hub 106.

As discussed above, one or more of the surgical instrument 112 used to treat tissue, the corresponding hub 106, and the cloud 104 may be used to receive, infer, or determine perioperative information in order to determine, infer, or predict the type and characteristics of the tissue currently being therapeutically treated. These closure situational awareness inferences and predictions are useful for adjusting closure rate of change thresholds. Accordingly, in addition to $FTC_d$, $\Delta FTC_d$ 22006, 22106, graphs 22000, 21000 show, for example, a second tissue closure rate of change threshold function $FTC_{L1}$, $\Delta FTC_{L1}$ 22008, 22108, which the closure algorithm used by the surgical instrument 112 can automatically incorporate. That is, the surgical instrument 112 can adjust the inputs to the current closure control program or adjust to a different control program to be executed by the control circuit 500. For example, the situationally aware surgical hub 106 could determine that the currently applied surgical procedure is a lung surgical procedure based on the targeted area being in the thoracic cavity. In turn, the thoracic cavity could be inferred as the targeted area based on ventilation output from another device used in the surgical theater, for example. Thus, it is determined that the treated tissue type is lung tissue. Accordingly, the surgical instrument 112 can adjust to using the default closure threshold function $FTC_{L1}$ 22008, 22108 for lung tissue from the threshold $FTC_d$ 22006, 22106, that was previously used. Such adjustments may be made during the surgical cycle spanning the y-axis 22004, 22104.

For example, the situationally aware surgical hub 106 may predict that the patient's lung will comprise relatively brittle tissue. Consequently, a closure threshold function could be adjusted to a lower FTC threshold function, as depicted in FIGS. 108 and 109. The closure threshold could be a maximum allowable FTC value applied by the end effector or a maximum allowable FTC rate of change, for example. The inference of relatively high stiffness of the lung tissue may be confirmed by other perioperative information. For example, a patient's EMR stored in the cloud 104 could be analyzed to determine that the patient has previously been diagnosed with cancer and has been subject to radiation treatments. This type of preoperative information may be used to infer that the tissue characteristics of the lung tissue include relative high stiffness and significant liquid content (e.g., percentage of water in tissue).

In addition to confirming the initial prediction, perioperative information could also be used to adapt from an inaccurate initial prediction. For example, the surgical instrument 112 could be applying a suboptimal closure algorithm based on an erroneous assumption that the tissue has more pliability than it actually has. In this situation, the patient history preoperative information may be used as part of a correction to the erroneous assumption. In general, perioperative information may be used in conjunction with sensor signals indicative of a closure parameter. Advantageously, the perioperative information could confirm an initial closure algorithm determined based on the sensor signals or could be used to adjust the initial closure algorithm to a different, more suitable closure algorithm. For example, the sensor signal could be indicative of the relationship between sensed applied closure force and end effector 702 aperture position (e.g., position of the first jaw 152002 relative to the second jaw 152004). Such a signal could be used to determine tissue stiffness and could be used in conjunction with other perioperative information to adjust the closure algorithm before or during the surgical operation.

Accordingly, the graphs 22000, 22100 of FIGS. 108 and 109 show that the default lung tissue threshold function $FTC_{L1}$ may be further adjusted based on patient specific tissue characteristics. As illustrated in FIGS. 108 and 109, the surgical instrument could further adjust from threshold function $FTC_{L1}$ 22008 to $FTC_{L2}$ 22010 or to $FTC_d$ 22006, for example, based on patient specific perioperative information. As such, the adjustment could occur before the surgical procedure begins or during the surgical procedure. Moreover, the adjustment could be made from $FTC_d$ 22006 to $FTC_{L2}$ 22010, or threshold function $FTC_{L2}$ 22010 could simply be directly implemented. Adjustment between any of the available closure threshold functions based on perioperative information is possible.

Although FIGS. 108 and 109 illustrate adjustment to lower thresholds, adjustment to higher thresholds is also possible. The threshold functions shown in FIGS. 108 and 109 may correspond to particular control processes, which could be implemented by a particular closure control program. Alternatively, the control processes could correspond to different closure control programs. The control circuit 500 may directly modify the selected closure control algorithm itself or switch to a different closure control algorithm, for example. That is, the closure threshold function for a particular closure control algorithm or a particular applied closure rate of change as represented by lines 22012, 22112, for example, may be modified. Closure threshold function modification could be performed during a surgical procedure based on perioperative information. Also, threshold functions may also be a function of some other parameter besides or in addition to time, such as staple size used, for example.

Additionally or alternatively, closure adjustment may comprise merely adjusting the inputs to a closure threshold function. For example, if a tissue characteristic such as tissue thickness is an input to a closure threshold function, perioperative information may be used to predictively or inferentially modify the inputs so that the output closure thresholds are modified according to the predicted or inferred tissue thickness input. As such, the applied closure threshold function can be modified based on perioperative information. As discussed above, the applied closure threshold function is defined by the applied closure control algorithm. Also, the applied FTC or closure force lines 22012, 22112 can be adjusted based on perioperative information.

In one aspect, the FTC or closure force lines 22012, 22112 represent a closure rate of change parameter of the corresponding closure control program executed by the control circuit 500. The FTC line 22012, 22112 is also defined by the applied closure control algorithm. In one aspect, the applied closure force can be dynamically adjusted during the cycle of a surgical procedure being performed, as indicated by the "x" in FIGS. 108 and 109. This dynamic adjustment could also be an application of situational awareness. In other words, perioperative information may be incorporated to infer or predict adjustments to the threshold or threshold function during the surgical procedure. In this way, as shown in FIGS. 108 and 109, at the time or times corresponding to the "x" denoted in FIGS. 108 and 109, the applied FTC is adjusted or modified to stay within the corresponding instantaneous closure threshold. In sum, the applied closure control algorithm can comprise both a closure threshold function and closure rate of change, both of which can be adjusted based on perioperative information.

In general, adjustment to different closure thresholds or different closure threshold functions may be performed based on a determined, inferred, or predicted characteristic or type of the tissue being treated. As discussed above, the tissue characteristics or type can be determined, inferred, or predicted based on perioperative information. Adjustment to another closure threshold may be understood as adjusting a maximum threshold with respect to a maximum torque generated by the motor 482 of the surgical instrument 112 or a rate of change of the motor speed. Various instances of perioperative information may be used to determine, infer, or predict tissue type or tissue characteristics. For example, the amount of water, the muscular properties, and the vasculature of tissue can influence the closure rate algorithm (including the closure threshold) that would be applied. In one aspect, these properties as well as other tissue type and tissue characteristic properties are used to determine the default closure threshold $FTC_D$ 22006 or any other initial closure control program parameter.

Thus, high vasculature might be a tissue characteristic used to infer a default closure threshold function with relatively low slope. Additionally to determining initial control program parameters, if preoperative information such as the surgical procedure being applied and the surgical history (e.g., the typical routine of the clinician performing the procedure with respect to surgical steps of the procedure) can be used to infer that a vascular tissue with high hemoglobin content is being targeted, then the closure rate of change applied by the surgical instrument may be adjusted to be slower. As such, these properties can be used to determine control program parameters preoperatively and intraoperatively. Also, perioperative information could be used to confirm that a suitable vascular stapler is being used for the procedure on the vascular tissue.

FIG. 110 is a flow diagram 22200 of an aspect of adjusting a closure rate algorithm by the computer-implemented interactive surgical system 100, according to one aspect of the present disclosure. At step 22202, the current closure algorithm is determined. This may refer to determining the closure control program currently executed by the control circuit 500 of a surgical instrument 112. As described above in connection with FIGS. 108 and 109, the current closure algorithm or control program may include a closure threshold function (e.g., closure threshold parameter) and applied closure force (FTC) function (e.g., closure rate of change parameter). The flow diagram 22200 proceeds next to step 22204, where preoperative information is received and analyzed. As discussed above, preoperative information may include initial tissue thickness based on tissue contact sensors 474, patient history including prior diagnoses and treatments (e.g., listed on a patient information EMR record stored in the hub or cloud), clinician history such as a surgeon's typical surgical routine, identified surgical instrument and associated materials, and identified current surgical procedure. This preoperative information can be used to determine, infer, or predict tissue type or tissue characteristics at step 22206.

For example, the undeformed initial tissue thickness as measured by tissue contact sensors 474 may be used to determine an initial closure algorithm. Preoperative information such as a patient history of lung issues might be used to determine that the current surgical procedure being performed is a thoracic procedure and the tissue type is a lung tissue. This preoperative information may further be used to determine an adjustment to the initial closure algorithm. Additionally or alternatively, an initial tissue stiffness measured via comparing a non-therapeutic (or quasi non-therapeutic) initial tissue compression measurement and a closure member position measurement (e.g., position of first and second jaws of end effector) could also be used in conjunction with the preoperative information. Ventilation preoperative information received from a ventilation device in the surgical theater could further be used to infer that the current procedure is thoracic. Other preoperative information could also be used to further predict the specific thoracic procedure being performed. For example, based on the patient EMR record in the cloud indicating that the patient has cancer, it could be inferred at step 22206 that the thoracic procedure is a pulmonary lobectomy to excise cancerous tissue in a lung lobe.

Moreover, the patient EMR record could further indicate that the patient history indicates the patient has previously undergone radiation treatments for the cancer. In this situation, it may be inferred or predicted that the irradiated lung tissue would be stiff, but also susceptible to the application of monopolar RF energy by the surgical instrument 112, for example. This would be one example of an inferred tissue characteristic. Also, the inference that a pulmonary lobectomy is being performed may also be used to determine that possible tissues for stapling by the surgical instrument 112 include blood vessels (PA/PV), bronchus, and parenchyma. At step 22208, adjustments to the current closure algorithm are determined based on the preoperative information and applied. As discussed above, the closure threshold and applied FTC may be adjusted based on the tissue type and tissue characteristics. For example, high tissue stiffness may necessitate a slower more conservative rate of change of applied FTC (e.g., as represented by FTC lines 22012, 22112) as well as a closure threshold that generally outputs a lower maximum threshold (e.g., as represented by $FTC_{L2}$ 22010 and $\Delta FTC_{L2}$ 22110).

The maximum threshold may indicate the threshold at which the first and second jaw members 152002, 152004 are in a sufficient position for the surgical instrument 112 to fire staples. A relatively thicker tissue may correspond to a slower closure force rate of change and also a generally higher maximum closure threshold, for example. Also, tissue type or structure could be inferred based on the determined surgical procedure and clinician history for identifying other closure algorithm adjustments at step 22208. For example, the treating surgeon's clinician history may indicate a practice of treating blood vessels first. It could be inferred that the tissue type and structure is vascular lung tissue with high blood content (i.e., high vasculature). Based on this inferred tissue type and characteristic information, it could be determined that adjustment to a slower applied FTC rate of change would be beneficial. In sum, adjustments to the current closure algorithm are determined based on the inferred information and applied at step 22208. Accordingly, the current surgical operation may be performed with the surgical instrument 112 using the adjusted current closure algorithm.

The flow diagram 22200 then proceeds to decision operation 22210, at which it is determined whether any steps of the identified surgical procedure are remaining. If there are no steps remaining (i.e., the answer to decision operation 22210 is no), the flow diagram 22200, in some aspects, terminates. However, if the answer to decision operation 22210 is yes, there are further steps of the surgical procedure remaining. Therefore, the current state of the flow diagram 22200 is intra-operation. In this case, the flow diagram proceeds to step 22212, where intraoperative information may be received and analyzed. For example, intraoperative information could indicate that the tissue type treated during this step of the surgical procedure is parenchyma. In particular, it could be inferred that the tissue is parenchyma based on clinician history, for example. This inference could be made in conjunction with tissue contact sensor 474 measurements and load sensor 474 versus closure member position measurements. Moreover, clinician history may indicate that the treating surgeon routinely completes a lung fissure (a double-fold of visceral pleura that folds inward to sheath lung parenchyma) after dissection with a monopolar RF energy surgical instrument. In this situation, it may be inferred based on the previously completed monopolar RF dissection that the current step of the surgical procedure is lung parenchyma tissue.

Additionally, the surgical hub 106 may determine whether the surgical instrument 112 being used is an appropriate stapler for parenchyma firings, for example. The initial tissue contact sensor 474 measurements may indicate that the tissue is relatively thick, such as based on tissue contacting the length of the first and second jaw members 152002, 152004 when the end effector 702 is fully open (at the maximum jaw aperture), which may be consistent with parenchyma. Furthermore, the load sensor 474 versus closure member position measurements as represented by a closure compared to jaw aperture curve may indicate relatively high tissue stiffness. This stiffness characteristic could be consistent with irradiated parenchyma, which is a prediction that could be confirmed by reference to patient EMR data in the cloud. In this way for example at step 22212, sensor signals and perioperative information could be used in conjunction.

Based on this received and analyzed intraoperative information, it may be determined at decision operation 22214, that further adjustment is necessary. On the other hand, if the answer is no at decision operation 22214, the flow diagram would proceed back to decision operation 22210. When the answer at decision operation 22214 is yes, tissue type and tissue characteristics are inferred such as determining parenchyma tissue structure and stiffness characteristics, similar to as described above at step 22206. Subsequently, adjustments to the currently applied closure algorithm can be determined and applied at step 22208. In particular, the inference that stiff and fragile parenchyma tissue is being treated could cause adjustment to a slower, more conservative rate of change of applied closure force.

Accordingly, the current closure algorithm may be adjusted to an algorithm that minimizes the closure threshold and rate of change. That is, the adjusted threshold may have a reduced maximum closure force threshold, a more gradual rate of change in closure force, a reduced rate of change of closure force threshold, or some combination or subcombination of the above. In situations in which the clinician inadvertently exceeds the closure threshold, a wait time can be instituted, for example. Exceeding the closure threshold may indicate that the tissue or material being compressed is too thick for firing staples, for example, so this wait time may be necessary. Thus, the wait time may enable some tissue material or fluid in the end effector 702 to evacuate or egress. Upon a suitable wait time, it is determined that the tissue can be properly compressed to achieve a proper end effector 702 configuration such that the stapling surgical instrument 112 can fire staples. Because the adjusted closure algorithm is more conservative, a long wait time may be used. However, the clinician may be able to override this long wait time or conservative adjusted closure algorithm by manually selecting a faster clamp protocol usage on the surgical instrument 112.

Upon applying this modified closure algorithm to the parenchyma tissue at step 22208, the flow diagram again proceeds to decision operation 22210. Here, the answer may again be yes because there are remaining steps of the surgical procedure. For example, the lobectomy procedure may then proceed to a vessel stapling step. Again, at step 22212, intraoperative information is received and analyzed. For example, the surgical hub could determine that the clinician has selected a vascular stapler surgical instrument. Also, an initial measurement from the tissue contact sensors 474 may indicate that tissue contact occurs almost immediately during closure. In addition, the tissue contact may be determined to encompass a small area of the vascular stapler 112 and is bounded on the distal side of the stapler 112. Load sensor 474 measurements may also indicate a compliant tissue structure. Further, it may be inferred that the tissue may have relatively low stiffness which may be consistent with a lung pulmonary vessel. Moreover, clinician history may indicate that the treating surgeon generally uses a vascular stapler 112 for blood vessels as the step subsequent to completing the lung fissure. Thus, intraoperative information, in conjunction with closure parameter sensor signals for example, may be used to infer tissue type and tissue characteristics. In particular, it can be predicted that vessel tissue is being treated based on the specific characteristics of the selected vascular stapler 112. The initial tissue contact and load sensor 474 measurements may confirm this initial prediction, for example.

Consequently, it can be determined at decision operation 22214 that further adjustment is necessary, which causes the flow diagram 22200 to proceed to step 22206. At step 22206, it may be inferred that the tissue is blood vessel tissue with relatively low tissue thickness and stiffness. Accordingly, the flow diagram 22200 proceeds to step 22208, where the previously applied conservative closure algorithm is adjusted to a normal closure algorithm. A normal closure algorithm may comprise a constant closure rate of change. Also, the closure threshold could be higher than the threshold used in the control algorithm for the parenchyma tissue. In other words, the normal closure algorithm may reach a higher maximum applied closure force and the closure rate of change may be faster than for parenchyma tissue. The surgical instrument can also inform the clinician of the adjustment to the normal closure algorithm via a suitable indicator, such as a light emitting diode (LED) indicator displaying a particular color. In another example, it could be determined at step 22206 that the patient has a complete lung fissure. Accordingly, there would not have been any staple firings of parenchyma tissue performed yet in the surgical procedure. In response to this determination, the surgical instrument may prompt the clinician for confirmation that this inference is correct, such as via a display of the surgical instrument. The clinician could then manually select an appropriate closure control algorithm for this step or stage of the surgical procedure. Additionally or alternatively, the surgical instrument 112 may default to a conservative closure algorithm because the inferences performed at step 22206 may not be definitive. In any case, the adjusted closure algorithm is applied at step 22208.

Continuing the description of the lung lobectomy procedure example, the flow diagram proceeds to decision operation 22210. At decision operation 22210, it may be determined that there are remaining steps of the surgical procedure. Accordingly, at step 22212, intraoperative information is received and analyzed. Based on intraoperative information, it may be inferred that the tissue type being treated is bronchus tissue. Furthermore, the initial tissue contact sensor 474 measurements could indicate that the tissue grasped between the end effector 702 contacts the first and second jaw members 152002, 152004 almost immediately during initial closure of the end effector 702 and that such contact corresponds to a small area of the stapling surgical instrument 112. Also, such contact is bounded on both sides of the jaw members 152002, 152004.

Consequently, it may be predicted that this tissue contact scenario corresponds to bronchus tissue. As discussed above, these initial tissue contact sensor 474 measurements may be non-therapeutic or quasi non-therapeutic. Furthermore, the closure load sensor 474 measurements as represented by a closure compared to jaw aperture curve may indicate a stiff tissue structure that is consistent with bronchus tissue. The indication by the surgical procedure history that a vascular stapler 112 has already been used in the surgical procedure may also mean it is likely that parenchyma staple firings have already been performed and significant monopolar RF energy usage has occurred. This surgical procedure history considered in conjunction with clinician history, for example, may be used to predict that the surgeon is treating bronchus tissue. This prediction would be consistent with the surgeon's routine practice of stapling the bronchus as the last step in a lobectomy procedure. Based on analyzing this type of and other suitable intraoperative information at step 22212, it can be determined at decision operation 22214 that further adjustment is necessary. Because the answer to decision operation 22214 is yes, the flow diagram proceeds to step 22206 where it is inferred that the treated tissue is bronchus tissue with a normal tissue stiffness and thickness.

In one aspect, it may be easy to conclude that the treated tissue is bronchus tissue because the surgical instrument 112 is only configured for a specific tissue type. For example, the surgical instrument 112 may only be adaptable to fire staples that are used for bronchus. Conversely, the surgical instrument 112 might only be adaptable to fire staples that are used for parenchyma tissue. In that scenario, a warning might be generated by the surgical instrument 112 because the surgeon is attempting to treat bronchus tissue with staples exclusively used for parenchyma tissue. This warning could be an auditory, visual, or some other appropriate warning. In another example, a warning may be provided by a vascular stapler 112 if the vascular stapler 112 is selected for use with bronchus tissue. As discussed above, it may be determined based on perioperative information that the tissue being treated is bronchus tissue that the vascular stapler is contraindicated for. Similarly, other perioperative information such as closure loads and stapler cartridge selection may be used to provide warnings when surgical instruments 112 are used for tissue types or characteristics that they are not compatible with. As discussed above, inferences made using perioperative information may be made in conjunction with closure parameter sensor signals. In all situations, safety checks may be implemented to ensure that the surgical instrument 112 being used is safe for the tissue being treated.

In accordance with the inferred tissue type and characteristics, at step 22208, an adjustment to the current closure algorithm is made. Although it may be determined that a constant closure rate is suitable, the closure rate may be adjusted to be faster or slower depending on the inferred tissue characteristics of the bronchus, for example. The closure threshold could be modified in the same or similar way. Moreover, the current closure algorithm may also be adjusted such that if and when the surgical instrument 112 exceeds the instantaneously applicable closure threshold, a longer wait time is automatically enabled or suggested. For example, this wait time for bronchus tissue may be longer than the wait time used for parenchyma tissue. As discussed above, the surgeon is informed of the selected adjustment to the closure algorithm via the LED indicators, for example. A clinician override to the longer wait time is also possible so that the surgeon may be permitted to fire the stapler surgical instrument 112 in appropriate circumstances. The flow diagram 22200 then proceeds to step 22212, where it may be determined that no further steps of the surgical procedure remain.

In one aspect, the flow diagram 22200 may be implemented by the control circuit. However, in other aspects, the flow diagram 22200 can be implemented by the surgical hub 106 or cloud 104. Additionally, although steps 22204 and 22212 are described in terms of preoperative information and intraoperative information respectively, they are not limited in this way. Specifically, perioperative information in general may be received and analyzed rather than specific preoperative or intraoperative information. As discussed above, perioperative information encompasses preoperative, intraoperative, and postoperative information. Moreover, sensor signals may be used in conjunction with perioperative information for contextual and inferential closure algorithm adjustments.

Irregularities in Tissue Distribution

Typically, in a surgical stapling procedure, a user places the jaws of the end effector around tissue to clamp and staple the tissue. In some instances, the majority of the tissue clamped between the jaws of the surgical stapling instrument can be concentrated in a portion of the gap between the jaws while the remainder of the gap remains unoccupied or slightly occupied. Irregularities in distribution of tissue positioned between the jaws of a surgical stapling instrument can reduce stapling outcome consistency. For example, the irregular tissue distribution can lead to excessive tissue compression in parts of the clamped tissue, and insufficient tissue compression in other parts of the clamped tissue, which may have a negative impact on the tissue being operated on. For example, excessive compression of tissue may result in tissue necrosis and, in certain procedures, staple line failure. Insufficient tissue compression also negatively impacts staple deployment and formation, and may cause the stapled tissue to leak or heal improperly.

Aspects of the present disclosure present a surgical stapling instrument that includes an end effector configured to staple tissue clamped between a first jaw and a second jaw of the end effector. The surgical stapling instrument is configured to sense and indicate irregularities in tissue distribution with respect to a number of predetermined zones between the first jaw and the second jaw, within the end effector. The surgical stapling instrument is further configured to sense and indicate irregularities in the amount and location of the tissue among the predetermined zones.

In one aspect, the surgical stapling instrument is configured to provide feedback on the most appropriate location and positioning of tissue in situations where tissue irregularities are detected.

Absolute measurements of the tissue impedance at the predetermined zones may be significantly influenced by the environment in which the end effector is immersed. For example, an end effector immersed in a fluid such as blood, for example, will yield different tissue impedance measurements than an end effector not immersed in blood. Also, an end effector clamped around a previously stapled tissue will yield different tissue impedance measurements than an end effector clamped around unstapled tissue. The present disclosure addresses such discrepancies when assessing tissue distribution in different predetermined zones by evaluating the tissue impedance measurements at the different predetermined zones in comparison to one another.

In one aspect, irregularities in the tissue clamped between the jaws of the surgical stapling instrument yield different tissue compressions at the predetermined zones. Aspects of the present disclosure present a surgical stapling instrument including a tissue-distribution assessment circuit configured to sense and indicate irregularities in the tissue compression among the predetermined zones by measuring impedance between the jaws of the end effector at each of the predetermined zones.

In one aspect, the tissue-distribution assessment circuit of the surgical stapling instrument comprises one or more tissue contact circuits at each of the predetermined zones configured to measure tissue impedance to assess position and amount of the clamped tissue.

For brevity, one or more of the embodiments of the present disclosure are described in connection with a specific type of surgical instruments. This should not be construed, however, as limiting. The embodiments of the present disclosure are applicable to various types of surgical stapling instruments such as, for example, linear surgical stapling instruments, curved surgical stapling instruments, and/or circular stapling instruments. The embodiments of the present disclosure are also equally applicable to surgical instrument that applies therapeutic energy to tissue such as, for example, ultrasonic or radio frequency (RF) energy.

Referring to FIG. 111, an end effector 25002 extending from a shaft 25004 of a curved surgical stapling instrument is depicted. The end effector 25002 includes a first jaw 25006 defining an anvil 25007 and a second jaw 25008 that includes a staple cartridge 25009. The staple cartridge 25009 and the anvil 25007 have as an arc-like shape in the cross-sectional plane. The staple cartridge 25009 can be removed from the rest of the end effector 25002 and is mounted in a cartridge holder slidably mounted in a guide portion. An arm 250010 supporting the anvil is rigidly connected to one end of the guide portion and runs in parallel to a longitudinal axis L defined by the shaft 25004.

Tissue is clamped between the anvil 25007 and the staple cartridge 25009 by moving the staple cartridge 25009 distally toward the anvil 25007. In certain aspects, the anvil 25007 is moved proximally toward the staple cartridge 25009 to clamp the tissue therebetween. In other aspects, the anvil and the staple cartridge are moved relative to one another to clamp the tissue therebetween. As illustrated in FIG. 111, the anvil 25007 and staple cartridge 25009 define a stapling plane perpendicular to the longitudinal axis L. Staples are deployed in curved rows from the staple cartridge 25009 into tissue clamped between the staple cartridge 25009 and the anvil 25007.

Referring again to FIG. 111, three tissue-distribution assessment zones (Zone 1, Zone 2, Zone 3) are defined along the curved length of the anvil 25007. Each of the three zones extends along a portion of the curved length of the anvil 25007. Tissue impedance is measured at each of the three zones to assess irregularities in tissue distribution between the anvil 25007 and the staple cartridge 25009. Zone 1, which is also referred to herein as the crotch zone, is an inner zone residing closest to the arm 25010 while zone 3 is an outer zone, and is farther away from the arm 25010 than Zone 1. Zone 2 is an intermediate zone extending between Zone 1 and Zone 3. Zone 1 and Zone 3 each extend along about one quarter of the curved length of the anvil 25007. On the other hand, Zone 2 extends along about one half of the curved length of the anvil between Zone 1 and Zone 3.

FIG. 112 is a partial cross-sectional view of the end effector of FIG. 111 shown grasping tissue between its jaws at the three tissue-distribution assessment zones (Zone 1, Zone 2, Zone 3). FIG. 113 illustrates a perspective view of an end effector 25020 of a surgical stapling and cutting instrument including tissue-distribution assessment zones (Zone 1, Zone 2, Zone 3), which are similar in many respects to the tissue-distribution assessment zones (Zone 1, Zone 2, Zone 3) of the end effector 25002.

In the embodiment of FIG. 111, the anvil 25007 has a tissue contacting surface 25012 that is divided into the three zones (Zone 1, Zone 2, Zone 3). Tissue impedance measurements at the three zones represent tissue distribution within the end effector 25002. In various aspects, the number of zones can be greater or less than three. In one example, a surgical stapling instrument may include four zones, as illustrated in FIG. 126. In another example, a surgical stapling instrument may include eight zones, as illustrated in FIG. 127. The size of the zones can be the same, or at least substantially the same. Alternatively, the size of the zones may vary, as illustrated in FIG. 111.

A suitable number, size, and location of the zones may be selected depending on the type of surgical instrument. For example, a linear surgical stapling instrument may include an inner or proximal zone, which is closest to the shaft, an outer or distal zone, which is farthest from the shaft, and one or more intermediate zones between the inner zone and the outer zone.

The three zones of the embodiment of FIG. 111 are defined with respect to the tissue contacting surface 25012 of the anvil 25007. In other embodiments, however, tissue-distribution assessment zones may be defined with respect to a tissue contacting surface of a staple cartridge. In other words, the tissue contacting surface of the staple cartridge can be divided into predetermined zones for the purpose of assessing tissue distribution within an end effector.

Each of the three zones of the embodiment of FIG. 111 includes one or more tissue contact circuits that are configured to measure impedance of a tissue portion residing at the predetermined zone. An example tissue contacting circuit is illustrated in FIG. 24. Tissue "T" contact with the anvil 25007 and staple cartridge 25009 at a predetermined zone closes the sensing circuit "SC" at the predetermined zone, which is otherwise open, by simultaneously establishing contact with a pair of opposed plates "P1, P2" provided on the anvil 25007 and staple cartridge 25009 at the predetermined zone.

Any of the contact circuits disclosed herein may include, and are not limited to, electrical contacts placed on an inner surface of a jaw which, when in contact with tissue, close a sensing circuit that is otherwise open.

The contact circuits may also include sensitive force transducers that determine the amount of force being applied to the sensor, which may be assumed to be the same amount of force being applied to the tissue "T". Such force being applied to the tissue "T" may then be translated into an amount of tissue compression. The force sensors measure the amount of compression a tissue "T" is under, and provide a surgeon with information about the force applied to the tissue "T".

As described above, excessive tissue compression may have a negative impact on the tissue "T" being operated on. For example, excessive compression of tissue "T" may result in tissue necrosis and, in certain procedures, staple line failure. Information regarding the pressure being applied to tissue "T" enables a surgeon to better determine that excessive pressure is not being applied to tissue "T".

The force transducers of the contact circuits may include, and are not limited to, piezoelectric elements, piezoresistive elements, metal film or semiconductor strain gauges, inductive pressure sensors, capacitive pressure sensors, and potentiometric pressure transducers that use bourbon tubes, capsules or bellows to drive a wiper arm on a resistive element.

In various aspects, the predetermined zones within an end effector 25002 may comprise one or more segmented flexible circuit configured to fixedly attach to at least one jaw member of the end effector 25002. Examples of suitable segmented flexible circuits are described in connection with FIG. 75 of the present disclosure. To measure tissue impedances, the segmented flexible circuit pass sub-therapeutic electrical signals through the tissue at each of the predetermined zones.

FIGS. 114-119 illustrate three tissue distribution examples ($T_1$, $T_2$, $T_3$) within an end effector 25002. Straightened cross-sectional views of the end effector 25002 in FIGS. 114-116 illustrate an initial distribution of tissue among the three zones (Zone 1, Zone 2, Zone 3) within the end effector 25002 according to each of the three examples. Straightened cross-sectional views of the end effector in FIGS. 117-119 illustrate the tissue of the three examples under an initial compression to close the sensing contact circuits between the tissue-contacting surfaces of the anvil 25007 and the staple cartridge 25009.

As described above, establishing contact between the tissue "T" and the tissue contacting surfaces of the anvil 25007 and the staple cartridge 25009 at a predetermined zone closes a sensing circuit at the predetermined zone. The closure of the sensing circuit causes a current to pass through the tissue "T" at the predetermined zone, as illustrated in FIG. 112, and the sensing circuit. Impedance of the tissue "T" at the predetermined zone can be calculated from the formula:

$$Z_{tissue} = \left(\frac{V}{I}\right) - Z_{sense\ circuit}$$

wherein $Z_{tissue}$ is tissue impedance, V is voltage, I is current, and $Z_{sense\ circuit}$ is impedance of the sense circuit.

As illustrated in FIG. 112, insulating elements 25014 can be positioned between adjacent plates (p) to separate adjacent sensing circuits. Although three sensing circuits are represented in FIG. 112, the number of sensing circuits can be different than three. In various examples, an end effector may include an "n" number of sensing circuits corresponding to an "n" number of predetermined zones, wherein "n" is an integer greater than or equal to the number 3.

FIG. 120 illustrates a logic flow diagram of a process 25030 depicting a control program or a logic configuration for identifying irregularities in tissue distribution within an end effector 25002 of a surgical instrument, in accordance with at least one aspect of the present disclosure. In one aspect, the process 25030 is executed by a control circuit 500 (FIG. 13). In another aspect, the process 25030 can be executed by a combinational logic circuit 510 (FIG. 14). In yet another aspect, the process 25030 can be executed by a sequential logic circuit 520 (FIG. 15).

The process 25030 includes receiving 25032 senor signals from sensor circuits of a sensing circuit assembly 25471 corresponding to predetermined zones (e.g. zone 1, Zone 2, and Zone 3) within the end effector 25002, determining 25034 tissue impedance $Z_{tissue}$ of tissue portions at such zones based on the received sensor signals. FIG. 121 illustrates tissue impedance $Z_{tissue}$ curves 25001, 25003, 25005, which correspond to the tissue examples $T_1$, $T_2$, $T_3$, respectively.

The process 25030 further includes conditional steps 25036, 25038. If it is determined that the average of the tissue impedances of an inner zone (e.g. Zone 1) and an outer zone (e.g. Zone 3) is greater than the tissue impedance of the intermediate zone (e.g. Zone 2), then tissue distribution is considered to be inadequate, instructions are provided for releasing 25040 the grasped tissue and repositioning the end effector 25002, as illustrated by the example in FIGS. 115, 118, 121, 123. In certain instances, during the release cycle the grasped tissue is only released to a minimum threshold and then re-clamped so that the tissue does not slip out of the end effector 25002.

If, however, the average of the tissue impedances of an outer zone (e.g. Zone 1) and an inner zone (e.g. Zone 3) is less than or equal to the tissue impedance of an intermediate zone (e.g. Zone 2), and tissue impedance of the inner zone is less than or equal to the tissue impedance of the outer zone, then tissue distribution is considered to be adequate, and the end effector closure is continued 25042 while maintaining a predetermined Force-To-Close (FTC) threshold rate, as illustrated by the example of FIGS. 114, 117, 121, 122.

If, however, the average of the tissue impedances of an outer zone (e.g. Zone 1) and an inner zone (e.g. Zone 3) is less than or equal to the tissue impedance of an intermediate zone (e.g. Zone 2), and tissue impedance of the inner zone is greater than the tissue impedance of the outer zone, then tissue distribution is considered to be adequate, but the FTC threshold rate is reduced 25044 to a slower rate, as illustrated by the example of FIGS. 116, 119, 121, 124.

FIG. 125 illustrates a logic diagram of a control system 25470, which can be employed to execute the process of FIG. 120. The control system 25470 is similar in many respects to the control system 470 (FIG. 12). In addition, the control system 25470 includes a sensing circuit assembly 25471 that includes an "n" number of sensing circuits $S_1$-$S_n$, wherein "n" is an integer greater than two. The sensing circuits $S_1$-$S_n$ define predetermined zones within an end effector, as described above.

In various examples, the sensing circuit assembly 25471 includes an "n" number of continuity sensors, wherein "n" is an integer greater than two. The continuity sensors define predetermined zones within an end effector, as described above.

In various examples, sensing circuits $S_1$-$S_n$ can be configured to provide sensor signals indicative of tissue compression using impedance measurements. Continuity sensors $S_1$-$S_n$ can be used to inform whether sufficient tissue extends within an end effector 25002. In addition, FTC sensors can be used in assessing tissue creep rates in order to determine tissue distribution within an end effector 25002.

In various aspects, the sensing circuits $S_1$-$S_n$ can be configured to measure tissue impedance by driving a sub-therapeutic RF current through the tissue grasped by an end effector 25002. One or more electrodes can be positioned on either or both jaws of the end effector 25002. The tissue compression/impedance of the grasped tissue can be measured over time.

In various aspects, various sensors such as a magnetic field sensor, a strain gauge, a pressure sensor, a force sensor, an inductive sensor such as, for example, an eddy current sensor, a resistive sensor, a capacitive sensor, an optical sensor, and/or any other suitable sensor, may be adapted and configured to measure tissue compression/impedance at predetermined zones within an end effector.

In various aspects, the rate of closure system advancement is changed by the microcontroller 461 if more tissue is sensed in an inner zone than an outer zone of an end effector 25002. The closure rate is slowed down to improve tissue distribution by allowing time for the tissue in the inner zone to creep outward within the end effector 25002.

In various aspects, monitoring the change in impedance as closure gap changes may be used to inform tissue properties and positioning as well.

FIG. 122 illustrates a graph 25400 depicting end effector FTC 25402 and closure velocity 25404 verse time 25406 for an illustrative firing of an end effector 25002 of a surgical instrument, in accordance with at least one aspect of the present disclosure. In the following description of the graph 25400, reference should also be made to FIGS. 114, 117, 120. The illustrative firings described herein are for the purpose of demonstrating the concepts discussed above with respect to FIGS. 114, 117, 120 and should not be interpreted as limiting in any way.

A firing of the end effector 25002, as illustrated in FIGS. 114, 117, can be represented by a FTC curve 25408 and a corresponding velocity curve 25408', which illustrate the change in FTC and closure velocity over time during the course of the firing, respectively. The firing can represent, for example, a firing of the end effector 25002 of a surgical instrument that includes a control circuit executing the process 25030 depicted in FIG. 120. As firing of the end effector 25002 is initiated, the processor 462 controls the motor 482 to begin driving the anvil 25007 from its open position, causing the closure velocity of the anvil 25007 to sharply increase 25416 until it plateaus 25418 at a particular closure velocity. As the anvil 25007 closes, the FTC increases 25410 until it peaks 25412 at a particular time. From the peak 25412, the FTC decreases 25414 until the tissue "T1" is fully clamped, at which point the processor 462 controls the motor 482 to halt the closure of the anvil 25007 and the closure velocity drops 25420 to zero.

The firing of FIGS. 114, 117 thus represents a firing of the end effector 25002 wherein tissue distribution between the jaws 25006, 25008 is within acceptable limits. In other words, the firing of FIGS. 114, 117 stays within all control parameters during the course of the jaw closure. Thus, the processor 462 does not pause the anvil 25007, adjust the closure velocity of the anvil 25007, or take any other corrective action during the course.

FIG. 100 illustrates a graph 25422 depicting end effector FTC 25402 and closure velocity 25404 verse time 25406 for an illustrative firing of an end effector 25007 of a surgical instrument, in accordance with at least one aspect of the present disclosure. In the following description of the graph 25422, reference should also be made to FIGS. 115, 118, 120. The illustrative firings described herein are for the purpose of demonstrating the concepts discussed above with respect to FIGS. 115, 118, 120 and should not be interpreted as limiting in any way.

A firing of the end effector 25002, as illustrated in FIGS. 115, 118, 120, can be represented by an FTC curve 25424 and a corresponding velocity curve 25424', which illustrate the change in FTC and closure velocity over time during the course of the firing, respectively. The firing of FIGS. 115, 118 can represent, for example, a firing of an end effector 25007 of a surgical instrument that includes a control circuit executing the process 25030 depicted in FIG. 120. As firing of the end effector 25007 is initiated, the processor 462 controls the motor 482 to begin driving the anvil 25007 from its open position, causing the closure velocity of the anvil 25007 to sharply increase 25432 until it reaches a particular closure velocity. As the anvil 25012 closes, the FTC increases 25426 until it peaks 25428 at a particular time. In this instance, the processor 462 receives input from the sensing circuit assembly 25471 indicating that tissue distribution between the jaws 25006, 2008 is skewed toward the third zone, as illustrated in FIGS. 115, 118.

In response, as outlined in the process 25030, the processor 462 instructs, through display 473, the operator of the end effector 25007 of the surgical instrument to open the jaws 25006, 25008 in order to readjust the tissue "T2" therein. Thus, the closure velocity drops 25434 until it reaches a negative closure velocity, indicating that the jaws 25006, 25008 are being opened in order to, for example, easily permit the tissue "T2" to be readjusted within the jaws 25006, 25008. The closure velocity then returns 25436 back to zero, the jaws 25006, 25008 stopped. Correspondingly, the FTC decreases 25430 to zero as the jaws 25006, 25008 are released from the tissue "T2".

FIG. 124 illustrates a graph 25438 depicting end effector FTC 25402 and closure velocity 25404 verse time 25406 for an illustrative firing of a surgical instrument, in accordance with at least one aspect of the present disclosure. In the following description of the seventh graph 25438, reference should also be made to FIGS. 116, 119, 120. The illustrative firings described herein are for the purpose of demonstrating the concepts discussed above with respect to FIGS. 116, 119, 120 and should not be interpreted as limiting in any way.

A firing of the end effector 25002, as illustrated in FIGS. 116, 119, 120 can be represented by an FTC curve 21440 and a corresponding velocity curve 25440', which illustrate the change in FTC and closure velocity over time during the course of the firing, respectively. The firing of FIGS. 116, 119 can represent, for example, an end effector 25002 of a surgical instrument that includes a control circuit executing the process 25030 depicted in FIG. 11. As firing of the end effector 25002 is initiated, the processor 462 controls the motor 482 to begin driving the anvil 25007 from its open position, causing the closure velocity of the anvil 25007 to sharply increase 25450 to a first closure velocity v1. As the anvil 25007 closes, the FTC increases 21442 until time t1. At time t1, the control circuit 21002 determines that tissue distribution is skewed toward zone 1, as depicted in FIGS. 116, 119. In response, as indicated by the process 25030, the processor 462 may adjust the speed of the motor 482 to allow the tissue "T3" sufficient time to creep outward toward the zone 2 and/or zone 3.

FIG. 126 illustrates a diagram 6000 of a surgical instrument 6002 centered on a staple line 6003 using the benefit of centering tools and techniques described in connection with FIGS. 127-129, in accordance with at least one aspect of the present disclosure. As used in the following description of FIGS. 127-137 a staple line may include multiple rows of staggered staples and typically includes two or three rows of staggered staples, without limitation. The staple line may be a double staple line 6004 formed using a double-stapling technique as described in connection with FIGS. 127-131 or may be a linear staple line 6052 formed using a linear transection technique as described in connection with FIGS. 131-137. The centering tools and techniques described herein can be used to align the instrument 6002 located in one part of the anatomy with either the staple line 6003 or with another instrument located in another part of the anatomy without the benefit of a line of sight. The centering tools and techniques include displaying the current alignment of the instrument 6002 adjacent to previous operations. The centering tool is useful, for example, during laparoscopic-assisted rectal surgery that employ a double-stapling technique, also referred to as an overlapping stapling technique. In the illustrated example, during a laparoscopic-assisted rectal surgical procedure, a circular stapler 6002 is positioned in the rectum 6006 of a patient within the pelvic cavity 6008 and a laparoscope is positioned in the peritoneal cavity.

During the laparoscopic-assisted rectal surgery, the colon is transected and sealed by the staple line 6003 having a length "1." The double-stapling technique uses the circular stapler 6002 to create an end-to-end anastomosis and is currently used widely in laparoscopic-assisted rectal surgery. For a successful formation of an anastomosis using a circular stapler 6002, the anvil trocar 6010 of the circular stapler 6002 should be aligned with the center "½" of the staple line 6003 transection before puncturing through the center "½" of the staple line 6003 and/or fully clamping on the tissue before firing the circular stapler 6002 to cut out the staple overlap portion 6012 and forming the anastomosis. Misalignment of the anvil trocar 6010 to the center of the staple line 6003 transection may result in a high rate of anastomotic failures. This technique may be applied to ultrasonic instruments, electrosurgical instruments, combination ultrasonic/electrosurgical instruments, and/or combination surgical stapler/electrosurgical instruments. Several techniques are now described for aligning the anvil trocar 6010 of the circular stapler 6002 to the center "½" of the staple line 6003.

In one aspect, as described in FIGS. 127-129 and with reference also to FIGS. 1-11, to show interaction with an interactive surgical system 100 environment including a surgical hub 106, 206, the present disclosure provides an apparatus and method for detecting the overlapping portion of the double staple line 6004 in a laparoscopic-assisted rectal surgery colorectal transection using a double stapling technique. The overlapping portion of the double staple line 6004 is detected and the current location of the anvil trocar 6010 of the circular stapler 6002 is displayed on a surgical hub display 215 coupled to the surgical hub 206. The surgical hub display 215 displays the alignment of a circular stapler 6002 cartridge relative to the overlapping portion of the double staple line 6004, which is located at the center of the double staple line 6004. The surgical hub display 215 displays a circular image centered around the overlapping double staple line 6004 region to ensure that the overlapping portion of the double staple line 6004 is contained within the knife of the circular stapler 6002 and therefore removed following the circular firing. Using the display, the surgeon aligns the anvil trocar 6010 with the center of the double staple line 6004 before puncturing through the center of the double staple line 6004 and/or fully clamping on the tissue before firing the circular stapler 6002 to cut out the staple overlap portion 6012 and form the anastomosis.

FIGS. 127-131 illustrate a process of aligning an anvil trocar 6010 of a circular stapler 6022 to a staple overlap portion 6012 of a double staple line 6004 created by a double-stapling technique, in accordance with at least one aspect of the present disclosure. The staple overlap portion 6012 is centered on the double staple line 6004 formed by a double-stapling technique. The circular stapler 6002 is inserted into the colon 6020 below the double staple line 6004 and a laparoscope 6014 is inserted through the abdomen above the double staple line 6004. A laparoscope 6014 and a non-contact sensor 6022 are used to determine an anvil trocar 6010 location relative to the staple overlap portion 6012 of the double staple line 6004. The laparoscope 6014 includes an image sensor to generate an image of the double staple line 6004. The image sensor image is transmitted to the surgical hub 206 via the imaging module 238. The sensor 6022 generates a signal 6024 that detects the metal staples using inductive or capacitive metal sensing technology. The signal 6024 varies based on the position of the anvil trocar 6010 relative to the staple overlap portion 6004. A centering tool 6030 presents an image 6038 of the double staple line 6004 and a target alignment ring 6032 circumscribing the image 6038 of the double staple line 6004 centered about an image 6040 of the staple overlap portion 6012 on the surgical hub display 215. The centering tool 6030 also presents a projected cut path 6034 of an anvil knife of a circular stapler 6002. The alignment process includes displaying an image 6038 of the double staple line 6004 and a target alignment ring 6032 circumscribing the image 6038 of the double staple line 6004 centered on the image 6040 of the staple overlap portion 6012 to be cut out by the circular knife of the circular stapler 6002. Also displayed is an image of a crosshair 6036 (X) relative to the image 6040 of the staple overlap portion 6012.

FIG. 127 illustrates an anvil trocar 6010 of a circular stapler 6002 that is not aligned with a staple overlap portion 6012 of a double staple line 6004 created by a double-stapling technique. The double staple line 6004 has a length "1" and the staple overlap portion 6012 is located midway along the double staple line 6004 at "½." As shown in FIG. 127, the circular stapler 6002 is inserted into a section of the colon 6020 and is positioned just below the double staple line 6004 transection. A laparoscope 6014 is positioned above the double staple line 6004 transection and feeds an image of the double staple line 6004 and staple overlap portion 6012 within the field of view 6016 of the laparoscope 6014 to the surgical hub display 215. The position of the anvil trocar 6010 relative to the staple overlap portion 6012 is detected by a sensor 6022 located on the circular stapler 6002. The sensor 6022 also provides the position of the anvil trocar 6010 relative to the staple overlap portion 6012 to the surgical hub display 215.

As shown in In FIG. 127, the projected path 6018 of the anvil trocar 6010 is shown along a broken line to a position marked by an X. As shown in FIG. 127, the projected path 6018 of the anvil trocar 6010 is not aligned with the staple overlap portion 6012. Puncturing the anvil trocar 6010 through the double staple line 6044 at a point off the staple overlap portion 6012 could lead to an anastomotic failure. Using the anvil trocar 6010 centering tool 6030 described in FIG. 129, the surgeon can align the anvil trocar 6010 with the staple overlap portion 6012 using the images displayed by the centering tool 6030. For example, in one implementation the sensor 6022 is an inductive sensor. Since the staple overlap portion 6012 contains more metal than the rest of the lateral portions of the double staple line 6004, the signal 6024 is maximum when the sensor 6022 is aligned with and proximate to the staple overlap portion 6012. The sensor 6022 provides a signal to the surgical hub 206 that indicates the location of the anvil trocar 6010 relative to the staple overlap portion 6012. The output signal is converted to a visualization of the location of the anvil trocar 6010 relative to the staple overlap portion 6012 that is displayed on the surgical hub display 215.

As shown in FIG. 128, the anvil trocar 6010 is aligned with the staple overlap portion 6012 at the center of the double staple line 6004 created by a double-stapling technique. The surgeon can now puncture the anvil trocar 6010 through the staple overlap portion 6012 of the double staple line 6004 and/or fully clamp on the tissue before firing the circular stapler 6002 to cut out the staple overlap portion 6012 and form an anastomosis.

FIG. 129 illustrates a centering tool 6030 displayed on a surgical hub display 215, the centering tool providing a display of a staple overlap portion 6012 of a double staple line 6004 created by a double-staling technique, where the anvil trocar 6010 is not aligned with the staple overlap portion 6012 of the double staple line 6004 as shown in FIG. 127. The centering tool 6030 presents an image 6038 on the surgical hub display 215 of the double staple line 6004 and an image 6040 of the staple overlap portion 6012 received from the laparoscope 6014. A target alignment ring 6032 centered about the image 6040 of the staple overlap portion 6012 circumscribes the image 6038 of the double staple line 6004 to ensure that the staple overlap portion 6012 is located within the circumference of the projected cut path 6034 of the circular stapler 6002 knife when the projected cut path 6034 is aligned to the target alignment ring 6032. The crosshair 6036 (X) represents the location of the anvil trocar 6010 relative to the staple overlap portion 6012. The crosshair 6036 (X) indicates the point through the double staple line 6004 where the anvil trocar 6010 would puncture if it were advanced from its current location.

As shown in FIG. 129, the anvil trocar 6010 is not aligned with the desired puncture through location designated by the image 6040 of the staple overlap portion 6012. To align the anvil trocar 6010 with the staple overlap portion 6012 the surgeon manipulates the circular stapler 6002 until the projected cut path 6034 overlaps the target alignment ring 6032 and the crosshair 6036 (X) is centered on the image 6040 of the staple overlap portion 6012. Once alignment is complete, the surgeon punctures the anvil trocar 6010 through the staple overlap portion 6012 of the double staple line 6004 and/or fully clamps on the tissue before firing the circular stapler 6002 to cut out the staple overlap portion 6012 and form the anastomosis.

As discussed above, the sensor 6022 is configured to detect the position of the anvil trocar 6010 relative to the staple overlap portion 6012. Accordingly, the location of the crosshair 6036 (X) presented on the surgical hub display 215 is determined by the surgical stapler sensor 6022. In another aspect, the sensor 6022 may be located on the laparoscope 6014, where the sensor 6022 is configured to detect the tip of the anvil trocar 6010. In other aspects, the sensor 6022 may be located either on the circular stapler 6022 or the laparoscope 6014, or both, to determine the location of the anvil trocar 6010 relative to the staple overlap portion 6012 and provide the information to the surgical hub display 215 via the surgical hub 206.

FIGS. 130 and 131 illustrate a before image 6042 and an after image 6043 of a centering tool 6030, in accordance with at least one aspect of the present disclosure. FIG. 130 illustrates an image of a projected cut path 6034 of an anvil trocar 6010 and circular knife before alignment with the target alignment ring 6032 circumscribing the image 6038 of the double staple line 6004 over the image 6040 of the staple overlap portion 6040 presented on a surgical hub display 215. FIG. 131 illustrates an image of a projected cut path 6034 of an anvil trocar 6010 and circular knife after alignment with the target alignment ring 6032 circumscribing the image 6038 of the double staple line 6004 over the image 6040 of the staple overlap portion 6040 presented on a surgical hub display 215. The current location of the anvil trocar 6010 is marked by the crosshair 6036 (X), which as shown in FIG. 130, is positioned below and to the left of center of the image 6040 of the staple overlap portion 6040. As shown in FIG. 131, as the surgeon moves the anvil trocar 6010 of the along the projected path 6046, the projected cut path 6034 aligns with the target alignment ring 6032. The target alignment ring 6032 may be displayed as a greyed out alignment circle overlaid over the current position of the anvil trocar 6010 relative to the center of the double staple line 6004, for example. The image may include indication marks as to which direction to move. The target alignment ring 6032 may be shown in bold, change color or highlight when it is located within a predetermined distance of center within acceptable limits.

In another aspect, the sensor 6022 may be configured to detect the beginning and end of a linear staple line in a colorectal transection and to provide the position of the current location of the anvil trocar 6010 of the circular stapler 6002. In another aspect, the present disclosure provides a surgical hub display 215 to present the circular stapler 6002 centered on the linear staple line, which would create even dog ears, and to provide the current position of the anvil trocar 6010 to allow the surgeon to center or align the anvil trocar 6010 as desired before puncturing and/or fully clamping on tissue prior to firing the circular stapler 6002.

In another aspect, as described in FIGS. 132-134 and with reference also to FIGS. 1-11, in a laparoscopic-assisted rectal surgery colorectal transection using a linear stapling technique, the beginning and end of the linear staple line 6052 is detected and the current location of the anvil trocar 6010 of the circular stapler 6002 is displayed on a surgical hub display 215 coupled to the surgical hub 206. The surgical hub display 215 displays a circular image centered on the double staple line 6004, which would create even dog ears and the current position of the anvil trocar 6002 is displayed to allow the surgeon to center or align the anvil trocar 6010 before puncturing through the linear staple line 6052 and/or fully clamping on the tissue before firing the circular stapler 6002 to cut out the center 6050 of the linear staple line 6052 to form an anastomosis.

FIGS. 132-135 illustrate a process of aligning an anvil trocar 6010 of a circular stapler 6022 to a center 6050 of a linear staple line 6052 created by a linear stapling technique, in accordance with at least one aspect of the present disclosure. FIGS. 132 and 133 illustrate a laparoscope 6014 and a sensor 6022 located on the circular stapler 6022 to determine the location of the anvil trocar 6010 relative to the center 6050 of the linear staple line 6052. The anvil trocar 6010 and the sensor 6022 is inserted into the colon 6020 below the linear staple line 6052 and the laparoscope 6014 is inserted through the abdomen above the linear staple line 6052.

FIG. 132 illustrates the anvil trocar 6010 out of alignment with the center 6050 of the linear staple line 6052 and FIG. 133 illustrates the anvil trocar 6010 in alignment with the center 6050 of the linear staple line 6052. The sensor 6022 is used to detect the center 6050 of the linear staple line 6052 to align the anvil trocar 6010 with the center of the staple line 6052. In one aspect, the center 6050 of the linear staple line 6052 may be located by moving the circular stapler 6002 until one end of the linear staple line 6052 is detected. An end may be detected when there are no more staples in the path of the sensor 6022. Once one of the ends is reached, the circular stapler 6002 is moved along the linear staple line 6053 until the opposite end is detected and the length "1" of the linear staple line 6052 is determined by measurement or by counting individual staples by the sensor 6022. Once the length of the linear staple line 6052 is determined, the center 6050 of the linear staple line 6052 can be determined by dividing the length by two "½."

FIG. 134 illustrates a centering tool 6054 displayed on a surgical hub display 215, the centering tool providing a display of a linear staple line 6052, where the anvil trocar 6010 is not aligned with the staple overlap portion 6012 of the double staple line 6004 as shown in FIG. 132. The surgical hub display 215 presents a standard reticle field of view 6056 of the laparoscopic field of view 6016 of the linear staple line 6052 and a portion of the colon 6020. The surgical hub display 215 also presents a target ring 6062 circumscribing the image center of the linear staple line and a projected cut path 6064 of the anvil trocar and circular knife. The crosshair 6066 represents the location of the anvil trocar 6010 relative to the center 6050 of the linear staple line 6052. The crosshair 6036 (X) indicates the point through the linear staple line 6052 where the anvil trocar 6010 would puncture if it were advanced from its current location.

As shown in FIG. 134, the anvil trocar 6010 is not aligned with the desired puncture through location designated by the offset between the target ring 6062 and the projected cut path 6064. To align the anvil trocar 6010 with the center 6050 of the linear staple line 6052 the surgeon manipulates the circular stapler 6002 until the projected cut path 6064 overlaps the target alignment ring 6062 and the crosshair 6066 is centered on the image 6040 of the staple overlap portion 6012. Once alignment is complete, the surgeon punctures the anvil trocar 6010 through the center 6050 of the linear staple line 6052 and/or fully clamps on the tissue before firing the circular stapler 6002 to cut out the staple overlap portion 6012 and form the anastomosis.

In one aspect, the present disclosure provides an apparatus and method for displaying an image of an linear staple line 6052 using a linear transection technique and an alignment ring or bullseye positioned as if the anvil trocar 6010 of the circular stapler 6022 were centered appropriately along the linear staple line 6052. The apparatus displays a greyed out alignment ring overlaid over the current position of the anvil trocar 6010 relative to the center 6050 of the linear staple line 6052. The image may include indication marks to assist the alignment process by indication which direction to move. the anvil trocar 6010. The target alignment ring 6032 may be shown in bold, change color or may be highlighted when it is located within a predetermined distance of center within acceptable limits.

With reference now to FIGS. 132-135, FIG. 135 is an image 6080 of a standard reticle field view 6080 of a linear staple line 6052 transection of a surgical as viewed through a laparoscope 6014 displayed on the surgical hub display 215, in accordance with at least one aspect of the present disclosure. In a standard reticle view 6080, it is difficult to see the linear staple line 6052 in the standard reticle field of view 6056. Further, there are no alignment aids to assist with alignment and introduction of the anvil trocar 6010 to the center 6050 of the linear staple line. This view does not show an alignment circle or alignment mark to indicate if the circular stapler is centered appropriately and does not show the projected trocar path. In this view it also difficult to see the staples because there is no contrast with the background image.

With reference now to FIGS. 132-136, FIG. 136 is an image 6082 of a laser-assisted reticle field of view 6072 of the surgical site shown in FIG. 135 before the anvil trocar 6010 and circular knife of the circular stapler 6002 are aligned to the center 6050 of the linear staple line 6052, in accordance with at least one aspect of the present disclosure. The laser-assisted reticle field of view 6072 provides an alignment mark or crosshair 6066 (X), currently positioned below and to the left of center of the linear staple line 6052 showing the projected path of the anvil trocar 6010 to assist positioning of the anvil trocar 6010. In addition to the projected path marked by the crosshair 6066 of the anvil trocar 6010, the image 6082 displays the staples of the linear staple line 6052 in a contrast color to make them more visible against the background. The linear staple line 6052 is highlighted and a bullseye target 6070 is displayed over the center 6050 of the linear staple line 6052. Outside of the laser-assisted reticle field of view 6072, the image 6082 displays a status warning box 6068, a suggestion box 6074, a target ring 6062, and the current alignment position of the anvil trocar 6010 marked by the crosshair 6066 relative to the center 6050 of the linear staple line 6052. As shown in FIG. 136, the status warning box 6068 indicates that the trocar is "MISALIGNED" and the suggestion box 6074 states "Adjust trocar to center staple line."

With reference now to FIGS. 132-137, FIG. 137 is an image 6084 of a laser-assisted reticle field of view 6072 of the surgical site shown in FIG. 136 after the anvil trocar 6010 and circular knife of the circular stapler 6002 are aligned to the center 6050 of the linear staple line 6052, in accordance with at least one aspect of the present disclosure.

The laser-assisted reticle field of view 6072 provides an alignment mark or crosshair 6066 (X), currently positioned below and to the left of center of the linear staple line 6052 showing the projected path of the anvil trocar 6010 to assist positioning of the anvil trocar 6010. In addition to the projected path marked by the crosshair 6066 of the anvil trocar 6010, the image 6082 displays the staples of the linear staple line 6052 in a contrast color to make them more visible against the background. The linear staple line 6052 is highlighted and a bullseye target 6070 is displayed over the center 6050 of the linear staple line 6052. Outside of the laser-assisted reticle field of view 6072, the image 6082 displays a status warning box 6068, a suggestion box 6074, a target ring 6062, and the current alignment position of the anvil trocar 6010 marked by the crosshair 6066 relative to the center 6050 of the linear staple line 6052. As shown in FIG. 136, the status warning box 6068 indicates that the trocar is "MISALIGNED" and the suggestion box 6074 states "Adjust trocar to center staple line."

FIG. 137 is a laser assisted view of the surgical site shown in FIG. 136 after the anvil trocar 6010 and circular knife are aligned to the center of the staple line 6052. In this view, inside the field of view 6072 of the laser-assisted reticle, the alignment mark crosshair 6066 (X) is positioned over the center of the staple line 6052 and the highlighted bullseye target to indicate alignment of the trocar to the center of the staple line. Outside the field of view 6072 of the laser-assisted reticle, the status warning box indicates that the trocar is "ALIGNED" and the suggestion is "Proceed trocar introduction."

Referring now to FIGS. 138-142, not only the amount and location of the tissue can affect the stapling outcome but also the nature, type, or state of the tissue. For example, irregular tissue distribution also manifests in situations that involve stapling previously stapled tissue such as, for example, in J-Pouch procedures, also known as Ileal Pouch Anal Anastomosis, and End-To End anastomosis procedures. Poor positioning and distribution of the previously stapled tissue within the end effector of a staple cartridge may cause the previously fired staple lines to be concentrated in one zone over another within the end effector, which negatively affects the outcome of such procedures.

Aspects of the present disclosure present a surgical stapling instrument that includes an end effector configured to staple tissue clamped between a first jaw and a second jaw of the end effector. In one aspect, positioning and orientation of previously stapled tissue within the end effector is determined by measuring and comparing tissue impedance at a number of predetermined zones within the end effector. In various aspects, tissue impedance measurements can also be utilized to identify overlapped layers of tissue and their position within an end effector.

FIGS. 138, 140, 141 illustrate an end effector 25500 of a circular stapler that includes a staple cartridge 25502 and an anvil 25504 configured to grasp tissue therebetween. The anvil 25504 and staple cavities 25505 of the staple cartridge 25502 are removed from FIG. 138 to highlight other features of the end effector 25500. The staple cartridge 25502 includes four predetermined zones (Zone 1, Zone 2, Zone 3, Zone4) defined by sensing circuits ($S_1$, $S_2$, $S_3$, $S_4$), in accordance with the present disclosure.

FIG. 139 illustrates another end effector 25510 of a circular stapler that includes staple cartridge 25512 and an anvil configured to grasp tissue therebetween. The anvil and staple cavities of the staple cartridge 25512 are removed to highlight other features of the end effector 25510. The staple cartridge 25512 includes eight predetermined zones (Zone 1-Zone 8) defined by sensing circuits ($S_1$-$S_8$), in accordance with the present disclosure. The zones defined in each of the circular staplers of FIGS. 138 and 139 are equal, or at least substantially equal, in size, and are arranged circumferentially around a longitudinal axis extending longitudinally through shafts of the circular staplers.

As described above, a previously stapled tissue is a tissue that includes staples that were previously deployed into the tissue. Circular staplers are often utilized in stapling previously stapled tissue to unstapled tissue (e.g. J-pouch procedures), as illustrated in FIG. 141, and stapling previously stapled tissue to other previously stapled tissue (e.g. End-To-End Anastomosis procedures), as illustrated in FIG. 140.

The presence of the staples in tissue affects the tissue impedance as the staples usually have different conductivity than tissue. The present disclosure presents various tools and techniques for monitoring and comparing tissue impedances at the predetermined zones of an end effector (e.g. end effectors 25500, 25510) of a circular stapler to determine an optimal positioning and orientation of a previously-stapled tissue with respect to the end effector.

The examples on the left sides of FIGS. 140, 141 demonstrate properly positioned and oriented previously-stapled tissue with respect to predetermined zones of a circular stapler. The previously-stapled tissue properly extends through the center of the staple cartridge 25502, and only once intersects a predetermined zone. The bottom left side of FIGS. 140, 141 demonstrate staples 25508 of the staple cartridge 25502 deployed into properly positioned and oriented previously-stapled tissue.

The examples on the right sides of FIGS. 140, 141 demonstrate poorly positioned and oriented previously-stapled tissue. The previously-stapled tissue is off center (FIG. 141) or overlaps (FIG. 31) at one or more predetermined zones. The bottom right side of FIGS. 140, 141 demonstrate staples 25508 of the staple cartridge 25502 deployed into poorly positioned and oriented previously-stapled tissue.

As used in connection with FIGS. 138-142 a staple line may include multiple rows of staggered staples and typically includes two or three rows of staggered staples, without limitation. In the examples of FIG. 140, a circular stapler of FIG. 138 is utilized to staple two tissues that include previously deployed staple lines SL1, SL2. In the example to the left of FIG. 140, which represents properly positioned and orientated staple lines SL1, SL2, each of Zone 1 through Zone 4 receives a discrete portion of one of the staple lines SL1, SL2. The first staple line SL1 extends across Zone 2 and Zone 4, while the second staple line SL2, which intersects the first staple line SL1 at a central point, extends across Zone 1 and Zone 3. Accordingly, the measured impedances in the four zones will be equal, or at least substantially equal, to one another, and will be less than the impedance of an unstapled tissue.

On the contrary, in the example to the right of FIG. 140, which represents improperly positioned and orientated staple lines SL1, SL2, the staple lines SL1, SL2 overlap, or extend substantially on top of one another, across Zone 1 and Zone 3 yielding lower impedance measurements in zone 1 and Zone 3 as compared to Zone 2 and Zone 4.

FIGS. 142 and 143 illustrate staple lines SL1, SL2 in an End-To-End anastomosis procedure performed by an end effector 25510 of a circular stapler of FIG. 116 that includes eight predetermined zones (zone 1: Zone 8) defined by eight sensing circuits $S_1$-$S_8$, as described above. The anvil of the end effector 25510 and staple cavities of the staple cartridge 25512 are removed from FIGS. 142 and 143 to highlight other features of the end effector 25510.

FIGS. 144 and 145 illustrate measured tissue impedances based on sensor signals from the sensing circuits $S_1$-$S_8$. The individual measurements define tissue impedance signatures. Vertical axes 25520, 25520' represent an angle of orientation (θ), while vertical axes 25522, 25522' list corresponding predetermined zones (Zone 1: Zone 8). Tissue impedance (Z) is depicted on horizontal axes 25524, 25524'.

In the example of FIGS. 142 and 144, the impedance measurements represent properly positioned and orientated staple lines SL1, SL2. As illustrated in FIG. 142, the staple lines SL1, SL2 extend through Zone 1, Zone 3, Zone 5, and Zone 7, and only overlap at a central point of the staple cartridge 25512. Since the previously-stapled tissue is evenly distributed among Zone 1, Zone 3, Zone 5, and Zone 7, tissue impedance measurements at such zones are the same, or at least substantially the same, in magnitude, and are significantly less than tissue impedance measurements at Zone 2, Zone 4, Zone 6, and Zone 8, which did not receive previously-stapled tissue.

Conversely, in the example of FIGS. 143, 145, the impedance measurements represent improperly positioned and orientated staple lines SL1, SL2. As illustrated in FIG. 143, the staple lines SL1, SL2 overlap on top of one another extending only through Zone 1 and Zone 5. Accordingly, tissue impedance measurements at Zone 1 and Zone 5 are significantly lower in magnitude than the remaining zones, which did not receive previously-stapled tissue.

FIGS. 146 and 147 illustrate a staple line SL3 in a J-Pouch procedure performed by an end effector 25510 of a circular stapler of FIG. 139 that includes eight predetermined zones (Zone 1: Zone 8) defined by eight sensing circuits $S_1$-$S_8$, as described above. The anvil of the end effector 25510 and staple cavities of the staple cartridge 25512 are removed from FIGS. 146 and 147 to highlight other features of the end effector 25510.

FIGS. 148 and 149 illustrate measured tissue impedances based on sensor signals from the sensing circuits $S_1$-$S_8$. The individual measurements define tissue impedance signatures. Vertical axes 25526, 25526' represent an angle of orientation (θ), while vertical axes 25528, 25528' list corresponding predetermined zones (Zone 1: Zone 8). Tissue impedance (Z) is depicted on horizontal axes 25530, 25530'.

In the example of FIGS. 146 and 148, the impedance measurements represent a properly positioned and orientated staple line SL3. As illustrated in FIG. 146, the staple line SL3 extends only through Zone 1 and Zone 5. Since the previously-stapled tissue is evenly distributed among Zone 1 and Zone 5, tissue impedance measurements at such zones are the same, or at least substantially the same, in magnitude, and are significantly less than tissue impedance measurements at the remaining zones, which did not receive previously-stapled tissue.

Conversely, in the example of FIGS. 147, 149, the impedance measurements represent an improperly positioned and orientated staple line SL3. As illustrated in FIG. 147, the staple line SL3 extends through Zone 4, Zone 5, and Zone 6, which are all on one side of the staple cartridge 25510. Accordingly, tissue impedance measurements at Zone 4, Zone 5, and Zone 6 are significantly lower in magnitude than the remaining zones, which did not receive previously-stapled tissue.

In various aspects, a circular stapler (e.g. the circular stapler of FIG. 138 and the circular stapler of FIG. 139) further includes a control system 25470 (FIG. 125), which can be configured to further analyze impedance measurements determined from the received sensor signals of the sensing circuits of the circular stapler. In certain aspects, the control system 25470, as illustrated in FIG. 125, includes a microcontroller 461 that can be configured to determine a geometric parameter of one or more previously deployed staple lines, as shown in connection with FIGS. 138-149. In certain instances, the microcontroller 461 can also be configured to determine an alignment aspect of the circular stapler, as shown in connection with FIGS. 126-137. In certain instances, the microcontroller 461 can also be configured to determine the location of a circular trocar of the circular staple, the length and centerline of a pre-existing staple line, and/or the center intersection of two sequential lines, as shown in in connection with FIGS. 126-137.

The microcontroller 461 may alert the surgical operator through the display 473, for example, of a detected improper positioning and/or orientation of previously stapled tissue. Other audio, haptic, and/or visual means can also be employed. The microcontroller 461 may also take steps to prevent the tissue stapling. For example, the microcontroller 461 may signal the motor driver 492 to deactivate the motor 482. In certain instances, the microcontroller 461 may recommend a new position and/or orientation to the surgical operator.

In various aspects, the circular staplers of the present disclosure are communicatively coupled to a surgical hub 106 (FIG. 3, FIG. 4), 206 (FIG. 9) through a wired and/or wireless communication channel. Data gathered by such circular stapler can be transmitted to the surgical hub 106, 206, which may further transmit the data to a cloud based system 104, 204, for additional analysis.

FIG. 150 illustrates a logic flow diagram of a process 25600 depicting a control program or a logic configuration for properly positioning a previously-stapled tissue within an end effector (e.g. end effectors 25500, 25510) of a surgical stapler. In one aspect, the process 25600 is executed by a control circuit 500 (FIG. 13). In another aspect, the process 25600 is executed by a combinational logic circuit 510 (FIG. 14). In yet another aspect, the process 25600 is executed by a sequential logic circuit 520 (FIG. 15).

For illustrative purposes, the following description depicts the process 25600 as being executable by a control circuit that includes a controller 461, which includes a processor 461. A memory 468 stores program instructions, which are executable by the processor 461 to perform the process 25600.

The process 25600 determines 25602 the type of surgical procedure being performed by the surgical stapler. The surgical procedure type can be determined using various techniques described under the heading "Situational Awareness". The processor 25600 then selects 25604, based on the determined surgical procedure type, a tissue impedance signature for a properly positioned previously-stapled tissue. As described above, a properly positioned previously-stapled tissue in a J-pouch procedure, for example, comprises a different tissue impedance signature than in an End-To-End Anastomosis procedure, for example.

The process 25600 then determines 25606 whether measured tissue impedances in the predetermined zones correspond to the selected tissue impedance signature. If not, the processor 461 may alert 25608 the user and/or override 25610 the tissue treatment. In one aspect, the processor 461 may alert 25608 the user through the display 473. In addition, the processor 461 may override 25610 the tissue treatment by preventing the end effector from completing its firing, which can be accomplished by causing the motor driver 492 to stop the motor 482 (FIG. 125), for example.

If, however, the measured tissue impedances in the predetermined zones correspond to the selected tissue impedance signature, the processor 461 permits the end effector to proceed 25612 with the tissue treatment.

Referring generally to FIGS. 151-157, tissue overhang is a phenomenon that occurs when tissue such as, for example, a blood vessel (BV), which is grasped between the jaws of a surgical end effector, extends beyond an optimal treatment region of the end effector. As such, the overhanging tissue may not receive the treatment applied by the end effector. In cases where the tissue includes a blood vessel, and the treatment involves sealing and cutting the blood vessel (BV), the unsealed overhanging portion of the blood vessel may leak leading to undesirable consequences.

Aspects of the present disclosure present a surgical instrument including a circuit configured to detect overhanging tissue in an end effector of the surgical instrument. Aspects of the present disclosure also present a surgical instrument including a circuit configured to detect tissue extending beyond a predetermined treatment region in an end effector of the surgical instrument.

In various examples, an end effector 25700 of a surgical instrument 25701 includes a first jaw 25702 and a second jaw 25704. The 25701 is similar in many respects to other surgical instruments discloses elsewhere herein such as, for example, the surgical instrument 150010. At least one of the first jaw 25702 and the second jaw 25704 is movable to transition the end effector 25700 between an open configuration (FIGS. 151, 152, 155) to a closed configuration (FIGS. 153, 154, 156, 157). In the example of FIGS. 151-157, the end effector 25700 includes a staple cartridge 25708 including staples deployable into tissue grasped between the jaws 25702 and 25704, and deformable by an anvil 25710. In other examples, an end effector in accordance with the present disclosure, may treat tissue by application of ultrasonic and/or radiofrequency energy.

The end effector 25700 further includes a flex circuit 25706 comprising a continuity sensor for detecting overhanging tissue. The overhanging tissue, when in contact with the continuity sensor, as illustrated in FIGS. 154, 157, establishes an electrical path that causes a flow of current through the flex circuit 25706. The current flow indicates the presence of overhanging tissue.

The jaws 25702, 25704 define a treatment region 25714 therebetween where tissue treatment is applied in the closed configuration, as illustrated in FIGS. 154, 157.

Bent tips or noses 25716, 25718 are defined in the jaws 25702, 25704 distal to the treatment region 25714. A stepped feature 25720 maintains a minimum distance or gap between the jaws 25702 and 25704 at the bent noses 25716, 25718 in the closed configuration.

The flex circuit 25706 is nestled in the nose 25716 of the first jaw 25702 such that, in the absence of tissue, a gap 25724 is maintained above the flex circuit 25706 by the stepped feature 25720.

In the example of FIG. 151-157, the end effector 25700 includes a treatment region 25714 residing between the anvil 25710 and the staple cartridge 25708. To staple tissue grasped by the end effector 25700 in the treatment region 25714, staples are deployed from the staple cartridge 25708 into the tissue, and are deformed by the anvil 25710. In other example, a treatment region of an end effector 25700 may seal tissue by application of radiofrequency and/or ultrasonic energy to tissue at a treatment region.

In the example of FIGS. 151-157, a continuity sensor is disposed onto a distal portion of the staple cartridge 25708, and is defined by an insulated flex circuit 25706 wired through contacts coupled to corresponding contacts in a channel 25726 of the first jaw 25702 that is configured to receive the staple cartridge. A sensor signal indicative of the presence of overhanding tissue passes through the contacts to a control system such as, for example, the control system 470 (FIG. 12).

The flex circuit 25706 extends distally from a flat, or substantially flat, portion 25728 of the staple cartridge 25708 between the stepped feature 25720 and the bent nose 25716. The flex circuit 25706 further extends down a ramp 25730 defined by the bent nose 25716, and extending from a distal edge of the flat portion 25728. Tissue extending beyond the stepped feature 25720 onto the flat portion 25728 and/or the ramp 25730, triggers the continuity sensor causing a sensor signal to be transmitted to the control system 470 (FIG. 12).

Distal ends of the bent noses include corresponding alignment features 25722, 25732 positioned distal to the continuity sensor. In the example of FIGS. 151-157, the alignment feature 25722 comprises a raised surface and the alignment feature 25732 comprises a corresponding recessed surface configured to receive the raised surface of the alignment feature 25722.

Although the continuity sensor is disposed onto the staple cartridge 25708, this should not be construed as limiting. For example, in certain instances, the continuity sensor can be disposed onto the distal nose 25718 of the anvil 25710.

In various aspects, a surgical instrument including an end effector 25700, as shown in FIGS. 128-157 can be a handheld surgical instrument. Alternatively, end effector 25700 can be incorporated into a robotic system as a component of a robotic arm. Additional details on robotic systems are disclosed in U.S. Provisional Patent Application No. 62/611,339, filed Dec. 28, 2017, which is incorporated herein by reference in its entirety.

In certain instances, a surgical instrument 25701 including an end effector 25700, as shown in FIGS. 151-134, can be communicatively coupled to a surgical hub (e.g. surgical hubs 106 (FIG. 3, FIG. 4), 206 (FIG. 9)) through a wired and/or wireless communication channel, as described in greater detail in connection with FIGS. 1-11.

In various aspects, when tissue overhanging is detected, a display 473 may show at least a partial view of the end effector 25700 such as, for example, a cartridge deck of the staple cartridge 25708 with tissue overhanging therefrom. Furthermore, impedance or another tissue compression estimation sensing means or 3D stacking or another visualization means can be employed to further indicate the amount of overhanging tissue sensed between the bent noses 25716, 25718.

Cancerous Tissue Proximity Detection

Cancer is a disease at the cellular level involving disorders in cellular control mechanisms. Tumor cells alter their metabolism to maintain unregulated cellular proliferation and survival, but this transformation leaves them reliant on constant supply of nutrients and energy. Cancer cells are shown to experience characteristic changes in their metabolic programs, including increased uptake of glucose. Many cancer cells have shown an increase in glycolysis (anaerobic metabolism) leading to decreased glucose and increased lactic acid in the interstitial fluid environment. Accordingly, glucose levels in normal tissue are higher than cancerous tissue. Also, due to the increase in lactic acid levels in cancerous tissue, cancerous tissue pH (potential of hydrogen) is lower than normal tissue pH.

One of the popular treatments of cancer is to excise the cancerous tissue. As illustrated in FIG. 158, a surgical instrument can be employed to seal and cut tissue along a perimeter defined in healthy tissue around the cancerous tissue. The sealing of the tissue can be achieved by application of energy (e.g., RF or ultrasonic) or by deployment of staples into the tissue. In a successful procedure, no cancer cells are detected at the outer edge of the tissue that was removed, which is referred to as a clear surgical margin.

Using various existing techniques, a surgeon may attempt to visually determine where tissue grasped by a surgical end effector is located relative to a desired clear surgical margin. Needless to say, such visual determination may be inefficient. Furthermore, unintentionally disturbing the cancerous tissue by cutting through the cancerous tissue may have undesirable consequences. For example, cancerous cells dislodged by this process may migrate into other healthy tissue through the blood stream, for example, causing the cancer to spread to other healthy tissue.

Aspects of the present disclosure present various surgical instruments utilized in cancer treatment, which employ various sensors and algorithms for assessing proximity to cancerous tissue and/or assisting a user in navigating a safe distance away from cancerous tissue before application of a cancer treatment by the end effector.

FIG. 160 is a logic flow diagram of a process 26120 depicting a control program or a logic configuration for assessing proximity of an end effector 26000 of a surgical instrument 26010 to cancerous tissue, in accordance with at least one aspect of the present disclosure. In one aspect, as described in greater detail below, the process 26120 is executed by a control circuit 500 (FIG. 13). In another aspect, the process 26120 can be executed by a combinational logic circuit 510 (FIG. 14). In yet another aspect, the process 26120 can be executed by a sequential logic circuit 520 (FIG. 15).

The process 26120 measures 26123 a physiological parameter of tissue in contact with the end effector 26000, the measured physiological parameter being one that indicates proximity of the end effector 26000 to cancerous tissue. The process 26120 further alerts 26125 a user and/or overrides 26126 a tissue treatment, if it is determined that the physiological parameter reaches or crosses a predetermined threshold.

FIG. 161 is a logic flow diagram of a process 26020 depicting a control program or a logic configuration for assessing proximity of an end effector 26000 of a surgical instrument 26010 to cancerous tissue, in accordance with at least one aspect of the present disclosure. In one aspect, as described in greater detail below, the process 26020 is executed by a control circuit 500 (FIG. 13). In another aspect, the process 26020 can be executed by a combinational logic circuit 510 (FIG. 14). In yet another aspect, the process 26020 can be executed by a sequential logic circuit 520 (FIG. 15).

The end effector 26000, as illustrated in FIGS. 162 and 163, includes a sensor array 26471 configured to generate or provide sensor signals indicative of a physiological parameter of the tissue that represents proximity of the end effector to cancerous tissue. FIG. 163 illustrates a control system 26470 including a control circuit coupled to the sensor array 26471. The control system 26470 is configured to assess proximity of the end effector 26000 to cancerous tissue based on the sensor signals of the sensor array 26471.

In one aspect, the physiological parameter is glucose level within the tissue. A low glucose level indicates a close proximity of the end effector to cancerous tissue.

In another aspect, the physiological parameter is a pH level. A low pH level indicates a close proximity of the end effector to cancerous tissue.

FIG. 159 is a graph illustrating a physiological parameter of tissue (Y-axis) plotted against distance from a tumor (x-axis). In the example of FIG. 159, the physiological parameter decreases with an increase in proximity to the tumor. Examples of physiological parameters that exhibit such characteristic include glucose, and pH, as described below in greater detail. Other examples may involve a physiological parameter that increases with an increase in proximity to the tumor.

In the example of FIG. 159, the physiological parameter of the tissue reaches a normal level (N) at a distance (d) from the tumor, which defines a clear margin, as illustrated in FIG. 158. The normal level (N) represents a typical level of the physiological parameter in normal tissue.

The surgical instrument 26010 is similar in many respects to the surgical instrument 150010. For example, the end effector 26000 and control system 26470 are similar in many respects to the end effector 150300 and the control system 470 (FIG. 12), respectively. For conciseness, components of the surgical instrument 26010 that are similar to above-described components of the surgical instrument 150010 are not repeated herein in detail.

The end effector 26000 includes a first jaw 26001 and a second jaw 26002 extending from an interchangeable shaft assembly 150200. The end effector 26000 further includes an anvil 26009 (FIG. 32) defined in the first jaw 26001 and a staple cartridge 26005 defined in the second jaw 26002. At least one of the first jaw 26001 and the second jaw 26002 is movable relative to the other to transition the end effector 26000 between an open configuration and a closed configuration to grasp tissue between the anvil 26009 and the staple cartridge 26005. In operation, a tissue treatment by the surgical instrument 26010 involves deploying staples from the staple cartridge 26005 by a firing member 26011 into the grasped tissue. The deployed staples are deformed by the anvil 26009.

In various aspects, a surgical instrument, in accordance with the present disclosure, may include an end effector that treats tissue by application of RF or ultrasonic energy to tissue. In various aspects, the surgical instrument 26010 can be a handheld surgical instrument. Alternatively, the surgical instrument 26010 can be incorporated into a robotic system as a component of a robotic arm. Additional details on robotic systems are disclosed in U.S. Provisional Patent Application No. 62/611,339, filed Dec. 28, 2017, which is incorporated herein by reference in its entirety.

Measuring the physiological parameter and assessing proximity of the end effector 26000 to cancerous tissue may begin with activation of the surgical instrument 26010 and can be continually performed as long as the surgical instrument 26010 remains operational. Alternatively, as described in connection with the process 26020, such activities can be triggered by, for example, detecting a tissue grasped by the end effector 26000. In certain instances, such activities can be triggered reaching or approaching a closed configuration.

The process 26020 detects 26021 whether tissue is grasped by a surgical end effector 26000. FIG. 112 illustrates an example of a tissue contact circuit that includes tissue contact or pressure sensors that determine when the jaws of an end effector initially come into contact with the tissue "T." Contact of the jaws with tissue "T" closes a sensing circuit "SC" that is otherwise open, by establishing contacting with a pair of opposed plates "P1, P2" provided on the jaw members.

The contact sensors may also include sensitive force transducers that determine the amount of force being applied to the sensor, which may be assumed to be the same amount of force being applied to the tissue "T." Such force being applied to the tissue may then be translated into an amount of tissue compression. In certain instances, measuring the physiological parameter and assessing proximity of the end effector 26000 to cancerous tissue can be triggered by reaching a predetermined tissue compression threshold.

Force transducers may include, and are not limited to, piezoelectric elements, piezoresistive elements, metal film or semiconductor strain gauges, inductive pressure sensors, capacitive pressure sensors, and potentiometric pressure transducers that use bourbon tubes, capsules, or bellows to drive a wiper arm on a resistive element. FIG. 112 and additional exemplifications are further described in U.S. Pat. No. 8,181,839, filed Jun. 27, 2011, titled SURGICAL INSTRUMENT EMPLOYING SENSORS, which issued May 5, 2012, the entire disclosure of which is incorporated by reference herein.

In certain instances, transition of the end effector 26000 to a closed configuration can trigger measuring the physiological parameter and assessing proximity of the end effector 26000 to cancerous tissue. A tracking system 480 (FIGS. 12 and 163), which is configured to determine the position of a longitudinally movable displacement member that transmits closure motions to the end effector 26000, can be employed in detecting the closed configuration.

The microcontroller 461 may consult one or more readings from one or more of the sensors 472, 474, 476 in performing the detection 26021. For example, readings from the strain gauge sensor 474, which can be used to measure the force applied to tissue grasped by the end effector 26000, can reflect whether tissue is grasped by the end effector 26000.

In any event, if it is determined 26021 that tissue is grasped by the end effector 26000, or that a closed configuration is reached, proximity of the end effector 26000 from cancerous tissue can be ascertained 26023 based upon a physiological parameter of grasped tissue. A sensor array 26471 including "n" sensors, wherein "n" is an integer greater than or equal to one, can be configured to provide the microcontroller 461 sensor signals according to a physiological parameter of the tissue that indicates proximity of the end effector 26000 to cancerous tissue.

If it is determined 26024 that the proximity of the end effector to cancerous tissue reaches or crosses a predetermined threshold, steps can be taken to alert 26025 a surgical operator and/or override 26026 a tissue treatment.

The microcontroller 461 may alert the surgical operator through the display 473, for example. Other audio, haptic, and/or visual means can also be employed. The microcontroller 461 may also take steps to prevent the tissue sealing. For example, the microcontroller 461 may signal the motor driver 492 to deactivate the motor 482.

In various aspects, one or more the processes 26020 and 26120 are implemented by program instructions stored in the memory 468, which can be executed by the processor 462 to perform one or more of the steps of the processes 26020 and 26120. The microcontroller 461 may also employ neural networks, look-up tables, defined functions, and/or real-time input from a cloud-based system 104 (FIG. 1) in performing one or more of the steps of the processes 26020 and 26120.

In one example, the microcontroller 461 may employ a look-up table or a defined function, which can be stored in the memory 468, in correlating sensor signals from the sensor array 26471 with values of the physiological parameter of the grasped tissue. Look-up tables can also define a proximity index for assessing proximity of the end effector 26000 to cancerous tissue based upon the determined values of the physiological parameter or, more directly, based on the received sensor signals. FIG. 164 illustrates an example proximity index 26030, which correlates sensor signal readings ($R_{1-n}$) received by the microcontroller 461 from the sensor array 26471 with corresponding distances ($D_{1-n}$) between the end effector and cancerous tissue.

In various instances, measuring the physiological parameter of the tissue and/or assessing proximity of an end effector 26000 to cancerous tissue is triggered by a user input. A user interface such as, for example, the display 473 can be employed to receive and transmit the user input to the microcontroller 461, for example.

In addition to detecting proximity of an end effector to cancerous tissue, it is desirable to provide a direction for navigating the end effector sufficiently away from the cancerous tissue. FIG. 165 is a logic flow diagram of a process 26040 depicting a control program or a logic configuration for navigating an end effector 26050 away from cancerous tissue. The end effector 26050 is similar in many respects to the end effector 26000. For example, the surgical instrument 26010 can be equipped with an end effector 26050 in lieu of the end effector 26000.

The process 26040 can be executed alone or in combination with the process 26020, or at least a portion thereof. In various aspects, the process 26040 is executed by a control circuit of a control system 26470 in communication with sensors 26055, 26056 on opposite sides 26053, 26054 of an end effector 26050. The sensors 26055, 26056 are spaced apart and separated by a transection path defined by a longitudinal axis "L" extending along an elongated channel configured to accommodate a transection member movable there through. The sensors 26055, 26056 are configured to provide sensor signals corresponding to a physiological parameter indicative of proximity of the end effector 26050 to cancerous tissue.

The process 26040 can be executed by program instructions stored in the memory 468, which can be executed by the processor 462 to perform the process 26040. The microcontroller 461 may also employ neural networks, look-up tables, defined functions, and/or real-time input from a cloud-based system 104 (FIG. 1) in performing the process 26040.

The process 26040 includes receiving 26041 the sensor signals from sensors 26055, 26056. If it is determined 26042 that the sensor signals represent values of the physiological parameter greater than or equal to a predetermined threshold, the process 26040 allows 26043 a treatment application to the tissue by the end effector 26050. Conversely, If it is determined 26044 that the sensor signals represent values of the physiological parameter less than or equal to the predetermined threshold, the process 26040 instructs 26045 the user to move the end effector in any suitable direction.

Further to the above, if it is determined 26046 that a first sensor signal represents a value of the physiological parameter greater than or equal to the predetermined threshold, while a second sensor signal represents a value less than the predetermined threshold, the process 26040 instructs the user to move the end effector 26050 in a first direction 26061. Conversely, if it is determined 26048 that the second sensor signal represents a value of the physiological parameter greater than or equal to the predetermined threshold, while the first sensor signal represents a value less than the predetermined threshold, the process 26040 instructs the user to move the end effector 26050 in a second direction 26062, opposite the first direction 26061.

As illustrated in FIG. 166, the longitudinal axis "L" defines a first side 26053 and a second side 26054. The first direction 26061 extends away from the longitudinal axis "L" on the first side 26053, while the second direction 26062 extends away from the longitudinal axis "L" on the second side 26054.

FIG. 167 is a graph illustrating sensor signals from sensors 26055, 26056 representing values of a physiological parameter of tissue (Y-axis) plotted against time (x-axis) for three different positions (Position A, Position B, Position C) of the end effector 26050 relative to cancerous tissue. The physiological parameter is glucose level within the tissue. As described above, a low glucose level indicates a close proximity to cancerous tissue. Alternatively, the physiological parameter can be pH level. A low pH level indicates a close proximity to cancerous tissue.

In various examples, an end effector, in accordance with at least one aspect of the present disclosure, may include sensors that measure two or more physiological parameters indicative of proximity to cancerous tissue. For example, an end effector may include one or more glucose sensors and one or more pH sensors. Sensor signals from sensor of different types can be received analyzed by the microcontroller 461 to assess proximity to cancerous tissue.

In Position A, sensor signals 26057, 26058 of the sensors 26055, 26056 are greater than or equal to the predetermined threshold "N." Accordingly, it can be concluded that the cancerous tissue is sufficiently far away from the end effector 26050. Accordingly, the microcontroller 461 may inform the surgical operator that is safe to treat tissue grasped by the end effector 26050.

In position C, the signals 26057, 26058 of the sensors 26055, 26056 are less than the predetermined threshold "N." Accordingly, it can be concluded that the tumor is on, or at least near, the transection path 26052 between the sensors 26055, 26056. Accordingly, the microcontroller 461 may instruct the surgical operator to release the grasped tissue, and reposition the end effector 26050 by moving it to the side in either direction, before application of a treatment to the tissue.

In position B, the sensor signal 26057 of the sensor 26055 is below the predetermined threshold "N," while the sensor signal 26058 of the sensor 26056 is greater than the predetermined threshold "N." Accordingly, it can be concluded that the tumor extends on the first side 56053 of the end effector 26050. Accordingly, the microcontroller 461 may instruct the surgical operator to release the grasped tissue, and reposition the end effector 26050 by moving it in the second direction 26062 away from the cancerous tissue, before treating the tissue.

In various examples, the sensor signals are directly proportional to the physiological parameter detected by the sensors. In other equivalent examples, however, the sensor signals can be inversely proportional to the physiological parameter detected by the sensors. In such other examples, the sensor signals decrease as the proximity to cancerous tissue increases. Nonetheless, an inverter can be utilized to invert the received sensor signals.

In various aspects, referring to FIGS. 163, 166, and 167, the microcontroller 461 further processes the sensor signals of the sensors 26055, 26056 by subtracting one sensor signal from the other sensor signal. The resulting delta can be further analyzed to determine the direction in which the end effector 26050 is to be moved. As illustrated in FIG. 167, in position A and position C, the sensor signals mostly cancel each other out. However, in position B of FIG. 167, a positive in the delta 26059 is detected. The delta positive transition indicates that the cancerous tissue extends on the first side 26053 of the end effector 26050 but not the second side 26054. In addition, whether the delta 26059 is above or below zero can give an indication as to the desired direction of motion for the end effector 26050.

With sensors 26055, 26056, as illustrated in the example of FIG. 166, the microcontroller 461 is able to assess relevant proximity to cancerous and determine how to navigate away from the cancerous tissue direction. In other example, a sensor array may include more than two sensors. In one example, a sensor array may include, in addition to the sensors 26055, 26056, a third sensor at a distal portion of the end effector.

In various aspects, as illustrated in FIG. 168, an end effector 26070 may be equipped with a sensor array 26080 that includes six sensors ($Sen_1$-$Sen_6$): two proximal sensors ($Sen_1$ and $Sen_6$), two medial sensors ($Sen_2$ and $Sen_5$), and two distal sensors ($Sen_3$ and $Sen_4$). The added sensors allow the microcontroller 461, among other things, to more accurately predict the position of the end effector 26070 with respect to cancerous tissue.

The end effector 26070 is similar in many respects to the end effectors 26000, 26050. For example, the end effector 26070 includes a first jaw 26071 and a second jaw 26072. At least one of the first jaw 26071 and the second jaw 26072 is movable relative to the other to grasp tissue therebetween.

Further to the above, the end effector 26070 includes an anvil defined in the second jaw 26072 and a staple cartridge 26075 defined in the first jaw 26071. To treat tissue grasped by the end effector 26070, staples are deployed from the staple cartridge 26075 into the grasped tissue, and are deformed by the anvil. To cut the tissue, a transection member is moved relative to an elongated slot that defines a transection path 26073 for the transection member. The transection path 26073 defines two opposite sides 26076, 26077 of the end effector 26070.

Further to the above, the sensor array 26080 is similar in many respects to the sensor array 26471. For example, the sensor array 26080 can also be coupled to the microcontroller 461. The sensor array 26080 includes six sensors ($Sen_1$-$Sen_6$) configured to provide the microcontroller 461 with sensor signals according to a physiological parameter of the tissue that indicates proximity of the end effector 26070 to cancerous tissue. In other examples, the sensor array 26080, like the sensor array 26471, may include more or less than six sensors.

The sensors of the sensor array 26080 are spaced apart and arranged on outer edges 26078, 26079 of the staple cartridge 26075. In the example of FIG. 168, $Sen_1$, $Sen_2$, and $Sen_3$ are arranged on the side 26076 while $Sen_4$, $Sen_5$, and $Sen_6$ are arranged on the side 26077. In other words, the transection path 26052 extends between the sensors of the sensor array 26080.

In various examples, the differential between the sensor signals and the mean of the signals can give insight into tumor proximity. If a signal indicates a sensor is on a tumor, the differential between that sensor and the other sensors will give insight if the tumor is along one side (not transected) or across the transection path (transected). If the differential between the signals and mean is small but the mean is high, the entire end effector is on the tumor.

FIGS. 169 and 172 are graphs illustrating sensor signals of sensors $Sen_1$-$Sen_6$ plotted on the Y-axis against time on the x-axis. The sensor signals of sensors $Sen_1$-$Sen_6$ measure a physiological parameter that changes with a change in distance from cancerous tissue. Accordingly, the sensor signals of $Sen_1$-$Sen_6$ represent a physiological parameter of tissue indicative of the position of the end effector 26070 with respect to cancerous tissue. The physiological parameter of FIGS. 169 and 172 is one that decreases with an increase in proximity to cancerous tissue, but the sensor signals of sensors $Sen_1$-$Sen_6$ were passed through an inverter. Each of the positions A-C of FIG. 169 and the positions A-E of FIG. 171 represents a distinct position of the end effector 26070 with respect to the cancerous tissue.

In the examples of FIGS. 169 and 172, an average (AVG) of the sensor signals may calculate microcontroller 461 from the formula:

$$AVG = \frac{Sen_1 + Sen_2 + Sen_3 \ \ldots + Sen_n}{n},$$

wherein $Sen_{1-n}$ represent sensor signal values at time (t), and wherein (n) represent the number of sensors. Then, the microcontroller 461 may employ a formula:

$$\Sigma|Sen_n - \text{AVG}| < X,$$

wherein (n) is an integer greater than zero, wherein (AVG) is the average of the sensor signals, and wherein (x) is a predetermined threshold, to determine proximity of the end effector 26070 to cancerous tissue. If the formula yields an outcome below the predetermined threshold (x), as illustrated in Positions A of FIGS. 169 and 172, the microcontroller 461 authorizes a tissue treatment by the end effector 26070. In positions B-D of FIG. 169 and positions B-E of FIG. 172, the formula yields an outcome that is greater than the predetermined threshold (x) indicating that one or more of the sensors are within a close proximity to the cancerous tissue.

The microcontroller 461 may compare the sensor signal of each of the sensors $Sen_1$-$Sen_6$ to the average of the sensor signals (AVG) to assess proximity of the sensors $Sen_1$-$Sen_6$ to cancerous tissue. The proximity of the end effector 26070 to tissue can be inferred from the assessed proximity of the sensors $Sen_1$-$Sen_6$ to cancerous tissue. The sensors providing sensor signals greater than (AVG) can be identified as sensors positioned within close proximity to the cancerous tissue. Other mathematical formulas can be applied to the sensor signals of the sensors $Sen_1$-$Sen_6$ to ascertain proximity of the sensors $Sen_1$-$Sen_6$ to cancerous tissue.

Further to the above, additional information can also be inferred from the spatial relation of the sensors $Sen_1$-$Sen_6$ on the end effector 26070. FIG. 170 is a logic flow diagram of a process 26090 depicting a control program or a logic configuration that provides instructions for navigating an end effector with respect to cancerous tissue, wherein the instructions are based on the spatial relation of sensors on the end effector that report readings indicative of close proximity of the sensors to cancerous tissue. The process 26090 can be executed by the microcontroller 461 based on sensor readings from the sensors $Sen_1$-$Sen_6$. The process 26090 includes receiving 26091 sensor signals from sensors $Sen_1$-$Sen_6$, and determining 26092, based on the above-described formulas, the sensors with close proximity to cancerous tissue. Furthermore, the process 26090 includes providing 26092 instructions for navigating an end effector 26050 away from the cancerous tissue based on the relative location of the sensors with close proximity to cancerous tissue on the end effector 26050.

Position C of FIG. 169 and Position B of FIG. 172 illustrate an example that implements the process 26090 of FIG. 170. In Position C of FIG. 169 and Position B of FIG. 172, the readings of $Sen_3$ and $Sen_4$ are greater than (AVG) while the remaining sensors report readings below (AVG). In addition, the $Sen_3$ and $Sen_4$ are located at a distal portion of the end effector 26070 on opposite sides 26076 and 26077. Accordingly, it can be concluded that the cancerous tissue extends over the transection path 26073, and is mainly located in front of the end effector 26070. In response, the microcontroller 461 may instruct the surgical operator to release the grasped tissue, and move the end effector 26070 backward to reach a clear margin before re-grasping the tissue.

Position D of FIG. 169 illustrates another example that implements the process 26090 of FIG. 170. In Position D of FIG. 38, the readings of $Sen_3$ and $Sen_2$ are greater than (AVG) while the remaining sensors report readings below (AVG). In addition, $Sen_2$ and $Sen_3$ are positioned on the same side 26076 of the end effector 26070. Accordingly, it can be concluded the cancerous tissue extends on the side 26076 of the end effector 26070. Since the readings of Sensors $Sen_4$, $Sen_5$, and $Sen_6$, which are located on the side 26077, indicate that these sensors are not in close proximity to cancerous tissue, the microcontroller 461 may instruct the surgical operator to release the grasped tissue, and move the end effector 26070 in a direction away from the transection path 26073 on the side 26077 in order to reach a clear margin on the side 26076.

FIG. 171 is a logic flow diagram of a process 26190 depicting a control program or a logic configuration that provides instructions for navigating an end effector with respect to cancerous tissue, wherein the instructions are based on the spatial relation and comparison of values of readings of sensors on the end effector that report readings indicative of close proximity of the sensors to cancerous tissue. The process 26190 can be executed by the microcontroller 461 based on sensor readings from the sensors $Sen_1$-$Sen_6$. The process 26190 includes receiving 26191 sensor signals from sensors $Sen_1$-$Sen_6$, and determining 26192, based on the above-described formulas, the sensors with close proximity to cancerous tissue. Furthermore, the process 26190 includes providing 26193 instructions for navigating an end effector 26070 away from the cancerous tissue based on the relative location and relative values of the readings of the sensors with close proximity to cancerous tissue on the end effector 26070.

Position E of FIG. 172 provides an example that implements the process 26190. In Position E of FIG. 172, the readings of $Sen_1$, $Sen_2$, and $Sen_3$ are all greater than or equal to (AVG) while the remaining sensors report readings below (AVG). In addition, $Sen_1$, $Sen_2$, and $Sen_3$ are all positioned on the side 26076 of the end effector 26070. Accordingly, it can be concluded that the cancerous tissue extends on the side 26076 of the end effector 26070. In addition, the reading of $Sen_2$ is greater than the reading of $Sen_1$. Also, the reading of $Sen_2$ is greater than the reading of $Sen_3$. Since $Sen_2$ is positioned between $Sen_1$ and $Sen_3$ on the same side 26076, I can be concluded that the cancerous tissue extends on the side 26076 of the end effector 26070 at a position closer to $Sen_2$ than $Sen_1$ and $Sen_3$.

In various examples the sensors of a sensor array such as the sensor array 26471 and/or the sensor array 26080 can be integrated into a staple cartridge and conducted through metallic portions of the staple cartridge that, when assembled with an end effector, engage contactor plates that transmit power and/or data.

In various examples, the physiological parameter of the tissue that is measured by the sensors of a sensor array, in accordance with the present disclosure, is pH. As discussed above, lactic acid is a byproduct of the glycolysis (anaerobic metabolism) process that is performed by cancerous tissue leading to decreased glucose and increased lactic acid in the interstitial fluid environment.

In various examples, the physiological parameter of the tissue that is measured by the sensors of a sensor array, in accordance with the present disclosure, is glucose. As described above, glucose levels have been measured to be very low in tumor microenvironments (0.1-0.4 mM). In normal tissue, glucose levels can be in the range of about 3.3-5.5 mM.

In various examples, the sensors of a sensor array, in accordance with the present disclosure, are Clark-type sensors, which can be used to measure glucose levels based on oxygen reaction with an enzyme. Clark-type sensors use an immobilized glucose oxidase embedded surface to catalyze the oxidation of beta-D-glucose to produce gluconic acid and hydrogen peroxide. Hydrogen peroxide is oxidized at a catalytic (usually platinum) anode which induces an electron transfer proportional to the number of glucose molecules present.

FIGS. 173 and 174 illustrate an example thick-film printed glucose sensor 26200, which can be employed with a sensor array of the present disclosure. This configuration uses iridium doped carbon ink, which has high specificity towards glucose detection that is not obscured by other common interference chemicals (e.g., ascorbic acid). The sensor 26200 comprises an electrode diameter of ~1 mm. In one example, as illustrated in FIG. 174, the sensor 26200 includes an Ir-Carbon counter electrode 26202, and Ir-Carbon working electrode 26203, an Ag/AgCl reference electrode 26204, and a silver conducting pad 26205. In addition, the sensor 26200 further includes an insulating layer 26206. Additional details of the sensor 26200 are described in a journal publication to Shen J et al., titled Sensors and Actuators B: Chemical, 2007, V125(1), pp. 16-113, which is incorporated by reference herein in its entirety. As illustrated in FIGS. 175-176, with an applied potential of 0.2-0.3V, a response current of ~15-20 uA can be observed with an increase of 5 mM of glucose.

In various aspects, the sensors of a sensor array, in accordance with the present disclosure, can be placed on a staple cartridge. An adhesive mask can be embedded with the sensors at predetermined locations. In various aspects, the sensors are attached to bumps on the staple cartridge so that the sensors are positioned higher than a cartridge deck of the staple cartridge to ensure contact with the tissue. The adhesive mask could be created in bulk using screen-printing technology on a polyester substrate, for example. Conducting pads can be printed to a common location.

In various examples, in addition to detection of proximity to cancerous tissue, an end effector of the present disclosure can also be configured to target specific cancer types in specific tissues. As indicated in the journal publication to Altenberg B and Greulich K O, Genomics 84(2004) pp. 1014-1020, which is incorporated herein by reference in its entirety, certain cancers are characterized by an overexpression of glycolysis genes while other cancers are not characterized by an overexpression of glycolysis genes. Accordingly, an end effector of the present disclosure can be equipped with a sensor array with a high specificity for cancerous tissue characterized by an overexpression of glycolysis genes such as lung cancer or liver cancer.

In various aspects, the sensor readings of a sensor array, in accordance with the present disclosure, are communicated by the surgical instrument to a surgical hub (e.g., surgical hub 106, 206) for additional analysis and/or for situational awareness.

Cartridge Sensor Assemblies

Typical sensor assemblies utilized in surgical instruments are only able to passively detect tissue and physical environmental conditions, which can limit the amount, type, and detail of the data that they are able to detect. Aspects of the present disclosure present a solution, wherein the cartridges for use with the surgical instruments include active sensors that can be utilized to dynamically evaluate the tissue by stimulating or perturbing the tissue during the course of a surgical procedure and then detecting the corresponding response in the tissue. By applying a stimulus to the tissue through an active sensor incorporated with the cartridge, the surgical instrument can sense additional or different information than could have been detected using passive sensors.

FIG. 177 illustrates a perspective view of a staple cartridge 27000 including an active sensor 27006, in accordance with at least one aspect of the present disclosure. The staple cartridge 27000 can be received within an end effector 150300 of a surgical instrument 150010, such as the surgical instrument 150010 described with respect to FIG. 25. In one aspect, the staple cartridge 27006 includes an active sensor 27006, which in turn includes an active element 27002 and a sensor 27004. The active sensor 27006 is configured to actively perturb or stimulate its environment, via the active element 27002, and then measure the corresponding environmental response, via the sensor 27004. The active sensor 27006 differs from passive sensors, which are configured to passively measure their environment.

The active element 27002 is configured to provide a stimulus to a tissue clamped by the end effector 150300 in which the staple cartridge 27000 is inserted (i.e., a tissue positioned or secured between the cartridge deck 27008 and the anvil 150306 of the end effector 150300). The sensor 27004 is configured to sense a tissue parameter associated with the perturbation or stimulus applied to the tissue and thereby determine the change in the tissue parameter resulting from the stimulus. In one aspect, the active element 27002 and the sensor 27004 are incorporated together or otherwise associated with each other to form an active sensor 27006 as single integral unit. In another aspect, the active element 27002 and the sensor 27004 are positioned separately from each other on or in the cartridge or otherwise disassociated with each other to form an active sensor 27006 as a distributed unit.

FIG. 178 illustrates a block diagram of a circuit 27010, in accordance with at least one aspect of the present disclosure. In one aspect, the cartridge 27000 includes a circuit 27010, which includes an active element 27002, a sensor 27004, a control circuit 27012 that is communicably connected to each of the active element 27002 and the sensor 27004, and a power source 27014 that is connected to the control circuit 27012 for supplying power thereto. The circuit 27010 and/or control circuit 27012 can include, for example, hardwired circuitry, programmable circuitry, state machine circuitry, firmware that stores instructions executed by programmable circuitry, and any combination thereof. In one aspect, the control circuit 27012 can be configured to activate the active element 27002, cause the active element 27002 to discharge or supply the stimulus to a tissue clamped by the end effector, or otherwise control the state of the active element 27002. The control circuit 27014 can be configured to activate the sensor 27004, receive data or an electrical signal indicative of a tissue property from the sensor 27004, or otherwise control the sensor 27004. In various aspects, either or both of the active element 27002 and the sensor 27004 can be exposed or positioned on the deck 27008 of the cartridge 27000 to contact a tissue positioned against the cartridge deck 27008, such as is illustrated in FIG. 177. In one aspect, the circuit 27010 illustrated in FIG. 178 can be embodied as a flex circuit. In one aspect, the circuit 27010 is a separate circuit from a cartridge circuit and/or a channel circuit, such as the cartridge circuit and channel circuit disclosed in U.S. patent application Ser. No. 15/636,096, filed Jun. 28, 2017, titled SURGICAL SYSTEM COUPLABLE WITH STAPLE CARTRIDGE AND RADIO FREQUENCY CARTRIDGE, AND METHOD OF USING SAME, which is hereby incorporated by reference herein in its entirety. In such aspects, the circuit 27010 may or may not be communicably coupled to the cartridge circuit and/or channel circuit. In another aspect, the circuit 27010 is integrated into the cartridge circuit and/or channel circuit.

In one aspect, the active element 27002 comprises a heating element and the sensor 27004 comprises a temperature sensor (e.g., a temperature measuring array). In this aspect, the active element 27002 is configured to provide a stimulus (perturbation) in the form of heat or thermal energy to a tissue grasped by the end effector 150300 and/or positioned against the cartridge deck 27008. Further, the sensor 27004 is configured to sense the physiologic response of the tissue to which the thermal energy from the active element 27002 is applied. The control circuit 27012 can thus be configured to evaluate the physiologic response of the tissue via data and/or signals received from the sensor 27004.

In one aspect, the active element 27002 is configured to apply thermal energy to a predetermined or localized area of a tissue grasped by the end effector 150300 and/or positioned against the cartridge deck 27008. For example, the heating element can comprise a heat sink (e.g., constructed from aluminum and/or copper) that is configured to convert electrical energy (e.g., from the power source 27014) into heat to apply thermal energy to a predetermined or localized area of a tissue adjacent or localized to the heat sink. In another aspect, the active element 27002 is configured to apply thermal energy across the entirety of or a larger portion of the surface of the cartridge deck 27008. For example, the heating element can comprise a flexible heating grid built into one or more of the layers of the cartridge circuit. In such aspects, the heating grid can be configured to enable the entirety or a large portion of the cartridge 27000 to emit thermal energy. Alternatively or additionally, the heating grid can be configured such that various regions of the heating grid can be activated to produce thermal energy. In this example, the heating grid can likewise be utilized to apply thermal energy at localized or predefined heating areas with a specified amount of thermal energy output to apply to a tissue.

Applying thermal energy to a tissue can be utilized to derive a variety of physiological information regarding the tissue. For example, the rate at which the temperature of a tissue rises is a function of its water content. Accordingly, applying thermal energy to a tissue can be utilized to determine the overall water content of the tissue by sensing the rate at which the temperature of the tissue increases in response to applied thermal energy. The water content of a tissue in turn corresponds to, for example, the tissue type. Further, applying thermal energy to different portions of a tissue can be utilized to determine the location(s) of high or low water content tissue by comparing the rates at which the temperatures of the different portions of the tissue increase in response to applied thermal energy.

In one aspect, the active element 27002 comprises a pressure-applying element and the sensor 27004 comprises a tissue compression sensor. The pressure-applying element can include, for example, a magnetic or electroactive polymer that, when energized, is configured to deform in shape and thereby apply a local pressure to a specific area of tissue situated thereagainst. The pressure-applying element can be disposed on, for example, the cartridge deck 27008 such that the pressure-applying element contacts and applies pressure to a tissue situated thereagainst. The tissue compression sensor can include, for example, an impedance sensor configured to measure an impedance of the tissue. As the impedance of the tissue can correspond to the thickness of the tissue (i.e., tissue compression), monitoring the time rate change of the tissue impedance can be utilized to monitor the change in the viscoelastic properties of the tissue over time in response to the pressure stimulus. Such viscoelastic properties of the tissue can include, for example, tissue creep and stability. The tissue compression sensor can also include, for example, a force sensor (e.g., a load cell or force-sensitive resistor) configured to sense a force or pressure exerted on the tissue or a gap sensor (e.g., a Hall effect sensor) configured to sense the gap or distance between the jaws (e.g., the anvil 150306 and/or channel 150302 of the surgical instrument 150010 depicted in FIG. 25) of the end effector 150300, which in turn corresponds to the degree to which a tissue grasped by the end effector 150300 is being compressed.

The magnetic or electroactive polymers can be configured to deform in a predetermined manner according to the manner in which they are manufactured. In one aspect, the control circuit 27012 can be configured to receive measurements from the sensor 27004 regarding the tissue compression while the added pressure is applied to determine accelerated creep aspects of the tissue. In one aspect, the control circuit 27012 can be configured to receive measurements from the sensor 27004 regarding the tissue pressure after the added pressure is relieved to evaluate the tissue recovery characteristics of the tissue.

Applying pressure to a tissue can be utilized to derive a variety of physiological information regarding the tissue. For example, the viscoelastic properties exhibited by a tissue correspond to its tissue type. In other words, different types of tissue each exhibit consistent viscoelastic properties. Accordingly, applying a pressure to a tissue can be utilized to determine the viscoelastic properties of a tissue by sensing the rate at which the tissue compresses, the rate at which the tissue returns to its prior shape when the pressure is removed, and other viscoelastic properties. Additional details regarding monitoring the viscoelastic properties of tissue can be found under the heading "Surgical Instrument Hardware" and in U.S. Patent Publication No. 2016/0256156, filed Sep. 14, 2015, titled TIME DEPENDENT EVALUATION OF SENSOR DATA TO DETERMINE STABILITY, CREEP, AND VISCOELASTIC ELEMENTS OF MEASURES, which is hereby incorporated by reference herein in its entirety.

FIG. 179 illustrates a logic flow diagram of a process 27050 for determining a tissue type. In the following description of the process 27050, reference should also be made for FIG. 178. The illustrated process can be executed by, for example, a control circuit 27012. Accordingly, the control circuit 27012 executing the process 27050 causes the active element 27002 to apply 27052 a stimulus to a tissue clamped at or by the end effector 150300. The stimulus can include, for example, heat or pressure. Accordingly, the control circuit 27012 detects 27054 a change in the tissue property sensed by the sensor 27004, wherein the tissue property sensed by the sensor 27004 corresponds to the stimulus imparted upon the tissue by the active element 27002. The tissue property sensed by the sensor 27004 can include, for example, the tissue temperature or the viscoelastic properties of the tissue. Accordingly, the control circuit 27012 determines 27056 the tissue type of the clamped tissue by characterizing the resulting change in the sensed property of the tissue in response to the application of the stimulus. The tissue type can include, for example, the physiological tissue type (e.g., lung tissue or stomach tissue) or the tissue type exhibiting particular tissue characteristics (e.g., tissue having a particular water content).

In aspects wherein the cartridge circuit is a flex circuit, the flex circuit can include reinforced sections for fixation of sensors, chips, and other electronics. In one aspect, the control circuitry can be disposed on a rigid substrate having positive attachment points within the molded cartridge. In another aspect, the control chips or circuitry could be disposed on a reinforced semi-rigid section of the flex circuit where the circuit is designed to be fixated to the cartridge (e.g., via adhesion by being sandwiched between layers of the cartridge or between the end effector channel and the cartridge). In another aspect, distal portions of the flex circuit could include the sensors 27004 or sensing arrays for use with the control circuits 27012 (which may or may not likewise be disposed on reinforced or semi-rigid sections of the circuit).

FIG. 180 illustrates a perspective view of a cartridge 27100 including hydrophobic areas 27102, in accordance with at least one aspect of the present disclosure. In one aspect, a cartridge (e.g., a stapling cartridge or an RF energy cartridge) can include hydrophobic areas 27102 disposed on the cartridge deck 27104. The hydrophobic areas 27102 can be configured to exclude liquid contact, unless a direct pressure of a tissue is forced into contact with the hydrophobic areas 27102. The hydrophobic areas 27102 can include, for example, regions constructed from one or more hydrophobic materials that are disposed along the cartridge deck 27104. Further, it should be noted that although the cartridge 27200 is depicted as a staple cartridge, the cartridge 27200 also includes RF cartridges and any other such cartridges.

In one aspect, the location of the hydrophobic area(s) 27102 can be positioned adjacent to, positioned around, or otherwise correspond to the locations of the various cartridge sensors. For example, a cartridge 27100 can include hydrophobic areas 27102 that correspond to the locations of a first electrode disposed on the end effector 150300 that is configured to receive an RF signal from a corresponding second electrode, such as in aspects discussed with respect to FIGS. 36-43. As the positions of the hydrophobic areas 27102 correspond to the positions of the electrodes illustrated in FIGS. 36-38 (i.e., RF electrodes 151038, 151048 and/or electrical contacts 151040, 151044, 151050, 151052), the hydrophobic areas 27102 thus prevent liquid contact against the electrodes unless a tissue is directly forced into contact therewith. As the electrodes utilize the liquid to transmit the RF signal, the control circuit coupled to the electrodes, such as circuit 151250 (FIG. 40), is configured to measure only the pressurized areas of the tissue.

In another aspect, the hydrophobic areas 27012 disposed on or otherwise integrated with RF or other energy cartridges that are configured to drive fluids out of a tissue in order to cut and/coagulate the tissue. In this aspect, the cartridge sensors can be positioned on, in, or adjacent to hydrophobic regions 27102. In aspects where the cartridge sensors include impedance sensors configured to sense an impedance of the tissue, the hydrophobic regions 27102 can make the impedance sensors more likely to sense resistive aspects of the tissue as it melts, as opposed to sensing the fluid being driven from the tissue.

In one aspect, the cartridge flex circuits and/or end effector flex circuits can include graphical overlays (e.g., printed pictures or icons) positioned on or at various locations of the cartridge 27100 and/or end effector 150300. The graphical overlays could be positioned to indicate, for example, where the sensing occurs on the flex circuit or where the tissue should be located with respect to the flex circuit to be sensed.

In one aspect, the cartridge flex circuits and/or end effector flex circuits can include floating flex circuit sensing arrays that are configured to allow the sensors to stay in contact with the tissue during tissue movement relative to the cartridge 27100, rather than the tissue moving relative to the sensing array. The floating flex circuit arrays can include, for example, a floating or movable layer that is configured to move relative to a fixed layer to maintain contact with the tissue. The floating layer and the fixed layer can be electrically connected such that movement of the floating layer does not break the electrical connection to the fixed layer. Additional detail regarding floating circuit sensing arrays can be found under the heading "Surgical Instrument Hardware."

In one aspect, the cartridge circuit can include an impedance circuit that is configured to apply a non-therapeutic level of electrical energy to the tissue (i.e., a degree of electrical energy that has no or minimal therapeutic effect) and then correspondingly sense the compression of the tissue, such as is discussed with respect to FIGS. 36-43. The cartridge circuit and/or a control circuit of the surgical instrument can be configured to monitor the force to close (FTC) the end effector and correlate the FTC to impedance changes in the tissue to determine the tissue configuration, tissue type, and/or tissue characteristics. The tissue configuration, tissue type, and/or tissue characteristics can then be utilized to determine the thresholds appropriate for force to fire (FTF), advancement speed, and/or creep rate to indicate stability.

The techniques described hereabove increase the amount and detail of data that is detectable by the surgical instrument's sensor assemblies and improved the surgical instrument's ability to differentiate between tissue types based on the tissues' responses to the applied stimulus.

Cartridge Identification and Status Detection

Surgical instrument cartridges may have multiple and/or duplicative means for storing or relaying data (i.e., data elements) associated with the cartridge. The data associated with the cartridge can include, for example, the cartridge type, characteristics of the cartridge, and whether the cartridge has been fired previously. Data redundancy is beneficial in avoiding total data loss if there is an error with one of the data elements or one of the data elements is destroyed. However, if one of the data elements incorrectly stores data, fails to store data, or has an error in transmitting the data, then an unresolvable conflict between the data elements may be created. When the surgical instrument or another system attempts to retrieve the data from the cartridge, the data conflict may cause errors in the surgical instrument or other system retrieving the data. Aspects of the present disclosure present a solution, wherein the surgical instruments are configured to resolve conflicts between data storage elements by prioritizing one of the data elements over the other data elements. In that way, the prioritized data element will supersede the other data elements, avoiding conflicts in attempting to select the proper cartridge data for use by the control circuit of the surgical instrument or another system.

FIG. 181 illustrates a perspective view of a cartridge 27200 including a pair of data elements, in accordance with at least one aspect of the present disclosure. In one aspect, the data elements include features, characteristics, and/or devices that are associated with the cartridge 27200 and are capable of storing, representing, and/or relaying data associated with the cartridge. The data elements can include, for example, a data storage element 27202 that is configured to store data related to the cartridge and a data-representative feature 27204 that is configured to represent data related to the cartridge. In some aspects, the data elements can be broadly characterized as automatic identification and data capture (AIDC) technologies. Although the cartridge depicted in FIG. 181 includes two data elements, in alternative aspects the cartridge can include one or more than two data elements in various combinations of data storage elements and data-representative features of the cartridge. Further, it should be noted that although the cartridge 27200 is depicted as a staple cartridge, the cartridge 27200 also includes RF cartridges and any other such cartridges.

In various aspects, the data-representative feature 27204 can include, for example, a physically or visually identifiable feature or structure that is associated with or disposed on the cartridge 27200. In one such aspect, the data-representative feature 27204 can include the material that the cartridge body 27205 is constructed from and/or the thickness of the cartridge body 27205. The cartridge body 27205 material and/or thickness can be different for the various cartridge types in order to create keyed resistance ranges for each cartridge type, which can then be detected by a sensor 27224 (FIG. 182) associated with the end effector 150300 of the surgical instrument 150302. The sensor 27224 for detecting the cartridge body 27205 material and/or thickness can be disposed in the channel 150302 of the end effector 150300 for example. In such aspects, the end effector 150300 could be electrically insulated.

In another such aspect, the data-representative feature 27204 can include a layer of material or a structure disposed on the cartridge deck 27206 (e.g., at the proximal end of cartridge deck 27206) that is configured to influence the initial phase of clamping force. For example, in FIG. 181 the data-representative feature 27204 includes a structure that extends generally orthogonally from the proximal end of the cartridge deck 27206 such that the anvil 150306 of the end effector 150300 would contact the structure as the anvil 150306 is clamped shut. The force as the anvil 150306 contacts the data-representative feature 27204 can then be detected by a control circuit 27222 (FIG. 182) via, e.g., a current sensor 786 (FIG. 18) detecting the motor current (which corresponds to the force exerted by the anvil 150306 as the anvil 150306 is driven closed by the motor 754). The material and/or geometry of the data-representative feature(s) 27204 disposed on the cartridge deck 27206 can be customized for each of the various cartridge types to yield different detectable responses in the force to close (FTC) the anvil 150306. A control circuit 27222 coupled to a sensor capable of detecting the data-representative feature 27204 can thus determine the cartridge type according to the degree or level of the maximum FTC, the characteristics of the FTC response (e.g., the shape of the FTC curve plotted verse time, as depicted in various graphs described under the heading "Surgical Instrument Hardware," such as FIG. 83), and other such characteristics of the FTC detected over time. For example, a first cartridge type can include a data-representative feature 27204 that is constructed from a stiff material and a second cartridge type can include a data-representative feature 27204 that is constructed from a flexible material. According to the type of FTC response detected by the control circuit 27222, the control circuit 27222 can thus determine whether the anvil 150306 is making contact with a stiff or flexible structure as the anvil 150306 is closed and thereby determine whether the cartridge 27200 is the first cartridge type or the second cartridge type, respectively.

In various aspects, the data storage element 27202 can, for example, be associated with or disposed on the cartridge 27200 and be configured to transmit data stored by the data storage element 27202 via a wired or wireless connection. In one aspect, the data storage element 27202 comprises a RFID micro-transponder or RFID chip including a digital signature. In another such aspect, the data storage elements comprise a battery-assisted passive RFID tag. A battery-assisted passive RFD tag can exhibit improved range and signal length as compared to RFID micro-transponders and/or RFID chips. In this aspect, the RFID tag can include a writable section that could be used to store data associated with the cartridge 27200, such as whether the cartridge 27200 has been fired. Data can be written to the writable section of the cartridge 27200 via a circuit, such as a control circuit of the cartridge 27200 or the surgical instrument. The writable section could then be read subsequently by a sensor of the surgical instrument so that the surgical instrument can determine, for example, that the cartridge 27200 should not be re-fired.

In aspects wherein the data storage element 27202 includes an RFID tag utilizing ultra high-frequencies and higher frequencies, the RFID tag may be more than one radio wavelength away from the reader (sensor) of the surgical instrument. Therefore, simply transmitting the RF signal may not be sufficient to communicate the data from the RFID tag. In these aspects, the RFID tag can be configured to backscatter a signal. The active RFID tags may contain transmitters and receivers that are functionally separated and the RFID tags need not respond on a frequency related to the reader's interrogation signal.

In another aspect, the data storage element 27202 can include a one-wire chip configured to store identification data. The data storage element 27202 can be configured to transmit or provide the stored identification data to the surgical instrument, either upon the cartridge 27200 being inserted in the end effector or in response to receiving a query from the surgical instrument. In such aspects, the one-wire chip can include a writable section that could be used to store data associated with the cartridge 27200, such as whether the cartridge 27200 has been fired. In another such aspect, the data storage elements comprise an integrated circuit (IC) executing a particular communication protocol, such as an I-squared-C (i.e., I-two-C), SPI, or other multi-master, multi-slave, packet-switched, single-ended, serial computer bus. Various additional details regarding wired electrical connections between the cartridge 27200 and the surgical instrument can be found in U.S. patent application Ser. No. 15/636,096, filed Jun. 28, 2017, titled SURGICAL SYSTEM COUPLABLE WITH STAPLE CARTRIDGE AND RADIO FREQUENCY CARTRIDGE, AND METHOD OF USING SAME, which is hereby incorporated by reference herein in its entirety.

Although FIG. 181 depicts a cartridge 27200 including a single data-representative feature 27204 and a single data storage element 27202, it should be noted that different aspects of the cartridge 27200 can include various combinations of the aforementioned data elements. In other words, various aspects of the cartridge 27200 can include combinations of multiple data-representative features 27204, multiple data storage elements 27202, different types of data storage elements 27202 and/or data-representative features 27204, and so on.

The data storage element 27202 can store or represent a variety of data pertaining to the cartridge 27200, including, for example, data identifying the cartridge type and data identifying characteristics of the cartridge (e.g., the cartridge size). In one aspect, the data storage element 27202 can be configured to store an Electronic Product Code (EPC). In aspects wherein the data storage element is an RFID tag, the EPC can be written into the tag by an RFID printer and can contain, for example, a 96-bit string of data. The string of data can include, for example, a header (e.g., of eight bits) identifying the version of the protocol; an organization number (e.g., of 28 bits) that identifies the organization that manages the data for this tag (which can be assigned by the EPC Global consortium); an object class (e.g., of 24 bits) identifying the kind of product; and a unique serial number (e.g., of 36 bits) for a particular tag. The object class and unique serial number fields can be set by the organization that issued the tag. Similarly to a URL, the EPC number can be used as a key into a global database to uniquely identify a particular product.

FIG. 182 illustrates a block diagram of a sensor assembly 27220 for detecting and/or receiving data from data elements associated with a cartridge 27200, in accordance with at least one aspect of the present disclosure. In the following description of the sensor assembly 27220, reference should also be made to FIG. 181. The sensor assembly 27220 can be included in or communicably coupled with a surgical instrument that is configured to receive a cartridge 27200. In one aspect, the sensor assembly 27220 includes a control circuit 27222 communicably connected to a sensor 27224 configured to detect a data-representative feature 27204 representing cartridge data and an I/O interface 27228 that is configured to receive data from a data storage element 27202 storing cartridge data. In one aspect, the sensor assembly 27220 be a component of or integrated with a circuit disposed in the channel 150302 (FIG. 25) of the end effector 150300, such as the channel circuit disclosed in U.S. patent application Ser. No. 15/636,096. In another aspect, the sensor assembly 27220 be a distinct or separate from the channel circuit, such as the channel circuit disclosed in U.S. patent application Ser. No. 15/636,096. The control circuit 27222 is further connected to a power source to draw power therefrom. The sensor 27224 can include any type of sensor that is able to identify a particular physical or visual feature identifying the cartridge 27200. In one aspect, the sensor 27224 can include a current sensor (e.g., current sensor 786 discussed in connection with FIGS. 18-19) that is configured to detect the current drawn by the motor 754 (FIG. 18) during at least the initial or clamping portion of the firing member stroke, thereby allowing the control circuit 27222 to determine the FTC and thereby determine whether the anvil 150306 of the end effector 150300 is encountering a physical feature disposed on the cartridge 27200 identifying the cartridge type, as described above. In another aspect, the sensor 27224 can include an optical sensor (e.g., sensor 152408 discussed in connection with FIGS. 73-74) configured to detect an icon, color, bar code, or other marking or series of markings disposed on the cartridge 27200 that identify the cartridge type. In one aspect, the I/O interface 27228 can include bus wires (e.g., cartridge and channel electrical contacts disclosed in U.S. patent application Ser. No. 15/636,096) configured to electrically connect to a data storage element 27202 storing data to receive the data stored thereon utilizing a wired communication protocol (e.g., I-squared-C). In another aspect, the I/O interface 27228 can include a wireless transmitter configured to wirelessly connect to a data storage element 27202 storing data to receive the data stored thereon utilizing a wireless communication protocol (e.g., Bluetooth).

Other aspects of the sensor assembly 27220 can include various combinations of sensors 27224 configured to detect data-representative features 27204 and I/O interfaces 27228 configured to receive data from data storage elements 27202 associated with a cartridge 2700, including multiple sensors 27224 (of the same or different types), multiple I/O interfaces 27228 (of the same or different types), no I/O interfaces 27228, no sensors 27224, and all combinations thereof. The particular combination of sensors 27224 and/or I/O interfaces 27228 included in the sensor assembly 27220 to detect data associated with the cartridge 27200 corresponds to the combination of data elements utilized by the cartridge 27200 to store cartridge data.

FIG. 183 illustrates a logic flow diagram of a process 27300 for resolving data identification conflicts, in accordance with at least one aspect of the present disclosure. In the following description of the process 27300, reference should also be made to FIGS. 181-182. The illustrated process 27300 can be executed by, for example, the control circuit 27222 of the sensor assembly 27220 depicted in FIG. 182.

Accordingly, the control circuit 27222 executing the illustrated process 27300 determines 27302, 27304 the cartridge data (i.e., data identifying the cartridge 27200 and/or data regarding characteristics of the cartridge 27200) associated with a first data element and a second data element. In aspects where the first data element is a data-representative feature, such as in FIG. 181, the control circuit 27222 determines 27302 the cartridge data by sensing the presence and identity of the data-representative feature 27204 via a sensor 27224, as described above, and then retrieving the appropriate cartridge data corresponding to the identified data-representative feature 27204. The cartridge data can be retrieved from, for example, a look-up table. In aspects where the second data element is a data storage element 27202, such as in FIG. 181, the control circuit 27222 determines the cartridge data by receiving the stored cartridge data from the data storage element 27202.

Accordingly, the control circuit 27222 determines 27306 whether the cartridge data from the two sources (i.e., the first data element and the second data element) correspond to each other. If the data from the two sources do correspond to each other, then the process 27300 continues along the YES branch and the control circuit 27222 selects one of the two matching data and proceeds accordingly. If the data from the two sources do not correspond to each other, then the process 27300 continues along the NO branch and the control circuit 27222 determines which of the two data elements has a higher priority and accordingly selects 27310 the cartridge data from the higher priority data storage element. The prioritization between different types of data elements can be preprogrammed by the manufacturer or set by a user, for example. The selected data can be, for example, stored in a memory 264 (FIG. 16) of the surgical instrument for subsequent use, utilized in a control algorithm for controlling one or more operations of the surgical instrument, or otherwise utilized by a control circuit of the surgical instrument.

The techniques described hereabove permit data redundancy in the cartridges without creating unresolvable processing conflicts.

Variable Output Cartridge Sensor Assembly

Backward Compatible Sensor Assembly

As new versions of surgical instruments and their associated modular components (e.g., stapler cartridges) are developed, older versions of the surgical instruments may become incompatible with newer versions of the modular components due to additional or alternative features being incorporated into the modular components, the sensor architecture of the modular components being changed, and other such updates being developed for the modular components. Therefore, the release of an updated modular component that is no longer compatible with the prior version(s) of the associated surgical instrument can cut short the effective lifespan of the surgical instrument, even if the surgical instrument is otherwise fully functioning. Aspects of the present disclosure provide a solution, wherein modular components can include sensors configured to output data in two or more different modes or formats. A first data output format from the sensors can be compatible with current versions of the surgical instrument, whereas a second data output format from the sensors can be compatible with prior versions of the surgical instrument (i.e., the second data output format can mimic the data output format of a prior version of the modular device). The modular components can further be configured to determine whether they are connected to an out-of-date or an up-to-date version of the surgical instrument and then cause their sensors to output data in a format that is compatible with the version of the surgical instrument.

FIG. 184 illustrates a block diagram of a circuit 28000 including a variable output sensor 28004, in accordance with at least one aspect of the present disclosure. In one aspect, the circuit 28000 includes a control circuit 28002 that is communicably coupled to a sensor 28004. In one aspect, the sensor 28004 can be configured to output data in a first mode **28006*a* or a second mode 28006*b*. The circuit 28000 further includes a power source 28008 connected to the control circuit 28002 for supplying power thereto. In one aspect, when the sensor 28004 is in the first output mode 28006*a*, the sensor data feed output by the sensor 28004 is configured for use by the current version of a surgical instrument, such as a surgical instrument 150010 described in connection with FIG. 25. In one aspect, when the sensor 28004 is in the second output mode 28006*b*, the sensor data feed output by the sensor 28004 is configured for use by a prior or older version of a surgical instrument. In various aspects, the sensor data feed of the first output mode 28006*a* can, for example, provide more complex data, more voluminous data, or data that is in an updated or alternate format suitable for use with the current version of the surgical instrument as compared to the second output mode's 28006*b* sensor data feed. In various aspects, the sensor data feed of the second output mode 28006*b* can, for example, provide data that is in a simpler or different format than the sensor data feed of the first output mode 28006*a*. In various aspects, the sensor data feed of the first output mode 28006*a* can be incompatible with an older version of the surgical instrument and/or the sensor data feed of the second output mode 28006*b*** can be incompatible with a current or more recent version of the surgical instrument.

In one aspect, the circuit 28000 can be included with a cartridge 150304 (FIG. 25), such as a stapler cartridge or an RF cartridge, that is configured to be received by an end effector 150300 (FIG. 25) of a surgical instrument 150010 (FIG. 25). The circuit 28000 and/or control circuit 28002 can be communicably coupled to a control circuit 760 (FIGS. 18-19) of the surgical instrument 150010 upon the cartridge 150304 being inserted into the end effector 15300 or otherwise connected to the surgical instrument 150010. In one aspect, the circuit 28000 and/or control circuit 28002 of the cartridge 150304 can be communicably connected to the control circuit 760 of the surgical instrument 150010 via corresponding electrical contacts that communicably couple the cartridge 150304 and the surgical instrument 150010 upon the cartridge 150304 being received within the end effector 150300, such as is disclosed in U.S. patent application Ser. No. 15/636,096, filed Jun. 28, 2017, titled SURGICAL SYSTEM COUPLABLE WITH STAPLE CARTRIDGE AND RADIO FREQUENCY CARTRIDGE, AND METHOD OF USING SAME, which is hereby incorporated by reference herein in its entirety.

In one aspect, the sensor 28004 can comprise a magnetoresistance and impedance combo array that is configured to provide better accuracy in measuring the magnetic field being sensed, as well as some tissue contact related data, as compared to a Hall effect sensor. In this example, the sensor 28004 comprises a first output mode **28006*a* that can output the magnetoresistance and impedance data feeds to provide a smart gap sensing metric. The magnetoresistance and impedance data feeds of the first output mode 28006*a* of the sensor 28004 could, for example, be combined using an algorithm (e.g., executed by the control circuit 28002 of the cartridge 150304) as an output signal. The sensor 28004 can further comprise a second output mode 28006*b* that can output a signal equivalent to a Hall effect sensor output. However, when the circuit 28000 of the modular component (e.g., a cartridge 150304) comprising the sensor 28004 detects that it is being utilized with an older generation surgical instrument, the circuit 28000 can be configured to cause the sensor 28004 to calculate and output the sensor data feed of the second output mode 28006*b*, which mimics the output of a Hall effect sensor for the gap measurement being sensed. Thus, the circuit 28000 can allow the sensor 28004** to also be compatible with older generation surgical instruments that are programmed to receive a data feed and/or signal from a Hall effect sensor.

In another aspect, the sensor 28004 can comprise a smaller Hall effect or other type of proximity sensor that is configured to replace a position or limit switch. Similarly as described above, when the circuit 28000 of the modular component (e.g., a cartridge 150304) detects that it is being utilized with an older generation surgical instrument, the circuit 28000 can be configured to cause the sensor 28004 to calculate and output a sensor data feed mimicking the output of a simulated switch closure, thereby allowing the sensor 28004 to also be compatible with older generation surgical instruments that are programmed to receive a data feed and/or signal from a position or limit switch.

FIG. 185 illustrates a logic flow diagram of a process 28050 for controlling an output mode of a sensor 28004, in accordance with at least one aspect of the present disclosure. In the following description of the process 28050, reference should also be made to FIG. 95. The illustrated process 28050 can be executed by, for example, the control circuit 28002. The sensor 28004 controlled by the process 28050 can be included with a modular component intended to be connected or otherwise associated with a surgical instrument 150010, such as a stapler cartridge.

Accordingly, the control circuit 28002 executing the illustrated process 28050 determines 28052 whether the version of the modular component corresponds to or is otherwise compatible with the version of the surgical instrument 150010. The control circuit 28002 can determine whether the modular device and the surgical instrument 150010 are compatible by, for example, retrieving a version number, EPC, or other identifier from the surgical instrument 150010 (e.g., when the modular device is connected to the surgical instrument) and then retrieving a look-up table (e.g., stored in a memory of the modular component) listing versions of the surgical instrument 150010 that are compatible with the modular component. If the modular component and the surgical instrument 150010 are compatible, then the process 28050 continues along the YES branch and the control circuit 280002 causes the sensor 28004 to output data in a first data mode 28006*a*. If the modular component and the surgical instrument 150010 are not compatible, then the process 28050 continues along the NO branch and the control circuit 28002 causes the sensor 28004 to output data in a second data mode 28006*b*.

In one aspect, sensor data stream output by the sensor 28004 when the sensor 28004 is in the first output mode 28006*a* may only be incompatible with the older versions of the surgical instruments when the data moves outside of certain tolerances or thresholds. In this aspect, the control circuit 28002 can be configured to cause the sensor 28004 to output data in the second output mode 28006*b* only when the sensor data stream moves outside of the acceptable thresholds for the older version of the surgical instrument.

The techniques described hereabove permit out-of-date versions of surgical instruments to utilize newer or current versions of modular components without losing any functionality and provide surgical instruments with a longer effective lifespan by not forcing users to upgrade to newer versions of the surgical instruments when new versions of the corresponding modular components are released.

Circuit Fabrication

In one aspect, all of the circuits (e.g., flex circuits) for the modular components (e.g., cartridges) are fabricated with all the sensor technology utilized by the various types and versions of the modular components. Once fabricated, laser trimming techniques can then be utilized to enable/disable sensors and features, as well as calibrate the sensors.

In one aspect, the circuits are fabricated utilizing selective etching and deposition of nonconductive coating techniques, including, for example, metal oxide nonconductive coatings as described in U.S. Pat. No. 5,942,333, filed Mar. 27, 1995, titled NON-CONDUCTIVE COATINGS FOR UNDERWATER CONNECTOR BACKSHELLS, which is hereby incorporated by reference herein; polyurethane and other polymer coatings; and plasma sprayed ceramic coatings.

In one aspect, the circuits are fabricated utilizing techniques of 3D printing conductive pathways into the cartridges and other modular components. Such techniques can include, for example, 3D printing dissolvable channels that can be impregnated with conductive epoxy or vapor deposition or utilizing graphene.

In one aspect, the circuits are fabricated by laser skiving openings within the circuit that have a known or predetermined dimension. For example, the laser skiving could create through holes or partial deep holes that only penetrate one of more layers of the circuit. As another example, the laser skiving could create a number of small openings in surface of the circuit to allow only certain amounts of fluid or certain size particles to permeate the surface. Circuits fabricated in such a manner can be useful for various sensor or detection arrangements described herein.

Sensing Internal Instrument Parameters

In one aspect, the surgical instrument 150010 and/or a system communicably coupled to the surgical instrument 150010 (e.g., a surgical hub 106 with which the surgical instrument 150010 is paired, as described above with respect to FIGS. 1-11) can be configured to sense internal parameters of the surgical instrument 150010. The sensed internal parameters of the surgical instrument 150010 can be utilized to better understand how the instrument is operating to adjust parameters during operation. For example, the surgical instrument 150010 can be configured to sense closure actuation (e.g., motor current and FTC), firing actuation (e.g., motor current and FTF), articulation (e.g., the angular position of the end effector), rotation of the shaft or the end effector, closed loop actuation strokes of the drive components, and local loading of drive components (resulting in the ability to run the drive system in load control without accounting for backlash and tolerances).

Device Feedback Display Capabilities

Surgical instruments described herein, such as the surgical instruments described under the heading "Surgical Instrument Hardware," can further be configured to detect and display tissue-specific data, such as margin perimeter, adhesions, tissue fragility, perfusion level, and vascularization.

In one aspect, a surgical instrument 150010 (FIG. 25) can be configured to display collateral contact of the jaws with anatomy and tissues around the perimeter of the device. In other words, the surgical instrument can be configured to display the position of the jaws or provide feedback when the jaws have made inadvertent contact with tissue surrounding the intended operating site. Various aspects of the surgical instrument can be configured to detect collateral tissue contact, and tissue contact more generally, via piezoelectric sensors, thin conductive films, impedance sensors, and/or photoacoustic sensors, as will be discussed in more detail below.

In one aspect, a surgical instrument can be configured to assess the viability of the grasped tissue utilizing one or more sensors. FIG. 186 illustrates an end effector 28100 comprising a first sensor 28102 and a second sensor 28104, in accordance with at least one aspect of the present disclosure. The end effector 28100 can include one or more sensors 28102, 28104 configured to sense pCO2, blood flow, and/or pathology of a tissue clamped by the end effector 3000, such as optical sensors, piezoacoustic sensors, impedance sensors, and/or photoacoustic sensors. Additional detail regarding various such sensors and sensor assemblies can be found under the heading "Surgical Instrument Hardware."

In one aspect, a surgical instrument is configured to assess the ventilation or pCO2 content of the grasped tissue via, for example, capnography. In this aspect, the surgical instrument includes an infrared (IR) emitting source (e.g., an LED), such as the light sources 28106 depicted in FIG. 187, and a sensor (photodetector), such as one or more of the sensors 28102, 28104 depicted in FIG. 186, that receives the IR light transmitted through the grasped tissue to measure the absorbance of the IR light in the tissue. The degree of absorbance of the IR light indicates the proportion of CO2 that is present in the tissue (more absorbance equates to more CO2). In one aspect, the IR light source can be disposed on the anvil 28108 and the photodetector can be disposed on the cartridge 28110. In another aspect, the IR light source can be disposed on the cartridge 28110 and the photodetector can be disposed on the anvil 28108 (as depicted in FIGS. 186-187).

In one aspect, a surgical instrument is configured to assess the perfusion of or blood flow in the grasped tissue via, for example, pulse oximetry. In this aspect, the surgical instrument includes one or more light sources, for example an LED, that are configured to emit light of two different wavelengths, such as, for example, IR and red. Such light sources can be, for example, the light sources 28106 depicted in FIG. 187. In various instances, the surgical instrument further includes a sensor, for example a photosensor, such as one or more of the sensors 28102, 28104 depicted in FIG. 186, that receives the light transmitted through the grasped tissue to measure the absorbance of the light in the tissue. As the two wavelengths of light, for example red and IR, are passed through the tissue, the change in absorbance of both wavelengths correlates to the oxygen saturation in the tissue. This is due to the fact that oxygenated hemoglobin absorbs more IR light and deoxygenated hemoglobin absorbs more red light. In one aspect, the surgical instrument can utilize a reflective pulse oximetry technique for measuring oxygen saturation, wherein, for example, the light sources 28106 are disposed on the anvil 28108 and the sensors are disposed on either the anvil 28108 or the cartridge 28110. In such instances where the sensors 28102, 28104 are disposed on the anvil 28108, a reflective cartridge can be used. In various instances, the reflective cartridge comprises a cartridge 28110 having a reflective layer or material disposed on the cartridge deck 28112. In another aspect, the surgical instrument can utilize a transmission pulse oximetry technique, wherein, for example, the light sources 28106 are disposed on the anvil 28108 and the sensors 28102, 28104 are disposed on the cartridge 28110. These aspects provide the ability to detect local oxygen saturation, such as, for example, if the tissue is losing oxygen and can indicate if tissue is being overcompressed. In various instances, these aspects can be used to help identify the ideal compressive force for staple firing if staple firing is able to occur at non-fixed tissue gaps and/or or provide go/no-go data on firing.

In one aspect, a surgical instrument is configured to assess the perfusion of or blood flow in the grasped tissue via, for example, general photoplethysmography. In this aspect, the surgical instrument includes one or more light sources, such as, for example, an LED, that are configured to emit light, such as the light sources 28106 depicted in FIG. 98. In various instances, the surgical instrument further includes a sensor, such as, for example a photodetector. Such sensors can include, for example, the one or more of the sensors 28102, 28104 depicted in FIG. 186. The sensors 28102, 28104 can be configured to receive the light transmitted through the grasped tissue by the light sources 28106 to measure the absorbance of the light in the tissue. As the light is transmitted through the tissue by the light sources 28106, pulsing blood in the tissue will cause a change in the amount or degree of absorbed light, which can then be detected by the sensor(s) 28102, 28104. The waveform frequency of the received light correlates to pulse and the amplitude correlates to pulse pressure. In one aspect, the surgical instrument can utilize a reflective photoplethysmography technique for measuring blood flow, wherein, for example, the light sources 28106 are disposed on the anvil 28108 and the sensors 28102, 28104 are disposed on either the anvil 28108 or the cartridge 28110. In instances where the sensors 28102, 28104 are disposed on the anvil 28108, a reflective cartridge can be used. The reflective cartridge can comprise a cartridge 28110 having a reflective layer or material disposed on the cartridge deck 28112. In another aspect, the surgical instrument can utilize a transmission photoplethysmography technique, wherein, for example, the light sources 28106 are disposed on the anvil 28108 and the sensors 28102, 28104 are disposed on the cartridge 28110. These aspects provide a sense of local perfusion, such as if the blood is flowing across a major vessel, prior to performing a staple firing stroke, and can indicate if tissue is being undercompressed. Further, these aspects could provide go/no-go data on firing.

In one aspect, a surgical instrument is configured to assess the tissue pathology or location of the grasped tissue via, for example, piezoacoustic sensors or a thin film coating. The surgical instrument can include piezoacoustic sensors, such as the one or more of the sensors 28102, 28104 depicted in FIG. 186, or a thin film coating (e.g., of a conductive material) that is disposed on, for example, the cartridge 28110. An example of a thin film coating can include, for example, a conductive material. The piezoacoustic sensors and thin film coating are configured to measure changes in tissue properties to determine content/characteristics and/or pathology of tissue prior to a staple firing stroke. Utilizing a conductive material to assess tissue conditions is discussed in more detail under the heading "Surgical Instrument Hardware," such as in connection with FIGS. 66-67, for example. The piezoacoustic sensors and/or thin film coating can be utilized to measure and/or distinguish between calcifications and non-calcifications in the tissue, plaques and non-plaques in the tissue, and/or fibrous ad non-fibrous tissue.

In one aspect, a surgical instrument is configured to assess the tissue pathology or location of the grasped tissue via, for example, electrical impedance sensors. The surgical instrument can include impedance sensors, such as one or more of the sensors 28102, 28104 depicted in FIG. 186. In one aspect, the impedance sensors can be located at a discrete location or discrete locations along the anvil 28108 and/or cartridge 28110. In this aspect, the impedance sensors can be utilized to determine whether there is tissue positioned at or against that discrete location(s) of the anvil 28108 and/or cartridge 28110. In another aspect, the impedance sensors can be located at multiple locations along the length of the anvil 28108 and/or cartridge 28110. In this aspect, the impedance sensors can be utilized to determine the presence of tissue at any one of the points along the anvil 28108 and/or cartridge 28110. In one aspect, the multiple locations of the impedance sensors can each be comprise a region of insulation and conduction. Further detail regarding impedance sensors can be found under the heading "Surgical Instrument Hardware," such as in connection with FIGS. 36-43, for example.

In one aspect, a surgical instrument is configured to assess the tissue pathology and/or location of the grasped tissue via, for example, photoacoustic sensors and/or a thin film coating. The surgical instrument can include photoacoustic sensors, such as the one or more of the sensors 28102, 28104 depicted in FIG. 186, or a thin film coating that is disposed on, for example, the cartridge 28110. The thin film coating can include, for example, a conductive material. The surgical instrument can include a tunable optical parametric oscillator based laser system with a broadband ultrasound detector. In this aspect, the surgical instrument can include fiber optics to transmit the light. The handle unit can include a control and/or analysis unit attached thereto or integral therewith. The photoacoustic sensors and thin film coating are configured to measure changes in tissue properties resulting from the parametric oscillator to determine characteristics and/or pathology of tissue prior to a staple firing stroke. Utilizing a conductive material to assess tissue conditions is discussed in more detail under the heading "Surgical Instrument Hardware," such as in connection with FIGS. 66-67, for example. The photoacoustic sensors or thin film coating can be utilized to measure and/or distinguish between calcifications and non-calcifications in the tissue, plaques and non-plaques in the tissue, and/or fibrous and non-fibrous tissue.

In various aspects, the sensors of a sensor array, in accordance with the present disclosure, can be placed on a staple cartridge. An adhesive mask can be embedded with the sensors at predetermined locations. In various aspects, the sensors are attached to bumps on the staple cartridge so that the sensors are positioned higher than a cartridge deck of the staple cartridge to ensure contact with the tissue. The adhesive mask could be created in bulk using screen-printing technology on a polyester substrate, for example. Conducting pads can be printed to a common location.

In various examples, in addition to detection of proximity to cancerous tissue, an end effector of the present disclosure can also be configured to target specific cancer types in specific tissues. As indicated in the journal publication to Altenberg B and Greulich K O, Genomics 84(2004) pp. 1014-1020, which is incorporated herein by reference in its entirety, certain cancers are characterized by an overexpression of glycolysis genes while other cancers are not characterized by an overexpression of glycolysis genes. Accordingly, an end effector of the present disclosure can be equipped with a sensor array with a high specificity for cancerous tissue characterized by an overexpression of glycolysis genes such as lung cancer or liver cancer.

In various aspects, the sensor readings of a sensor array, in accordance with the present disclosure, are communicated by the surgical instrument to a surgical hub (e.g., surgical hub 106, 206) for additional analysis and/or for situational awareness.

EXAMPLES

Various aspects of the subject matter described herein are set out in the following examples:

Example 1: A method of compressing tissue during a surgical procedure is disclosed. The method comprises obtaining a surgical instrument comprising an end effector, wherein the end effector comprises a first jaw and a second jaw, establishing a communication pathway between the surgical instrument and a surgical hub, and inserting the surgical instrument into a surgical site. The method further comprises compressing tissue between the first jaw and the second jaw, determining a location of the compressed tissue with respect to at least one of the first jaw and the second jaw, communicating the determined location of the compressed tissue to the surgical hub, and displaying the determined location of the compressed tissue on a visual feedback device.

Example 2: The method of Example 1, wherein the location of the compressed tissue is determined using an impedance sensor.

Example 3: The method of Example 2, wherein the impedance sensor is positioned on the first jaw of the surgical instrument.

Example 4: The method of any one of Examples 2 and 3, wherein the impedance sensor is configured to determine if tissue is positioned against the impedance sensor to determine the location of the compressed tissue.

Example 5: The method of any one of Examples 1-4, wherein the location of the compressed tissue is determined using a photoacoustic sensor.

Example 6: The method of any one of Examples 1-5, wherein location of the compressed tissue is determined using a thin film coating positioned on the first jaw of the surgical instrument.

Example 7: The method of any one of Examples 1-6, wherein the method comprises simultaneously displaying the determined location of the compressed tissue on the visual feedback device.

Example 8: The method of any one of Examples 1-7, wherein the visual feedback device comprises a display screen.

Example 9: A method of compressing tissue during a surgical procedure is disclosed. The method comprises inserting a surgical instrument comprising an end effector into a surgical site, wherein the end effector comprises a first jaw and a second jaw and compressing tissue between the first jaw and the second jaw. The method further comprises determining a location of the compressed tissue within a surgical site, communicating the determined location of the compressed tissue to a surgical hub, and displaying the determined location of the compressed tissue on a display.

Example 10: The method of Example 9, wherein the location of the compressed tissue is determined using an impedance sensor.

Example 11: The method of Example 10, wherein the impedance sensor is configured to determine if tissue is positioned against the impedance sensor to determine the location of the compressed tissue.

Example 12: The method of any one of Examples 9-11, wherein the location of the compressed tissue is determined using a photoacoustic sensor.

Example 13: The method of any one of Examples 9-12, wherein location of the compressed tissue is determined using a thin film coating positioned on the first jaw of the surgical instrument.

Example 14: The method of any one of Examples 9-13, wherein the method comprises simultaneously displaying the determined location of the compressed tissue on the display.

Example 15: A method of grasping tissue during a surgical procedure is disclosed. The method comprises obtaining a surgical instrument comprising an end effector, wherein the end effector comprises a first jaw and a second jaw, establishing a communication pathway between the surgical instrument and a surgical hub, and grasping tissue between the first jaw and the second jaw. The method further comprises determining a location of the grasped tissue with respect to at least one of the first jaw and the second jaw, communicating the determined location of the grasped tissue to the surgical hub, and displaying the determined location of the grasped tissue on a visual feedback display.

Example 16: The method of Example 15, wherein the location of the grasped tissue is determined using an impedance sensor.

Example 17: The method of Example 16, wherein the impedance sensor is configured to determine if tissue is positioned against the impedance sensor to determine the location of the grasped tissue.

Example 18: The method of any one of Examples 15-17, wherein the location of the compressed tissue is determined using a photoacoustic sensor.

Example 19: The method of any one of Examples 15-18, wherein location of the compressed tissue is determined using a thin film coating positioned on the first jaw of the surgical instrument.

Example 20: The method of any one of Examples 15-19, wherein the method comprises simultaneously displaying the determined location of the compressed tissue on the visual feedback display.

Various additional aspects of the subject matter described herein are set out in the following examples:

Example 1: A surgical system comprises a surgical instrument. The surgical instrument comprises an end effector comprising a first jaw and a second jaw. The first jaw is configured to move relative to the second jaw. The surgical instrument further comprises a motor configured to move the first jaw relative to the second jaw according to a closure rate of change parameter and a closure threshold parameter. The surgical instrument further comprises a sensor configured to transmit a sensor signal indicative of a closure parameter of the end effector. The surgical system further comprises a control circuit communicatively coupled to the sensor. The control circuit is configured to receive perioperative information, wherein the perioperative information comprises one or more of a perioperative disease, a perioperative treatment, and a type of a surgical procedure. The control circuit is further configured to receive the sensor signal from the sensor and determine an adjustment to the closure rate of change parameter and the closure threshold parameter based on the perioperative information and the sensor signal.

Example 2: The surgical system of Example 1, wherein the control circuit is further configured to determine a characteristic of a tissue to be treated by the surgical instrument based on one or more of the perioperative information and the sensor signal.

Example 3: The surgical system of Example 2, wherein the tissue characteristic comprises one or more of a tissue type characteristic, muscular characteristic, vasculature characteristic, water content characteristic, stiffness characteristic, and thickness characteristic.

Example 4: The surgical system of any one of Examples 1-3, wherein the control circuit is further configured to change a speed of the motor based on the determined adjustment to the closure rate of change parameter and closure threshold parameter.

Example 5: The surgical system of any one of Examples 1-4, wherein the control circuit is further configured to generate an alert based on an inconsistency between a type of the surgical instrument and one or more of the perioperative information and the sensor signal.

Example 6: The surgical system of any one of Examples 1-5, wherein the perioperative information further comprises one or more of a type of a tissue to be treated by the surgical instrument, a tissue characteristic, a clinician history, and a type of staple cartridge for use with the surgical instrument.

Example 7: The surgical system of any one of Examples 1-6, wherein the closure threshold parameter is a maximum closure force threshold and the control circuit is further configured to disable the motor for a predetermined period of time based on reaching the maximum closure force threshold.

Example 8: A surgical system comprises a surgical hub configured to receive perioperative information transmitted from a remote database of a cloud computing system. The surgical hub is communicatively coupled to the cloud computing system. The surgical system further comprises a surgical instrument communicatively coupled to the surgical hub. The surgical instrument comprises an end effector comprising a first jaw and a second jaw. The first jaw is configured to move relative to the second jaw. The end effector further comprises a motor configured to move the first jaw relative to the second jaw according to a closure rate of change parameter and a closure threshold parameter of a closure control program received from the surgical hub. The end effector further comprises a sensor configured to transmit a sensor signal indicative of a closure parameter of the end effector. The surgical hub is further configured to receive the sensor signal from the sensor and determine an adjustment to the closure rate of change parameter and the closure threshold parameter based on the perioperative information and the sensor signal.

Example 9: The surgical system of Example 8, wherein the closure control program is a first closure control program, the surgical hub is further configured to transmit a second closure control program to the surgical instrument, and the second closure control program defines the adjustment to the closure rate of change parameter and the adjustment to the closure threshold parameter.

Example 10: The surgical system of Example 9, wherein the cloud computing system is configured to transmit the second closure control program to the surgical hub, and the adjustment to the closure rate of change parameter and the adjustment to the closure threshold parameter of the second control program is adjusted based on perioperative information.

Example 11: The surgical system of any one of Examples 8-10, wherein the surgical instrument is configured to generate an alert based on an inconsistency between a type of the surgical instrument and one or more of the perioperative information and the sensor signal.

Example 12: The surgical system of any one of Examples 8-11, wherein the closure threshold parameter is a maximum closure force threshold, and the surgical hub is further configured to disable the motor for a predetermined period of time based on reaching the maximum closure force threshold.

Example 13: The surgical system of any one of Examples 8-12, wherein the perioperative information comprises one or more of a perioperative disease, a perioperative treatment, a type of a surgical procedure, a clinician history, a type of the surgical instrument, a type of a tissue being treated by the surgical instrument, and a characteristic of the tissue.

Example 14: The surgical system of Example 9, wherein the surgical hub is further configured to change a speed of the motor based on the determined adjustment to the closure rate of change parameter and closure threshold parameter.

Example 15: A surgical instrument comprises an end effector comprising a first jaw and a second jaw. The first jaw is configured to move relative to the second jaw. The surgical instrument further comprises a motor configured to move the first jaw relative to the second jaw according to a closure rate of change parameter and a closure threshold parameter of a first closure control program received from a surgical hub. The surgical instrument further comprises a sensor configured to transmit a sensor signal indicative of a closure parameter of the end effector and a control circuit communicatively coupled to the sensor and the motor. The control circuit is configured to receive the sensor signal from the sensor and determine an adjustment to the closure rate of change parameter and the closure threshold parameter based on perioperative information and the sensor signal.

Example 16: The surgical system of Example 15, wherein the surgical instrument is configured to generate an alert based on an inconsistency between a type of the surgical instrument and one or more of the perioperative information and the sensor signal.

Example 17: The surgical system of Example 15 or 16, wherein the control circuit is further configured to switch from the first closure control program to a second closure control program received from a cloud computing system and change a speed of the motor based on the second closure control program.

Example 18: The surgical system of any one of Examples 15-17, wherein the control circuit is further configured to determine a characteristic and a type of a tissue to be treated by the surgical instrument based on one or more of the perioperative information and the sensor signal.

Example 19: The surgical system of any one of Examples 15-18, wherein the closure threshold parameter is a maximum closure force threshold.

Example 20: The surgical system of Example 19, wherein the closure threshold parameter is a maximum closure force threshold.

Various additional aspects of the subject matter described herein are set out in the following examples:

Example 1: A surgical system comprises a surgical instrument. The surgical instrument comprises an end effector comprising a first jaw and a second jaw. The first jaw is configured to move relative to the second jaw. The surgical instrument further comprises a motor configured to move the first jaw relative to the second jaw according to a closure rate of change parameter and a closure threshold parameter. The surgical instrument further comprises a sensor configured to transmit a sensor signal indicative of a closure parameter of the end effector. The surgical system further comprises a control circuit communicatively coupled to the sensor. The control circuit is configured to receive perioperative information, wherein the perioperative information comprises one or more of a perioperative disease, a perioperative treatment, and a type of a surgical procedure. The control circuit is further configured to receive the sensor signal from the sensor and determine an adjustment to the closure rate of change parameter and the closure threshold parameter based on the perioperative information and the sensor signal.

Example 2: The surgical system of Example 1, wherein the control circuit is further configured to determine a characteristic of a tissue to be treated by the surgical instrument based on one or more of the perioperative information and the sensor signal.

Example 3: The surgical system of Example 2, wherein the tissue characteristic comprises one or more of a tissue type characteristic, muscular characteristic, vasculature characteristic, water content characteristic, stiffness characteristic, and thickness characteristic.

Example 4: The surgical system of any one of Examples 1-3, wherein the control circuit is further configured to change a speed of the motor based on the determined adjustment to the closure rate of change parameter and closure threshold parameter.

Example 5: The surgical system of any one of Examples 1-3, wherein the control circuit is further configured to generate an alert based on an inconsistency between a type of the surgical instrument and one or more of the perioperative information and the sensor signal.

Example 6: The surgical system of any one of Examples 1-5, wherein the perioperative information further comprises one or more of a type of a tissue to be treated by the surgical instrument, a tissue characteristic, a clinician history, and a type of staple cartridge for use with the surgical instrument.

Example 7: The surgical system of any one of Examples 1-6, wherein the closure threshold parameter is a maximum closure force threshold and the control circuit is further configured to disable the motor for a predetermined period of time based on reaching the maximum closure force threshold.

Example 8: A surgical system comprises a surgical hub configured to receive perioperative information transmitted from a remote database of a cloud computing system. The surgical hub is communicatively coupled to the cloud computing system. The surgical system further comprises a surgical instrument communicatively coupled to the surgical hub. The surgical instrument comprises an end effector comprising a first jaw and a second jaw. The first jaw is configured to move relative to the second jaw. The end effector further comprises a motor configured to move the first jaw relative to the second jaw according to a closure rate of change parameter and a closure threshold parameter of a closure control program received from the surgical hub. The end effector further comprises a sensor configured to transmit a sensor signal indicative of a closure parameter of the end effector. The surgical hub is further configured to receive the sensor signal from the sensor and determine an adjustment to the closure rate of change parameter and the closure threshold parameter based on the perioperative information and the sensor signal.

Example 9: The surgical system of Example 8, wherein the closure control program is a first closure control program, the surgical hub is further configured to transmit a second closure control program to the surgical instrument, and the second closure control program defines the adjustment to the closure rate of change parameter and the adjustment to the closure threshold parameter.

Example 10: The surgical system of Example 9, wherein the cloud computing system is configured to transmit the second closure control program to the surgical hub, and the adjustment to the closure rate of change parameter and the adjustment to the closure threshold parameter of the second control program is adjusted based on perioperative information.

Example 11: The surgical system of any one of Examples 8-10, wherein the surgical instrument is configured to generate an alert based on an inconsistency between a type of the surgical instrument and one or more of the perioperative information and the sensor signal.

Example 12: The surgical system of any one of Examples 8-11, wherein the closure threshold parameter is a maximum closure force threshold, and the surgical hub is further configured to disable the motor for a predetermined period of time based on reaching the maximum closure force threshold.

Example 13: The surgical system o any one of Examples 8-12, wherein the perioperative information comprises one or more of a perioperative disease, a perioperative treatment, a type of a surgical procedure, a clinician history, a type of the surgical instrument, a type of a tissue being treated by the surgical instrument, and a characteristic of the tissue.

Example 14: The surgical system of Example 9, wherein the surgical hub is further configured to change a speed of the motor based on the determined adjustment to the closure rate of change parameter and closure threshold parameter.

Example 15: A surgical instrument comprises an end effector comprising a first jaw and a second jaw. The first jaw is configured to move relative to the second jaw. The surgical instrument further comprises a motor configured to move the first jaw relative to the second jaw according to a closure rate of change parameter and a closure threshold parameter of a first closure control program received from a surgical hub. The surgical instrument further comprises a sensor configured to transmit a sensor signal indicative of a closure parameter of the end effector and a control circuit communicatively coupled to the sensor and the motor. The control circuit is configured to receive the sensor signal from the sensor and determine an adjustment to the closure rate of change parameter and the closure threshold parameter based on perioperative information and the sensor signal.

Example 16: The surgical system of Example 15, wherein the surgical instrument is configured to generate an alert based on an inconsistency between a type of the surgical instrument and one or more of the perioperative information and the sensor signal.

Example 17: The surgical system of Example 15 or 16, wherein the control circuit is further configured to switch from the first closure control program to a second closure control program received from a cloud computing system and change a speed of the motor based on the second closure control program.

Example 18: The surgical system of any one of Examples 15-17, wherein the control circuit is further configured to determine a characteristic and a type of a tissue to be treated by the surgical instrument based on one or more of the perioperative information and the sensor signal.

Example 19: The surgical system of any one of Examples 15-18, wherein the closure threshold parameter is a maximum closure force threshold.

Example 20: The surgical system of Example 19, wherein the closure threshold parameter is a maximum closure force threshold.

Various additional aspects of the subject matter described herein are set out in the following examples:

Example 1: A surgical system comprises a surgical instrument. The surgical instrument comprises an end effector comprising a first jaw and a second jaw. The first jaw is configured to move relative to the second jaw. The surgical instrument further comprises a motor configured to move the first jaw relative to the second jaw according to a closure rate of change parameter and a closure threshold parameter. The surgical instrument further comprises a sensor configured to transmit a sensor signal indicative of a closure parameter of the end effector. The surgical system further comprises a control circuit communicatively coupled to the sensor. The control circuit is configured to receive perioperative information, wherein the perioperative information comprises one or more of a perioperative disease, a perioperative treatment, and a type of a surgical procedure. The control circuit is further configured to receive the sensor signal from the sensor and determine an adjustment to the closure rate of change parameter and the closure threshold parameter based on the perioperative information and the sensor signal.

Example 2: The surgical system of Example 1, wherein the control circuit is further configured to determine a characteristic of a tissue to be treated by the surgical instrument based on one or more of the perioperative information and the sensor signal.

Example 3: The surgical system of Example 2, wherein the tissue characteristic comprises one or more of a tissue type characteristic, muscular characteristic, vasculature characteristic, water content characteristic, stiffness characteristic, and thickness characteristic.

Example 4: The surgical system of any one of Examples 1-3, wherein the control circuit is further configured to change a speed of the motor based on the determined adjustment to the closure rate of change parameter and closure threshold parameter.

Example 5: The surgical system of any one of Examples 1-4, wherein the control circuit is further configured to generate an alert based on an inconsistency between a type of the surgical instrument and one or more of the perioperative information and the sensor signal.

Example 6: The surgical system of any one of Examples 1-5, wherein the perioperative information further comprises one or more of a type of a tissue to be treated by the surgical instrument, a tissue characteristic, a clinician history, and a type of staple cartridge for use with the surgical instrument.

Example 7: The surgical system of any one of Examples 1-6, wherein the closure threshold parameter is a maximum closure force threshold and the control circuit is further configured to disable the motor for a predetermined period of time based on reaching the maximum closure force threshold.

Example 8: A surgical system comprises a surgical hub configured to receive perioperative information transmitted from a remote database of a cloud computing system. The surgical hub is communicatively coupled to the cloud computing system. The surgical system further comprises a surgical instrument communicatively coupled to the surgical hub. The surgical instrument comprises an end effector comprising a first jaw and a second jaw. The first jaw is configured to move relative to the second jaw. The end effector further comprises a motor configured to move the first jaw relative to the second jaw according to a closure rate of change parameter and a closure threshold parameter of a closure control program received from the surgical hub. The end effector further comprises a sensor configured to transmit a sensor signal indicative of a closure parameter of the end effector. The surgical hub is further configured to receive the sensor signal from the sensor and determine an adjustment to the closure rate of change parameter and the closure threshold parameter based on the perioperative information and the sensor signal.

Example 9: The surgical system of Example 8, wherein the closure control program is a first closure control program, the surgical hub is further configured to transmit a second closure control program to the surgical instrument, and the second closure control program defines the adjustment to the closure rate of change parameter and the adjustment to the closure threshold parameter.

Example 10: The surgical system of Example 9, wherein the cloud computing system is configured to transmit the second closure control program to the surgical hub, and the adjustment to the closure rate of change parameter and the adjustment to the closure threshold parameter of the second control program is adjusted based on perioperative information.

Example 11: The surgical system of any one of Examples 8-10, wherein the surgical instrument is configured to generate an alert based on an inconsistency between a type of the surgical instrument and one or more of the perioperative information and the sensor signal.

Example 12: The surgical system of any one of Examples 8-11, wherein the closure threshold parameter is a maximum closure force threshold, and the surgical hub is further configured to disable the motor for a predetermined period of time based on reaching the maximum closure force threshold.

Example 13: The surgical system of any one of Examples 8-12, wherein the perioperative information comprises one or more of a perioperative disease, a perioperative treatment, a type of a surgical procedure, a clinician history, a type of the surgical instrument, a type of a tissue being treated by the surgical instrument, and a characteristic of the tissue.

Example 14: The surgical system of Example 9, wherein the surgical hub is further configured to change a speed of the motor based on the determined adjustment to the closure rate of change parameter and closure threshold parameter.

Example 15: A surgical instrument comprises an end effector comprising a first jaw and a second jaw. The first jaw is configured to move relative to the second jaw. The surgical instrument further comprises a motor configured to move the first jaw relative to the second jaw according to a closure rate of change parameter and a closure threshold parameter of a first closure control program received from a surgical hub. The surgical instrument further comprises a sensor configured to transmit a sensor signal indicative of a closure parameter of the end effector and a control circuit communicatively coupled to the sensor and the motor. The control circuit is configured to receive the sensor signal from the sensor and determine an adjustment to the closure rate of change parameter and the closure threshold parameter based on perioperative information and the sensor signal.

Example 16: The surgical system of Example 15, wherein the surgical instrument is configured to generate an alert based on an inconsistency between a type of the surgical instrument and one or more of the perioperative information and the sensor signal.

Example 17: The surgical system of Example 15 or 16, wherein the control circuit is further configured to switch from the first closure control program to a second closure control program received from a cloud computing system and change a speed of the motor based on the second closure control program.

Example 18: The surgical system of any one of Examples 15-17, wherein the control circuit is further configured to determine a characteristic and a type of a tissue to be treated by the surgical instrument based on one or more of the perioperative information and the sensor signal.

Example 19: The surgical system of any one of Examples 15-18, wherein the closure threshold parameter is a maximum closure force threshold.

Example 20: The surgical system of Example 19, wherein the closure threshold parameter is a maximum closure force threshold.

Various additional aspects of the subject matter described herein are set out in the following examples:

Example 1: A surgical system comprises a surgical instrument. The surgical instrument comprises an end effector comprising a first jaw and a second jaw. The first jaw is configured to move relative to the second jaw. The surgical instrument further comprises a motor configured to move the first jaw relative to the second jaw according to a closure rate of change parameter and a closure threshold parameter. The surgical instrument further comprises a sensor configured to transmit a sensor signal indicative of a closure parameter of the end effector. The surgical system further comprises a control circuit communicatively coupled to the sensor. The control circuit is configured to receive perioperative information, wherein the perioperative information comprises one or more of a perioperative disease, a perioperative treatment, and a type of a surgical procedure. The control circuit is further configured to receive the sensor signal from the sensor and determine an adjustment to the closure rate of change parameter and the closure threshold parameter based on the perioperative information and the sensor signal.

Example 2: The surgical system of Example 1, wherein the control circuit is further configured to determine a characteristic of a tissue to be treated by the surgical instrument based on one or more of the perioperative information and the sensor signal.

Example 3: The surgical system of Example 2, wherein the tissue characteristic comprises one or more of a tissue type characteristic, muscular characteristic, vasculature characteristic, water content characteristic, stiffness characteristic, and thickness characteristic.

Example 4: The surgical system of any one of Examples 1-3, wherein the control circuit is further configured to change a speed of the motor based on the determined adjustment to the closure rate of change parameter and closure threshold parameter.

Example 5: The surgical system of any one of Examples 1-4, wherein the control circuit is further configured to generate an alert based on an inconsistency between a type of the surgical instrument and one or more of the perioperative information and the sensor signal.

Example 6: The surgical system of any one of Examples 1-5, wherein the perioperative information further comprises one or more of a type of a tissue to be treated by the surgical instrument, a tissue characteristic, a clinician history, and a type of staple cartridge for use with the surgical instrument.

Example 7: The surgical system of any one of Examples 1-6, wherein the closure threshold parameter is a maximum closure force threshold and the control circuit is further configured to disable the motor for a predetermined period of time based on reaching the maximum closure force threshold.

Example 8: A surgical system comprises a surgical hub configured to receive perioperative information transmitted from a remote database of a cloud computing system. The surgical hub is communicatively coupled to the cloud computing system. The surgical system further comprises a surgical instrument communicatively coupled to the surgical hub. The surgical instrument comprises an end effector comprising a first jaw and a second jaw. The first jaw is configured to move relative to the second jaw. The end effector further comprises a motor configured to move the first jaw relative to the second jaw according to a closure rate of change parameter and a closure threshold parameter of a closure control program received from the surgical hub. The end effector further comprises a sensor configured to transmit a sensor signal indicative of a closure parameter of the end effector. The surgical hub is further configured to receive the sensor signal from the sensor and determine an adjustment to the closure rate of change parameter and the closure threshold parameter based on the perioperative information and the sensor signal.

Example 9: The surgical system of Example 8, wherein the closure control program is a first closure control program, the surgical hub is further configured to transmit a second closure control program to the surgical instrument, and the second closure control program defines the adjustment to the closure rate of change parameter and the adjustment to the closure threshold parameter.

Example 10: The surgical system of Example 9, wherein the cloud computing system is configured to transmit the second closure control program to the surgical hub, and the adjustment to the closure rate of change parameter and the adjustment to the closure threshold parameter of the second control program is adjusted based on perioperative information.

Example 11: The surgical system of any one of Examples 8-10, wherein the surgical instrument is configured to generate an alert based on an inconsistency between a type of the surgical instrument and one or more of the perioperative information and the sensor signal.

Example 12: The surgical system of any one of Examples 8-11, wherein the closure threshold parameter is a maximum closure force threshold, and the surgical hub is further configured to disable the motor for a predetermined period of time based on reaching the maximum closure force threshold.

Example 13: The surgical system of any one of Examples 8-12, wherein the perioperative information comprises one or more of a perioperative disease, a perioperative treatment, a type of a surgical procedure, a clinician history, a type of the surgical instrument, a type of a tissue being treated by the surgical instrument, and a characteristic of the tissue.

Example 14: The surgical system of Example 9, wherein the surgical hub is further configured to change a speed of the motor based on the determined adjustment to the closure rate of change parameter and closure threshold parameter.

Example 15: A surgical instrument comprises an end effector comprising a first jaw and a second jaw. The first jaw is configured to move relative to the second jaw. The surgical instrument further comprises a motor configured to move the first jaw relative to the second jaw according to a closure rate of change parameter and a closure threshold parameter of a first closure control program received from a surgical hub. The surgical instrument further comprises a sensor configured to transmit a sensor signal indicative of a closure parameter of the end effector and a control circuit communicatively coupled to the sensor and the motor. The control circuit is configured to receive the sensor signal from the sensor and determine an adjustment to the closure rate of change parameter and the closure threshold parameter based on perioperative information and the sensor signal.

Example 16: The surgical system of Example 15, wherein the surgical instrument is configured to generate an alert based on an inconsistency between a type of the surgical instrument and one or more of the perioperative information and the sensor signal.

Example 17: The surgical system of Example 15 or 16, wherein the control circuit is further configured to switch from the first closure control program to a second closure control program received from a cloud computing system and change a speed of the motor based on the second closure control program.

Example 18: The surgical system of any one of Examples 15-17, wherein the control circuit is further configured to determine a characteristic and a type of a tissue to be treated by the surgical instrument based on one or more of the perioperative information and the sensor signal.

Example 19: The surgical system of any one of Examples 15-18, wherein the closure threshold parameter is a maximum closure force threshold.

Example 20: The surgical system of Example 19, wherein the closure threshold parameter is a maximum closure force threshold.

Various additional aspects of the subject matter described herein are set out in the following examples:

Example 1: A surgical stapling instrument comprises an end effector. The end effector comprises a first jaw and a second jaw movable relative to the first jaw between an open configuration and a closed configuration to grasp tissue between the first jaw and the second jaw. The end effector further comprises an anvil and a staple cartridge. The staple cartridge comprises staples deployable into the tissue and deformable by the anvil. The surgical stapling system further comprises a control circuit. The control circuit is configured to determine tissue impedances at predetermined zones, detect an irregularity in tissue distribution within the end effector based on the tissue impedances, and adjust a closure parameter of the end effector in accordance with the irregularity.

Example 2: The surgical stapling instrument of Example 1, wherein the end effector comprises sensing circuits at the predetermined zones.

Example 3: The surgical stapling instrument of Example 1 or 2, wherein the predetermined zones are separated by insulating elements.

Example 4: The surgical stapling instrument of any one of Examples 1-3, wherein the predetermined zones comprise an inner predetermined zone, an outer predetermined zone, and an intermediate predetermined zone between the inner predetermined zone and the outer predetermined zone.

Example 5: The surgical stapling instrument of Example 4, wherein detecting the irregularity in tissue distribution within the end effector comprises determining that an average of the tissue impedances at the inner predetermined zone and the outer predetermined zone is greater than the tissue impedance at the intermediate predetermined zone.

Example 6: The surgical stapling instrument of any one of Examples 1-5, wherein detecting the irregularity in tissue distribution within the end effector causes the control circuit to alert a user to release and reposition the tissue grasped by the end effector.

Example 7: The surgical stapling instrument of Example 4, wherein detecting the irregularity in tissue distribution within the end effector comprises determining that an average of the tissue impedances at the inner predetermined zone and the outer predetermined zone is less than or equal to the tissue impedance at the intermediate predetermined zone. Detecting the irregularity in tissue distribution within the end effector further comprises determining that the tissue impedance of the inner predetermined zone is greater than the tissue impedance of the outer predetermined zone.

Example 8: The surgical stapling instrument of any one of Examples 1-7, further comprising a motor configured to motivate the end effector to transition to the closed configuration, wherein detecting the irregularity in tissue distribution within the end effector causes the control circuit to reduce a speed of the motor.

Example 9: The surgical stapling instrument of any one of Examples 1-8, wherein the closure parameter is closure velocity.

Example 10: The surgical stapling instrument of any one of Examples 1-9, wherein the control circuit is configured to pass at least one therapeutic signal through tissue at each of the predetermined zones to determine the tissue impedances.

Example 11: A surgical stapling instrument for stapling a previously-stapled tissue comprises a shaft defining a longitudinal axis extending there through, and an end effector extending from the shaft. The end effector comprises a first jaw and a second jaw movable relative to the first jaw between an open configuration and a closed configuration to grasp tissue between the first jaw and the second jaw. The end effector further comprises an anvil and a staple cartridge. The staple cartridge comprises staples deployable into the previously-stapled tissue and deformable by the anvil. The end effector further comprises predetermined zones between the anvil and the staple cartridge. The surgical stapling instrument further comprises a circuit. The circuit is configured to measure tissue impedances at the predetermined zones, compare the measured tissue impedances to a predetermined tissue impedance signature of the predetermined zones, and detect an irregularity in at least one of position and orientation of the previously-stapled tissue within the end effector from the comparison.

Example 12: The surgical stapling instrument of Example 11, wherein the end effector comprises sensing circuits at the predetermined zones.

Example 13: The surgical stapling instrument of Example 11 or 12, wherein the predetermined zones are separated by insulating elements.

Example 14: The surgical stapling instrument of any one of Examples 11-13, wherein the predetermined zones are circumferentially arranged about the longitudinal axis.

Example 15: The surgical stapling instrument of any one of Examples 11-14, wherein detecting the irregularity causes the control circuit to alert a user.

Example 16: The surgical stapling instrument of any one of Examples 11-15, wherein the control circuit is configured to pass at least one therapeutic signal through tissue at each of the predetermined zones to determine the tissue impedances.

Example 17: A surgical stapling instrument comprises an end effector. The end effector comprises a first jaw and a second jaw movable relative to the first jaw between an open configuration and a closed configuration to grasp tissue between the first jaw and the second jaw. The end effector further comprises an anvil and a staple cartridge. The staple cartridge comprises staples deployable into the tissue and deformable by the anvil. The end effector further comprises predetermined zones between the anvil and the staple cartridge. The surgical stapling instrument further comprises a control circuit. The control circuit is configured to determine an electrical parameter of the tissue at each of the predetermined zones, detect an irregularity in tissue distribution within the end effector based on the determined electrical parameters, and adjust a closure parameter of the end effector in accordance with the irregularity.

Example 18: The surgical stapling instrument of Example 17, wherein the end effector comprises sensing circuits at the predetermined zones.

Example 19: The surgical stapling instrument of Example 17 or 18, wherein the predetermined zones are separated by insulating elements.

Example 20: The surgical stapling instrument of any one of Examples 17-19, wherein the closure parameter is closure velocity.

Various additional aspects of the subject matter described herein are set out in the following numbered examples.

Example 1: A surgical instrument is disclosed. The surgical instrument comprises an end effector and a control circuit. The end effector comprises a first jaw, a second jaw movable relative to the first jaw to grasp tissue therebetween, an anvil, a staple cartridge comprising staples deployable into the tissue, wherein the staples are deformable by the anvil, and a sensor configured to provide a sensor signal according to a physiological parameter of the tissue. The control circuit is coupled to the sensor, wherein the control circuit is configured to receive the sensor signal, and assess proximity of the sensory to cancerous tissue based on the sensor signal.

Example 2: The surgical instrument of Example 1, wherein the control circuit is further configured to generate an alert in the event the proximity of the sensor to cancerous tissue reaches or crosses a predetermined threshold.

Example 3: The surgical instrument of any one of Examples 1 and 2, wherein the control circuit is further configured to prevent deployment of the staples in the event the proximity of the sensor to cancerous tissue reaches or crosses a predetermined threshold.

Example 4: The surgical instrument of any one of Examples 1-3, further comprising a motor configured to cause deployment of the staples, wherein the control circuit is further configured to prevent activation of the motor in the event the value of the physiological parameter reaches or crosses a predetermined threshold.

Example 5: The surgical instrument of any one of Examples 1-4, wherein the physiological parameter is tissue glucose level.

Example 6: The surgical instrument of any one of Examples 1-4, wherein the physiological parameter is tissue pH level.

Example 7: The surgical instrument of any one of Examples 1-6, wherein the sensor is a Clark-type sensor.

Example 8: The surgical instrument of any one of Examples 1-7, wherein the control circuit is further configured to provide instructions to move the end effector in a predetermined direction away from the cancerous tissue.

Example 9: A surgical stapling instrument is disclosed. The surgical stapling instrument comprises an end effector and a control circuit. The end effector comprises a first jaw, a second jaw movable relative to the first jaw to grasp tissue therebetween, an anvil, a staple cartridge comprising staples deployable into the tissue, wherein the staples are deformable by the anvil, and a sensor configured to provide a sensory signal according to a physiological parameter indicative of proximity of the sensor to cancerous tissue. The control circuit is coupled to the sensor, wherein the control circuit is configured to receive the sensor signal, determine a value of the physiological parameter based on the sensor signal, and compare the value of the physiological parameter to a predetermined threshold.

Example 10: The surgical stapling instrument of Example 9, wherein the control circuit is further configured to generate an alert based on comparing the value of the physiological parameter to a predetermined threshold.

Example 11: The surgical stapling instrument of any one of Examples 9 and 10, wherein the control circuit is further configured to prevent deployment of the staples in the event the value of the physiological parameter reaches or crosses the predetermined threshold.

Example 12: The surgical stapling instrument of any one of Examples 9-11, further comprising a motor configured to cause deployment of the staples, wherein the control circuit is further configured to prevent activation of the motor in the event the value of the physiological parameter reaches or crosses the predetermined threshold.

Example 13: The surgical stapling instrument of any one of Examples 9-12, wherein the physiological parameter is tissue glucose level.

Example 14: The surgical stapling instrument of any one of Examples 9-12, wherein the physiological parameter is tissue pH level.

Example 15: The surgical stapling instrument of any one of Examples 9-14, wherein the sensor is a Clark-type sensor.

Example 16: The surgical stapling instrument of any one of Examples 9-15, wherein the control circuit is further configured to provide instructions to move the end effector in a predetermined direction away from the cancerous tissue.

Example 17: A surgical instrument is disclosed. The surgical instrument comprises an end effector and a control circuit. The end effector comprises a first jaw, a second jaw movable relative to the first jaw to grasp tissue therebetween, an anvil, a staple cartridge comprising staples deployable into the tissue, wherein the staples are deformable by the anvil, and a sensor assembly configured to provide sensor signals according to a physiological parameter indicative of proximity of the sensors to cancerous tissue. The sensor assembly comprises a first sensor on a first side of a longitudinal axis extending through the staple cartridge and a second sensor on a second side of the longitudinal axis. The control circuit is coupled to the sensor assembly, wherein the control circuit is configured to receive a first sensor signal from the first sensor, receive a second sensor signal from the second sensor, determine a first value of the physiological parameter based on the first sensor signal, determine a second value of the physiological parameter based on the second sensor signal, and compare the first value and the second value to a predetermined threshold.

Example 18: The surgical instrument of Example 17, wherein the control circuit is further configured to provide instructions to move the end effector in a first direction in the event the first value but not the second value reaches or crosses the predetermined threshold, and wherein the first direction extends away from the longitudinal axis on the first side.

Example 19: The surgical instrument of Example 18, wherein the control circuit is further configured to provide instructions to move the end effector in a second direction in the event the second value but not the first value reaches or crosses the predetermined threshold, and wherein the second directions extends away from the longitudinal axis on the second side.

Example 20: The surgical instrument of Example 19, wherein the control circuit is further configured to approve position of the end effector in the event the first value and the second value are below the predetermined threshold.

Various additional aspects of the subject matter described herein are set out in the following numbered examples:

Example 1: A cartridge for a surgical instrument configured to grasp a tissue, the cartridge comprising a circuit, comprising: an active element configured to stimulate the tissue; and a sensor configured to take measurements corresponding to a tissue parameter associated with the tissue; wherein the circuit is configured to determine a tissue type of the tissue according to a change in the tissue parameter detected by the sensor resulting from a stimulus from the active element.

Example 2: The cartridge of Example 1, wherein the active element comprises a heating element and the stimulus comprises thermal energy.

Example 3: The cartridge of Example 2, wherein the sensor is configured to measure a change in a temperature of the tissue resulting from the thermal energy applied by the heating element.

Example 4: The cartridge of Example 1, wherein the active element comprises a pressure-applying element and the stimulus comprises pressure.

Example 5: The cartridge of Example 4, wherein the pressure-applying element comprises an electroactive polymer.

Example 6: The cartridge of Example 4 or 5, wherein the sensor is configured to measure a viscoelastic response of the tissue resulting from the pressure applied by the pressure-applying element.

Example 7: The cartridge of any one of Examples 1-6, wherein the circuit comprises a flex circuit.

Example 8: The cartridge of any one of Examples 1-7, wherein the cartridge comprises a stapler cartridge.

Example 9: A surgical instrument for use with a cartridge comprising a data-representative feature representing a first cartridge data and a data storage element storing a second cartridge data, the surgical instrument comprising: an end effector configured to receive the cartridge; a sensor configured to take measurements associated with the data-representative feature that are representative of the first cartridge data; and a control circuit coupled to the sensor, the control circuit configured to: determine the first cartridge data according to measurements taken by the sensor; receive the second cartridge data from the data storage element; determine whether the first cartridge data corresponds to the second cartridge data; and select one of the first cartridge data or the second cartridge data in response to the first cartridge data not corresponding to the second cartridge data.

Example 10: The surgical instrument of Example 9, wherein the cartridge comprises an RFID tag and the sensor comprises an RFID reader.

Example 11: The surgical instrument of Example 9, wherein the data storage element comprises a chip coupled to a first electrical contact, wherein the control circuit comprises a second electrical contact, and wherein the control circuit is configured to receive the second cartridge data through contact between the first electrical contact and the second electrical contact.

Example 12: The surgical instrument of any one of Examples 9-11, wherein the data-representative feature comprises a deformable structure disposed at a proximal end of the cartridge, wherein the deformable structure is configured to deform when the end effector transitions from an open configuration to a closed configuration, and wherein the sensor is configured to detect a force exerted on the deformable structure by a jaw of the end effector as the jaw closes.

Example 13: The surgical instrument of any one of Examples 9-11, wherein the data-representative feature comprises a bar code and the sensor is configured to optically scan the bar code.

Example 14: The surgical instrument of any one of Examples 9-13, wherein the first cartridge data and the second cartridge data correspond to a cartridge type.

Example 15: The surgical instrument of any one of Examples 9-13, wherein the first cartridge data and the second cartridge data correspond to a cartridge characteristic.

Example 16: A cartridge for a surgical instrument, the cartridge comprising: a data-representative feature comprising one or more physical characteristics, the one or more physical characteristics indicative of a first cartridge data; and a data storage element comprising a memory, the memory storing a second cartridge data.

Example 17: The cartridge of Example 16, comprising an RFID tag that is readable by an RFID reader.

Example 18: The cartridge of Example 16, wherein the data storage element comprises a chip coupled to a first electrical contact, the first electrical contact configured to electrically couple to a second electrical contact to define a wired connection therebetween.

Example 19: The cartridge of any one of Examples 16-18, wherein the data-representative feature comprises a deformable structure disposed at a proximal end of the cartridge, the deformable structure configured to deform when an end effector of the surgical instrument transitions from an open configuration to a closed configuration.

Example 20: The cartridge of any one of Examples 16-18, wherein the data-representative feature comprises a bar code optically scannable by a sensor.

Various additional aspects of the subject matter described herein are set out in the following numbered examples:

Example 1: A modular component is used with a surgical instrument. The modular component comprises a sensor;

and a control circuit coupled to the sensor. The control circuit is configured to: determine whether a version of the modular component corresponds to a version of the surgical instrument in the event that the modular component is coupled to the surgical instrument; and cause the sensor to output data detected by the sensor in one of a first output mode or a second output mode according to whether the version of the modular component corresponds to the version of the surgical instrument; wherein the data of the first output mode is compatible with a first version of the surgical instrument and data of the second output mode is compatible with a second version of the surgical instrument.

Example 2: The modular component of Example 1, wherein the modular component comprises a staple cartridge.

Example 3: The modular component of Example 1 or 2, wherein the first version comprises a current version of the surgical instrument and the second version comprises a prior version of the surgical instrument.

Example 4: The modular component of any one of Examples 1-3, wherein: the first output mode corresponds to a magnetoresistance and impedance data feed; and the second output mode corresponds to a Hall effect data feed.

Example 5: The modular component of any one of Examples 1-3, wherein: the first output mode corresponds to a Hall effect data feed; and the second output mode corresponds to a limit switch data feed.

Example 6: A modular component for use with a surgical instrument, the modular component comprises: a sensor; and a control circuit coupled to the sensor. The control circuit is configured to: receive data output from the sensor; determine whether a modular component version corresponds to a surgical instrument version in the event that the modular component is coupled to the surgical instrument; and convert the data output from a first format to a second format according to whether the modular component version corresponds to the surgical instrument version; wherein the first format is compatible with a first version of the surgical instrument and second format is compatible with a second version of the surgical instrument.

Example 7: The modular component of Example 6, wherein the modular component comprises a staple cartridge.

Example 8: The modular component of Example 6 or 7, wherein the first version comprises a current version of the surgical instrument and the second version comprises a prior version of the surgical instrument.

Example 9: The modular component of any one of Examples 6-8, wherein: the first format corresponds to a magnetoresistance and impedance data feed; and the second format corresponds to a Hall effect data feed.

Example 10: The modular component of any one of Examples 6-8, wherein: the first format corresponds to a Hall effect data feed; and the second format corresponds to a limit switch data feed.

Example 11: A surgical system comprises a surgical instrument; and a modular component connectable to the surgical instrument, the modular component comprising: a sensor; and a control circuit coupled to the sensor. the control circuit IS configured to: determine whether a version of the modular component corresponds to a version of the surgical instrument in the event that the modular component is coupled to the surgical instrument; and cause the sensor to output data detected by the sensor in one of a first output mode or a second output mode according to whether the version of the modular component corresponds to the version of the surgical instrument; wherein the data of the first output mode is compatible with a first version of the surgical instrument and data of the second output mode is compatible with a second version of the surgical instrument.

Example 12: The surgical system of Example 11, wherein the modular component comprises a staple cartridge.

Example 13: The surgical system of Example 11 or 12, wherein the first version comprises a current version of the surgical instrument and the second version comprises a prior version of the surgical instrument.

Example 14: The surgical system of any one of Examples 11-13, wherein: the first output mode corresponds to a magnetoresistance and impedance data feed; and the second output mode corresponds to a Hall effect data feed.

Example 15: The surgical system of any one of Examples 11-13, wherein: the first output mode corresponds to a Hall effect data feed; and the second output mode corresponds to a limit switch data feed.

Example 16: The surgical system of any one of Examples 11-15, wherein the surgical instrument comprising a surgical stapler.

Various additional aspects of the subject matter described herein are set out in the following examples:

Example 1: A surgical system comprises a control circuit and a surgical instrument. The surgical instrument comprises a handle assembly, a shaft assembly extending distally from the handle assembly, and an end effector assembly coupled to a distal end of the shaft assembly. The end effector assembly comprises a first jaw, a second jaw pivotably coupled to the first jaw, and a sensor. The sensor is configured to detect a parameter associated with a function of the end effector and transmit the detected parameter to the control circuit. The control circuit is configured to analyze the detected parameter based on a system-defined constraint and prevent at least one function of the surgical instrument based on a result of the analysis. The surgical system further comprises a user interface configured to provide a current status regarding at least one prevented function of the surgical instrument.

Example 2: The surgical system of Example 1, wherein the system-defined constraint comprises at least one of a predefined parameter or a predefined parameter range based on historical data associated with a surgical procedure being performed by the surgical system.

Example 3: The surgical system of Example 1 or 2, wherein the current status comprises a first message that the at least one function of the surgical instrument is prevented and a second message indicating a reason why the at least one function of the surgical instrument is prevented.

Example 4: The surgical system of any one of Examples 1-3, wherein the user interface comprises a user-interface element selectable to override the control circuit to permit the at least one function of the surgical instrument.

Example 5: The surgical system of any one of Examples 1-4, wherein the sensor comprises a force sensor coupled to the end effector, wherein the detected parameter comprises a force applied to at least one of the first jaw or the second jaw of the end effector, and wherein the at least one function prevented via the control circuit comprises one or more than one of preventing use of an attached shaft, preventing a firing cycle from commencing, preventing articulation of the end effector, preventing shaft rotation, or preventing one or more than one of the first jaw or the second jaw from opening.

Example 6: The surgical system of any one of Examples 1-5, wherein the function of the end effector associated with the detected parameter comprises a clamping function, and wherein the at least one function of the surgical instrument prevented via the control circuit comprises one or more than one of a dissect function, a coagulation function, a staple function, or a cut function.

Example 7: The surgical system of any one of Examples 1-6, further comprising a surgical hub communicatively coupled to the surgical instrument, wherein the surgical hub comprises the control circuit.

Example 8: The surgical system of Example 7, wherein one of the handle assembly or the surgical hub comprises the user interface.

Example 9: The surgical system of any one of Examples 1-8, wherein one of the handle assembly, the shaft assembly, or the end effector assembly of the surgical instrument comprises the control circuit.

Example 10: The surgical system of any one of Examples 1-9, wherein the shaft assembly comprises a sensor configured to detect a shaft parameter associated with a function of the shaft and transmit the detected shaft parameter to the control circuit. The control circuit is further configured to prevent the at least one function of the surgical instrument further based on the detected shaft parameter.

Example 11: A surgical system comprises a surgical hub and a surgical instrument communicatively coupled to the surgical hub. The surgical instrument comprises a handle assembly, a shaft assembly extending distally from the handle assembly, and an end effector assembly coupled to a distal end of the shaft assembly. The end effector assembly comprises a first jaw, a second jaw pivotably coupled to the first jaw, and a sensor. The sensor is configured to detect a parameter associated with a function of the end effector and transmit the detected parameter to the surgical hub. The surgical hub comprises a processor and a memory coupled to the processor. The memory stores instructions executable by the processor to analyze the detected parameter based on a system-defined constraint and prevent at least one function of the surgical instrument based on a result of the analysis. The surgical system further comprises a user interface configured to provide a current status regarding at least one prevented function of the surgical instrument.

Example 12: The surgical system of Example 11, wherein the system-defined constraint comprises at least one of a predefined parameter or a predefined parameter range based on historical data associated with a surgical procedure being performed by the surgical system.

Example 13: The surgical system of Example 11 or 12, wherein the current status comprises a first message that the at least one function of the surgical instrument is prevented and a second message indicating a reason why the at least one function of the surgical instrument is prevented.

Example 14: The surgical system of any one of Examples 11-13, wherein the user interface comprises a user-interface element selectable to override the surgical hub to permit the at least one function of the surgical instrument.

Example 15: The surgical system of any one of Example 11-14, wherein the sensor comprises a force sensor coupled to the end effector, wherein the detected parameter comprises a force applied to at least one of the first jaw or the second jaw of the end effector, and wherein the at least one function prevented via the surgical hub comprises one or more than one of preventing use of an attached shaft, preventing a firing cycle from commencing, preventing articulation of the end effector, preventing shaft rotation, or preventing one or more than one of the first jaw or the second jaw from opening.

Example 16: The surgical system of any one of Examples 11-15, wherein the function of the end effector associated with the detected parameter comprises a clamping function, and wherein the at least one function of the surgical instrument prevented via the surgical hub comprises one or more than one of a dissect function, a coagulation function, a staple function, or a cut function.

Example 17: The surgical system of any one of Examples 11-16, wherein at least one of the handle assembly or the surgical hub comprises the user interface.

Example 18: The surgical system of any one of Examples 11-17, wherein the shaft assembly comprises a sensor configured to detect a shaft parameter associated with a function of the shaft and transmit the detected shaft parameter to the surgical hub. The memory further stores instructions executable by the processor to prevent the at least one function of the surgical instrument further based on the detected shaft parameter.

Example 19—A non-transitory computer readable medium stores computer readable instructions which, when executed, causes a machine to analyze a detected parameter, associated with a function of an end effector of a surgical system, based on a system-defined constraint, the surgical system including a handle assembly, a shaft assembly extending distally from the handle assembly, and an end effector assembly coupled to a distal end of the shaft assembly. The end effector assembly comprises a first jaw, a second jaw pivotably coupled to the first jaw, and a sensor configured to detect the detected parameter and transmit the detected parameter to the machine. The instructions, when executed, further cause the machine to prevent at least one function of the surgical system based on a result of the analysis, and generate a user interface. The user interface provides a current status regarding at least one prevented function of the surgical system.

Example 20: The non-transitory computer readable medium of Example 19 further comprises instructions that, when executed, further cause the machine to generate an override element on the user interface. The override element is selectable to permit the at least one function of the surgical system.

Various additional aspects of the subject matter described herein are set out under the heading in the following examples:

Example 1: A surgical system comprises a control circuit and a surgical instrument. The surgical instrument comprises a plurality of components and a sensor. Each of the plurality of components of the surgical instrument comprises a device parameter. Each component is configured to transmit its respective device parameter to the control circuit. The sensor is configured to detect a tissue parameter associated with a proposed function of the surgical instrument and transmit the detected tissue parameter to the control circuit. The control circuit is configured to analyze the detected tissue parameter in cooperation with each respective device parameter based on a system-defined constraint. The surgical system further comprises a user interface configured to indicate whether the surgical instrument comprising the plurality of components is appropriate to perform the proposed function.

Example 2: The surgical system of Example 1, wherein the detected tissue parameter comprises at least one of a type of the tissue, a thickness of the tissue, a stiffness of the tissue, a location of the tissue, or vascularization of the tissue.

Example 3: The surgical system of Example 1 or 2, wherein a component of the surgical instrument includes a staple cartridge, and wherein the device parameter includes at least one of a type of the staple cartridge, a color of the staple cartridge, adjuncts to the staple cartridge, a clamp load limit of the staple cartridge, a gap range for the staple cartridge, and a firing rate for the staple cartridge.

Example 4: The surgical system of any one of Examples 1-3, wherein a component of the surgical instrument includes an end effector, and wherein the detected tissue parameter comprises at least one of a closure angle of the end effector on the tissue, a length of the tissue in contact with a tissue-contacting surface of the end effector, and a force to compress the tissue within the end effector.

Example 5: The surgical system of Example 4, wherein the control circuit is further configured to identify the tissue as parenchyma, vessel or bronchus based on the at least one detected tissue parameter.

Example 6: The surgical system of any one of Examples 1-5, wherein the control circuit is further configured to recommend at least one alternative component for use with the surgical instrument to perform the proposed function.

Example 7: The surgical system of any one of Examples 1-6, wherein the system-defined constraint comprises at least one of a predetermined tissue parameter or a predetermined tissue parameter range associated with each transmitted device parameter.

Example 8: The surgical system of any one of Examples 1-7, wherein the control circuit is further configured to prevent the proposed function when the system-defined constraint is exceeded.

Example 9: The surgical system of Example 8, wherein the user interface comprises a user-interface element selectable to override the control circuit to permit the proposed function of the surgical instrument.

Example 10: The surgical system of any one of Examples 1-9, wherein the proposed function of the surgical instrument comprises one or more than one of clamping the tissue, coagulating the tissue, cutting the tissue, and stapling the tissue.

Example 11—The surgical system of any one of Examples 1-10, further comprising a surgical hub communicatively coupled to the surgical instrument, wherein the surgical hub comprises the control circuit.

Example 12: The surgical system of Example 11, wherein one of the surgical instrument or the surgical hub comprises the user interface.

Example 13: A surgical system comprises a surgical hub and a surgical instrument communicatively coupled to the surgical hub. The surgical instrument comprises a plurality of components and a sensor. Each of the plurality of components of the surgical instrument comprises a device parameter. Each component is configured to transmit its respective device parameter to the surgical hub. The sensor is configured to detect a tissue parameter associated with a proposed function of the surgical instrument and transmit the detected tissue parameter to the surgical hub. The surgical hub comprises a processor and a memory coupled to the processor. The memory stores instructions executable by the processor to analyze the detected tissue parameter in cooperation with each respective device parameter based on a system-defined constraint. The surgical system further comprises a user interface configured to indicate whether the surgical instrument comprising the plurality of components is appropriate to perform the proposed function.

Example 14: The surgical system of Example 13, wherein the detected tissue parameter comprises at least one of a type of the tissue, a thickness of the tissue, a stiffness of the tissue, a location of the tissue, or vascularization of the tissue.

Example 15: The surgical system of Example 13 or 14, wherein a component of the surgical instrument includes a staple cartridge, and wherein the device parameter includes at least one of a type of the staple cartridge, a color of the staple cartridge, adjuncts to the staple cartridge, a clamp load limit of the staple cartridge, a gap range for the staple cartridge, and a firing rate for the staple cartridge.

Example 16: The surgical system of any one of Examples 13-15, wherein a component of the surgical instrument includes an end effector, and wherein the detected tissue parameter comprises at least one of a closure angle of the end effector on the tissue, a length of the tissue in contact with a tissue-contacting surface of the end effector, and a force to compress the tissue within the end effector.

Example 17: The surgical system of any one of Examples 13-16, wherein the instructions are further executable by the processor of the surgical hub to recommend at least one alternative component for use with the surgical instrument to perform the proposed function.

Example 18: The surgical system of any one of Examples 13-17, wherein the instructions are further executable by the processor of the surgical hub to prevent the proposed function when the system-defined constraint is exceeded.

Example 19: A non-transitory computer readable medium stores computer readable instructions which, when executed, causes a machine to analyze a detected tissue parameter in cooperation with a device parameter, of each of a plurality of components of a surgical instrument of a surgical system, based on a system-defined constraint, wherein the detected tissue parameter is associated with a proposed function of the surgical instrument. The surgical system includes the surgical instrument which includes a plurality of components. Each component is configured to transmit its respective device parameter to the machine. The surgical system further includes a sensor configured to detect the detected tissue parameter and transmit the detected tissue parameter to the machine. The instructions, when executed, further cause the machine to generate a user interface, wherein the user interface provides an indication whether the surgical instrument including the plurality of components is appropriate to perform the proposed function of the surgical system.

Example 20: The non-transitory computer readable medium of Example 19, wherein the instructions, when executed, further cause the machine to generate an override element on the user interface, wherein the override element is selectable to permit the proposed function of the surgical instrument.

In various aspects, the sensors of a sensor array, in accordance with the present disclosure, can be placed on a staple cartridge. An adhesive mask can be embedded with the sensors at predetermined locations. In various aspects, the sensors are attached to bumps on the staple cartridge so that the sensors are positioned higher than a cartridge deck of the staple cartridge to ensure contact with the tissue. The adhesive mask could be created in bulk using screen-printing technology on a polyester substrate, for example. Conducting pads can be printed to a common location.

In various examples, in addition to detection of proximity to cancerous tissue, an end effector of the present disclosure can also be configured to target specific cancer types in specific tissues. As indicated in the journal publication to Altenberg B and Greulich K O, Genomics 84(2004) pp. 1014-1020, which is incorporated herein by reference in its entirety, certain cancers are characterized by an overexpression of glycolysis genes while other cancers are not characterized by an overexpression of glycolysis genes. Accordingly, an end effector of the present disclosure can be equipped with a sensor array with a high specificity for cancerous tissue characterized by an overexpression of glycolysis genes such as lung cancer or liver cancer.

In various aspects, the sensor readings of a sensor array, in accordance with the present disclosure, are communicated by the surgical instrument to a surgical hub (e.g., surgical hub 106, 206) for additional analysis and/or for situational awareness.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor comprising one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol.

The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A surgical system, comprising:

- a surgical instrument configured to perform a surgical procedure, wherein the surgical instrument comprises:
  - a housing;
  - a shaft assembly extending from the housing;
  - an end effector extending from the shaft assembly, wherein the end effector comprises a first jaw and a second jaw, wherein the first jaw is movable relative to the second jaw from an open position toward a closed position to capture tissue within the end effector; and
  - a sensor configured to sense a parameter associated with a function of the surgical instrument;
- a surgical hub comprising a processor and a memory communicatively coupled to the processor, wherein the memory stores instructions executable by the processor to:
  - receive data from the sensor, wherein the data comprises the parameter associated with the function of the surgical instrument;
  - infer a step of the surgical procedure being performed by the surgical instrument, based on the data from the sensor;
  - receive data from a database, wherein the data from the database is associated with the step of the surgical procedure;
  - compare a value of the parameter to the data received from the database; and
  - control the surgical instrument based on the comparison.

2. The surgical system of claim 1, wherein controlling the surgical instrument comprises controlling the housing, the shaft assembly, or the end effector, or combinations thereof.

3. The surgical system of claim 1, wherein the data from the database comprises a threshold parameter associated with the step of the surgical procedure, and wherein comparing the value of the parameter to the data received from the database comprises comparing the value of the parameter to the threshold parameter.

4. The surgical system of claim 1, wherein the data from the database comprises a threshold range associated with the step of the surgical procedure, and wherein comparing the value of the parameter to the data received from the database comprises comparing the value of the parameter to the threshold range.

5. The surgical system of claim 1, wherein the memory further stores instructions executable by the processor to infer a next surgical function to be performed by the surgical instrument, and wherein controlling the surgical instrument comprises preventing the surgical instrument from performing the next surgical function.

6. The surgical system of claim 1, wherein the function comprises the end effector rotating relative to the shaft assembly about an articulation joint.

7. The surgical system of claim 1, wherein the function comprises the shaft assembly rotating relative to the housing.

8. The surgical system of claim 1, wherein the function comprises the second jaw clamping the tissue within the end effector.

9. The surgical system of claim 1, wherein the end effector further comprises an electrode, and wherein the function comprises the surgical instrument applying energy to the tissue via the electrode.

10. The surgical system of claim 1, wherein the end effector further comprises a knife, and wherein the function comprises cutting the tissue with the knife.

11. The surgical system of claim 1, wherein the end effector further comprises a staple cartridge including staples removably stored therein, and wherein the function comprises deploying the staples into the tissue.

12. A surgical system, comprising:

- a surgical instrument configured to perform a surgical procedure, wherein the surgical instrument comprises:
  - a housing;
  - a shaft assembly extending from the housing;
  - an end effector extending from the shaft assembly, wherein the end effector comprises a first jaw and a second jaw, wherein the first jaw is movable relative to the second jaw from an open position toward a closed position to capture tissue within the end effector; and
  - a sensor configured to sense a parameter associated with a function of the surgical instrument;
- a surgical hub comprising a control circuit, configured to:
  - receive data from the sensor, wherein the data comprises the parameter associated with the function of the surgical instrument;
  - infer a step of the surgical procedure being performed by the surgical instrument, based on the data from the sensor;
  - infer a next function of the surgical procedure to be performed by the surgical instrument;
  - receive data from a database, wherein the data from the database is associated with the step of the surgical procedure;
  - compare a value of the parameter to the data received from the database; and
  - select between permitting the surgical instrument to perform the next function and preventing the surgical instrument from performing the next function based on the comparison.

13. The surgical system of claim 12, wherein the data from the database comprises a threshold parameter associated with the step of the surgical procedure, and wherein comparing the value of the parameter to the data received from the database comprises comparing the value of the parameter to the threshold parameter.

14. The surgical system of claim 12, wherein the data from the database comprises a threshold range associated with the step of the surgical procedure, and wherein comparing the value of the parameter to the data received from the database comprises comparing the value of the parameter to the threshold range.

* * * * *